US012460006B2

(12) United States Patent
Kurtagic et al.

(10) Patent No.: US 12,460,006 B2
(45) Date of Patent: Nov. 4, 2025

(54) ANTIBODIES AGAINST INTEGRIN ALPHA 11 BETA 1

(71) Applicant: Momenta Pharmaceuticals, Inc., Titusville, NJ (US)

(72) Inventors: Elma Kurtagic, Milton, MA (US); James W. Meador, III, Needham, MA (US); Christopher Beneduce, Jr., Medford, MA (US)

(73) Assignee: Momenta Pharmaceuticals, Inc., Titusville, NJ (US)

( * ) Notice: Subject to any disclaimer, the term of this patent is extended or adjusted under 35 U.S.C. 154(b) by 647 days.

(21) Appl. No.: 17/757,607

(22) PCT Filed: Dec. 18, 2020

(86) PCT No.: PCT/US2020/066107

§ 371 (c)(1),
(2) Date: Jun. 17, 2022

(87) PCT Pub. No.: WO2021/127500

PCT Pub. Date: Jun. 24, 2021

(65) Prior Publication Data

US 2023/0050972 A1 Feb. 16, 2023

Related U.S. Application Data

(60) Provisional application No. 63/054,717, filed on Jul. 21, 2020, provisional application No. 62/983,155, filed on Feb. 28, 2020, provisional application No. 62/951,723, filed on Dec. 20, 2019.

(51) Int. Cl.

| | |
|---|---|
| ***C07K 16/28*** | (2006.01) |
| ***A61P 1/16*** | (2006.01) |
| ***A61P 11/00*** | (2006.01) |
| ***A61P 35/00*** | (2006.01) |
| ***C12N 15/63*** | (2006.01) |

(52) U.S. Cl.

CPC ............ *C07K 16/2842* (2013.01); *A61P 1/16* (2018.01); *A61P 11/00* (2018.01); *A61P 35/00* (2018.01); *C12N 15/63* (2013.01); *C07K 2317/24* (2013.01); *C07K 2317/565* (2013.01)

(58) Field of Classification Search

None

See application file for complete search history.

(56) References Cited

U.S. PATENT DOCUMENTS

| | | | |
|---|---|---|---|
| 4,439,196 | A | 3/1984 | Higuchi |
| 4,447,224 | A | 5/1984 | DeCant, Jr. et al. |
| 4,447,233 | A | 5/1984 | Mayfield |
| 4,487,603 | A | 12/1984 | Harris |
| 4,596,556 | A | 6/1986 | Morrow et al. |
| 4,790,824 | A | 12/1988 | Morrow et al. |
| 4,816,567 | A | 3/1989 | Cabilly et al. |
| 4,868,116 | A | 9/1989 | Morgan et al. |
| 4,941,880 | A | 7/1990 | Burns |
| 4,946,778 | A | 8/1990 | Ladner et al. |
| 4,980,286 | A | 12/1990 | Morgan et al. |
| 5,013,556 | A | 5/1991 | Woodle et al. |
| 5,064,413 | A | 11/1991 | McKinnon et al. |
| 5,260,203 | A | 11/1993 | Ladner et al. |
| 5,308,341 | A | 5/1994 | Chanoch |
| 5,312,335 | A | 5/1994 | McKinnon et al. |
| 5,383,851 | A | 1/1995 | McKinnon, Jr. et al. |
| 5,399,163 | A | 3/1995 | Peterson et al. |
| 5,641,640 | A | 6/1997 | Hanning |
| 6,005,079 | A | 12/1999 | Casterman et al. |
| 6,096,002 | A | 8/2000 | Landau |
| 6,146,361 | A | 11/2000 | DiBiasi et al. |
| 6,192,891 | B1 | 2/2001 | Gravel et al. |
| 6,200,296 | B1 | 3/2001 | Dibiasi et al. |
| 6,277,099 | B1 | 8/2001 | Strowe et al. |
| 6,302,855 | B1 | 10/2001 | Lav et al. |
| 6,620,135 | B1 | 9/2003 | Weston et al. |
| 7,556,615 | B2 | 7/2009 | Pettis et al. |
| 7,670,600 | B2 | 3/2010 | Dall'Acqua et al. |
| 8,394,925 | B2 | 3/2013 | Chamberlain et al. |
| 11,634,470 | B2 | 4/2023 | Prakash |
| 2011/0256061 | A1 | 10/2011 | Lundgren-Akerlund |
| 2016/0202265 | A1 | 7/2016 | Kurosawa et al. |
| 2020/0262912 | A1 | 8/2020 | Orengo et al. |
| 2021/0079099 | A1 | 3/2021 | Gullberg |

FOREIGN PATENT DOCUMENTS

| | | | |
|---|---|---|---|
| EP | 0404097 | A2 | 12/1990 |
| EP | 1181317 | B1 | 7/2011 |
| EP | 3524625 | B1 | 8/2019 |
| WO | 1988001649 | A1 | 3/1988 |
| WO | 1989002468 | A1 | 3/1989 |
| WO | 1989005345 | A1 | 6/1989 |

(Continued)

OTHER PUBLICATIONS

Reichmann et al., "Single domain antibodies: comparison of camel VH and camelised human VH domains," J. Immunol. Methods (1999) vol. 231, 25-38.
Reichmann et al., "Reshaping human bodies for therapy," Nature (1988) vol. 332, pp. 323-327.
Romaine et al., "Overexpression of Integrin Alpha 11 Induces Cardiac Fibrosis in Mice," Acta Physiol. (2018) vol. 222 (2) e12932.
Rosenfeld et al., "Adenovirus-Mediated Transfer of a Recombinant Alpha1-Antitrypsin Gene to the Lung Epithelium in Vivo," Science (1991) vol. 252, No. 5004, pp. 431-434.

(Continued)

*Primary Examiner* — Gary B Nickol
*Assistant Examiner* — Cheom-Gil Cheong
(74) *Attorney, Agent, or Firm* — Troutman Pepper Locke LLP

(57) ABSTRACT

The present disclosure includes antibodies that specifically bind integrin alpha 11 beta 1 ($\alpha 11\beta 1$), as well as methods of making and using such antibodies.

9 Claims, 29 Drawing Sheets

Specification includes a Sequence Listing.

(56) References Cited

FOREIGN PATENT DOCUMENTS

| | | | |
|---|---|---|---|
| WO | 1989007136 | A2 | 8/1989 |
| WO | 1992007573 | A1 | 5/1992 |
| WO | 1993011161 | A1 | 6/1993 |
| WO | 1994004678 | A1 | 3/1994 |
| WO | 1994025591 | A1 | 11/1994 |
| WO | 2004060407 | A1 | 7/2004 |
| WO | 2008068481 | A1 | 6/2008 |
| WO | 2015161247 | A1 | 10/2015 |
| WO | 2017069627 | A1 | 4/2017 |
| WO | 2017201491 | A1 | 11/2017 |
| WO | 2019145404 | A1 | 8/2019 |
| WO | 2019154961 | A1 | 8/2019 |
| WO | 2019168176 | A1 | 9/2019 |
| WO | 2022130318 | A2 | 6/2022 |

OTHER PUBLICATIONS

Rosenfeld et al., "In Vivo Transfer of the Human Cystic Fibrosis Transmembrane Conductance Regulator Gene to the Airway Epithelium," Cell (Jan. 10, 1992) vol. 68, No. 1, pp. 143-155.
Rudikoff et al., "Single Amino Acid Substitution Altering Antigen-Binding Specificity," Proc. Natl. Acad. Sci. (Mar. 1, 1982) vol. 79, No. 6, pp. 1979-1983.
Ruiz-Ortega et al., "Targeting the Progression of Chronic Kidney Disease," Nature Reviews (2020) vol. 16, No. 5, pp. 269-288.
Samulski et al., "Helper-Free Stocks of Recombinant Adeno-Associated Viruses: Normal Integration Does Not Require Viral Gene Expression," J. Virol. (1989) vol. 63, No. 9, pp. 3822-3828.
Sassoon et al., "Antibody-Drug Conjugate (ADC) Clinical Pipeline: A Review," Methods Mol. Biol. (2013) vol. 1045, pp. 1-27.
Schnittert et al., "Integrin Alpha11 in Pancreatic Stellate Cells Regulates Tumor Stroma Interaction in Pancreatic Cancer," FASEB J. (May 2019) vol. 33, pp. 6609-6621.
Sjolander et al., "Integrated fluid handling system for biomolecular interaction analysis," Anal. Chem. (1991) vol. 63 (20), pp. 2338-2345.
Slamon et al., "Use of Chemotherapy Plus a Monoclonal Antibody Against Her2 for Metastatic Breast Cancer that Overexpresses Her2," New Engl. J. Med. (2001) vol. 344, pp. 783-792.
Smeland et al., "Integrin ?11?1 is Expressed in Breast Cancer Stroma and Associates with Aggressive Tumor Phenotypes," J. Pathol. Clin. Res. (Dec. 3, 2019) vol. 6, pp. 69-82.
Song et al., "Epitope Mapping of Ibalizumab, a Humanized Anti-CD4 Monoclonal Antibody with Anti-HIV-1 Activity in Infected Patients," J. Virol. (Jul. 2010) vol. 84, No. 14, pp. 6935-6942.
Stahli et al., "Distinction of Epitopes by Monoclonal Antibodies," Methods in Enzymology (1983) vol. 92, pp. 242-253.
Szabo et al., "Surface Plasmon Resonance and its Use in Biomolecular Interaction Analysis (BIA)," Curr. Opin. Struct. Biol. (1995) vol. 5, No. 5, pp. 699-705.
Tsurushita et al., "Humanization of a chicken anti-IL-12 monoclonal antibody," Journal of Immunological Methods (2004) vol. 295(1-2), pp. 9-19.
Van Beusechem et al., "Long-Term Expression of Human Adenosine Deaminase in Rhesus Monkeys Transplanted with Retrovirus-Infected Bone-Marrow Cells," Proc. Natl. Acad. Sci. USA (Aug. 15, 1992) vol. 89(16), pp. 7640-7644.
Van Gurp et al., "Phase 1 Dose-Escalation Study of CP-690 550 in Stable Renal Allograft Recipients: Preliminary Findings of Safety, Tolerability, Effects on Lymphocyte Subsets and Pharmacokinetics," Am J. Transplantation (2008) vol. 8, No. 8, pp. 1711-1718.
Wen et al., "Poly(ethylene glycol)-Conjugated Anti-EGF Receptor Antibody C225 with Radiometal Chelator Attached to the Termini of Plymer Chains," Bioconjugate Chem (2001), vol. 12, pp. 545-553.
Wilson et al., "Retrovirus-Mediated Transduction of Adult Hepatocytes," Proc. Natl. Acad. Sci. USA (May 1988) vol. 85 (9), pp. 3014-3018.
Wynn, "Cellular and molecular mechanisms of fibrosis," J. Pathol (2008) vol. 214, pp. 199-210.
Yang et al., "A Randomized Trial of Bevacizumab, an Anti-Vascular Endothelial Growth Factor Antibody, for Metastatic Renal Cancer," New Engl. J. Med. (2003) vol. 349(5), pp. 427-434.
Zeltz et al., "Alpha11Beta1 Integrin is Induced in a Subset of Cancer-Associated Fibroblasts in Desmoplastic Tumor Stroma and Mediates In Vitro Cell Migration," Cancers (Jun. 1, 2019) vol. 11, No. 6, 765, pp. 1-21.
Clackson et al., "Making antibody fragments using phage display libraries," Nature (1991) vol. 352, pp. 624-628.
Berkner et al., "Development of Adenovirus Vectors for the Expression of Heterologous Genes," BioTechniques (1988), vol. 6(7), pp. 616-629.
Nygren, J., "Conjugation of horseradish peroxidase to Fab fragments with different homobifuncational and heterobifunctional cross-linking reagents. A comparative study," Histochem. And Cytochem. (1982) vol. 30(5), pp. 407-412.
McLaughlin et al., "Adeno-Associated Virus General Transduction Vectors: Analysis of Proviral Structures," Journal of Virology (1988) vol. 62(6), pp. 1963-1973.
Lefranc, "Unique database numbering system for immunogenetic analysis," Immunol. Today (1997), vol. 18(11), p. 509.
Kozbar et al., "The production of monoclonal antibodies from human lymphocytes," Immunol. Today (1983), vol. 4(3), pp. 72-79.
Hunter et al., "Preparation of Iodine-131 Labelled Human Growth Hormone of High Specific Activity," Nature (1962), vol. 194, pp. 495-496.
Hanouske et al., "Phase 1b Dose Escalation Study of Erlotinib in Combination with Infusional 5-Fluorouracil, Leucovorin, and Oxaliplatin in Patients with Advanced Solid Tumors," Clin Cancer Res (2007) vol. 13(2), pp. 523-531.
Ando et al., Integrin a11 in non-small cell lung cancer is associated with tumor progression and postoperative recurrence, Cancer Sci. 111(1): 200-208 (2020).
Bansal et al., Integrin alpha 11 in the regulation of the myofibroblast phenotype: implications for fibrotic diseases, Exp. Mol. Med. 49(11):e396. doi: 10.1038/emm.2017.213 (2017).
Altshuler et al., "Production of Recombinant Antibodies and Methods for Increasing their Affinity," Advances in Biological Chemistry (2010) vol. 50, p. 207.
Armentano et al., "Expression of human factor IX in rabbit hepatocytes by retrovirus-mediated gene transfer: Potential for gene therapy of hemophilia B," Proc. Natl. Sci. USA (1990) vol. 87, pp. 6141-6145.
Baert et al., "Influence of Immunogenicity on the Long-Term Efficacy of Infliximab in Crohn's Disease," New Engl. J. Med. (2003) vol. 348, pp. 601-608.
Beniaminovitz et al., "Prevention of Rejection in Cardiac Transplantation by Blockade of the Interleukin-2 Receptor with a Monoclonal Antibody," New Engl. J. Med. (2000) vol. 342, pp. 613-619.
Bouchard et al., "Antibody-Drug Conjugates—A New Wave of Cancer Drugs," Bioorganic Med. Chem. Lett. (Dec. 1, 2014) vol. 24, No. 23, pp. 5357-5363.
Chothia et al., "Canonical Structures for the Hypervariable Regions of Immunoglobulins," J. Mol. Biol. (1987) vol. 196, pp. 901-917.
Chothia et al., "Conformations of immunoglobulin hypervariable regions," Nature (1989) vol. 342, pp. 877-883.
Chowdhury et al., "Long-Term Improvement of Hypercholesterolemia After Ex Vivo Gene Therapy in LDLR-Deficient Rabbits," Science (Dec. 20, 1991) vol. 254, No. 5039, pp. 1802-1805.
Dai et al., "Gene Therapy via Primary Myoblasts: Long-Term Expression of Factor IX Protein Following Transplantation in Vivo," Proc. Natl. Acad. Sci. USA (Nov. 15, 1992) vol. 89(22), pp. 10892-10895.
Danos et al., "Safe and Efficient Generation of Recombinant Retroviruses with Amphotropic and Ecotropic Host Ranges," Proc. Natl. Acad. Sci. USA (Sep. 1, 1988) vol. 85(17), pp. 6460-6464.
Dondelinger et al., "Understanding the Significance and Implications of Antibody Numbering and Antigen-Binding Surface/Residue Definition," Frontiers in Immunology (2018) vol. 9(2278), pp. 1-15.
David et al., "Protein iodination with solid state lactoperoxidase," Biochemistry (1974) vol. 13(5), pp. 1014-1021.
Eglitis et al., "Gene Expression in Mice After High Efficiency Retroviral-Mediated Gene Transfer," Science (1985) vol. 230, No. 4732, pp. 1395-1398.

(56) References Cited

OTHER PUBLICATIONS

Ferry et al., "Retroviral-Mediated Gene Transfer into Hepatocytes in Vivo," Proc. Natl. Acad. Sci. USA (Oct. 1, 1991) vol. 88(19) pp. 8377-8381.
Flotte et al., "Gene Expression from Adeno-Associated Virus Vectors in Airway Epithelial Cells," Am J. Respir Cell Mol. Biol. (Jan. 13, 1992) vol. 7, No. 3, pp. 349-356.
Gallo et al., "In Situ Antibody Phage Display Yields Optimal Inhibitors of Integrin ?11/?1," mAbs (Jan. 24, 2020) vol. 12, No. 1, e1717265, pp. 1-11.
Ghosh et al., "Natalizumab for Active Crohn's Disease," New Engl. J. Med. (2003) vol. 348(1), pp. 24-32.
Herold et al., "Anti-CD3 Monoclonal Antibody in New-Onset Type 1 Diabetes Mellitus," New Engl. J. Med. (2002) vol. 346(22), pp. 1692-1698.
Hetherington et al., "Phase I Dose Escalation Study to Evaluate the Safety and Pharmacokinetic Profile of Tefibazumab in Subjects with End-Stage Renal Disease Requiring Hemodialysis," Antimicrobial Agents and Chemotherapy (Oct. 1, 2006) vol. 50, No. 10, pp. 3499-3500.
Holliger et al., "Diabodies': Small bivalent and bispecific antibody fragments," Proc. Natl. Acad. Sci. USA (1993) vol. 90, pp. 6444-6448.
Holliger et al., "Engineered antibody fragments and the rise of single domains," Nat. Biotechnol. (2005) vol. 23(9), pp. 1126-1136.
Huber et al., "Retroviral-Mediated Gene Therapy for the Treatment of Hepatocellular Carcinoma: An Innovative Approach for Cancer Therapy," Proc. Natl. Acad. Sci. USA (Sep. 15, 1991) vol. 88(18), pp. 8039-8043.
Hwu et al., "Functional and Molecular Characterization of Tumor-Infiltrating Lymphocytes Transduced with Tumor Necrosis Factor-Alpha cDNA for the Gene Therapy of Cancer in Humans," J. Immunol. (1993) vol. 150(9), pp. 4104-4115.
International Preliminary Report on Patentability for International PCT Application No. PCT/IB2021/061926 dated Jun. 13, 2023.
International Preliminary Report on Patentability for International PCT Application No. PCT/US2020/066107 dated Nov. 1, 2021.
International Search Report and Written Opinion for International PCT Application No. PCT/IB2021/061926 dated Jun. 29, 2022.
International Search Report and Written Opinion for International PCT Application No. PCT/US2020/066107 dated May 7, 2021.
Jia et al., "A Novel Method of Multiplexed Competitive Antibody Binning for the Characterization of Monoclonal Antibodies," J. Immunological Methods (2004) vol. 288, Nos. 1-2, pp. 91-98.
Kabat, "The Structural Basis for Antibody Complementary," Adv. Prot. Chem. (1978) vol. 32, pp. 1-75.
Kabat et al., "Unusual Distributions of Amino Acids in Complementarity-determining (Hypervariable) Segments of Heavy and Light Chains of Immunoglobulins and Their Possible Roles in Specificity of Antibody-combining Sites," J. Biol. Chem (1977) vol. 252(19), pp. 6609-6616.
Kay et al., "Hepatic Gene Therapy: Persistent Expression of Human Alpha1-Antitrypsin in Mice after Direct Gene Delivery in Vivo," Human Gene Therapy (1992), vol. 3, pp. 641-647.
Koiko, "Immunology: A Textbook," Moscow: Publishing Center Academy (2008), pp. 61-62.
Kirkland et al., "Analysis of the fine specificity and cross-reactivity of monoclonal anti-lipid A antibodies," J. Immunol. (1986) vol. 137(11), pp. 3614-3619.
Kohler et al., "Continuous cultures of fused cells secreting antibody of predefined specificity," Nature (1975) vol. 256, pp. 495-497.
Lathe et al., "Synthetic Oligonucleotide Probes Deduced from Amino Acid Sequence Data: Theoretical and Practice Considerations," J. Mol. Biol. (1985) vol. 183, pp. 1-12.
Lee et al., "Prolonged Circulating Lives of Single-Chain Fv Proteins Conjugated with Polyethylene Glycol: A Comparison of Conjugation Chemistries and Compounds," Bioconj. Chem. (1999) vol. 10(6), pp. 973-981.
Lipsky et al., "Infliximab and Methotrexate in the Treatment of Rheumatoid Arthritis," New Engl. J. Med. (2000) vol. 343(22), pp. 1594-1602.
Liu et al., "Chimeric mouse-human IgG1 antibody that can mediate lysis of cancer cells," Proc. Natl. Acad. Sci. USA (1987) vol. 84, pp. 3439-3443.
Liu et al., "Production of a mouse-human chimeric monoclonal antibody to CD20 with potent Fc-dependent biologic activity," J. Immunology (1987) vol. 139(10), pp. 3521-3526.
Liu et al., "Randomised, double blind, placebo controlled study of interferon B-1a relapsing-remitting multiple sclerosis analysed by area under disability/time curves," J. Neurol. Neurosurg. Psych. (1999) vol. 67, pp. 451-456.
Marks et al., "By-passing Immunization: Human Antibodies from V-gene Libraries Displayed on Phage," J. Mol. Biol. (1991) vol. 222, pp. 581-597.
Milgrom et al., "Treatment of Allergic Asthma with Monoclonal Anti-IgE Antibody," New Engl. J. Med. (1999) vol. 341 (26), pp. 1966-1973.
Morrison et al., "Chimeric human antibody molecules: Mouse antigen-binding domains with human constant region domains," Proc. Natl. Acad. Sci. USA (1984) vol. 81, pp. 6851-6855.
Muyldermans et al., "Recognition of antigens by single-domain antibody fragments: the superfluous luxury of paired domains," Trends Biochem. Sci. (2001) vol. 26(4), pp. 230-235.
Pain et al., "Preparation of protein A-peroxidase monoconjugate using a heterobifunctional reagent, and its use in enzyme immunoassays," J. Immunol. Meth. (1981) vol. 40(2), pp. 219-230.
Parajuli et al., "Integrin Alpha11 is Overexpressed by Tumour Stroma of Head and Neck Squamous Cell Carcinoma and Correlates Positively with Alpha Smooth Muscle Actin Expression," J. Oral Pathol. Med. (2017) vol. 46, No. 4, pp. 267-275.
Presta, "Selection, design, and engineering of therapeutic antibodies," J. Allergy Clin. Immunol. (2005) vol. 116(4), pp. 731-736.
International Search Report and Written Opinion for International PCT Application No. PCT/US2023/068875 dated Dec. 20, 2023.
Extended European Search Report for Patent Application No. 20903433.9 dated Mar. 4, 2024.
Muller, "Determination of affinity and specificity of anti-hapten antibodies by competitive radioimmunoassay," Meth. Enzymol. (1983) vol. 92, pp. 589-601.

| Antibody | EC50 (μg/ml) | EC50 (nM) |
|---|---|---|
| 1994-01-C07 | 0.53 | 3.5 |
| 16E10 | 0.051 | 0.3 |
| 79E3E3 | 0.5 | 3.35 |

Shading omitted in symbols

ANTIBODIES AGAINST INTEGRIN ALPHA 11 BETA 1

CROSS-REFERENCE TO RELATED APPLICATIONS

The present application is a 35 U.S.C. § 371 national stage application of International Application Number PCT/US2020/066107, filed Dec. 18, 2020, which claims priority to U.S. Provisional Application No. 62/951,723, filed Dec. 20, 2019; U.S. Provisional Application No. 62/983,155, filed Feb. 28, 2020; and U.S. Provisional Application No. 63/054,717, filed Jul. 21, 2020, each of which is incorporated herein in its entirety.

BACKGROUND

Fibrosis is a process of scarring that manifests itself in many tissues in the body, typically as a result of inflammation or tissue damage. Increased production of extracellular matrix results in organ failure and, often, death. Diseases associated with fibrosis account for approximately 45% of all deaths in industrialized nations (Wynn, T. A., 2008, *J Pathol.* 214:199-210). One such disease is Systemic Sclerosis (SSc). SSc is a complex autoimmune disease with a chronic progressive course and high interpatient variability. It is characterized by inflammation, vascular dysfunction and fibrosis. Fibrosis of the skin and visceral organs results in irreversible scarring and ultimately organ failure, accounting for high mortality. There is currently no approved targeted therapy with disease-modifying potential.

SUMMARY

The present disclosure provides novel, function-blocking antibodies against type I collagen receptor integrin alpha 11 beta 1 (α11β1). The present disclosure also provides use of such antibodies to treat fibrotic disorders and/or cancers.

In one aspect, the present disclosure provides an anti-α11β1 antibody, or antigen-binding fragment thereof, comprising an amino acid sequence selected from a group consisting of SEQ ID NO: 103-443. In another aspect, the present disclosure provides an anti-α11β1 antibody, or antigen-binding fragment thereof, comprising a CDR sequence encompassed within any one of SEQ ID NO: 103-207, 209, 211, 213, 216, 218, 220, 223, 225, 228, 233, 234, 236, 240, 241, 245, 247, 253, 255, 257, 259, 261, 265, 267, 269, 271, 275, 277, 279, 281, 283, 287, 289, 291, 293, 296, 300, 304, 306, 308, 310, 312, 314, 316, 318, 320, 322, 324, 325, 327, 329, 334, 336, 338, 340, 342, 344, 348, 351, 353, 355, 358, 360, 361, 364, 366, 368, 369, 374, 376, 377, 379, 380, 381, 383, 384, 385, 387, 389, 392, 393, 396, 398, 400, 402, 405, 408, 411, 413-435, or 436-443. In another aspect, the present disclosure provides an anti-α11β1 antibody, or antigen-binding fragment thereof, comprising CDR1, CDR2, and CDR3 encompassed within any one of SEQ ID NO: 103-206, or 413-435. In some embodiments, an anti-α11β1 antibody, or antigen-binding fragment thereof, comprises an amino acid sequence selected from a group consisting of SEQ ID NO: 103-114, 207-311 or 436-442, and 312-435 or 443. In some embodiments, an anti-α11β1 antibody, or antigen-binding fragment thereof, comprises a CDR sequence encompassed within any one of SEQ ID NO: 103-114, 207, 209, 211, 213, 216, 218, 220, 223, 225, 228, 233, 234, 236, 240, 241, 245, 247, 253, 255, 257, 259, 261, 265, 267, 269, 271, 275, 277, 279, 281, 283, 287, 289, 291, 293, 296, 300, 304, 306, 308, 310, 312, 314, 316, 318, 320, 322, 324, 325, 327, 329, 334, 336, 338, 340, 342, 344, 348, 351, 353, 355, 358, 360, 361, 364, 366, 368, 369, 374, 376, 377, 379, 380, 381, 383, 384, 385, 387, 389, 392, 393, 396, 398, 400, 402, 405, 408, 411, 413-435, or 436-443. In some embodiments, an anti-α11β1 antibody, or antigen-binding fragment thereof, comprises one or more CDR sequences encompassed within any one of SEQ ID NO: 103-114, or 413-434. In some embodiments, an anti-α11β1 antibody, or antigen-binding fragment thereof, comprises CDR1, CDR2, and CDR3 encompassed within any one of SEQ ID NO: 103-114 or 413-434.

In some embodiments, an anti-α11β1 antibody, or antigen-binding fragment thereof, is a monoclonal antibody, or antigen-binding fragment thereof. In some embodiments, an anti-α11β1 antibody, or antigen-binding fragment thereof, is a humanized antibody, or antigen-binding fragment thereof. In some embodiments, an anti-α11β1 antibody, or antigen-binding fragment thereof, reduces interaction of α11β1 with collagen in human α11β1-expressing cells. In some embodiments, an anti-α11β1 antibody, or antigen-binding fragment thereof, competes with an antibody, or antigen-binding fragment thereof, described herein.

In another aspect, the present disclosure provides a nucleic acid, comprising a nucleic acid sequence encoding an antibody, or antigen-binding fragment thereof, described herein. In some embodiments, a nucleic acid sequence comprises a sequence selected from a group consisting of SEQ ID NO: 1-102.

In another aspect, the present disclosure provides a vector comprising a nucleic acid described herein.

In another aspect, the present disclosure provides a host cell comprising a nucleic acid described herein or a vector described herein.

In another aspect, the present disclosure provides a method of producing an antibody, or antigen-binding fragment thereof, comprising culturing a host cell described herein under conditions suitable for expression of the antibody or antigen-binding fragment thereof.

In another aspect, the present disclosure provides a method of treating a subject having or at risk of a fibrotic disorder, the method comprising administering to a subject in need thereof a therapeutically effective amount of an antibody, or antigen-binding fragment thereof, described herein. In some embodiments, a fibrotic disorder is idiopathic pulmonary fibrosis (IPF), chronic kidney disease, diabetic cardiomyopathy, primary sclerosing cholangitis (PSC), primary biliary cirrhosis (PBC), non-alcoholic fatty liver disease (NAFLD/NASH), Crohn's disease, ulcerative colitis, or systemic sclerosis.

In another aspect, the present disclosure provides a method of treating a subject having or at risk of cancer, the method comprising administering to a subject in need thereof a therapeutically effective amount of an antibody, or antigen-binding fragment thereof, described herein. In some embodiments, the cancer is one or more of head and neck squamous cell carcinomas, pancreatic ductal adenocarcinoma, non-small cell lung cancer, adrenocortical carcinoma, acute myeloid leukemia, bladder urothelial carcinoma, invasive breast carcinoma, cervical squamous cell carcinoma, cholangiocarcinoma, colorectal adenocarcinoma, diffuse large B-cell lymphoma, esophageal adenocarcinoma, glioblastoma multiforme, liver hepatocellular carcinoma, lung adenocarcinoma, lung squamous cell carcinoma, skin cutaneous melanoma, mesothelioma, ovarian serous cystadenocarcinoma, pheochromocytoma and paraganglioma, prostate adenocarcinoma, sarcoma, stomach adenocarcinoma, testicular germ cell tumors, thymoma, thyroid carcinoma, uterine corpus endometrial carcinoma, uterine carcinosarcoma, uveal melanoma, kidney renal clear cell carcinoma, kidney chromophobe, and kidney renal papillary cell carcinoma.

BRIEF DESCRIPTION OF THE DRAWING

The present teachings described herein will be more fully understood from the following description of various illustrative embodiments, when read together with the accompanying drawings. It should be understood that the drawings described below are for illustration purposes only and are not intended to limit the scope of the present teachings in any way.

DETAILED DESCRIPTION

Figure 1:
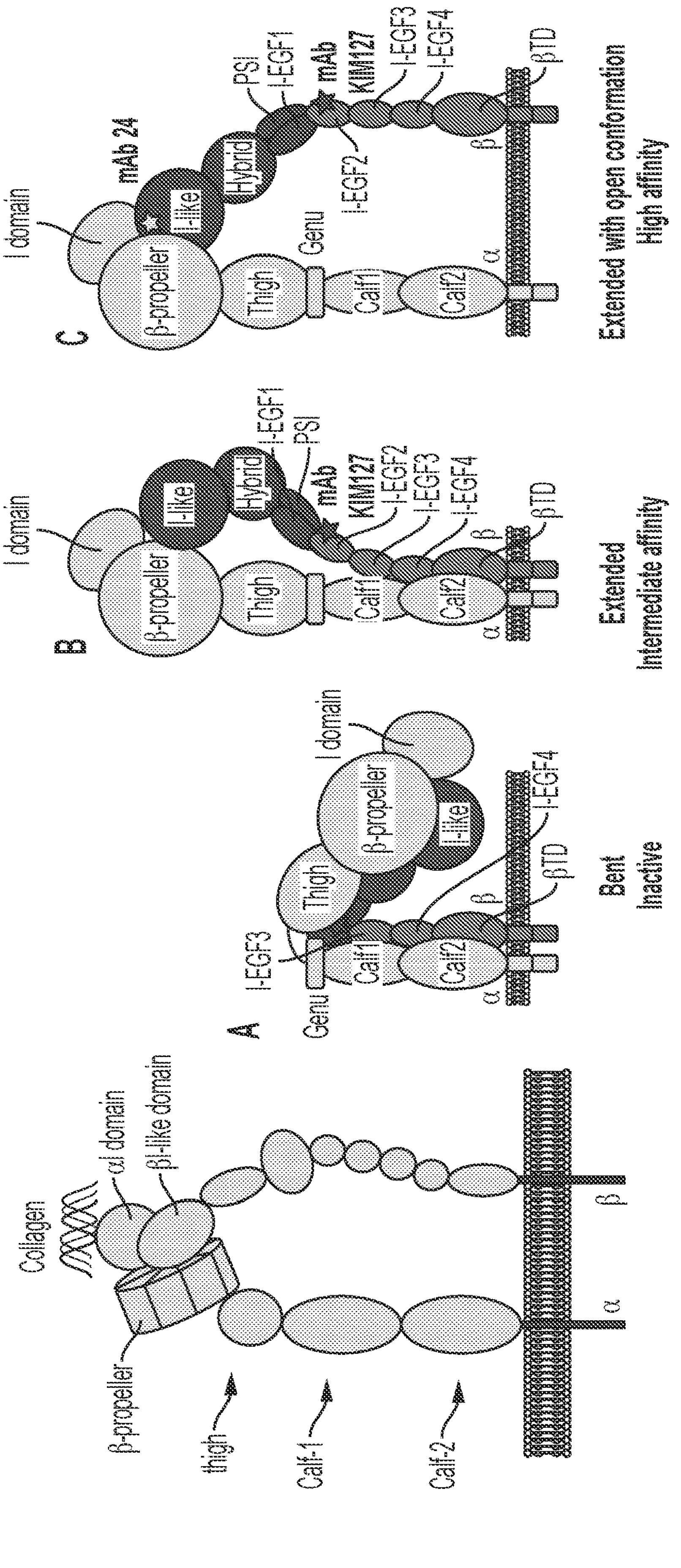
FIG. 1 shows representations of an integrin structure. The panels illustrate the structure of collagen-binding integrins and three different conformations integrins can exist in on the surface of a cell.

The present disclosure is based, in part, on the discovery of novel antibodies that selectively bind to α11β1. The disclosure also relates to nucleic acids encoding said antibodies and methods of use in the treatment of fibrosis and diseases comprising a fibrotic component.

Fibrosis and Diseases

Fibrosis is a process of scarring that manifests itself in many tissues in the body, typically as a result of inflammation or tissue damage. Increased production of extracellular matrix results in organ failure and, often, death. Diseases associated with fibrosis account for approximately 45% of all deaths in industrialized nations (Wynn, T. A., 2008, *J Pathol.* 214:199-210). One such disease is Systemic Sclerosis (SSc). SSc is a complex autoimmune disease with a chronic progressive course and high interpatient variability. It is characterized by inflammation, vascular dysfunction and fibrosis. Fibrosis of the skin and visceral organs results in irreversible scarring and ultimately organ failure, accounting for high mortality. There is currently no approved targeted therapy with disease-modifying potential.

The cells responsible for producing extracellular matrix (ECM) for tissue repair (and in fibrosis) are a specialized type of fibroblasts called myofibroblasts (MF). Although mechanisms of fibrosis have been extensively studied, this complex process is far from well understood. In order to focus on the most important drivers of fibrosis, published patient-derived datasets (SSc patient data and normal controls) were interrogated using an in-house derived novel data analysis methodology. This analysis lead to the identification of the type I collagen-binding integrin alpha 11 beta 1 (α11β1) as one of the top targets for modulating fibrosis.

To this date, there are no truly disease-modifying therapeutics for fibrosis. Two of the approved therapies for idiopathic pulmonary fibrosis (IPF), nintedanib and pirfenidone, work poorly and do not modify the disease, and there is no approved therapy for systemic sclerosis (SSc) to date. In some embodiments, a fibrotic disorder is or comprises idiopathic pulmonary fibrosis (IPF), chronic kidney disease, diabetic cardiomyopathy, primary sclerosing cholangitis (PSC), primary biliary cirrhosis (PBC), non-alcoholic fatty liver disease (NAFLD/NASH), Crohn's disease, ulcerative colitis, or systemic sclerosis (SSc). In some embodiments, a fibrotic disorder is or comprises atrial fibrosis, endomyocardial fibrosis, arthrofibrosis, mediastinal fibrosis, myelofibrosis, progressive massive fibrosis, retroperitoneal fibrosis or skeletal muscle fibrosis.

One clinical feature of the tumor microenvironment is the interaction between tumor and stroma, which mainly relies on various integrins that interact with ECM components as well as growth factors. Such interaction can influence tumor survival, progression and eventually metastasis. α11β1 has been reported to be overexpressed in cancer-associated fibroblasts (CAFs) of metastatic tumors, and its expression has been correlated with aggressive tumors in patients. For example, integrin α11 was overexpressed in the stroma of most head and neck squamous cell carcinomas (HNSCC) and correlated positively with alpha smooth muscle actin expression (Parajuli et al., J. Oral Pathol. Med. 46:267-275 (2017)). Integrin α11 was also overexpressed by CAFs in Pancreatic Ductal Adenocarcinoma (PDAC) stroma (Schnittert et al., FASEB J. 33:6609-6621 (2019)). In addition, integrin α11β1 overexpression in the tumor stroma has been associated with tumor growth and metastatic potential of non-small cell lung cancer (NSCLC), and high expression of ITGA11 (gene encoding integrin alpha-11 in humans) was associated with lower recurrence-free survival in all NSCLC patients; the same study showed that all overexpression in lung cancer cell lines resulted in increased migration and invasion (Ando et al., Cancer Sci. 111:200-208 (2020)).

Integrins

Integrins are a large family of type I transmembrane heterodimeric glycoprotein receptors and act as major receptors for cell adhesion. The integrin family of receptors plays key roles in modulating signal transduction pathways that control cell adhesion, migration, proliferation, differentiation and apoptosis. There are 18 α and 8 β subunits, which combine to form 24 integrin heterodimers. Each integrin receptor comprises two non-covalently bound subunits, α and β. Integrins α1β1, α2β1, α10β1, and α11β1 are the primary collagen receptors. α and β subunits are transmembrane proteins with large, modular, extracellular domains, single transmembrane helices, and short cytoplasmic regions, which mediate cytoskeletal interactions. Extracellular domain of integrins are generally large, approximately 80-150 kDa structures. The extracellular domains can be seen as comprising a headpiece connected to two legs (see FIG. 1 for structure of collagen-binding integrins). Collagen binding integrins contain an I domain, which serves as the ligand-binding site. The αI-domain contains a conserved "metal-ion-dependent adhesion site" (MIDAS) that binds divalent metal cations (Mg2+) and plays important role in ligand binding.

Integrins can exist in three different conformations: 1) a resting, low affinity state (bent conformation, FIG. 1, panel A) where the head piece containing ligand binding site is turned towards the membrane; 2) an extended, intermediate affinity state, where the integrin is extended but the head piece remains 'closed' (FIG. 1, panel B) and 3) an extended, high affinity state where the integrin is fully activated and readily binds the ligand. The complexity of the different integrin states allows for both allosteric and ligand-blocking ways of inhibiting integrin function. As marked with a star in FIG. 1, one of the allosteric ways to block the function of an integrin is to generate a monoclonal antibody that prevents the integrin from reaching the fully extended conformation from the extended intermediate conformation. Another allosteric option is to bind an integrin in its bent/inactive conformation and to keep it from extending to either of the two other states. A non-allosteric way of inhibiting integrin function is to bind to the I domain a prevent the integrin from attaching to collagen. Binding to the ligand binding site directly runs the risk of generating a recombinant activator of integrin function.

As cell surface receptors, integrins sense the stiffness of the surrounding matrix, triggering the cells to further produce and remodel connective tissue, which can perpetuate a fibrotic phenotype. Many integrins are overexpressed in fibrosis, but it is not clear which alpha subunit is sufficient for fibrosis to occur. α11β1 integrin is specifically expressed on a subset of fibroblasts and myofibroblasts (i.e., terminal scar producing cells). Recent literature has provided strong evidence that α11β1 is one of the main drivers of a fibrotic phenotype in cardiac tissue, liver, lungs and kidney (Romaine, A. et. al. Overexpression of integrin alpha 11 induces cardiac fibrosis in mice. Acta Physiol February 2018, 222 (2); Bansal, R. et. al. Integrin alpha 11 in the regulation of the myofibroblast phenotype: implications for fibrotic diseases. Exp Mol Med. 2017 November 17:49(11)). Blocking α11β1 function may inhibit myofibroblast differentiation and extracellular matrix deposition (i.e., the major event in scar formation) and blocking α11β1 function may provide a mechanism for local, injury-specific attenuation of fibrosis which could fundamentally change fibrotic microenvironment and modify disease progression in all diseases that have a fibrotic component.

In some embodiments, an anti-α11β1 antibody, or antigen-binding fragment thereof, of the present disclosure reduces interaction of α11β1 with collagen in human α11β1-expressing cells. In some embodiments, reducing interaction of α11β1 with collagen in human α11β1-expressing cells comprises an anti-α11β1 antibody, or antigen-binding fragment thereof, interacting with α11β1 that is in a resting, low affinity state (bent conformation). In some embodiments, reducing interaction of α11β1 with collagen in human α11β1-expressing cells comprises an anti-α11β1 antibody, or antigen-binding fragment thereof, interacting with α11β1 that is in an extended, intermediate affinity state. In some embodiments, reducing interaction of α11β1 with collagen in human α11β1-expressing cells comprises an anti-α11β1 antibody, or antigen-binding fragment thereof, interacting with α11β1 that is in an extended, high affinity state.

Antibodies

The term "antibody" is used herein in the broadest sense and encompasses various antibody structures, including but not limited to monoclonal antibodies, polyclonal antibodies, multispecific antibodies (e.g., bispecific antibodies), and/or antibody fragments (preferably those fragments that exhibit the desired antigen-binding activity). An antibody described herein can be an immunoglobulin, heavy chain antibody, light chain antibody, LRR-based antibody, or other protein scaffold with antibody-like properties, as well as other immunological binding moiety known in the art, including, e.g., a Fab, Fab', Fab'2, Fab2, Fab3, F(ab')2, Fd, Fv, Feb, scFv, SMIP, antibody, diabody, triabody, tetrabody, minibody, maxibody, tandab, DVD, BiTe, TandAb, or the like, or any combination thereof. The subunit structures and three-dimensional configurations of different classes of antibodies are known in the art.

A "monoclonal antibody" or "mAb" refers to an antibody obtained from a population of substantially homogeneous antibodies, i.e., the individual antibodies comprising the population are identical and/or bind the same epitope, except for possible variant antibodies (e.g., containing naturally occurring mutations or arising during production of a monoclonal antibody preparation), such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

An "antigen-binding fragment" refers to a portion of an intact antibody that binds the antigen to which the intact antibody binds. An antigen-binding fragment of an antibody includes any naturally occurring, enzymatically obtainable, synthetic, or genetically engineered polypeptide or glycoprotein that specifically binds an antigen to form a complex. Exemplary antibody fragments include, but are not limited to, Fv, Fab, Fab', Fab'-SH, F(ab')2; diabodies; linear antibodies; single-chain antibody molecules (e.g. scFv or VHH or VH or VL domains only); and multispecific antibodies formed from antibody fragments. In some embodiments, the antigen-binding fragments of the antibodies described herein are scFvs. As with full antibody molecules, antigen-binding fragments may be mono-specific or multispecific (e.g., bispecific). A multispecific antigen-binding fragment of an antibody may comprise at least two different variable domains, wherein each variable domain is capable of specifically binding to a separate antigen or to a different epitope of the same antigen.

A "multispecific antibody" refers to an antibody comprising at least two different antigen binding domains that recognize and specifically bind to at least two different antigens. A "bispecific antibody" is a type of multispecific antibody and refers to an antibody comprising two different antigen binding domains that recognize and specifically bind to at least two different antigens.

A "different antigen" may refer to different and/or distinct proteins, polypeptides, or molecules; as well as different and/or distinct epitopes, which epitopes may be contained within one protein, polypeptide, or other molecule.

The term "epitope" refers to an antigenic determinant that interacts with a specific antigen binding site in the variable region of an antibody molecule known as a paratope. A single antigen may have more than one epitope. Thus, different antibodies may bind to different areas of an antigen and may have different biological effects. The term "epitope" also refers to a site of an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

As used herein, "selective binding", "selectively binds" "specific binding", or "specifically binds" refers, with respect to an antigen binding moiety and an antigen target, preferential association of an antigen binding moiety to an antigen target and not to an entity that is not the antigen target. A certain degree of non-specific binding may occur between an antigen binding moiety and a non-target. In some embodiments, an antigen binding moiety selectively binds an antigen target if binding between the antigen binding moiety and the antigen target is greater than 2-fold, greater than 5-fold, greater than 10-fold, or greater than 100-fold as compared with binding of the antigen binding moiety and a non-target. In some embodiments, an antigen binding moiety selectively binds an antigen target if the binding affinity is less than about $10^{-5}$ M, less than about $10^{-6}$ M, less than about $10^{-7}$ M, less than about $10^{-8}$ M, or less than about $10^{-9}$ M.

In some embodiments, antibodies or fragments thereof that selectively bind to an identical epitope or overlapping epitope that will often cross-compete for binding to an antigen. Thus, in some embodiments, the disclosure provides an antibody or fragment thereof that cross-competes with an exemplary antibody or fragment thereof as disclosed herein. In some embodiments, to "cross-compete", "compete", "cross-competition", or "competition" means antibodies or fragments thereof compete for the same epitope or binding site on a target. Such competition can be determined by an assay in which the reference antibody or fragment thereof prevents or inhibits specific binding of a test antibody or fragment thereof, and vice versa. Numerous types of competitive binding assays can be used to determine if a test molecule competes with a reference molecule for binding. Examples of assays that can be employed include solid phase direct or indirect radioimmunoassay (RIA), solid phase direct or indirect enzyme immunoassay (EIA), sandwich competition assay (see, e.g., Stahli et al. (1983) Methods in Enzymology 9:242-253), solid phase direct biotin-avidin EIA (see, e.g., Kirkland et al., (1986) J. Immunol. 137:3614-9), solid phase direct labeled assay, solid phase direct labeled sandwich assay, Luminex (Jia et al. "A novel method of Multiplexed Competitive Antibody Binning for the characterization of monoclonal antibodies" J. Immunological Methods (2004) 288, 91-98) and surface plasmon resonance (Song et al. "Epitope Mapping of Ibalizumab, a Humanized Anti-CD4 Monoclonal Antibody with Anti-HIV-1 Activity in Infected Patients" J. Virol. (2010) 84, 6935-42). Usually, when a competing antibody or fragment thereof is present in excess, it will inhibit binding of a reference antibody or fragment thereof to a common antigen by at least 50%, 55%, 60%, 65%, 70%, or 75%. In some instances, binding is inhibited by at least 80%, 85%, 90%, 95%, 96%, 97%, 98%, 99%, or more.

An antibody can be an immunoglobulin molecule of four polypeptide chains, e.g., two heavy (H) chains and two light (L) chains. In some embodiments, a light chain is a lambda light chain. In some embodiments, a light chain is a kappa light chain. A heavy chain can include a heavy chain variable domain and a heavy chain constant domain. A heavy chain constant domain can include CH1, hinge, CH2, CH3, and in some instances CH4 regions. A light chain can include a light chain variable domain and a light chain constant domain. A light chain constant domain can include a CL.

A heavy chain variable domain of a heavy chain and a light chain variable domain of a light chain can typically be further subdivided into regions of variability, termed complementarity determining regions (CDRs), interspersed with regions that are more conserved, termed framework regions (FR). Such heavy chain and light chain variable domains can each include three CDRs and four framework regions, arranged from amino-terminus to carboxyl-terminus in the following order: FR1, CDR1, FR2, CDR2, FR3, CDR3, FR4, one or more of which can be engineered as described herein. The CDRs in a heavy chain are designated "CDRH1", "CDRH2", and "CDRH3", respectively, and the CDRs in a light chain are designated "CDRL1", "CDRL2", and "CDRL3".

There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

Exemplary Antibodies

The present disclosure provides antibodies that can include various heavy chains and light chains described herein. In some embodiments, an antibody comprises two heavy chains and light chains. In some embodiments, the present disclosure encompasses an antibody including at least one heavy chain and/or light chain as disclosed herein, at least one heavy chain and/or light chain framework domain as disclosed herein, at least one heavy chain and/or light chain CDR domain as disclosed herein, and/or any heavy chain and/or light chain constant domain as disclosed herein.

In some embodiments, an antibody disclosed herein is a homodimeric monoclonal antibody. In some embodiments, an antibody disclosed herein is a heterodimeric antibody. In some embodiments, an antibody is, e.g., a typical antibody or a diabody, triabody, tetrabody, minibody, maxibody, tandab, DVD, BiTe, scFv, TandAb scFv, Fab, Fab2, Fab3, F(ab')2, or the like, or any combination thereof.

The present disclosure provides, among other things, an anti-integrin alpha 11 beta 1 (α11β1) antibody, or antigen-binding fragment thereof. In some embodiments, an α11β1 antibody, or antigen-binding fragment thereof, comprises an amino acid sequence selected from a group consisting of SEQ ID NO: 103-443. In some embodiments, an anti-α11β1 antibody, or antigen-binding fragment thereof, comprises a CDR sequence encompassed within any one of SEQ ID NO: 103-207, 209, 211, 213, 216, 218, 220, 223, 225, 228, 233, 234, 236, 240, 241, 245, 247, 253, 255, 257, 259, 261, 265, 267, 269, 271, 275, 277, 279, 281, 283, 287, 289, 291, 293, 296, 300, 304, 306, 308, 310, 312, 314, 316, 318, 320, 322, 324, 325, 327, 329, 334, 336, 338, 340, 342, 344, 348, 351, 353, 355, 358, 360, 361, 364, 366, 368, 369, 374, 376, 377, 379, 380, 381, 383, 384, 385, 387, 389, 392, 393, 396, 398, 400, 402, 405, 408, 411, 413-435, or 436-443. In some embodiments, an anti-α11β1 antibody, or antigen-binding fragment thereof, comprises CDR1, CDR2, and CDR3 encompassed within any one of SEQ ID NO: 103-206, or 413-435. In some embodiments, an anti-α11β1 antibody, or antigen-binding fragment thereof, comprises an amino acid sequence selected from a group consisting of SEQ ID NO: 103-114, 207-311 or 436-442, and 312-435 or 443. In some embodiments, an anti-α11β1 antibody, or antigen-binding fragment thereof, comprises a CDR sequence encompassed within any one of SEQ ID NO: 103-114, 207, 209, 211, 213, 216, 218, 220, 223, 225, 228, 233, 234, 236, 240, 241, 245, 247, 253, 255, 257, 259, 261, 265, 267, 269, 271, 275, 277, 279, 281, 283, 287, 289, 291, 293, 296, 300, 304, 306, 308, 310, 312, 314, 316, 318, 320, 322, 324, 325, 327, 329, 334, 336, 338, 340, 342, 344, 348, 351, 353, 355, 358, 360, 361, 364, 366, 368, 369, 374, 376, 377, 379, 380, 381, 383, 384, 385, 387, 389, 392, 393, 396, 398, 400, 402, 405, 408, 411, 413-435, or 436-443. In some embodiments, an anti-α11β1 antibody, or antigen-binding fragment thereof, comprises one or more CDR sequences encompassed within any one of SEQ ID NO: 103-114, or 413-434. In some embodiments, an anti-α11β1 antibody, or antigen-binding fragment thereof, comprises CDR1, CDR2, and CDR3 encompassed within any one of SEQ ID NO: 103-114, or 413-434. In some embodiments, an anti-α11β1 antibody, or antigen-binding fragment thereof, is a monoclonal antibody, or antigen-binding fragment thereof. In some embodiments, an anti-α11β1 antibody, or antigen-binding fragment thereof, is a humanized antibody, or antigen-binding fragment thereof. In some embodiments, an anti-α11β1 antibody, or antigen-binding fragment thereof, reduces interaction of α11β1 with collagen in human α11β1-expressing cells. In some embodiments, the present disclosure provides an anti-α11β1 antibody, or antigen-binding fragment thereof, that competes with an antibody, or antigen-binding fragment thereof, comprising an amino acid sequence selected from a group consisting of SEQ ID NO: 103-443. In some embodiments, the present disclosure provides an anti-α11β1 antibody, or antigen-binding fragment thereof, that competes with an antibody, or antigen-binding fragment thereof, comprising an amino acid sequence selected from a group consisting of SEQ ID NO: 103-443.

In some embodiments, the present disclosure provides an anti-α11β1 antibody, or antigen-binding fragment thereof, comprising a heavy chain provided herein and a light chain provided herein. In some embodiments, the present disclosure provides an anti-α11β1 antibody, or antigen-binding fragment thereof, comprising a heavy chain variable domain provided herein and a light chain variable region provided herein. In some embodiments, the present disclosure provides an anti-α11β1 antibody, or antigen-binding fragment thereof, comprising a specific combination of heavy chain variable domain and light chain variable domain. For example, in some embodiments, an anti-α11β1 antibody, or antigen-binding fragment thereof, comprises a combination of heavy chain variable domain and light chain variable domain selected from Table 1.

TABLE 1

Combinations of 16E10 variant heavy chain variable regions and light chain variable regions

| Light Chain Variable Region | Heavy Chain Variable Region | Description |
|---|---|---|
| 16E10_VL (SEQ ID NO: 428) | 16E10_VH (SEQ ID NO: 421) | Parental light chain variable region; Parental heavy chain variable region |
| 16E10_VL_1 (SEQ ID NO: 429) | 16E10_VH_1 (SEQ ID NO: 422) | Conservatively humanized light chain variable region; Conservatively humanized heavy chain variable region |
| 16E10_VL_2 (SEQ ID NO: 430) | 16E10_VH_2 (SEQ ID NO: 423) | Humanized light chain variable region; humanized heavy chain variable region |
| 16E10_VL_3 (SEQ ID NO: 431) | 16E10_VH_1 (SEQ ID NO: 422) | Deimmunized conservatively humanized light chai variable region; Conservatively humanized heavy chain variable region |
| 16E10_VL_4 (SEQ ID NO: 432) | 16E10_VH_2 (SEQ ID NO: 423) | Deimmunized humanized light chain variable region; Humanized heavy chain variable region |
| 16E10_VL_1 (SEQ ID NO: 429) | 16E10_VH_3 (SEQ ID NO: 424) | Conservatively humanized light chain variable region; Deimmunized conservatively humanized heavy chain variable region |
| 16E10_VL_2 (SEQ ID NO: 430) | 16E10_VH_4 (SEQ ID NO: 425) | Humanized light chain variable region; Deimmunized humanized heavy chain variable region |
| 16E10_VL_3 (SEQ ID NO: 431) | 16E10_VH_3 (SEQ ID NO: 424) | Deimmunized conservatively humanized light chain variable region; Deimmunized conservatively humanized heavy chain variable region |

TABLE 1-continued

Combinations of 16E10 variant heavy chain variable regions and light chain variable regions

| Light Chain Variable Region | Heavy Chain Variable Region | Description |
|---|---|---|
| 16E10_VL_4 (SEQ ID NO: 432) | 16E10_VH_4 (SEQ ID NO: 425) | Deimmunized humanized light chain variable region; Deimmunized humanized heavy chain variable region |
| 16E10_VL_5 (SEQ ID NO: 433) | 16E10_VH_3 (SEQ ID NO: 424) | De-risked deimmunized conservatively humanized light chain variable region; Deimmunized conservatively humanized heavy chain variable region |
| 16E10_VL_6 (SEQ ID NO: 434) | 16E10_VH_4 (SEQ ID NO: 425) | De-risked deimmunized humanized light chain variable region; Deimmunised humanised heavy chain variable region |
| 16E10_VL_3 (SEQ ID NO: 431) | 16E10_VH_5 (SEQ ID NO: 426) | Deimmunised conservatively humanised light chain variable region; De-risked deimmunised conservatively humanised heavy chain variable region |
| 16E10_VL_4 (SEQ ID NO: 432) | 16E10_VH_6 (SEQ ID NO: 427) | Deimmunised humanised light chain variable region; De-risked deimmunised humanised heavy chain variable region |
| 16E10_VL_5 (SEQ ID NO: 433) | 16E10_VH_5 (SEQ ID NO: 426) | De-risked deimmunised conservatively humanised light chain variable region; De-risked deimmunised conservatively humanised heavy chain variable region |
| 16E10_VL_6 (SEQ ID NO: 434) | 16E10_VH_6 (SEQ ID NO: 427) | De-risked deimmunised humanised light chain variable region; De-risked deimmunised humanised heavy chain variable region |

In some embodiments, the present disclosure provides an anti-α11β1 antibody, or antigen-binding fragment thereof, comprising between 1 and 30 (e.g., 1, 2, 3, 4, 5, 10, or more) additions, deletions, or substitutions relative to an anti-α11β1 antibody, or antigen-binding fragment thereof, wherein the anti-α11β1 antibody comprises an amino acid sequence selected from a group consisting of SEQ ID NO: 103-158, 413, 414 and 421-434 and, e.g., the antibody or fragment selectively binds α11β1. In some embodiments, the present disclosure provides an anti-α11β1 antibody, or antigen-binding fragment thereof, comprising between 1 and 30 additions, deletions, or substitutions relative to an anti-α11β1 antibody, or antigen-binding fragment thereof, wherein the anti-α11β1 antibody comprises an amino acid sequence selected from a group consisting of SEQ ID NO: 103-114, 413, 414 and 421-434 and, e.g., the antibody or fragment selectively binds α11β1. In some embodiments, the present disclosure provides an anti-α11β1 antibody, or antigen-binding fragment thereof, comprising an amino acid sequence having at least 80%, 85%, 90%, 91%, 92%, 93%, 94%, 95%, 96%, 97%, 98%, or 99% sequence identity to an amino acid sequence selected from a group consisting of SEQ ID NO: 103-158, 413, 414 and 421-434 and, e.g., the antibody or fragment selectively binds α11β1. In some embodiments, the present disclosure provides an anti-α11β1 antibody, or antigen-binding fragment thereof, comprising an amino acid sequence having at least 80%, 85%, 90%, 91%, 92%, 93%, 94%, 95%, 96%, 97%, 98%, or 99% identity to an amino acid sequence selected from a group consisting of SEQ ID NO: 103-114, 413, 414 and 421-434 and, e.g., the antibody or fragment selectively binds α11β1.

In some embodiments, the present disclosure provides an anti-α11β1 antibody, or antigen-binding fragment thereof, comprising between 1 and 90 (e.g., between 1 and 50, e.g., at least 1, 2, 3, 4, 5, 6, 7, 8, 9, 10 or more) additions, deletions, or substitutions relative to an anti-α11β1 antibody, or antigen-binding fragment thereof, wherein the anti-α11β1 antibody, or antigen-binding fragment thereof comprises an amino acid sequence selected from a group consisting of SEQ ID NO: 159-206 and 415-420 and, e.g., the antibody or fragment selectively binds α11β1. In some embodiments, the present disclosure provides an anti-α11β1 antibody, or antigen-binding fragment thereof, comprising an amino acid sequence having at least 80%, 85%, 90%, 91%, 92%, 93%, 94%, 95%, 96%, 97%, 98%, or 99% identity to an amino acid sequence selected from the group consisting of SEQ ID NO: 159-206 and 415-420 and, e.g., the antibody or fragment selectively binds α11β1.

In some embodiments, the disclosure provides an antibody or fragment thereof that selectively binds α11β1, wherein the antibody or fragment comprises one or more CDR sequences depicted in the list of exemplary sequences provided herein. For example, in some embodiments, an antibody or fragment thereof comprises one or more CDRs from SEQ ID NOs: 103-114. In some embodiments, the disclosure provides an antibody or fragment thereof that selectively binds α11β1, wherein the antibody or fragment comprises an amino acid sequence that is at least 95%, 96%, 97%, 98%, or 99% identical to one or more CDRs from SEQ ID NOs: 103-114. In some embodiments, an antibody or fragment comprises an amino acid sequence having at least 90%, 91%, 92%, 93%, 94%, 95%, 96%, 97%, 98%, or 99% identity to one of SEQ ID NOs: 103-114, wherein the antibody comprises one or more CDRs depicted in one of SEQ ID NOs: 103-114. For example, the antibody or fragment comprises an amino acid sequence having at least 90%, 91%, 92%, 93%, 94%, 95%, 96%, 97%, 98%, or 99% identity to SEQ ID NO: 103, wherein the antibody comprises one or more CDRs (e.g., 1, 2, or 3 CDRs) depicted in SEQ ID NO:103.

In some embodiments, the disclosure provides an antibody or fragment thereof that selectively binds α11β1, wherein the antibody or fragment comprises one or more CDR sequences depicted in the list of exemplary sequences provided herein. For example, in some embodiments, an antibody or fragment thereof comprises one or more CDRs from SEQ ID NOs: 103-207, 209, 211, 213, 216, 218, 220, 223, 225, 228, 233, 234, 236, 240, 241, 245, 247, 253, 255, 257, 259, 261, 265, 267, 269, 271, 275, 277, 279, 281, 283, 287, 289, 291, 293, 296, 300, 304, 306, 308, 310, 312, 314, 316, 318, 320, 322, 324, 325, 327, 329, 334, 336, 338, 340, 342, 344, 348, 351, 353, 355, 358, 360, 361, 364, 366, 368, 369, 374, 376, 377, 379, 380, 381, 383, 384, 385, 387, 389, 392, 393, 396, 398, 400, 402, 405, 408, 411, 413-435, or 436-443. In some embodiments, the disclosure provides an antibody or fragment thereof that selectively binds α11β1, wherein the antibody or fragment comprises an amino acid sequence that is at least 95%, 96%, 97%, 98%, or 99% identical to one or more CDRs from SEQ ID NOs: 103-207, 209, 211, 213, 216, 218, 220, 223, 225, 228, 233, 234, 236, 240, 241, 245, 247, 253, 255, 257, 259, 261, 265, 267, 269, 271, 275, 277, 279, 281, 283, 287, 289, 291, 293, 296, 300, 304, 306, 308, 310, 312, 314, 316, 318, 320, 322, 324, 325, 327, 329, 334, 336, 338, 340, 342, 344, 348, 351, 353, 355, 358, 360, 361, 364, 366, 368, 369, 374, 376, 377, 379, 380, 381, 383, 384, 385, 387, 389, 392, 393, 396, 398, 400, 402, 405, 408, 411, 413-435, or 436-443. In some embodiments, an antibody or fragment comprises an amino acid sequence having at least 90%, 91%, 92%, 93%, 94%, 95%, 96%, 97%, 98%, or 99% identity to one of SEQ ID NOs: 103-207, 209, 211, 213, 216, 218, 220, 223, 225, 228, 233, 234, 236, 240, 241, 245, 247, 253, 255, 257, 259, 261, 265, 267, 269, 271, 275, 277, 279, 281, 283, 287, 289, 291, 293, 296, 300, 304, 306, 308, 310, 312, 314, 316, 318, 320, 322, 324, 325, 327, 329, 334, 336, 338, 340, 342, 344, 348, 351, 353, 355, 358, 360, 361, 364, 366, 368, 369, 374, 376, 377, 379, 380, 381, 383, 384, 385, 387, 389, 392, 393, 396, 398, 400, 402, 405, 408, 411, 413-435, or 436-443, wherein the antibody comprises one or more CDRs depicted in one of SEQ ID NOs: 103-207, 209, 211, 213, 216, 218, 220, 223, 225, 228, 233, 234, 236, 240, 241, 245, 247, 253, 255, 257, 259, 261, 265, 267, 269, 271, 275, 277, 279, 281, 283, 287, 289, 291, 293, 296, 300, 304, 306, 308, 310, 312, 314, 316, 318, 320, 322, 324, 325, 327, 329, 334, 336, 338, 340, 342, 344, 348, 351, 353, 355, 358, 360, 361, 364, 366, 368, 369, 374, 376, 377, 379, 380, 381, 383, 384, 385, 387, 389, 392, 393, 396, 398, 400, 402, 405, 408, 411, 413-435, or 436-443. For example, the antibody or fragment comprises an amino acid sequence having at least 90%, 91%, 92%, 93%, 94%, 95%, 96%, 97%, 98%, or 99% identity to SEQ ID NO: 103, wherein the antibody comprises one or more CDRs (e.g., 1, 2, or 3 CDRs) depicted in SEQ ID NO:103.

The present disclosure provides, among other things, methods of making an anti-α11β1 antibody, or antigen-binding fragment thereof. Methods of making antibodies are known in the art. In some embodiments, the present disclosure provides methods of producing an antibody, or antigen-binding fragment thereof, comprising culturing a host cell comprising a nucleic acid comprising a nucleic acid sequence selected from a group consisting of SEQ ID NO: 1-102 under conditions suitable for expression of the antibody or antigen-binding fragment thereof.

Exemplary Nucleotide Sequences

The present disclosure includes nucleotide sequences encoding one or more heavy chains, heavy chain variable domains, heavy chain framework regions, heavy chain CDRs, heavy chain constant domains, light chains, light chain variable domains, light chain framework regions, light chain CDRs, light chain constant domains, or other immunoglobulin-like sequences, antibodies, or binding molecules disclosed herein. In some embodiments, such nucleotide sequences may be present in a vector. In some embodiments such nucleotides may be present in the genome of a cell, e.g., a cell of a subject in need of treatment or a cell for production of an antibody, e.g. a mammalian cell for production of a an antibody.

In some embodiments, the present disclosure provides a nucleic acid comprising a nucleic acid sequence encoding an antibody, or antigen-binding fragment thereof, comprising an amino acid sequence selected from a group consisting of SEQ ID NO: 103-206. In some embodiments, the present disclosure provides a nucleic acid comprising a nucleic acid sequence encoding an antibody, or antigen-binding fragment thereof, comprising an amino acid sequence selected from a group consisting of SEQ ID NO: 103-114. In some embodiments, the present disclosure provides a nucleic acid comprising a nucleic acid sequence selected from a group consisting of SEQ ID NO: 1-102. In some embodiments, the present disclosure provides a vector comprising a nucleic acid comprising a nucleic acid sequence selected from a group consisting of SEQ ID NO: 1-102. In some embodiments, the present disclosure provides a host cell comprising a nucleic acid comprising a nucleic acid sequence selected from a group consisting of SEQ ID NO: 1-102. In some embodiments, the present disclosure provides a vector comprising a nucleic acid comprising a nucleic acid sequence selected from a group consisting of SEQ ID NO: 1-102.

In some embodiments, the present disclosure provides a nucleic acid comprising a nucleic acid sequence having at least 80%, 85%, 90%, 91%, 92%, 93%, 94%, 95%, 96%, 97%, 98%, or 99% sequence identity a nucleic acid sequence selected from a group consisting of SEQ ID NO: 1-102.

Measuring Interactions of Antibodies and α11β1

The binding properties of an antibody described herein to α11β1 can be measured by methods known in the art, e.g., one of the following methods: BIACORE analysis, Enzyme Linked Immunosorbent Assay (ELISA), x-ray crystallography, sequence analysis and scanning mutagenesis. The binding interaction of an antibody and α11β1 can be analyzed using surface plasmon resonance (SPR). SPR or Biomolecular Interaction Analysis (BIA) detects bio-specific interactions in real time, without labeling any of the interactants. Changes in the mass at the binding surface (indicative of a binding event) of the BIA chip result in alterations of the refractive index of light near the surface. The changes in the refractivity generate a detectable signal, which are measured as an indication of real-time reactions between biological molecules. Methods for using SPR are described, for example, in U.S. Pat. No. 5,641,640; Raether (1988) Surface Plasmons Springer Verlag; Sjolander and Urbaniczky (1991) Anal. Chem. 63:2338-2345; Szabo et al. (1995) Curr. Opin. Struct. Biol. 5:699-705 and on-line resources provide by BIAcore International AB (Uppsala, Sweden). Additionally, a KinExA® (Kinetic Exclusion Assay) assay, available from Sapidyne Instruments (Boise, Id.) can also be used.

Information from SPR can be used to provide an accurate and quantitative measure of the equilibrium dissociation constant ($K_D$), and kinetic parameters, including $K_{on}$ and $K_{off}$, for the binding of an antibody to α11β1. Such data can be used to compare different molecules. Information from SPR can also be used to develop structure-activity relationships (SAR). Variant amino acids at given positions can be identified that correlate with particular binding parameters, e.g., high affinity.

In certain embodiments, an antibody described herein exhibits high affinity for binding α11β1. In various embodiments, $K_D$ of an antibody as described herein for α11β1 is less than about $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, $10^{-14}$, or $10^{-15}$ M. In certain instances, $K_D$ of an antibody as described herein for α11β1 is between 0.001 and 1 nM, e.g., 0.001 nM, 0.005 nM, 0.01 nM, 0.05 nM, 0.1 nM, 0.5 nM, or 1 nM.

Methods of Treatment

In some embodiments, one or more anti-α11β1 antibodies described herein are used in a method of treating one or more disorders described herein, e.g., one or more fibrotic disorders and/or one or more cancers. In some embodiments, the method comprises administering to a subject in need thereof a therapeutically effective amount of an antibody, or antigen-binding fragment thereof, described herein. In some embodiments, a fibrotic disorder is or comprises idiopathic pulmonary fibrosis (IPF), chronic kidney disease, diabetic cardiomyopathy, primary sclerosing cholangitis (PSC), primary biliary cirrhosis (PBC), non-alcoholic fatty liver disease (NAFLD/NASH), Crohn's disease, ulcerative colitis, or systemic sclerosis. In some embodiments, a fibrotic disorder is or comprises atrial fibrosis, endomyocardial fibrosis, arthrofibrosis, mediastinal fibrosis, myelofibrosis, progressive massive fibrosis, retroperitoneal fibrosis or skeletal muscle fibrosis.

In some embodiments, one or more anti-α11β1 antibodies described herein are used in a method of treating cancer, such as one or more of the following: head and neck squamous cell carcinomas, pancreatic ductal adenocarcinoma, non-small cell lung cancer, adrenocortical carcinoma, acute myeloid leukemia, bladder urothelial carcinoma, invasive breast carcinoma, cervical squamous cell carcinoma, cholangiocarcinoma, colorectal adenocarcinoma, diffuse large B-cell lymphoma, esophageal adenocarcinoma, glioblastoma multiforme, liver hepatocellular carcinoma, lung adenocarcinoma, lung squamous cell carcinoma, skin cutaneous melanoma, mesothelioma, ovarian serous cystadenocarcinoma, pheochromocytoma and paraganglioma, prostate adenocarcinoma, sarcoma, stomach adenocarcinoma, testicular germ cell tumors, thymoma, thyroid carcinoma, uterine corpus endometrial carcinoma, uterine carcinosarcoma, uveal melanoma, kidney renal clear cell carcinoma, kidney chromophobe, and kidney renal papillary cell carcinoma.

Combination Therapy

In some embodiments, an anti-α11β1 antibody described herein is administered in combination with one or more additional therapeutic agents, such as a chemotherapeutic agent or an oncolytic therapeutic agent. "Combination therapy", as used herein, refers to those situations in which two or more different pharmaceutical agents are administered in overlapping regimens so that the subject is simultaneously exposed to both agents. When used in combination therapy, two or more different agents may be administered simultaneously or separately. Administration in combination can include simultaneous administration of the two or more agents in the same dosage form, simultaneous administration in separate dosage forms, and separate administration. That is, two or more agents can be formulated together in the same dosage form and administered simultaneously. Alternatively, two or more agents can be simultaneously administered, wherein the agents are present in separate formulations. In another alternative, a first agent can be administered just followed by one or more additional agents. In the separate administration protocol, two or more agents may be administered a few minutes apart, or a few hours apart, or a few days apart.

As used herein, the term "chemotherapeutic agent" or "oncolytic therapeutic agent" (e.g., anti-cancer drug, e.g., anti-cancer therapy, e.g., immune cell therapy) has its art-understood meaning referring to one or more pro-apoptotic, cytostatic and/or cytotoxic agents, and/or hormonal agents, for example, specifically including agents utilized and/or recommended for use in treating one or more diseases, disorders or conditions associated with undesirable cell proliferation. In some embodiments, a chemotherapeutic agent and/or oncolytic therapeutic agent may be or comprise platinum compounds (e.g., cisplatin, carboplatin, and oxaliplatin), alkylating agents (e.g., cyclophosphamide, ifosfamide, chlorambucil, nitrogen mustard, thiotepa, melphalan, busulfan, procarbazine, streptozocin, temozolomide, dacarbazine, and bendamustine), antitumor antibiotics (e.g., daunorubicin, doxorubicin, idarubicin, epirubicin, mitoxantrone, bleomycin, mytomycin C, plicamycin, and dactinomycin), taxanes (e.g., paclitaxel and docetaxel), antimetabolites (e.g., 5-fluorouracil, cytarabine, premetrexed, thioguanine, floxuridine, capecitabine, and methotrexate), nucleoside analogues (e.g., fludarabine, clofarabine, cladribine, pentostatin, and nelarabine), topoisomerase inhibitors (e.g., topotecan and irinotecan), hypomethylating agents (e.g., azacitidine and decitabine), proteosome inhibitors (e.g., bortezomib), epipodophyllotoxins (e.g., etoposide and teniposide), DNA synthesis inhibitors (e.g., hydroxyurea), vinca alkaloids (e.g., vicristine, vindesine, vinorelbine, and vinblastine), tyrosine kinase inhibitors (e.g., imatinib, dasatinib, nilotinib, sorafenib, and sunitinib), nitrosoureas (e.g., carmustine, fotemustine, and lomustine), hexamethylmelamine, mitotane, angiogenesis inhibitors (e.g., thalidomide and lenalidomide), steroids (e.g., prednisone, dexamethasone, and prednisolone), hormonal agents (e.g., tamoxifen, raloxifene, leuprolide, bicaluatmide, granisetron, and flutamide), aromatase inhibitors (e.g., letrozole and anastrozole), arsenic trioxide, tretinoin, nonselective cyclooxygenase inhibitors (e.g., nonsteroidal anti-inflammatory agents, salicylates, aspirin, piroxicam, ibuprofen, indomethacin, naprosyn, diclofenac, tolmetin, ketoprofen, nabumetone, and oxaprozin), selective cyclooxygenase-2 (COX-2) inhibitors, or any combination thereof.

In certain embodiments, chemotherapeutic agents and/or oncolytic therapeutic agents for anti-cancer treatment comprise biological agents such as tumor-infiltrating lymphocytes, CAR T-cells, antibodies, antigens, therapeutic vaccines (e.g., made from a patient's own tumor cells or other substances such as antigens that are produced by certain tumors), immune-modulating agents (e.g., cytokines, e.g., immunomodulatory drugs or biological response modifiers), checkpoint inhibitors or other immunologic agents. In certain embodiments, immunologic agents include immunoglobins, immunostimulants (e.g., bacterial vaccines, colony stimulating factors, interferons, interleukins, therapeutic vaccines, vaccine combinations, viral vaccines) and/or immunosuppressive agents (e.g., calcineurin inhibitors, interleukin inhibitors, TNF alpha inhibitors). In certain embodiments, hormonal agents include agents for anti-androgen therapy (e.g., Ketoconazole, ABiraterone, TAK-700, TOK-OOl, Bicalutamide, Nilutamide, Flutamide, Enzalutamide, ARN-509).

Additional chemotherapeutic agents and/or oncolytic therapeutic agents include immune checkpoint therapeutics (e.g., pembrolizumab, nivolumab, ipilimumab, atezolizumab, avelumab, durvalumab, tremelimumab, or cemiplimab), other monoclonal antibodies (e.g., rituximab, cetuximab, panetumumab, tositumomab, trastuzumab, alemtuzumab, gemtuzumab ozogamicin, bevacizumab, catumaxomab, denosumab, obinutuzumab, ofatumumab, ramucirumab, pertuzumab, nimotuzumab, lambrolizumab, pidilizumab, siltuximab, BMS-936559, RG7446/MPDL3280A, MEDI4736), antibody-drug conjugates (e.g., brentuximab vedotin (ADCETRIS®, Seattle Genetics); ado-trastuzumab emtansine (KADCYLA®, Roche); Gemtuzumab ozogamicin (Wyeth); CMC-544; SAR3419; CDX-011; PSMA-ADC; BT-062; and IMGN901 (see, e.g., Sassoon et al., Methods Mol. Biol. 1045:1-27 (2013); Bouchard et al., Bioorganic Med. Chem. Lett. 24: 5357-5363 (2014)), or any combination thereof.

In some embodiments, combined administration of an anti-α11β1 antibody and an additional therapeutic agent results in an improvement in cancer to an extent that is greater than one produced by either the anti-α11β1 antibody or the additional therapeutic agent alone. The difference between the combined effect and the effect of each agent alone can be a statistically significant difference. In some embodiments, the combined effect can be a synergistic effect. In some embodiments, combined administration of an anti-α11β1 antibody and an additional therapeutic agent allows administration of the additional therapeutic agent at a reduced dose, at a reduced number of doses, and/or at a reduced frequency of dosage compared to a standard dosing regimen, e.g., an approved dosing regimen for the additional therapeutic agent.

In some embodiments, treatment methods described herein are performed on subjects for whom other treatments of the medical condition have failed or have had less success in treatment through other means. Additionally, the treatment methods described herein can be performed in conjunction with one or more additional treatments of the medical condition. For instance, the method can comprise administering a cancer regimen, e.g., non-myeloablative chemotherapy, surgery, hormone therapy, and/or radiation, prior to, substantially simultaneously with, or after the administration of an anti-α11β1 antibody described herein, or composition thereof.

Formulations and Administration

In various embodiments, an antibody described herein can be incorporated into a pharmaceutical composition. Such a pharmaceutical composition can be useful, e.g., for the prevention and/or treatment of diseases, e.g., fibrotic disorders. Pharmaceutical compositions can be formulated by methods known to those skilled in the art (such as described in Remington's Pharmaceutical Sciences, 17th edition, ed. Alfonso R. Gennaro, Mack Publishing Company, Easton, Pa. (1985)).

In some embodiments, a pharmaceutical composition can be formulated to include a pharmaceutically acceptable carrier or excipient. Examples of pharmaceutically acceptable carriers include, without limitation, any and all solvents, dispersion media, coatings, antibacterial and antifungal agents, isotonic and absorption delaying agents, and the like that are physiologically compatible. Compositions of the present invention can include a pharmaceutically acceptable salt, e.g., an acid addition salt or a base addition salt.

In some embodiments, a composition including an antibody as described herein, e.g., a sterile formulation for injection, can be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, such as, for example, an alcohol such as ethanol and/or a polyalcohol such as propylene glycol or polyethylene glycol, and/or a nonionic surfactant such as polysorbate 80™ or HCO-50.

As disclosed herein, a pharmaceutical composition may be in any form known in the art. Such forms include, e.g., liquid, semi-solid and solid dosage forms, such as liquid solutions (e.g., injectable and infusible solutions), dispersions or suspensions, tablets, pills, powders, liposomes and suppositories.

Selection or use of any particular form may depend, in part, on the intended mode of administration and therapeutic application. For example, compositions containing a composition intended for systemic or local delivery can be in the form of injectable or infusible solutions. Accordingly, compositions can be formulated for administration by a parenteral mode (e.g., intravenous, subcutaneous, intraperitoneal, or intramuscular injection). As used herein, parenteral administration refers to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion.

Route of administration can be parenteral, for example, administration by injection, transnasal administration, transpulmonary administration, or transcutaneous administration. Administration can be systemic or local by intravenous injection, intramuscular injection, intraperitoneal injection, or subcutaneous injection.

In some embodiments, a pharmaceutical composition of the present invention can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filter sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

A pharmaceutical composition can be administered parenterally in the form of an injectable formulation comprising a sterile solution or suspension in water or another pharmaceutically acceptable liquid. For example, the pharmaceutical composition can be formulated by suitably combining the therapeutic molecule with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of active ingredient included in a pharmaceutical preparation is such that a suitable dose within the designated range is provided. Non-limiting examples of oily liquid include sesame oil and soybean oil, and may be combined with benzyl benzoate or benzyl alcohol as a solubilizing agent. Other items that may be included are a buffer such as a phosphate buffer, or sodium acetate buffer, a soothing agent such as procaine hydrochloride, a stabilizer such as benzyl alcohol or phenol, and an antioxidant. A formulated injection can be packaged in a suitable ampule.

In various embodiments, subcutaneous administration can be accomplished by means of a device, such as a syringe, a prefilled syringe, an auto-injector (e.g., disposable or reusable), a pen injector, a patch injector, a wearable injector, an ambulatory syringe infusion pump with subcutaneous infusion sets, or other device for combining with antibody drug for subcutaneous injection.

An injection system of the present disclosure may employ a delivery pen as described in U.S. Pat. No. 5,308,341. Pen devices, most commonly used for self-delivery of insulin to patients with diabetes, are well known in the art. Such devices can comprise at least one injection needle (e.g., a 31 gauge needle of about 5 to 8 mm in length), are typically prefilled with one or more therapeutic unit doses of a therapeutic solution, and are useful for rapidly delivering solution to a subject with as little pain as possible. One medication delivery pen includes a vial holder into which a vial of a therapeutic or other medication may be received. The pen may be an entirely mechanical device or it may be combined with electronic circuitry to accurately set and/or indicate the dosage of medication that is injected into the user. See, e.g., U.S. Pat. No. 6,192,891. In some embodiments, the needle of the pen device is disposable and the kits include one or more disposable replacement needles. Pen devices suitable for delivery of any one of the presently featured compositions are also described in, e.g., U.S. Pat. Nos. 6,277,099; 6,200,296; and 6,146,361, the disclosures of each of which are incorporated herein by reference in their entirety. A microneedle-based pen device is described in, e.g., U.S. Pat. No. 7,556,615, the disclosure of which is incorporated herein by reference in its entirety. See also the Precision Pen Injector (PPI) device, MOLLY™, manufactured by Scandinavian Health Ltd.

In some embodiments, a composition described herein can be therapeutically delivered to a subject by way of local administration. As used herein, “local administration” or “local delivery,” can refer to delivery that does not rely upon transport of the composition or agent to its intended target tissue or site via the vascular system. For example, the composition may be delivered by injection or implantation of the composition or agent or by injection or implantation of a device containing the composition or agent. In certain embodiments, following local administration in the vicinity of a target tissue or site, the composition or agent, or one or more components thereof, may diffuse to an intended target tissue or site that is not the site of administration.

In some embodiments, a composition can be formulated for storage at a temperature below 0° C. (e.g., −20° C. or −80° C.). In some embodiments, the composition can be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, in some embodiments, the compositions described herein are stable in storage for at least 1 year at 2-8° C. (e.g., 4° C.).

In some embodiments, a pharmaceutical composition can be formulated as a solution. In some embodiments, a composition can be formulated, for example, as a buffered solution at a concentration suitable for storage at 2-8° C. (e.g., 4° C.).

Compositions including one or more antibodies as described herein can be formulated in immunoliposome compositions. Such formulations can be prepared by methods known in the art. Liposomes with enhanced circulation time are disclosed in, e.g., U.S. Pat. No. 5,013,556.

In certain embodiments, compositions can be formulated with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) “Sustained and Controlled Release Drug Delivery Systems,” Marcel Dekker, Inc., New York.

In some embodiments, administration of an antibody as described herein is achieved by administering to a subject a nucleic acid encoding the antibody. Nucleic acids encoding a therapeutic antibody described herein can be incorporated into a gene construct to be used as a part of a gene therapy protocol to deliver nucleic acids that can be used to express and produce antibody within cells. Expression constructs of such components may be administered in any therapeutically effective carrier, e.g. any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1 (HSV-1), or recombinant bacterial or eukaryotic plasmids. Viral vectors can transfect cells directly; plasmid DNA can be delivered with the help of, for example, cationic liposomes (lipofectin) or derivatized, polylysine conjugates, gramicidin S, artificial viral envelopes or other such intracellular carriers, as well as direct injection of the gene construct or $CaPO_4$ precipitation (see, e.g., WO04/060407). Examples of suitable retroviruses include pLJ, pZIP, pWE and pEM which are known to those skilled in the art (see, e.g., Eglitis et al. (1985) Science 230:1395-1398; Danos and Mulligan (1988) Proc Natl Acad Sci USA 85:6460-6464; Wilson et al. (1988) Proc Natl Acad Sci USA 85:3014-3018; Armentano et al. (1990) Proc Natl Acad Sci USA 87:6141-6145; Huber et al. (1991) Proc Natl Acad Sci USA 88:8039-8043; Ferry et al. (1991) Proc Natl Acad Sci USA 88:8377-8381; Chowdhury et al. (1991) Science 254:1802-1805; van Beusechem et al. (1992) Proc Natl Acad Sci USA 89:7640-7644; Kay et al. (1992) Human Gene Therapy 3:641-647; Dai et al. (1992) Proc Natl Acad Sci USA 89:10892-10895; Hwu et al. (1993) J Immunol 150:4104-4115; U.S. Pat. Nos. 4,868,116 and 4,980,286; and PCT Publication Nos. WO89/07136, WO89/02468, WO89/05345, and WO92/07573). Another viral gene delivery system utilizes adenovirus-derived vectors (see, e.g., Berkner et al. (1988) BioTechniques 6:616; Rosenfeld et al. (1991) Science 252:431-434; and Rosenfeld et al. (1992) Cell 68:143-155). Suitable adenoviral vectors derived from the adenovirus strain Ad type 5 d1324 or other strains of adenovirus (e.g., Ad2, Ad3, Ad7, etc.) are known to those skilled in the art. Yet another viral vector system useful for delivery of the subject gene is the adeno-associated virus (AAV). See, e.g., Flotte et al. (1992) Am J Respir Cell Mol Biol 7:349-356; Samulski et al. (1989) J Virol 63:3822-3828; and McLaughlin et al. (1989) J Virol 62:1963-1973.

In some embodiments, the compositions provided herein are present in unit dosage form, which unit dosage form can be suitable for self-administration. Such a unit dosage form may be provided within a container, typically, for example, a vial, cartridge, prefilled syringe or disposable pen. A doser such as the doser device described in U.S. Pat. No. 6,302,855, may also be used, for example, with an injection system as described herein.

A suitable dose of a composition described herein, which dose is capable of treating or preventing a disorder in a subject, can depend on a variety of factors including, e.g., the age, sex, and weight of a subject to be treated and the particular inhibitor compound used. For example, a different dose of one composition including an antibody as described herein may be required to treat a subject with a fibrotic disorder as compared to the dose of a different formulation of that antibody. Other factors affecting the dose administered to the subject include, e.g., the type or severity of the disorder. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject can also be adjusted based upon the judgment of the treating medical practitioner.

A composition described herein can be administered as a fixed dose, or in a milligram per kilogram (mg/kg) dose. In some embodiments, the dose can also be chosen to reduce or avoid production of antibodies or other host immune responses against one or more of the antigen-binding molecules in the composition. Exemplary dosages of an antibody, such as a composition described herein, include, e.g., 0.0001 to 100 mg/kg, 0.01 to 5 mg/kg, 1-1000 mg/kg, 1-100 mg/kg, 0.5-50 mg/kg, 0.1-100 mg/kg, 0.5-25 mg/kg, 1-20 mg/kg, and 1-10 mg/kg of the subject body weight. For example dosages can be 0.1 mg/kg, 0.3 mg/kg, 0.5 mg/kg, 1.0 mg/kg, 2.0 mg/kg, 3.0 mg/kg, 4.0 mg/kg, 5.0 mg/kg, 10 mg/kg or 20 mg/kg body weight or within the range of 1-20 mg/kg body weight. An exemplary treatment regime entails administration once per week, once every two weeks, once every three weeks, once every four weeks, once a month, once every 3 months or once every three to 6 months, or with a short administration interval at the beginning (such as once per week to once every three weeks), and then an extended interval later (such as once a month to once every three to 6 months).

A pharmaceutical solution can include a therapeutically effective amount of a composition described herein. Such effective amounts can be readily determined by one of ordinary skill in the art based, in part, on the effect of the administered composition, or the combinatorial effect of the composition and one or more additional active agents, if more than one agent is used. A therapeutically effective amount of a composition described herein can also vary according to factors such as the disease state, age, sex, and weight of the individual, and the ability of the composition (and one or more additional active agents) to elicit a desired response in the individual, e.g., amelioration of at least one condition parameter, e.g., amelioration of at least one symptom of a fibrotic disorder. For example, a therapeutically effective amount of a composition described herein can inhibit (lessen the severity of or eliminate the occurrence of) and/or prevent a particular disorder, and/or any one of the symptoms of the particular disorder known in the art or described herein. A therapeutically effective amount is also one in which any toxic or detrimental effects of the composition are outweighed by the therapeutically beneficial effects.

Suitable human doses of any of the compositions described herein can further be evaluated in, e.g., Phase I dose escalation studies. See, e.g., van Gurp et al. (2008) Am J Transplantation 8(8):1711-1718; Hanouska et al. (2007) Clin Cancer Res 13(2, part 1):523-531; and Hetherington et al. (2006) Antimicrobial Agents and Chemotherapy 50(10): 3499-3500.

Toxicity and therapeutic efficacy of compositions can be determined by known pharmaceutical procedures in cell cultures or experimental animals (e.g., animal models of any of the fibrotic disorders described herein). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A composition described herein that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

Those of skill in the art will appreciate that data obtained from cell culture assays and animal studies can be used in formulating a range of dosage for use in humans. Appropriate dosages of compositions described herein lie generally within a range of circulating concentrations of the compositions that include the $ED_{50}$ with little or no toxicity. The dosage may vary within this range depending upon the dosage form employed and the route of administration utilized. For a composition described herein, the therapeutically effective dose can be estimated initially from cell culture assays. A dose can be formulated in animal models to achieve a circulating plasma concentration range that includes the $IC_{50}$ (i.e., the concentration of the antibody which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration (e.g., to the eye or a joint) is desired, cell culture or animal modeling can be used to determine a dose required to achieve a therapeutically effective concentration within the local site.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

The disclosure is further illustrated by the following examples. The examples are provided for illustrative purposes only. They are not to be construed as limiting the scope or content of the disclosure in any way.

EXAMPLES

Methods

Generation of Novel Antibodies Against α11β1

Rat Immunization

Wistar rats were immunized with recombinant human α11β1 protein. An enzyme-linked immunosorbent assay (ELISA) was used to test an immune response against target human and mouse proteins. Subsequently, cell fusion (by electro fusion) was performed with animals that produced a good immune response. All fused cells were plated in a 96-well plate and supernatants were screened by ELISA against soluble human and mouse α11β1. Positive clones were counter-screened against human α1β1, α2β1 and α10β1. Clones that specifically bound to human and mouse α11β1 and did not bind to α1β1, α2β1 and α10β1 were selected, subcloned, expanded and cryopreserved. Purified antibodies were then generated from the selected clones and heavy chain and light chain variable domain sequences were obtained from each purified antibody.

Rabbit Immunization

Rabbits were immunized employing a cell-based monoclonal antibody platform. Two rabbits were immunized with recombinant human α11β1 protein. Splenocytes from the immunized rabbits were sorted and selected against human β1, in order to reduce the number of β1-specific B cell clones. Sorted splenocytes were then cultured for approximately 1 week and culture supernatants were screened for binding to human α11β1. Top results were sequenced and subsequently rabbit antibodies were recombinantly produced using a HEK cell system.

Mouse Immunization 10 mice from 5 different strains were immunized with an appropriate mixture of human α11β1, mouse α11β1 and tolerance breaking protein. Plasma titers were evaluated by ELISA against a mixture of human and mouse α11β1. Popliteal, inguinal, and iliac lymph nodes were collected. ELISA-positive anti-human/mouse α11β1 hybridomas were expanded and subjected to a secondary screen against human and mouse α11β1, control HIS protein, and a counter-screen was performed against human α11β1, α2β1 and α10β1. Supernatant IgG concentration was sufficient for functional screening. Selected hybridomas satisfying all the criteria were cloned and clonal hybridomas were confirmed by ELISA against human and mouse α11β1 and subsequently scaled-up and IgGs were purified. Heavy and light chain variable regions of selected hybridomas were then sequenced.

Phage Library Display

Phage library display was employed for generation of fully human anti-α11β1 antibodies. Fully human anti-α11β1 antibodies were discovered using single chain fragment variable (scFv) antigen-binding fragments displayed on phages (phage display library). Three rounds of selection were performed on purified human and mouse α11β1 antigen as well as deselection against α10β1, to enrich for all subunit-specific antibodies. Subsequently, optimal populations were subcloned into a bacterial soluble expression vector, recombinant antibody expression was induced and supernatant was screened for binding via ELISA assays. Antibodies with appropriate binding profiles were sequenced and subsequently converted from scFv to IgG.

ELISA 0.25 μg/mL of target antigen (recombinant human or mouse α11β1) was plated in a 96-well plate over night at 4° C. Plates were washed (PBS with 0.1% Tween-20), blocked (PBS with 2% BSA and 0.05% Tween-20) for 1 hour at room temperature and incubated with a range of antibody concentrations for 1 hour at room temperature. Subsequently, plates were washed and incubated with biotinylated anti-rabbit/mouse/human IgG in a 1:1000 dilution buffer and incubated for 1 hour at room temperature. After washing the plates, Streptavidin HRP was added at 1:200 in dilution buffer and incubated for 1 hour at room temperature. Ultra TMB ELISA substrate solution was added and the plates incubated for 5 minutes on a plate shaker. The reaction was stopped by adding stop solution to each well and plates were read at 450 nm.

FACS

Antibody Binding to CHO-K1

200,000 cells (wild-type CHO-K1 cells or CHO-K1 cells expressing human α11) were incubated with each antibody at desired concentrations in FACS buffer for 30 min at 4° C. Then, the cells were washed with FACS buffer and incubated with secondary antibody at 1:100 dilution for 30 minutes at 4° C. Cells were then washed and fixed with 1% PFA in PBS for 20 minutes at room temperature; washed again and read on a cytometer in FACS buffer.

Antibody Binding to HPF/MF

Human Pulmonary Fibroblasts (ScienCell) were cultured in complete Fibroblast Growth Medium (ScienCell) until 80% confluent in T-150 flasks. Cells were washed and harvested using Accutase. Cells were seeded into T-150 flasks at 7,500 cells/cm$^2$ in complete FGF and cultured for 72 hours. Cells were then washed and starved in serum reduced medium for 24 hours. After starvation, cells were treated with TGFβ-1 (R&D Systems) for 72 hours. Cells were harvested using Accutase and seeded in 96-well conical bottom plates. Cells were blocked with Heat Inactived Fetal Bovine Serum (Gibco) for 30 minutes at 4° C. Cells were then incubated with anti-α11 antibodies at the doses described in each figure for 30 minutes at 4° C. A human anti-α11 antibody (Creative BioLabs) was included as a positive control as well as the appropriate IgG isotype negative controls. Cells were washed twice and incubated with PE conjugated secondary antibodies specific to the IgG class of the anti-α11 antibodies being tested for 30 minutes at 4° C. Cells were washed twice and fixed in 1% PFA for 30 minutes. Cells were acquired on a FACS Verse (Benton Dickson) binding of each antibody. Data were analyzed by gating on single cells and determining the geometric Mean Fluorescence Intensity (gMFI) in the PE channel for each sample.

Surface Plasmon Resonance (SPR)

The affinity of antibodies for human α11β1 was measured by surface plasmon resonance assay (SPR). Affinity was measured at pH 7.6 and 25° C. with a Biacore T200 instrument. Anti-HIS antibody was immobilized on the SPR sensor surface using EDC/NHS covalent attachment. HIS-tagged human α11β1 was captured on the sensor surface and a single-cycle kinetics assay was used. Increasing concentrations of test antibody were injected in series over the sensor-bound α11β1. Dissociation was monitored for 1000 seconds. A sensor surface with only anti-HIS antibody and a series of blank injections were used to double-reference subtract the data. A 1:1 Langmuir model was fit to the data to estimate the kinetic association and dissociation constants. The affinity (equilibrium dissociation constant) of the interaction was calculated by dividing the kinetic dissociation constant by the kinetic association constant. Between injection cycles α11β1 and bound antibody were removed with an injection of 10 mM glycine at pH 1.5.

Cell Adhesion Inhibition 0.6×10$^6$ cells/mL were incubated with each antibody at a range of concentrations for 20 minutes at 37° C. E-Plate VIEW 96 PET plate coated with 100 ng/mL type I collagen or PBS overnight at room temperature was blocked in 3% BSA for 1 house at room temperature. After washing the plate with PBS, cell and antibody mixture was added to the wells and the plate was places into an xCelligence machine. Cell adhesion was recorded over 6 hours. The time point of maximum cell adhesion was used for comparison relative to control.

Fibroblast-to-Myofibroblasts Transition (FMT)

Human Pulmonary Fibroblasts (ScienCell) were cultured in complete Fibroblast Growth Medium (ScienCell) until 80% confluent. Cells were washed and harvested using Accutase. Cells were seeded onto tissue culture-treated 96 well plates at 20,000 cells/well in complete Fibroblast Growth Medium. After 24 hours, cells were washed and starved in serum reduced medium for an additional 24 hours. After starvation, cells were treated with TGFβ-1 (R&D Systems) with or without anti-α11 antibodies. A polyclonal rabbit anti-human α11 antibody was used as a positive control. Appropriate IgG isotype controls were also included. After 48 hours, cells were harvested, fixed, permeabilized and stained with AlexaFluor488 Labeled Anti-αSMA (α-smooth muscle actin) (Invitrogen). Cells were acquired on a FACS Verse (Benton Dickson) to determine expression levels of αSMA. Data were analyzed by gating on single cells and determining the geometric Mean Fluorescence Intensity (gMFI) in the FITC channel for each sample. gMFI for each sample was normalized to the untreated control and presented as % inhibition.

Collagen Gel Contraction Assay 24-well plates were blocked with 2% BSA in PBS overnight at 37° C. The following day, the plates were washed 3 times with PBS before being used in the assay. Human CHO cell lines expressing α11 were harvested and resuspended at $1.25\times10^6$ in ExpiCHO Expression Medium (Gibco™ Cat #A2910002). The collagen gel solution was prepared by diluting 3 mg/mL stock collagen type I (Gibco™ Collagen I Rat Protein, Tail Cat #A1048301) to 1 mg/mL in the media containing the CHO cells. Sodium hydroxide was added to the solution to neutralize the pH and 400 μL of the collagen solution was added to each well of the 24-well plates. For the wells where the antibodies were included in the collagen gel solution, CHO cells were prepared at $2.5\times10^6$ and the antibodies were prepared at 2× final concentration in ExpiCHO media. The cells and antibodies were then combined 1:1 before the addition of the stock collagen type 1. The gels were allowed to polymerize for 60 minutes at 37° C. Antibodies were added to the ExpiCHO media, which was then layered on top of the polymerized gel (400 μL/well). The gels were incubated for 6 days at 37° C. before gel contraction was quantified. Images of each well were analyzed using Image J and gel contraction was determined as a percentage of the initial gel area.

Tumor Xenograft Model

Fifty-six female C.B-17 SCID mice were inoculated with A549 cells ($5\times10^6$ cells/mouse) subcutaneously in the flank. Once tumor volume reached ~100 $mm^3$, animals were randomized amongst 7 groups of 8 mice each. Mice were then treated intraperitonealy every 3 days for a total of 7 doses with isotype controls or novel mAbs 79E3E3, 16E10 and 9G04 (2 and 20 mg/kg) or with docetaxel at 10 mg/kg every 4 days for a total of 6 doses. Tumor volumes and body weights were recorded twice a week with a gap of 2-3 days in between two measurements until any of the following conditions defined were observed: loss of 20% or more body weight; tumors that inhibit normal physiological function such as eating, drinking, and mobility; ulcerated tumors; tumor size greater than 2000 $mm^3$ and clinical observations of prostration, paralysis, seizures and hemorrhages.

Precision-Cut Liver Slices (PCLS)

Precision-Cut Liver Slices (PCLS) were prepared from resected liver tissue and rested for 24 hours to allow the post-slicing stress period to elapse before experiments began. PCLS were cultured without exogenous challenge (Group 1), with 100 μg/mL control antibodies (Groups 2 and 3—either mouse IgG2a or rabbit IgG), or with a combination of TGF-β1 (3 ng/mL) and PDGF-ββ (50 ng/mL) (Groups 2-10). PCLS were cultured in the presence or absence of 10 μM Alk5i (Group 4) as a positive control or novel inhibitors (16E10, 79E3E3, and 9G05) at 2 escalating doses (10 and 100 μg/mL) in Groups 5-10. Each of the 10 groups included n=6 human PCLS prepared from a single human liver. PCLS culture media, including all stimuli and compounds, was refreshed and harvested at 24 hour intervals. Cell culture supernatant (n=⅔ paired wells) was collected every 24 hours and snap frozen for quantification of soluble outputs. All PCLS were harvested at 96 hours.

Tissue culture levels of markers of liver damage (lactate dehydrogenase (LDH) and aspartate transaminase (AST)) and hepatocyte function/viability (albumin) were quantified on all PCLS at all time points. Albumin secretion was quantified by ELISA as a marker of PCLS integrity and function. Levels of collagen 1a1, IL-6, hyaluronic acid and Timp-1 in the cell culture supernatants were quantified using R&D Duoset ELISA kits.

Total RNA extraction from PCLS was performed on all samples. RNeasy Mini kits (Qiagen) were used for RNA extraction. RNA was reverse-transcribed to cDNA and used in qPCR to measure transcript levels of Col1a1, αSMA, TIMP-1, TGF-β1, IL-6 and β-actin/GAPDH.

Example 1. Generation of Novel Monoclonal Antibodies Against α11β1 and Determination of Binding Affinity Antibody discovery was performed by immunizing rats and rabbits with recombinant human α11β1, and by immunizing mice with both human and mouse α11β1. 51 novel anti-human α11β1 monoclonal antibodies were generated (24 rabbit, 7 rat and 20 mouse). Heavy chain and light chain variable region sequences were determined for the mouse and rat antibodies, while full heavy chain and light chain sequences were determined for the rabbit antibodies.

Figure 2A:
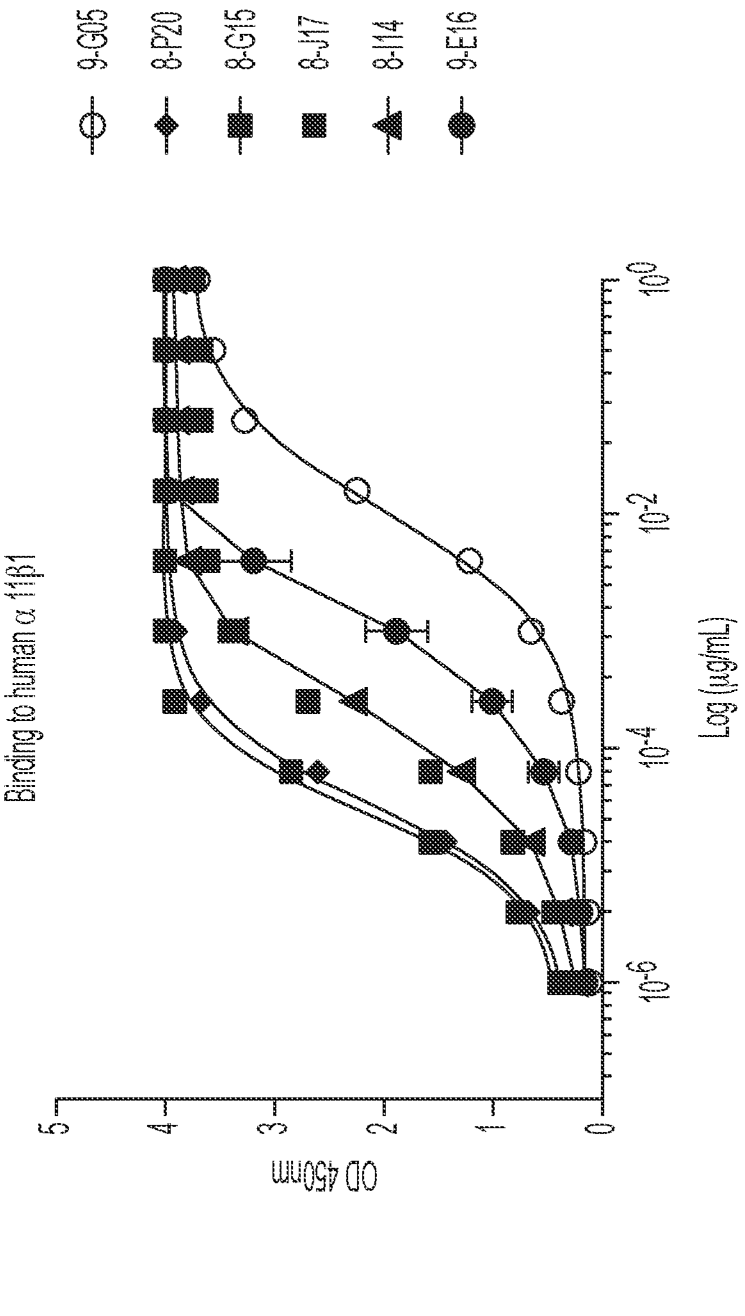
FIG. 2A shows a chart illustrating an ELISA analysis of binding of exemplary mouse monoclonal antibodies to human α11β1.
Figure 2B:
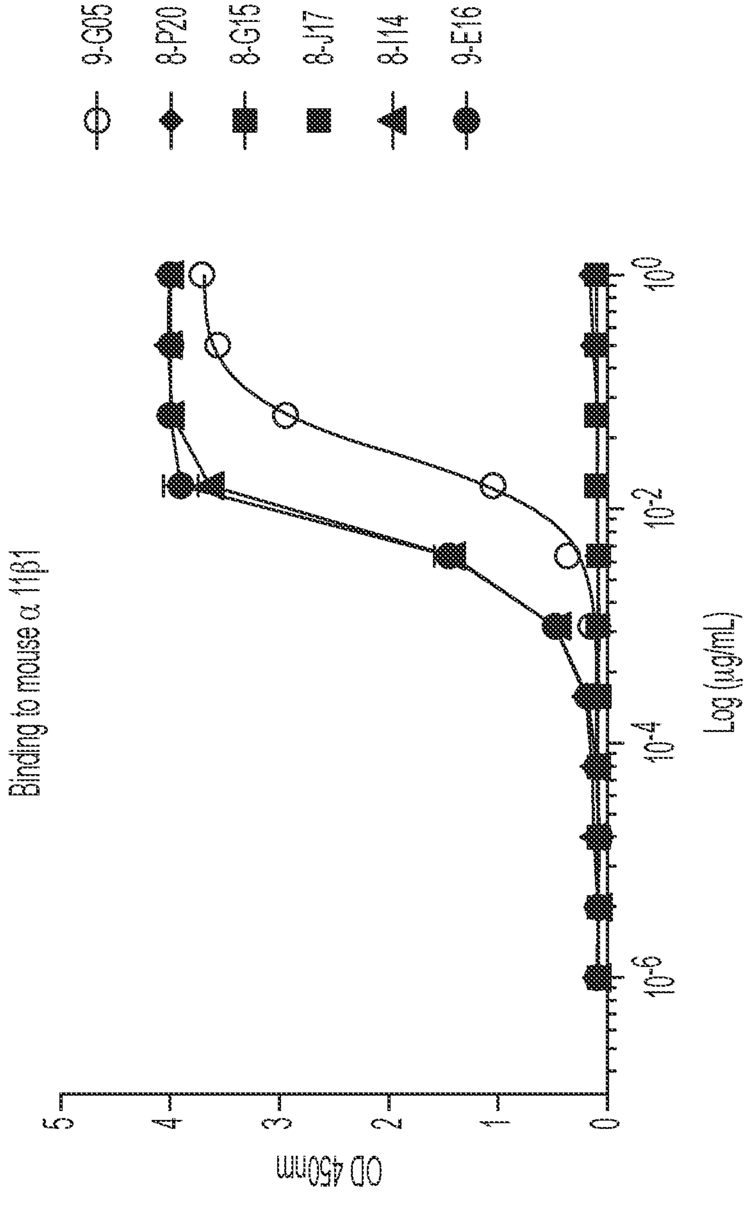
FIG. 2B shows a chart illustrating an exemplary ELISA analysis of binding of mouse monoclonal antibodies to mouse α11β1.

ELISA results illustrating exemplary binding of selected mouse monoclonal antibodies to recombinant human α11β1 are shown in FIG. 2A. Three of those mAbs also bound to mouse α11β1, as shown in FIG. 2B.

Figure 3A:
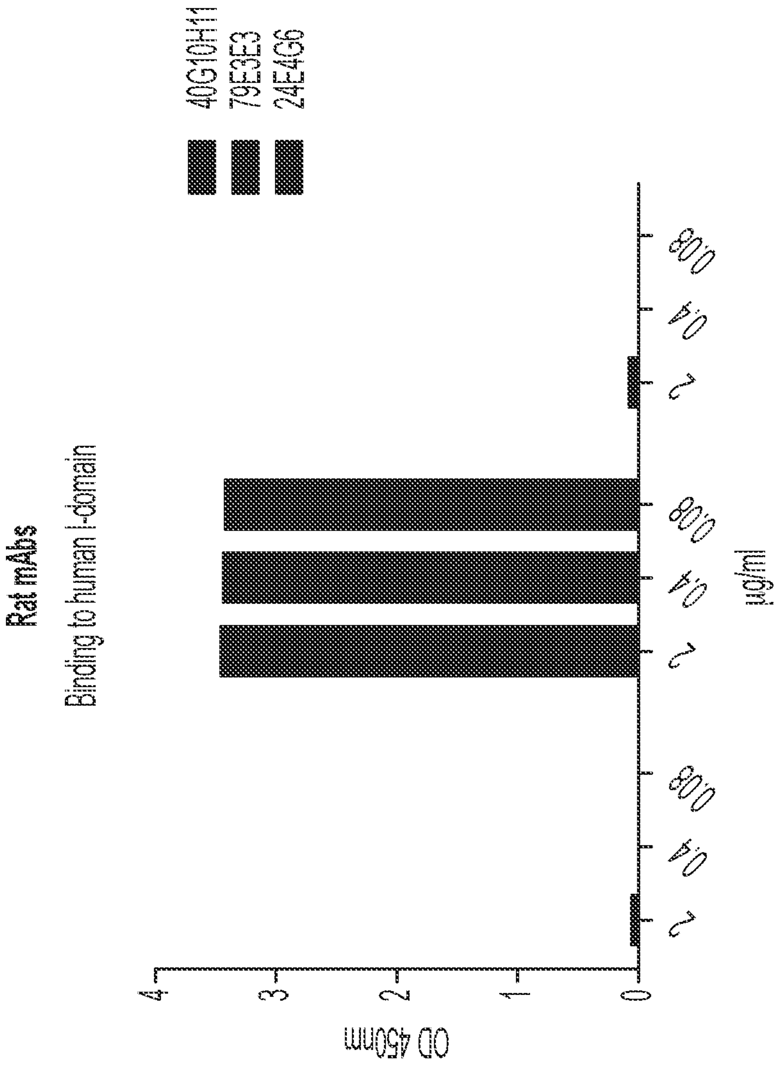
FIG. 3A shows a graph illustrating an ELISA analysis of binding of exemplary rat monoclonal antibodies to a human α11β1 I domain.
Figure 3B:
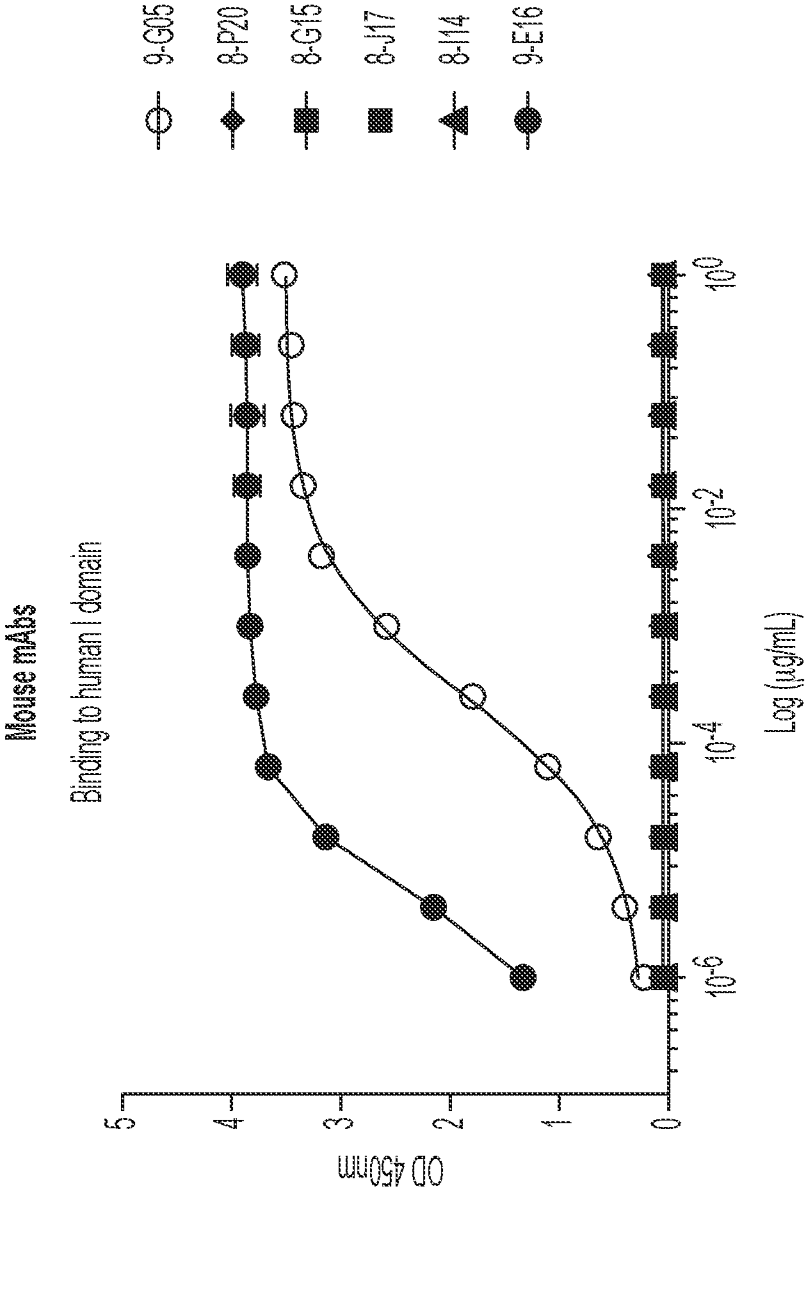
FIG. 3B shows a graph illustrating an ELISA analysis of binding of exemplary mouse monoclonal antibodies to a human α11β1 I domain.

22 Data was also collected to determine whether antibodies of interest bind to the I domain of α11β1. An in-house generated I domain of α11β1 was used. The rat clones 79E3E3, 8H8E9 and 6E5C11 exhibited high, medium, and low binding, respectively, as determined by ELISA. Mouse antibodies 10-F23, 10-L15, 7-O8, 6-A12, 9-G05 and 9-E16 and rabbit antibodies 7-H12 and 2-D3 were also tested for binding against the in-house generated α11031 domain. FIGS. 3A and 3B show graphs illustrating binding data from exemplary mAbs.

α11β1 belongs to a family of collagen receptors and has a relatively high homology to them. Therefore, the novel antibodies of this invention were counter-screened against α1β1, α2β1 and/or α10β1. Table 2 includes results of cross-reactivity to the other receptors.

TABLE 2

Data summary of tested monoclonal antibodies

| | Clone ID | Human α11β1 ELISA | Murine α11β1 ELISA | Off Target | I Domain binding | CHO-K1 FACS | HPF FACS | MF FACS | Inhibition of CHO-K1 adhesion to collagen | Inhibition of FMT | Inhibition of CHO-K1 gel contraction |
|---|---|---|---|---|---|---|---|---|---|---|---|
| MOUSE | 10-L15 | Yes | Yes | No | Yes | No | No | No | No | No | |
| | 8-I14 | Yes | Yes | No | No | Yes | No | Yes | No | Yes | No |
| | 3-G5 | Yes | Yes/Low | No | No | No | No | No | No | No | |
| | 2-A3 | Yes | Yes/Low | No | No | No | No | No | No | No | |

TABLE 2-continued

Data summary of tested monoclonal antibodies

| | Clone ID | Human α11β1 ELISA | Murine α11β1 ELISA | Off Target | I Domain binding | CHO-K1 FACS | HPF FACS | MF FACS | Inhibition of CHO-K1 adhesion to collagen | Inhibition of FMT | Inhibition of CHO-K1 gel contraction |
|---|---|---|---|---|---|---|---|---|---|---|---|
| | 8-G15 | Yes | No | No | No | Yes | No | Yes | Yes | Yes | |
| | 8-P20 | Yes | No | No | No | Yes | No | Yes | No | No | |
| | 10-F23 | Yes | Yes/Low | No | Yes | Yes | No | Yes | Yes | No | |
| | 7-O8 | Yes | Yes/Low | Yes (α10β1) | Yes | Yes | No | Yes | No | No | |
| | 8-J17 | Yes | No | Yes (at high doses) | No | Yes | No | Yes | No | Yes | |
| | 9-E16 | Yes | Yes | No | Yes | Yes | Low | Yes | Yes | Yes | |
| | 9-G05 | Yes | Yes | No | Yes | Yes | No | Yes | Yes | Yes | Yes |
| | 10-K10 | Yes | Yes/Low | No | No | No | No | Yes | No | No | |
| | 6-O12 | Yes | No | No | No | No | No | No | No | No | |
| | 6-A15 | Yes | Yes/Low | No | No | No | No | No | No | No | |
| | 6-B21 | Yes | Yes/Low | No | No | No | No | No | No | No | |
| | 6-A12 | Yes | Yes/Low | No | Yes | Yes | No | Yes | Yes | No | |
| | 6-M8 | Yes | No | No | No | No | No | No | No | No | |
| | 6-P20 | Yes | No | No | No | Yes | No | No | No | No | |
| | 6-O17 | Yes | Yes/Low | No | No | Yes | No | Yes | No | No | |
| | 9-B11 | Yes | No | No | Yes | Yes | No | Yes | Yes | Yes | No |
| | 7-H14 | Yes | Yes/Low | No | No | Yes | No | Yes | No | No | |
| RAT | 24E4G6 | Yes | No/Low | No | No | Yes | No | Yes | No | Yes | Yes |
| | 40G10H11 | Yes | Yes | Yes (all) | No | Yes | N/A | N/A | Yes | Yes | |
| | 18E10F10 | Yes | No | No | No | Yes | N/A | N/A | Yes | Yes | |
| | 8H8E9 | Yes | No | No | No | Yes | N/A | N/A | Yes | Yes | |
| | 6E5C11 | Yes | No | No | No | Yes | N/A | N/A | No | Yes | |
| | 7D8B10 | Yes | No | No | No | Yes | No | Yes | No | Yes | |
| | 79E3E3 | Yes | Yes | No | Yes | Yes | No | Yes | Yes | No | Yes |
| RABBIT | 16E10 | Yes | No | No | No | Yes | No | Yes | Yes | Yes | Yes |
| | 6F9 | Yes | No | No | No | Yes | No | Yes | Yes | No | |
| | 6G4 | Yes | No | No | No | Yes | No | Yes | Yes | No | |
| | 4E1 | Yes | No | No | No | Yes | No | Yes | Yes | No | |
| | 6C7 | Yes | No | No | No | Yes | No | Yes | Yes | No | |
| | 5D7 | Yes | No | No | No | Yes | No | Yes | Yes | No | |
| | 5A7 | Yes | No | No | No | Yes | No | Yes | Yes | No | |
| | 3B1 | Yes | No | No | No | Yes | No | Yes | Yes | No | |
| | 16G7 | Yes | Yes | No | No | Yes | No | Yes | No | Yes | No |

N/A = not tested

Since integrins are large, transmembrane receptors that exist in different conformational shapes, experiments were performed to confirm that the novel antibodies also bound cell-expressed α11β1. A CHO-K1 cell line that endogenously expressed high levels of the β1 subunit was engineered to stably express human α11 (CHO-K1 hu α11).

Figure 4A:
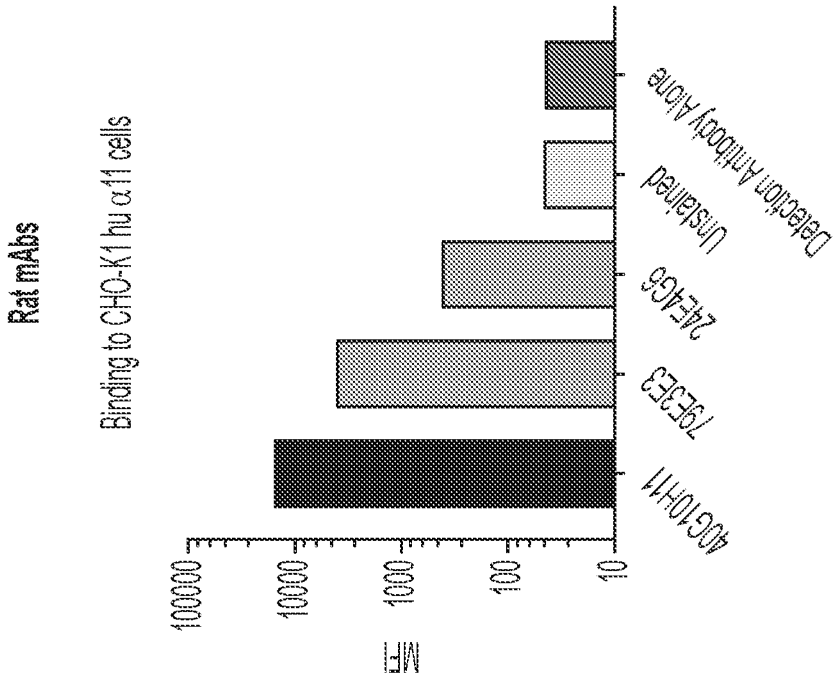
FIG. 4A shows a graph illustrating an FACS analysis of binding of exemplary rat monoclonal antibodies to CHO-K1 cells expressing human α11β1.
Figure 4B:
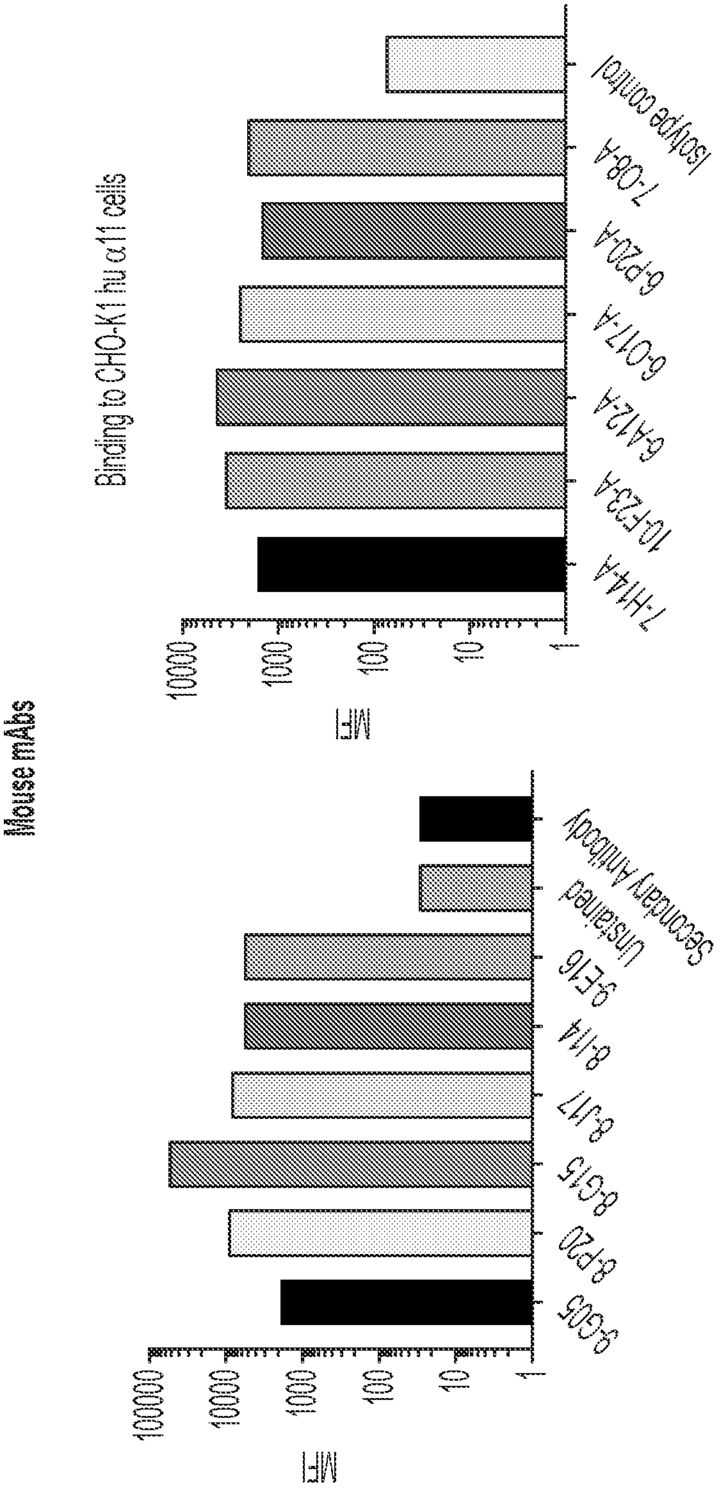
FIG. 4B shows a graph illustrating an FACS analysis of binding of exemplary mouse monoclonal antibodies to CHO-K1 cells expressing human α11β.
Figure 11A:
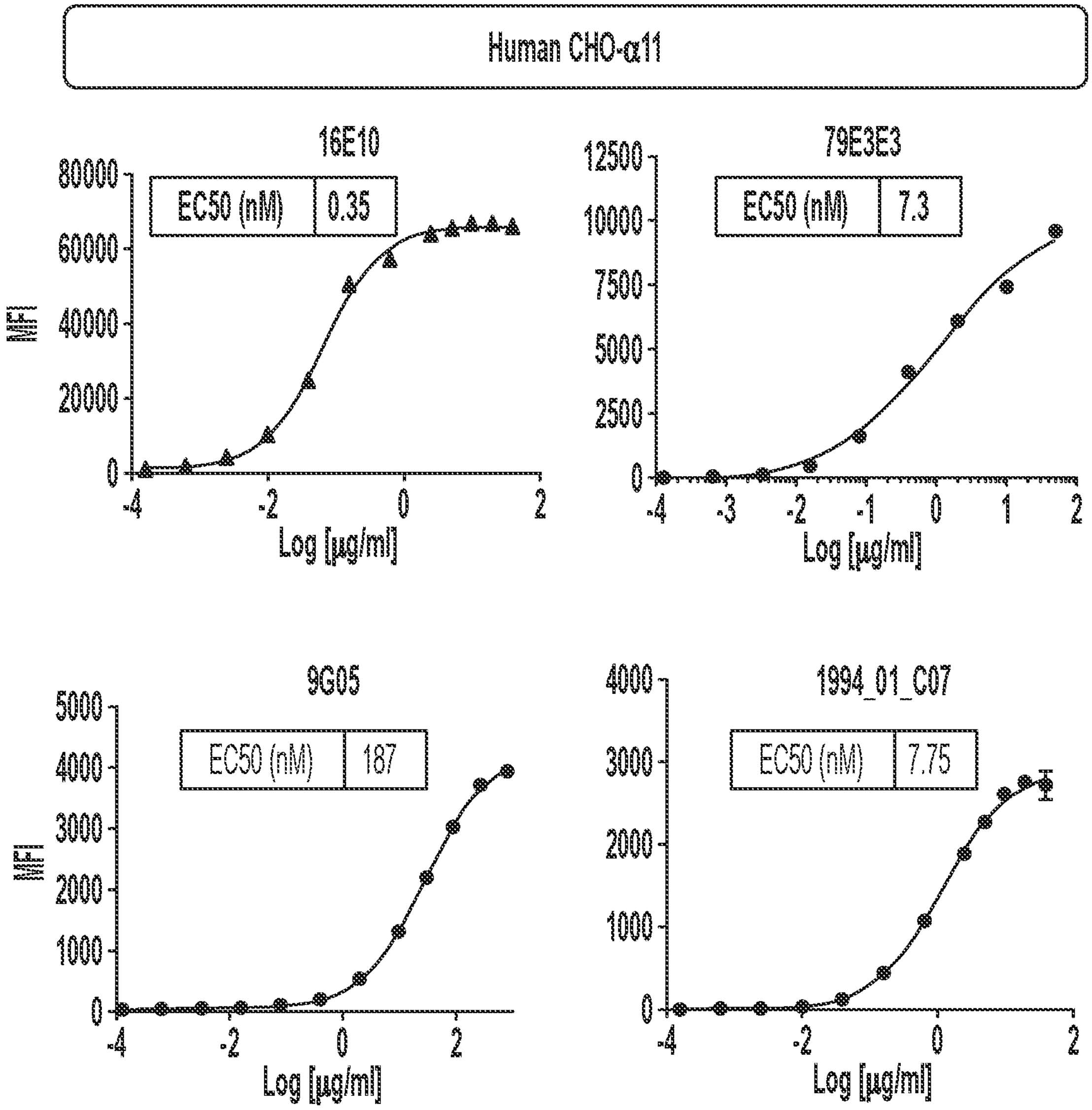
FIG. 11A and FIG. 11B show graphs illustrating the binding ability of selected rabbit, rat, mouse and human monoclonal antibodies to α11β1 expressed on the surface of CHO cells.
Figure 11B:
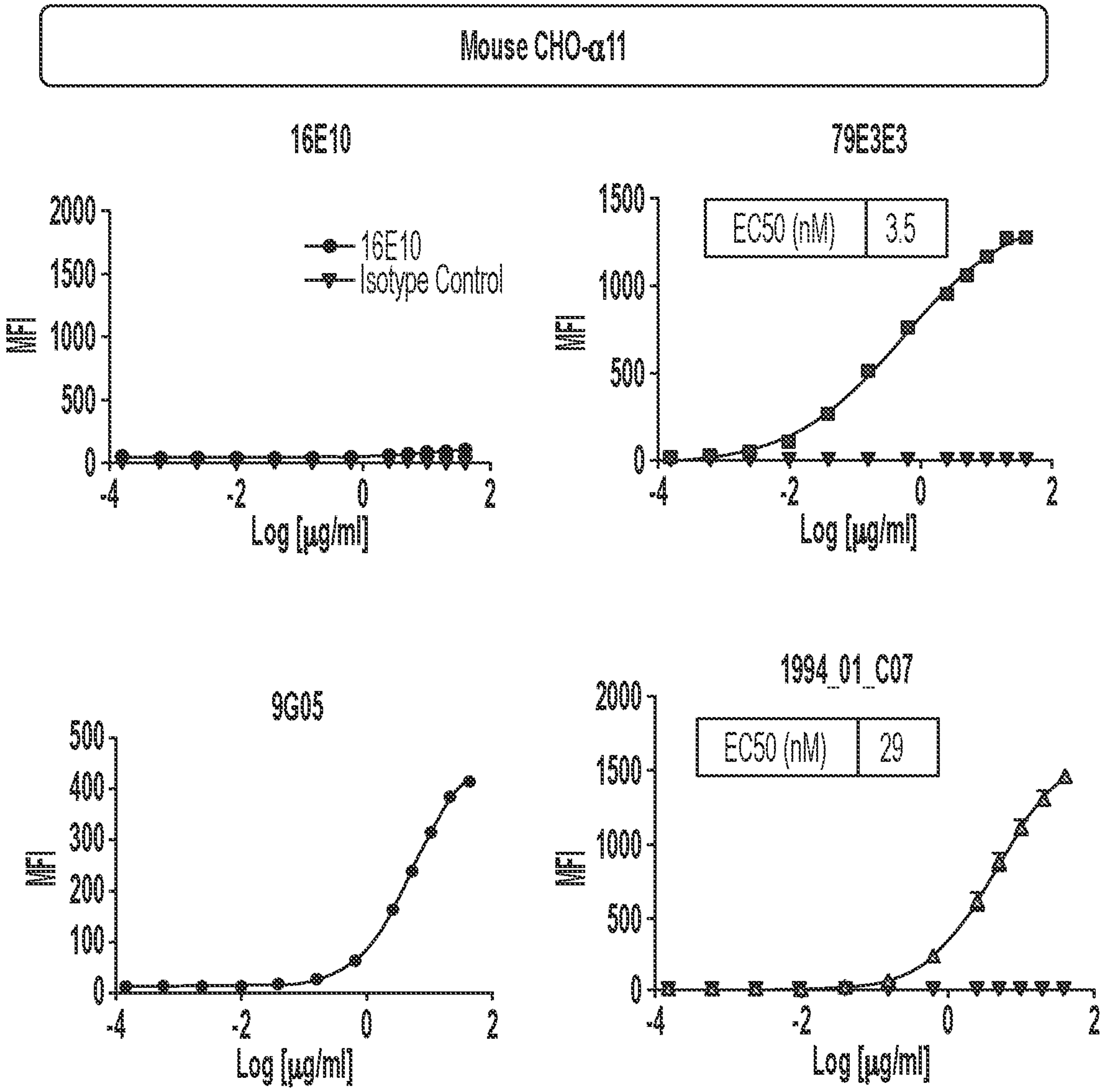
Figure 14:
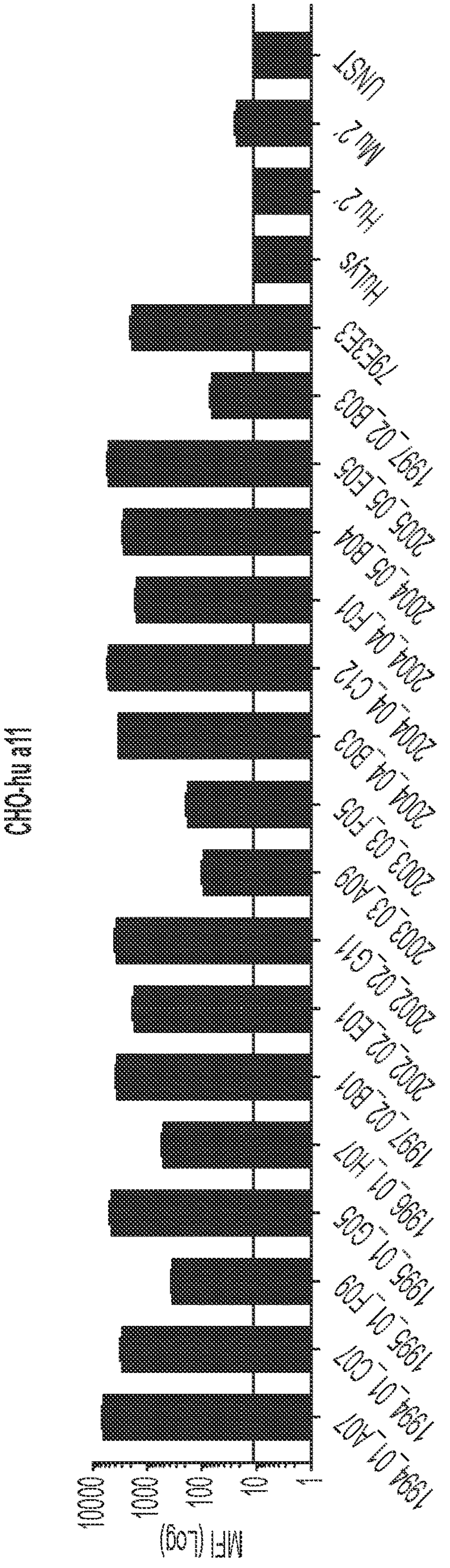
FIG. 14 shows a graph illustrating the binding ability of selected monoclonal antibodies to α11β1 expressed on the surface of CHO cells.

FIGS. 4A and 4B show selected rat and mouse mAbs that bound human α11β1 (as tested by ELISA) and also demonstrated binding ability to α11β1 expressed on the surface of CHO-K1 cells. FIGS. 11A and 11B show selected rabbit, rat, mouse and human mAbs that demonstrated binding ability to α11β1 expressed on the surface of CHO cells. Additionally, FIG. 14 shows selected fully human mAbs that demonstrated binding ability to α11β1 expressed on the surface of CHO cells. However, as shown in Table 1, there were several mAbs that were shown to bind α11β1 by ELISA, but did not bind cell-expressed α11β1.

Binding $EC_{50}$ was estimated using data from Fluorescence-activated cell sorting (FACS) performed with CHO-K1 hu α11β1 cells. The results are shown in Table 3. Four out of six mAbs tested had $EC_{50}$ results in the low nanomolar range (8-P20, 8-G15, 8-J17, 8-I14), while the remaining two mAbs were not as potent (9-G05 and 9-E16; both I domain binders).

TABLE 3

Estimated CHO-K1 binding EC50 for mouse mAbs

| mAb | Conc. (μg/mL) | Molarity (nM) |
|---|---|---|
| 9-G05 | 21.03 | 140.2 |
| 8-P20 | 0.12 | 0.8 |
| 8-G15 | 0.22 | 1.5 |
| 8-J17 | 0.33 | 2.2 |
| 8-I14 | 1.22 | 8.1 |
| 9-E16 | 42.80 | 285.3 |

Figure 9:
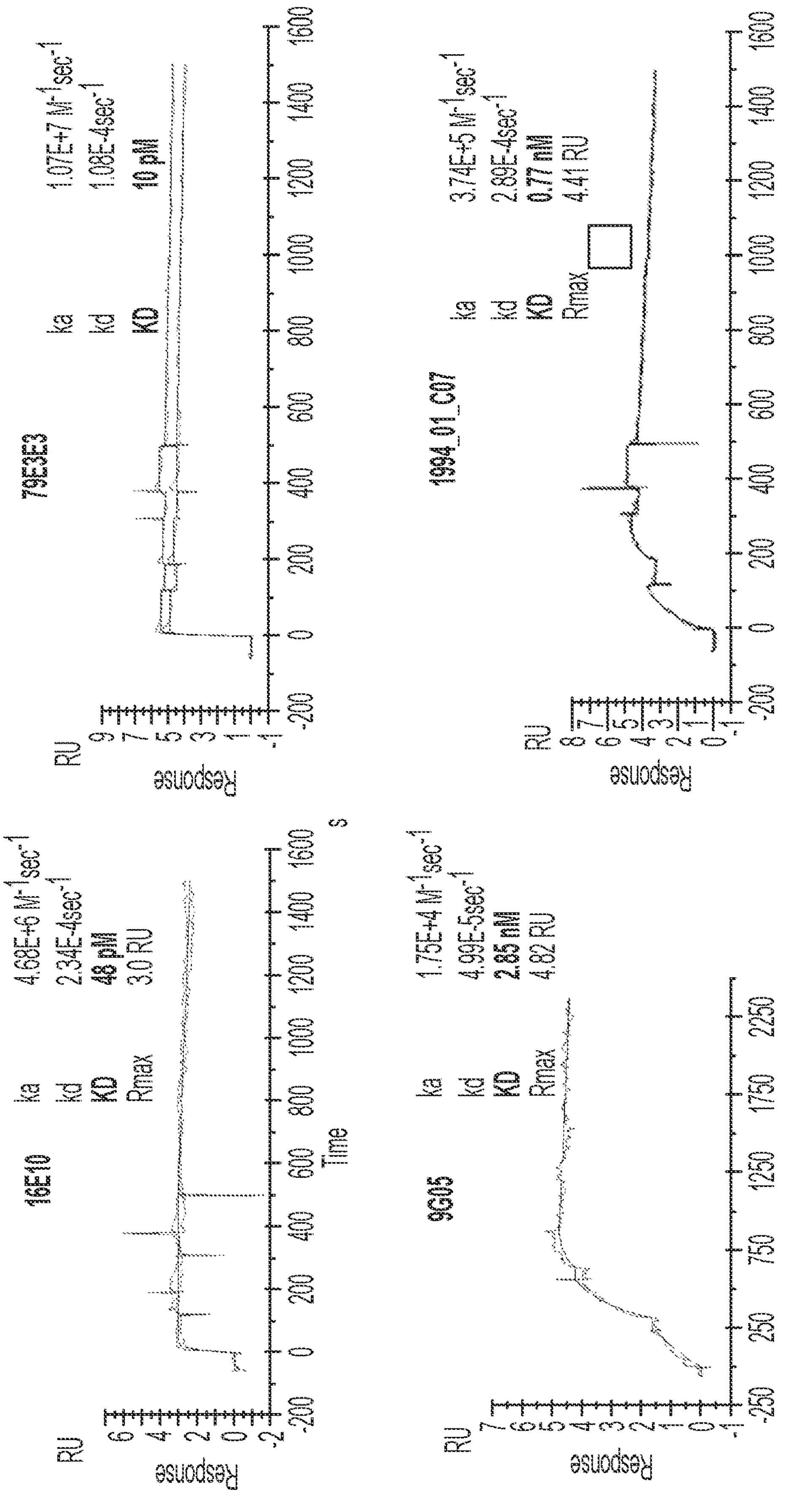
FIG. 9 shows graphs illustrating the affinity of exemplary monoclonal antibodies for human α11β1 via surface plasmon resonance (SPR).
Figure 10A:
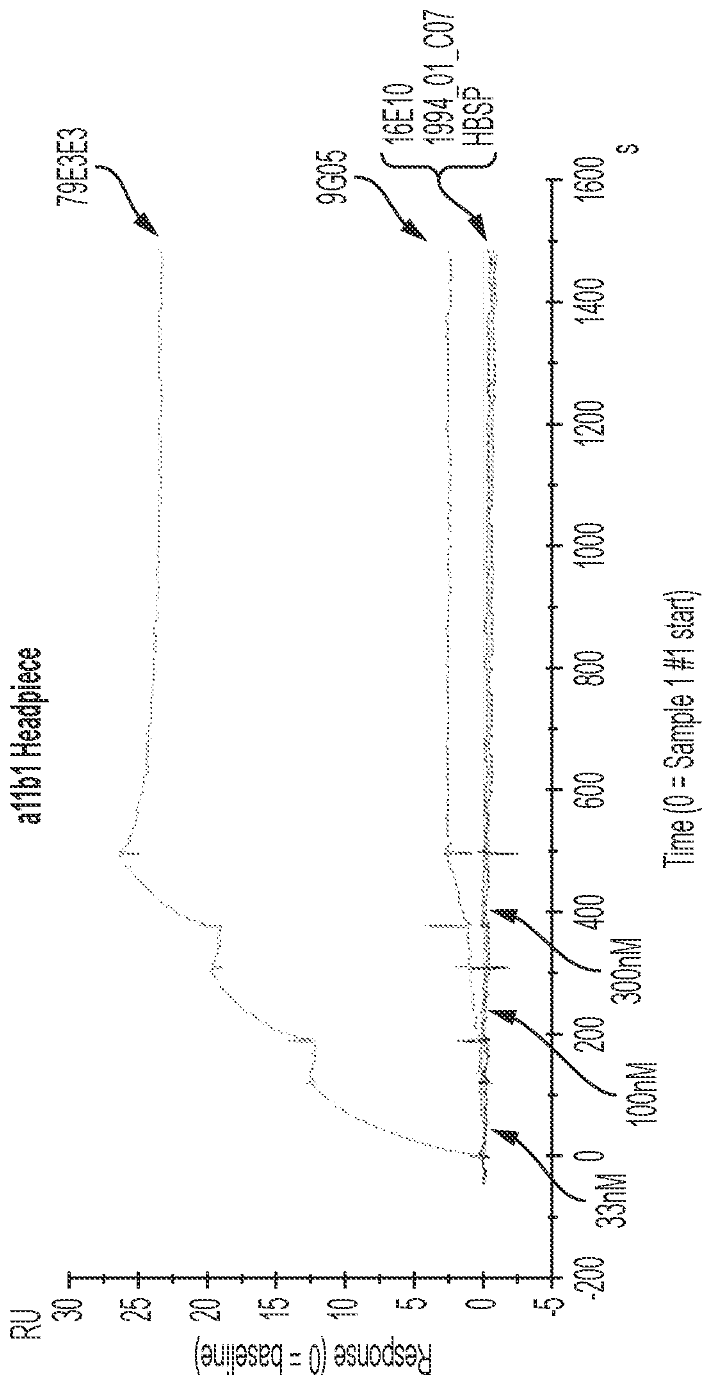
FIG. 10A and FIG. 10B show graphs illustrating the affinity of exemplary monoclonal antibodies for human α11β1 via surface plasmon resonance (SPR).
Figure 10B:
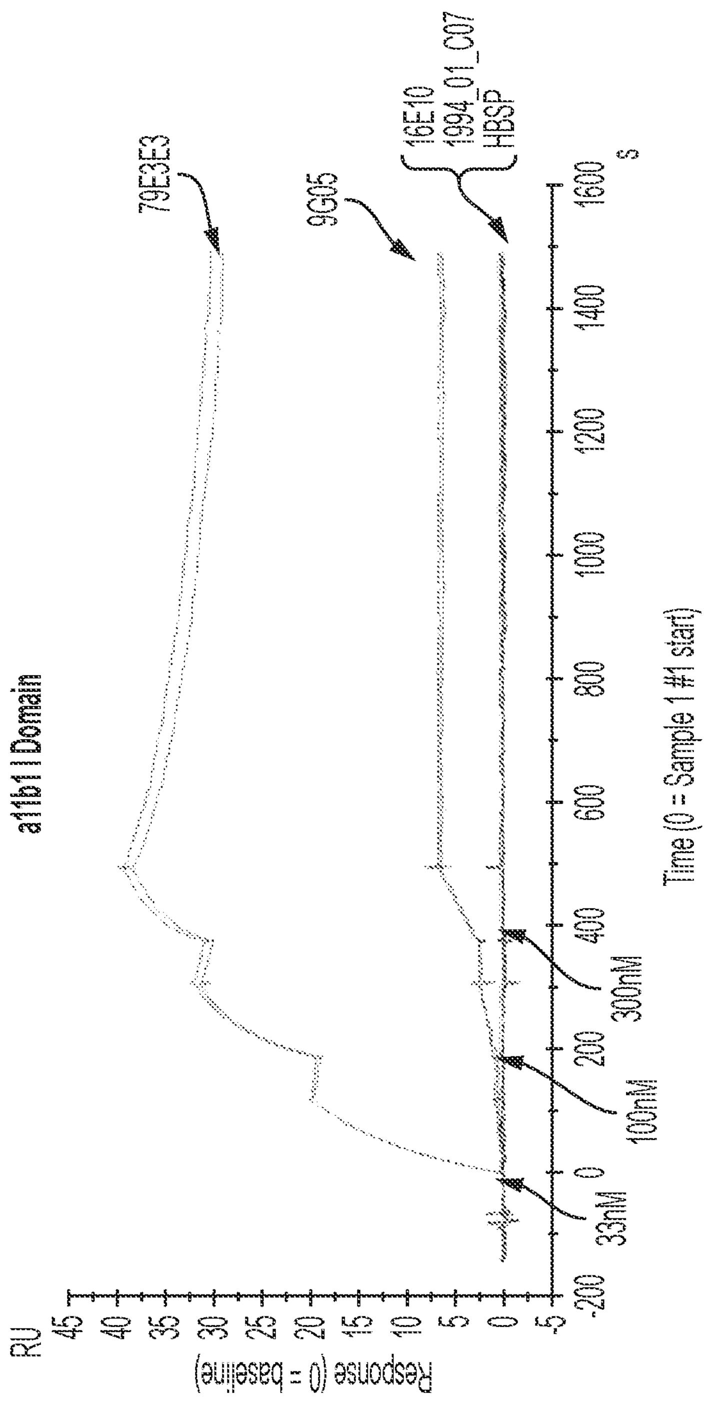

As shown in FIG. 9, when antibodies 16E10, 79E3E3, 9G05 and 1994_01_C07 were tested for their affinity to human α11β1 via surface plasmon resonance (SPR), they exhibited KDs of 48 pM, 10 pM, 2.85 nM and 0.77 nM, respectively. Interestingly, 16E10 and 1994_01_C07 do not bind either the I domain or the headpiece domain of α11β1, which indicates that both might act as allosteric inhibitors by not binding to the ligand binding domain but still inhibiting α11β1 function. 9G05 and 79E3E3 do bind to the I domain (the ligand binding domain) and therefore might directly inhibit the ligand binding site. The binding affinity of antibodies for the α11β1 Headpiece and α11β1 I Domain as measured by SPR is shown in FIG. 10A and FIG. 10B, respectively.

Figure 5:
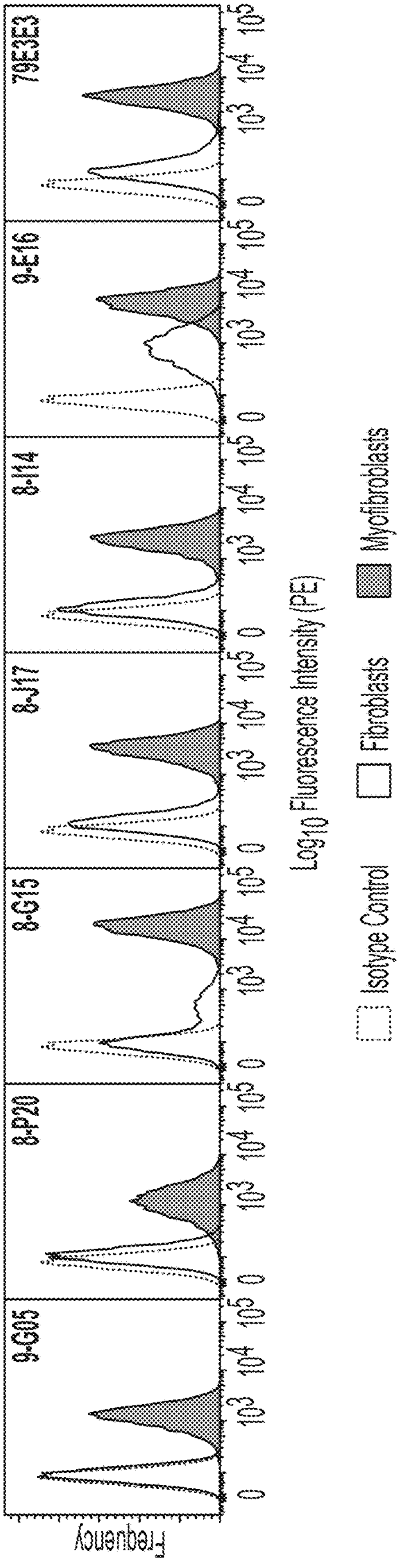
FIG. 5 shows graphs illustrating a FACS analysis of binding of exemplary mouse monoclonal antibodies to human pulmonary fibroblasts (HPFs) and myofibroblasts (MF).
Figure 12:
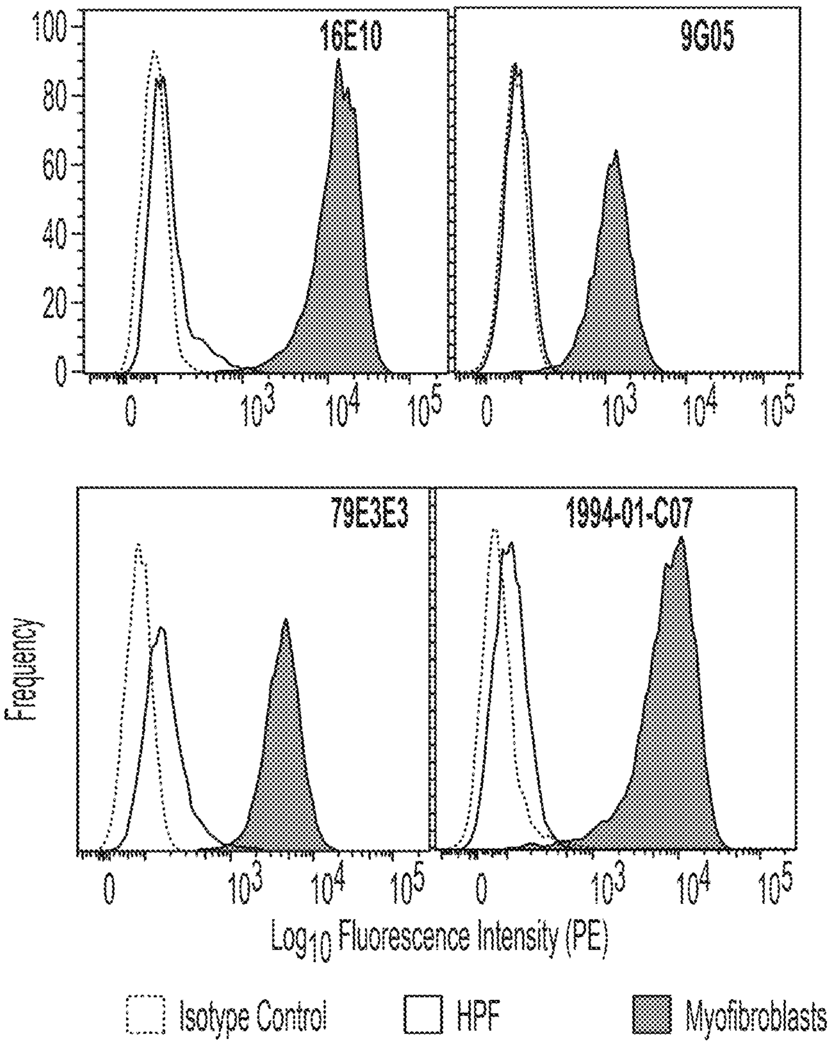
FIG. 12 shows graphs illustrating a FACS analysis of binding of exemplary monoclonal antibodies to human pulmonary fibroblasts (HPFs) and myofibroblasts (MF).
Figure 13:
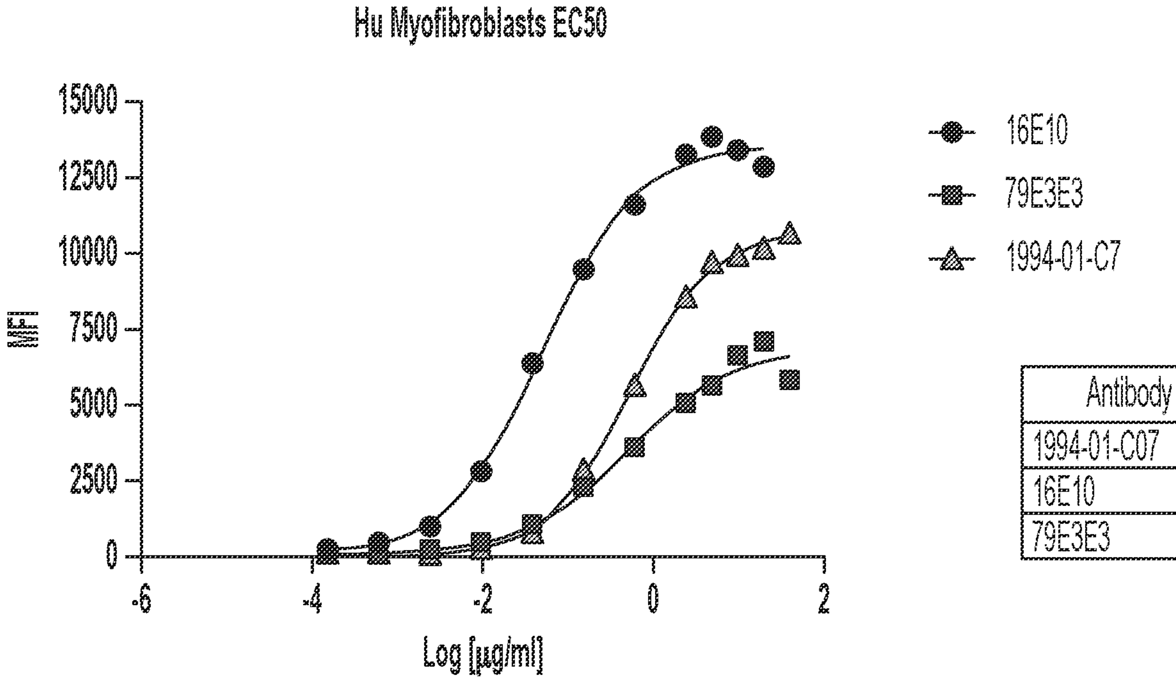
FIG. 13 shows a graph and table illustrating a FACS analysis of binding of exemplary monoclonal antibodies to human myofibroblasts (MF).

Binding to a physiologically relevant primary human cell type was also tested. Human pulmonary fibroblasts (HPF)

and TGFβ treatment were used to induce a fibroblast-to-myofibroblast transition (FMT), giving rise to myofibroblasts (MF). While HPFs do not express α11β1, significant expression of α11β1 is exhibited by MFs. Additionally, HPFs express α11 and α2β1, other collagen binding receptors, which means that HPFs can be to test cross-reactivity of antibodies of interest. Selected mAbs were assessed for binding to HPFs and MFs, and as shown in FIG. 5, FIG. 12, and FIG. 13, it is apparent that the tested antibodies bound MFs strongly while not binding HPFs, with the exception of 9-E16, which showed some HPF binding, indicative of off-target binding.

Example 2. Biological Activity of Novel Monoclonal Antibodies Against α11β1

Myofibroblasts are responsible for secreting fibrotic matrix, so blocking and/or reducing MF accumulation is an important step for treating and/or preventing fibrosis. This can be achieved by using anti-α11β1 antibodies to inhibit the fibroblast-to-myofibroblast transition. Typical functional inhibitors of a receptor block ligand binding, and while preventing the binding of α11β1 to type I collagen is a desired feature of anti-α11β1 antibodies, it may not be necessary for therapeutic efficacy. Unlike many other receptors, integrins are able to perform both "outside-in" (canonical, ligand-mediated) signaling and also "inside-out" signaling. Therefore, it might be possible for an antibody to bind α11β1 in a way that affects the structure of α11β1 in a way that prevents inside-out signaling and FMT, but does not affect the ability of α11β1 to bind type I collagen. For this reason, both mAbs that block ligand binding and those that do not were included these studies.

Figure 6A:
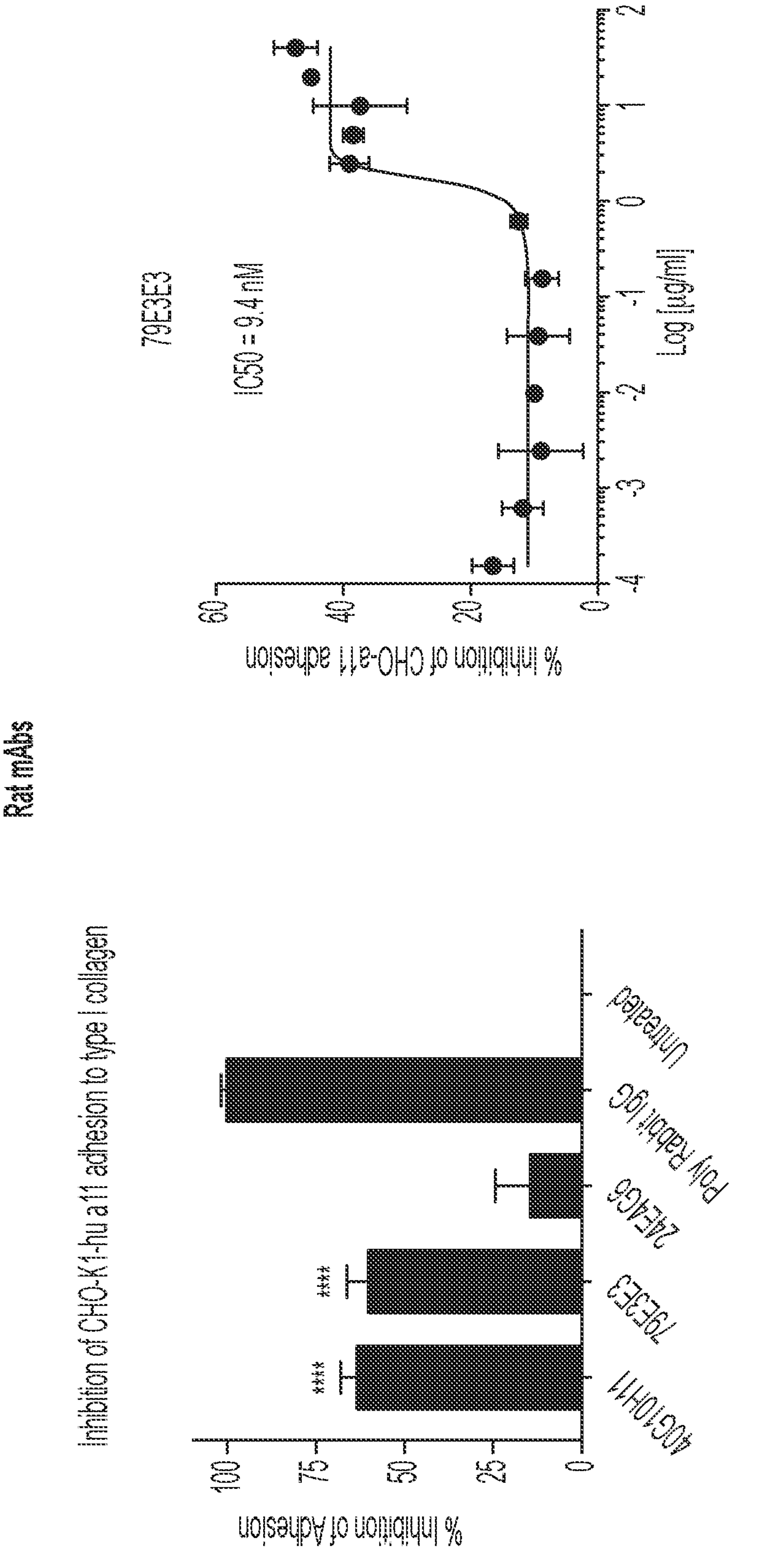
FIG. 6A shows graphs illustrating the ability of exemplary rat monoclonal antibodies to inhibit adhesion of CHO-K1 cells expressing human α11 to rat tail type I collagen.
Figure 6B:
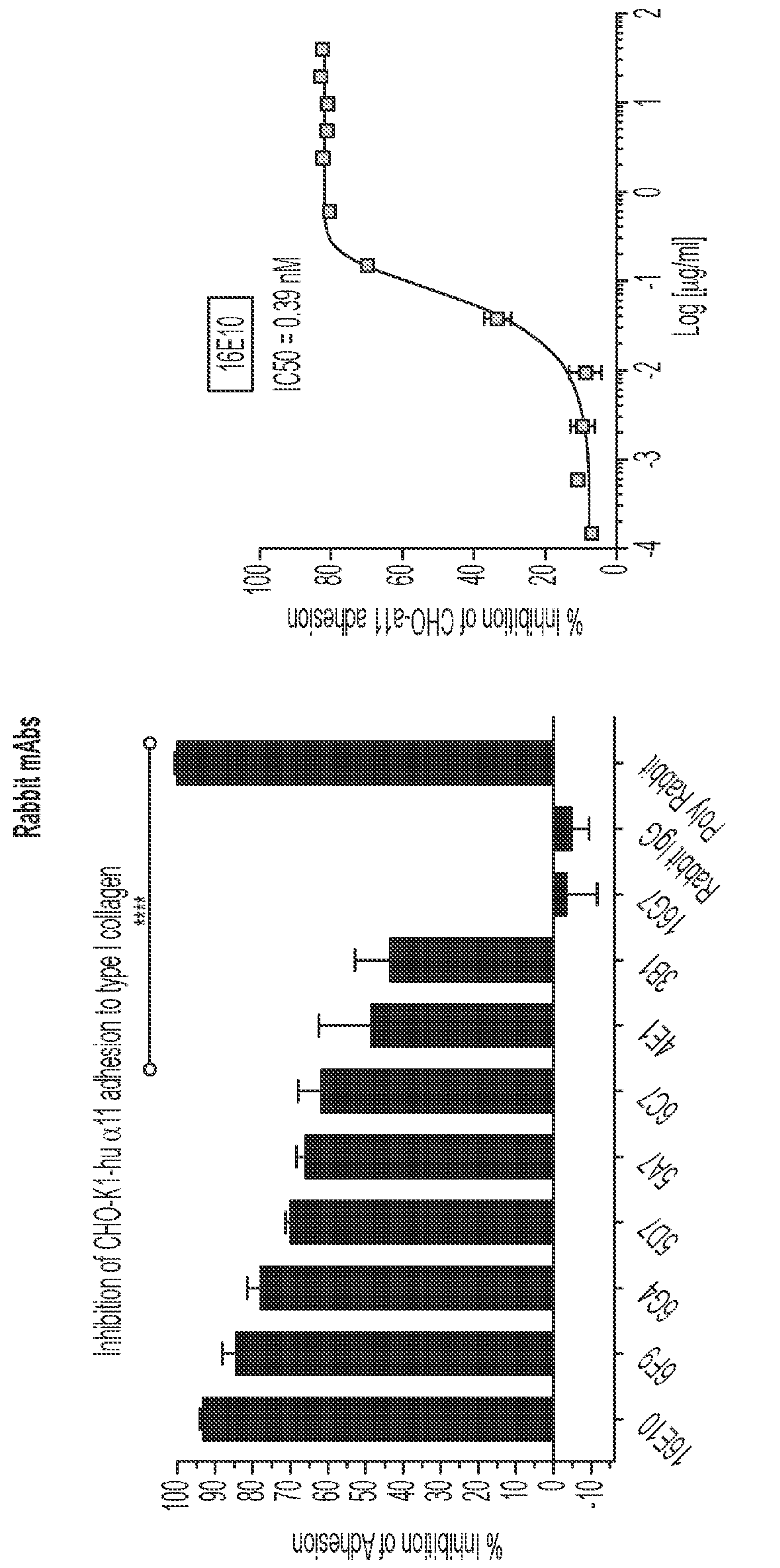
FIG. 6B shows graphs illustrating the ability of exemplary rabbit monoclonal antibodies to inhibit adhesion of CHO-K1 cells expressing human α11 to rat tail type I collagen.
Figure 6C:
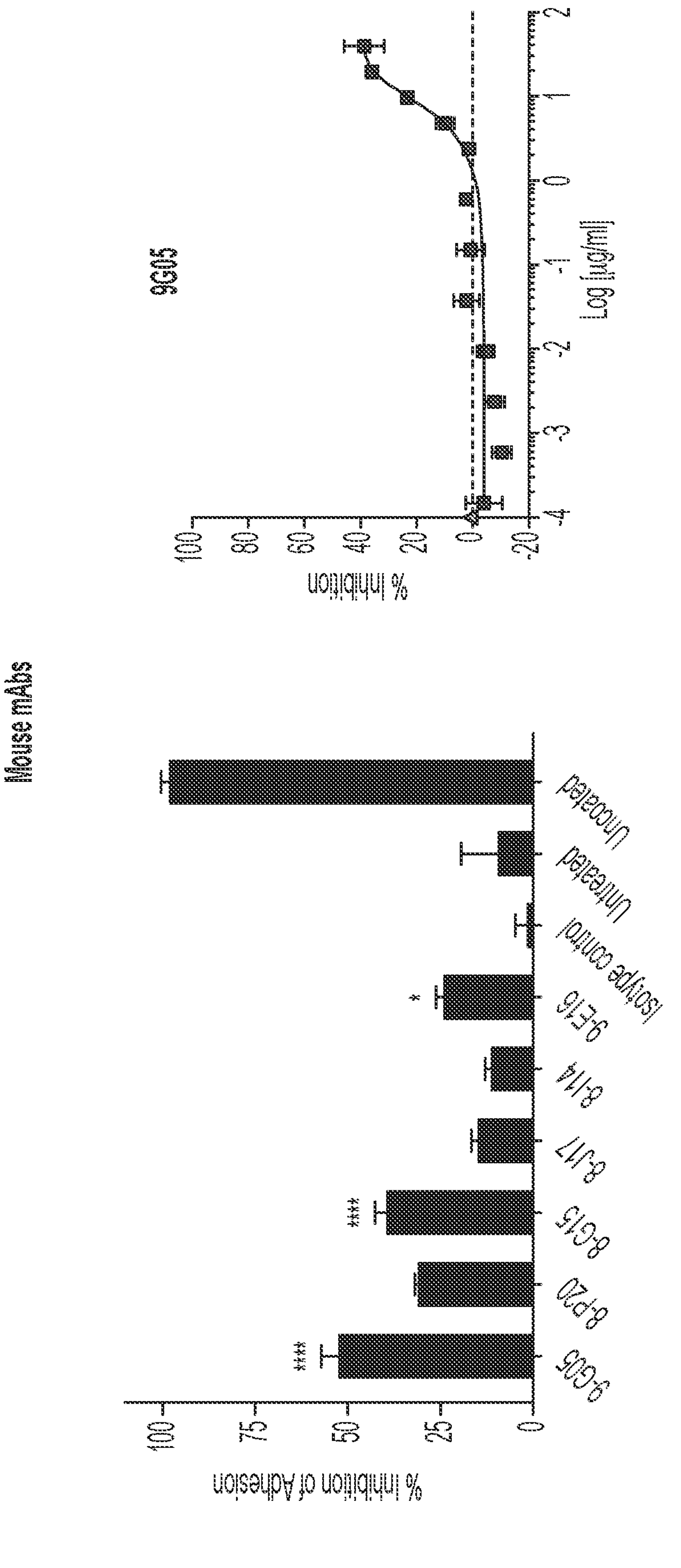
FIG. 6C shows graphs illustrating the ability of exemplary mouse monoclonal antibodies to inhibit adhesion of CHO-K1 cells expressing human α11 to rat tail type I collagen.
Figure 15A:
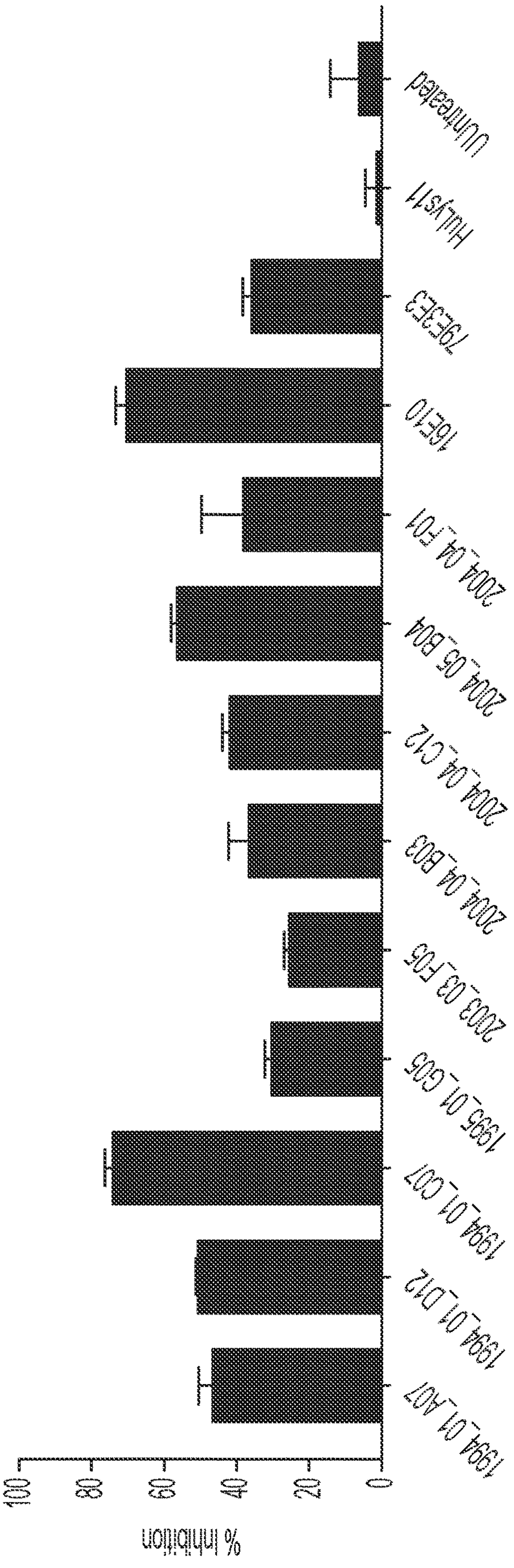
FIG. 15A and FIG. 15B show graphs illustrating the ability of exemplary monoclonal antibodies to inhibit adhesion of CHO cells expressing human α11 to rat tail type I collagen.
Figure 15B:
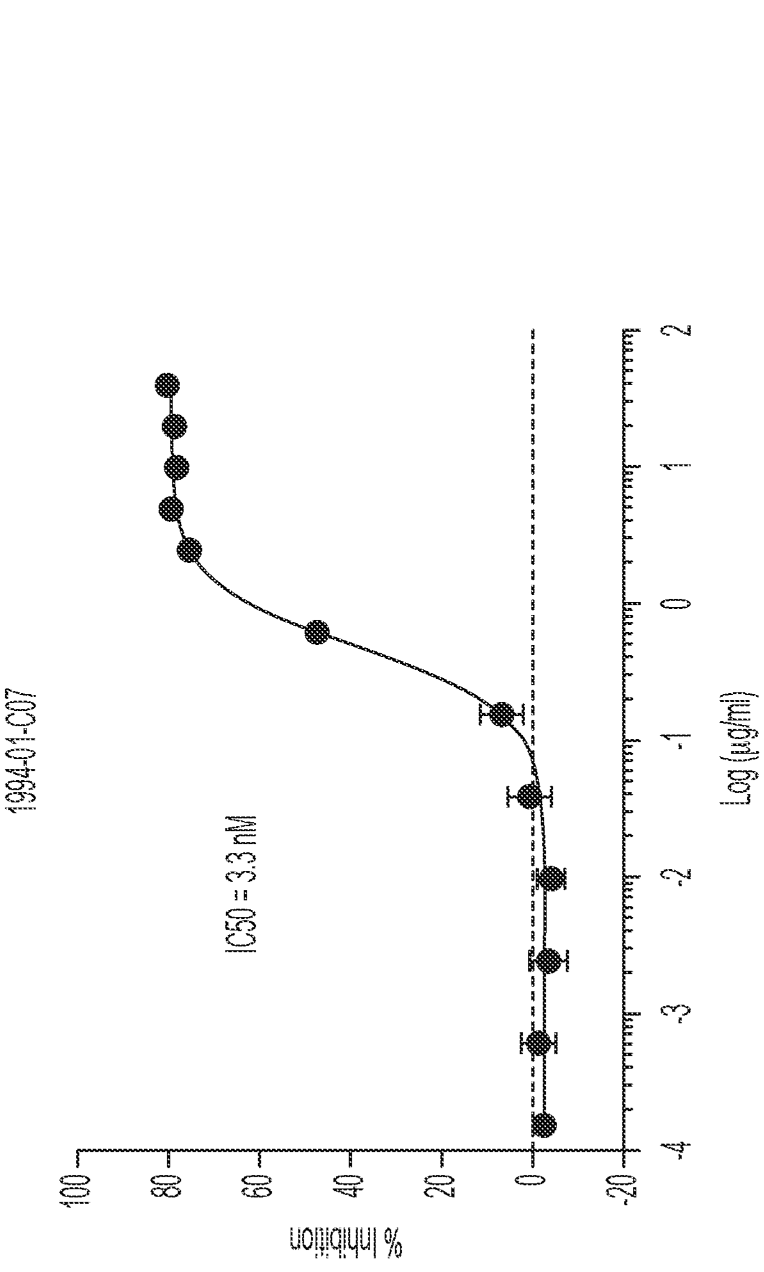

A CHO-K1 hu α11 cell line was used to assess the ability of mAbs to block α11β1-mediated binding to type I collagen. As shown in FIG. 6A, out of three rat mAbs tested, two significantly inhibited adhesion of CHO-K1 hu α11 cells to type I collagen-coated plates. In the "Untreated" condition, cells were plated on type I collagen but no antibody was added and in the "Uncoated" condition, cells were seeded onto BSA-coated wells containing no type I collagen. Statistics were performed using one-way ANOVA followed by Dunnett's multiple comparisons test. 79E3E3, which is an I-domain binder, was able to block cell adhesion with an IC50 of 9.4 nM. However, 40G10H11 strongly inhibited cell adhesion but was not found to be an I-domain binder, though it does cross-react with other collagen receptors (α1β1, a2β1 and a10β1). 24E4G6 did not bind to the I-domain nor did it inhibit cell adhesion to collagen. When rabbit mAbs were tested, eight of the nine mAbs strongly and significantly inhibited cell adhesion and none of those mAbs were found to be I-domain binders (FIG. 6B). Therefore, it is possible that these mAbs bind on an α11β1 domain that keeps the integrin in a low or intermediate affinity state. FIG. 6C shows the activity of selected mouse mAbs. Three of six mAbs significantly blocked cell adhesion, and two of those mAbs were found to be I-domain binders (9-G05 and 9-E16). 8-G15, however, is a strong blocker of cell adhesion but was not found to bind the I-domain. 8-P20, 8-J17 and 8-I14 did not block cell adhesion to type I collagen. Nine human mAbs were also tested for their ability to inhibit the binding of human CHO-α11 cells to type I collagen. As shown in FIGS. 15A and 15B, all of the human Abs inhibited cell adhesion relative to the control, with 1994-01-C07 having an IC50 of 3.3 nM. As illustrated by these data (and summarized in Table 1), some anti-α11β1 mAbs were found to strongly bind human α11β1 when tested by ELISA and FACS, but not all of those antibodies were able to block ligand interaction. Furthermore, binding to the I-domain (ligand binding domain on α11β1) was found to not be necessary for blocking the interaction of α11β1 with type I collagen.

In addition to the binding abilities described above, it is important for an anti-α11β1 antibody to inhibit the fibroblast-to-myofibroblast transition (FMT). It is now appreciated that myofibroblasts are a heterogeneous cell population, existing in different activation states, with the main function of producing and contracting collagen extracellular matrix (ECM). FMT is a multi-step event that is controlled by a changing mechanical environment in tissues undergoing repair. TGFβ is one of the potent factors that potentiates this process and alpha smooth muscle actin (αSMA) is one of the main markers that becomes overexpressed when fibroblasts are undergoing the transition to becoming myofibroblasts. The presence of αSMA enhances fibroblast contraction and guides myofibroblast activation through an intracellular feedback loop. Because αSMA is the main molecular marker of myofibroblasts, the ability of the novel anti-α11β1 mAbs to inhibit αSMA expression in TGFβ-induced FMT was tested.

Figure 7A:
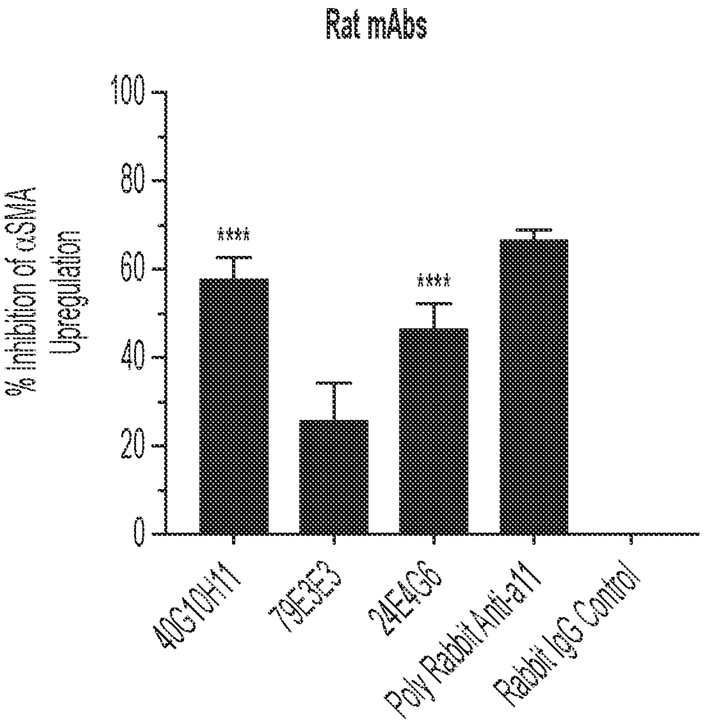
FIG. 7A shows a graph illustrating the ability of exemplary rat monoclonal antibodies to inhibit Fibroblast-to-Myofibroblasts Transition (FMT) as measured by percent inhibition of αSMA upregulation.
Figure 7B:
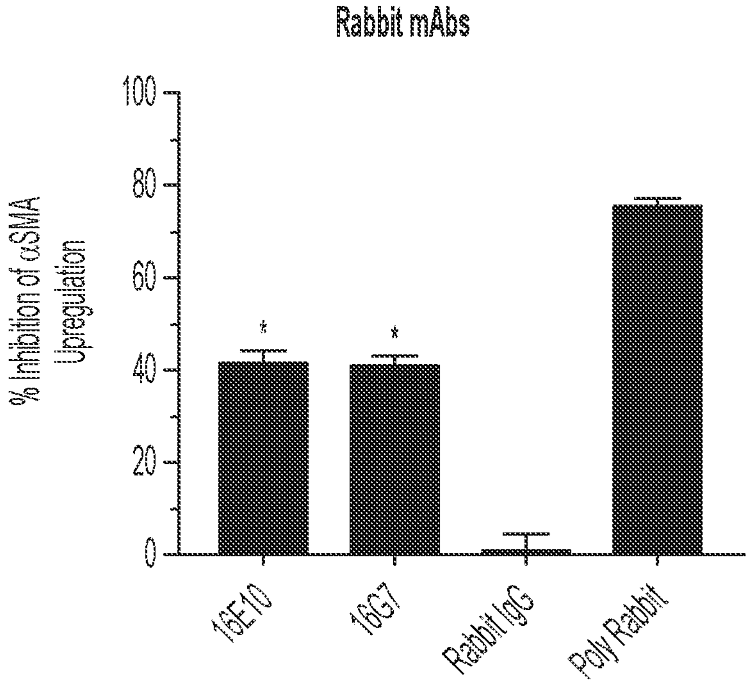
FIG. 7B shows a graph illustrating the ability of exemplary rabbit monoclonal antibodies to inhibit Fibroblast-to-Myofibroblasts Transition (FMT) as measured by percent inhibition of αSMA upregulation.
Figure 7C:
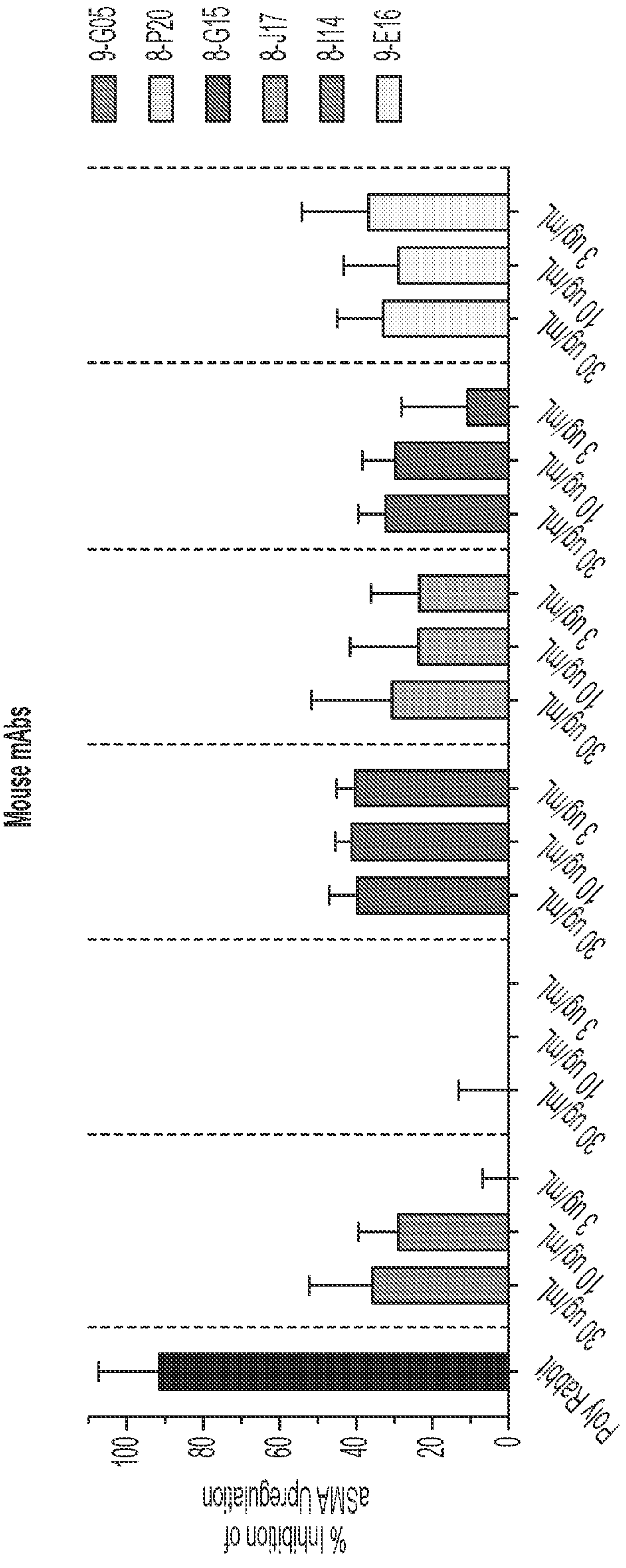
FIG. 7C shows a graph illustrating the ability of exemplary mouse monoclonal antibodies to inhibit Fibroblast-to-Myofibroblasts Transition (FMT) as measured by percent inhibition of αSMA upregulation.

As shown in FIG. 7A, two rat mAbs (40G10H11 and 24E4G6) significantly inhibited αSMA expression compared to control, but neither of the antibodies was found to be an I-domain binder. Statistics were performed using one-way ANOVA followed by Dunnett's multiple comparisons test. Furthermore, only 40G10H11 inhibited cell adhesion to type I collagen. Interestingly, the 79E3E3 mAb was found to be an I-domain binder and strongly inhibited cell adhesion to collagen but failed to decrease αSMA expression (a surrogate for myofibroblast generation). As shown in FIG. 7B, two rabbit mAbs significantly inhibited αSMA expression compared to control, but neither of the antibodies was found to be an I-domain binder. 16E10 was found to inhibit both ligand binding and FMT (% inhibition of αSMA upregulation), but 16G7 was found to inhibit FMT but didn't have an effect on cell adhesion to collagen. Finally, as shown in FIG. 7C, five of the six tested mouse mAb significantly inhibited αSMA expression compared to control. Three of the FMT inhibitors (9-G05, 8-G15, 9-E16) were also found to decrease cell adhesion to collagen and two of those (9-G05, 9-E16) also bound the I domain. Mouse antibodies 8-J17 and 8-I14 only inhibited FMT and had effect on ligand binding.

Example 3. Ability of Selected Antibodies to Inhibit Cell-Mediated Contraction of Collagen Gels Cell-mediated contraction of CD collagen I gels is a process previously shown to be α11β1-mediated, and a more recent study showed that α11β1-mediated downstream signaling was indispensable for gel contraction to occur. Selected exemplary antibodies were tested for the ability to inhibit cell-mediated 3D gel contraction because this ability is directly linked to the functionality of the exemplary antibodies.

Figure 8:
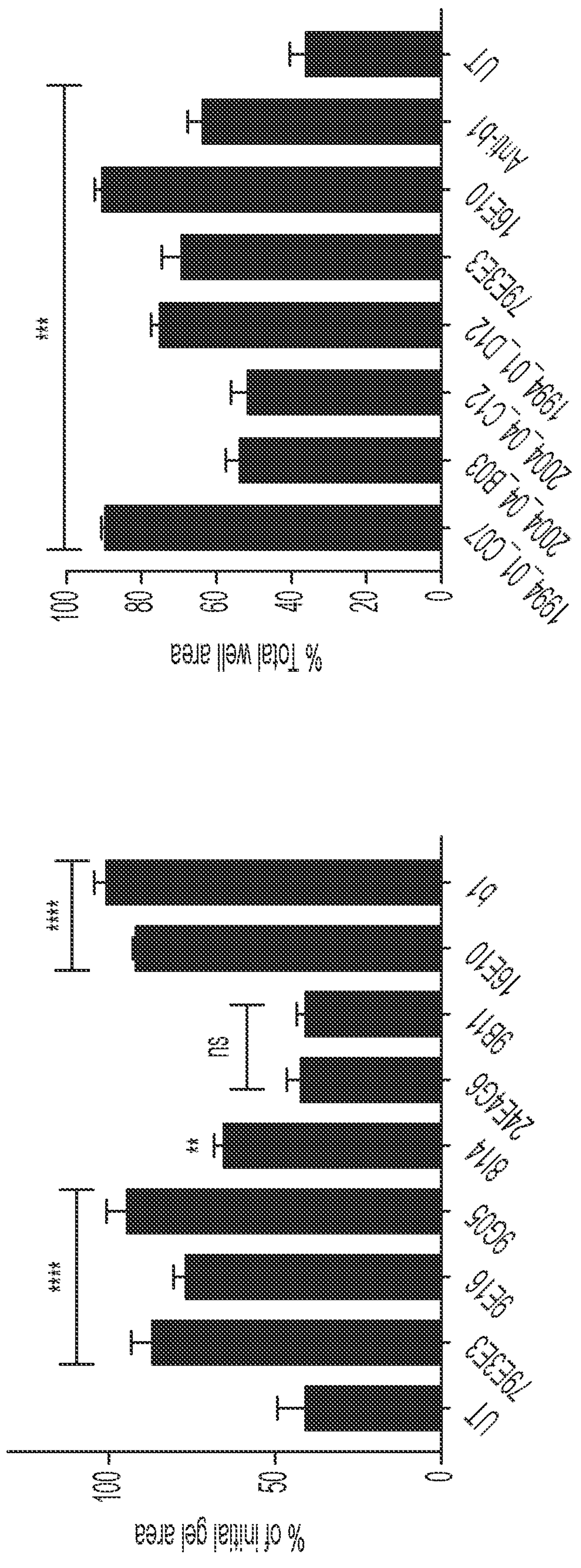
FIG. 8 shows graphs illustrating the ability of exemplary monoclonal antibodies to inhibit CHO-K1 human α11-mediated rat tail type I collagen gel contraction.

As can be seen in FIG. 8, rat 79E3E3, mouse 9E16, 9G05 and 8114, rabbit 16E10, and human 1994_01_C07, 2004_04_B03, 2004_04_C12, and 1994_01_D12 antibodies all inhibited CHO-hu α11-mediated collagen gel contraction. Of note, CHO-hu α11 cells were able to contract collagen gel without the addition of TGFβ, as shown in the UT (untreated) condition. In the untreated condition, cells were embedded in the collagen gel but no antibody was added. Statistics were performed using one-way ANOVA followed by Dunnett's multiple comparisons test; each treatment conditions was compared to untreated condition. Asterisks indicate statistical significance and "ns" indicates that the difference was not statistically significant.

Figure 16:
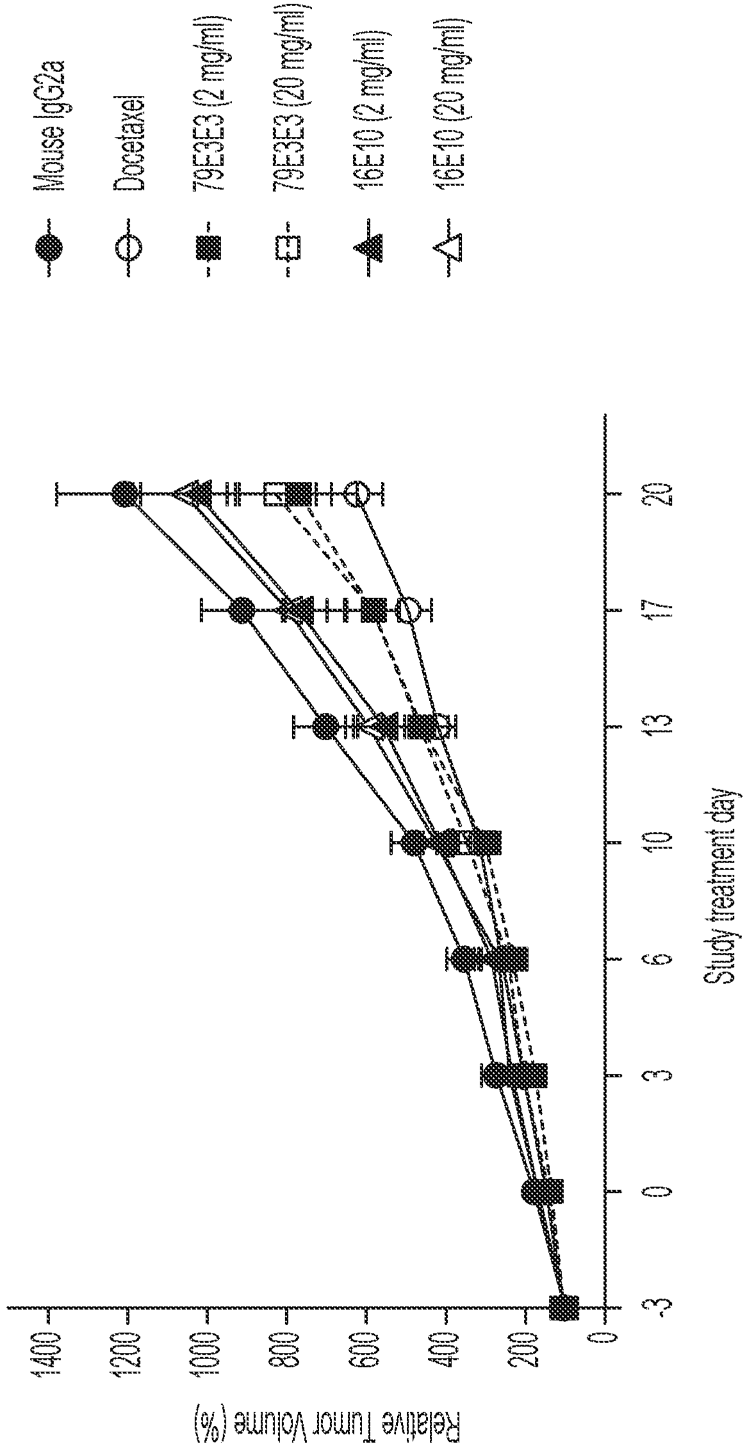
FIG. 16 shows a graph illustrating the effect of exemplary monoclonal antibodies on xenograft growth in SCID mice.

Example 4. Assessing Effect of Selected Antibodies on Tumor Xenograpt Growth Previous studies have shown growth of A549 cell xenografts in α11 knockout SCID mice to be significantly impeded compared to wild-type mice. In this example, studies were performed to determine if inhibition of α11β1 function with mAb results in xenograft growth inhibition. As shown in FIG. 16 and Table 4, blocking α11β1 on mouse CAFs impeded xenograft growth in SCID mice. Specifically, 79E3E3, an effectorless mAb that cross-reacts with mouse α11β1, significantly inhibited tumor growth compared to isotype control, while 16E10, a mAb that does not bind mouse α11β1, showed no significant inhibition of tumor growth. Inhibition of tumor-expressed α11β1 did not affect tumor growth as 16E10 did not show any effect.

TABLE 4

Days to volume doubling after treatment with mAbs

| Treatment | Days to Volume Doubling (ave, 95% CI) |
|---|---|
| Mouse IgG2a | 7.6 (7.3, 8.0) |
| Docetaxel | 11.0 (10.0, 12.0) |
| 79E3E3 2mpk | 8.5 (8.0, 9.0) |
| 79E3E3 20mpk | 8.5 (8.0, 9.0) |

TABLE 4-continued

Days to volume doubling after treatment with mAbs

| Treatment | Days to Volume Doubling (ave, 95% CI) |
|---|---|
| 16E10 2mpk | 7.9 (7.5, 8.3) |
| 16E10 20mpk | 7.9 (7.5, 8.3) |

Example 5. Effect of Anti-α11β1 Antibodies on Human Precision-Cut Liver Slices (PCLS)

Precision-Cut Liver Slices (PCLS) from human liver tissue are physiologically and structurally representative of the tissue architecture and testing therapeutic targets in human PCLS allow for assessment of their effectiveness and relevance to the clinical situation, overcoming the limitations of in vivo rodent models and in vitro 2D cell culture methods. Tissue bioreactor technology maintains viability and functionality of PCLS from human liver tissue for at least 6 days in vitro.

Figure 17A:
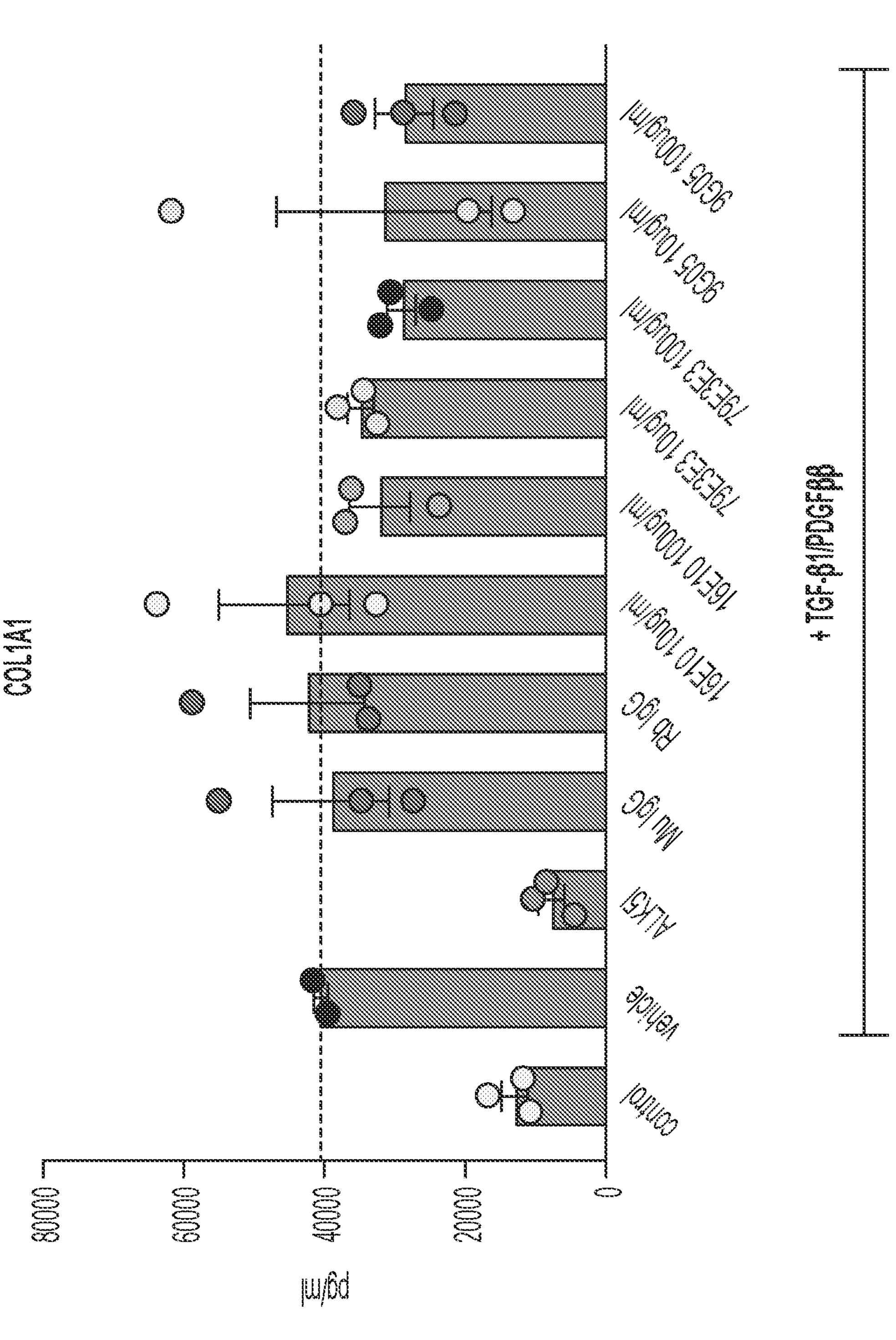
FIG. 17A, FIG. 17B and FIG. 17 C illustrate the effect of exemplary monoclonal antibodies on soluble pro-fibrogenic markers from Precision-Cut Liver Slices (PCLS).
Figure 17B:
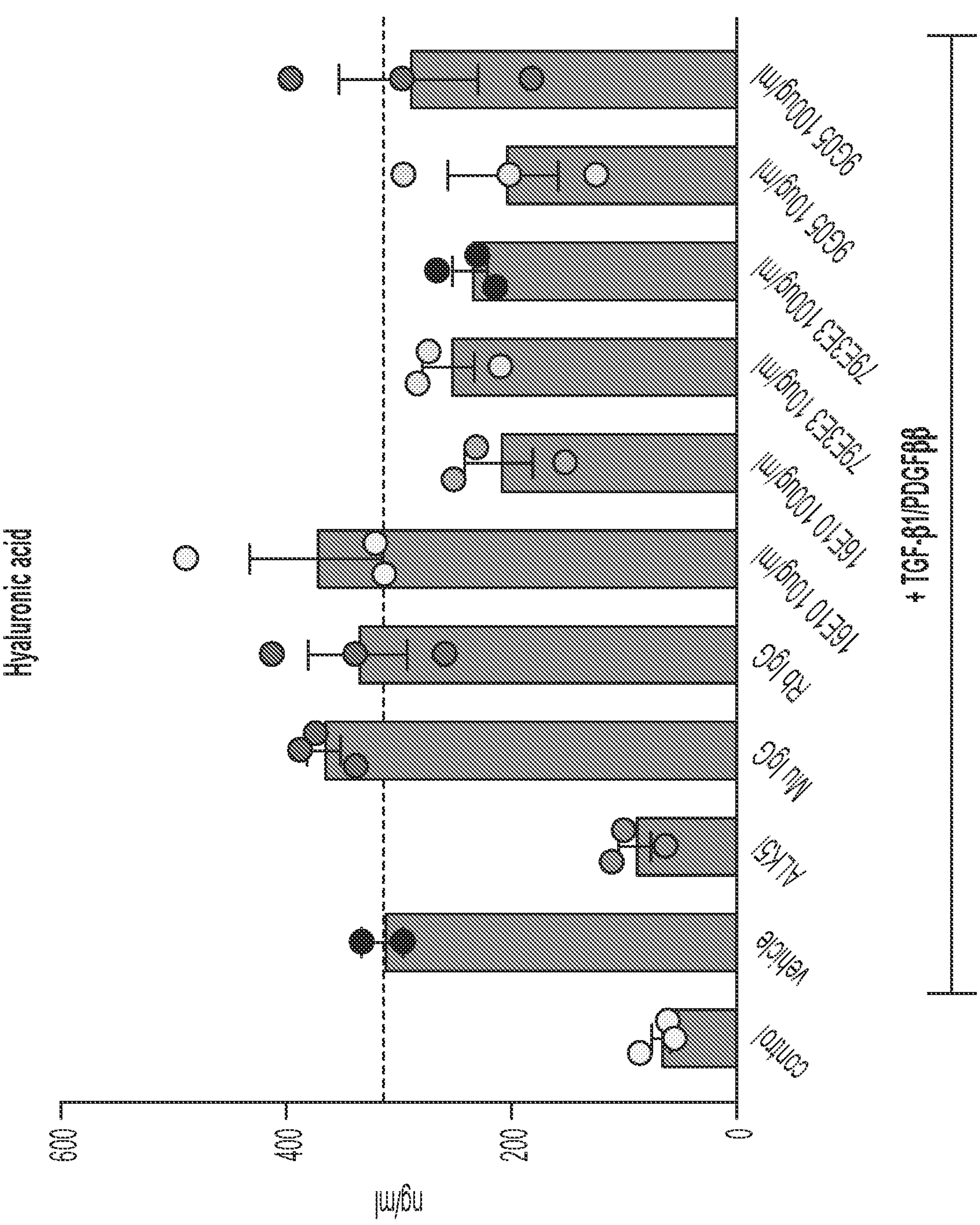
Figure 17C:
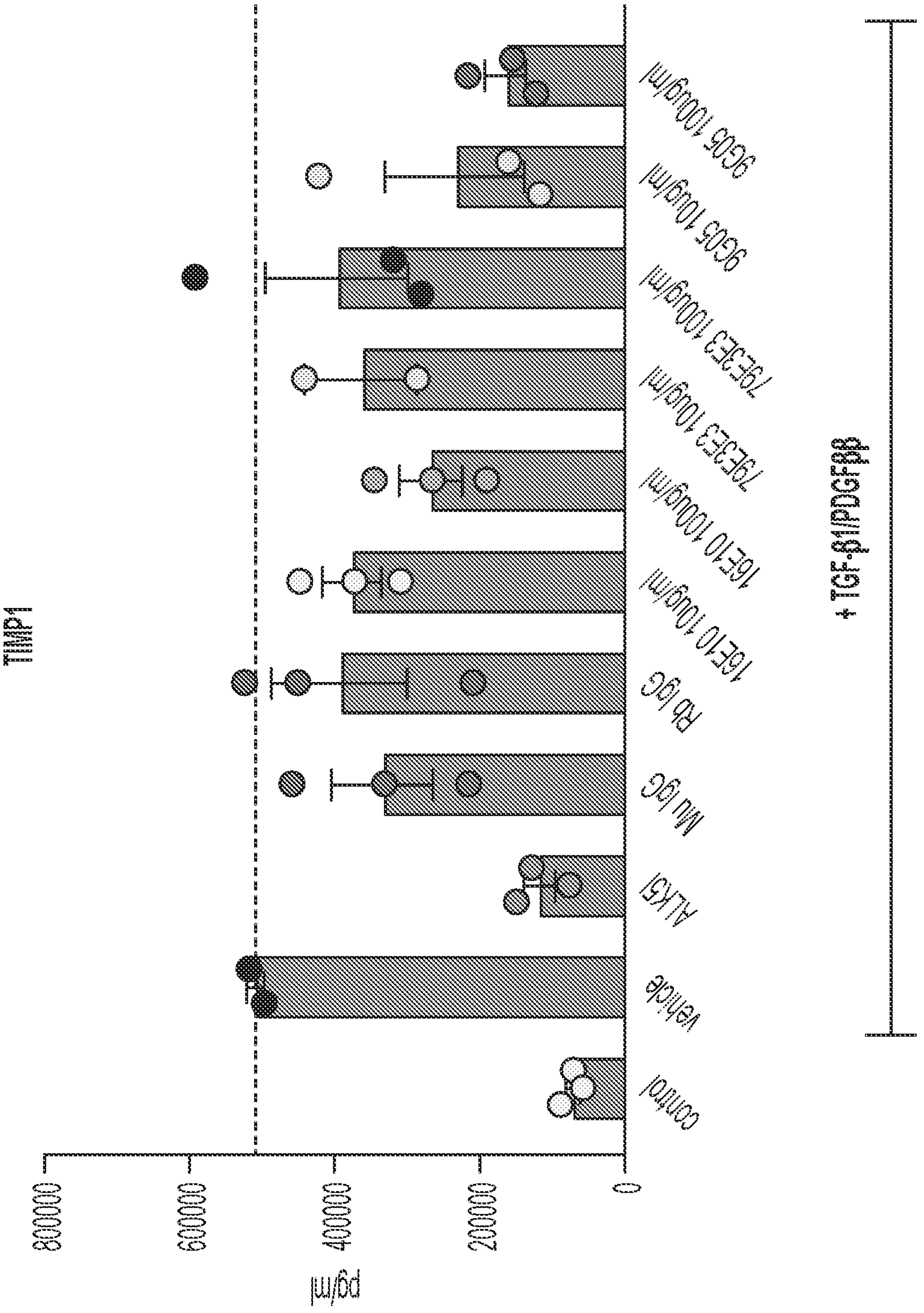

As shown in FIGS. 17A-17C, all anti-α11-β1 antibodies that were tested provided partial inhibition of soluble pro-fibrogenic markers (COL1A1, hyaluronic acid and TIMP1) either in a dose-dependent manner or at the highest dose tested. No toxicity was observed after treatment with any of the antibodies (i.e., no elevation in ALT, AST, or albumin; data not shown).

EXEMPLARY SEQUENCES

DNA Sequences of Anti-α11β1 Monoclonal Antibodies
Rat mAb Sequences

Signal sequence-FR1-CDR1-FR2-CDR2-FR3-CDR3-FR4
79E3E3 Heavy Chain Variable Region
Signal sequence-FR1-CDR1-FR2-CDR2-FR3-CDR3-FR4

(SEQ ID NO: 1)

*ATGGATTGGTTGTGGAACTTGCTATTCCTGATGGTAGTTGCCCAAAGTGCTCAAGCA*CAG

ATCCAGTTGGTACAGTCTGGACCTGAAGTAAAGAAGCCTGGAGAGTCAGTGAAGAT

CTCCTGCAAGGCCTCTGGGTATACCTTCACAGACTATGCAATGAACTGGGTGAAAC

AGGCTCCAGGAAATGGCCTGAAGTGGATGGGCTGGATCAACACCCAAACTGGAAA

GCCAACATATGCGGATGATTTCAAACAACGGTTTGTCTTCTCTTTGGAAACTTCTG

CCAGAACTACATATTTGCAGATCAACAACCTCAATATTGAAGACACAGCTACATATT

TCTGTACGAGATTGGGTACAGGTAATACGAAGGGGTTTGCTTACTGGGGCCAAG

GCACTCTGGTCACTGTCTCTTCA

79E3E3 Light Chain Variable Region (SEQ ID NO: 2)

*ATGGAATCACAGACGCATGTCCTCATTTCCCTTCTGCTCTGTGTATCAGGTACCTGTGGG*G

ACATTTTGATAAACCAGTCTCCAGCCTCTCTGACTGTGTCAGCAGGAGAGAGGGTCA

CTATGAGCTGCAAGTCCAGTCAGAGTCTTCTATACAGTGAAAACAACCAGGACT

ATTTGGCTTGGTACCAGCAGAAACCAGGACAGTTTCCTAAATTGCTTATCTATGGG

GCATCCAACCGGCACACTGGGGTCCCTGATCGCTTCACAGGCAGTGGATCTGGGA

CAGACTTCACTCTGACCATCAGCAGTGTGCAGGCTGAAGACCTGGCTGATTATTATT

GTGAGCAGACCTACAGATATCCATTCACGTTCGGCTCAGGGACGAAGTTGGAAAT

AAAA

-continued

24E4G6 Heavy Chain Variable Region (SEQ ID NO: 3)

*ATGGAGTTGGAATTGAGCTTAATTTTTATTTTTCTCTTTTAAAAGATGTCCAGTGT*GA

AGTACAGCTGGTGGAGTCTGGAGGAAGCTTGGTTCAACCTGGGGGTTCTCTGAAACTCT

CCTGTGTAGCCTCAGGATACACTTTCAGTAACTACTGGATGGACTGGGTTCGGCAGT

CTCCTGGAAAGTCCCTGGAATGGATTGGAGAGATTAACACGGATGGCAGAAGGAC

CAACTATGCACCATCCATAAAGGATCGATTCACAATCTCCAGAGACAATGCCAAG

AGCACCCTGTATCTGCAGATGAGCAATGTGAAATCAGATGACACAGCCATTTATTAC

TGTACCATACTACGGGTATACCCCCACTACTTTGATTACTGGGGCCAAGGAGTCA

TGGTCACAGTCTCCTCA

24E4G6 Light Chain Variable Region (SEQ ID NO: 4)

ATGATGAGTCCTGCCCAGTTCCTGTTTCTGCTAATGCTCTGGATCCAGGAAGCCCGC

GGAGATGTTGTGATGACCCAGACACCACCGTCTTTGTCGGTTGCCATTGGACAATCA

GTCTCCATCTCTTGCAAGTCAAGTCAGAGCCTCGTATATAGTGATGGAGAGACAT

ATTTGCATTGGTTTTTACAGAGTCCTGGCAGGTCTCCGAAGCGCCTAATTTATCACG

TGTCTAATCTGGGCTCTGGAGTCCCTGACAGGTTCAGTGGCACTGGATCACTGACA

GATTTTACACTTAGAATCAGCAGAGTGGAGGCTGAGGATTTGGGAGTTTATTACTGC

GCGCAAACTACACATTTTCCTCCCACGTTTGGAGCTGGGACCAAGCTGGAACTGA

AA

8H8E9 Heavy Chain Variable Region (SEQ ID NO: 5)

*ATGGCTGTCCTGGTGCTGTTGCTCTGCCTGGTGACATTTCCAAGCTGTGCCCTGTCC*CAG

GTGCAGTTGAAGGAGTCAGGACCTGGTCTGGTGCAGCCCTCACAGACCCTGTCCCTC

ACCTGCACTGTCTCTGGGTTCTCATTAACCAGCAATAGTGTTAGCTGGGTTCGCCA

GGCTCCGGGAAAGGGTCTGGAGTGGATGGGAGCAATATGGAGTGGTGGAAGCAC

AGATTATAATTCAGCTCTCAAATCCCGACTGAGCATCAGCAGGGACACCTCCAAG

AGCCAAGTTTTCTTAAAAATGAACAGTCTGCAAACTGAAGACACAGCCATTTACTTC

TGTACCAGATCTCACTGGGAGCCCTTTGATTACTGGGGCCAAGGAGTCATGGTCA

CAGTCTCCTCA

8H8E9 Light Chain Variable Region (SEQ ID NO: 6)

*ATGGAATCACAAACTCAGGCCCTCATATCCCTGCTGCTCTGGGTATATGGTACCTGTGGG*

GACATTGTGATGACCCAGTCTCCATTCTCCCTGGCTGTGTCAGAAGGAGAGATGGTC

ACTATAAACTGCAAGTCCAGTCAGGGTCTTTTATCCAGTGGAAACCAAAAGAAC

TACTTGGCCTGGTACCAGCAGAGACCAGGGCAGTCTCCTAAACTACTGATCTACTA

TGCATCCACTAGGCAATCAGGGGTCCCTGATCGCTTCATAGGCGGTGGATCTGGGA

CAGACTTCACTCTGACCATCAGCGATGTGCAGGCTGAAGACCTGGCAGATTATTACT

GCCTGCAGCATTACAGCTATCCTCCCACGTTCGGTTCTGGGACCAAGCTGGAGAT

CAAA

6E5C11 Heavy Chain Variable Region (SEQ ID NO: 7)

*ATGGCTGTCCTGGTGCTGTTGCTCTGCCTGGTGACATTTCCAAGCTGTGCCCTGTCC*CAG

GTGCAGCTGAGGGAGTCAGGACCTGGTCTGGTGCAGCCCTCACAGACCCTGTCCCTC

ACCTGCACTGTCTCTGGGTTCTCATTGACCAGCAATAGTGTGACCTGGGTTCGCCA

-continued

GCCTCCGGGAAAGGGTCTGGAGTGGATGGGAGCGATATGGAGTGATGGAAGCAC

AGATTATAATTCAACTCTCAAATCCCGACTGAGCATCAGTAGGGACACCTCCAAG

AGCCAAGTTTTCTTAAAAATGAGCAGTCTGCAAACTGAAGACACAGCCATTTACTTC

TGTACCAGATCCCACTGGGAGCCCTTTGATTACTGGGGCCAAGGAGTCATGGTCA

CAGTCTCCTCA

6E5C11 Light Chain Variable Region (SEQ ID NO: 8)

*ATGGAATCACAAACTCAGGCCCTCATATCCCTGCTGCTCTGGGTATATGGTACCTGTGGG*

GACATTGTGATGACCCAGTCTCCACTCTCCCTGGCTGTGTCAGAAGGAGAGACGGTC

ACTATGAACTGCAAGTCCAGTCAGAGTCTTTTTTCCAGTGGAAATCAAAAGAAC

TACTTGGCCTGGTACCAGCAGAAACCAGGGCAGTCTCCTAAACTACTGATCTACTA

TGCATCCACTAGGCAATCAGGGGTCCCTGATCGCTTCATAGGCAGTGGATCTGGGA

CAGACTTCACTCTGACCATCAGCGATGTGCAGACTGAAGACCTGGCAGATTATTACT

GCCTGCAGCATTACAACTATCCTCCCACGTTCGGTTCTGGGACCAAGCTGGAGA

7D8B10 Heavy Chain Variable Region (SEQ ID NO: 9)

*ATGGACTTGCGACTGACTTATGTCTTTATTGTTGCTATTTTAAAAGGTGTCTTGTGT*GAG

GTGAAACTGGAGGAATCTGGGGGAGGTTTGGTGCAACCTGGAATGTCCGTGAAACTCT

CTTGTGCAACCTCTGGATTCATTTTCAGTGACTACTGGATGGAATGGGTCCGCCAG

GCTCCAGGGAAGGGGCTAGAATGGGTAGCCGAAATTAGAAACAAAGCTAATAATT

ATGCAACATACTATGGGAAGTCTATGAAAGGCAGATTCACCATCTCAAGAGATGA

TTCCAAAAGTATAGTCTACCTACAAGTGAACAGCATAAGATCTGAAGATACTGCTAT

TTATTACTGTGCACCGAATTTTGATTACTGGGGCCAAGGAGTCATGGTCACGGTCTC

CTCA

7D8B10 Light Chain Variable Region (SEQ ID NO: 10)

*ATGAGTCCTGTCCAGTCCCTGTTTTTGCTATTGCTTTGGATTCTGGGAACCCATGGT*GA

AGTTGTGCTGACCCAGACTCCACCCACTTTATCGGCTACCATTGGACAATCAGTCTCTA

TCTCTTGCAGGTCAAGTCAGAGTCTCTTACATAGTACTGGAAACACCTATTTAAAT

TGGTTGCTACAGAGGCCAGGCCAACCTCCGCAACTTCTAATTTATTTGGTTTCCAG

ACTGGAATCTGGGGTCCCCAACAGGTTCAGTGCCAGTGGGTCAGGAACTGATTTCA

CACTCAAAATCAGTGGAATAGAGGCTGAGGATTTGGGGGTTTATTACTGCGTGCAA

AGTTCCCATACTCCGTACACGTTTGGGACTGGGACCAAGCTGGAACTGAAA

18E10F10 Heavy Chain Variable Region (SEQ ID NO: 11)

*ATGGACATCAGGCTCAGCTTGGTTTTCCTTGTCCTTTTTATGAAAGGTGTCCAGTGT*GA

GGTGCAGTTGGTGGAGTCTGGGGGAGGCTTAGTGCAGCCTGGAAGGTCCCTGAAACTCT

CCTGTGCAGCCTCACGATTCACTTTTAGTGACTATAACATGGCCTGGGTCCGCCAG

GCTCCAAAGAAGGGTCTGGAGTGGGTCGCAACCATTTATCATGATGATAGTGGTT

CTTACTATCGAGACTCCGTGAAGGGCCGATTCACCATCTCCAGAAATAATGCAAA

AAGCACTCTGTACCTGCAGATGGACAGTCTGAGGTCTGAGGACATGGCCACTTATTA

CTGTGCAAGACATAACAATGGCTTTGATTACTGGGGCCAAGGAGTCATGGTCACA

GTCGCCTCA

-continued

18E10F10 Light Chain Variable Region
(SEQ ID NO: 12)
*ATGAAGTGGCCTGTTAGGCTGTTGGTGCTGTTCTTCTGGATTCCTGCTTCCGGGGGT*GAT

GTTGTGATGACACAAACTCCAGTCTCCCTGCCTGTCCGCCTTGGAGGTCAAGCCTCT

ATCTCTTGCCGGTCAAGTCAGAGCCTGGTACACAGTAATGGAAACACCTACTTG

CATTGGTACCTACAGAAGCCAGGCCAGTCTCCACAGCTCCTCATCAATCGGGTTTC

CAACAGATTTTCTGGGGTGCCAGACAGGTTCAGTGGCAGTGGGTCAGGGACAGATT

TCACCCTCAAGATCAACAGAGTAGAGCCTGAGGACTTGGGAGATTATTACTGCTTA

CAAAGTACACATTTTCCACTCACGTTCGGTTCTGGGACCAAGCTGGAGACCAAA

40G10H11 Heavy Chain Variable Region
(SEQ ID NO: 13)
*ATGGACATCAGGCTCAGCTTGGGTTTCCTTGTCCTTTTCATAAAAGGTGACCAGTGT*GC

GGTGCAACTGGTGGAGTCTGGGGGAGGCTTAGTGCAGCCTGGAAGGTCCCTGAAACTC

TCCTGTGCAGCCTCAAGAATCACTTTCACTGACTATTACATGGCCTGGGTCCGCCA

GGCTCCAACGAAGGGTCTGGAGTGGGTCGCAACCATTAGTTCTGATGGTGGTGAC

ACTTTCTATCGAGACTCCGTGAAGGGCCGATTTACTATCTCCAGAGACAATGCAA

AAAGCACCCTATATTTGCAAATGGTCAGTCTGAGGTCTGAGGACACGGCCACTTATT

ACTGTTCAACAGATCGGGGAGCTCAGTTTGGTTACTGGGGCCAAGGCACTCTGGT

CACTGTCTCTTCA

40G10H11 Light Chain Variable Region
(SEQ ID NO: 14)
*ATGGCTCCAGTCCAGCTCTTAGGGCTGCTGCTGATTTGGCTCCCAGCCATGAGATGT*G

ACATCCAGATGACCCAGTCTCCTTCATTCCTGTCTGCATCTGTGGGAGACAGAGTCTC

TATCAACTGCAAAGCAAGTCAGAATGTTCACGAGAACCTAAACTGGTATCAGCAAA

AGCTTGGAGAAGCTCCCAAACGCCTGATATATAATACAAACAATTTGCAAACAGG

CATCCCATCAAGGTTCAGTGGCAGTGGATCTGGTGCAGATTACACACTCACCATCAG

CAGCCTGCAGCCTGAAGATTTTGCCACATATTTCTGTTTGCAGCATAATGCTTTTC

CGTACACGTTTGGACCTGGGACGAAGCTGGAACTGAAA

Mouse mAb Sequences

9-G05 Heavy Chain Variable Region
(SEQ ID NO: 15)
GAGGTCCAGCTGCAACAGTCTGGACCTGAGCTGGT

GAAGCCTGGGGCTTCAGTGAAGATACCCTGCAAGG

CTTCTGGATACACATTCCCTGACTACAACATGGAC

TGGGTGAAGCAGAGCCATGGAAAGAGCCTTGAGTG

GATTGGATATATTAATCCTGACAATGGTGGTACTA

TCTACAACCAGAAGTTCAAGGGCAAGGCCACATTG

ACTGTAGACAAGTCCTCCAGCACAGCCTACATGGA

GCTCCGCAGCCTGACATCTGAGGACACTGCAGTCT

ATTACTGTGCAAGATTAGACAGCTCAGGCTACGGT

TACTATGCTATGGACTACTGGGGTCAAGGAACCTC

AGTCACCGTCTCCTCA

-continued

9-G05 Light Chain Variable Region
(SEQ ID NO: 16)
GACATTGTGCTGACCCAATCTCCAGCTTCTTTGGC

TGTGTCTCTAGGGCAGAGGGCCACCATCTCCTGCA

GAGCCAGCGAAAGTGTTGATAATTATGGCATTAGT

TTTATGCACTGGTACCAGCAGAAACCAGGACAGCC

ACCCAAACTCCTCATCTATCGTGCATCCAACCTAG

ACTCTGAGATCCCTGCCAGGTTCAGTGGCAGTGGG

TCTAGGACAGACTTCACCCTCACCATTGATCCTGT

GGAGACTGATGATGTTGCAACCTATTACTGTCAGC

AAAGTTATAAGGATCCTCGGACGTTCGGTGGAGGC

ACCAAGCTGGAAATCAAA

8-P20 Heavy Chain Variable Region
(SEQ ID NO: 17)
AAAGTGATGCTGGTGGAGTCTGGGGGAGCCTTAGT

GAAGCCTGGAGGGTCCCTGAAACTCTCCTGTGTAG

-continued

CCTCTGGATTCACTTTCAGTAACTATGCCATGTCT
TGGGTTCGCCAGACTCCAGAGAAGAGGCTGGAGTG
GGTCGCAACCATTAGTAGTGGTGGTTATTACACTT
ACTATCCAGACAGTGTGAAGGGTCGATTCACCATC
TCCAGAGACAATGCCAGGAACACCCTGTTCCTGCA
AATGAGCAGTCTGAGGTCTGAGGACACGGCCATGT
TTTACTGTGCAAGAGAGGATGATTACGGAAGATAT
TCCTATACTATGGACTACTGGGGTCAAGGAACCTC
AGTCACCGTCTCCTCA

8-P20 Light Chain Variable Region
(SEQ ID NO: 18)
GATGTTGTGATGACCCAAACTCCACTCTCCCTGCC
TGTCAGTCTTGGAGATCAAGTCTCCATCTCTTGCA
GATGTAGTCAGAGCCTTGTACACAGTAATGGAAAC
ACCTATTTACATTGGTACCTGCAGAAGCCAGGCCA
GTCTCCACAGCTCCTGATCTACAAAATTTCCAACC
GATTTTCTGGGGTCCCAGACAGGTTCAGTGGCAGT
GGATCAGGGACAGATTTCACACTCAAGATCAGCAG
AGTGGAGGCTGAGGATCTGGGAGTTTATTTCTGCT
CTCAAAGTACACATGTTCCGTACACGTTCGGAGGG
GGGACCGAGCTGGAAATAAAA 8-G15 Heavy Chain Variable Region
(SEQ ID NO: 19)
GAGGTCCAGCTGCAGCAGTCTGGACCTGAGCTGGT
AAAGCCTGGGGCTTCAGTGAGGATATCCTGCAAGG
CTTCTGGATACACATTCACTGACTACTACATACAC
TGGGTGAAGCAGAAGCCTGGGCAGGGCCTTGAATG
CATTGGAGAGATTTATCCTGGAACTGATAATACTT
ACTACAGTAAAAAATTCAGGGGCAAGGCCACACTG
ACTGCAGACAAATCCTCCGACACAGCCTACATGCA
GCTCAGCAGCCTGACATCTGAGGACTCTGCAGTCT
ATTTCTGTGCAAGAGGAGACTACTATAGGGGGTAC
TTCGATGTCTGGGGCGCAGGGACCACGGTCACCGT
CTCCTCA 8-G15 Light Chain Variable Region
(SEQ ID NO: 20)
GATGTTGTGATGACTCAGACCTCACTCACTTTGTC
GGTTACCATTGGACAACCAGCCTCCATCTCTTGCA
AGTCAAGTCAGAGCCTCTTACATAGTAATGGAAAG
ACATATTTGAATTGGTTATTACAGAGGCCAGGCCA
GTCTCCAAAGTTCCTAATCTATCTGGTGTCTAAAC
TGGAATCTGGAGTCCCTGACAGGTTCAGTGGCAGT
GGATCAGGGACAGATTTCACACTGAAAATCAGCAG
AGTGGAGGCTGAGGATTTGGGGGTTTATTACTGCT -continued

TGCAATCTACACATTTTCCTTGGACGTTCGGTGGA
GGCACCAAGCTGGAAATCAAA

8-I14 Heavy Chain Variable Region
(SEQ ID NO: 21)
GAGGTCCAGCTGCAGCAGTCTGGACCTGAGCTGGT
AAAGCCTGGGGCTTCAGTGAAGAAATCCTGCAAGG
CTTCTGGATACACATTCACTGACTACTACATGCAC
TGGGTGAAGCAGAAGCCTGGGCAGGGCCTTGAGTG
GATTGGAAAGATTTATCCTGGAAGTGGTAATACTC
ACTACAATGAGAAGTTCAAGGGCAAGGCCACACTG
ACTGCAGACAAATCCTCCAGCACAGCCTACATGCA
GCTCAGCAGCCTGACATCTGAGGACTCTGCAGTCT
ATTTCTGTGCAACCAATTACTACGGCTACAGGGCA
ATGAACTATTGGGGTCAAGGATCCTCAGTCACCGT
CTCCTCA 8-I14 Light Chain Variable Region
(SEQ ID NO: 22)
GACATCCATTTGACCCAGTCTCCATCCTCCTTATC
TGCCTCTCTGGGAGAAAGAATCAGTCTCACTTGCC
GGGCAAGTCAGGACATTTATATTAGCTTAAACTGG
TTTCAGCAGAAACCAGATGGAACTATTAAACTCCT
GATCTACGGCACATCCAGTTTAGATTCTGGTGTCC
CCAAAAGGTTCAGTGGCAGTAGGTCTGGGTCAGAT
TATTCTCTCACCATCAGCAGCCTTGAGTCTGAAGA
TTTTGCAGACTATTACTGTCTACAATATGCTAGTT
CTCCGTACACGTTCGGAGGGGGGACCAAGCTGGAA
ATAAAA 9-E16 Heavy Chain Variable Region
(SEQ ID NO: 23)
GAGGTCCAGCTGCAGCAGTCTGGACCTGAGCTGGT
AAAGCCTGGGGCTTCAGTGAAGATATCCTGCAAGG
CTTCTGGATACACATTCACTGACTACTACATGCAC
TGGGTGAAGCAGAAGCCTGGGCAGGGCCTTGAGTG
GATTGGAGAGATTTATCCTGGAAGTGGTAATCCTT
ACTACAATGAGAAGTTCAAGGGCAAGGCCACACTG
ACTGCAGACAAATCATCCAGCTCAGCCTACATGCA
GCTCAGCAGCCTGACATCTGAGGACTCTGCAGTCT
ATTTCTGTGCAAGAACCTCCTACGGTAGAGTAGGG
ACAGGGTTTGCTTACTGGGGCCAAGGGACTCTGGT
CACTGTCTCTGCA 9-E16 Light Chain Variable Region
(SEQ ID NO: 24)
AATTTTGTGATGACCCAAACTCCACTCTCCCTGCC
TGTCAGTCTTGGAGATCAAGCCTCCATCTCTTGCA -continued

GATCTAGTCAGAGCCTTCTACACAGTAACGGAAAC

ACCTATTTACATTGGTACCTGCAGAAGCCAGGCCA

GTCTCCAAAGCTCCTGATCTACAAAGTTTCCAACC

GATTTTCTGGGGTCCCAGACAGGTTCAGTGGCAGT

GGATCAGGGACAGATTTCACACTCAAGATCAACAG

AGTGGAGACTGAGGATCTGGGAATTTATTTCTGCT

CTCAAAGTTCACATGTTCCCACGTTCGGTGCTGGG

ACCAAGCTGGAGCTGAAA

8-J17 Heavy Chain Variable Region (SEQ ID NO: 25)

CAGGTCCAGCTGCAGCAGTCTGGGGCTGAACTGGC

AAAACCTGGGGCCTCAGTGAAGATGTCCTGCAAGG

CTTCTGGCTACACCTTTACTAACTACTGGATGCAC

TGGGTAAAACAGAGGCCTGGACAGGGTCTGGAATG

GATTGGATACATTAATCCTAACAATGGTTATACTG

AGTACAATCAGCGATTCAAGGACAAGGCCACATTG

ACTGCAGACAGATCCTCCACCACAGCCTACATGCA

ACTAAGCAGCCTGACATCTGAGGACTCTGCAGTCT

ATTACTGTGCAAGATCCGATATCATTACGACAGAC

TACTGGGGCCAAGGCACCACTCTCACAGTCTCCTC

A

8-J17 Light Chain Variable Region (SEQ ID NO: 26)

GATGTTGTGATGACCCAAACTCCACTCTCCCTGCC

TGTCAGTCTTGGAGATCAAGCCTCCATCTCTTGCA

GATCTAGTCAGAGCCTTGTATATAGTAATGGAAAT

ACCTATTTACATTGGTACCTGCAGAAGCCAGGCCA

GTCTCCAAAGCTCCTGATCTACAAAGTTTCCAACC

GATTTTCTGGGGTCCCAGACAGGTTCAGTGGCAGT

GGATCAGGGACAGATTTCACACTCAAGATAAGCAG

AGTGGAGGCTGAGGATCTGGGAGTTTATTTCTGCT

CTCAAAGTACACATGTTCCGTGGACGTTCGGTGGA

GGCACCAAGCTGGAAATCAAA

6-O12 Heavy Chain Variable Region (SEQ ID NO: 27)

GAAGTGAAGCTTGAGGAGTCTGGAGGAGGCTTGGT

GCAACCTGGAGGATCCATGAAACTCTCTTGTGCTG

CCTCTGGATTCACTTTTAGTGACGCCTGGATGGAC

TGGGTCCGCCAGTCTCCAGAGGCGGGGCTTGAGTG

GGTTGCTGAAATTAGAAACAAAGCTCATAATCCTG

CAACATACTATGCTGAGTCTGTGAAAGGGAGATTC

ACCATCTCAAGAGATGATTCCAAAAGTAGTGTCTA

CCTGCAAATGAACAGCTTAAGAGCTGAAGACACTG

GCATTTATTACTGTACCTTAGTAGCCCCTGATGCT

-continued

ATGGACTACTGGGGTCAAGGAACCTCAGTCACCGT

CTCCTCA

6-O12 Light Chain Variable Region (SEQ ID NO: 28)

GACATTGTGATGTCACTGTCTCCATCCTCCCTAGC

TGTGTCAGTTGGAGAGAAGGTTACTATGAGCTGCA

AGTCCAGTCAGAGCCTTTTATATAGTCGCAATCAA

AAGAACTACTTGGCCTGGTACCAGCAGAAACCAGG

GCAGTCTCCTAAACTGCTGATTTACTGGGCATCCA

CTAGGGCATCTGGAGTCCCTGATCGCTTCACAGGC

AGTGGATCTGGGACAGATTTCACTCTCACCATCAG

CAGTGTGAAGGCTGAAGACCTGGCAGTTTATTACT

GTCAGCAATATTATAGCTATCCGTACACGTTCGGA

GGGGGGACCAAGCTGGAAATAAAA

10-L15 Heavy Chain Variable Region (SEQ ID NO: 29)

CAGGTCCAACTGCAGCAGTCTGGGCCTGAGCTGGT

GAGGCCTGGGGCTTCAGTGAAGATGTCCTGCAAGG

CTTCAGGCTATACCTTCACCAGCTACTGGATGCAC

TGGGTGAAACAGAGGCCTGGACAAGGCCTTGAGTG

GATTGGCATGATTGATCCTTCCAATAGTGAAACTT

GGTTAAATCAGAAGTTCAAGGACAAGGCCACATTG

AATGTAGACAAATCCTCCAACACAGCCTACATGCA

GCTCAGCAGCCTGACATCTGAGGACTCTGCAGTCT

ATTACTGTGCAAGATATGATGGTTACTACGACTAC

TGGGGCCAAGGCACCACTCTCACAGTCTCCTCA

10-L15 Light Chain Variable Region (SEQ ID NO: 30)

AACATTGTGCTGACCCAATCTCCAGCTTCTTTGGC

TGTGTCTCTAGGGCAGAGGGCCACCATATCCTGCA

GAGCCAGTGAAAGTGTTGATAGTTATGGCAATAGT

TTTATGCACTGGTACCAGCAGAAACCAGGACAGCC

ACCCAAACTCCTCATCTATCTTGCATCCAACGTAG

AATCTGGGGTCCCTGCCAGGTTCAGTGGCAGTGGG

TCTAGGACAGACTTCACCCTCACCATTGATCCTGT

GGAGGCTGATGATGCTGCAACCTATTACTGTCAGC

AAAATAATGAGGATCCGTGGACGTTCGGTGGAGGC

ACCAAGCTGGAAATCAAA

7-H14 Heavy Chain Variable Region (SEQ ID NO: 31)

CAGGTCCAACTGCAGCAGCCTGGGGCTGAGCTGGT

GAGGCCTGGGGCTTCAGTGAAGCTGTCCTGCAAGC

CTTCTGGCTACACCTTCACCAGCTACTGGATGAAC

TGGGTGAAGCAGAGGCCTGGACAAGGCCTTGAATG

-continued

GATTGGTATGATTGATCCTTCAGACAGTGAAACTC
ACTACAATCAAATGTTCAAGGACAAGGCCACATTG
ACTGTTGACAAATCCTCCAACACAGCCTACATGCA
GCTCAGCAGCCTGACATCTGAGGACTCTGCGGTCT
ATTACTGTGCGCAGATCTACTATGCTTACGACAAG
GCTTACTGGGGCCAAGGGACTCTGGTCACTGTCTC
TGCA

7-H14 Light Chain Variable Region
(SEQ ID NO: 32)

GACATTGTGATGTCACAGTCTCCATCCTCCCTAGC
TGTGTCAGTTGGAGAGAAGGTTACTATGAGCTGCA
AGTCCAGTCAGAGCCTTTTATATAGTAGCCATCAA
AAGAACTACTTGGCCTGGTACCAGCAGAAACCAGG
GCAGTCTCCTAAACTGCTGATTTACTGGGCATCCA
CTAGGGAATCTGGGGTCCCTGATCGCTTCACAGGC
AGTGGATCTGGGACAGATTTCAGTCTCACCATCAG
CAGTGTGAAGGCTGAAGACCTGGCAGTTTATTACT
GTCAGGAATATTATAGCTGGACGTTCGGTGGAGGC
ACCAAGCTGGAAATCAAA

6-B21 Heavy Chain Variable Region
(SEQ ID NO: 33)

GAGGTCCAGCTGCAACAATCTGGACCTGAGCTGGT
GAAGCCTGGGGCTTCAGTGAAGATATCCTGTAAGG
CTTCTGGATACACGTTCACTGACTACTACATGAAC
TGGGTGAAGCAGAGCCATGGAAAGAGCCTTGAGTG
GATTGGAGATATTAATCCTCACAATGGTGGTACTA
GCTTCATCCAGAAGTTCAAGGGCAAGGCCACATTG
ACTGTAGACAAGTCCTCCAGCACAGCCTACATGGA
GCTCCGCAGCCTGACATCTGAGGACTCTGCAGTCT
ATTATTGTGCCCCTCTGGGACGAAAGGAGGGGTTT
GCTTACTGGGGCCAAGGGACTCTGGTCACTGTCTC
TGCA

6-B21 Light Chain Variable Region
(SEQ ID NO: 34)

GACACTGTGCTGACACAGTCTCCTGCTTCCTTAGT
TGTATCTCTGGGGCAGAGGGCCACCATCTCATGCA
GGGCCAGCAAAAGTGTCAGTACATCTGGCTATAGT
TATATGCACTGGTACCAACAGAAACCAGGACAGCC
ACCCAAACTCCTCATCTATCTTGCATCCAACCTAG
AATCTGGGGTCCCTGCCAGGTTCAGTGGCAGTGGG
TCTGGGACAGCCTTCACCCTCAACATCCATCCTGT
GGAGGAGGAGGATGCTGCAACCTATTACTGTCAGC
ACAGTAGGGAGCTTCCGTACACGTTCGGAGGGGGG
ACCAAGCTGGAAATAAAA

-continued

10-F23 Heavy Chain Variable Region
(SEQ ID NO: 35)

CAGGTTACTCTGAAAGAGTCTGGCCCTGGGATATT
GCAGCCCTCCCAGACCCTCAGTCTGACTTGTTCTT
TCTCTGGGTTTTCACTGAGCACTTTTGCTATGGGT
GTAGGCTGGATTCGTCAGCCTTCAGGGAAGGGTCT
GGAGTGGCTGGCACACATTTGGTGGGATGATGATA
AGTACTATAACCCAGCCCTGAAGAGCCGGCTCACA
ATCTCCAAGGATACCTCCAAAAACCATGTATTCCT
CAAGATCGCCAATGTGGACACTGCAGATACTGCCA
CATACTACTGTGCTCGAATGCCGCTAACTTTCTAC
TTTGACTACTGGGGCCAAGGCACCACTCTCACAGT
CTCCTCA

10-F23 Light Chain Variable Region
(SEQ ID NO: 36)

GATGTTTTGCTGACCCAAACTCCACTCTCCCTGCC
TGTCAGTCTTGGAGATCAAGCCTCCATCTCTTGCA
GATCTAGTCAGAGCATTGTACATAGTAATGGACAC
ACCTATTTAGAATGGTACCTGCAGAAACCAGGCCA
GTCTCCAAAGCTCCTGATCTACAAAGTTTCCAACC
GATTTTCTGGGGTCCCAGACAGGTTCAGTGGCAGT
GGATCAGGGACAGATTTCACACTCAAGATCAGCAG
AGTGGAGGCTGAGGATCTGGGAGTTTATTACTGCT
TTCAAGGTTCACATGTTCCGTTCACGTTCGGAGGG
GGGACCAAGCTGGAAATAAAA

6-A12 Heavy Chain Variable Region
(SEQ ID NO: 37)

CAGGTTACTCTGAAAGAGTCTGGCCCTGGGATATT
GCAGCCCTCCCAGACCCTCAGTCTGACTTGTTCTT
TCTCTGGGTTTTCACTGAGAACTTTTGCTATGGGT
GTAGGCTGGATTCGTCAGCCTTCAGGGAAGGGTCT
GGAGTGGCTGGCACACATTTGGTGGGATGATGATA
AGTACTATAACCCAGCCCTGAAGAGCCGGCTCACA
ATCTCCAAGGATACCTCCAAAAACCAGGTATTCCT
CAAGATCGCCAATGTGGACACTGCAGATACTGCCA
CATACTACTGTGCTCGAATGCCGCTAACTTTCTAC
TTTGACTACTGGGGCCAAGGCACCACTCTCACAGT
CTCCTCA

6-A12 Light Chain Variable Region
(SEQ ID NO: 38)

GATGTTTTGATGACCCAAACTCCACTCTCCCTGCC
TGTCAGTCTTGGAGATCAAGCCTCCATCTCTTGTA
GATCTAGTCAGAGCATTGTACATAGTAATGGAAAC
ACCTATTTAGAATGGTACCTGCAGAAACCAGGCCA

-continued

GTCTCCAAAGCTCCTGATCTACAAAGTTTCCACCC
GATTTTCTGGGGTCCCAGACAGGTTCAGTGGCAGT
GGATCAGGGACAGATTTCACACTCAAGATCAGCAG
AGTGGAGGCTGAGGATCTGGGAGTTTATTACTGCT
TTCAAGGTTCACATGTTCCGTTCACGTTCGGAGGG
GGGACCAAGCTGGAAATAAAA

6-M8 Heavy Chain Variable Region
(SEQ ID NO: 39)
CAGGTCCAACTGCAGCAGCCTGGGGCTGAACTTGT
GATGCCTGGGGCTTCAGTGAAGCTGTCCTGCAAGG
CTTCTGGCTACACCTTCACCAACTACTGGATGCAC
TGGGTGAAACAGAGGCCTGGACAAGGCCTTGAGTG
GATCGGAGAGATTGATCCTTCTGATAGTTATACTA
ACTACAATCAAAAGTTCAAGGGCAAGGCCACATTG
ACTGTAGACAAATCCTCCAGCACAGCCTACATGCA
GCTCAGCAGCCTGACATCTGAGGACTCTGCGGTCT
ATTACTGTACAAGACAGGGTAGTACCTACGCGTGG
GGTCAAGGAACCTCAGTCACCGTCTCCTCA 6-M8 Light Chain Variable Region
(SEQ ID NO: 40)
GATATTGTGATGACGCAGGCTGCATTCTCCAATCC
AGTCACTCTTGGAACATCAGCTTCCATCTCCTGCA
GGTCTAGTAAGAGTCTCCTACATAGTAATGGCATC
ACTTATTTGTATTGGTATCTGCAGAAGCCAGGCCA
GTCTCCTCAGCTCCTGATTTATCAGATGTCCAACC
TTGCCTCAGGAGTCCCAGACAGGTTCAGTAGCAGT
GGGTCAGGAACTGATTTCACACTGAGAATCAGCAG
AGTGGAGGCTGAGGATGTGGGTGTTTATTACTGTG
CTCAAAATCTAGAACTTCCTCCGACGTTCGGTGGA
GGCACCAAGCTGGAAATCAAA 2-A3 Heavy Chain Variable Region
(SEQ ID NO: 41)
GAGGTCCAGCTGCAACAATCTGGACCTGAGCTGGT
GAAGCCTGGGGCTTCAGTGAAGATGTCCTGTAAGG
CTTCTGGATACACATTCACTGACTACTACATGATG
TGGGTGAAGCAGAGTCATGGAAAGAGCCTTGAGTG
GATTGGAGATATTAATCCTTACAATGGTGGTTCTA
GCTACAACCCGAAGTTCAAGGGCAGGGCCACATTG
ACTGTAGACAAATCCTCCAGCACAGCCTACATGCA
GCTCAACAGCCTGACATCTGAGGACTCTGCAGTCT
ATTACTGTGCAAGAGGGACTTACTGGGGCCAAGGG
ACTCTGGTCACTGTCTCTGCA -continued 2-A3 Light Chain Variable Region
(SEQ ID NO: 42)
GATGTTGTGATGACCCAGACTCCACTCACTTTGTC
GGTTACCATTGGACAACCAGCCTCCATCTCTTGCA
AGTCAAGTCAGAGCCTCTTAGATAGTGCTGGAAAG
ACATATTTGAATTGGTTGTTACAGAGGCCAGGCCA
GTCTCCAAAGCGCCTAATGTATCTGGTGTCTAAAC
TGGACTCTGGAGTCCCTGACAGGTTCACTGGCAGC
GGATCAGGGACAGATTTCACACTGAAAATCAGCAG
AGTGGAGGCTGAGGATTTGGGAGTTTATTATTGCT
GGCAAGGTACACATTTTCCGTACACGTTCGGAGGG
GGGACCAAGCTGGAAATAAAA 6-O17 Heavy Chain Variable Region
(SEQ ID NO: 43)
CAGGTCCAACTGCAGCAGCCTGGGGCTGAGCTTGT
GAAGCCTGGGGCTTCAGTGAAGTTGTCCTGCAAGG
CTTCTGGCTACACCTTCACCAGCTACTGGATGCAC
TGGATAAAGCAGAGACCTGGACAAGGCCTTGAGTG
GATTGGAGAGATTAACCCTAGCAATGGTGGTTCTA
ACTACAATGAGAAGTTCAAGAGCAAGGCCACACTG
ACTGTAGACAAATCCTCCAGCACAGCCTACATGCA
ACTCAGCAGCCTGACATCTGAGGACTCTGCGGTCT
ATCACTGTAAAAGCAGAGGCTACTGGGGCCAAGGC
ACCACTCTCACAGTCTCCTCA 6-O17 Light Chain Variable Region
(SEQ ID NO: 44)
GATGTTGTGATGACCCAGACTCCACTCACTTTGTC
GGTTACCATTGGACAACCAGCCTCCATCTCTTGCA
AGTCAAGTCAGAGCCTCTTAGATAGTTATGGAAAG
ACATATTTGAATTGGTTGTTACAGCGGCCAGGCCA
GTCTCCAAAGCGCCTAATCTATCTGGTGTCTAAAT
TGGACTCTGGAGTCCCTGACAGGTTCACTGGCAGT
GGATCAGGGACAGATTTCACACTGAAAATCAGCAG
AGTGGAGGCTGAGGATTTGGGAATTTATTATTGCT
GGCAAGGTACACATTTTCCTCACACGTTCGGCTCG
GGGACAAAGTTGGAAATAAAA 3-G5 Heavy Chain Variable Region
(SEQ ID NO: 45)
CAGGTTCAGCTGCAGCAGTCTGGAGCTGAGCTGGC
GAGGCCTGGGGCTTCAGTGAAACTGTCCTGCAAGG
CTTCTGGCTACACCTTCACAAGCTATGGTATAAGC
TGGGTGAAACAGAGAACTGGACAGGGCCTTGAGTG
GATTGGAGAGATTTTTCCTAGAAGTAGTAATACTT
ACTATAATGAGAAGTTCAAGGGCAAGGCCACACTG -continued ACTGCAGACAAGTCCTCCAGCACAGTGTACATGGA
GTTCCGCAGCCTGACATCTGAGGACTCTGCGGTCT
ATTTCTGTGCAAGAGAGGGGGGCCTGGCCTGGTTT
GCTTACTGGGGCCAAGGGACTCTGGTCACTGTCTC
TGCA 3-G5 Light Chain Variable Region
(SEQ ID NO: 46)
GATGTTGTGATGACCCAGACTCCACTCACTTTGTC
GGTTACCATTGGACAACCAGCTTCCATCTCTTGCA
AGTCAAGTCAGAGCCTCTTATATACTAATGGAAAC
ACCTATTTGAATTGGTTATTACAGAGGCCAGGCCA
GTCTCCAAAACGCCTAATCTATCTGGTGTCTAAAT
TGGACTCTGGAATCCCTGACAGGTTCAGTGGCAGT
GGATCAGGGACAGATTTCACACTGAGAATCAGCAG
AGTGGAGGCTGAGGATTTGGGAGTTTATTACTGCT
TGCAGAGTACACATTTTCCATTCACGTTCGGCTCG
GGGACAAAGTTGGAAATAAAA 6-A15 Heavy Chain Variable Region
(SEQ ID NO: 47)
GAGGTCCAGCTGCAACAATCTGGACCTGAGCTGGT
GAAGCCTGGGGCTTCAGTGAAGATGTCCTGTAAGG
CTTCTGGATACACAATCACTGACTACTACATGATG
TGGTTGAAGCAGAGTCATGGAAAGAGCCTTGAATG
GATTGGAGATATTAATCCTTACACTGGTGGTACTA
GCTACAACCAGAAGTTCAAGGGCAAGGCCACATTG
ACTGTAGACAAATCCTCCAGCACAGCCTACCTGCA
GCTCCACAGCCTGACATCTGAGGACTCTGCAGTCT
ATTACTGTGCAAGAGGGGCCTACTGGGGCCAAGGC
ACCACTCTCACAGTCTCCTCA 6-A15 Light Chain Variable Region
(SEQ ID NO: 48)
GATGTTGTGATGACCCAGACTCCACTCACTTTGTC
GGTTACCATTGGACAACCAGCCTCCATCTCTTGCA
AGTCAAGTCAGAGCCTCTTAGATAGTGATGGAAAG
ACATATTTGAATTGGTTGTTACAGAGGCCAGGCCA
GTCTCCAAAGCGCCTAATCTATCTGGTGTCTAAAC
TGGACTCTGGAGTCCCTGACAGGTTCACTGGCAGT
GGATCAGGGACAGATTTCACACTGAAAATCAGCAG
AGTGGAGGCTGAGGATTTGGGAGTTTATTATTGCT
GGCAAGGTACACATTTTCCGTACACGTTCGGAGGG
GGGACCAAGCTGGAAATAAAA 10-K10 Heavy Chain Variable Region
(SEQ ID NO: 49)
GAGGTCCAGCTGCAACAATCTGGACCTGAGCTGGT
GAAGCCTGGGGCTTCAGTGAAGATGTCCTGTAAGG -continued CTTCTGGATACACAATCACTGACTACTACATGATG
TGGTTGAAGCAGAGTCATGGAAAGAGCCTTGAATG
GATTGGAGATATTAATCCTTACACTGGTGGTACTA
GCTACAACCAGAAGTTCAAGGGCAAGGCCACATTG
ACTGTAGACAAATCCTCCAGCACAGCCTACATGCA
GCTCAACAGCCTGACATCTGAGGACTCTGCAGTCT
ATTACTGTGCAAGAGGGGCCTACTGGGGCCAAGGC
ACCACTCTCACAGTCTCCTCA 10-K10 Light Chain Variable Region
(SEQ ID NO: 50)
GATGTTGTGATGACCCAGACTCCACTCACTTTGTC
GGTTACCATTGGACAACCAGCCTCCATCTCTTGCA
AGTCAAGTCAGAGCCTCTTAGATAGTGATGGAAAG
ACATATTTGAATTGGTTGTTACAGAGGCCAGGCCA
GTCTCCAAAGCGCCTAATCTATCTGGTGTCTAAAC
TGGACTCTGGAGTCCCTGACAGGTTCACTGGCAGT
GGATCAGGGACAGATTTCACACTGAAAATCAGCAG
AGTGGAGGCTGAGGATTTGGGAGTTTATTATTGCT
GGCAAGGTACACATTTTCCGTACACGTTCGGAGGG
GGGACCAAGCTGGAAATAAAA 6-P20 Heavy Chain Variable Region
(SEQ ID NO: 51)
GAGGTCCAGCTGCAACAATCTGGACCTGAGCTGGT
GAAGCCTGGGGCTTCAGTGAAGATATCCTGTAAGG
CTTCTGGATACACGTTCACTGACTACTACATGAAC
TGGGTGAAGCAGAGCCATGGCAGGAGCCTTGAGTT
GATTGGAGATATTAATCCTAACAATGGTGGTTCTA
ACTTCAACCAGAAGTTCAGGGGCAAGGCCACATTG
ACTGTAGACAAGTCCTCCAGCACAGCCTATATGGA
GCTCCGCAGCCTGACATCTGAGGACTCTGCAATCT
ATTACTGTGCAAGAATGGGTTACTGGGGCCAAGGG
ACTCTGGTCACTGTCTCTGCA 6-P20 Light Chain Variable Region
(SEQ ID NO: 52)
GATGTTGTGATGACCCAGACTCCACTCACTTTGTC
GGTTACCATTGGACAACCAGCCTCCATCTCTTGCA
AGTCAAGTCAGAGCCTCTTACATAGTGATGGAAAG
ACATATTTGAATTGGATGTTCCAGAGGCCAGGCCA
GTCTCCAAAGCGCCTAATCTATCTGGTGTCTAAAC
TGGACTCTGGAGTCCCTTACAGGTTCACTGGCGGT
GGATCAGGGACAGATTTCACACTGCAAATCAGCAG -continued

AGTGGAGACTGAGGATTTGGGAGTTTATTATTGCT

GGCAAGGTACACATTTTCCTCGGACGTTCGGTGGA

GGCACCAAGCTGGAAATCAAA

7-O8 Heavy Chain Variable Region
(SEQ ID NO: 53)
GAGGTCCAGCTGCAGCAGTCTGGACCTGAACTGGT

CAAGCCTGGGGCTTCAGTGAAGATGTCCTGCAAGG

CTTCTGGATACACATTCACTGACTACTACATACAC

TGGGTGAAGCAGAAGCCTGGGCAGGGCCTTGAGTA

CATTGGAGAGATTTATCCTGGAAGTGGTAATACTT

ACTACAATGGGAAGTTCAGGGGCAAGGCCACACTG

ACTGCAGACAAGTCCTCCAGCACAGCCTACATGCA

GCTCAGCAGCCTGACATCTGAGGACTCTGCAGTCT

ATTTCTGTGGTAGTGGCTACTTTGACTACTGGGGC

CAAGGCACCACTCTCACAGTCTCCTCA

7-O8 Light Chain Variable Region
(SEQ ID NO: 54)
GATGTTGTGATGACCCAGACTCCACTCACTTTGTC

TGTTACCATTGGACAGCCAGCTTCCATTTCTTGCA

AGTCAAGTCAGAGCCTCTTATATAGTAATGGAAAA

ACCTATTTGAATTGGTTATTACAGAGTCCAGGCCA

GTCTCCAAAGCTCCTAATCTATCTGGTGTCTAAAC

TGGAATCTGGAGTCCCTGACAGATTCAGTGGCAGT

GGATCAGGGACAGATTTTACACTGAAACTCAGCAG

AGTGGAGGCTGAGGATTTGGGAGTATATTACTGCG

TGCAAGGTACACATTTCCCATTCACGTTCGGCTCG

GGGACAAAGTTGGAAATAAAA

Rabbit mAb Sequences

A11B1_16G7 Heavy Chain
(SEQ ID NO: 55)
ATGGAGACTGGGCTGCGCTGGCTTCTCCTGGTCGCTGTGTTCAAAG

GTGTCCAGTGTCAGGAGCAACTGGTGGAGTCCGGGGGAGACCTGGT

CAAGCCTGGGGCATCCCTGACACTCACCTGCACAGCCTCTGGATTC

TCCTTCAATAAGAATTATTGGATGTGCTGGGTCCGCCAGGCTCCAG

GGAAGGGGCTGGAGTGGATCGGATGCATTTATAATGGTGATGGCAA

CACATACTACGCGAGCTGGGTGAATGGCCGATTCACCATCTCCAAA

ACCTCGTCGACCACGGTGACTCTGCAAATGACCAGTCTGACAGTCG

CGGACACGGCCATCTATTTCTGTGCGAGACTACTTAATATGTGGGG

CCCAGGCACCCTGGTCACCGTCTCCTCAGGGCAACCTAAGGCTCCA

TCAGTCTTCCCACTGGCCCCCTGCTGCGGGGACACACCCAGCTCCA

CGGTGACCCTGGGCTGCCTGGTCAAAGGCTACCTCCCGGAGCCAGT

GACCGTGACCTGGAACTCGGGCACCCTCACCAATGGGGTACGCACC

-continued

TTCCCGTCCGTCCGGCAGTCCTCAGGCCTCTACTCGCTGAGCAGCG

TGGTGAGCGTGACCTCAAGCAGCCAGCCCGTCACCTGCAACGTGGC

CCACCCAGCCACCAACACCAAAGTGGACAAGACCGTTGCGCCCTCG

ACATGCAGCAAGCCCATGTGCCCACCCCCTGAACTCCCGGGGGGAC

CGTCTGTCTTCATCTTCCCCCCAAAACCCAAGGACACCCTCATGAT

CTCACGCACCCCCGAGGTCACATGCGTGGTGGTGGACGTGAGCCAG

GATGACCCCGAGGTGCAGTTCACATGGTACATAAACAACGAGCAGG

TGCGCACCGCCCGGCCGCCGCTACGGGAGCAGCAGTTCAACAGCAC

GATCCGCGTGGTCAGCACCCTCCCCATCGCGCACCAGGACTGGCTG

AGGGGCAAGGAGTTCAAGTGCAAAGTCCACAACAAGGCACTCCCGG

CCCCCATCGAGAAAACCATCTCCAAAGCCAGAGGGCAGCCCCTGGA

GCCGAAGGTCTACACCATGGGCCCTCCCCGGGAGGAGCTGAGCAGC

AGGTCGGTCAGCCTGACCTGCATGATCAACGGCTTCTACCCTTCCG

ACATCTCGGTGGAGTGGGAGAAGAACGGGAAGGCAGAGGACAACTA

CAAGACCACGCCGACCGTGCTGGACAGCGACGGCTCCTACTTCCTC

TACAGCAAGCTCTCAGTGCCCACGAGTGAGTGGCAGCGGGGCGACG

TCTTCACCTGCTCCGTGATGCACGAGGCCTTGCACAACCACTACAC

GCAGAAGTCCATCTCCCGCTCTCCGG GTAAATAG

A11B1_16G7 Light Chain
(SEQ ID NO: 56)
ATGGACACGAGGGCCCCCACTCAGCTGCTGGGGCTCCTACTGCTCT

GGCTCCCAGGTGCCAGATGTGCTGACATTGTGATGACCCAGACTCC

AGCCTCCGTGGAGGCAGCTGTGGGAGGCACAGTCACCATCAAGTGC

CAGGCCAGTGAGAGCATTGGCAATGCATTAGCCTGGTATCAGCAGA

AACCAGGGCAGCCTCCCAAGCTCCTGATCTATACTGCAGCCACTCT

GGCATCTGGGGTCCCATCGCGGTTCAGCGGCAGTGGATCTGGGACA

GAGTTCACTCTCACCATCAGTGGCGTGCAGTGTGACGATGCTGCCA

CTTACTACTGTCAAAGCTATTATTTTACTAGTGTTAGTAGTTATGG

CAATGCTTTCGGCGGAGGGACCGAGGTGGTGGTCAAAGGTGATCCA

GTTGCACCTACTGTCCTCATCTTCCCACCAGCTGCTGATCAGGTGG

CAACTGGAACAGTCACCATCGTGTGTGTGGCGAATAAATACTTTCC

CGATGTCACCGTCACCTGGGAGGTGGATGGCACCACCCAAACAACT

GGCATCGAGAACAGTAAAACACCGCAGAATTCTGCAGATTGTACCT

ACAACCTCAGCAGCACTCTGACACTGACCAGCACACAGTACAACAG

CCACAAAGAGTACACCTGCAAGGTGACCCAGGGCACGACCTCAGTC

GTCCAGAGCTTCAATAGGGGTGACTGTTAG

A11B1_16E10 Heavy Chain
(SEQ ID NO: 57)
ATGGAGACTGGGCTGCGCTGGCTTCTCCTGGTCGCTGTGCTCAAAG

GTGTCCAGTGTCAGTCGTTGGAGGAGTCCGGGGGAGACCTGGTCAA

GCCTGGGGCATCCCTGACACTCACCTGCAGAGTCTCTGGATTCTCC

TTCAGTAGCAGTTATTATATGTGTTGGGTCCGCCAGGCTCCAGGGA

AGGGGCTGGAATGGATCGCATGTATTGGTACTACTCGTGGTAGCAC

-continued

TTACTACGCGACCTGGGCGAAAGGCCGATTCACCATTTCTAAAATC
TCGTCGACCACGGTGACTCTACAAATGACCAGTCTGACAGACGCGG
ACACGGCCACCTATTTCTGTGCGAGAGATGCTACTGGTTATAGGAT
TAACACGATTGGCCTCTATTTTAATTTGTGGGGCCCAGGCACCCTG
GTCACCGTCTCCTCAGGGCAACCTAAGGCTCCATCAGTCTTCCCAC
TGGCCCCCTGCTGCGGGGACACACCCAGCTCCACGGTGACCCTGGG
CTGCCTGGTCAAAGGCTACCTCCCGGAGCCAGTGACCGTGACCTGG
AACTCGGGCACCCTCACCAATGGGGTACGCACCTTCCCGTCCGTCC
GGCAGTCCTCAGGCCTCTACTCGCTGAGCAGCGTGGTGAGCGTGAC
CTCAAGCAGCCAGCCCGTCACCTGCAACGTGGCCCACCCAGCCACC
AACACCAAAGTGGACAAGACCGTTGCGCCCTCGACATGCAGCAAGC
CCATGTGCCCACCCCCTGAACTCCCGGGGGGACCGTCTGTCTTCAT
CTTCCCCCCAAAACCCAAGGACACCCTCATGATCTCACGCACCCCC
GAGGTCACATGCGTGGTGGTGGACGTGAGCCAGGATGACCCCGAGG
TGCAGTTCACATGGTACATAAACAACGAGCAGGTGCGCACCGCCCG
GCCGCCGCTACGGGAGCAGCAGTTCAACAGCACGATCCGCGTGGTC
AGCACCCTCCCCATCGCGCACCAGGACTGGCTGAGGGGCAAGGAGT
TCAAGTGCAAAGTCCACAACAAGGCACTCCCGGCCCCCATCGAGAA
AACCATCTCCAAAGCCAGAGGGCAGCCCCTGGAGCCGAAGGTCTAC
ACCATGGGCCCTCCCCGGGAGGAGCTGAGCAGCAGGTCGGTCAGCC
TGACCTGCATGATCAACGGCTTCTACCCTTCCGACATCTCGGTGGA
GTGGGAGAAGAACGGGAAGGCAGAGGACAACTACAAGACCACGCCG
ACCGTGCTGGACAGCGACGGCTCCTACTTCCTCTACAGCAAGCTCT
CAGTGCCCACGAGTGAGTGGCAGCGGGGCGACGTCTTCACCTGCTC
CGTGATGCACGAGGCCTTGCACAACCACTACACGCAGAAGTCCATC
TCCCGCTCTCCGGGTAAATAG

A11B1_16E10 Light Chain (SEQ ID NO: 58)

ATGGACACGAGGGCCCCCACTCAGCTGCTGGGGCTCCTGCTGCTCT
GGCTCCCAGGTGCCAGATGTGCGTTCGAATTGACCCAGACTCCATC
CTCCGTGGAGGCTGCTGTGGGAGGCACGCCCACCATCAAGTGCCAG
GCCAGTCAGACCATTTACAGTTACTTATCCTGGTATCAGCAGAAAC
CAGGGCAGCCTCCCAAGCTCCTGATCTATGAAGCGTCCAAACTGGC
CTCTGGGGTCCCATCGCGGTTCAGCGGCAGTGGATCTGGGACAGAC
TACACTCTCACCATCAGCGACCTGGAGTGTGCCGATGCTGCCACTT
ACTACTGTCAAAGCTATCATGGTACTGCTAGTACTGAATATAATAC
TTTCGGCGGGGGGACCGAGGTGGTGGTCAGAGGTGATCCAGTTGCA
CCTACTGTCCTCATCTTCCCACCAGCTGCTGATCAGGTGGCAACTG
GAACAGTCACCATCGTGTGTGTGGCGAATAAATACTTTCCCGATGT
CACCGTCACCTGGGAGGTGGATGGCACCACCCAAACAACTGGCATC
GAGAACAGTAAAACACCGCAGAATTCTGCAGATTGTACCTACAACC

-continued

TCAGCAGCACTCTGACACTGACCAGCACACAGTACAACAGCCACAA
AGAGTACACCTGCAAGGTGACCCAGGGCACGACCTCAGTCGTCCAG
AGCTTCAATAGGGGTGACTGTTAG

A11B1_15G10 Heavy Chain (SEQ ID NO: 59)

ATGGAGACTGGGCTGCGCTGGCTTCTCCTGGTCGCTGTGCTCAAAG
GTGTCCAGTGTCAGCAGCAGCTGGTGGAGTCCGGGGGAGGCCTGGT
CAAGCCTGGGGCAGCCCTGACATTCACCTGCACAGCCTCTGGATTC
TCCTTCAGTGGCAATTATTGGATATGCTGGGTCCGCCAGGCTCCAG
GGAAGGGGTTGGAGTGGATCGCGTGCATTGGTACTATTACTAGTAG
GACATACTACGCGAGCTGGGCGAAAGGCCGATTCACCATTTCCAAA
ACCTCGTCGACCACGGTGACTCTGCAAATGACCAGTCTGACAGCCG
CGGACACGGCCACGTATTTCTGTGCGAGAGGTGCGGTTGTTAGTAG
TGGTAATGCTCCCTACTACTTTACCTTGTGGGGCCCAGGCACCCTG
GTCACCGTCTCCTCAGGGCAACCTAAGGCTCCATCAGTCTTCCCAC
TGGCCCCCTGCTGCGGGGACACACCCAGCTCCACGGTGACCCTGGG
CTGCCTGGTCAAAGGCTACCTCCCGGAGCCAGTGACCGTGACCTGG
AACTCGGGCACCCTCACCAATGGGGTACGCACCTTCCCGTCCGTCC
GGCAGTCCTCAGGCCTCTACTCGCTGAGCAGCGTGGTGAGCGTGAC
CTCAAGCAGCCAGCCCGTCACCTGCAACGTGGCCCACCCAGCCACC
AACACCAAAGTGGACAAGACCGTTGCGCCCTCGACATGCAGCAAGC
CCATGTGCCCACCCCCTGAACTCCCGGGGGGACCGTCTGTCTTCAT
CTTCCCCCCAAAACCCAAGGACACCCTCATGATCTCACGCACCCCC
GAGGTCACATGCGTGGTGGTGGACGTGAGCCAGGATGACCCCGAGG
TGCAGTTCACATGGTACATAAACAACGAGCAGGTGCGCACCGCCCG
GCCGCCGCTACGGGAGCAGCAGTTCAACAGCACGATCCGCGTGGTC
AGCACCCTCCCCATCGCGCACCAGGACTGGCTGAGGGGCAAGGAGT
TCAAGTGCAAAGTCCACAACAAGGCACTCCCGGCCCCCATCGAGAA
AACCATCTCCAAAGCCAGAGGGCAGCCCCTGGAGCCGAAGGTCTAC
ACCATGGGCCCTCCCCGGGAGGAGCTGAGCAGCAGGTCGGTCAGCC
TGACCTGCATGATCAACGGCTTCTACCCTTCCGACATCTCGGTGGA
GTGGGAGAAGAACGGGAAGGCAGAGGACAACTACAAGACCACGCCG
ACCGTGCTGGACAGCGACGGCTCCTACTTCCTCTACAGCAAGCTCT
CAGTGCCCACGAGTGAGTGGCAGCGGGGCGACGTCTTCACCTGCTC
CGTGATGCACGAGGCCTTGCACAACCACTACACGCAGAAGTCCATC
TCCCGCTCTCCGGGTAAATAG

A11B1_15G10 Light Chain (SEQ ID NO: 60)

ATGGACACGAGGGCCCCCACTCAGCTGCTGGGGCTCCTGCTGCTCT
GGCTCCCAGGTGCCAGATGTGCATTCGAATTGACGCAGACTCCATC
CTCCGTGGAGGCAGCTGTGGGAGGCACAGTCACCATCAAGTGCCAG
GCCAGTCAGAGCATTAGTAGTTACTTATCCTGGTATCAGCAGAAAC
CAGGGCAGCCTCCCAAGCTCCTGATCTACAGGGCATCCACTCTGGA

-continued

ATCTGGGGTCCCATCGCGGTTTAAAGGCAGTGGATCTGGGACAGAG
TTCACTCTCACCATCAGCGACCTGGAGTGTGCCGATGCTGCCACTT
ACTTCTGTCAAAGCTATTATGGTGTTACTTTTAGTGGTTTTGCTTT
CGGCGGAGGGACCGAGGTGGTGGTCAAAGGTGATCCAGTTGCACCT
ACTGTCCTCATCTTCCCACCAGCTGCTGATCAGGTGGCAACTGGAA
CAGTCACCATCGTGTGTGTGGCGAATAAATACTTTCCCGATGTCAC
CGTCACCTGGGAGGTGGATGGCACCACCCAAACAACTGGCATCGAG
AACAGTAAAACACCGCAGAATTCTGCAGATTGTACCTACAACCTCA
GCAGCACTCTGACACTGACCAGCACACAGTACAACAGCCACAAAGA
GTACACCTGCAAGGTGACCCAGGGCACGACCTCAGTCGTCCAGAGC
TTCAATAGGGGTGACTGTTAG

A11B1_14H1 Heavy Chain (SEQ ID NO: 61)

ATGGAGACTGGGCTGCGCTGGCTTCTCCTGGTCGCTGTGCTCAAAG
GTGTCCAGTGTCAGTCGTTGGAGGAGTCCGGGGGAGACCTGGTCAA
GCCTGGGGCATCCCTGACACTCACCTGCAAAGCCTCTGGAATCGAC
TTCAATAACTATTGGATAACCTGGGTCCGCCAGGCTCCAGGGAAGG
GGCTGGAGTGGATCGCATGCATTTATGTTGGAATTACCGGCCGCAC
ATGGTACGCGAACTGGGCGAAAGGCCGATTCACCATCTCCAAGGCC
TCGAGCACGGTGGATCTGAAAATGACCAGTCTGACAGCCGCGGACA
CGGCCACCTATTTCTGTGCGAGGAATGGTGATGGTGGTATTTATGC
TCTTAACTTGTGGGGCCCAGGCACCCTGGTCACCGTCTCCTCAGGG
CAACCTAAGGCTCCATCAGTCTTCCCACTGGCCCCCTGCTGCGGGG
ACACACCCAGCTCCACGGTGACCCTGGGCTGCCTGGTCAAAGGCTA
CCTCCCCGGAGCCAGTGACCGTGACCTGGAACTCGGGCACCCTCACC
AATGGGGTACGCACCTTCCCGTCCGTCCGGCAGTCCTCAGGCCTCT
ACTCGCTGAGCAGCGTGGTGAGCGTGACCTCAAGCAGCCAGCCCGT
CACCTGCAACGTGGCCCACCCAGCCACCAACACCAAAGTGGACAAG
ACCGTTGCGCCCTCGACATGCAGCAAGCCCATGTGCCCACCCCCTG
AACTCCCGGGGGGACCGTCTGTCTTCATCTTCCCCCCAAAACCCAA
GGACACCCTCATGATCTCACGCACCCCCGAGGTCACATGCGTGGTG
GTGGACGTGAGCCAGGATGACCCCGAGGTGCAGTTCACATGGTACA
TAAACAACGAGCAGGTGCGCACCGCCCGGCCGCCGCTACGGGAGCA
GCAGTTCAACAGCACGATCCGCGTGGTCAGCACCCTCCCCATCGCG
CACCAGGACTGGCTGAGGGGCAAGGAGTTCAAGTGCAAAGTCCACA
ACAAGGCACTCCCGGCCCCCATCGAGAAAACCATCTCCAAAGCCAG
AGGGCAGCCCCTGGAGCCGAAGGTCTACACCATGGGCCCTCCCCGG
GAGGAGCTGAGCAGCAGGTCGGTCAGCCTGACCTGCATGATCAACG
GCTTCTACCCTTCCGACATCTCGGTGGAGTGGGAGAAGAACGGGAA
GGCAGAGGACAACTACAAGACCACGCCGACCGTGCTGGACAGCGAC
GGCTCCTACTTCCTCTACAGCAAGCTCTCAGTGCCCACGAGTGAGT

-continued

GGCAGCGGGGCGACGTCTTCACCTGCTCCGTGATGCACGAGGCCTT
GCACAACCACTACACGCAGAAGTCCATCTCCCGCTCTCCGGGTAAA
TAG

A11B1_14H1 Light Chain (SEQ ID NO: 62)

ATGGACACGAGGGCCCCCACTCAGCTGCTGGGGCTCCTGCTGCTCT
GGCTCCCAGGTGCCACATTTGCACAAGTGCTGACCCAGACTGCATC
GTCCGTGTCTGCAGCTGTGGGAGGCACAGTCACCATCAGTTGCCAG
TCCAGTCAGAGTGTTTATAATAATAATTGGTTAGCCTGGTATCAGC
AGAAACCAGGGCAGCCTCCCAAGCTCCTGATCTACAGGGCATCCAC
TCTGACATCTGGGGTCCCATCGCGGTTCAAAGGCAGTGGATCTGGG
ACACAGTTCACTCTCACCATCAGCGACCTGGAGTGTGACGATGCTG
CCACTTACTACTGTGCAGGCGGTTATAGTGGTAATATTTACGTAAA
TGATTTCGGCGGAGGGACCGAGGTGGTGGTCAAAGGTGATCCAGTT
GCACCTACTGTCCTCATCTTCCCACCAGCTGCTGATCAGGTGGCAA
CTGGAACAGTCACCATCGTGTGTGTGGCGAATAAATACTTTCCCGA
TGTCACCGTCACCTGGGAGGTGGATGGCACCACCCAAACAACTGGC
ATCGAGAACAGTAAAACACCGCAGAATTCTGCAGATTGTACCTACA
ACCTCAGCAGCACTCTGACACTGACCAGCACACAGTACAACAGCCA
CAAAGAGTACACCTGCAAGGTGACCCAGGGCACGACCTCAGTCGTC
CAGAGCTTCAATAGGGGTGACTGTTAG

A11B1_13G4 Heavy Chain (SEQ ID NO: 63)

ATGGAGACTGGGCTGCGCTGGCTTCTCCTGGTCGCTGTGCTCAAAG
GTGTCCAGTGTCAGGAGCAGCTGGAGGAGTCCGGGGGAGACCTGGT
CAAGCCTGGGGGATCCCTGACACTCACCTGCAAAGCCTCTGGATTC
TCCTTCAGTAATACCTACTGGGCATGCTGGGTCCGCCAGGCTCCAG
GGAAGGGGCTGGAGTGGATCGCATGCATGAATCCTGCTAGTAGTGG
TAGCTCTTACTACGCGAGCTGGGCGAAAGGCCGATTCACCATCTCC
AAAACCTCGTCGACCACGGTGACTCTGCACATGCCCAGTCTGACAG
CCGCGGACACGGCCACCTATTTCTGTGCGAAATGGGATACTGCTTT
CGATGTGTGGGGCCCAGGCACCCTGGTCACCGTCTCCTCAGGGCAA
CCTAAGGCTCCATCAGTCTTCCCACTGGCCCCCTGCTGCGGGGACA
CACCCAGCTCCACGGTGACCCTGGGCTGCCTGGTCAAAGGCTACCT
CCCGGAGCCAGTGACCGTGACCTGGAACTCGGGCACCCTCACCAAT
GGGGTACGCACCTTCCCGTCCGTCCGGCAGTCCTCAGGCCTCTACT
CGCTGAGCAGCGTGGTGAGCGTGACCTCAAGCAGCCAGCCCGTCAC
CTGCAACGTGGCCCACCCAGCCACCAACACCAAAGTGGACAAGACC
GTTGCGCCCTCGACATGCAGCAAGCCCATGTGCCCACCCCCTGAAC
TCCCGGGGGGACCGTCTGTCTTCATCTTCCCCCCAAAACCCAAGGA
CACCCTCATGATCTCACGCACCCCCGAGGTCACATGCGTGGTGGTG
GACGTGAGCCAGGATGACCCCGAGGTGCAGTTCACATGGTACATAA
ACAACGAGCAGGTGCGCACCGCCCGGCCGCCGCTACGGGAGCAGCA

-continued

GTTCAACAGCACGATCCGCGTGGTCAGCACCCTCCCCATCGCGCAC

CAGGACTGGCTGAGGGGCAAGGAGTTCAAGTGCAAAGTCCACAACA

AGGCACTCCCGGCCCCCATCGAGAAAACCATCTCCAAAGCCAGAGG

GCAGCCCCTGGAGCCGAAGGTCTACACCATGGGCCCTCCCCGGGAG

GAGCTGAGCAGCAGGTCGGTCAGCCTGACCTGCATGATCAACGGCT

TCTACCCTTCCGACATCTCGGTGGAGTGGGAGAAGAACGGGAAGGC

AGAGGACAACTACAAGACCACGCCGACCGTGCTGGACAGCGACGGC

TCCTACTTCCTCTACAGCAAGCTCTCAGTGCCCACGAGTGAGTGGC

AGCGGGGCGACGTCTTCACCTGCTCCGTGATGCACGAGGCCTTGCA

CAACCACTACACGCAGAAGTCCATCTCCCGCTCTCCGGGTAAATAG

A11B1_13G4 Light Chain (SEQ ID NO: 64)

ATGGACACGAGGGCCCCCACTCAGCTGCTGGGGCTCCTGCTGCTCT

GGCTCCCAGGTGCCAGATGTGCCGATGTTGTGATGACCCAGACTCC

ATCCTCCGTGGAGGCAGCTGTGGGAGGCACAGTCACCATCAAGTGC

CAGGCCAGTCAGAGCATTAGTAGCTACTTAGCCTGGTATCAGCAGA

AACCAGGGCAGCCTCCCAAGCTCCTGATCTATGGTGCATCCAATCT

GGAGTCTGGGGTCCCATCGCGGTTCAAAGGCAGTGGATCTGGGACA

GAGTACACTCTCACCATCAGCGGCGTGCAGTGTGACGATGCTGCCA

CTTACTACTGTCAAAACTATTATGCTATTGATACTTATGGTCATGC

TTTCGGCGGAGGGACCGAGGTGGTGGTCAAAGGTGATCCAGTTGCA

CCTACTGTCCTCATCTTCCCACCAGCTGCTGATCAGGTGGCAACTG

GAACAGTCACCATCGTGTGTGTGGCGAATAAATACTTTCCCGATGT

CACCGTCACCTGGGAGGTGGATGGCACCACCCAAACAACTGGCATC

GAGAACAGTAAAACACCGCAGAATTCTGCAGATTGTACCTACAACC

TCAGCAGCACTCTGACACTGACCAGCACACAGTACAACAGCCACAA

AGAGTACACCTGCAAGGTGACCCAGGGCACGACCTCAGTCGTCCAG

AGCTTCAATAGGGGTGACTGTTAG

A11B1_13C3 Heavy Chain (SEQ ID NO: 65)

ATGGAGACTGGGCTGCGCTGGCTTCTCCTGGTCGCTGTGCTCAAAG

GTGTCCAGTGTCAGGAGCAGCTGGAGGAGTCCGGGGGAGACCTGGT

CAAGCCTGGGGCATCCCTGACACTCACCTGCACAGCCTCTGGATTC

TCCTTTAGTAGCAACTATCACATCTGCTGGGTCCGCCAGGCTCCAG

GAAAGGGGCTGGAGTTGATCGCATGCATTTATGTTGGTGATGGCAG

CACATACTACGCGAGCTGGGCGAAAGGCCGATTCACCATCTCCAAA

TCCTCGTCGACCACGGTAGCTCTGCAAATGACCAGTCTGACAGCCG

CGGACACGGCCACCTATTTCTGTGGGAGAATGTTTAACTTGTGGGG

CCCAGGCACCCTGGTCACCGTCTCCTCAGGGCAACCTAAGGCTCCA

TCAGTCTTCCCACTGGCCCCCTGCTGCGGGGACACACCCAGCTCCA

CGGTGACCCTGGGCTGCCTGGTCAAAGGCTACCTCCCGGAGCCAGT

GACCGTGACCTGGAACTCGGGCACCCTCACCAATGGGGTACGCACC

-continued

TTCCCGTCCGTCCGGCAGTCCTCAGGCCTCTACTCGCTGAGCAGCG

TGGTGAGCGTGACCTCAAGCAGCCAGCCCGTCACCTGCAACGTGGC

CCACCCAGCCACCAACACCAAAGTGGACAAGACCGTTGCGCCCTCG

ACATGCAGCAAGCCCATGTGCCCACCCCCTGAACTCCCGGGGGGAC

CGTCTGTCTTCATCTTCCCCCCAAAACCCAAGGACACCCTCATGAT

CTCACGCACCCCCGAGGTCACATGCGTGGTGGTGGACGTGAGCCAG

GATGACCCCGAGGTGCAGTTCACATGGTACATAAACAACGAGCAGG

TGCGCACCGCCCGGCCGCCGCTACGGGAGCAGCAGTTCAACAGCAC

GATCCGCGTGGTCAGCACCCTCCCCATCGCGCACCAGGACTGGCTG

AGGGGCAAGGAGTTCAAGTGCAAAGTCCACAACAAGGCACTCCCGG

CCCCCATCGAGAAAACCATCTCCAAAGCCAGAGGGCAGCCCCTGGA

GCCGAAGGTCTACACCATGGGCCCTCCCCGGGAGGAGCTGAGCAGC

AGGTCGGTCAGCCTGACCTGCATGATCAACGGCTTCTACCCTTCCG

ACATCTCGGTGGAGTGGGAGAAGAACGGGAAGGCAGAGGACAACTA

CAAGACCACGCCGACCGTGCTGGACAGCGACGGCTCCTACTTCCTC

TACAGCAAGCTCTCAGTGCCCACGAGTGAGTGGCAGCGGGGCGACG

TCTTCACCTGCTCCGTGATGCACGAGGCCTTGCACAACCACTACAC

GCAGAAGTCCATCTCCCGCTCTCCGGGTAAATAG

A11B1_13C3 Light Chain (SEQ ID NO: 66)

ATGGACACGAGGGCCCCCACTCAGCTGCTGGGGCTCCTGCTGCTCT

GGCTCCCAGGTGCCATATGTGACCCTGTGCTGACCCAGACTCCATC

CTCCGTGTCTGCGGCTGTGGGAGTCACAGTCACCATCAACTGCCAG

TCCAGTCCGAGTGTTTATAGTAACTACTTATCCTGGTATCAGCAGA

AACCAGGGCAGCCTCCCAAGCTCCTCATCTATCTGGCATCTACTCT

GGCATCTGGGGTCCCATCGCGGTTCAAAGGCAGTGGATCTGGGACA

CAGTTCACTCTCACCATCAGCGACGTGCAGTGTGACGATGCTGCCA

CTTACTACTGTGCAGGCACTTATAGTGGTAATATTTGGTCTTTCGG

CGGAGGGACCGAGGTGGTGGTCAAAGGTGATCCAGTTGCACCTACT

GTCCTCATCTTCCCACCAGCTGCTGATCAGGTGGCAACTGGAACAG

TCACCATCGTGTGTGTGGCGAATAAATACTTTCCCGATGTCACCGT

CACCTGGGAGGTGGATGGCACCACCCAAACAACTGGCATCGAGAAC

AGTAAAACACCGCAGAATTCTGCAGATTGTACCTACAACCTCAGCA

GCACTCTGACACTGACCAGCACACAGTACAACAGCCACAAAGAGTA

CACCTGCAAGGTGACCCAGGGCACGACCTCAGTCGTCCAGAGCTTC

AATAGGGGTGACTGTTAG

A11B1_12F2 Heavy Chain (SEQ ID NO: 67)

ATGGAGACTGGGCTGCGCTGGCTTCTCCTGGTCGCTGTGCTCAAAG

GTGTCCAGTGTCAGCAGCAGCTGGTGGAGTCCGGGGGAGGCCTGGT

CAAGCCTGGGGCATCCCTGACACTCACCTGCACAGCCTCTGGATTC

TCCTTCAGTAGCGGCTATCACATGTGCTGGGTCCGCCAGGCTCCAG

GGAAGGGGCTGGAGTGGATCGCATGCTTTGGTGTTTATACTGGTAC

CACTACCTACGCGAGCTGGGCGAAAGGTCGATTCACCATCTCCAAA
ACCTCGTCGACCACGGTGACTCTACAAATGACCAGTCTAACAGTCG
CGGACACGGCCACCTATTTCTGTGCGAGAATCAGTGCTGAAAATGG
TGGGGACTTGTGGGGCCCAGGCACCCTGGTCACCGTCTCCTCAGGG
CAACCTAAGGCTCCATCAGTCTTCCCACTGGCCCCCTGCTGCGGGG
ACACACCCAGCTCCACGGTGACCCTGGGCTGCCTGGTCAAAGGCTA
CCTCCCGGAGCCAGTGACCGTGACCTGGAACTCGGGCACCCTCACC
AATGGGGTACGCACCTTCCCGTCCGTCCGGCAGTCCTCAGGCCTCT
ACTCGCTGAGCAGCGTGGTGAGCGTGACCTCAAGCAGCCAGCCCGT
CACCTGCAACGTGGCCCACCCAGCCACCAACACCAAAGTGGACAAG
ACCGTTGCGCCCTCGACATGCAGCAAGCCCATGTGCCCACCCCCTG
AACTCCCGGGGGGACCGTCTGTCTTCATCTTCCCCCCAAAACCCAA
GGACACCCTCATGATCTCACGCACCCCCGAGGTCACATGCGTGGTG
GTGGACGTGAGCCAGGATGACCCCGAGGTGCAGTTCACATGGTACA
TAAACAACGAGCAGGTGCGCACCGCCCGGCCGCCGCTACGGGAGCA
GCAGTTCAACAGCACGATCCGCGTGGTCAGCACCCTCCCCATCGCG
CACCAGGACTGGCTGAGGGGCAAGGAGTTCAAGTGCAAAGTCCACA
ACAAGGCACTCCCGGCCCCCATCGAGAAAACCATCTCCAAAGCCAG
AGGGCAGCCCCTGGAGCCGAAGGTCTACACCATGGGCCCTCCCCGG
GAGGAGCTGAGCAGCAGGTCGGTCAGCCTGACCTGCATGATCAACG
GCTTCTACCCTTCCGACATCTCGGTGGAGTGGGAGAAGAACGGGAA
GGCAGAGGACAACTACAAGACCACGCCGACCGTGCTGGACAGCGAC
GGCTCCTACTTCCTCTACAGCAAGCTCTCAGTGCCCACGAGTGAGT
GGCAGCGGGGCGACGTCTTCACCTGCTCCGTGATGCACGAGGCCTT
GCACAACCACTACACGCAGAAGTCCATCTCCCGCTCTCCGGGTAAA
TAG

A11B1_12F2 Light Chain (SEQ ID NO: 68)

ATGGACACGAGGGCCCCCACTCAGCTGCTGGGGCTCCTGCTGCTCT
GGCTCCCAGGTGCCAGATGTGATGTTGTGATGACCCAGACTCCAGC
CTCCGTGGAGGCAGCTGTGGGAGGCACAGTCACCATCAAGTGCCAG
GCCAGTCAGAGCATTAGCAACTACTTTTCTTGGTATCAGCAGAAAC
CAGGGCAGCCTCCCAAGCTCCTGATCTACAGGGCGTCCACTCTGGC
ATCTGGGGTCCCATCGCGGTTCAGCGGCAGTGGATCTGGGACAGAG
TTCACTCTCACCATCAGCGACCTGGAGTGTGCCGATTCTGCCACTT
ACTACTGTCAGTGCACTTATGGTAGTAGTAGTACTGGTTTTGGTTT
CGGCGGAGGGACCGAGGTGGTGGTCAAAGGTGATCCAGTTGCACCT
ACTGTCCCCATCTTCCCACCAGCTGCTGATCAGGTGGCAACTGGAA
CAGTCACCATCGTGTGTGTGGCGAATAAATACTTTCCCGATGTCAC
CGTCACCTGGGAGGTGGATGGCACCACCCAAACAACTGGCATCGAG
AACAGTAAAACACCGCAGAATTCTGCAGATTGTACCTACAACCTCA
GCAGCACTCTGACACTGACCAGCACACAGTACAACAGCCACAAAGA
GTACACCTGCAAGGTGACCCAGGGCACGACCTCAGTCGTCCAGAGC
TTCAATAGGGGTGACTGTTAG

A11B1_11D10 Heavy Chain (SEQ ID NO: 69)

ATGGAGACTGGGCTGCGCTGGCTTCTCCTGGTCGCTGTGCTCAAAG
GTGTCCAGTGTCAGTCGTTGGAGGAGTCCGGGGGAGACCTGGTCAA
GCCTGGGGCATCCCTGACACTCACCTGCATGGCCTCTGGAATCGAC
TTCAGTAGCGGCTACGGCATGTGGTGGGTCCGCCAGGCTCCAGGGA
AGGGACTGGAGTATATCGGATACATTGATACTGGTGATGATAACAC
ATACTACGCGAACTGGGCGAAAGGCCGATTCACCATCTCCAAAACC
TCGTCGACCACGGTGACTCTGCAAATGACCAGTCTGACAGTCGCGG
ACACGGCCACCTATTTCTGTGCGAAAGGGGGCGCCATAGACCTCTG
GGGCCCAGGGACCCTCGTCACCGTCTCTTCAGGGCAACCTAAGGCT
CCATCAGTCTTCCCACTGGCCCCCTGCTGCGGGGACACACCCAGCT
CCACGGTGACCCTGGGCTGCCTGGTCAAAGGCTACCTCCCGGAGCC
AGTGACCGTGACCTGGAACTCGGGCACCCTCACCAATGGGGTACGC
ACCTTCCCGTCCGTCCGGCAGTCCTCAGGCCTCTACTCGCTGAGCA
GCGTGGTGAGCGTGACCTCAAGCAGCCAGCCCGTCACCTGCAACGT
GGCCCACCCAGCCACCAACACCAAAGTGGACAAGACCGTTGCGCCC
TCGACATGCAGCAAGCCCATGTGCCCACCCCCTGAACTCCCGGGGG
GACCGTCTGTCTTCATCTTCCCCCCAAAACCCAAGGACACCCTCAT
GATCTCACGCACCCCCGAGGTCACATGCGTGGTGGTGGACGTGAGC
CAGGATGACCCCGAGGTGCAGTTCACATGGTACATAAACAACGAGC
AGGTGCGCACCGCCCGGCCGCCGCTACGGGAGCAGCAGTTCAACAG
CACGATCCGCGTGGTCAGCACCCTCCCCATCGCGCACCAGGACTGG
CTGAGGGGCAAGGAGTTCAAGTGCAAAGTCCACAACAAGGCACTCC
CGGCCCCCATCGAGAAAACCATCTCCAAAGCCAGAGGGCAGCCCCT
GGAGCCGAAGGTCTACACCATGGGCCCTCCCCGGGAGGAGCTGAGC
AGCAGGTCGGTCAGCCTGACCTGCATGATCAACGGCTTCTACCCTT
CCGACATCTCGGTGGAGTGGGAGAAGAACGGGAAGGCAGAGGACAA
CTACAAGACCACGCCGACCGTGCTGGACAGCGACGGCTCCTACTTC
CTCTACAGCAAGCTCTCAGTGCCCACGAGTGAGTGGCAGCGGGGCG
ACGTCTTCACCTGCTCCGTGATGCACGAGGCCTTGCACAACCACTA
CACGCAGAAGTCCATCTCCCGCTCTCCGGGTAAATAG

A11B1_11D10 Light Chain (SEQ ID NO: 70)

ATGGACACGAGGGCCCCCACTCAGCTGCTGGGACTCCTACTGCTCT
GGCTCCCAGGTGCCAGATGTGCTGACATTGTGATGACCCAGACTCC
AGCCTCCGTGGAGGCAGCTGTGGGAGGCACAGTCACCATCAAGTGC
CAGGCCAGTCAGAGCATTAGTAGTTACTTAGCCTGGTATCAGCAGA
AACCAGGGCAGCGTCCCAAGCTCCTGATCTACAGGGCATCCACTCT
AAAATCTGGGGTCCCATCGCGGTTCAAAGGCAGTGGATCTGGGACA

-continued

GAGTACACTCTCACCATCAGCGACCTGGAGTGTGCCGATGCTGCCA
CTTATTATTGTCAAGCGTATTATCTTAGTAGTAGTATCAGTTATGG
TAATACTTTCGGCGGAGGGACCGAGGTGGTGGTCAAAGGTGATCCA
GTTGCACCTACTGTCCTCATCTTCCCACCAGCTGCTGATCAGGTGG
CAACTGGAACAGTCACCATCGTGTGTGTGGCGAATAAATACTTTCC
CGATGTCACCGTCACCTGGGAGGTGGATGGCACCACCCAAACAACT
GGCATCGAGAACAGTAAAACACCGCAGAATTCTGCAGATTGTACCT
ACAACCTCAGCAGCACTCTGACACTGACCAGCACACAGTACAACAG
CCACAAAGAGTACACCTGCAAGGTGACCCAGGGCACGACCTCAGTC
GTCCAGAGCTTCAATAGGGGTGACTGTTAG

A11B1_10F9 Heavy Chain (SEQ ID NO: 71)

ATGGAGACTGGGCTGCGCTGGCTTCTCCTGGTCGCTGTGCTCAAAG
GTGTCCAGTGTCAGTCGTTGGAGGAGTCCGGGGGAGACCTGGTCAA
GCCTGGGGCGTCCCTGACACTCACCTGCACAGCCTCTGGATTCTCC
CTCAGTAGCGGGTATGGCATGTGCTGGGTCCGCCAGGCTCCAGGGA
AGGGACTGGAGTGGATCGGATACACTGATACTGCTACTGGTACCAT
TCACTACGCGAGCTGGGCGAAAGGCCGATTCACCATCTCCAAAACC
TCGTCGACCACGGTGACTCTGCAAATGACCAGTCTGACAGCCGCGG
ACACGGCCACCTATTTCTGTGCGAAAGGGGGCGCCATGGACCTCTG
GGGCCCAGGGACCCTCGTCACCGTCTCTTCAGGGCAACCTAAGGCT
CCATCAGTCTTCCCACTGGCCCCCTGCTGCGGGGACACACCCAGCT
CCACGGTGACCCTGGGCTGCCTGGTCAAAGGCTACCTCCCGGAGCC
AGTGACCGTGACCTGGAACTCGGGCACCCTCACCAATGGGGTACGC
ACCTTCCCGTCCGTCCGGCAGTCCTCAGGCCTCTACTCGCTGAGCA
GCGTGGTGAGCGTGACCTCAAGCAGCCAGCCCGTCACCTGCAACGT
GGCCCACCCAGCCACCAACACCAAAGTGGACAAGACCGTTGCGCCC
TCGACATGCAGCAAGCCCATGTGCCCACCCCCTGAACTCCCGGGGG
GACCGTCTGTCTTCATCTTCCCCCCAAAACCCAAGGACACCCTCAT
GATCTCACGCACCCCCGAGGTCACATGCGTGGTGGTGGACGTGAGC
CAGGATGACCCCGAGGTGCAGTTCACATGGTACATAAACAACGAGC
AGGTGCGCACCGCCCGGCCGCCGCTACGGGAGCAGCAGTTCAACAG
CACGATCCGCGTGGTCAGCACCCTCCCCATCGCGCACCAGGACTGG
CTGAGGGGCAAGGAGTTCAAGTGCAAAGTCCACAACAAGGCACTCC
CGGCCCCCATCGAGAAAACCATCTCCAAAGCCAGAGGGCAGCCCCT
GGAGCCGAAGGTCTACACCATGGGCCCTCCCCGGGAGGAGCTGAGC
AGCAGGTCGGTCAGCCTGACCTGCATGATCAACGGCTTCTACCCTT
CCGACATCTCGGTGGAGTGGGAGAAGAACGGGAAGGCAGAGGACAA
CTACAAGACCACGCCGACCGTGCTGGACAGCGACGGCTCCTACTTC

-continued

CTCTACAGCAAGCTCTCAGTGCCCACGAGTGAGTGGCAGCGGGGCG
ACGTCTTCACCTGCTCCGTGATGCACGAGGCCTTGCACAACCACTA
CACGCAGAAGTCCATCTCCCGCTCTCCGGGTAAATAG

A11B1_10F9 Light Chain (SEQ ID NO: 72)

ATGGACACGAGGGCCCCCACTCAGCTGCTGGGGCTCCTACTGCTCT
GGCTCCCAGGTGCCAGATGTGCTGACATTGTGATGACCCAGACTCC
AGCCTCCGTGGAGGCAGCTGTGGGAGGCACAGTCACCATCAAGTGC
CAGGCCAGTCAGAGCATTAGTAGCTACTTAGCCTGGTATCAGCAGA
AACCAGGGCAGCCTCCCAAGCTCCTGATCTACAGGACATCCACTCT
GGCATCTGGGGTCCCATCGCGGTTCAAAGGCAGTGGATCTGGGACA
GAGTACACTCTCACCATCAGCGACCTGGAGTGTGCCGATGCTGCCA
CTTACTATTGTCAAAGCTATGCTTATAGTAGTAGTAGCAGTTATGG
TAATGCTTTCGGCGGAGGGACCGAGGTGGTGGTCAAAGGTGATCCA
GTTGCACCTACTGTCCTCATCTTCCCACCAGCTGCTGATCAGGTGG
CAACTGGAACAGTCACCATCGTGTGTGTGGCGAATAAATACTTTCC
CGATGTCACCGTCACCTGGGAGGTGGATGGCACCACCCAAACAACT
GGCATCGAGAACAGTAAAACACCGCAGAATTCTGCAGATTGTACCT
ACAACCTCAGCAGCACTCTGACACTGACCAGCACACAGTACAACAG
CCACAAAGAGTACACCTGCAAGGTGACCCAGGGCACGACCTCAGTC
GTCCAGAGCTTCAATAGGGGTGACTGTTAG

A11B1_7H12 Heavy Chain (SEQ ID NO: 73)

ATGGAGACTGGGCTGCGCTGGCTTCTCCTGGTCGCTGTGCTCAAAG
GTGTCCAGTGTCAGTCGTTGGAGGAGTCCGGGGGAGACCTGGTCAA
GCCTGGGGCATCCCTGACACTCACCTGCACAGGCTCTGGAATCGAC
TTCAGTAGCAGCTACTGGATATGCTGGGTCCGCCAGGCTCCAGGGA
AGGGGCTGGAGTGGATCGCATGCATCGATGGTAGTGATGGTAACAC
TTACTACGCGAGCTGGGCGAGAGGCCGATTCACCATCTCCAAAACC
TCGTCGACCACGGTGACTCTGCAAATGGCCAGTCTGACAGCCGCGG
ACACGGCCACCTATTTCTGTACGAGAGATCTCAGGTTGTGGGGCCC
AGGCACCCTGGTCACCGTCTCCTCAGGGCAACCTAAGGCTCCATCA
GTCTTCCCACTGGCCCCCTGCTGCGGGGACACACCCAGCTCCACGG
TGACCCTGGGCTGCCTGGTCAAAGGCTACCTCCCGGAGCCAGTGAC
CGTGACCTGGAACTCGGGCACCCTCACCAATGGGGTACGCACCTTC
CCGTCCGTCCGGCAGTCCTCAGGCCTCTACTCGCTGAGCAGCGTGG
TGAGCGTGACCTCAAGCAGCCAGCCCGTCACCTGCAACGTGGCCCA
CCCAGCCACCAACACCAAAGTGGACAAGACCGTTGCGCCCTCGACA
TGCAGCAAGCCCATGTGCCCACCCCCTGAACTCCCGGGGGGACCGT
CTGTCTTCATCTTCCCCCCAAAACCCAAGGACACCCTCATGATCTC
ACGCACCCCCGAGGTCACATGCGTGGTGGTGGACGTGAGCCAGGAT
GACCCCGAGGTGCAGTTCACATGGTACATAAACAACGAGCAGGTGC

-continued

GCACCGCCCGGCCGCCGCTACGGGAGCAGCAGTTCAACAGCACGAT
CCGCGTGGTCAGCACCCTCCCCATCGCGCACCAGGACTGGCTGAGG
GGCAAGGAGTTCAAGTGCAAAGTCCACAACAAGGCACTCCCGGCCC
CCATCGAGAAAACCATCTCCAAAGCCAGAGGGCAGCCCCTGGAGCC
GAAGGTCTACACCATGGGCCCTCCCCGGGAGGAGCTGAGCAGCAGG
TCGGTCAGCCTGACCTGCATGATCAACGGCTTCTACCCTTCCGACA
TCTCGGTGGAGTGGGAGAAGAACGGGAAGGCAGAGGACAACTACAA
GACCACGCCGACCGTGCTGGACAGCGACGGCTCCTACTTCCTCTAC
AGCAAGCTCTCAGTGCCCACGAGTGAGTGGCAGCGGGGCGACGTCT
TCACCTGCTCCGTGATGCACGAGGCCTTGCACAACCACTACACGCA
GAAGTCCATCTCCCGCTCTCCGGGTAAATAG

A11B1_7H12 Light Chain (SEQ ID NO: 74)

ATGGACACGAGGGCCCCCACTCAGCTGCTGGGGCTCCTGCTGCTCT
GGCTCCCAGGTGCCAGATGTGCTGACATTGTGCTGACCCAGACTCC
AGCCTCGGTGTCTGCAGCTGTGGGAGGCACAGTCACCATCAACTGC
CAGGCCAGTCAGAATGTTTATAGTAACAATGCCTTAGCCTGGCATC
AGCAGAAACCAGGGCAGCGTCCCAACCTCCTGATCTACAAGGCTTC
CACTCTGGCATCTGGGGTCCCATCGCGGTTCAAAGGCAGTGGATCT
GGGACACAGTTTACTCTCACCATCAGCGACGTGCAGTGTGACGATG
CTGCCACTTACTACTGTCTAGGCGAATTTAGTTGTAGTAGTGGTGA
TTGTTTTGTTTTCGGCGGAGGGACCGAGGTGGTGGTCAAAGGTGAT
CCAGTTGCACCTACTGTCCTCATCTTCCCACCAGCTGCTGATCAGG
TGGCAACTGGAACAGTCACCATCGTGTGTGTGGCGAATAAATACTT
TCCCGATGTCACCGTCACCTGGGAGGTGGATGGCACCACCCAAACA
ACTGGCATCGAGAACAGTAAAACACCGCAGAATTCTGCAGATTGTA
CCTACAACCTCAGCAGCACTCTGACACTGACCAGCACACAGTACAA
CAGCCACAAAGAGTACACCTGCAAGGTGACCCAGGGCACGACCTCA
GTCGTCCAGAGCTTCAATAGGGGTGACTGTTAG

A11B1_7G12 Heavy Chain (SEQ ID NO: 75)

ATGGAGACTGGGCTGCGCTGGCTTCTCCTGGTCGCTGTGCTCAAAG
GTGTCCAGTGTCAGTCGTTGGAGGAGTCCGGGGGAGACCTGGTCAA
GCCTGGGGCATCCCTGACACTCACCTGCATGGCCTCTGGAATCGAC
TTCAGTAGCGGCTACGGCATGTGGTGGGTCCGCCAGGCTCCAGGGA
AGGGACTGGAGTATATCGGATACATTGATACTGGTGATGATAACAC
ATACTACGCGAACTGGGCGAAAGGCCGATTCACCATCTCCAAAACC
TCGTCGACCACGGTGACTCTGCAAATGACCAGTCTGACAGTCGCGG
ACACGGCCACCTATTTCTGTGCGAAAGGGGGCGCCATAGACCTCTG
GGGCCCAGGGACCCTCGTCACCGTCTCTTCAGGGCAACCTAAGGCT
CCATCAGTCTTCCCACTGGCCCCCTGCTGCGGGGACACACCCAGCT
CCACGGTGACCCTGGGCTGCCTGGTCAAAGGCTACCTCCCGGAGCC
AGTGACCGTGACCTGGAACTCGGGCACCCTCACCAATGGGGTACGC

-continued

ACCTTCCCGTCCGTCCGGCAGTCCTCAGGCCTCTACTCGCTGAGCA
GCGTGGTGAGCGTGACCTCAAGCAGCCAGCCCGTCACCTGCAACGT
GGCCCACCCAGCCACCAACACCAAAGTGGACAAGACCGTTGCGCCC
TCGACATGCAGCAAGCCCATGTGCCCACCCCCTGAACTCCCGGGGG
GACCGTCTGTCTTCATCTTCCCCCCAAAACCCAAGGACACCCTCAT
GATCTCACGCACCCCCGAGGTCACATGCGTGGTGGTGGACGTGAGC
CAGGATGACCCCGAGGTGCAGTTCACATGGTACATAAACAACGAGC
AGGTGCGCACCGCCCGGCCGCCGCTACGGGAGCAGCAGTTCAACAG
CACGATCCGCGTGGTCAGCACCCTCCCCATCGCGCACCAGGACTGG
CTGAGGGGCAAGGAGTTCAAGTGCAAAGTCCACAACAAGGCACTCC
CGGCCCCCATCGAGAAAACCATCTCCAAAGCCAGAGGGCAGCCCCT
GGAGCCGAAGGTCTACACCATGGGCCCTCCCCGGGAGGAGCTGAGC
AGCAGGTCGGTCAGCCTGACCTGCATGATCAACGGCTTCTACCCTT
CCGACATCTCGGTGGAGTGGGAGAAGAACGGGAAGGCAGAGGACAA
CTACAAGACCACGCCGACCGTGCTGGACAGCGACGGCTCCTACTTC
CTCTACAGCAAGCTCTCAGTGCCCACGAGTGAGTGGCAGCGGGGCG
ACGTCTTCACCTGCTCCGTGATGCACGAGGCCTTGCACAACCACTA
CACGCAGAAGTCCATCTCCCGCTCTCCGGGTAAATAG

A11B1_7G12 Light Chain (SEQ ID NO: 76)

ATGGACACGAGGGCCCCCACTCAGCTGCTGGGACTCCTACTGCTCT
GGCTCCCAGGTGCCAGATGTGCTGACATTGTGATGACCCAGACTCC
AGCCTCCGTGGAGGCAGCTGTGGGAGGCACAGTCACCATCAAGTGC
CAGGCCAGTCAGAGCATTAGTAGTTACTTAGCCTGGTATCAGCAGA
AACCAGGGCAGCGTCCCAAGCTCCTGATCTACAGGGCATCCACTCT
AAAATCTGGGGTCCCATCGCGGTTCAAAGGCAGTGGATCTGGGACA
GAGTACACTCTCACCATCAGCGACCTGGAGTGTGCCGATGCTGCCA
CTTATTATTGTCAAGCGTATTATCTTAGTAGTAGTATCAGTTATGG
TAATACTTTCGGCGGAGGGACCGAGGTGGTGGTCAAAGGTGATCCA
GTTGCACCTACTGTCCTCATCTTCCCACCAGCTGCTGATCAGGTGG
CAACTGGAACAGTCACCATCGTGTGTGTGGCGAATAAATACTTTCC
CGATGTCACCGTCACCTGGGAGGTGGATGGCACCACCCAAACAACT
GGCATCGAGAACAGTAAAACACCGCAGAATTCTGCAGATTGTACCT
ACAACCTCAGCAGCACTCTGACACTGACCAGCACACAGTACAACAG
CCACAAAGAGTACACCTGCAAGGTGACCCAGGGCACGACCTCAGTC
GTCCAGAGCTTCAATAGGGGTGACTGTTAG

A11B1_6G4 Heavy Chain (SEQ ID NO: 77)

ATGGAGACTGGGCTGCGCTGGCTTCTCCTGGTCGCTGTGCTCAAAG
GTGTCCAGTGTCAGCAGCAGCTGGAGGAGTCCGGGGGAGGCCTGGT
CAAGCCTGGAGGAACCCTGACACTCACCTGCAAAGCCTCTGGAGTC
GCCCTCAATCCCTACTACTATATGTGCTGGGTCCGCCAGGCTCCAG

-continued

GGAAGGGGCTGGAGTGGATCGCATGCGTGGATGCTGATAGTAGTGG
TAGCACTTACTACGCGAGCTGGGCGAAAGGCCGATTCACCATCTCC
AAAACCTCGTCGACCACGGTGACTCTGAAAATGACCAGTCTGACAG
CCGCGGACACGGCCACCTATTTCTGTGCGAGAGAATCGGTTGACTA
TAGTTCTGTTGGTATTGGCTATGTACATGGTACGGATGGCTTGTGG
GGCCCAGGCACCCTGGTCACCGTCTCCTCAGGGCAACCTAAGGCTC
CATCAGTCTTCCCACTGGCCCCCTGCTGCGGGGACACACCCAGCTC
CACGGTGACCCTGGGCTGCCTGGTCAAAGGCTACCTCCCGGAGCCA
GTGACCGTGACCTGGAACTCGGGCACCCTCACCAATGGGGTACGCA
CCTTCCCGTCCGTCCGGCAGTCCTCAGGCCTCTACTCGCTGAGCAG
CGTGGTGAGCGTGACCTCAAGCAGCCAGCCCGTCACCTGCAACGTG
GCCCACCCAGCCACCAACACCAAAGTGGACAAGACCGTTGCGCCCT
CGACATGCAGCAAGCCCATGTGCCCACCCCCTGAACTCCCGGGGGG
ACCGTCTGTCTTCATCTTCCCCCCAAAACCCAAGGACACCCTCATG
ATCTCACGCACCCCCGAGGTCACATGCGTGGTGGTGGACGTGAGCC
AGGATGACCCCGAGGTGCAGTTCACATGGTACATAAACAACGAGCA
GGTGCGCACCGCCCGGCCGCCGCTACGGGAGCAGCAGTTCAACAGC
ACGATCCGCGTGGTCAGCACCCTCCCCATCGCGCACCAGGACTGGC
TGAGGGGCAAGGAGTTCAAGTGCAAAGTCCACAACAAGGCACTCCC
GGCCCCCATCGAGAAAACCATCTCCAAAGCCAGAGGGCAGCCCCTG
GAGCCGAAGGTCTACACCATGGGCCCTCCCCGGGAGGAGCTGAGCA
GCAGGTCGGTCAGCCTGACCTGCATGATCAACGGCTTCTACCCTTC
CGACATCTCGGTGGAGTGGGAGAAGAACGGGAAGGCAGAGGACAAC
TACAAGACCACGCCGACCGTGCTGGACAGCGACGGCTCCTACTTCC
TCTACAGCAAGCTCTCAGTGCCCACGAGTGAGTGGCAGCGGGGCGA
CGTCTTCACCTGCTCCGTGATGCACGAGGCCTTGCACAACCACTAC
ACGCAGAAGTCCATCTCCCGCTCTCCGGGTAAATAG

A11B1_6G4 Light Chain (SEQ ID NO: 78)

ATGGACACGAGGGCCCCCACTCAGCTGCTGGGGCTCCTGCTGCTCT
GGCTCCCAGGTGCCAGATGTGCCGACATCGTGGTGACCCAGACTCC
ATCCTCCGTGTCTGCAGCTGTGGGAGGCACAGTCACCATCAAGTGC
CAGGCCAGTCAGAGCATTAGCAACTACTTTTCTTGGTATCAGCAGA
AACCAGGGCAGCCTCCCAAGCTCCTGATCTACAGGGCGTCCACTCT
GGCATCTGGGGTCCCATCGCGGTTCAAAGGCAGTGGATCTGGGACA
GAGTTCACTCTCACCATCAGCGACCTGGAGTGTGCCGATGCTGCCA
CTTACTACTGTCAATGCACTTACGGTAGAAGTAATAGTAATTTTTT
TTATGGTTTCGGCGGAGGGACCGAGGTGGTGGTCAAAGGTGATCCA
GTTGCACCTACTGTCCTCATCTTCCCACCAGCTGCTGATCAGGTGG
CAACTGGAACAGTCACCATCGTGTGTGTGGCGAATAAATACTTTCC
CGATGTCACCGTCACCTGGGAGGTGGATGGCACCACCCAAACAACT
GGCATCGAGAACAGTAAAACACCGCAGAATTCTGCAGATTGTACCT
ACAACCTCAGCAGCACTCTGACACTGACCAGCACACAGTACAACAG
CCACAAAGAGTACACCTGCAAGGTGACCCAGGGCACGACCTCAGTC
GTCCAGAGCTTCAATAGGGGTGACTGTTAG

A11B1_6F9 Heavy Chain (SEQ ID NO: 79)

ATGGAGACTGGGCTGCGCTGGCTTCTCCTGGTCGCCGTGCTCAAAG
GTGTCCAGTGTCAGTCGTTGGAGGAGTCCGGGGGAGACCTGGTCAA
GCCTGGGGCCTCCCTGACACTCACCTGCACAGCCTCTGGATCCTCC
TTCAGTAGTACCTACTGGAACTGCTGGGTCCGCCAGGCTCCAGGGA
AGGGGCTGGAGTGGATCGCATGCATTAATGCTGGTAGTGGTACCAC
TTACTACGCGAGCTGGGCGAAAGGCCGATTCACCGTCTCCAAAACC
TCGTCGACCACGGTGACTCTGCAAATGACCAGTCTGACAGCCGCGG
ACACGGCCACCTATTTCTGTACGAGAGATAGTGATGGTCGTTTTAG
TAGTGGCTACTATTTTAACTTGTGGGGCCCAGGCACCCTGGTCACC
GTCTCCTCAGGGCAACCTAAGGCTCCATCAGTCTTCCCACTGGCCC
CCTGCTGCGGGGACACACCCAGCTCCACGGTGACCCTGGGCTGCCT
GGTCAAAGGCTACCTCCCGGAGCCAGTGACCGTGACCTGGAACTCG
GGCACCCTCACCAATGGGGTACGCACCTTCCCGTCCGTCCGGCAGT
CCTCAGGCCTCTACTCGCTGAGCAGCGTGGTGAGCGTGACCTCAAG
CAGCCAGCCCGTCACCTGCAACGTGGCCCACCCAGCCACCAACACC
AAAGTGGACAAGACCGTTGCGCCCTCGACATGCAGCAAGCCCATGT
GCCCACCCCCTGAACTCCCGGGGGGACCGTCTGTCTTCATCTTCCC
CCCAAAACCCAAGGACACCCTCATGATCTCACGCACCCCCGAGGTC
ACATGCGTGGTGGTGGACGTGAGCCAGGATGACCCCGAGGTGCAGT
TCACATGGTACATAAACAACGAGCAGGTGCGCACCGCCCGGCCGCC
GCTACGGGAGCAGCAGTTCAACAGCACGATCCGCGTGGTCAGCACC
CTCCCCATCGCGCACCAGGACTGGCTGAGGGGCAAGGAGTTCAAGT
GCAAAGTCCACAACAAGGCACTCCCGGCCCCCATCGAGAAAACCAT
CTCCAAAGCCAGAGGGCAGCCCCTGGAGCCGAAGGTCTACACCATG
GGCCCTCCCCGGGAGGAGCTGAGCAGCAGGTCGGTCAGCCTGACCT
GCATGATCAACGGCTTCTACCCTTCCGACATCTCGGTGGAGTGGGA
GAAGAACGGGAAGGCAGAGGACAACTACAAGACCACGCCGACCGTG
CTGGACAGCGACGGCTCCTACTTCCTCTACAGCAAGCTCTCAGTGC
CCACGAGTGAGTGGCAGCGGGGCGACGTCTTCACCTGCTCCGTGAT
GCACGAGGCCTTGCACAACCACTACACGCAGAAGTCCATCTCCCGC
TCTCCGGGTAAATAG

A11B1_16F9 Light Chain (SEQ ID NO: 80)

ATGGACACGAGGGCCCCCACTCAGCTGCTGGGGCTCCTGCTGCTCT
GGCTCCCAGGTGCCACATTTGCCCAAGTGCTGACCCAGACTGCATC
CCCTGTGTCTGCAGCTGTGGGAGGCACAGTCACCATCAATTGTCAG
TCCAGTCAGAGTGTTTATGATAACAACTGGTTAGCCTGGTATCAGC

-continued

AAAAACCAGGGCAGCCTCCCAAACTCTTGATCGACGATGCATCCAA

ATTGACATCTGGGGTCTCATCGCGGTTCAAAGGCAGTGGATCTGGG

ACGCAGTTCACTCTCACCATCAGCGGCGTGCAGTGTGACGATGCTG

CCACTTACTACTGTCAAGGCGCTTATTATAGTAGTGGTTGGTACTG

GGCTTTCGGCGGAGGGACCGAGGTGGTGGTCAAAGGTGATCCAGTT

GCACCTACTGTCCTCATCTTCCCACCAGCTGCTGATCAGGTGGCAA

CTGGAACAGTCACCATCGTGTGTGTGGCGAATAAATACTTTCCCGA

TGTCACCGTCACCTGGGAGGTGGATGGCACCACCCAAACAACTGGC

ATCGAGAACAGTAAAACACCGCAGAATTCTGCAGATTGTACCTACA

ACCTCAGCAGCACTCTGACACTGACCAGCACACAGTACAACAGCCA

CAAAGAGTACACCTGCAAGGTGACCCAGGGCACGACCTCAGTCGTC

CAGAGCTTCAATAGGGGTGACTGTTAG

A11B1_6C7 Heavy Chain (SEQ ID NO: 81)

ATGGAGACTGGGCTGCGCTGGCTTCTCCTGGTCGCTGTGCTCAAAG

GTGTCCAGTGTCAGCAGCAGCTGGAGGAGTCCGGGGGAGGCCTGGT

CAAGCCTGGAGGAACCCTGACACTCACCTGCAAAGCCTCTGGAATC

GACTTCAGTAGCTACTACTACATGTGTTGGGTCCGCCAGGCTCCAG

GGAAGGGGCTGGAGTTGATCGTATGTATTTATACTAGTAGTGGTGG

CACATGGTACGCGAGCTGGGTGAATGGCCGACTCACCATCTCCAGA

AGCACCAGCCTAAACACGGTGGATCTGAAAATGACCAGTCTGACAG

CCGCGGACACGGCCACCTATTTCTGTGCCAGAGGGGTTTATTCTGG

TAGTAGTGATTATCCAACTCGGTTGGATCTCTGGGGCCAGGGCACC

CTGGTCACCGTCTCCTTAGGGCAACCTAAGGCTCCATCAGTCTTCC

CACTGGCCCCCTGCTGCGGGGACACACCCAGCTCCACGGTGACCCT

GGGCTGCCTGGTCAAAGGCTACCTCCCGGAGCCAGTGACCGTGACC

TGGAACTCGGGCACCCTCACCAATGGGGTACGCACCTTCCCGTCCG

TCCGGCAGTCCTCAGGCCTCTACTCGCTGAGCAGCGTGGTGAGCGT

GACCTCAAGCAGCCAGCCCGTCACCTGCAACGTGGCCCACCCAGCC

ACCAACACCAAAGTGGACAAGACCGTTGCGCCCTCGACATGCAGCA

AGCCCATGTGCCCACCCCCTGAACTCCCGGGGGGACCGTCTGTCTT

CATCTTCCCCCCAAAACCCAAGGACACCCTCATGATCTCACGCACC

CCCGAGGTCACATGCGTGGTGGTGGACGTGAGCCAGGATGACCCCG

AGGTGCAGTTCACATGGTACATAAACAACGAGCAGGTGCGCACCGC

CCGGCCGCCGCTACGGGAGCAGCAGTTCAACAGCACGATCCGCGTG

GTCAGCACCCTCCCCATCGCGCACCAGGACTGGCTGAGGGGCAAGG

AGTTCAAGTGCAAAGTCCACAACAAGGCACTCCCGGCCCCCATCGA

GAAAACCATCTCCAAAGCCAGAGGGCAGCCCCTGGAGCCGAAGGTC

TACACCATGGGCCCTCCCCGGGAGGAGCTGAGCAGCAGGTCGGTCA

GCCTGACCTGCATGATCAACGGCTTCTACCCTTCCGACATCTCGGT

GGAGTGGGAGAAGAACGGGAAGGCAGAGGACAACTACAAGACCACG

CCGACCGTGCTGGACAGCGACGGCTCCTACTTCCTCTACAGCAAGC

-continued

TCTCAGTGCCCACGAGTGAGTGGCAGCGGGGCGACGTCTTCACCTG

CTCCGTGATGCACGAGGCCTTGCACAACCACTACACGCAGAAGTCC

ATCTCCCGCTCTCCGGGTAAATAG

A11B1_6C7 Light Chain (SEQ ID NO: 82)

ATGGACACGAGCACCTCCACTGCGCTCCTGGGGCTCCTGCTGCTCT

GGCTCACAGGTGCCAGATGTGCCATCGAGATGACCCAGTCTCCACC

CTCCCTGTCTGCATCTGTGGGAGAAACTGTCAGGATTAGGTGCCTG

GCCAGTGAGGACATTTACAGTGGTATATCCTGGTACCAACAGAAGC

CAGAGAAACCTCCTACACTCCTGATCTCTGGTGCATCCAATTTAGA

ATCTGGGGTCCCACCACGGTTCAGTGGCGGTGGATCCGGGACAGAT

TACACCCTCACCATCGGCGGCGTGCAGGCTGAAGATGTTGCCACCT

ACTACTGTCTAGGCGGTTATAGTTTCAGTAGTACCGGTTTGACTTT

TGGAGCTGGCACCAAGGTGGAAATCAAACGTGATCCAGTTGCGCCT

TCTGTCCTCCTCTTCCCACCATCTAAGGAGGAGCTGACAACTGGAA

CAGCCACCATCGTGTGTGTGGCGAATAAATACTTTCCCGATGTCAC

CGTCACCTGGGAGGTGGATGGCACCACCCAAACAACTGGCATCGAG

AACAGTAAAACACCGCAGAATTCTGCAGATTGTACCTACAACCTCA

GCAGCACTCTGACACTGACCAGCACACAGTACAACAGCCACAAAGA

GTACACCTGCAAGGTGACCCAGGGCACGACCTCAGTCGTCCAGAGC

TTCAATAGGGGTGACTGTTAG

A11B1_6B6 Heavy Chain (SEQ ID NO: 83)

ATGGAGACTGGGCTGCGCTGGCTTCTCCTGGTCGCTGTGCTCAAAG

GTGTCCAGTGTCAGCAACATCTGGTGGAGTCCGGGGGAGGCCTGGT

CAAGCCTGGGGCATCCCTGACACTCACCTGCACAGCCTCTGGATTC

TCCTTCACTACCGGCTATCACATGTGCTGGGTCCGCCAGGCTCCAG

GGAAGGGGCTGGAGTGGATCGCATGTTTTGGTGTTTATACTAGTAC

CACTACCTACGCGAGCTGGGCGAAAGGTCGATTCACCATCTCCAAA

ACCTCGTCGACCACGGTGACTCTACAAATGACCAGTCTAACAGTCG

CGGACACGGCCACCTATTTCTGTGCGAGAATCAGTGCTGAAGATGG

TGGGGACTTGTGGGGCCCAGGCACCCTGGTCACCGTCTCCTCAGGG

CAACCTAAGGCTCCATCAGTCTTCCCACTGGCCCCCTGCTGCGGGG

ACACACCCAGCTCCACGGTGACCCTGGGCTGCCTGGTCAAAGGCTA

CCTCCCGGAGCCAGTGACCGTGACCTGGAACTCGGGCACCCTCACC

AATGGGGTACGCACCTTCCCGTCCGTCCGGCAGTCCTCAGGCCTCT

ACTCGCTGAGCAGCGTGGTGAGCGTGACCTCAAGCAGCCAGCCCGT

CACCTGCAACGTGGCCCACCCAGCCACCAACACCAAAGTGGACAAG

ACCGTTGCGCCCTCGACATGCAGCAAGCCCATGTGCCCACCCCCTG

AACTCCCGGGGGGACCGTCTGTCTTCATCTTCCCCCCAAAACCCAA

GGACACCCTCATGATCTCACGCACCCCCGAGGTCACATGCGTGGTG

GTGGACGTGAGCCAGGATGACCCCGAGGTGCAGTTCACATGGTACA

-continued

TAAACAACGAGCAGGTGCGCACCGCCCGGCCGCCGCTACGGGAGCA
GCAGTTCAACAGCACGATCCGCGTGGTCAGCACCCTCCCCATCGCG
CACCAGGACTGGCTGAGGGGCAAGGAGTTCAAGTGCAAAGTCCACA
ACAAGGCACTCCCGGCCCCCATCGAGAAAACCATCTCCAAAGCCAG
AGGGCAGCCCCTGGAGCCGAAGGTCTACACCATGGGCCCTCCCCGG
GAGGAGCTGAGCAGCAGGTCGGTCAGCCTGACCTGCATGATCAACG
GCTTCTACCCTTCCGACATCTCGGTGGAGTGGGAGAAGAACGGGAA
GGCAGAGGACAACTACAAGACCACGCCGACCGTGCTGGACAGCGAC
GGCTCCTACTTCCTCTACAGCAAGCTCTCAGTGCCCACGAGTGAGT
GGCAGCGGGGCGACGTCTTCACCTGCTCCGTGATGCACGAGGCCTT
GCACAACCACTACACGCAGAAGTCCATCTCCCGCTCTCCGGGTAAA
TAG

A11B1_6B6 Light Chain (SEQ ID NO: 84)

ATGGACACGAGGGCCCCCACTCAGCTGCTGGGGCTCCTGCTGCTCT
GGCTCCCAGGTGCCAGATGTGATGTTGTGATGACCCAGACTCCAGC
CTCCGTGGAGGCAGCTGTGGGAGGCACAGTCACCATCACGTGCCAG
GCCAGTCAGAGCATTAGCAACTACTTTTCTTGGTATCAGCAGAAAC
CAGGGCAGCCTCCCAAGCTCCTGATCTACAGGGCGTCCACTCTGGC
ATCTGGGGTCCCATCGCGGTTCAGCGGCAGTGGATCTGGGACACAG
TTCACTCTCACCATCAGCGACCTGGAGTGTGCCGATTCTGCCACTT
ACGCCTGTCAGTGCACTTATGGTAGTAGTAGTACTGGTTTTGGTTT
CGGCGGAGGGACCGAGGTGGTGGTCAAAGGTGATCCAGTTGCACCT
ACTGTCCTCATCTTCCCACCAGCTGCTGATCAGGTGGCAACTGGAA
CAGTCACCATCGTGTGTGTGGCGAATAAATACTTTCCCGATGTCAC
CGTCACCTGGGAGGTGGATGGCACCACCCAAACAACTGGCATCGAG
AACAGTAAAACACCGCAGAATTCTGCAGATTGTACCTACAACCTCA
GCAGCACTCTGACACTGACCAGCACACAGTACAACAGCCACAAAGA
GTACACCTGCAAGGTGACCCAGGGCACGACCTCAGTCGTCCAGAGC
TTCAATAGGGGTGACTGTTAG

A11B1_5F7 Heavy Chain (SEQ ID NO: 85)

ATGGAGACTGGGCTGCGCTGGCTTCTCCTGGTCGCTGTGCTCAAAG
GTGTCCAGTGTCAGTCGTTGGAGGAGTCCGGGGGAGACCTGGTCAA
GCCTGGGGCATCCCTGACACTCACCTGCAAAGCCTCTGGATTCTCC
TTCAGTAGTTACTTCTGGATATGCTGGGTCCGCCAGGCTCCAGGGA
AGGGGCTGGAGTGGAGCGCATGCATCTATGGTGATAGTAGTGGTAG
TAGTTACTACGCGAGCTGGGCGAAAGGCCGATTCACCATCTCCAAA
ACCTCGTCGACCACGGTGACTCTGCAAATGACCAGTCTGACAGCCG
CGGACACGGCCACCTATTTCTGTGCGAGTTATGGTAGTAGTAGTTA
TTACTACTCTAATTTATGGGGCCCAGGCACCCTGGTCACCGTCTCC
TCAGGGCAACCTAAGGCTCCATCAGTCTTCCCACTGGCCCCCTGCT
GCGGGGACACACCCAGCTCCACGGTGACCCTGGGCTGCCTGGTCAA
AGGCTACCTCCCGGAGCCAGTGACCGTGACCTGGAACTCGGGCACC
CTCACCAATGGGGTACGCACCTTCCCGTCCGTCCGGCAGTCCTCAG
GCCTCTACTCGCTGAGCAGCGTGGTGAGCGTGACCTCAAGCAGCCA
GCCCGTCACCTGCAACGTGGCCCACCCAGCCACCAACACCAAAGTG
GACAAGACCGTTGCGCCCTCGACATGCAGCAAGCCCATGTGCCCAC
CCCCTGAACTCCCGGGGGGACCGTCTGTCTTCATCTTCCCCCCAAA
ACCCAAGGACACCCTCATGATCTCACGCACCCCCGAGGTCACATGC
GTGGTGGTGGACGTGAGCCAGGATGACCCCGAGGTGCAGTTCACAT
GGTACATAAACAACGAGCAGGTGCGCACCGCCCGGCCGCCGCTACG
GGAGCAGCAGTTCAACAGCACGATCCGCGTGGTCAGCACCCTCCCC
ATCGCGCACCAGGACTGGCTGAGGGGCAAGGAGTTCAAGTGCAAAG
TCCACAACAAGGCACTCCCGGCCCCCATCGAGAAAACCATCTCCAA
AGCCAGAGGGCAGCCCCTGGAGCCGAAGGTCTACACCATGGGCCCT
CCCCGGGAGGAGCTGAGCAGCAGGTCGGTCAGCCTGACCTGCATGA
TCAACGGCTTCTACCCTTCCGACATCTCGGTGGAGTGGGAGAAGAA
CGGGAAGGCAGAGGACAACTACAAGACCACGCCGACCGTGCTGGAC
AGCGACGGCTCCTACTTCCTCTACAGCAAGCTCTCAGTGCCCACGA
GTGAGTGGCAGCGGGGCGACGTCTTCACCTGCTCCGTGATGCACGA
GGCCTTGCACAACCACTACACGCAGAAGTCCATCTCCCGCTCTCCG
GGTAAATAG

A11B1_5F7 Light Chain (SEQ ID NO: 86)

ATGGACACGAGGGCCCCCACTCAGCTGCTGGGGCTCCTGCTGCTCT
GGCTCCCAGGTGCCATATGTGACCCTGTGATGACCCAGACTCCATC
TTCCACGTCTGCGGCTGTGGGAGGCACAGTCACCATCAGTTGCCAG
TCCAGTCAGAGTGTTTATAATAACAACTACTTAGCCTGGTATCAGC
AGAAACCAGGGCAGCCTCCCAAACGCCTGATCTACGAATCATCCAA
ACTGGCATCTGGGGTCCCATCGCGGTTCAGAGGCAGTGGATCTGGG
GCACAGTTCACTCTCACCATCAGCGACCTGGAGTGTGACGATGCTG
CCACTTACTACTGTCTAGGCGCATATTATACTACTCTTGATTTCGG
CGGAGGGACCGAGGTGGTGGTCAGAGGTGATCCAGTTGCACCTACT
GTCCTCATCTTCCCACCAGCTGCTGATCAGGTGGCAACTGGAACAG
TCACCATCGTGTGTGTGGCGAATAAATACTTTCCCGATGTCACCGT
CACCTGGGAGGTGGATGGCACCACCCAAACAACTGGCATCGAGAAC
AGTAAAACACCGCAGAATTCTGCAGATTGTACCTACAACCTCAGCA
GCACTCTGACACTGACCAGCACACAGTACAACAGCCACAAAGAGTA
CACCTGCAAGGTGACCCAGGGCACGACCTCAGTCGTCCAGAGCTTC
AATAGGGGTGACTGTTAG

A11B1_5D7 Heavy Chain (SEQ ID NO: 87)

ATGGAGACTGGGCTGCGCTGGCTTCTCCTGGTCGCTGTGCTCAAAG
GTGTCCAGTGTCAGGAGCAGTTGGTGGAGTCCGGGGGAGGCCTGGT

-continued

CCAGCCTGAGGGATCCCTGACACTCACCTGCAAAGCCTCTGGATTC

GACTTCAGTAGCAATGCAATGTGCTGGGTCCGCCAGGCTCCAGGGA

AGGGGCTGGAGTGGATCGCATGCATTTATAATGGTGATGGCAGCAC

ATACTACGCGAGCTGGGTGAATGGCCGATTCACCATCTCCAAGACC

TCGTCGACCACGGTGACTCTGCAAATGACCAGTCTGACAGCCGCGG

ACACGGCCACCTATTTCTGTGCGAGAGGTCTCTCTAATTGGAATAG

GGATAACTTATGGGGCCCTGGCACCCTGGTCACCGTCTCCTCAGGG

CAACCTAAGGCTCCATCAGTCTTCCCACTGGCCCCCTGCTGCGGGG

ACACACCCAGCTCCACGGTGACCCTGGGCTGCCTGGTCAAAGGCTA

CCTCCCGGAGCCAGTGACCGTGACCTGGAACTCGGGCACCCTCACC

AATGGGGTACGCACCTTCCCGTCCGTCCGGCAGTCCTCAGGCCTCT

ACTCGCTGAGCAGCGTGGTGAGCGTGACCTCAAGCAGCCAGCCCGT

CACCTGCAACGTGGCCCACCCAGCCACCAACACCAAAGTGGACAAG

ACCGTTGCGCCCTCGACATGCAGCAAGCCCATGTGCCCACCCCCTG

AACTCCCGGGGGGACCGTCTGTCTTCATCTTCCCCCCAAAACCCAA

GGACACCCTCATGATCTCACGCACCCCCGAGGTCACATGCGTGGTG

GTGGACGTGAGCCAGGATGACCCCGAGGTGCAGTTCACATGGTACA

TAAACAACGAGCAGGTGCGCACCGCCCGGCCGCCGCTACGGGAGCA

GCAGTTCAACAGCACGATCCGCGTGGTCAGCACCCTCCCCATCGCG

CACCAGGACTGGCTGAGGGGCAAGGAGTTCAAGTGCAAAGTCCACA

ACAAGGCACTCCCGGCCCCCATCGAGAAAACCATCTCCAAAGCCAG

AGGGCAGCCCCTGGAGCCGAAGGTCTACACCATGGGCCCTCCCCGG

GAGGAGCTGAGCAGCAGGTCGGTCAGCCTGACCTGCATGATCAACG

GCTTCTACCCTTCCGACATCTCGGTGGAGTGGGAGAAGAACGGGAA

GGCAGAGGACAACTACAAGACCACGCCGACCGTGCTGGACAGCGAC

GGCTCCTACTTCCTCTACAGCAAGCTCTCAGTGCCCACGAGTGAGT

GGCAGCGGGGCGACGTCTTCACCTGCTCCGTGATGCACGAGGCCTT

GCACAACCACTACACGCAGAAGTCCATCTCCCGCTCTCCGGGTAAA

TAG

A11B1_5D7 Light Chain (SEQ ID NO: 88)

ATGGACACGAGGGCCCCCACTCAGCTGCTGGGGCTCCTGCTGCTCT

GGCTCCCAGGTGCCACATTTGCCCAAGTGCTGACCCAGACTCCATC

CTCCGTGTCTGCAGCTGTGGGAGGCACAGCCACCATCAACTGCCAG

GCCAGTCAGAGTCTTTATAGTCCCAAGAATTTAGCCTGGTATCAGC

AGACACCAGGGCAGCCTCCCAAGCTCCTGATCTATTCTGCATCGAA

ACTGGCATCTGGGGTCCCATCGCGGTTCAAAGGCAGTGGATCTGGG

ACACAGTTCACTCTCACCATCAGCGGCGTGCAGTGTGACGATGCTG

CAATTTACTACTGTCAAGGCGAATTTAGTTGTACTACTGCTGCTTG

TTTTGCTTTTGGCGGAGGGACCGAGGTGGTGGTCAAAGGTGATCCA

GTTGCACCTACTGTCCTCATCTTCCCACCAGCTGCTGATCAGGTGG

CAACTGGAACAGTCACCATCGTGTGTGTGGCGAATAAATACTTTCC

-continued

CGATGTCACCGTCACCTGGGAGGTGGATGGCACCACCCAAACAACT

GGCATCGAGAACAGTAAAACACCGCAGAATTCTGCAGATTGTACCT

ACAACCTCAGCAGCACTCTGACACTGACCAGCACACAGTACAACAG

CCACAAAGAGTACACCTGCAAGGTGACCCAGGGCACGACCTCAGTC

GTCCAGAGCTTCAATAGGGGTGACTGTTAG

A11B1_5A7 Heavy Chain (SEQ ID NO: 89)

ATGGAGACTGGGCTGCGCTGGCTTCTCCTGGTCGCTGTGCTCAAAG

GTGTCCAGTGTCAGTCTTTGGAGGAGTCCGGGGGAGGCCTGGTCCA

GCCTGAGGGATCCCTGACACTCGCCTGCACAGCTTCGGGATTCTCC

TTCAGTAGCTACTACTACATCTGCTGGGTCCGCCAGGCTCCAGGGA

CGGGGCTGGAGTGGATCGGATGCATTAATACTGGTAGTGATGACAC

TCACTACGCGAGCTGGTTGAAAGGCCGATTCACCTTCTCCAAGGCC

TCGTCGACCACGTTGACTCTGCAAATGACCAGTCTGACAGCCGCGG

ACACGGCCACCTATTTCTGTGCGAGATCATCTGGTAGTAGTGATGA

TGCTTATGATCTCTGGGGCCCAGGCACCCTGGTCACTGTCTCCTCA

GGGCAACCTAAGGCTCCATCAGTCTTCCCACTGGCCCCCTGCTGCG

GGGACACACCCAGCTCCACGGTGACCCTGGGCTGCCTGGTCAAAGG

CTACCTCCCGGAGCCAGTGACCGTGACCTGGAACTCGGGCACCCTC

ACCAATGGGGTACGCACCTTCCCGTCCGTCCGGCAGTCCTCAGGCC

TCTACTCGCTGAGCAGCGTGGTGAGCGTGACCTCAAGCAGCCAGCC

CGTCACCTGCAACGTGGCCCACCCAGCCACCAACACCAAAGTGGAC

AAGACCGTTGCGCCCTCGACATGCAGCAAGCCCATGTGCCCACCCC

CTGAACTCCCGGGGGGACCGTCTGTCTTCATCTTCCCCCCAAAACC

CAAGGACACCCTCATGATCTCACGCACCCCCGAGGTCACATGCGTG

GTGGTGGACGTGAGCCAGGATGACCCCGAGGTGCAGTTCACATGGT

ACATAAACAACGAGCAGGTGCGCACCGCCCGGCCGCCGCTACGGGA

GCAGCAGTTCAACAGCACGATCCGCGTGGTCAGCACCCTCCCCATC

GCGCACCAGGACTGGCTGAGGGGCAAGGAGTTCAAGTGCAAAGTCC

ACAACAAGGCACTCCCGGCCCCCATCGAGAAAACCATCTCCAAAGC

CAGAGGGCAGCCCCTGGAGCCGAAGGTCTACACCATGGGCCCTCCC

CGGGAGGAGCTGAGCAGCAGGTCGGTCAGCCTGACCTGCATGATCA

ACGGCTTCTACCCTTCCGACATCTCGGTGGAGTGGGAGAAGAACGG

GAAGGCAGAGGACAACTACAAGACCACGCCGACCGTGCTGGACAGC

GACGGCTCCTACTTCCTCTACAGCAAGCTCTCAGTGCCCACGAGTG

AGTGGCAGCGGGGCGACGTCTTCACCTGCTCCGTGATGCACGAGGC

CTTGCACAACCACTACACGCAGAAGTCCATCTCCCGCTCTCCGGGT

AAATAG

A11B1_5A7 Light Chain (SEQ ID NO: 90)

ATGGACACGAGGGCCCCCACTCAGCTGCTGGGGCTCCTGCTGCTCT

GGCTCCCAGGTGCCAGATGTGATGTTGTGATGACCCAGACTCCAGC

-continued

CTCCGTGTCTGAACCTGTGGGAGGCGCAGTCACCATCAAGTGCCAG

GCCAGTCAGAGCATTGGTAGTAATTTAGCCTGGTATCAGCACAAAC

CAGGGCAGCCTCCCAAGCTCCTGATCTATTTTGCATCCAGCCTGGC

ATCTGGGGTCTCGTCGCGGTTCAAGGGCGGTAGATCTGGGACACAG

TTCACTCTCACCATCAGCGACCTGGAGTGTGCCGATGCTGCCACTT

ACTACTGTCACTGTACTTATTATCCTCTTAGTTATGTTACTTTCGG

CGGAGGGACCGAGGTGGTGGTCAAAGGTGATCCAGTTGCACCTACT

GTCCTCATCTTCCCACCAGCTGCTGATCAGGTGGCAACTGGAACAG

TCACCATCGTGTGTGTGGCGAATAAATACTTTCCCGATGTCACCGT

CACCTGGGAGGTGGATGGCACCACCCAAACAACTGGCATCGAGAAC

AGTAAAACACCGCAGAATTCTGCAGATTGTACCTACAACCTCAGCA

GCACTCTGACACTGACCAGCACACAGTACAACAGCCACAAAGAGTA

CACCTGCAAGGTGACCCAGGGCACGACCTCAGTCGTCCAGAGCTTC

AATAGGGGTGACTGTTAG

A11B1_4E1 Heavy Chain (SEQ ID NO: 91)

ATGGAGACTGGGCTGCGCTGGCTTCTCCTGGTCGCTGTGCTCAAAG

GTGTCCAGTGTCAGTCGTTGGAGGAGTCCGGGGGAGACCTGGTCAA

GCCTGGGACATCCCTGACACTCTCCTGCACAGCCTCTGGATTCTCC

TTCGGTAGCTATTATTATATGTGCTGGGTCCGCCAGGCTCCAGGGA

AGGGGCTGGAGTGGATCGCATGCATTGATGTTGGTAGTAGTGGTGA

CACATACTACGCGAGCTGGGTGAATGGCCGATTCACCATCTCCAAA

ACCTCGTCGACCACGGTGACTCTGCAAATGACCAGTCTGACAGCCG

CGGACACGGCCACCTATTTCTGTGCGAGAGATGATACTGCTGCTGG

TGGTTTTGGTAATTTGGAATTGTGGGGCCCAGGCACCCTGGTCACC

GTCTCCTCAGGGCAACCTAAGGCTCCATCAGTCTTCCCACTGGCCC

CCTGCTGCGGGGACACACCCAGCTCCACGGTGACCCTGGGCTGCCT

GGTCAAAGGCTACCTCCCGGAGCCAGTGACCGTGACCTGGAACTCG

GGCACCCTCACCAATGGGGTACGCACCTTCCCGTCCGTCCGGCAGT

CCTCAGGCCTCTACTCGCTGAGCAGCGTGGTGAGCGTGACCTCAAG

CAGCCAGCCCGTCACCTGCAACGTGGCCCACCCAGCCACCAACACC

AAAGTGGACAAGACCGTTGCGCCCTCGACATGCAGCAAGCCCATGT

GCCCACCCCCTGAACTCCCGGGGGGACCGTCTGTCTTCATCTTCCC

CCCAAAACCCAAGGACACCCTCATGATCTCACGCACCCCCGAGGTC

ACATGCGTGGTGGTGGACGTGAGCCAGGATGACCCCGAGGTGCAGT

TCACATGGTACATAAACAACGAGCAGGTGCGCACCGCCCGGCCGCC

GCTACGGGAGCAGCAGTTCAACAGCACGATCCGCGTGGTCAGCACC

CTCCCCATCGCGCACCAGGACTGGCTGAGGGGCAAGGAGTTCAAGT

GCAAAGTCCACAACAAGGCACTCCCGGCCCCCATCGAGAAAACCAT

CTCCAAAGCCAGAGGGCAGCCCCTGGAGCCGAAGGTCTACACCATG

GGCCCTCCCCGGGAGGAGCTGAGCAGCAGGTCGGTCAGCCTGACCT

GCATGATCAACGGCTTCTACCCTTCCGACATCTCGGTGGAGTGGGA

-continued

GAAGAACGGGAAGGCAGAGGACAACTACAAGACCACGCCGACCGTG

CTGGACAGCGACGGCTCCTACTTCCTCTACAGCAAGCTCTCAGTGC

CCACGAGTGAGTGGCAGCGGGGCGACGTCTTCACCTGCTCCGTGAT

GCACGAGGCCTTGCACAACCACTACACGCAGAAGTCCATCTCCCGC

TCTCCGGGTAAATAG

A11B1_4E1 Light Chain (SEQ ID NO: 92)

ATGGACACGAGGGCCCCCACTCAGCTGCTGGGGCTCCTGCTGCTCT

GGCTCCCAGGTGCCAGATGTGCATTCGAATTGACCCAGACTCCATC

CTCCGTGTCTGAACCTGTGGGAGGCACAGTCACCATCAAGTGCCAG

GCCAGTCAGAGCATTTACAGCTACTTTTCCTGGTATCAGCAGAAAC

CAGGGCAGCCTCCCAAGCGCCTGATTTACCAGGCATCCACTCTGGC

TTCTGGGGTCCCATCGCGGTTCAAAGGCAGTGGATCTGGGACAGAT

TTCACTCTCACCATCAGCGACCTGGAGTGTGCCGATGCTGCCACTT

ACTACTGTCAAAACAATTATGGTAGGGGTAGTGGTAGTTATTTTTT

TGGTTTCGGCGGAGGGACCGAGGTGGTGGTCAAAGGTGATCCAGTT

GCACCTACTGTCCTCATCTTCCCACCAGCTGCTGATCAGGTGGCAA

CTGGAACAGTCACCATCGTGTGTGTGGCGAATAAATACTTTCCCGA

TGTCACCGTCACCTGGGAGGTGGATGGCACCACCCAAACAACTGGC

ATCGAGAACAGTAAAACACCGCAGAATTCTGCAGATTGTACCTACA

ACCTCAGCAGCACTCTGACACTGACCAGCACACAGTACAACAGCCA

CAAAGAGTACACCTGCAAGGTGACCCAGGGCACGACCTCAGTCGTC

CAGAGCTTCAATAGGGGTGACTGTTAG

A11B1_3H9 Heavy Chain (SEQ ID NO: 93)

ATGGAGACTGGGCTGCGCTGGCTTCTCCTGGTCGCTGTGCTCAAAG

GTGTCCAGTGTCAGTCGTTGGAGGAGTCCGGGGGAGACCTGGTCAA

GCCTGGGGCATCCCTGACACTCACCTGCAAAGCCTCTGGAATCGAC

TTCAGTAGCGGCTACGGCATGTGGTGGGTCCGCCAGGCTCCAGGGA

AGGGACTGGAGTATATCGGATACATTGATACTGGTAGTGGTAGCAC

TTACTACGCGAACTGGGCGAAAGGCCGATTCACCATCTCCAAAACC

TCGTCGACCATGGTGACTCTGCAAATGACCAGTCTGACAGTCGCGG

ACACGGCCACCTATTTCTGTGCGAAAGGGGGCGCCATAGACCTCTG

GGGCCCAGGGACCCTCGTCACCGTCTCTTCAGGGCAACCTAAGGCT

CCATCAGTCTTCCCACTGGCCCCCTGCTGCGGGGACACACCCAGCT

CCACGGTGACCCTGGGCTGCCTGGTCAAAGGCTACCTCCCGGAGCC

AGTGACCGTGACCTGGAACTCGGGCACCCTCACCAATGGGGTACGC

ACCTTCCCGTCCGTCCGGCAGTCCTCAGGCCTCTACTCGCTGAGCA

GCGTGGTGAGCGTGACCTCAAGCAGCCAGCCCGTCACCTGCAACGT

GGCCCACCCAGCCACCAACACCAAAGTGGACAAGACCGTTGCGCCC

TCGACATGCAGCAAGCCCATGTGCCCACCCCCTGAACTCCCGGGGG

GACCGTCTGTCTTCATCTTCCCCCCAAAACCCAAGGACACCCTCAT

-continued

GATCTCACGCACCCCCGAGGTCACATGCGTGGTGGTGGACGTGAGC
CAGGATGACCCCGAGGTGCAGTTCACATGGTACATAAACAACGAGC
AGGTGCGCACCGCCCGGCCGCCGCTACGGGAGCAGCAGTTCAACAG
CACGATCCGCGTGGTCAGCACCCTCCCCATCGCGCACCAGGACTGG
CTGAGGGGCAAGGAGTTCAAGTGCAAAGTCCACAACAAGGCACTCC
CGGCCCCCATCGAGAAAACCATCTCCAAAGCCAGAGGGCAGCCCCT
GGAGCCGAAGGTCTACACCATGGGCCCTCCCCGGGAGGAGCTGAGC
AGCAGGTCGGTCAGCCTGACCTGCATGATCAACGGCTTCTACCCTT
CCGACATCTCGGTGGAGTGGGAGAAGAACGGGAAGGCAGAGGACAA
CTACAAGACCACGCCGACCGTGCTGGACAGCGACGGCTCCTACTTC
CTCTACAGCAAGCTCTCAGTGCCCACGAGTGAGTGGCAGCGGGGCG
ACGTCTTCACCTGCTCCGTGATGCACGAGGCCTTGCACAACCACTA
CACGCAGAAGTCCATCTCCCGCTCTCCGGGTAAATAG

A11B1_3H9 Light Chain (SEQ ID NO: 94)

ATGGACACGAGGGCCCCCACTCAGCTGCTGGGACTCCTACTGCTCT
GGCTCCCAGGTGCCAGATGTGCTGACATTGTGATGACCCAGACTCC
AGCCTCCGTGGAGGCAGCTGTGGGAGGCACAGTCACCATCAAGTGC
CAGGCCAGTCAGAGCATTAGTAGTTACTTAGCCTGGTATCAGCAGA
AACCAGGGCAGCGTCCCAAGCTCCTGATCTACAGGGCATCCACTCT
GGCATCTGGGGTCCCATCGCGGTTCAAAGGCAGTGGATCTGGGACA
GACTACACTCTCACCATCAGCGACCTGGAGTGTGCCGATGCTGCCA
CTTATTATTGTCATACCTATTATCTTAGTAGTAGTATCAGTTATGG
TAATACTTTCGGCGGAGGGACCGAGGTGGTGGTCAAAGGTGATCCA
GTTGCACCTACTGTCCTCATCTTCCCACCAGCTGCTGATCAGGTGG
CAACTGGAACAGTCACCATCGTGTGTGTGGCGAATAAATACTTTCC
CGATGTCACCGTCACCTGGGAGGTGGATGGCACCACCCAAACAACT
GGCATCGAGAACAGTAAAACACCGCAGAATTCTGCAGATTGTACCT
ACAACCTCAGCAGCACTCTGACACTGACCAGCACACAGTACAACAG
CCACAAAGAGTACACCTGCAAGGTGACCCAGGGCACGACCTCAGTC
GTCCAGAGCTTCAATAGGGGTGACTGTTAG

A11B1_3G2 Heavy Chain (SEQ ID NO: 95)

ATGGAGACTGGGCTGCGCTGGCTTCTCCTGGTCGCTGTGCTCAAAG
GTGTCCAGTGTCAGGAGCAGCTGGAGGAGTCCGGGGGAGACCTGGT
CAAGCCTGAGGGATCCCTGACACTCACCTGCAAAGCCTCTGGATTC
TCCTTCAGTAGCATCTACTGGATTTGCTGGGTCCGCCAGGCTCCAG
GGAAGGGGCTGGAGTGGATCGCATGCACTACTGTTGTCAAAAGTGG
TAGAACTTACTACGCGAACTGGGCGAAAGGCCGATTCACCATCTCC
AAAACCTCGTCGACCACGGTGACTCTGCAAATGACCAGTCTGACAG
CCGCGGACACGGCCACCTATTTCTGTGCGAGAGAATTTGTTGATGG
TGGTGGTAGTAGTGGTAGGGACTTGTGGGGCCCAGGCACCCTGGTC
ACCGTCTCCTCAGGGCAACCTAAGGCTCCATCAGTCTTCCCACTGG

-continued

CCCCCTGCTGCGGGGACACACCCAGCTCCACGGTGACCCTGGGCTG
CCTGGTCAAAGGCTACCTCCCGGAGCCAGTGACCGTGACCTGGAAC
TCGGGCACCCTCACCAATGGGGTACGCACCTTCCCGTCCGTCCGGC
AGTCCTCAGGCCTCTACTCGCTGAGCAGCGTGGTGAGCGTGACCTC
AAGCAGCCAGCCCGTCACCTGCAACGTGGCCCACCCAGCCACCAAC
ACCAAAGTGGACAAGACCGTTGCGCCCTCGACATGCAGCAAGCCCA
TGTGCCCACCCCCTGAACTCCCGGGGGGACCGTCTGTCTTCATCTT
CCCCCCAAAACCCAAGGACACCCTCATGATCTCACGCACCCCCGAG
GTCACATGCGTGGTGGTGGACGTGAGCCAGGATGACCCCGAGGTGC
AGTTCACATGGTACATAAACAACGAGCAGGTGCGCACCGCCCGGCC
GCCGCTACGGGAGCAGCAGTTCAACAGCACGATCCGCGTGGTCAGC
ACCCTCCCCATCGCGCACCAGGACTGGCTGAGGGGCAAGGAGTTCA
AGTGCAAAGTCCACAACAAGGCACTCCCGGCCCCCATCGAGAAAAC
CATCTCCAAAGCCAGAGGGCAGCCCCTGGAGCCGAAGGTCTACACC
ATGGGCCCTCCCCGGGAGGAGCTGAGCAGCAGGTCGGTCAGCCTGA
CCTGCATGATCAACGGCTTCTACCCTTCCGACATCTCGGTGGAGTG
GGAGAAGAACGGGAAGGCAGAGGACAACTACAAGACCACGCCGACC
GTGCTGGACAGCGACGGCTCCTACTTCCTCTACAGCAAGCTCTCAG
TGCCCACGAGTGAGTGGCAGCGGGGCGACGTCTTCACCTGCTCCGT
GATGCACGAGGCCTTGCACAACCACTACACGCAGAAGTCCATCTCC
CGCTCTCCGGGTAAATAG

A11B1_3G2 Light Chain (SEQ ID NO: 96)

ATGGACACGAGGGCCCCCACTCAGCTGCTGGGGCTCCTGCTGCTCT
GGCTCCCAGGTGCCAGATGTGCCTATGATATGACCCAGACTCCAGC
CTCCGTGGAGGCAGCTGTGGGAGGCACAGTCACCATCAAGTGCCAG
GCCAGTCAGAGCATTAGTAGGGACTTATCCTGGTATCAGCAGAAAC
CTGGACAGCCTCCCAAGCGCCTAATCTACAAGGCATCCACTCTGGC
ATCTGGGGTCCCATCGCGGTTCAAAGGCAGTGGATCTGGGACAGAT
TTCACTCTCACCATCAGCGACCTGGAGTGTGCCGATGCTGCCACTT
ACTACTGTCAACAGGGTTATAGTAGTATTGATGTTGATAATGATTT
CGGCGGAGGGACCGAGGTGGTGGTCAAAGGTGATCCAGTTGCACCT
ACTGTCCTCATCTTCCCACCAGCTGCTGATCAGGTGGCAACTGGAA
CAGTCACCATCGTGTGTGTGGCGAATAAATACTTTCCCGATGTCAC
CGTCACCTGGGAGGTGGATGGCACCACCCAAACAACTGGCATCGAG
AACAGTAAAACACCGCAGAATTCTGCAGATTGTACCTACAACCTCA
GCAGCACTCTGACACTGACCAGCACACAGTACAACAGCCACAAAGA
GTACACCTGCAAGGTGACCCAGGGCACGACCTCAGTCGTCCAGAGC
TTCAATAGGGGTGACTGTTAG

-continued

A11B1_3B1 Heavy Chain (SEQ ID NO: 97)

ATGGAGACTGGGCTGCGCTGGCTTCTCCTGGTCGCTGTGCTCAAAG
GTGTCCAGTGTCAGGAGCAGCTGGAGGAGTCCGGGGGAGGCCTGGT
CAAGCCTGAGGGATCCCTGACACTCACCTGCAAAGCCTCTGGATTC
GACCTCAGTAGCGGCTATGACATGTGCTGGGTCCGCCAGGCTCCAG
GGAAGGGGCTGGAGTGGATCGCATGCATTTATGCTGATTATAGTGG
TAGCACATACTACGCGAGCTGGGTGAATGGCCGATTCACCATCTCC
AGCAGCACCAGCCTAAACACGGTGGATCTGAAAATGACCAGTCTGA
CAGCCGCGGACACGGCCACCTATTTCTGTGCCAGAGGGGCTACTGG
TAATGGTGGTTATGGATACTACTTTAACTTGTGGGGCCCAGGCACC
CTGGTCACCGTCTCCTCAGGGCAACCTAAGGCTCCATCAGTCTTCC
CACTGGCCCCCTGCTGCGGGGACACACCCAGCTCCACGGTGACCCT
GGGCTGCCTGGTCAAAGGCTACCTCCCGGAGCCAGTGACCGTGACC
TGGAACTCGGGCACCCTCACCAATGGGGTACGCACCTTCCCGTCCG
TCCGGCAGTCCTCAGGCCTCTACTCGCTGAGCAGCGTGGTGAGCGT
GACCTCAAGCAGCCAGCCCGTCACCTGCAACGTGGCCCACCCAGCC
ACCAACACCAAAGTGGACAAGACCGTTGCGCCCTCGACATGCAGCA
AGCCCATGTGCCCACCCCCTGAACTCCCGGGGGGACCGTCTGTCTT
CATCTTCCCCCCAAAACCCAAGGACACCCTCATGATCTCACGCACC
CCCGAGGTCACATGCGTGGTGGTGGACGTGAGCCAGGATGACCCCG
AGGTGCAGTTCACATGGTACATAAACAACGAGCAGGTGCGCACCGC
CCGGCCGCCGCTACGGGAGCAGCAGTTCAACAGCACGATCCGCGTG
GTCAGCACCCTCCCCATCGCGCACCAGGACTGGCTGAGGGGCAAGG
AGTTCAAGTGCAAAGTCCACAACAAGGCACTCCCGGCCCCCATCGA
GAAAACCATCTCCAAAGCCAGAGGGCAGCCCCTGGAGCCGAAGGTC
TACACCATGGGCCCTCCCCGGGAGGAGCTGAGCAGCAGGTCGGTCA
GCCTGACCTGCATGATCAACGGCTTCTACCCTTCCGACATCTCGGT
GGAGTGGGAGAAGAACGGGAAGGCAGAGGACAACTACAAGACCACG
CCGACCGTGCTGGACAGCGACGGCTCCTACTTCCTCTACAGCAAGC
TCTCAGTGCCCACGAGTGAGTGGCAGCGGGGCGACGTCTTCACCTG
CTCCGTGATGCACGAGGCCTTGCACAACCACTACACGCAGAAGTCC
ATCTCCCGCTCTCCGGGTAAATAG

A11B1_3B1 Light Chain (SEQ ID NO: 98)

ATGGACACGAGGGCCCCCACTCAGCTGCTGGGGCTCCTACTGCTCT
GGCTCCCAGGTGCCAGATGTGCTGACATTGTGATGACCCAGACTCC
AGCCTCCGTGTCTGAACCTGTGGGAGGCACAGTCACCATCAAGTGT
CAGGCCAGTCAGAACATTAATAGCGGCTTAGCCTGGTATCAGCAGA
AACCAGGGCAGCCTCCCAAGCTCCTGATCTACAAGGCATCCACTCT
GGCATCTGGGGTCTCATCGCGGTTCAAAGGCAGTGGATCTGGGACA
GAATTCACTCTCACCATCAGCGACCTGGAGTGTGCCGATGCTGCCA
CTTACTACTGTCAAACCTATTATTATAGTAGTAGTAGTAGTGATAA
TGCTTTCGGCGGAGGGACCGAGGTGGTGGTCAAAGGTGATCCAGTT
GCACCTACTGTCCTCATCTTCCCACCAGCTGCTGATCAGGTGGCAA
CTGGAACAGTCACCATCGTGTGTGTGGCGAATAAATACTTTCCCGA
TGTCACCGTCACCTGGGAGGTGGATGGCACCACCCAAACAACTGGC
ATCGAGAACAGTAAAACACCGCAGAATTCTGCAGATTGTACCTACA
ACCTCAGCAGCACTCTGACACTGACCAGCACACAGTACAACAGCCA
CAAAGAGTACACCTGCAAGGTGACCCAGGGCACGACCTCAGTCGTC
CAGAGCTTCAATAGGGGTGACTGTTAG

A11B1_2D3 Heavy Chain (SEQ ID NO: 99)

ATGGAGACTGGGCTGCGCTGGCTTCTCCTGGTCGCTGTGCTCAAAGG
TGTCCAGTGTCAGTCGTTGGAGGAGTCCGGGGGAGACCTGGTCAAG
CCTGGGGCATCCCTGACACTCACCTGCACAGCTTCTGGATTCTCCT
TCAGTAGCAGTTATTGGATATGCTGGGTCCGCCAGGCTCCAGGGAA
GGGGCTGGAGTGGATCGCATGTATTTATGGTGGTAGTAGTGGTAAC
ATTGCCTACGCGAGCTGGGCGAAAGGCCGATTCACCATCTCCAAAA
CCTCGTCGACCACGGTGACTCTACAAATGACCAGTCTGACAGCCGC
GGACACGGCCACCTATTTCTGTGCGAGAGATATTCCTAGTGATGCT
TTCACCTTAGACTTGTGGGGCCCAGGCACCCTGGTCACCGTCTCCT
CAGGGCAACCTAAGGCTCCATCAGTCTTCCCACTGGCCCCCTGCTG
CGGGGACACACCCAGCTCCACGGTGACCCTGGGCTGCCTGGTCAAA
GGCTACCTCCCGGAGCCAGTGACCGTGACCTGGAACTCGGGCACCC
TCACCAATGGGGTACGCACCTTCCCGTCCGTCCGGCAGTCCTCAGG
CCTCTACTCGCTGAGCAGCGTGGTGAGCGTGACCTCAAGCAGCCAG
CCCGTCACCTGCAACGTGGCCCACCCAGCCACCAACACCAAAGTGG
ACAAGACCGTTGCGCCCTCGACATGCAGCAAGCCCATGTGCCCACC
CCCTGAACTCCCGGGGGGACCGTCTGTCTTCATCTTCCCCCCAAAA
CCCAAGGACACCCTCATGATCTCACGCACCCCCGAGGTCACATGCG
TGGTGGTGGACGTGAGCCAGGATGACCCCGAGGTGCAGTTCACATG
GTACATAAACAACGAGCAGGTGCGCACCGCCCGGCCGCCGCTACGG
GAGCAGCAGTTCAACAGCACGATCCGCGTGGTCAGCACCCTCCCCA
TCGCGCACCAGGACTGGCTGAGGGGCAAGGAGTTCAAGTGCAAAGT
CCACAACAAGGCACTCCCGGCCCCCATCGAGAAAACCATCTCCAAA
GCCAGAGGGCAGCCCCTGGAGCCGAAGGTCTACACCATGGGCCCTC
CCCGGGAGGAGCTGAGCAGCAGGTCGGTCAGCCTGACCTGCATGAT
CAACGGCTTCTACCCTTCCGACATCTCGGTGGAGTGGGAGAAGAAC
GGGAAGGCAGAGGACAACTACAAGACCACGCCGACCGTGCTGGACA
GCGACGGCTCCTACTTCCTCTACAGCAAGCTCTCAGTGCCCACGAG
TGAGTGGCAGCGGGGCGACGTCTTCACCTGCTCCGTGATGCACGAG
GCCTTGCACAACCACTACACGCAGAAGTCCATCTCCCGCTCTCCGG
GTAAATAG

-continued

A11B1_2D3 Light Chain
(SEQ ID NO: 100)
ATGGACACGAGGGCCCCCACTCAGCTGCTGGGGCTCCTGCTGCTCT
GGCTCCCAGGTGCCACATTTGCCCAAGTGCTGACCCAGACTCCATC
CTCCGTGTCTGCAGCTGTGGGAAGCACAGTCACCATCAATTGCCAG
GCCAGTCAGAGTGTTTATAAAGACAACAATTTAGCCTGGTATCAGC
AGAAACCAGGGCAGCCTCCCAAGCTCCTGATCTACAAGGCTTCCAC
TCTGGCATCTGGGGTCCCATCGCGGTTCAAAGGCAGTGGATCTGGG
ACACAGTTCACTCTCACCATCAGCGGCGTGCAGTGTGAAGATGCTG
CCACTTACTACTGTCAAGGCGAATTCAGTTGTGGTAGTGCTGATTG
TATTGCTTTCGGCGGAGGGACCGAGGTGGTGGTCAAAGGTGATCCA
GTTGCACCTACTGTCCTCATCTTCCCACCAGCTGCTGATCAGGTGG
CAACTGGAACAGTCACCATCGTGTGTGTGGCGAATAAATACTTTCC
CGATGTCACCGTCACCTGGGAGGTGGATGGCACCACCCAAACAACT
GGCATCGAGAACAGTAAAACACCGCAGAATTCTGCAGATTGTACCT
ACAACCTCAGCAGCACTCTGACACTGACCAGCACACAGTACAACAG
CCACAAAGAGTACACCTGCAAGGTGACCCAGGGCACGACCTCAGTC
GTCCAGAGCTTCAATAGGGGTGACTGTTAG A11B1_2A7 Heavy Chain
(SEQ ID NO: 101)
ATGGAGACTGGGCTGCGCTGGCTTCTCCTGGTCGCTGTGCTCAAAG
GTGTCCAGTGTCAGTCGTTGGAGGAGTCCGGGGGAGACCTGGTCAA
GCCTGGGGCATCCCTGACACTCACCTGCAAAGGCTCTGGAATCGAC
TTCAGTAGCGGCTACGGCATGTGGTGGGTCCGCCAGGCTCCAGGGA
AGGGACTGGAGTATATCGGATACATTGATACTGGTTATGGTAGCAC
TTACTACGCGAGCTGGGCGAAAGGCCGATTCACCATCTCCAAGACC
TCGTCGACCACGGTGACTCTGCAAATGACCAGTCTGACAGTCGCGG
ACACGGCCACCTATTTCTGTGCGAAAGGGGGCGCCATAGACCTCTG
GGGCCCAGGGACCCTCGTCACCGTCTCTTCAGGGCAACCTAAGGCT
CCATCAGTCTTCCCACTGGCCCCCTGCTGCGGGGACACACCCAGCT
CCACGGTGACCCTGGGCTGCCTGGTCAAAGGCTACCTCCCGGAGCC
AGTGACCGTGACCTGGAACTCGGGCACCCTCACCAATGGGGTACGC
ACCTTCCCGTCCGTCCGGCAGTCCTCAGGCCTCTACTCGCTGAGCA
GCGTGGTGAGCGTGACCTCAAGCAGCCAGCCCGTCACCTGCAACGT
GGCCCACCCAGCCACCAACACCAAAGTGGACAAGACCGTTGCGCCC
TCGACATGCAGCAAGCCCATGTGCCCACCCCCTGAACTCCCGGGGG
GACCGTCTGTCTTCATCTTCCCCCCAAAACCCAAGGACACCCTCAT
GATCTCACGCACCCCCGAGGTCACATGCGTGGTGGTGGACGTGAGC
CAGGATGACCCCGAGGTGCAGTTCACATGGTACATAAACAACGAGC
AGGTGCGCACCGCCCGGCCGCCGCTACGGGAGCAGCAGTTCAACAG
CACGATCCGCGTGGTCAGCACCCTCCCCATCGCGCACCAGGACTGG
CTGAGGGGCAAGGAGTTCAAGTGCAAAGTCCACAACAAGGCACTCC
CGGCCCCCATCGAGAAAACCATCTCCAAAGCCAGAGGGCAGCCCCT
GGAGCCGAAGGTCTACACCATGGGCCCTCCCCGGGAGGAGCTGAGC
AGCAGGTCGGTCAGCCTGACCTGCATGATCAACGGCTTCTACCCTT
CCGACATCTCGGTGGAGTGGGAGAAGAACGGGAAGGCAGAGGACAA
CTACAAGACCACGCCGACCGTGCTGGACAGCGACGGCTCCTACTTC
CTCTACAGCAAGCTCTCAGTGCCCACGAGTGAGTGGCAGCGGGGCG
ACGTCTTCACCTGCTCCGTGATGCACGAGGCCTTGCACAACCACTA
CACGCAGAAGTCCATCTCCCGCTCTCCGGGTAAATAG A11B1_2A7 Light Chain
(SEQ ID NO: 102)
ATGGACACGAGGGCCCCCACTCAGCTGCTGGGGCTCCTGCTGCTCT
GGCTCCCAGGTGCCACATTTGCAGCCGTGCTGACCCAGACTCCGGC
TTCCACGTCTGCAGCTGTGGGAGGCACAGTCACCATCAATTGTCAG
TCCAGTCAGAGCGTGTATCGTAGCAACTGGTTAGCCTGGTATCAGC
AGAAACCAGGGCAGCCTCCCAAGCTCCTGATCTATGATGTATTTAA
TTTGGCATCTGGGGTCCCATCCCGGTTCAAGGGCAGTGGATCTGGG
ACACAGTTCACTCTCACCATCAGCGGCGTGCAGTGTGCCGATGCTG
CCACTTACTACTGTCAAGGCAGTTATTATAGTGGTAATTGGTACAG
TGCTTTCGGCGGAGGGACCGAGGTGGTGGTCAAAGGTGATCCAGTT
GCACCTACTGTCCTCATCTTCCCACCAGCTGCTGATCAGGTGGCAA
CTGGAACAGTCACCATCGTGTGTGTGGCGAATAAATACTTTCCCGA
TGTCACCGTCACCTGGGAGGTGGATGGCACCACCCAAACAACTGGC
ATCGAGAACAGTAAAACACCGCAGAATTCTGCAGATTGTACCTACA
ACCTCAGCAGCACTCTGACACTGACCAGCACACAGTACAACAGCCA
CAAAGAGTACACCTGCAAGGTGACCCAGGGCACGACCTCAGTCGTC
CAGAGCTTCAATAGGGGTGACTGTTAG Protein Sequences of Anti-α11β1 Monoclonal Antibodies
Rat mAb Sequences Signal peptide-FR1-CDR1-FR2-CDR2-FR3-CDR3-FR4
79E3E3 Heavy Chain Variable Region
(SEQ ID NO: 145)
*MDWLWNLLFLMVVAQSAQA*QIQLVQSGPEVKKPGESVKISCKASGYTFTDYAMNWVKQ
APGNGLKWMGWINTQTGKPTYADDFKQRFVFSLETSARTTYLQINNLNIEDTATYFCT
RLGTGNTKGFAYWGQGTLVTVSS -continued 79E3E3 Light Chain Variable Region
(SEQ ID NO: 146)
*MESQTHVLISLLLCVSGTCG*DILINQSPASLTVSAGERVTMSCKSSQSLLYSENNQDYLA
WYQQKPGQFPKLLIYGASNRHTGVPDRFTGSGSGTDFTLTISSVQAEDLADYYCEQTY
RYPFTFGSGTKLEIK 24E4G6 Heavy Chain Variable Region
(SEQ ID NO: 147)
*MELELSLIFIFSLLKDVQC*EVQLVESGGSLVQPGGSLKLSCVASGYTFSNYWMDWVRQSP
GKSLEWIGEINTDGRRTNYAPSIKDRFTISRDNAKSTLYLQMSNVKSDDTAIYYCTILR
VYPHYFDYWGQGVMVTVSS 24E4G6 Light Chain Variable Region
(SEQ ID NO: 148)
*MMSPAQFLFLLMLWIQEARG*DVVMTQTPPSLSVAIGQSVSISCKSSQSLVYSDGETYLH
WFLQSPGRSPKRLIYHVSNLGSGVPDRFSGTGSLTDFTLRISRVEAEDLGVYYCAQTTH
FPPTFGAGTKLELK 8H8E9 Heavy Chain Variable Region
(SEQ ID NO: 149)
*MAVLVLLLCLVTFPSCALS*QVQLKESGPGLVQPSQTLSLTCTVSGFSLTSNSVSWVRQAPG
KGLEWMGAIWSGGSTDYNSALKSRLSISRDTSKSQVFLKMNSLQTEDTAIYFCTRSHW
EPFDYWGQGVMVTVSS 8H8E9 Light Chain Variable Region
(SEQ ID NO: 150)
*MESQTQALISLLLWVYGTCG*DIVMTQSPFSLAVSEGEMVTINCKSSQGLLSSGNQKNYLA
WYQQRPGQSPKLLIYYASTRQSGVPDRFIGGGSGTDFTLTISDVQAEDLADYYCLQHYS
YPPTFGSGTKLEIK 6E5C11 Heavy Chain Variable Region
(SEQ ID NO: 151)
*MAVLVLLLCLVTFPSCALS*QVQLRESGPGLVQPSQTLSLTCTVSGFSLTSNSVTWVRQPPG
KGLEWMGAIWSDGSTDYNSTLKSRLSISRDTSKSQVFLKMSSLQTEDTAIYFCTRSHW
EPFDYWGQGVMVTVSS 6E5C11 Light Chain Variable Region
(SEQ ID NO: 152)
*MESQTQALISLLLWVYGTCG*DIVMTQSPLSLAVSEGETVTMNCKSSQSLFSSGNQKNYLA
WYQQKPGQSPKLLIYYASTRQSGVPDRFIGSGSGTDFTLTISDVQTEDLADYYCLQHYN
YPPTFGSGTKLEIK 7D8B10 Heavy Chain Variable Region
(SEQ ID NO: 153)
*MDLRLTYVFIVAILKGVLC*EVKLEESGGGLVQPGMSVKLSCATSGFIFSDYWMEWVRQAP
GKGLEWVAEIRNKANNYATYYGKSMKGRFTISRDDSKSIVYLQVNSIRSEDTAIYYCA
PNFDYWGQGVMVTVSS 7D8B10 Light Chain Variable Region
(SEQ ID NO: 154)
*MSPVQSLFLLLLWILGTHG*DVVLTQTPPTLSATIGQSVSISCRSSQSLLHSTGNTYLNWLL
QRPGQPPQLLIYLVSRLESGVPNRFSASGSGTDFTLKISGIEAEDLGVYYCVQSSHTPYT
FGTGTKLELK 18E10F10 Heavy Chain Variable Region
(SEQ ID NO: 155)
*MDIRLSLVFLVLFMKGVQC*EVQLVESGGGLVQPGRSLKLSCAASRFTFSDYNMAWVRQA
PKKGLEWVATIYHDDSGSYYRDSVKGRFTISRNNAKSTLYLQMDSLRSEDMATYYCA
RHNNGFDYWGQGVMVTVAS -continued 18E10F10 Light Chain Variable Region (SEQ ID NO: 156)

*MKWPVRLLVLFFWIPASGG*DVVMTQTPVSLPVRLGGQASISCRSSQSLVHSNGNTYLHW

YLQKPGQSPQLLINRVSNRFSGVPDRFSGSGSGTDFTLKINRVEPEDLGDYYCLQSTHFP

LTFGSGTKLETK

40G10H11 Heavy Chain Variable Region (SEQ ID NO: 157)

*MDIRLSLGFLVLFIKGDQC*AVQLVESGGGLVQPGRSLKLSCAASRITFTDYYMAWVRQA

PTKGLEWVATISSDGGDTFYRDSVKGRFTISRDNAKSTLYLQMVSLRSEDTATYYCST

DRGAQFGYWGQGTLVTVSS

40G10H11 Light Chain Variable Region (SEQ ID NO: 158)

*MAPVQLLGLLLIWLPAMRC*DIQMTQSPSFLSASVGDRVSINCKASQNVHENLNWYQQKL

GEAPKRLIYNTNNLQTGIPSRFSGSGSGADYTLTISSLQPEDFATYFCLQHNAFPYTFGP

GTKLELK

Mouse mAb Sequences

FR1-CDR1-FR2-CDR2-FR3-CDR3-FR4

9-G05 Heavy Chain Variable Region (SEQ ID NO: 103)

EVQLQQSGPELVKPGASVKIPCKASGYTFPDYNMDWVKQSHGKSLEWIGYINPDNGGT

IYNQKFKGKATLTVDKSSSTAYMELRSLTSEDTAVYYCARLDSSGYGYYAMDYWGQG

TSVTVSS

9-G05 Light Chain Variable Region (SEQ ID NO: 104)

DIVLTQSPASLAVSLGQRATISCRASESVDNYGISFMHWYQQKPGQPPKLLIYRASNLD

SEIPARFSGSGSRTDFTLTIDPVETDDVATYYCQQSYKDPRTFGGGTKLEIK

8-P20 Heavy Chain Variable Region (SEQ ID NO: 105)

KVMLVESGGALVKPGGSLKLSCVASGFTFSNYAMSWVRQTPEKRLEWVATISSGGYY

TYYPDSVKGRFTISRDNARNTLFLQMSSLRSEDTAMFYCAREDDYGRYSYTMDYWGQ

GTSVTVSS

8-P20 Light Chain Variable Region (SEQ ID NO: 106)

DVVMTQTPLSLPVSLGDQVSISCRCSQSLVHSNGNTYLHWYLQKPGQSPQLLIYKISNR

FSGVPDRFSGSGSGTDFTLKISRVEAEDLGVYFCSQSTHVPYTFGGGTELEIK

8-G15 Heavy Chain Variable Region (SEQ ID NO: 107)

EVQLQQSGPELVKPGASVRISCKASGYTFTDYYIHWVKQKPGQGLECIGEIYPGTDNTY

YSKKFRGKATLTADKSSDTAYMQLSSLTSEDSAVYFCARGDYYRGYFDVWGAGTTVT

VSS

8-G15 Light Chain Variable Region (SEQ ID NO: 108)

DVVMTQTSLTLSVTIGQPASISCKSSQSLLHSNGKTYLNWLLQRPGQSPKFLIYLVSKL

ESGVPDRFSGSGSGTDFTLKISRVEAEDLGVYYCLQSTHFPWTFGGGTKLEIK

8-I14 Heavy Chain Variable Region (SEQ ID NO: 109)

EVQLQQSGPELVKPGASVKKSCKASGYTFTDYYMHWVKQKPGQGLEWIGKIYPGSGN

THYNEKFKGKATLTADKSSSTAYMQLSSLTSEDSAVYFCATNYYGYRAMNYWGQGSS

VTVSS

-continued

8-I14 Light Chain Variable Region
(SEQ ID NO: 110)
DIHLTQSPSSLSASLGERISLTCRASQDIYISLNWFQQKPDGTIKLLIYGTSSLDSGVPKRF

SGSRSGSDYSLTISSLESEDFADYYCLQYASSPYTFGGGTKLEIK

9-E16 Heavy Chain Variable Region
(SEQ ID NO: 111)
EVQLQQSGPELVKPGASVKISCKASGYTFTDYYMHWVKQKPGQGLEWIGEIYPGSGNP

YYNEKFKGKATLTADKSSSSAYMQLSSLTSEDSAVYFCARTSYGRVGTGFAYWGQGT

LVTVSA

9-E16 Light Chain Variable Region
(SEQ ID NO: 112)
NFVMTQTPLSLPVSLGDQASISCRSSQSLLHSNGNTYLHWYLQKPGQSPKLLIYKVSNR

FSGVPDRFSGSGSGTDFTLKINRVETEDLGIYFCSQSSHVPTFGAGTKLELK

8-J17 Heavy Chain Variable Region
(SEQ ID NO: 113)
QVQLQQSGAELAKPGASVKMSCKASGYTFTNYWMHWVKQRPGQGLEWIGYINPNNG

YTEYNQRFKDKATLTADRSSTTAYMQLSSLTSEDSAVYYCARSDIITTDYWGQGTTLT

VSS

8-J17 Light Chain Variable Region
(SEQ ID NO: 114)
DVVMTQTPLSLPVSLGDQASISCRSSQSLVYSNGNTYLHWYLQKPGQSPKLLIYKVSNR

FSGVPDRFSGSGSGTDFTLKISRVEAEDLGVYFCSQSTHVPWTFGGGTKLEIK

9-B11 Heavy Chain Variable Region
(SEQ ID NO: 115)
QVQLQQPGAELVRPGTSVKLSCKASGYTFTSYWMHWVQQRPGQGLEWIGVIDPSDSY

TNYNQKFKGKATLTVDTSSSSAYMQLSSLTSEDSAVYYCARDDVAMDYWGQGTSVTV

SS

9-B11 Light Chain Variable Region
(SEQ ID NO: 116)
DIVVTQSPASLAVSLGQRATISCRASESVDSYGNSFIHWYQQKPGQPPKLLIYRASNLKS

GIPARFSGSGSRTDFTLTINPVEADDVATYYCQQSNEDPYTFGGGTKLEIK

For SEQ ID NO: 117-144, CDR3 is represented by bold and underlined text.
6-O12 Heavy Chain Variable Region
(SEQ ID NO: 117)
EVKLEESGGGLVQPGGSMKLSCAASGFTFSDAWMDWVRQSPEAGLEWVAEIRNKAHN

PATYYAESVKGRFTISRDDSKSSVYLQMNSLRAEDTGIYYCTLVAPDAMDYWGQGTS

VTVSS

6-O12 Light Chain Variable Region
(SEQ ID NO: 118)
DIVMSLSPSSLAVSVGEKVTMSCKSSQSLLYSRNQKNYLAWYQQKPGQSPKLLIYWAST

RASGVPDRFTGSGSGTDFTLTISSVKAEDLAVYYCQQYYSYPYTFGGGTKLEIK

10-L15 Heavy Chain Variable Region
(SEQ ID NO: 119)
QVQLQQSGPELVRPGASVKMSCKASGYTFTSYWMHWVKQRPGQGLEWIGMIDPSNSE

TWLNQKFKDKATLNVDKSSNTAYMQLSSLTSEDSAVYYCARYDGYYDYWGQGTTLT

VSS

10-L15 Light Chain Variable Region
(SEQ ID NO: 120)
NIVLTQSPASLAVSLGQRATISCRASESVDSYGNSFMHWYQQKPGQPPKLLIYLASNVES

GVPARFSGSGSRTDFTLTIDPVEADDAATYYCQQNNEDPWTFGGGTKLEIK

-continued

7-H14 Heavy Chain Variable Region (SEQ ID NO: 121)

QVQLQQPGAELVRPGASVKLSCKPSGYTFTSYWMNWVKQRPGQGLEWIGMIDPSDSET

HYNQMFKDKATLTVDKSSNTAYMQLSSLTSEDSAVYYCAQIYYAYDKAYWGQGTLV

TVSA

7-H14 Light Chain Variable Region (SEQ ID NO: 122)

DIVMSQSPSSLAVSVGEKVTMSCKSSQSLLYSSHQKNYLAWYQQKPGQSPKLLIYWAST

RESGVPDRFTGSGSGTDFSLTISSVKAEDLAVYYCQEYYSWTFGGGTKLEIK

6-B21 Heavy Chain Variable Region (SEQ ID NO: 123)

EVQLQQSGPELVKPGASVKISCKASGYTFTDYYMNWVKQSHGKSLEWIGDINPHNGGT

SFIQKFKGKATLTVDKSSSTAYMELRSLTSEDSAVYYCAPLGRKEGFAYWGQGTLVTV

SA

6-B21 Light Chain Variable Region (SEQ ID NO: 124)

DTVLTQSPASLVVSLGQRATISCRASKSVSTSGYSYMHWYQQKPGQPPKLLIYLASNLES

GVPARFSGSGSGTAFTLNIHPVEEEDAATYYCQHSRELPYTFGGGTKLEIK

10-F23 Heavy Chain Variable Region (SEQ ID NO: 125)

QVTLKESGPGILQPSQTLSLTCSFSGFSLSTFAMGVGWIRQPSGKGLEWLAHIWWDDDK

YYNPALKSRLTISKDTSKNHVFLKIANVDTADTATYYCARMPLTFYFDYWGQGTTLTV

SS

10-F23 Light Chain Variable Region (SEQ ID NO: 126)

DVLLTQTPLSLPVSLGDQASISCRSSQSIVHSNGHTYLEWYLQKPGQSPKLLIYKVSNRFS

GVPDRFSGSGSGTDFTLKISRVEAEDLGVYYCFQGSHVPFTFGGGTKLEIK

6-A12 Heavy Chain Variable Region (SEQ ID NO: 127)

QVTLKESGPGILQPSQTLSLTCSFSGFSLRTFAMGVGWIRQPSGKGLEWLAHIWWDDDK

YYNPALKSRLTISKDTSKNQVFLKIANVDTADTATYYCARMPLTFYFDYWGQGTTLTV

SS

6-A12 Light Chain Variable Region (SEQ ID NO: 128)

DVLMTQTPLSLPVSLGDQASISCRSSQSIVHSNGNTYLEWYLQKPGQSPKLLIYKVSTRF

SGVPDRFSGSGSGTDFTLKISRVEAEDLGVYYCFQGSHVPFTFGGGTKLEIK

6-M8 Heavy Chain Variable Region (SEQ ID NO: 129)

QVQLQQPGAELVMPGASVKLSCKASGYTFTNYWMHWVKQRPGQGLEWIGEIDPSDSY

TNYNQKFKGKATLTVDKSSSTAYMQLSSLTSEDSAVYYCTRQGSTYAWGQGTSVTVS

S

6-M8 Light Chain Variable Region (SEQ ID NO: 130)

DIVMTQAAFSNPVTLGTSASISCRSSKSLLHSNGITYLYWYLQKPGQSPQLLIYQMSNLA

SGVPDRFSSSGSGTDFTLRISRVEAEDVGVYYCAQNLELPPTFGGGTKLEIK

2-A3 Heavy Chain Variable Region (SEQ ID NO: 131)

EVQLQQSGPELVKPGASVKMSCKASGYTFTDYYMMWVKQSHGKSLEWIGDINPYNGG

SSYNPKFKGRATLTVDKSSSTAYMQLNSLTSEDSAVYYCARGTYWGQGTLVTVSA

-continued

2-A3 Light Chain Variable Region (SEQ ID NO: 132)

DVVMTQTPLTLSVTIGQPASISCKSSQSLLDSAGKTYLNWLLQRPGQSPKRLMYLVSKL

DSGVPDRFTGSGSGTDFTLKISRVEAEDLGVYYCWQGTHFPYTFGGGTKLEIK

6-O17 Heavy Chain Variable Region (SEQ ID NO: 133)

QVQLQQPGAELVKPGASVKLSCKASGYTFTSYWMHWIKQRPGQGLEWIGEINPSNGGS

NYNEKFKSKATLTVDKSSSTAYMQLSSLTSEDSAVYHCKSRGYWGQGTTLTVSS

6-O17 Light Chain Variable Region (SEQ ID NO: 134)

DVVMTQTPLTLSVTIGQPASISCKSSQSLLDSYGKTYLNWLLQRPGQSPKRLIYLVSKLD

SGVPDRFTGSGSGTDFTLKISRVEAEDLGIYYCWQGTHFPHTFGSGTKLEIK

3-G5 Heavy Chain Variable Region (SEQ ID NO: 135)

QVQLQQSGAELARPGASVKLSCKASGYTFTSYGISWVKQRTGQGLEWIGEIFPRSSNTY

YNEKFKGKATLTADKSSSTVYMEFRSLTSEDSAVYFCAREGGLAWFAYWGQGTLVTV

SA

3-G5 Light Chain Variable Region (SEQ ID NO: 136)

DVVMTQTPLTLSVTIGQPASISCKSSQSLLYTNGNTYLNWLLQRPGQSPKRLIYLVSKLD

SGIPDRFSGSGSGTDFTLRISRVEAEDLGVYYCLQSTHFPFTFGSGTKLEIK

6-A15 Heavy Chain Variable Region (SEQ ID NO: 137)

EVQLQQSGPELVKPGASVKMSCKASGYTITDYYMMWLKQSHGKSLEWIGDINPYTGGT

SYNQKFKGKATLTVDKSSSTAYLQLHSLTSEDSAVYYCARGAYWGQGTTLTVSS

6-A15 Light Chain Variable Region (SEQ ID NO: 138)

DVVMTQTPLTLSVTIGQPASISCKSSQSLLDSDGKTYLNWLLQRPGQSPKRLIYLVSKLD

SGVPDRFTGSGSGTDFTLKISRVEAEDLGVYYCWQGTHFPYTFGGGTKLEIK

10-K10 Heavy Chain Variable Region (SEQ ID NO: 139)

EVQLQQSGPELVKPGASVKMSCKASGYTITDYYMMWLKQSHGKSLEWIGDINPYTGGT

SYNQKFKGKATLTVDKSSSTAYMQLNSLTSEDSAVYYCARGAYWGQGTTLTVSS

10-K10 Light Chain Variable Region (SEQ ID NO: 140)

DVVMTQTPLTLSVTIGQPASISCKSSQSLLDSDGKTYLNWLLQRPGQSPKRLIYLVSKLD

SGVPDRFTGSGSGTDFTLKISRVEAEDLGVYYCWQGTHFPYTFGGGTKLEIK

6-P20 Heavy Chain Variable Region (SEQ ID NO: 141)

EVQLQQSGPELVKPGASVKISCKASGYTFTDYYMNWVKQSHGRSLELIGDINPNNGGSN

FNQKFRGKATLTVDKSSSTAYMELRSLTSEDSAIYYCARMGYWGQGTLVTVSA

6-P20 Light Chain Variable Region (SEQ ID NO: 142)

DVVMTQTPLTLSVTIGQPASISCKSSQSLLHSDGKTYLNWMFQRPGQSPKRLIYLVSKLD

SGVPYRFTGGGSGTDFTLQISRVETEDLGVYYCWQGTHFPRTFGGGTKLEIK

7-O8 Heavy Chain Variable Region (SEQ ID NO: 143)

EVQLQQSGPELVKPGASVKMSCKASGYTFTDYYIHWVKQKPGQGLEYIGEIYPGSGNT

YYNGKFRGKATLTADKSSSTAYMQLSSLTSEDSAVYFCGSGYFDYWGQGTTLTVSS

7-O8 Light Chain Variable Region (SEQ ID NO: 144)

DVVMTQTPLTLSVTIGQPASISCKSSQSLLYSNGKTYLNWLLQSPGQSPKLLIYLVSKLES

GVPDRFSGSGSGTDFTLKLSRVEAEDLGVYYCVQGTHFPFTFGSGTKLEIK

Rabbit mAb Sequences

A11B1_16G7 Heavy Chain (SEQ ID NO: 159)

METGLRWLLLVAVFKGVQCQEQLVESGGDLVKPGASLTLT
CTASGFSFNKNYWMCWVRQAPGKGLEWIGCIYNGDGNTYY
ASWVNGRFTISKTSSTTVTLQMTSLTVADTAIYFCARLLN
MWGPGTLVTVSSGQPKAPSVFPLAPCCGDTPSSTVTLGCL
VKGYLPEPVTVTWNSGTLTNGVRTFPSVRQSSGLYSLSSV
VSVTSSSQPVTCNVAHPATNTKVDKTVAPSTCSKPMCPPP
ELPGGPSVFIFPPKPKDTLMISRTPEVTCVVVDVSQDDPE
VQFTWYINNEQVRTARPPLREQQFNSTIRVVSTLPIAHQD
WLRGKEFKCKVHNKALPAPIEKTISKARGQPLEPKVYTMG
PPREELSSRSVSLTCMINGFYPSDISVEWEKNGKAEDNYK
TTPTVLDSDGSYFLYSKLSVPTSEWQRGDVFTCSVMHEAL
HNHYTQKSISRSPGK*

A11B1_16G7 Light Chain (SEQ ID NO: 160)

MDTRAPTQLLGLLLLWLPGARCADIVMTQTPASVEAAVGG
TVTIKCQASESIGNALAWYQQKPGQPPKLLIYTAATLASG
VPSRFSGSGSGTEFTLTISGVQCDDAATYYCQSYYFTSVS
SYGNAFGGGTEVVVKGDPVAPTVLIFPPAADQVATGTVTI
VCVANKYFPDVTVTWEVDGTTQTTGIENSKTPQNSADCTY
NLSSTLTLTSTQYNSHKEYTCKVTQGTTSVVQSFNRGDC*

A11B1_16E10 Heavy Chain (SEQ ID NO: 161)

METGLRWLLLVAVLKGVQCQSLEESGGDLVKPGASLTLTC
RVSGFSFSSSYYMCWVRQAPGKGLEWIACIGTTRGSTYYA
TWAKGRFTISKISSTTVTLQMTSLTDADTATYFCARDATG
YRINTIGLYFNLWGPGTLVTVSSGQPKAPSVFPLAPCCGD
TPSSTVTLGCLVKGYLPEPVTVTWNSGTLTNGVRTFPSVR
QSSGLYSLSSVVSVTSSSQPVTCNVAHPATNTKVDKTVAP
STCSKPMCPPPELPGGPSVFIFPPKPKDTLMISRTPEVTC
VVVDVSQDDPEVQFTWYINNEQVRTARPPLREQQFNSTIR
VVSTLPIAHQDWLRGKEFKCKVHNKALPAPIEKTISKARG
QPLEPKVYTMGPPREELSSRSVSLTCMINGFYPSDISVEW
EKNGKAEDNYKTTPTVLDSDGSYFLYSKLSVPTSEWQRGD
VFTCSVMHEALHNHYTQKSISRSPGK*

A11B1_16E10 Light Chain (SEQ ID NO: 162)

MDTRAPTQLLGLLLLWLPGARCAFELTQTPSSVEAAVGGT
PTIKCQASQTIYSYLSWYQQKPGQPPKLLIYEASKLASGV
PSRFSGSGSGTDYTLTISDLECADAATYYCQSYHGTASTE
YNTFGGGTEVVVRGDPVAPTVLIFPPAADQVATGTVTIVC

-continued

VANKYFPDVTVTWEVDGTTQTTGIENSKTPQNSADCTYNL
SSTLTLTSTQYNSHKEYTCKVTQGTTSVVQSFNRGDC*

A11B1_15G10 Heavy Chain (SEQ ID NO: 163)

METGLRWLLLVAVLKGVQCQQQLVESGGGLVKPGAALTFT
CTASGFSFSGNYWICWVRQAPGKGLEWIACIGTITSRTYY
ASWAKGRFTISKTSSTTVTLQMTSLTAADTATYFCARGAV
VSSGNAPYYFTLWGPGTLVTVSSGQPKAPSVFPLAPCCGD
TPSSTVTLGCLVKGYLPEPVTVTWNSGTLTNGVRTFPSVR
QSSGLYSLSSVVSVTSSSQPVTCNVAHPATNTKVDKTVAP
STCSKPMCPPPELPGGPSVFIFPPKPKDTLMISRTPEVTC
VVVDVSQDDPEVQFTWYINNEQVRTARPPLREQQFNSTIR
VVSTLPIAHQDWLRGKEFKCKVHNKALPAPIEKTISKARG
QPLEPKVYTMGPPREELSSRSVSLTCMINGFYPSDISVEW
EKNGKAEDNYKTTPTVLDSDGSYFLYSKLSVPTSEWQRGD
VFTCSVMHEALHNHYTQKSISRSPGK*

A11B1_15G10 Light Chain (SEQ ID NO: 164)

MDTRAPTQLLGLLLLWLPGARCAFELTQTPSSVEAAVGGT
VTIKCQASQSISSYLSWYQQKPGQPPKLLIYRASTLESGV
PSRFKGSGSGTEFTLTISDLECADAATYFCQSYYGVTFSG
FAFGGGTEVVVKGDPVAPTVLIFPPAADQVATGTVTIVCV
ANKYFPDVTVTWEVDGTTQTTGIENSKTPQNSADCTYNLS
STLTLTSTQYNSHKEYTCKVTQGTTSVVQSFNRGDC*

A11B1_14H1 Heavy Chain (SEQ ID NO: 165)

METGLRWLLLVAVLKGVQCQSLEESGGDLVKPGASLTLTC
KASGIDFNNYWITWVRQAPGKGLEWIACIYVGITGRTWYA
NWAKGRFTISKASSTVDLKMTSLTAADTATYFCARNGDGG
IYALNLWGPGTLVTVSSGQPKAPSVFPLAPCCGDTPSSTV
TLGCLVKGYLPEPVTVTWNSGTLTNGVRTFPSVRQSSGLY
SLSSVVSVTSSSQPVTCNVAHPATNTKVDKTVAPSTCSKP
MCPPPELPGGPSVFIFPPKPKDTLMISRTPEVTCVVVDVS
QDDPEVQFTWYINNEQVRTARPPLREQQFNSTIRVVSTLP
IAHQDWLRGKEFKCKVHNKALPAPIEKTISKARGQPLEPK
VYTMGPPREELSSRSVSLTCMINGFYPSDISVEWEKNGKA
EDNYKTTPTVLDSDGSYFLYSKLSVPTSEWQRGDVFTCSV
MHEALHNHYTQKSISRSPGK*

A11B1_14H1 Light Chain (SEQ ID NO: 166)

MDTRAPTQLLGLLLLWLPGATFAQVLTQTASSVSAAVGGT
VTISCQSSQSVYNNNWLAWYQQKPGQPPKLLIYRASTLTS
GVPSRFKGSGSGTQFTLTISDLECDDAATYYCAGGYSGNI
YVNDFGGGTEVVVKGDPVAPTVLIFPPAADQVATGTVTIV

-continued

CVANKYFPDVTVTWEVDGTTQTTGIENSKTPQNSADCTYN
LSSTLTLTSTQYNSHKEYTCKVTQGTTSVVQSFNRGDC*

A11B1_13G4 Heavy Chain (SEQ ID NO: 167)

METGLRWLLLVAVLKGVQCQEQLEESGGDLVKPGGSLTLT
CKASGFSFSNTYWACWVRQAPGKGLEWIACMNPASSGSSY
YASWAKGRFTISKTSSTTVTLHMPSLTAADTATYFCAKWD
TAFDVWGPGTLVTVSSGQPKAPSVFPLAPCCGDTPSSTVT
LGCLVKGYLPEPVTVTWNSGTLTNGVRTFPSVRQSSGLYS
LSSVVSVTSSSQPVTCNVAHPATNTKVDKTVAPSTCSKPM
CPPPELPGGPSVFIFPPKPKDTLMISRTPEVTCVVVDVSQ
DDPEVQFTWYINNEQVRTARPPLREQQFNSTIRVVSTLPI
AHQDWLRGKEFKCKVHNKALPAPIEKTISKARGQPLEPKV
YTMGPPREELSSRSVSLTCMINGFYPSDISVEWEKNGKAE
DNYKTTPTVLDSDGSYFLYSKLSVPTSEWQRGDVFTCSVM
HEALHNHYTQKSISRSPGK*

A11B1_13G4 Light Chain (SEQ ID NO: 168)

MDTRAPTQLLGLLLLWLPGARCADVVMTQTPSSVEAAVGG
TVTIKCQASQSISSYLAWYQQKPGQPPKLLIYGASNLESG
VPSRFKGSGSGTEYTLTISGVQCDDAATYYCQNYYAIDTY
GHAFGGGTEVVVKGDPVAPTVLIFPPAADQVATGTVTIVC
VANKYFPDVTVTWEVDGTTQTTGIENSKTPQNSADCTYNL
SSTLTLTSTQYNSHKEYTCKVTQGTTSVVQSFNRGDC*

A11B1_13C3 Heavy Chain (SEQ ID NO: 169)

METGLRWLLLVAVLKGVQCQEQLEESGGDLVKPGASLTLT
CTASGFSFSSNYHICWVRQAPGKGLELIACIYVGDGSTYY
ASWAKGRFTISKSSSTTVALQMTSLTAADTATYFCGRMFN
LWGPGTLVTVSSGQPKAPSVFPLAPCCGDTPSSTVTLGCL
VKGYLPEPVTVTWNSGTLTNGVRTFPSVRQSSGLYSLSSV
VSVTSSSQPVTCNVAHPATNTKVDKTVAPSTCSKPMCPPP
ELPGGPSVFIFPPKPKDTLMISRTPEVTCVVVDVSQDDPE
VQFTWYINNEQVRTARPPLREQQFNSTIRVVSTLPIAHQD
WLRGKEFKCKVHNKALPAPIEKTISKARGQPLEPKVYTMG
PPREELSSRSVSLTCMINGFYPSDISVEWEKNGKAEDNYK
TTPTVLDSDGSYFLYSKLSVPTSEWQRGDVFTCSVMHEAL
HNHYTQKSISRSPGK*

A11B1_13C3 Light Chain (SEQ ID NO: 170)

MDTRAPTQLLGLLLLWLPGAICDPVLTQTPSSVSAAVGVT
VTINCQSSPSVYSNYLSWYQQKPGQPPKLLIYLASTLASG
VPSRFKGSGSGTQFTLTISDVQCDDAATYYCAGTYSGNIW
SFGGGTEVVVKGDPVAPTVLIFPPAADQVATGTVTIVCVA

-continued

NKYFPDVTVTWEVDGTTQTTGIENSKTPQNSADCTYNLSS
TLTLTSTQYNSHKEYTCKVTQGTTSVVQSFNRGDC*

A11B1_12F2 Heavy Chain (SEQ ID NO: 171)

METGLRWLLLVAVLKGVQCQQQLVESGGGLVKPGASLTLT
CTASGFSFSSGYHMCWVRQAPGKGLEWIACFGVYTGTTTY
ASWAKGRFTISKTSSTTVTLQMTSLTVADTATYFCARISA
ENGGDLWGPGTLVTVSSGQPKAPSVFPLAPCCGDTPSSTV
TLGCLVKGYLPEPVTVTWNSGTLTNGVRTFPSVRQSSGLY
SLSSVVSVTSSSQPVTCNVAHPATNTKVDKTVAPSTCSKP
MCPPPELPGGPSVFIFPPKPKDTLMISRTPEVTCVVVDVS
QDDPEVQFTWYINNEQVRTARPPLREQQFNSTIRVVSTLP
IAHQDWLRGKEFKCKVHNKALPAPIEKTISKARGQPLEPK
VYTMGPPREELSSRSVSLTCMINGFYPSDISVEWEKNGKA
EDNYKTTPTVLDSDGSYFLYSKLSVPTSEWQRGDVFTCSV
MHEALHNHYTQKSISRSPGK*

A11B1_12F2 Light Chain (SEQ ID NO: 172)

MDTRAPTQLLGLLLLWLPGARCDVVMTQTPASVEAAVGGT
VTIKCQASQSISNYFSWYQQKPGQPPKLLIYRASTLASGV
PSRFSGSGSGTEFTLTISDLECADSATYYCQCTYGSSSTG
FGFGGGTEVVVKGDPVAPTVPIFPPAADQVATGTVTIVCV
ANKYFPDVTVTWEVDGTTQTTGIENSKTPQNSADCTYNLS
STLTLTSTQYNSHKEYTCKVTQGTTSVVQSFNRGDC*

A11B1_11D10 Heavy Chain (SEQ ID NO: 173)

METGLRWLLLVAVLKGVQCQSLEESGGDLVKPGASLTLTC
MASGIDFSSGYGMWWVRQAPGKGLEYIGYIDTGDDNTYYA
NWAKGRFTISKTSSTTVTLQMTSLTVADTATYFCAKGGAI
DLWGPGTLVTVSSGQPKAPSVFPLAPCCGDTPSSTVTLGC
LVKGYLPEPVTVTWNSGTLTNGVRTFPSVRQSSGLYSLSS
VVSVTSSSQPVTCNVAHPATNTKVDKTVAPSTCSKPMCPP
PELPGGPSVFIFPPKPKDTLMISRTPEVTCVVVDVSQDDP
EVQFTWYINNEQVRTARPPLREQQFNSTIRVVSTLPIAHQ
DWLRGKEFKCKVHNKALPAPIEKTISKARGQPLEPKVYTM
GPPREELSSRSVSLTCMINGFYPSDISVEWEKNGKAEDNY
KTTPTVLDSDGSYFLYSKLSVPTSEWQRGDVFTCSVMHEA
LHNHYTQKSISRSPGK*

A11B1_11D10 Light Chain (SEQ ID NO: 174)

MDTRAPTQLLGLLLLWLPGARCADIVMTQTPASVEAAVGG
TVTIKCQASQSISSYLAWYQQKPGQRPKLLIYRASTLKSG
VPSRFKGSGSGTEYTLTISDLECADAATYYCQAYYLSSSI
SYGNTFGGGTEVVVKGDPVAPTVLIFPPAADQVATGTVTI

-continued

VCVANKYFPDVTVTWEVDGTTQTTGIENSKTPQNSADCTY

NLSSTLTLTSTQYNSHKEYTCKVTQGTTSVVQSFNRGDC*

A11B1_10F9 Heavy Chain
(SEQ ID NO: 175)
METGLRWLLLVAVLKGVQCQSLEESGGDLVKPGASLTLTC

TASGFSLSSGYGMCWVRQAPGKGLEWIGYTDTATGTIHYA

SWAKGRFTISKTSSTTVTLQMTSLTAADTATYFCAKGGAM

DLWGPGTLVTVSSGQPKAPSVFPLAPCCGDTPSSTVTLGC

LVKGYLPEPVTVTWNSGTLTNGVRTFPSVRQSSGLYSLSS

VVSVTSSSQPVTCNVAHPATNTKVDKTVAPSTCSKPMCPP

PELPGGPSVFIFPPKPKDTLMISRTPEVTCVVVDVSQDDP

EVQFTWYINNEQVRTARPPLREQQFNSTIRVVSTLPIAHQ

DWLRGKEFKCKVHNKALPAPIEKTISKARGQPLEPKVYTM

GPPREELSSRSVSLTCMINGFYPSDISVEWEKNGKAEDNY

KTTPTVLDSDGSYFLYSKLSVPTSEWQRGDVFTCSVMHEA

LHNHYTQKSISRSPGK*

A11B1_10F9 Light Chain
(SEQ ID NO: 176)
MDTRAPTQLLGLLLLWLPGARCADIVMTQTPASVEAAVGG

TVTIKCQASQSISSYLAWYQQKPGQPPKLLIYRTSTLASG

VPSRFKGSGSGTEYTLTISDLECADAATYYCQSYAYSSSS

SYGNAFGGGTEVVVKGDPVAPTVLIFPPAADQVATGTVTI

VCVANKYFPDVTVTWEVDGTTQTTGIENSKTPQNSADCTY

NLSSTLTLTSTQYNSHKEYTCKVTQGTTSVVQSFNRGDC*

A11B1_7H12 Heavy Chain
(SEQ ID NO: 177)
METGLRWLLLVAVLKGVQCQSLEESGGDLVKPGASLTLTC

TGSGIDFSSSYWICWVRQAPGKGLEWIACIDGSDGNTYYA

SWARGRFTISKTSSTTVTLQMASLTAADTATYFCTRDLRL

WGPGTLVTVSSGQPKAPSVFPLAPCCGDTPSSTVTLGCLV

KGYLPEPVTVTWNSGTLTNGVRTFPSVRQSSGLYSLSSVV

SVTSSSQPVTCNVAHPATNTKVDKTVAPSTCSKPMCPPPE

LPGGPSVFIFPPKPKDTLMISRTPEVTCVVVDVSQDDPEV

QFTWYINNEQVRTARPPLREQQFNSTIRVVSTLPIAHQDW

LRGKEFKCKVHNKALPAPIEKTISKARGQPLEPKVYTMGP

PREELSSRSVSLTCMINGFYPSDISVEWEKNGKAEDNYKT

TPTVLDSDGSYFLYSKLSVPTSEWQRGDVFTCSVMHEALH

NHYTQKSISRSPGK*

A11B1_7H12 Light Chain
(SEQ ID NO: 178)
MDTRAPTQLLGLLLLWLPGARCADIVLTQTPASVSAAVGG

TVTINCQASQNVYSNNALAWHQQKPGQRPNLLIYKASTLA

SGVPSRFKGSGSGTQFTLTISDVQCDDAATYYCLGEFSCS

-continued

SGDCFVFGGGTEVVVKGDPVAPTVLIFPPAADQVATGTVT

IVCVANKYFPDVTVTWEVDGTTQTTGIENSKTPQNSADCT

YNLSSTLTLTSTQYNSHKEYTCKVTQGTTSVVQSFNRGDC

*

A11B1_7G12 Heavy Chain
(SEQ ID NO: 179)
METGLRWLLLVAVLKGVQCQSLEESGGDLVKPGASLTLTC

MASGIDFSSGYGMWWVRQAPGKGLEYIGYIDTGDDNTYYA

NWAKGRFTISKTSSTTVTLQMTSLTVADTATYFCAKGGAI

DLWGPGTLVTVSSGQPKAPSVFPLAPCCGDTPSSTVTLGC

LVKGYLPEPVTVTWNSGTLTNGVRTFPSVRQSSGLYSLSS

VVSVTSSSQPVTCNVAHPATNTKVDKTVAPSTCSKPMCPP

PELPGGPSVFIFPPKPKDTLMISRTPEVTCVVVDVSQDDP

EVQFTWYINNEQVRTARPPLREQQFNSTIRVVSTLPIAHQ

DWLRGKEFKCKVHNKALPAPIEKTISKARGQPLEPKVYTM

GPPREELSSRSVSLTCMINGFYPSDISVEWEKNGKAEDNY

KTTPTVLDSDGSYFLYSKLSVPTSEWQRGDVFTCSVMHEA

LHNHYTQKSISRSPGK*

A11B1_7G12 Light Chain
(SEQ ID NO: 180)
MDTRAPTQLLGLLLLWLPGARCADIVMTQTPASVEAAVGG

TVTIKCQASQSISSYLAWYQQKPGQRPKLLIYRASTLKSG

VPSRFKGSGSGTEYTLTISDLECADAATYYCQAYYLSSSI

SYGNTFGGGTEVVVKGDPVAPTVLIFPPAADQVATGTVTI

VCVANKYFPDVTVTWEVDGTTQTTGIENSKTPQNSADCTY

NLSSTLTLTSTQYNSHKEYTCKVTQGTTSVVQSFNRGDC*

A11B1_6G4 Heavy Chain
(SEQ ID NO: 181)
METGLRWLLLVAVLKGVQCQQQLEESGGGLVKPGGTLTLT

CKASGVALNPYYYMCWVRQAPGKGLEWIACVDADSSGSTY

YASWAKGRFTISKTSSTTVTLKMTSLTAADTATYFCARES

VDYSSVGIGYVHGTDGLWGPGTLVTVSSGQPKAPSVFPLA

PCCGDTPSSTVTLGCLVKGYLPEPVTVTWNSGTLTNGVRT

FPSVRQSSGLYSLSSVVSVTSSSQPVTCNVAHPATNTKVD

KTVAPSTCSKPMCPPPELPGGPSVFIFPPKPKDTLMISRT

PEVTCVVVDVSQDDPEVQFTWYINNEQVRTARPPLREQQF

NSTIRVVSTLPIAHQDWLRGKEFKCKVHNKALPAPIEKTI

SKARGQPLEPKVYTMGPPREELSSRSVSLTCMINGFYPSD

ISVEWEKNGKAEDNYKTTPTVLDSDGSYFLYSKLSVPTSE

WQRGDVFTCSVMHEALHNHYTQKSISRSPGK*

A11B1_6G4 Light Chain
(SEQ ID NO: 182)
MDTRAPTQLLGLLLLWLPGARCADIVVTQTPSSVSAAVGG

TVTIKCQASQSISNYFSWYQQKPGQPPKLLIYRASTLASG

-continued

VPSRFKGSGSGTEFTLTISDLECADAATYYCQCTYGRSNS

NFFYGFGGGTEVVVKGDPVAPTVLIFPPAADQVATGTVTI

VCVANKYFPDVTVTWEVDGTTQTTGIENSKTPQNSADCTY

NLSSTLTLTSTQYNSHKEYTCKVTQGTTSVVQSFNRGDC*

A11B1_6F9 Heavy Chain (SEQ ID NO: 183)

METGLRWLLLVAVLKGVQCQSLEESGGDLVKPGASLTLTC

TASGSSFSSTYWNCWVRQAPGKGLEWIACINAGSGTTYYA

SWAKGRFTVSKTSSTTVTLQMTSLTAADTATYFCTRDSDG

RFSSGYYFNLWGPGTLVTVSSGQPKAPSVFPLAPCCGDTP

SSTVTLGCLVKGYLPEPVTVTWNSGTLTNGVRTFPSVRQS

SGLYSLSSVVSVTSSSQPVTCNVAHPATNTKVDKTVAPST

CSKPMCPPPELPGGPSVFIFPPKPKDTLMISRTPEVTCVV

VDVSQDDPEVQFTWYINNEQVRTARPPLREQQFNSTIRVV

STLPIAHQDWLRGKEFKCKVHNKALPAPIEKTISKARGQP

LEPKVYTMGPPREELSSRSVSLTCMINGFYPSDISVEWEK

NGKAEDNYKTTPTVLDSDGSYFLYSKLSVPTSEWQRGDVF

TCSVMHEALHNHYTQKSISRSPGK*

A11B1_6F9 Light Chain (SEQ ID NO: 184)

MDTRAPTQLLGLLLLWLPGATFAQVLTQTASPVSAAVGGT

VTINCQSSQSVYDNNWLAWYQQKPGQPPKLLIDDASKLTS

GVSSRFKGSGSGTQFTLTISGVQCDDAATYYCQGAYYSSG

WYWAFGGGTEVVVKGDPVAPTVLIFPPAADQVATGTVTIV

CVANKYFPDVTVTWEVDGTTQTTGIENSKTPQNSADCTYN

LSSTLTLTSTQYNSHKEYTCKVTQGTTSVVQSFNRGDC*

A11B1_6C7 Heavy Chain (SEQ ID NO: 185)

METGLRWLLLVAVLKGVQCQQQLEESGGGLVKPGGTLTLT

CKASGIDFSSYYYMCWVRQAPGKGLELIVCIYTSSGGTWY

ASWVNGRLTISRSTSLNTVDLKMTSLTAADTATYFCARGV

YSGSSDYPTRLDLWGQGTLVTVSLGQPKAPSVFPLAPCCG

DTPSSTVTLGCLVKGYLPEPVTVTWNSGTLTNGVRTFPSV

RQSSGLYSLSSVVSVTSSSQPVTCNVAHPATNTKVDKTVA

PSTCSKPMCPPPELPGGPSVFIFPPKPKDTLMISRTPEVT

CVVVDVSQDDPEVQFTWYINNEQVRTARPPLREQQFNSTI

RVVSTLPIAHQDWLRGKEFKCKVHNKALPAPIEKTISKAR

GQPLEPKVYTMGPPREELSSRSVSLTCMINGFYPSDISVE

WEKNGKAEDNYKTTPTVLDSDGSYFLYSKLSVPTSEWQRG

DVFTCSVMHEALHNHYTQKSISRSPGK*

A11B1_6C7 Light Chain (SEQ ID NO: 186)

MDTSTSTALLGLLLLWLTGARCAIEMTQSPPSLSASVGET

VRIRCLASEDIYSGISWYQQKPEKPPTLLISGASNLESGV

PPRFSGGGSGTDYTLTIGGVQAEDVATYYCLGGYSFSSTG

-continued

LTFGAGTKVEIKRDPVAPSVLLFPPSKEELTTGTATIVCV

ANKYFPDVTVTWEVDGTTQTTGIENSKTPQNSADCTYNLS

STLTLTSTQYNSHKEYTCKVTQGTTSVVQSFNRGDC*

A11B1_6B6 Heavy Chain (SEQ ID NO: 187)

METGLRWLLLVAVLKGVQCQQHLVESGGGLVKPGASLTLT

CTASGFSFTTGYHMCWVRQAPGKGLEWIACFGVYTSTTTY

ASWAKGRFTISKTSSTTVTLQMTSLTVADTATYFCARISA

EDGGDLWGPGTLVTVSSGQPKAPSVFPLAPCCGDTPSSTV

TLGCLVKGYLPEPVTVTWNSGTLTNGVRTFPSVRQSSGLY

SLSSVVSVTSSSQPVTCNVAHPATNTKVDKTVAPSTCSKP

MCPPPELPGGPSVFIFPPKPKDTLMISRTPEVTCVVVDVS

QDDPEVQFTWYINNEQVRTARPPLREQQFNSTIRVVSTLP

IAHQDWLRGKEFKCKVHNKALPAPIEKTISKARGQPLEPK

VYTMGPPREELSSRSVSLTCMINGFYPSDISVEWEKNGKA

EDNYKTTPTVLDSDGSYFLYSKLSVPTSEWQRGDVFTCSV

MHEALHNHYTQKSISRSPGK*

A11B1_6B6 Light Chain (SEQ ID NO: 188)

MDTRAPTQLLGLLLLWLPGARCDVVMTQTPASVEAAVGGT

VTITCQASQSISNYFSWYQQKPGQPPKLLIYRASTLASGV

PSRFSGSGSGTQFTLTISDLECADSATYACQCTYGSSSTG

FGFGGGTEVVVKGDPVAPTVLIFPPAADQVATGTVTIVCV

ANKYFPDVTVTWEVDGTTQTTGIENSKTPQNSADCTYNLS

STLTLTSTQYNSHKEYTCKVTQGTTSVVQSFNRGDC*

A11B1_5F7 Heavy Chain (SEQ ID NO: 189)

METGLRWLLLVAVLKGVQCQSLEESGGDLVKPGASLTLTC

KASGFSFSSYFWICWVRQAPGKGLEWSACIYGDSSGSSYY

ASWAKGRFTISKTSSTTVTLQMTSLTAADTATYFCASYGS

SSYYYSNLWGPGTLVTVSSGQPKAPSVFPLAPCCGDTPSS

TVTLGCLVKGYLPEPVTVTWNSGTLTNGVRTFPSVRQSSG

LYSLSSVVSVTSSSQPVTCNVAHPATNTKVDKTVAPSTCS

KPMCPPPELPGGPSVFIFPPKPKDTLMISRTPEVTCVVVD

VSQDDPEVQFTWYINNEQVRTARPPLREQQFNSTIRVVST

LPIAHQDWLRGKEFKCKVHNKALPAPIEKTISKARGQPLE

PKVYTMGPPREELSSRSVSLTCMINGFYPSDISVEWEKNG

KAEDNYKTTPTVLDSDGSYFLYSKLSVPTSEWQRGDVFTC

SVMHEALHNHYTQKSISRSPGK*

A11B1_5F7 Light Chain (SEQ ID NO: 190)

MDTRAPTQLLGLLLLWLPGAICDPVMTQTPSSTSAAVGGT

VTISCQSSQSVYNNNYLAWYQQKPGQPPKRLIYESSKLAS

GVPSRFRGSGSGAQFTLTISDLECDDAATYYCLGAYYTTL

-continued

DFGGGTEVVVRGDPVAPTVLIFPPAADQVATGTVTIVCVA

NKYFPDVTVTWEVDGTTQTTGIENSKTPQNSADCTYNLSS

TLTLTSTQYNSHKEYTCKVTQGTTSVVQSFNRGDC*

A11B1_5D7 Heavy Chain (SEQ ID NO: 191)

METGLRWLLLVAVLKGVQCQEQLVESGGGLVQPEGSLTLT

CKASGFDFSSNAMCWVRQAPGKGLEWIACIYNGDGSTYYA

SWVNGRFTISKTSSTTVTLQMTSLTAADTATYFCARGLSN

WNRDNLWGPGTLVTVSSGQPKAPSVFPLAPCCGDTPSSTV

TLGCLVKGYLPEPVTVTWNSGTLTNGVRTFPSVRQSSGLY

SLSSVVSVTSSSQPVTCNVAHPATNTKVDKTVAPSTCSKP

MCPPPELPGGPSVFIFPPKPKDTLMISRTPEVTCVVVDVS

QDDPEVQFTWYINNEQVRTARPPLREQQFNSTIRVVSTLP

IAHQDWLRGKEFKCKVHNKALPAPIEKTISKARGQPLEPK

VYTMGPPREELSSRSVSLTCMINGFYPSDISVEWEKNGKA

EDNYKTTPTVLDSDGSYFLYSKLSVPTSEWQRGDVFTCSV

MHEALHNHYTQKSISRSPGK*

A11B1_5D7 Light Chain (SEQ ID NO: 192)

MDTRAPTQLLGLLLLWLPGATFAQVLTQTPSSVSAAVGGT

ATINCQASQSLYSPKNLAWYQQTPGQPPKLLIYSASKLAS

GVPSRFKGSGSGTQFTLTISGVQCDDAAIYYCQGEFSCTT

AACFAFGGGTEVVVKGDPVAPTVLIFPPAADQVATGTVTI

VCVANKYFPDVTVTWEVDGTTQTTGIENSKTPQNSADCTY

NLSSTLTLTSTQYNSHKEYTCKVTQGTTSVVQSFNRGDC*

A11B1_5A7 Heavy Chain (SEQ ID NO: 193)

METGLRWLLLVAVLKGVQCQSLEESGGGLVQPEGSLTLAC

TASGFSFSSYYYICWVRQAPGTGLEWIGCINTGSDDTHYA

SWLKGRFTFSKASSTTLTLQMTSLTAADTATYFCARSSGS

SDDAYDLWGPGTLVTVSSGQPKAPSVFPLAPCCGDTPSST

VTLGCLVKGYLPEPVTVTWNSGTLTNGVRTFPSVRQSSGL

YSLSSVVSVTSSSQPVTCNVAHPATNTKVDKTVAPSTCSK

PMCPPPELPGGPSVFIFPPKPKDTLMISRTPEVTCVVVDV

SQDDPEVQFTWYINNEQVRTARPPLREQQFNSTIRVVSTL

PIAHQDWLRGKEFKCKVHNKALPAPIEKTISKARGQPLEP

KVYTMGPPREELSSRSVSLTCMINGFYPSDISVEWEKNGK

AEDNYKTTPTVLDSDGSYFLYSKLSVPTSEWQRGDVFTCS

VMHEALHNHYTQKSISRSPGK*

A11B1_5A7 Light Chain (SEQ ID NO: 194)

MDTRAPTQLLGLLLLWLPGARCDVVMTQTPASVSEPVGGA

VTIKCQASQSIGSNLAWYQHKPGQPPKLLIYFASSLASGV

SSRFKGGRSGTQFTLTISDLECADAATYYCHCTYYPLSYV

TFGGGTEVVVKGDPVAPTVLIFPPAADQVATGTVTIVCVA

-continued

NKYFPDVTVTWEVDGTTQTTGIENSKTPQNSADCTYNLSS

TLTLTSTQYNSHKEYTCKVTQGTTSVVQSFNRGDC*

A11B1_4E1 Heavy Chain (SEQ ID NO: 195)

METGLRWLLLVAVLKGVQCQSLEESGGDLVKPGTSLTLSC

TASGFSFGSYYYMCWVRQAPGKGLEWIACIDVGSSGDTYY

ASWVNGRFTISKTSSTTVTLQMTSLTAADTATYFCARDDT

AAGGFGNLELWGPGTLVTVSSGQPKAPSVFPLAPCCGDTP

SSTVTLGCLVKGYLPEPVTVTWNSGTLTNGVRTFPSVRQS

SGLYSLSSVVSVTSSSQPVTCNVAHPATNTKVDKTVAPST

CSKPMCPPPELPGGPSVFIFPPKPKDTLMISRTPEVTCVV

VDVSQDDPEVQFTWYINNEQVRTARPPLREQQFNSTIRVV

STLPIAHQDWLRGKEFKCKVHNKALPAPIEKTISKARGQP

LEPKVYTMGPPREELSSRSVSLTCMINGFYPSDISVEWEK

NGKAEDNYKTTPTVLDSDGSYFLYSKLSVPTSEWQRGDVF

TCSVMHEALHNHYTQKSISRSPGK*

A11B1_4E1 Light Chain (SEQ ID NO: 196)

MDTRAPTQLLGLLLLWLPGARCAFELTQTPSSVSEPVGGT

VTIKCQASQSIYSYFSWYQQKPGQPPKRLIYQASTLASGV

PSRFKGSGSGTDFTLTISDLECADAATYYCQNNYGRGSGS

YFFGFGGGTEVVVKGDPVAPTVLIFPPAADQVATGTVTIV

CVANKYFPDVTVTWEVDGTTQTTGIENSKTPQNSADCTYN

LSSTLTLTSTQYNSHKEYTCKVTQGTTSVVQSFNRGDC*

A11B1_3H9 Heavy Chain (SEQ ID NO: 197)

METGLRWLLLVAVLKGVQCQSLEESGGDLVKPGASLTLTC

KASGIDFSSGYGMWWVRQAPGKGLEYIGYIDTGSGSTYYA

NWAKGRFTISKTSSTMVTLQMTSLTVADTATYFCAKGGAI

DLWGPGTLVTVSSGQPKAPSVFPLAPCCGDTPSSTVTLGC

LVKGYLPEPVTVTWNSGTLTNGVRTFPSVRQSSGLYSLSS

VVSVTSSSQPVTCNVAHPATNTKVDKTVAPSTCSKPMCPP

PELPGGPSVFIFPPKPKDTLMISRTPEVTCVVVDVSQDDP

EVQFTWYINNEQVRTARPPLREQQFNSTIRVVSTLPIAHQ

DWLRGKEFKCKVHNKALPAPIEKTISKARGQPLEPKVYTM

GPPREELSSRSVSLTCMINGFYPSDISVEWEKNGKAEDNY

KTTPTVLDSDGSYFLYSKLSVPTSEWQRGDVFTCSVMHEA

LHNHYTQKSISRSPGK*

A11B1_3H9 Light Chain (SEQ ID NO: 198)

MDTRAPTQLLGLLLLWLPGARCADIVMTQTPASVEAAVGG

TVTIKCQASQSISSYLAWYQQKPGQRPKLLIYRASTLASG

VPSRFKGSGSGTDYTLTISDLECADAATYYCHTYYLSSSI

SYGNTFGGGTEVVVKGDPVAPTVLIFPPAADQVATGTVTI

-continued

VCVANKYFPDVTVTWEVDGTTQTTGIENSKTPQNSADCTY
NLSSTLTLTSTQYNSHKEYTCKVTQGTTSVVQSFNRGDC*

A11B1_3G2 Heavy Chain
(SEQ ID NO: 199)
METGLRWLLLVAVLKGVQCQEQLEESGGDLVKPEGSLTLT
CKASGFSFSSIYWICWVRQAPGKGLEWIACTTVVKSGRTY
YANWAKGRFTISKTSSTTVTLQMTSLTAADTATYFCAREF
VDGGGSSGRDLWGPGTLVTVSSGQPKAPSVFPLAPCCGDT
PSSTVTLGCLVKGYLPEPVTVTWNSGTLTNGVRTFPSVRQ
SSGLYSLSSVVSVTSSSQPVTCNVAHPATNTKVDKTVAPS
TCSKPMCPPPELPGGPSVFIFPPKPKDTLMISRTPEVTCV
VVDVSQDDPEVQFTWYINNEQVRTARPPLREQQFNSTIRV
VSTLPIAHQDWLRGKEFKCKVHNKALPAPIEKTISKARGQ
PLEPKVYTMGPPREELSSRSVSLTCMINGFYPSDISVEWE
KNGKAEDNYKTTPTVLDSDGSYFLYSKLSVPTSEWQRGDV
FTCSVMHEALHNHYTQKSISRSPGK*

A11B1_3G2 Light Chain
(SEQ ID NO: 200)
MDTRAPTQLLGLLLLWLPGARCAYDMTQTPASVEAAVGGT
VTIKCQASQSISRDLSWYQQKPGQPPKRLIYKASTLASGV
PSRFKGSGSGTDFTLTISDLECADAATYYCQQGYSSIDVD
NDFGGGTEVVVKGDPVAPTVLIFPPAADQVATGTVTIVCV
ANKYFPDVTVTWEVDGTTQTTGIENSKTPQNSADCTYNLS
STLTLTSTQYNSHKEYTCKVTQGTTSVVQSFNRGDC*

A11B1_3B1 Heavy Chain
(SEQ ID NO: 201)
METGLRWLLLVAVLKGVQCQEQLEESGGGLVKPEGSLTLT
CKASGFDLSSGYDMCWVRQAPGKGLEWIACIYADYSGSTY
YASWVNGRFTISSSTSLNTVDLKMTSLTAADTATYFCARG
ATGNGGYGYYFNLWGPGTLVTVSSGQPKAPSVFPLAPCCG
DTPSSTVTLGCLVKGYLPEPVTVTWNSGTLTNGVRTFPSV
RQSSGLYSLSSVVSVTSSSQPVTCNVAHPATNTKVDKTVA
PSTCSKPMCPPPELPGGPSVFIFPPKPKDTLMISRTPEVT
CVVVDVSQDDPEVQFTWYINNEQVRTARPPLREQQFNSTI
RVVSTLPIAHQDWLRGKEFKCKVHNKALPAPIEKTISKAR
GQPLEPKVYTMGPPREELSSRSVSLTCMINGFYPSDISVE
WEKNGKAEDNYKTTPTVLDSDGSYFLYSKLSVPTSEWQRG
DVFTCSVMHEALHNHYTQKSISRSPGK*

A11B1_3B1 Light Chain
(SEQ ID NO: 202)
MDTRAPTQLLGLLLLWLPGARCADIVMTQTPASVSEPVGG
TVTIKCQASQNINSGLAWYQQKPGQPPKLLIYKASTLASG
VSSRFKGSGSGTEFTLTISDLECADAATYYCQTYYYSSSS -continued SDNAFGGGTEVVVKGDPVAPTVLIFPPAADQVATGTVTIV
CVANKYFPDVTVTWEVDGTTQTTGIENSKTPQNSADCTYN
LSSTLTLTSTQYNSHKEYTCKVTQGTTSVVQSFNRGDC*

A11B1_2D3 Heavy Chain
(SEQ ID NO: 203)
METGLRWLLLVAVLKGVQCQSLEESGGDLVKPGASLTLTC
TASGFSFSSSYWICWVRQAPGKGLEWIACIYGGSSGNIAY
ASWAKGRFTISKTSSTTVTLQMTSLTAADTATYFCARDIP
SDAFTLDLWGPGTLVTVSSGQPKAPSVFPLAPCCGDTPSS
TVTLGCLVKGYLPEPVTVTWNSGTLTNGVRTFPSVRQSSG
LYSLSSVVSVTSSSQPVTCNVAHPATNTKVDKTVAPSTCS
KPMCPPPELPGGPSVFIFPPKPKDTLMISRTPEVTCVVVD
VSQDDPEVQFTWYINNEQVRTARPPLREQQFNSTIRVVST
LPIAHQDWLRGKEFKCKVHNKALPAPIEKTISKARGQPLE
PKVYTMGPPREELSSRSVSLTCMINGFYPSDISVEWEKNG
KAEDNYKTTPTVLDSDGSYFLYSKLSVPTSEWQRGDVFTC
SVMHEALHNHYTQKSISRSPGK*

A11B1_2D3 Light Chain
(SEQ ID NO: 204)
MDTRAPTQLLGLLLLWLPGATFAQVLTQTPSSVSAAVGST
VTINCQASQSVYKDNNLAWYQQKPGQPPKLLIYKASTLAS
GVPSRFKGSGSGTQFTLTISGVQCEDAATYYCQGEFSCGS
ADCIAFGGGTEVVVKGDPVAPTVLIFPPAADQVATGTVTI
VCVANKYFPDVTVTWEVDGTTQTTGIENSKTPQNSADCTY
NLSSTLTLTSTQYNSHKEYTCKVTQGTTSVVQSFNRGDC*

A11B1_2A7 Heavy Chain
(SEQ ID NO: 205)
METGLRWLLLVAVLKGVQCQSLEESGGDLVKPGASLTLTC
KGSGIDFSSGYGMWWVRQAPGKGLEYIGYIDTGYGSTYYA
SWAKGRFTISKTSSTTVTLQMTSLTVADTATYFCAKGGAI
DLWGPGTLVTVSSGQPKAPSVFPLAPCCGDTPSSTVTLGC
LVKGYLPEPVTVTWNSGTLTNGVRTFPSVRQSSGLYSLSS
VVSVTSSSQPVTCNVAHPATNTKVDKTVAPSTCSKPMCPP
PELPGGPSVFIFPPKPKDTLMISRTPEVTCVVVDVSQDDP
EVQFTWYINNEQVRTARPPLREQQFNSTIRVVSTLPIAHQ
DWLRGKEFKCKVHNKALPAPIEKTISKARGQPLEPKVYTM
GPPREELSSRSVSLTCMINGFYPSDISVEWEKNGKAEDNY
KTTPTVLDSDGSYFLYSKLSVPTSEWQRGDVFTCSVMHEA
LHNHYTQKSISRSPGK*

A11B1_2A7 Light Chain
(SEQ ID NO: 206)
MDTRAPTQLLGLLLLWLPGATFAAVLTQTPASTSAAVGGT
VTINCQSSQSVYRSNWLAWYQQKPGQPPKLLIYDVFNLAS
GVPSRFKGSGSGTQFTLTISGVQCADAATYYCQGSYYSGN -continued

WYSAFGGGTEVVVKGDPVAPTVLIFPPAADQVATGTVTIV

CVANKYFPDVTVTWEVDGTTQTTGIENSKTPQNSADCTYN

LSSTLTLTSTQYNSHKEYTCKVTQGTTSVVQSFNRGDC*

Human mAb Sequences

| Heavy Chain and Light Chain Variable Region Sequences | |
|---|---|
| 2004_04B03 | |
| Heavy Chain FR1 | QVQLVESGGGVVQPGRSLRLSCAAS (SEQ ID NO: 208) |
| Heavy Chain CDR1 | GFTFSNYG (SEQ ID NO: 209) |
| Heavy Chain FR2 | MNWVRQAPGKGLEWVSY (SEQ ID NO: 210) |
| Heavy Chain CDR2 | ISSSGSTV (SEQ ID NO: 211) |
| Heavy Chain FR3 | YYADSVKGRFTISRDNAKNSLYLQMNSLRDEDTAVYYCAS (SEQ ID NO: 212) |
| Heavy Chain CDR3 | GQLDTSDAFDI (SEQ ID NO: 213) |
| Heavy Chain FR4 | WGQGTLVTVSS (SEQ ID NO: 214) |
| Heavy Chain V Gene Segment | IGHV3-48 |
| Light Chain FR1 | DIEMTQSPSSPSASVGDRVTITCRAS (SEQ ID NO: 215) |
| Light Chain CDR1 | QSISSY (SEQ ID NO: 216) |
| Light Chain FR2 | LNWYQQKPGKAPKLLIY (SEQ ID NO: 217) |
| Light Chain CDR2 | AAS (SEQ ID NO: 218) |
| Light Chain FR3 | SLQSGVPSRFSGSGSGTDFTLTISSLQPEDFATYYC (SEQ ID NO: 219) |
| Light Chain CDR3 | QQSYSTPLT (SEQ ID NO: 220) |
| Light Chain FR4 | FGGGTKVEIK (SEQ ID NO: 221) |
| Light Chain V Gene Segment | IGKV1-39; IGKV1D-39 |
| Light Chain Locus | kappa |
| 2004_05_A06 | |
| Heavy Chain FR1 | EVQLLESGGGVVQSGRSLRVSCAAS (SEQ ID NO: 222) |
| Heavy Chain CDR1 | GFSFSSYG (SEQ ID NO: 223) |
| Heavy Chain FR2 | MHWVRQAPGKGLEWVSY (SEQ ID NO: 224) |
| Heavy Chain CDR2 | ISSSGSTI (SEQ ID NO: 225) |
| Heavy Chain FR3 | YYADSVKGRFTISRDNAENSLYLQMNSLRAEDTAVYYCAR (SEQ ID NO: 226) |
| Heavy Chain CDR3 | DLGHFDSGSSYFDY (SEQ ID NO: 442) |
| Heavy Chain FR4 | WGQGTLVTVSS (SEQ ID NO: 214) |
| Heavy Chain V Gene Segment | IGHV3-48 |
| Light Chain FR1 | DIQMTQSPSSLSASVGDRVTITCRAS (SEQ ID NO: 227) |
| Light Chain CDR1 | QGISNY (SEQ ID NO: 228) |
| Light Chain FR2 | LAWYQQKPGKVPKLLIY (SEQ ID NO: 229) |
| Light Chain CDR2 | AAS (SEQ ID NO: 218) |
| Light Chain FR3 | TLQSGVPSRFSGSGSGTDFTLTISSLQPEDFATYYC (SEQ ID NO: 230) |

-continued

| Heavy Chain and Light Chain Variable Region Sequences | |
|---|---|
| Light Chain CDR3 | QQSYSTPLT (SEQ ID NO: 220) |
| Light Chain FR4 | FGGGTKVEVK (SEQ ID NO: 231) |
| Light Chain V Gene Segment | IGKV1-27 |
| Light Chain Locus | kappa |
| 2004_04_C12 | |
| Heavy Chain FR1 | EVQLLESGGGVVQPGRSLRLSCAAS (SEQ ID NO: 232) |
| Heavy Chain CDR1 | GFTFSNYG (SEQ ID NO: 209) |
| Heavy Chain FR2 | MNWVRQAPGKGLEWVSY (SEQ ID NO: 210) |
| Heavy Chain CDR2 | ISSSSSTI (SEQ ID NO: 233) |
| Heavy Chain FR3 | YYADSVKGRFTISRDNAKNSLYLQMNSLRDEDTAVYYCAS (SEQ ID NO: 212) |
| Heavy Chain CDR3 | GQXDXSDAFDI (SEQ ID NO: 234) |
| Heavy Chain FR4 | WGQGTLVTVSS (SEQ ID NO: 214) |
| Heavy Chain V Gene Segment | IGHV3OR16-8 |
| Light Chain FR1 | DIEMTQSPSSPSASVGDRVTITCRAS (SEQ ID NO: 215) |
| Light Chain CDR1 | QSISSY (SEQ ID NO: 216) |
| Light Chain FR2 | LNXYQQKPGKAPKLLXY (SEQ ID NO: 235) |
| Light Chain CDR2 | XAS (SEQ ID NO: 236) |
| Light Chain FR3 | SLQSGVPSRFSGSGSGTDFTLTISSLQPEDXATYYC (SEQ ID NO: 237) |
| Light Chain CDR3 | QQSYSTPLT (SEQ ID NO: 220) |
| Light Chain FR4 | FGGGXKXEIK (SEQ ID NO: 238) |
| Light Chain V Gene Segment | IGKV1-39; IGKV1D-39 |
| Light Chain Locus | kappa |
| 2002_02_B07 | |
| Heavy Chain FR1 | EVQLLESGGGVVQPGRSLRLSCAAS (SEQ ID NO: 232) |
| Heavy Chain CDR1 | GFTFSTYG (SEQ ID NO: 436) |
| Heavy Chain FR2 | MHWVRQAPGKGLEWVSY (SEQ ID NO: 224) |
| Heavy Chain CDR2 | ISSSGSTI (SEQ ID NO: 225) |
| Heavy Chain FR3 | YYADSVKGRFAISRDNAKNTLYLQMNSLRAEDTALYYCAK (SEQ ID NO: 239) |
| Heavy Chain CDR3 | ATRYDILTGYSDGVDYFDY (SEQ ID NO: 240) |
| Heavy Chain FR4 | WGQGTLVTVSS (SEQ ID NO: 214) |
| Heavy Chain V Gene Segment | IGHV3-48 |
| Light Chain FR1 | DIQMTQSPSSLSASVGDRVTITCRAS (SEQ ID NO: 227) |
| Light Chain CDR1 | QSISSY (SEQ ID NO: 216) |
| Light Chain FR2 | LNWYQQKPGKAPKLLIY (SEQ ID NO: 217) |
| Light Chain CDR2 | AAS (SEQ ID NO: 218) |

-continued

| Heavy Chain and Light Chain Variable Region Sequences | |
|---|---|
| Light Chain FR3 | SLQSGVPSRFSGSGSGTDFTLTISSLQPEDFATYYC (SEQ ID NO: 219) |
| Light Chain CDR3 | HQSYSTPYT (SEQ ID NO: 241) |
| Light Chain FR4 | FGQGTKLEIK (SEQ ID NO: 242) |
| Light Chain V Gene Segment | IGKV1-39; IGKV1D-39 |
| Light Chain Locus | kappa |
| 2004_05_B04 | |
| Heavy Chain FR1 | QVQLVESGGGLVQPGGSLRLSCAAS (SEQ ID NO: 243) |
| Heavy Chain CDR1 | GFTFSSYW (SEQ ID NO: 437) |
| Heavy Chain FR2 | MSWVRQAPGKGLEWVAN (SEQ ID NO: 244) |
| Heavy Chain CDR2 | IKQDGSEK (SEQ ID NO: 245) |
| Heavy Chain FR3 | YYVDSVKGRFTISRDNAKNSLYLQMNSLRAEDTAVYYCAR (SEQ ID NO: 246) |
| Heavy Chain CDR3 | VTSPHAFDI (SEQ ID NO: 247) |
| Heavy Chain FR4 | WGRGTLVTVSS (SEQ ID NO: 248) |
| Heavy Chain V Gene Segment | IGHV3-7 |
| Light Chain FR1 | DIQMTQSPSAMSASVGDRVTITCRAS (SEQ ID NO: 249) |
| Light Chain CDR1 | QGISNY (SEQ ID NO: 228) |
| Light Chain FR2 | LAWFQQKPGKVPKRLIY (SEQ ID NO: 250) |
| Light Chain CDR2 | AAS (SEQ ID NO: 218) |
| Light Chain FR3 | SLQSGVPSRFSGSGSGTDFTLTISSLQPEDFATYYC (SEQ ID NO: 219) |
| Light Chain CDR3 | QQSYSTPLT (SEQ ID NO: 220) |
| Light Chain FR4 | FGGGTKVEVK (SEQ ID NO: 231) |
| Light Chain V Gene Segment | IGKV1-39; IGKV1D-17; IGKV1D-39 |
| Light Chain Locus | kappa |
| 2003_03_E12 | |
| Heavy Chain FR1 | QVQLVESGGGVVRPGGSLRLSCAAS (SEQ ID NO: 251) |
| Heavy Chain CDR1 | GFTFDDYG (SEQ ID NO: 438) |
| Heavy Chain FR2 | MSWVRQAPGKGLEWVSG (SEQ ID NO: 252) |
| Heavy Chain CDR2 | INWNGGST (SEQ ID NO: 253) |
| Heavy Chain FR3 | GYADSVKGRFTISRDNSKNTLYLQMNSLRGEDTAVYYCVT (SEQ ID NO: 254) |
| Heavy Chain CDR3 | QGSAFDI (SEQ ID NO: 255) |
| Heavy Chain FR4 | WGRGTLVTVSS (SEQ ID NO: 248) |
| Heavy Chain V Gene Segment | IGHV3-20 |
| Light Chain FR1 | SYELTQPPSLSVSPGQTARITCSGD (SEQ ID NO: 256) |
| Light Chain CDR1 | ALAKQY (SEQ ID NO: 257) |

-continued

| Heavy Chain and Light Chain Variable Region Sequences | |
|---|---|
| Light Chain FR2 | AYWYQQTPGQAPVLVIY (SEQ ID NO: 258) |
| Light Chain CDR2 | KDT (SEQ ID NO: 259) |
| Light Chain FR3 | ERPSGIPERFSGSSSGTTVTLTISGVQAEDEVDYYC (SEQ ID NO: 260) |
| Light Chain CDR3 | QSTDSSGTYQV (SEQ ID NO: 261) |
| Light Chain FR4 | FGGGTKLTVL (SEQ ID NO: 262) |
| Light Chain V Gene Segment | IGLV3-25 |
| Light Chain Locus | lambda |
| 1994_01_C07 | |
| Heavy Chain FR1 | QVQLVQSGAEVKKPGASVKVSCKAS (SEQ ID NO: 263) |
| Heavy Chain CDR1 | GYTFTSYG (SEQ ID NO: 439) |
| Heavy Chain FR2 | ISWVRQAPGQGLEWMGW (SEQ ID NO: 264) |
| Heavy Chain CDR2 | ISAYNGNT (SEQ ID NO: 265) |
| Heavy Chain FR3 | NYAQKLQGRVTMTTDTSTSTAYMELRSLRSDDTAAYYCAR (SEQ ID NO: 266) |
| Heavy Chain CDR3 | VTGITGTTIDP (SEQ ID NO: 267) |
| Heavy Chain FR4 | WGQGTMVTVSS (SEQ ID NO: 268) |
| Heavy Chain V Gene Segment | IGHV1-18 |
| Light Chain FR1 | DIQMTQSPSSLSASVGDRVTITCRAS (SEQ ID NO: 227) |
| Light Chain CDR1 | QSISSY (SEQ ID NO: 216) |
| Light Chain FR2 | LNWYQQKPGKAPKLLIY (SEQ ID NO: 217) |
| Light Chain CDR2 | DAS (SEQ ID NO: 269) |
| Light Chain FR3 | SLESGVPSRFSGSGSGTEFTLTISSLQPDDFAVYYC (SEQ ID NO: 270) |
| Light Chain CDR3 | QQYNNWPQT (SEQ ID NO: 271) |
| Light Chain FR4 | FGQGTKVEIK (SEQ ID NO: 272) |
| Light Chain V Gene Segment | IGKV1-13; IGKV1D-13 |
| Light Chain Locus | kappa |
| 1995_01_G07 | |
| Heavy Chain FR1 | QVQLVESGGGLVKPGGSLRLSCAAS (SEQ ID NO: 273) |
| Heavy Chain CDR1 | GFTFSSYA (SEQ ID NO: 440) |
| Heavy Chain FR2 | MSWVRQAPGKGLEWVSA (SEQ ID NO: 274) |
| Heavy Chain CDR2 | ISGSGGST (SEQ ID NO: 275) |
| Heavy Chain FR3 | YYADSVKGRFTISRDNSKNTLYLQMNSLRAEDTAVYYCAR (SEQ ID NO: 276) |
| Heavy Chain CDR3 | DYGGYDGVYFDY (SEQ ID NO: 277) |
| Heavy Chain FR4 | WGRGTLVTVSS (SEQ ID NO: 248) |

-continued

| Heavy Chain and Light Chain Variable Region Sequences | |
|---|---|
| Heavy Chain V Gene Segment | IGHV3-23 |
| Light Chain FR1 | SYELTQDPAVSVALGQTVRITCQGD (SEQ ID NO: 278) |
| Light Chain CDR1 | SLRSYY (SEQ ID NO: 279) |
| Light Chain FR2 | ASWYQQKPGQAPVLVIY (SEQ ID NO: 280) |
| Light Chain CDR2 | GKN (SEQ ID NO: 281) |
| Light Chain FR3 | NRPSGIPDRFSGSSSGNTASLTITGAQAEDEADYYC (SEQ ID NO: 282) |
| Light Chain CDR3 | NSRDSSGNHVV (SEQ ID NO: 283) |
| Light Chain FR4 | FGGGTKVTVL (SEQ ID NO: 284) |
| Light Chain V Gene Segment | IGLV3-19 |
| Light Chain Locus | lamdba |
| 1995_01_G05 | |
| Heavy Chain FR1 | EVQLLESGGGLVKPGGSLRLSCAAS (SEQ ID NO: 285) |
| Heavy Chain CDR1 | GFTFSSYA (SEQ ID NO: 440) |
| Heavy Chain FR2 | MHWVRQAPGKGLEWVAV (SEQ ID NO: 286) |
| Heavy Chain CDR2 | ISYDGSNK (SEQ ID NO: 287) |
| Heavy Chain FR3 | YYADSVKGRFAISRDNSKNTLYLQMNSLRAEDTAVYYCAR (SEQ ID NO: 288) |
| Heavy Chain CDR3 | DRDVGPTYYYYGMDV (SEQ ID NO: 289) |
| Heavy Chain FR4 | WGQGTMVTVSS (SEQ ID NO: 268) |
| Heavy Chain V Gene Segment | IGHV3-30 |
| Light Chain FR1 | SYELTQPPSLSVSPGQTARITCSGH (SEQ ID NO: 290) |
| Light Chain CDR1 | ALPKQY (SEQ ID NO: 291) |
| Light Chain FR2 | AYWYQQTPGQAPVLVIY (SEQ ID NO: 258) |
| Light Chain CDR2 | KDT (SEQ ID NO: 259) |
| Light Chain FR3 | ERPSGIPERFSGSSSGTTVTLTISGVQAEDEADYYC (SEQ ID NO: 292) |
| Light Chain CDR3 | QSADSSGPYQV (SEQ ID NO: 293) |
| Light Chain FR4 | FGGGTQLTVL (SEQ ID NO: 294) |
| Light Chain V Gene Segment | IGLV3-25 |
| Light Chain Locus | lamdba |
| 2004_03_G10 | |
| Heavy Chain FR1 | EVQLLESGGGVVQPGRSLRLSCAAS (SEQ ID NO: 232) |
| Heavy Chain CDR1 | GFTFSSYA (SEQ ID NO: 440) |
| Heavy Chain FR2 | MSWVRQAPGKGLEWVSA (SEQ ID NO: 274) |
| Heavy Chain CDR2 | ISGSGGST (SEQ ID NO: 275) |
| Heavy Chain FR3 | YYADSVKGRFTISRDNSKNTLYLQMNSLRAEDTAVYYCAK (SEQ ID NO: 295) |

-continued

| Heavy Chain and Light Chain Variable Region Sequences | |
|---|---|
| Heavy Chain CDR3 | DREYIAVAADY (SEQ ID NO: 296) |
| Heavy Chain FR4 | WGQGTTVTVSS (SEQ ID NO: 297) |
| Heavy Chain V Gene Segment | IGHV3-23 |
| Light Chain FR1 | DIQMTQSPSSLSASVGDTISITCRAS (SEQ ID NO: 298) |
| Light Chain CDR1 | QSISSY (SEQ ID NO: 216) |
| Light Chain FR2 | LNWYQQKPGKAPKLLIY (SEQ ID NO: 217) |
| Light Chain CDR2 | AAS (SEQ ID NO: 218) |
| Light Chain FR3 | SLQSGVPSRFSGSGSRTDFTLTISSVQPEDFATYYC (SEQ ID NO: 299) |
| Light Chain CDR3 | QQSYSTPFT (SEQ ID NO: 300) |
| Light Chain FR4 | FGPGTKVEIK (SEQ ID NO: 301) |
| Light Chain V Gene Segment | IGKV1-39; IGKV1D-39 |
| Light Chain Locus | kappa |
| 2002_02_B05 | |
| Heavy Chain FR1 | EVQLLESGGGVVQPGRSLRLSCAAS (SEQ ID NO: 232) |
| Heavy Chain CDR1 | GFTFSTYG (SEQ ID NO: 436) |
| Heavy Chain FR2 | MHWVRQAPGKGLEWVSY (SEQ ID NO: 224) |
| Heavy Chain CDR2 | ISSSGSTI (SEQ ID NO: 225) |
| Heavy Chain FR3 | YYADSVKGRFAISRDNAKNTLYLQMNSLRAEDTALYYCAK (SEQ ID NO: 239) |
| Heavy Chain CDR3 | ATRYDILTGYSDGVDYFDY (SEQ ID NO: 240) |
| Heavy Chain FR4 | WGQGTLVTVSS (SEQ ID NO: 214) |
| Heavy Chain V Gene Segment | IGHV3-48 |
| Light Chain FR1 | DIQMTQSPSSLSASVGDRVTITCRAS (SEQ ID NO: 227) |
| Light Chain CDR1 | QSISSY (SEQ ID NO: 216) |
| Light Chain FR2 | LNWYQQKPGKAPKLLIY (SEQ ID NO: 217) |
| Light Chain CDR2 | AAS (SEQ ID NO: 218) |
| Light Chain FR3 | SLQSGVPSRFSGSGSGTDFTLTISSLQPEDFATYYC (SEQ ID NO: 219) |
| Light Chain CDR3 | QQSYSTPFT (SEQ ID NO: 300) |
| Light Chain FR4 | FGPGTKVEIK (SEQ ID NO: 301) |
| Light Chain V Gene Segment | IGKV1-39; IGKV1D-39 |
| Light Chain Locus | kappa |
| 2003_03_F05 | |
| Heavy Chain FR1 | EVQLVESGAEVKKPGASVKVSCKAS (SEQ ID NO: 302) |
| Heavy Chain CDR1 | GYTFTRYY (SEQ ID NO: 441) |
| Heavy Chain FR2 | MHWVRQAPGQGLEWMGI (SEQ ID NO: 303) |
| Heavy Chain CDR2 | INPSGGST (SEQ ID NO: 304) |

-continued

| Heavy Chain and Light Chain Variable Region Sequences | |
|---|---|
| Heavy Chain FR3 | IYAQKFQGRVTMTRDTSTSTVYMELSSLRSEDTAVYYCAR (SEQ ID NO: 305) |
| Heavy Chain CDR3 | SLRDGYNYIGSLGY (SEQ ID NO: 306) |
| Heavy Chain FR4 | WGQGTLVTVSS (SEQ ID NO: 214) |
| Heavy Chain V Gene Segment | IGHV1-46 |
| Light Chain FR1 | QSELTQPPSASGTPGQRVTISCSGS (SEQ ID NO: 307) |
| Light Chain CDR1 | SSNIGSNY (SEQ ID NO: 308) |
| Light Chain FR2 | VYWYQQLPGTAPKLLIY (SEQ ID NO: 309) |
| Light Chain CDR2 | RNN (SEQ ID NO: 310) |
| Light Chain FR3 | QRPSGVPDRFSGSKSGTSASLAIRGLQSEDEAGYYC (SEQ ID NO: 311) |
| Light Chain CDR3 | AAWDDSLNGLNWV (SEQ ID NO: 207) |
| Light Chain FR4 | FGGGTQLTVL (SEQ ID NO: 294) |
| Light Chain V Gene Segment | IGLV1-44; IGLV1-47 |
| Light Chain Locus | lambda |
| 1994_01_A07 | |
| Heavy Chain FR1 | QVQLVESGGGLVQPGGSLRLSCAAS (SEQ ID NO: 243) |
| Heavy Chain CDR1 | GFTFDDYA (SEQ ID NO: 312) |
| Heavy Chain FR2 | MHWVRQAPGKGLEWVSG (SEQ ID NO: 313) |
| Heavy Chain CDR2 | ISWNSGST (SEQ ID NO: 314) |
| Heavy Chain FR3 | YYADSVKGRFTISRDNSKNTLYLQMNSLRAEDTAVYYCAG (SEQ ID NO: 315) |
| Heavy Chain CDR3 | GSRRYDSSGYYYESFDY (SEQ ID NO: 316) |
| Heavy Chain FR4 | WGQGTTVTVSS (SEQ ID NO: 297) |
| Light Chain FR1 | DIQMTQSPSSLSASVGDRVTITCRAS (SEQ ID NO: 227) |
| Light Chain CDR1 | QSISSY (SEQ ID NO: 216) |
| Light Chain FR2 | LNWYQQKPGKAPKLLIY (SEQ ID NO: 217) |
| Light Chain CDR2 | DAS (SEQ ID NO: 269) |
| Light Chain FR3 | NLETGVPSRFSGSGSGTDFTLTISSLQPEDFATYYC (SEQ ID NO: 317) |
| Light Chain CDR3 | QQSYHTPYT (SEQ ID NO: 318) |
| Light Chain FR4 | FGQGTKVEIK (SEQ ID NO: 272) |
| Light Chain Locus | kappa |
| 1994_01_A09 | |
| Heavy Chain FR1 | QMQLVQSGAEVKKPGSSVKVSCKAS (SEQ ID NO: 319) |
| Heavy Chain CDR1 | GGTFSSYA (SEQ ID NO: 320) |
| Heavy Chain FR2 | ISWVRQAPGQGLEWMGR (SEQ ID NO: 321) |
| Heavy Chain CDR2 | IIPILGIA (SEQ ID NO: 322) |
| Heavy Chain FR3 | NYAQKFQGRVTITADKSTSTAYMELSSLRSEDTAVYYCAR (SEQ ID NO: 323) |

-continued

| Heavy Chain and Light Chain Variable Region Sequences | |
|---|---|
| Heavy Chain CDR3 | DINRYNWNFRAFDI (SEQ ID NO: 324) |
| Heavy Chain FR4 | WGQGTLVTVSS (SEQ ID NO: 214) |
| Light Chain FR1 | DIVMTQSPDSLAVSLGERATINCKSS (SEQ ID NO: 435) |
| Light Chain CDR1 | QSVLYSSNNKNY (SEQ ID NO: 325) |
| Light Chain FR2 | LAWYQQKPRQPPKLLIY (SEQ ID NO: 326) |
| Light Chain CDR2 | WAS (SEQ ID NO: 327) |
| Light Chain FR3 | TRESGVPDRFSGNGSGTDFTLTISSLQAEDVAAYYC (SEQ ID NO: 328) |
| Light Chain CDR3 | QQHYSTPLT (SEQ ID NO: 329) |
| Light Chain FR4 | FGPGTKVEIK (SEQ ID NO: 301) |
| Light Chain Locus | kappa |
| 1994_01_D12 | |
| Heavy Chain FR1 | QVQLVQSGAEVKKPGSSVKVSCKAS (SEQ ID NO: 330) |
| Heavy Chain CDR1 | GYTFTSYG (SEQ ID NO: 439) |
| Heavy Chain FR2 | ISWVRQAPGQGLEWMGW (SEQ ID NO: 264) |
| Heavy Chain CDR2 | ISAYNGNT (SEQ ID NO: 265) |
| Heavy Chain FR3 | NYAQKLQGRVTMTTNTSTSTAYMELRSLRSDDTAVYYCAR (SEQ ID NO: 331) |
| Heavy Chain CDR3 | VTGITGTTIDP (SEQ ID NO: 267) |
| Heavy Chain FR4 | WGQGTLVTVSS (SEQ ID NO: 214) |
| Light Chain FR1 | DIQMTQSPSSLSASVGDRVTITCRAS (SEQ ID NO: 227) |
| Light Chain CDR1 | QSISSY (SEQ ID NO: 216) |
| Light Chain FR2 | LNWYRQKPGKAPKLLIY (SEQ ID NO: 332) |
| Light Chain CDR2 | AAS (SEQ ID NO: 218) |
| Light Chain FR3 | SLQSGVPSRFSGSGSGTDFTLTISSLQPEDAATYYC (SEQ ID NO: 333) |
| Light Chain CDR3 | QQYDSQSGT (SEQ ID NO: 334) |
| Light Chain FR4 | FGQGTKLEIK (SEQ ID NO: 242) |
| Light Chain Locus | kappa |
| 1995_01_F05 | |
| Heavy Chain FR1 | EVQLVESGGGVVQPGRSLRLSCAAS (SEQ ID NO: 335) |
| Heavy Chain CDR1 | GFTFSSYA (SEQ ID NO: 440) |
| Heavy Chain FR2 | MHWVRQAPGKGLEWVAV (SEQ ID NO: 286) |
| Heavy Chain CDR2 | ISYDGVKK (SEQ ID NO: 336) |
| Heavy Chain FR3 | YYADSVKGRFTISRDNSKSTLYLQMNSLRVDDTAVYYCAK (SEQ ID NO: 337) |
| Heavy Chain CDR3 | DLGWQNDY (SEQ ID NO: 338) |
| Heavy Chain FR4 | WGQGTLVTVSS (SEQ ID NO: 214) |
| Light Chain FR1 | QSVLTQPASVSGSPGQSITISCTGT DLGWQNDY (SEQ ID NO: 339) |
| Light Chain CDR1 | SSDVGGHNY (SEQ ID NO: 340) |

-continued

| Heavy Chain and Light Chain Variable Region Sequences | |
|---|---|
| Light Chain FR2 | VSWYQQHPGKAPKLMIY (SEQ ID NO: 341) |
| Light Chain CDR2 | DVS (SEQ ID NO: 342) |
| Light Chain FR3 | NRPSGVSNRFSGSKSGNTASLTISGLQAEDEADYYC (SEQ ID NO: 343) |
| Light Chain CDR3 | SSYTSSSPWV (SEQ ID NO: 344) |
| Light Chain FR4 | FGGGTKLTVLG (SEQ ID NO: 345) |
| Light Chain Locus | lambda |
| 1995_01_F09 | |
| Heavy Chain FR1 | EVQLVESGGGLVQPGGSLRLSCAAS (SEQ ID NO: 346) |
| Heavy Chain CDR1 | GFTFSSYA (SEQ ID NO: 440) |
| Heavy Chain FR2 | MSWVRQAPGKGLEWVSA (SEQ ID NO: 274) |
| Heavy Chain CDR2 | ISGSGGST (SEQ ID NO: 275) |
| Heavy Chain FR3 | YYADSVKGRFTISRDNSKNALYLQMNSLRAEDTAVYYCRG (SEQ ID NO: 347) |
| Heavy Chain CDR3 | YCSSTSCYGRRGAFDI (SEQ ID NO: 348) |
| Heavy Chain FR4 | SGQGTLVTVSS (SEQ ID NO: 349) |
| Light Chain FR1 | QAVLTQPPSASGTPGQRVTISCSGR (SEQ ID NO: 350) |
| Light Chain CDR1 | NSNIGSNN (SEQ ID NO: 351) |
| Light Chain FR2 | VNWYQHLPGTAPKLLIY (SEQ ID NO: 352) |
| Light Chain CDR2 | SNN (SEQ ID NO: 353) |
| Light Chain FR3 | QRPSGVPDRFSASKSGTSASLAISGLQSEDEADYYC (SEQ ID NO: 354) |
| Light Chain CDR3 | AAWDDRMNGPV (SEQ ID NO: 355) |
| Light Chain FR4 | IGGGTKVTVLG (SEQ ID NO: 356) |
| Light Chain Locus | lambda |
| 1996_01_H07 | |
| Heavy Chain FR1 | QVQLVESGGGLVQPGGSLRLSCAAS (SEQ ID NO: 243) |
| Heavy Chain CDR1 | GFTFSSYW (SEQ ID NO: 437) |
| Heavy Chain FR2 | MHWVRQAPAKGLVWVSR (SEQ ID NO: 357) |
| Heavy Chain CDR2 | INSDGSST (SEQ ID NO: 358) |
| Heavy Chain FR3 | SYADSVKGRFTISRDNSKNTLYLQMNSLRAEDTAVYYCAR (SEQ ID NO: 359) |
| Heavy Chain CDR3 | DFWSGRPYYYYMDV (SEQ ID NO: 360) |
| Heavy Chain FR4 | WGQGTTVTVSS (SEQ ID NO: 297) |
| Light Chain FR1 | DIQMTQSPSSLSASVGDRVTITCRAS (SEQ ID NO: 227) |
| Light Chain CDR1 | QDIGDD (SEQ ID NO: 361) |
| Light Chain FR2 | LAWFQQKPGKAPKRLIY (SEQ ID NO: 362) |
| Light Chain CDR2 | AAS (SEQ ID NO: 218) |
| Light Chain FR3 | TLQGGVPSRFSGSGSGTDFTLTISSLQPEDFATYYC (SEQ ID NO: 363) |
| Light Chain CDR3 | QQSYSTPRT (SEQ ID NO: 364) |

-continued

| Heavy Chain and Light Chain Variable Region Sequences | |
|---|---|
| Light Chain FR4 | FGPGTKVEIK (SEQ ID NO: 301) |
| Light Chain Locus | kappa |
| 1997_02_B01 | |
| Heavy Chain FR1 | EVQLVESGGGVVQPGRSLRLSCAAS (SEQ ID NO: 335) |
| Heavy Chain CDR1 | GFTFSSYA (SEQ ID NO: 440) |
| Heavy Chain FR2 | MHWVRQAPGKGLEWVAV (SEQ ID NO: 286) |
| Heavy Chain CDR2 | ISYDGSNK (SEQ ID NO: 287) |
| Heavy Chain FR3 | YYADSVKGRFTISRDNSKNTLYLQMNSRRAEDTAVYYCAR (SEQ ID NO: 365) |
| Heavy Chain CDR3 | WGIVAARPNYYYGMDV (SEQ ID NO: 366) |
| Heavy Chain FR4 | WGQGTLVTVSS (SEQ ID NO: 214) |
| Light Chain FR1 | QSALTQPRSVSGSPGQSVTISCTGT (SEQ ID NO: 367) |
| Light Chain CDR1 | SSDVGGYNY (SEQ ID NO: 368) |
| Light Chain FR2 | VSWYQQHPGKAPKLMIY (SEQ ID NO: 341) |
| Light Chain CDR2 | DVS (SEQ ID NO: 342) |
| Light Chain FR3 | KRPSGVPDRFSGSKSGNTASLTISGLQAEDEADYHC (SEQ ID NO: 443) |
| Light Chain CDR3 | SSYANNSPWV (SEQ ID NO: 369) |
| Light Chain FR4 | FGGGTKVTVLG (SEQ ID NO: 370) |
| Light Chain Locus | lambda |
| 2002_02_E01 | |
| Heavy Chain FR1 | QVQLVQSGAEVRKPGASVKVSCKAS (SEQ ID NO: 371) |
| Heavy Chain CDR1 | GYTFTSYG (SEQ ID NO: 439) |
| Heavy Chain FR2 | ISWVRQAPGQGLEWMGW (SEQ ID NO: 264) |
| Heavy Chain CDR2 | ISAYNGNT (SEQ ID NO: 265) |
| Heavy Chain FR3 | NYAQKLQGRVTMTTDTSTSTAYMELRSLRSDDTAVYYCAR (SEQ ID NO: 372) |
| Heavy Chain CDR3 | VTGITGTTIDP (SEQ ID NO: 267) |
| Heavy Chain FR4 | WGQGTLVTVSS (SEQ ID NO: 214) |
| Light Chain FR1 | DIQMTQSPSSLSASVGDRVTITCQAS (SEQ ID NO: 373) |
| Light Chain CDR1 | QDISNY (SEQ ID NO: 374) |
| Light Chain FR2 | LNWYQQKPGKAPKLLIY (SEQ ID NO: 217) |
| Light Chain CDR2 | DAS (SEQ ID NO: 269) |
| Light Chain FR3 | NLETGVPSRFSGSGSGTDFTFTISSLQPEDIATYYC (SEQ ID NO: 375) |
| Light Chain CDR3 | QQYANLPLT (SEQ ID NO: 376) |
| Light Chain FR4 | FGGGTKVEIK (SEQ ID NO: 221) |
| Light Chain Locus | kappa |
| 2002_02_G11 | |
| Heavy Chain FR1 | EVQLVESGGGLVQPGGSLRLSCAAS (SEQ ID NO: 346) |
| Heavy Chain CDR1 | GFTVSSNY (SEQ ID NO: 377) |

-continued

| Heavy Chain and Light Chain Variable Region Sequences | |
|---|---|
| Heavy Chain FR2 | MSWVRQAPGKGLEWVSV (SEQ ID NO: 378) |
| Heavy Chain CDR2 | IYSGGST (SEQ ID NO: 379) |
| Heavy Chain FR3 | YYADSVKGRFTISRDNSKNTLYLQMNSLRAEDTAVYYCAR (SEQ ID NO: 276) |
| Heavy Chain CDR3 | GGLTGDDAFDI (SEQ ID NO: 380) |
| Heavy Chain FR4 | WGQGTLVTVSS (SEQ ID NO: 214) |
| Light Chain FR1 | DIQMTQSPSSLSASVGDRVTITCRAS (SEQ ID NO: 227) |
| Light Chain CDR1 | QSISSF (SEQ ID NO: 381) |
| Light Chain FR2 | LNWYQQKPGTAPKLLIY (SEQ ID NO: 382) |
| Light Chain CDR2 | TTS (SEQ ID NO: 383) |
| Light Chain FR3 | SLQSGVPSRFSGSGSGTDFTLTISSLQPEDFATYYC (SEQ ID NO: 219) |
| Light Chain CDR3 | QQGNSLPLT (SEQ ID NO: 384) |
| Light Chain FR4 | FGGGTKVEIK (SEQ ID NO: 221) |
| Light Chain Locus | kappa |
| 2003_03_A09 | |
| Heavy Chain FR1 | QVQLVESGGGVVQPGRSLRLSCAAS (SEQ ID NO: 208) |
| Heavy Chain CDR1 | GFTFSSYA (SEQ ID NO: 440) |
| Heavy Chain FR2 | MHWVRQAPGKGLEWVAV (SEQ ID NO: 286) |
| Heavy Chain CDR2 | ISYDGSNK (SEQ ID NO: 287) |
| Heavy Chain FR3 | YYADSVKGRFTISRDNSKNTLYLQMNSLRAEDTAVYYCAR (SEQ ID NO: 276) |
| Heavy Chain CDR3 | DKELSY (SEQ ID NO: 385) |
| Heavy Chain FR4 | WGQGTLVTVSS (SEQ ID NO: 214) |
| Light Chain FR1 | QSGLTQPASVSGSPGQSITISCTGT (SEQ ID NO: 386) |
| Light Chain CDR1 | SSDVGGYNY (SEQ ID NO: 368) |
| Light Chain FR2 | VSWYQQHPGKAPKLMIY (SEQ ID NO: 341) |
| Light Chain CDR2 | EVS (SEQ ID NO: 387) |
| Light Chain FR3 | NRPSGVPDRFSGSKSGNTASLTISGLQAEDEADYYC (SEQ ID NO: 388) |
| Light Chain CDR3 | SSYTSSSPWV (SEQ ID NO: 344) |
| Light Chain FR4 | FGGGTKLTVLG (SEQ ID NO: 345) |
| Light Chain Locus | lambda |
| 2004_04_D03 | |
| Heavy Chain FR1 | QVQLVESGGGVVQPGRSLRLSCAAS (SEQ ID NO: 208) |
| Heavy Chain CDR1 | GFTFSNYG (SEQ ID NO: 209) |
| Heavy Chain FR2 | MNWVRQAPGKGLEWVSY (SEQ ID NO: 210) |
| Heavy Chain CDR2 | ISSSSSTI (SEQ ID NO: 233) |
| Heavy Chain FR3 | YYADSVKGRFTISRDNAKNSLYLQMNSLRDEDTAVYYCAS (SEQ ID NO: 212) |
| Heavy Chain CDR3 | GQLDTSDAFDI (SEQ ID NO: 213) |

-continued

| Heavy Chain and Light Chain Variable Region Sequences | |
|---|---|
| Heavy Chain FR4 | WGQGTTVTVSS (SEQ ID NO: 297) |
| Light Chain FR1 | DIQMTQSPSSLSASVGDRVTITCRAS (SEQ ID NO: 227) |
| Light Chain CDR1 | QSISSY (SEQ ID NO: 216) |
| Light Chain FR2 | LNWYQQKPGKAPKLLIY (SEQ ID NO: 217) |
| Light Chain CDR2 | KTS (SEQ ID NO: 389) |
| Light Chain FR3 | NLQSGVPSRFSGSGSGTDFTLTISSLQPEDFATYYC (SEQ ID NO: 390) |
| Light Chain CDR3 | QQSYSTPLT (SEQ ID NO: 220) |
| Light Chain FR4 | FGGGTKVEIK (SEQ ID NO: 221) |
| Light Chain Locus | kappa |
| 2004_04_F01 | |
| Heavy Chain FR1 | EVQLVESGGGLVQPGGSLRLSCAAS (SEQ ID NO: 346) |
| Heavy Chain CDR1 | GFTFSSYA (SEQ ID NO: 440) |
| Heavy Chain FR2 | MSWVRQAPAKGLEWVSA (SEQ ID NO: 391) |
| Heavy Chain CDR2 | ISGSGGST (SEQ ID NO: 275) |
| Heavy Chain FR3 | YYADSVKGRFTISRDNSKNTLYLQMNSLRAEDTAVYYCAK (SEQ ID NO: 295) |
| Heavy Chain CDR3 | DRPYSYGKNDAFDI (SEQ ID NO: 392) |
| Heavy Chain FR4 | WGQGTTVTVSS (SEQ ID NO: 297) |
| Light Chain FR1 | DIQMTQSPSSLSASVGDRVTITCQAS (SEQ ID NO: 373) |
| Light Chain CDR1 | QDVSNY (SEQ ID NO: 393) |
| Light Chain FR2 | LNWYRQKPGKAPKLLIY (SEQ ID NO: 332) |
| Light Chain CDR2 | AAS (SEQ ID NO: 218) |
| Light Chain FR3 | SLQSGVPSRFSGSGSGTDFTLTISSLQPEDFATYYC (SEQ ID NO: 219) |
| Light Chain CDR3 | QQSYSTPLT (SEQ ID NO: 220) |
| Light Chain FR4 | FGGGTKLEIK (SEQ ID NO: 394) |
| Light Chain Locus | kappa |
| 2005_05_E05 | |
| Heavy Chain FR1 | EVQLVQSGAEVKKPGASVKVSCKAS (SEQ ID NO: 395) |
| Heavy Chain CDR1 | GYTFTSYY (SEQ ID NO: 396) |
| Heavy Chain FR2 | MHWVRQAPGQGLEWMGI (SEQ ID NO: 303) |
| Heavy Chain CDR2 | INPSGGST (SEQ ID NO: 304) |
| Heavy Chain FR3 | SYAQKFQGRVTMTRDTSTSTVYMELSSLRSEDTAVYYCAR (SEQ ID NO: 397) |
| Heavy Chain CDR3 | SPWLITFGGVIAMGY (SEQ ID NO: 402) |
| Heavy Chain FR4 | WGQGTLVTVSS (SEQ ID NO: 214) |
| Light Chain FR1 | QSVLTQPPSASGTPGQRVTISCSGS (SEQ ID NO: 403) |
| Light Chain CDR1 | SSNIGSNY (SEQ ID NO: 308) |
| Light Chain FR2 | VYWYQQLPGTAPKLLIY (SEQ ID NO: 309) |

-continued

| Heavy Chain and Light Chain Variable Region Sequences | |
|---|---|
| Light Chain CDR2 | RNN (SEQ ID NO: 310) |
| Light Chain FR3 | QRPSGVPDRFSGSKSGTSASLAISGLRSEDEADYYC (SEQ ID NO: 404) |
| Light Chain CDR3 | AAWDDSLSGVV (SEQ ID NO: 405) |
| Light Chain FR4 | FGGGTQLTVLG (SEQ ID NO: 406) |
| Light Chain Locus | lambda |
| 1994_01_D04 | |
| Heavy Chain FR1 | QVQLVQSGAEVRKPGASVKVSCKAS (SEQ ID NO: 371) |
| Heavy Chain CDR1 | GYTFTSYG (SEQ ID NO: 439) |
| Heavy Chain FR2 | ISWVRQAPGQGLEWMGW (SEQ ID NO: 264) |
| Heavy Chain CDR2 | ISAYNGNT (SEQ ID NO: 265) |
| Heavy Chain FR3 | NYAQKLQGRVTMTTDTSTSTAYMELRSLRSDDTAVYYCAR (SEQ ID NO: 372) |
| Heavy Chain CDR3 | VTGITGTTIDP (SEQ ID NO: 267) |
| Heavy Chain FR4 | WGQGTLVTVSS (SEQ ID NO: 214) |
| Light Chain FR1 | DIVMTQSPSSLSASVGDRVTITCRAS (SEQ ID NO: 407) |
| Light Chain CDR1 | QSISSY (SEQ ID NO: 216) |
| Light Chain FR2 | LNWYQQKPGKAPKLLIY (SEQ ID NO: 217) |
| Light Chain CDR2 | DAS (SEQ ID NO: 269) |
| Light Chain FR3 | NLETGVPSRFSGSGSGTDFTLTISSLQPEDFATYYC (SEQ ID NO: 317) |
| Light Chain CDR3 | QQFNNYPLT (SEQ ID NO: 408) |
| Light Chain FR4 | FGGGTKLEIK (SEQ ID NO: 394) |
| Light Chain Locus | kappa |
| 1997_02_B03 | |
| Heavy Chain FR1 | QVQLVESGAEVKKPGASVKVSCKAS (SEQ ID NO: 409) |
| Heavy Chain CDR1 | GYTFTSYY (SEQ ID NO: 396) |
| Heavy Chain FR2 | MHWVRQAPGQGLEWMGI (SEQ ID NO: 303) |
| Heavy Chain CDR2 | INPSGGST (SEQ ID NO: 304) |
| Heavy Chain FR3 | SYAQKFQGRVTMTRDTSTSTVYMELSSLRSEDTAVYYCAR (SEQ ID NO: 397) |
| Heavy Chain CDR3 | AGGYYYYYMDV (SEQ ID NO: 398) |
| Heavy Chain FR4 | WGQGTLVTVSS (SEQ ID NO: 214) |
| Light Chain FR1 | QSGLTQPPSASGTPGQRVTISCSGS (SEQ ID NO: 399) |
| Light Chain CDR1 | GPNIGNNY (SEQ ID NO: 400) |
| Light Chain FR2 | VYWYQQLPGTAPKLLMY (SEQ ID NO: 401) |
| Light Chain CDR2 | RNN (SEQ ID NO: 310) |
| Light Chain FR3 | QRPSGVPDRFSGSKSGTSASLAISGLQSEDEADYYC (SEQ ID NO: 410) |
| Light Chain CDR3 | AAWDDSLNGYV (SEQ ID NO: 411) |

-continued

| Heavy Chain and Light Chain Variable Region Sequences | |
|---|---|
| Light Chain FR4 | FGTGTKLTVLG (SEQ ID NO: 412) |
| Light Chain Locus | lambda |

Humanized mAb Sequences

Humanized 79E3E3 Heavy Chain Variable Region
(SEQ ID NO: 413)
QIQLVQSGAEVKKPGESLKISCKASGYTFTDYAIGWVRQMPGKGLEWMGIINTQTGKPK

YSPSFQGQFIFSLDTSINTTYLQWSSLKASDTAIYFCTRLGTGNTKGFAYWGQGTTVTV

SS

Humanized 79E3E3 Light Chain Variable Region
(SEQ ID NO: 414)
DIQITQSPSSLSASLGDKVTITCRSSQSLLYSENNQDYLAWYQQKPGKAPKLLIYGAS

NLQSGVPSRFSGRGSGTDFTLTISSLQPEDFATYYCEQTYRYPFTFGPGTKVDIKR

Humanized 9-G05 Heavy Chain VH_1
Leader sequence-VH-hIgG1CH-Stop codon*
(SEQ ID NO: 415)
*MGWSCIILFIVATATGVHS*QVQLVQSGAEVKKPGASVKVSCKASGYTFPDYNMDWVR

QAPGQRLEWMGYINPDNGGTIYNQKFKGRVTLTVDTSASTAYMELSSLRSEDTAVYYC

ARLDSSGYGYYAMDYWGQGTSVTVSSASTKGPSVFPLAPSSKSTSGGTAALGCLVKD

YFPEPVTVSWNSGALTSGVHTFPAVLQSSGLYSLSSVVTVPSSSLGTQTYICNVNHK

PSNTKVDKKVEPKSCDKTHTCPPCPAPELLGGPSVFLFPPKPKDTLMISRTPEVTCV

WDVSHEDPEVKFNWYVDGVEVHNAKTKPREEQYASTYRVVSVLTVLHQDWLNG

KEYKCKVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVFSCSVM

HEALHNHYTQKSLSLSPGK*

Humanized 9-G05 Heavy Chain VH_2
Leader sequence-VH-hIgG1CH-Stop codon*
(SEQ ID NO: 416)
*MGWSCIILFIVATATGVHS*QVQLVQSGAEVKKPGASVKVSCKASGYTFPDYNMDWVR

QAPGQRLEWIGYINPDNGGTIYNQKFKGRVTLTVDTSASTAYMELSSLRSEDTAVYYCA

RLDSSGYGYYAMDYWGQGTSVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPS

NTKVDKKVEPKSCDKTHTCPPCPAPELLGGPSVFLFPPKPKDTLMISRTPEVTCVV

VDVSHEDPEVKFNWYVDGVEVHNAKTKPREEQYASTYRVVSVLTVLHQDWLNGK

EYKCKVSNKALPAPIEKTISKAKGQPREPQVYTLPPSRDELTKNQVSLTCLVKGFYP

SDIAVEWESNGQPENNYKTTPPVLDSDGSFFLYSKLTVDKSRWQQGNVFSCSVMHE

ALHNHYTQKSLSLSPGK*

Humanized 9-G05 Heavy Chain VH_3
Leader sequence-VH-hIgG1CH-Stop codon*
(SEQ ID NO: 417)
*MGWSCIILFIVATATGVHS*QVQLVQSGAEVKKPGASVKVSCKASGYTFPDYNMDWVR

QAPGQRLEWMGYINPDNGGTIYNQKFKGRATLTVDTSASTAYMELSSLRSEDTAVYYC

ARLDSSGYGYYAMDYWGQGTSVTVSSASTKGPSVFPLAPSSKSTSGGTAALGCLVKD

YFPEPVTVSWNSGALTSGVHTFPAVLQSSGLYSLSSVVTVPSSSLGTQTYICNVNHK

-continued

PSNTKVDKKVEPKSCDKTHTCPPCPAPELLGGPSVFLFPPKPKDTLMISRTPEVTCV

WDVSHEDPEVKFNWYVDGVEVHNAKTKPREEQYASTYRVVSVLTVLHQDWLNG

KEYKCKVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVFSCSVM

HEALHNHYTQKSLSLSPGK*

Humanized 9-G05 Heavy Chain VH_4
Leader sequence-VH-hIgG1CH-Stop codon*

(SEQ ID NO: 418)

*MGWSCIILFLVATATGVHS*QVQLVQSGAEVKKPGASVKVSCKASGYTFPDYNMDWVR

QAPGQSLEWIGYINPDNGGTIYNQKFKGRATLTVDTSASTAYMELSSLRSEDTAVYYCA

RLDSSGYGYYAMDYWGQGTSVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPS

NTKVDKKVEPKSCDKTHTCPPCPAPELLGGPSVFLFPPKPKDTLMISRTPEVTCVV

VDVSHEDPEVKFNWYVDGVEVHNAKTKPREEQYASTYRVVSVLTVLHQDWLNGK

EYKCKVSNKALPAPIEKTISKAKGQPREPQVYTLPPSRDELTKNQVSLTCLVKGFYP

SDIAVEWESNGQPENNYKTTPPVLDSDGSFFLYSKLTVDKSRWQQGNVFSCSVMHE

ALHNHYTQKSLSLSPGK*

Humanized 9-G05 Light Chain VL_1
Leader sequence-VL-hIgKCL-Stop codon*

(SEQ ID NO: 419)

*MGWSCIILFLVATATGVHS*SDIVMTQSPDSLAVSLGERATINCRASESVDNYGISFMHWY

QQKPGQPPKLLIYRASNLDSGVPDRFSGSGSGTDFTLTISSLQAEDVATYYCQQSYKDPR

TFGGGTKLEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSPVTKSFN

RGEC*

Humanized 9-G05 Light Chain VL_2
Leader sequence-VL-hIgKCL-Stop codon*

(SEQ ID NO: 420)

*MGWSCIILFLVATATGVHS*SDIVLTQSPASLAVSPGQRATITCRASESVDNYGISFMHWYQ

QKPGQPPKLLIYRASNLDSEVPARFSGSGSRTDFTLTINPVEANDTATYYCQQSYKDPRT

FGGGTKLEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNR

GEC*

16E10 Heavy Chain Variable Region (SEQ ID NO: 421)

QSLEESGGDLVKPGASLTLTCRVSGFSFSSSYYMCWVRQAPGKGLEWIACIGTTRGSTY

YATWAKGRFTISKISSTTVTLQMTSLTDADTATYFCARDATGYRINTIGLYFNLWGPGTL

VTVSS

Humanized 16E10 Heavy Chain Variable Region VH_1

(SEQ ID NO: 422)

QSLLESGGGLVKPGGSLRLSCAVSGFSFSSSYYMCWVRQAPGKGLEWVSCIGTTRGSTY

YADSAKGRFTISKISKNTVYLQMTSLRAEDTAVYFCARDATGYRINTIGLYFNLWGPGT

LVTVSS

Humanized 16E10 Heavy Chain Variable Region VH_2

(SEQ ID NO: 423)

EVQLLESGGGLVKPGGSLRLSCAVSGFSFSSSYYMCWVRQAPGKGLEWVSCIGTTRGST

YYADSAKGRFTISKDNSKNTVYLQMTSLRAEDTAVYFCARDATGYRINTIGLYFNLWG

QGTLVTVSS

-continued

Humanized 16E10 Heavy Chain Variable Region VH_3

(SEQ ID NO: 424)

QSLLESGGGLVKPGGSLRLSCAVSGFSFSSSYYMCWVRQAPGKGLEWVSCIGTTRGSTY

YADSAKGRFTISKESKNTVYLQMSSLRAEDTAVYFCARDATGYRINTIGLYFNLWGPGT

LVTVSS

Humanized 16E10 Heavy Chain Variable Region VH_4

(SEQ ID NO: 425)

EVQLLESGGGLVKPGGSLRLSCAVSGFSFSSSYYMCWVRQAPGKGLEWVSCIGTTRGST

YYADSAKGRFTISKDNSKNTVYLQMSSLRAEDTAVYFCARDATGYRINTIGLYFNLWG

QGTLVTVSS

Humanized 16E10 Heavy Chain Variable Region VH_5

(SEQ ID NO: 426)

QSLLESGGGLVKPGGSLRLSCAVSGFSFSSSYYMCWVRQAPGKGLEWVSCIGTTRGSTY

YADSAKGRFTISKESKNTVYLQMSSLRAEDTAVYFCARDATGYRIQTIGLYFNLWGPGT

LVTVSS

Humanized 16E10 Heavy Chain Variable Region VH_6

(SEQ ID NO: 427)

EVQLLESGGGLVKPGGSLRLSCAVSGFSFSSSYYMCWVRQAPGKGLEWVSCIGTTRGST

YYADSAKGRFTISKDNSKNTVYLQMSSLRAEDTAVYFCARDATGYRIQTIGLYFNLWG

QGTLVTVSS

16E10 Light Chain Variable Region (SEQ ID NO: 428)

ELTQTPSSVEAAVGGTPTIKCQASQTIYSYLSWYQQKPGQPPKLLIYEASKLASGVPSRFS

GSGSGTDYTLTISDLECADAATYYCQSYHGTASTEYNTFGGGTEVVVK

Humanized 16E10 Light Chain Variable Region VL_1

(SEQ ID NO: 429)

QLTQSPSSLSASVGDRVTITCQASQTIYSYLSWYQQKPGKPPKLLIYEASKLASGVPSRFS

GSGSGTDYTLTISSLQPEDFATYYCQSYHGTASTEYNTFGGGTKVEIK

Humanized 16E10 Light Chain Variable Region VL_2

(SEQ ID NO: 430)

DIQLTQSPSSLSASVGDRVTITCQASQTIYSYLSWYQQKPGKPPKLLIYEASKLASGVPSR

FSGSGSGTDYTLTISSLQPEDFATYYCQSYHGTASTEYNTFGGGTKVEIK

Humanized 16E10 Light Chain Variable Region VL_3

(SEQ ID NO: 431)

QLTQSPSSLSASVGDRVTITCQASQTIYSYLSWYQQKPGKPPKLLIYEASKLASGVPSRFS

GSGSGTDYTLTISSLQPEDTATYYCQSYHGTASTEYNTFGGGTKVEIK

Humanized 16E10 Light Chain Variable Region VL_4

(SEQ ID NO: 432)

DIQLTQSPSSLSASVGDRVTITCQASQTIYSYLSWYQQKPGKPPKLLIYEASKLASGVPSR

FSGSGSGTDYTLTISSLQPEDTATYYCQSYHGTASTEYNTFGGGTKVEIK

Humanized 16E10 Light Chain Variable Region VL_5

(SEQ ID NO: 433)

QLTQSPSSLSASVGDRVTITCQASQTIYSYLSWYQQKPGKPPKLLIYEASKLASGVPSRFS

GSGSGTDYTLTISSLQPEDTATYYCQSYHGTASTEYQTFGGGTKVEIK

Humanized 16E10 Light Chain Variable Region VL_6

(SEQ ID NO: 434)

DIQLTQSPSSLSASVGDRVTITCQASQTIYSYLSWYQQKPGKPPKLLIYEASKLASGVPSR

FSGSGSGTDYTLTISSLQPEDTATYYCQSYHGTASTEYQTFGGGTKVEIK

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An anti-integrin alpha 11 beta 1 (α11β1) antibody, or antigen-binding fragment thereof, wherein the antibody or antigen-binding fragment thereof comprises: (1) a heavy chain comprising a heavy chain complementarity determining region 1 (CDRH1), a heavy chain complementarity determining region 2 (CDRH2), and a heavy chain complementarity determining region 3 (CDRH3) and (2) a light chain comprising a light chain complementarity determining region 1 (CDRL1), a light chain complementarity determining region 2 (CDRL2), and a light chain complementarity determining region 3 (CDRL3), and wherein the CDRH1 comprises the sequence GYTFTSYG (SEQ ID NO: 439), the CDRH2 comprises the sequence ISAYNGNT (SEQ ID NO: 265), the CDRH3 comprises the sequence VTGITGTTIDP (SEQ ID NO: 267), the CDRL1 comprises the sequence QSISSY (SEQ ID NO: 216), the CDRL2 comprises the sequence DAS (SEQ ID NO: 269), and the CDRL3 comprises the sequence QQYNNWPQT (SEQ ID NO: 271).

2. The anti-integrin α11β1 antibody, or antigen-binding fragment thereof, of claim 1, wherein the antibody, or antigen-binding fragment thereof, is a monoclonal antibody, or antigen-binding fragment thereof.

3. The anti-integrin α11β1 antibody, or antigen-binding fragment thereof, of claim 1, wherein the antibody, or antigen-binding fragment thereof, is a humanized antibody, or antigen-binding fragment thereof.

4. The anti-integrin α11β1 antibody, or antigen-binding fragment thereof, of claim 1, wherein the antibody, or antigen-binding fragment thereof, reduces interaction of α11β1 with collagen in human α11β1-expressing cells.

5. A nucleic acid, comprising a nucleic acid sequence encoding the antibody, or antigen-binding fragment thereof, of claim 1.

6. A vector comprising the nucleic acid of claim 5.

7. A host cell comprising the vector of claim 6.

8. A method of producing an antibody, or antigen-binding fragment thereof, comprising culturing the host cell of claim 7 under conditions suitable for expression of the antibody or antigen-binding fragment thereof.

9. The anti-integrin α11β1 antibody, or antigen-binding fragment thereof, of claim 1, wherein the heavy chain further comprises: a heavy chain framework region 1 (FRH1), a heavy chain framework region 2 (FRH2), a heavy chain framework region 3 (FRH3), and a heavy chain framework region 4 (FRH4);

wherein the light chain further comprises a light chain framework region 1 (FRL1), a light chain framework region 2 (FRL2), a light chain framework region 3 (FRL3), and a light chain framework region 4 (FRL4); and wherein the FRH1 comprises the sequence QVQLVQSGAEVKKPGASVKVSCKAS (SEQ ID NO: 263), the FRH2 comprises the sequence ISWVRQAPGQ-GLEWMGW (SEQ ID NO: 264), the FRH3 comprises the sequence NYAQKLQGRVTMTTDTST-STAYMELRSLRSDDTAAYYCAR (SEQ ID NO: 266), the FRH4 comprises the sequence WGQGTMVTVSS (SEQ ID NO: 268), the FRL1 comprises the sequence DIQMTQSPSSL-SASVGDRVTITCRAS (SEQ ID NO: 227), the FRL2 comprises the sequence LNWYQQKPGKAPKLLIY (SEQ ID NO: 217), the FRL3 comprises the sequence SLESGVPSRFSGSGSGTEFTLTISSLQPDD-FAVYYC (SEQ ID NO: 270), and the FRL4 comprises the sequence FGQGTKVEIK (SEQ ID NO: 272).

* * * * *

SEQUENCE LISTING

<160> NUMBER OF SEQ ID NOS: 443

<210> SEQ ID NO 1
<211> LENGTH: 417
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1
atggattggt tgtggaactt gctattcctg atggtagttg cccaaagtgc tcaagcacag 60
atccagttgg tacagtctgg acctgaagta aagaagcctg gagagtcagt gaagatctcc 120
tgcaaggcct ctgggtatac cttcacagac tatgcaatga actgggtgaa acaggctcca 180
ggaaatggcc tgaagtggat gggctggatc aacacccaaa ctggaaagcc aacatatgcg 240
gatgatttca aacaacggtt tgtcttctct ttggaaactt ctgccagaac tacatatttg 300
cagatcaaca acctcaatat tgaagacaca gctacatatt tctgtacgag attgggtaca 360
ggtaatacga aggggtttgc ttactggggc caaggcactc tggtcactgt ctcttca 417

<210> SEQ ID NO 2
<211> LENGTH: 399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2
atggaatcac agacgcatgt cctcatttcc cttctgctct gtgtatcagg tacctgtggg 60
gacattttga taaaccagtc tccagcctct ctgactgtgt cagcaggaga gagggtcact 120
atgagctgca agtccagtca gagtcttcta tacagtgaaa acaaccagga ctatttggct 180
tggtaccagc agaaaccagg acagtttcct aaattgctta tctatggggc atccaaccgg 240
cacactgggg tccctgatcg cttcacaggc agtggatctg ggacagactt cactctgacc 300
atcagcagtg tgcaggctga agacctggct gattattatt gtgagcagac ctacagatat 360
ccattcacgt tcggctcagg gacgaagttg gaaataaaa 399

<210> SEQ ID NO 3
<211> LENGTH: 414
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3
atggagttgg aattgagctt aatttttatt ttttctcttt taaaagatgt ccagtgtgaa 60
gtacagctgg tggagtctgg aggaagcttg gttcaacctg ggggttctct gaaactctcc 120
tgtgtagcct caggatacac tttcagtaac tactggatgg actgggttcg gcagtctcct 180
ggaaagtccc tggaatggat tggagagatt aacacggatg gcagaaggac caactatgca 240
ccatccataa aggatcgatt cacaatctcc agagacaatg ccaagagcac cctgtatctg 300
cagatgagca atgtgaaatc agatgacaca gccatttatt actgtaccat actacgggta 360 taccccccact actttgatta ctggggccaa ggagtcatgg tcacagtctc ctca 414

<210> SEQ ID NO 4
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4
atgatgagtc ctgcccagtt cctgtttctg ctaatgctct ggatccagga agcccgcgga 60
gatgttgtga tgacccagac accaccgtct ttgtcggttg ccattggaca atcagtctcc 120
atctcttgca agtcaagtca gagcctcgta tatagtgatg gagagacata tttgcattgg 180
tttttacaga gtcctggcag gtctccgaag cgcctaattt atcacgtgtc taatctgggc 240
tctggagtcc ctgacaggtt cagtggcact ggatcactga cagattttac acttagaatc 300
agcagagtgg aggctgagga tttgggagtt tattactgcg cgcaaactac acattttcct 360
cccacgtttg gagctgggac caagctggaa ctgaaa 396

<210> SEQ ID NO 5
<211> LENGTH: 405
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5
atggctgtcc tggtgctgtt gctctgcctg gtgacatttc caagctgtgc cctgtcccag 60
gtgcagttga aggagtcagg acctggtctg gtgcagccct cacagaccct gtccctcacc 120
tgcactgtct ctgggttctc attaaccagc aatagtgtta gctgggttcg ccaggctccg 180
ggaaagggtc tggagtggat gggagcaata tggagtggtg gaagcacaga ttataattca 240
gctctcaaat cccgactgag catcagcagg gacacctcca agagccaagt tttcttaaaa 300
atgaacagtc tgcaaactga agacacagcc atttacttct gtaccagatc tcactgggag 360
ccctttgatt actggggcca aggagtcatg gtcacagtct cctca 405

<210> SEQ ID NO 6
<211> LENGTH: 399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6
atggaatcac aaactcaggc cctcatatcc ctgctgctct gggtatatgg tacctgtggg 60
gacattgtga tgacccagtc tccattctcc ctggctgtgt cagaaggaga gatggtcact 120
ataaactgca agtccagtca gggtctttta tccagtggaa accaaaagaa ctacttggcc 180
tggtaccagc agagaccagg gcagtctcct aaactactga tctactatgc atccactagg 240
caatcagggg tccctgatcg cttcataggc ggtggatctg ggacagactt cactctgacc 300
atcagcgatg tgcaggctga agacctggca gattattact gcctgcagca ttacagctat 360
cctcccacgt tcggttctgg gaccaagctg gagatcaaa 399

<210> SEQ ID NO 7
<211> LENGTH: 405
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 7
atggctgtcc tggtgctgtt gctctgcctg gtgacatttc caagctgtgc cctgtcccag 60
gtgcagctga gggagtcagg acctggtctg gtgcagccct cacagaccct gtccctcacc 120
tgcactgtct ctgggttctc attgaccagc aatagtgtga cctgggttcg ccagcctccg 180
ggaaagggtc tggagtggat gggagcgata tggagtgatg gaagcacaga ttataattca 240
actctcaaat cccgactgag catcagtagg gacacctcca agagccaagt tttcttaaaa 300
atgagcagtc tgcaaactga agacacagcc atttacttct gtaccagatc ccactgggag 360
ccctttgatt actggggcca aggagtcatg gtcacagtct cctca 405

<210> SEQ ID NO 8
<211> LENGTH: 394
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8
atggaatcac aaactcaggc cctcatatcc ctgctgctct gggtatatgg tacctgtggg 60
gacattgtga tgacccagtc tccactctcc ctggctgtgt cagaaggaga gacggtcact 120
atgaactgca agtccagtca gagtcttttt tccagtggaa atcaaaagaa ctacttggcc 180
tggtaccagc agaaaccagg gcagtctcct aaactactga tctactatgc atccactagg 240
caatcagggg tccctgatcg cttcataggc agtggatctg ggacagactt cactctgacc 300
atcagcgatg tgcagactga agacctggca gattattact gcctgcagca ttacaactat 360
cctcccacgt tcggttctgg gaccaagctg gaga 394

<210> SEQ ID NO 9
<211> LENGTH: 402
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9
atggacttgc gactgactta tgtctttatt gttgctattt taaaaggtgt cttgtgtgag 60
gtgaaactgg aggaatctgg gggaggtttg gtgcaacctg gaatgtccgt gaaactctct 120
tgtgcaacct ctggattcat tttcagtgac tactggatgg aatgggtccg ccaggctcca 180
gggaaggggc tagaatgggt agccgaaatt agaaacaaag ctaataatta tgcaacatac 240
tatgggaagt ctatgaaagg cagattcacc atctcaagag atgattccaa aagtatagtc 300
tacctacaag tgaacagcat aagatctgaa gatactgcta tttattactg tgcaccgaat 360
tttgattact ggggccaagg agtcatggtc acggtctcct ca 402

<210> SEQ ID NO 10
<211> LENGTH: 393

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10
atgagtcctg tccagtccct gtttttgcta ttgctttgga ttctgggaac ccatggtgat 60
gttgtgctga cccagactcc acccacttta tcggctacca ttggacaatc agtctctatc 120
tcttgcaggt caagtcagag tctcttacat agtactggaa acacctattt aaattggttg 180
ctacagaggc caggccaacc tccgcaactt ctaatttatt tggtttccag actggaatct 240
ggggtcccca acaggttcag tgccagtggg tcaggaactg atttcacact caaaatcagt 300
ggaatagagg ctgaggattt gggggtttat tactgcgtgc aaagttccca tactccgtac 360
acgtttggga ctgggaccaa gctggaactg aaa 393

<210> SEQ ID NO 11
<211> LENGTH: 405
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 11
atggacatca ggctcagctt ggttttcctt gtccttttta tgaaaggtgt ccagtgtgag 60
gtgcagttgg tggagtctgg gggaggctta gtgcagcctg gaaggtccct gaaactctcc 120
tgtgcagcct cacgattcac ttttagtgac tataacatgg cctgggtccg ccaggctcca 180
aagaagggtc tggagtgggt cgcaaccatt tatcatgatg atagtggttc ttactatcga 240
gactccgtga agggccgatt caccatctcc agaaataatg caaaaagcac tctgtacctg 300
cagatggaca gtctgaggtc tgaggacatg gccacttatt actgtgcaag acataacaat 360
ggctttgatt actggggcca aggagtcatg gtcacagtcg cctca 405

<210> SEQ ID NO 12
<211> LENGTH: 393
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 12
atgaagtggc ctgttaggct gttggtgctg ttcttctgga ttcctgcttc cgggggtgat 60
gttgtgatga cacaaactcc agtctccctg cctgtccgcc ttggaggtca agcctctatc 120
tcttgccggt caagtcagag cctggtacac agtaatggaa acacctactt gcattggtac 180
ctacagaagc caggccagtc tccacagctc ctcatcaatc gggtttccaa cagattttct 240
ggggtgccag acaggttcag tggcagtggg tcagggacag atttcaccct caagatcaac 300
agagtagagc ctgaggactt gggagattat tactgcttac aaagtacaca ttttccactc 360
acgttcggtt ctgggaccaa gctggagacc aaa 393

<210> SEQ ID NO 13
<211> LENGTH: 408
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
atggacatca ggctcagctt gggtttcctt gtccttttca taaaaggtga ccagtgtgcg 60
gtgcaactgg tggagtctgg gggaggctta gtgcagcctg gaaggtccct gaaactctcc 120
tgtgcagcct caagaatcac tttcactgac tattacatgg cctgggtccg ccaggctcca 180
acgaagggtc tggagtgggt cgcaaccatt agttctgatg gtggtgacac tttctatcga 240
gactccgtga agggccgatt tactatctcc agagacaatg caaaaagcac cctatatttg 300
caaatggtca gtctgaggtc tgaggacacg gccacttatt actgttcaac agatcgggga 360
gctcagtttg gttactgggg ccaaggcact ctggtcactg tctcttca 408

<210> SEQ ID NO 14
<211> LENGTH: 378
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 14
atggctccag tccagctctt agggctgctg ctgatttggc tcccagccat gagatgtgac 60
atccagatga cccagtctcc ttcattcctg tctgcatctg tgggagacag agtctctatc 120
aactgcaaag caagtcagaa tgttcacgag aacctaaact ggtatcagca aaagcttgga 180
gaagctccca aacgcctgat atataataca aacaatttgc aaacaggcat cccatcaagg 240
ttcagtggca gtggatctgg tgcagattac acactcacca tcagcagcct gcagcctgaa 300
gattttgcca catatttctg tttgcagcat aatgcttttc cgtacacgtt tggacctggg 360
acgaagctgg aactgaaa 378

<210> SEQ ID NO 15
<211> LENGTH: 366
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 15
gaggtccagc tgcaacagtc tggacctgag ctggtgaagc ctggggcttc agtgaagata 60
ccctgcaagg cttctggata cacattccct gactacaaca tggactgggt gaagcagagc 120
catggaaaga gccttgagtg gattggatat attaatcctg acaatggtgg tactatctac 180
aaccagaagt tcaagggcaa ggccacattg actgtagaca agtcctccag cacagcctac 240
atggagctcc gcagcctgac atctgaggac actgcagtct attactgtgc aagattagac 300
agctcaggct acggttacta tgctatggac tactggggtc aaggaacctc agtcaccgtc 360
tcctca 366

<210> SEQ ID NO 16
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 16
gacattgtgc tgacccaatc tccagcttct ttggctgtgt ctctagggca gagggccacc 60
atctcctgca gagccagcga aagtgttgat aattatggca ttagttttat gcactggtac 120
cagcagaaac caggacagcc acccaaactc ctcatctatc gtgcatccaa cctagactct 180
gagatccctg ccaggttcag tggcagtggg tctaggacag acttcaccct caccattgat 240
cctgtggaga ctgatgatgt tgcaacctat tactgtcagc aaagttataa ggatcctcgg 300
acgttcggtg gaggcaccaa gctggaaatc aaa 333

<210> SEQ ID NO 17
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17
aaagtgatgc tggtggagtc tgggggagcc ttagtgaagc ctggagggtc cctgaaactc 60
tcctgtgtag cctctggatt cactttcagt aactatgcca tgtcttgggt tcgccagact 120
ccagagaaga ggctggagtg ggtcgcaacc attagtagtg gtggttatta cacttactat 180
ccagacagtg tgaagggtcg attcaccatc tccagagaca atgccaggaa caccctgttc 240
ctgcaaatga gcagtctgag gtctgaggac acggccatgt tttactgtgc aagagaggat 300
gattacggaa gatattccta tactatggac tactggggtc aaggaacctc agtcaccgtc 360
tcctca 366

<210> SEQ ID NO 18
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18
gatgttgtga tgacccaaac tccactctcc ctgcctgtca gtcttggaga tcaagtctcc 60
atctcttgca gatgtagtca gagccttgta cacagtaatg gaaacaccta tttacattgg 120
tacctgcaga agccaggcca gtctccacag ctcctgatct acaaaatttc caaccgattt 180
tctggggtcc cagacaggtt cagtggcagt ggatcaggga cagatttcac actcaagatc 240
agcagagtgg aggctgagga tctgggagtt tatttctgct ctcaaagtac acatgttccg 300
tacacgttcg gaggggggac cgagctggaa ataaaa 336

<210> SEQ ID NO 19
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19
gaggtccagc tgcagcagtc tggacctgag ctggtaaagc ctggggcttc agtgaggata 60
tcctgcaagg cttctggata cacattcact gactactaca tacactgggt gaagcagaag 120
cctgggcagg gccttgaatg cattggagag atttatcctg gaactgataa tacttactac 180
agtaaaaaat tcaggggcaa ggccacactg actgcagaca aatcctccga cacagcctac 240
atgcagctca gcagcctgac atctgaggac tctgcagtct atttctgtgc aagaggagac 300
tactataggg ggtacttcga tgtctggggc gcagggacca cggtcaccgt ctcctca 357

<210> SEQ ID NO 20
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 20
gatgttgtga tgactcagac ctcactcact ttgtcggtta ccattggaca accagcctcc 60
atctcttgca agtcaagtca gagcctctta catagtaatg gaaagacata tttgaattgg 120
ttattacaga ggccaggcca gtctccaaag ttcctaatct atctggtgtc taaactggaa 180
tctggagtcc ctgacaggtt cagtggcagt ggatcaggga cagatttcac actgaaaatc 240
agcagagtgg aggctgagga tttgggggtt tattactgct tgcaatctac acattttcct 300
tggacgttcg gtggaggcac caagctggaa atcaaa 336

<210> SEQ ID NO 21
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 21
gaggtccagc tgcagcagtc tggacctgag ctggtaaagc ctggggcttc agtgaagaaa 60
tcctgcaagg cttctggata cacattcact gactactaca tgcactgggt gaagcagaag 120
cctgggcagg gccttgagtg gattggaaag atttatcctg gaagtggtaa tactcactac 180
aatgagaagt tcaagggcaa ggccacactg actgcagaca aatcctccag cacagcctac 240
atgcagctca gcagcctgac atctgaggac tctgcagtct atttctgtgc aaccaattac 300
tacggctaca gggcaatgaa ctattggggt caaggatcct cagtcaccgt ctcctca 357

<210> SEQ ID NO 22
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 22
gacatccatt tgacccagtc tccatcctcc ttatctgcct ctctgggaga aagaatcagt 60
ctcacttgcc gggcaagtca ggacatttat attagcttaa actggtttca gcagaaacca 120
gatggaacta ttaaactcct gatctacggc acatccagtt tagattctgg tgtccccaaa 180
aggttcagtg gcagtaggtc tgggtcagat tattctctca ccatcagcag ccttgagtct 240
gaagattttg cagactatta ctgtctacaa tatgctagtt ctccgtacac gttcggaggg 300
gggaccaagc tggaaataaa a 321

<210> SEQ ID NO 23
<211> LENGTH: 363
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 23
gaggtccagc tgcagcagtc tggacctgag ctggtaaagc ctggggcttc agtgaagata 60
tcctgcaagg cttctggata cacattcact gactactaca tgcactgggt gaagcagaag 120
cctgggcagg gccttgagtg gattggagag atttatcctg gaagtggtaa tccttactac 180
aatgagaagt tcaagggcaa ggccacactg actgcagaca aatcatccag ctcagcctac 240
atgcagctca gcagcctgac atctgaggac tctgcagtct atttctgtgc aagaacctcc 300
tacggtagag tagggacagg gtttgcttac tggggccaag ggactctggt cactgtctct 360
gca 363

<210> SEQ ID NO 24
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 24
aattttgtga tgacccaaac tccactctcc ctgcctgtca gtcttggaga tcaagcctcc 60
atctcttgca gatctagtca gagccttcta cacagtaacg gaaacaccta tttacattgg 120
tacctgcaga agccaggcca gtctccaaag ctcctgatct acaaagtttc caaccgattt 180
tctggggtcc cagacaggtt cagtggcagt ggatcaggga cagatttcac actcaagatc 240
aacagagtgg agactgagga tctgggaatt tatttctgct ctcaaagttc acatgttccc 300
acgttcggtg ctgggaccaa gctggagctg aaa 333

<210> SEQ ID NO 25
<211> LENGTH: 351
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 25
caggtccagc tgcagcagtc tggggctgaa ctggcaaaac ctggggcctc agtgaagatg 60
tcctgcaagg cttctggcta cacctttact aactactgga tgcactgggt aaaacagagg 120
cctggacagg gtctggaatg gattggatac attaatccta acaatggtta tactgagtac 180
aatcagcgat tcaaggacaa ggccacattg actgcagaca gatcctccac cacagcctac 240
atgcaactaa gcagcctgac atctgaggac tctgcagtct attactgtgc aagatccgat 300
atcattacga cagactactg gggccaaggc accactctca cagtctcctc a 351

<210> SEQ ID NO 26
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 26
gatgttgtga tgacccaaac tccactctcc ctgcctgtca gtcttggaga tcaagcctcc 60
atctcttgca gatctagtca gagccttgta tatagtaatg gaaataccta tttacattgg 120
tacctgcaga agccaggcca gtctccaaag ctcctgatct acaaagtttc caaccgattt 180
tctggggtcc cagacaggtt cagtggcagt ggatcaggga cagatttcac actcaagata 240
agcagagtgg aggctgagga tctgggagtt tatttctgct ctcaaagtac acatgttccg 300
tggacgttcg gtggaggcac caagctggaa atcaaa 336

<210> SEQ ID NO 27
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
gaagtgaagc ttgaggagtc tggaggaggc ttggtgcaac ctggaggatc catgaaactc 60
tcttgtgctg cctctggatt cacttttagt gacgcctgga tggactgggt ccgccagtct 120
ccagaggcgg ggcttgagtg ggttgctgaa attagaaaca aagctcataa tcctgcaaca 180
tactatgctg agtctgtgaa agggagattc accatctcaa gagatgattc caaaagtagt 240
gtctacctgc aaatgaacag cttaagagct gaagacactg gcatttatta ctgtacctta 300
gtagcccctg atgctatgga ctactggggt caaggaacct cagtcaccgt ctcctca 357

<210> SEQ ID NO 28
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gacattgtga tgtcactgtc tccatcctcc ctagctgtgt cagttggaga gaaggttact 60
atgagctgca agtccagtca gagcctttta tatagtcgca atcaaaagaa ctacttggcc 120
tggtaccagc agaaaccagg gcagtctcct aaactgctga tttactgggc atccactagg 180
gcatctggag tccctgatcg cttcacaggc agtggatctg ggacagattt cactctcacc 240
atcagcagtg tgaaggctga agacctggca gtttattact gtcagcaata ttatagctat 300
ccgtacacgt tcggaggggg gaccaagctg gaaataaaa 339

<210> SEQ ID NO 29
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
caggtccaac tgcagcagtc tgggcctgag ctggtgaggc ctggggcttc agtgaagatg 60
tcctgcaagg cttcaggcta taccttcacc agctactgga tgcactgggt gaaacagagg 120
cctggacaag gccttgagtg gattggcatg attgatcctt ccaatagtga aacttggtta 180
aatcagaagt tcaaggacaa ggccacattg aatgtagaca aatcctccaa cacagcctac 240
atgcagctca gcagcctgac atctgaggac tctgcagtct attactgtgc aagatatgat 300
ggttactacg actactgggg ccaaggcacc actctcacag tctcctca 348

<210> SEQ ID NO 30
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 30
aacattgtgc tgacccaatc tccagcttct ttggctgtgt ctctagggca gagggccacc 60
atatcctgca gagccagtga aagtgttgat agttatggca atagttttat gcactggtac 120
cagcagaaac caggacagcc acccaaactc ctcatctatc ttgcatccaa cgtagaatct 180
ggggtccctg ccaggttcag tggcagtggg tctaggacag acttcaccct caccattgat 240
cctgtggagg ctgatgatgc tgcaacctat tactgtcagc aaaataatga ggatccgtgg 300
acgttcggtg gaggcaccaa gctggaaatc aaa 333

<210> SEQ ID NO 31
<211> LENGTH: 354
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 31
caggtccaac tgcagcagcc tggggctgag ctggtgaggc ctggggcttc agtgaagctg 60
tcctgcaagc cttctggcta caccttcacc agctactgga tgaactgggt gaagcagagg 120
cctggacaag gccttgaatg gattggtatg attgatcctt cagacagtga aactcactac 180
aatcaaatgt tcaaggacaa ggccacattg actgttgaca aatcctccaa cacagcctac 240
atgcagctca gcagcctgac atctgaggac tctgcggtct attactgtgc gcagatctac 300
tatgcttacg acaaggctta ctggggccaa gggactctgg tcactgtctc tgca 354

<210> SEQ ID NO 32
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 32
gacattgtga tgtcacagtc tccatcctcc ctagctgtgt cagttggaga gaaggttact 60
atgagctgca agtccagtca gagcctttta tatagtagcc atcaaaagaa ctacttggcc 120
tggtaccagc agaaaccagg gcagtctcct aaactgctga tttactgggc atccactagg 180
gaatctgggg tccctgatcg cttcacaggc agtggatctg ggacagattt cagtctcacc 240
atcagcagtg tgaaggctga agacctggca gtttattact gtcaggaata ttatagctgg 300
acgttcggtg gaggcaccaa gctggaaatc aaa 333

<210> SEQ ID NO 33
<211> LENGTH: 354
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 33
gaggtccagc tgcaacaatc tggacctgag ctggtgaagc ctggggcttc agtgaagata 60
tcctgtaagg cttctggata cacgttcact gactactaca tgaactgggt gaagcagagc 120
catggaaaga gccttgagtg gattggagat attaatcctc acaatggtgg tactagcttc 180
atccagaagt tcaagggcaa ggccacattg actgtagaca agtcctccag cacagcctac 240
atggagctcc gcagcctgac atctgaggac tctgcagtct attattgtgc cctctggga 300 cgaaaggagg ggtttgctta ctggggccaa gggactctgg tcactgtctc tgca 354

<210> SEQ ID NO 34
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34
gacactgtgc tgacacagtc tcctgcttcc ttagttgtat ctctggggca gagggccacc 60
atctcatgca gggccagcaa aagtgtcagt acatctggct atagttatat gcactggtac 120
caacagaaac caggacagcc acccaaactc ctcatctatc ttgcatccaa cctagaatct 180
ggggtccctg ccaggttcag tggcagtggg tctgggacag ccttcaccct caacatccat 240
cctgtggagg aggaggatgc tgcaacctat tactgtcagc acagtaggga gcttccgtac 300
acgttcggag gggggaccaa gctggaaata aaa 333

<210> SEQ ID NO 35
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35
caggttactc tgaaagagtc tggccctggg atattgcagc cctcccagac cctcagtctg 60
acttgttctt tctctgggtt ttcactgagc acttttgcta tgggtgtagg ctggattcgt 120
cagccttcag ggaagggtct ggagtggctg gcacacattt ggtgggatga tgataagtac 180
tataacccag ccctgaagag ccggctcaca atctccaagg atacctccaa aaaccatgta 240
ttcctcaaga tcgccaatgt ggacactgca gatactgcca catactactg tgctcgaatg 300
ccgctaactt tctactttga ctactggggc caaggcacca ctctcacagt ctcctca 357

<210> SEQ ID NO 36
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36
gatgttttgc tgacccaaac tccactctcc ctgcctgtca gtcttggaga tcaagcctcc 60
atctcttgca gatctagtca gagcattgta catagtaatg gacacaccta tttagaatgg 120
tacctgcaga aaccaggcca gtctccaaag ctcctgatct acaaagtttc caaccgattt 180
tctggggtcc cagacaggtt cagtggcagt ggatcaggga cagatttcac actcaagatc 240
agcagagtgg aggctgagga tctgggagtt tattactgct ttcaaggttc acatgttccg 300
ttcacgttcg gaggggggac caagctggaa ataaaa 336

<210> SEQ ID NO 37
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37
caggttactc tgaaagagtc tggccctggg atattgcagc cctcccagac cctcagtctg 60
acttgttctt tctctgggtt ttcactgaga acttttgcta tgggtgtagg ctggattcgt 120
cagccttcag ggaagggtct ggagtggctg gcacacattt ggtgggatga tgataagtac 180
tataacccag ccctgaagag ccggctcaca atctccaagg atacctccaa aaaccaggta 240
ttcctcaaga tcgccaatgt ggacactgca gatactgcca catactactg tgctcgaatg 300
ccgctaactt tctactttga ctactggggc caaggcacca ctctcacagt ctcctca 357

<210> SEQ ID NO 38
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38
gatgttttga tgacccaaac tccactctcc ctgcctgtca gtcttggaga tcaagcctcc 60
atctcttgta gatctagtca gagcattgta catagtaatg gaaacaccta tttagaatgg 120
tacctgcaga aaccaggcca gtctccaaag ctcctgatct acaaagtttc cacccgattt 180
tctggggtcc cagacaggtt cagtggcagt ggatcaggga cagatttcac actcaagatc 240
agcagagtgg aggctgagga tctgggagtt tattactgct ttcaaggttc acatgttccg 300
ttcacgttcg gaggggggac caagctggaa ataaaa 336

<210> SEQ ID NO 39
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39
caggtccaac tgcagcagcc tggggctgaa cttgtgatgc ctggggcttc agtgaagctg 60
tcctgcaagg cttctggcta caccttcacc aactactgga tgcactgggt gaaacagagg 120
cctggacaag gccttgagtg gatcggagag attgatcctt ctgatagtta tactaactac 180
aatcaaaagt tcaagggcaa ggccacattg actgtagaca aatcctccag cacagcctac 240
atgcagctca gcagcctgac atctgaggac tctgcggtct attactgtac aagacagggt 300
agtacctacg cgtggggtca aggaacctca gtcaccgtct cctca 345

<210> SEQ ID NO 40
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40
gatattgtga tgacgcaggc tgcattctcc aatccagtca ctcttggaac atcagcttcc 60
atctcctgca ggtctagtaa gagtctccta catagtaatg gcatcactta tttgtattgg 120
tatctgcaga agccaggcca gtctcctcag ctcctgattt atcagatgtc caaccttgcc 180
tcaggagtcc cagacaggtt cagtagcagt gggtcaggaa ctgatttcac actgagaatc 240
agcagagtgg aggctgagga tgtgggtgtt tattactgtg ctcaaaatct agaacttcct 300
ccgacgttcg gtggaggcac caagctggaa atcaaa 336

<210> SEQ ID NO 41
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 41
gaggtccagc tgcaacaatc tggacctgag ctggtgaagc ctggggcttc agtgaagatg 60
tcctgtaagg cttctggata cacattcact gactactaca tgatgtgggt gaagcagagt 120
catggaaaga gccttgagtg gattggagat attaatcctt acaatggtgg ttctagctac 180
aacccgaagt tcaagggcag ggccacattg actgtagaca aatcctccag cacagcctac 240
atgcagctca acagcctgac atctgaggac tctgcagtct attactgtgc aagagggact 300
tactggggcc aagggactct ggtcactgtc tctgca 336

<210> SEQ ID NO 42
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 42
gatgttgtga tgacccagac tccactcact ttgtcggtta ccattggaca accagcctcc 60
atctcttgca agtcaagtca gagcctctta gatagtgctg gaaagacata tttgaattgg 120
ttgttacaga ggccaggcca gtctccaaag cgcctaatgt atctggtgtc taaactggac 180
tctggagtcc ctgacaggtt cactggcagc ggatcaggga cagatttcac actgaaaatc 240
agcagagtgg aggctgagga tttgggagtt tattattgct ggcaaggtac acattttccg 300
tacacgttcg gaggggggac caagctggaa ataaaa 336

<210> SEQ ID NO 43
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 43
caggtccaac tgcagcagcc tggggctgag cttgtgaagc ctggggcttc agtgaagttg 60
tcctgcaagg cttctggcta caccttcacc agctactgga tgcactggat aaagcagaga 120
cctggacaag gccttgagtg gattggagag attaacccta gcaatggtgg ttctaactac 180
aatgagaagt tcaagagcaa ggccacactg actgtagaca aatcctccag cacagcctac 240
atgcaactca gcagcctgac atctgaggac tctgcggtct atcactgtaa aagcagaggc 300
tactggggcc aaggcaccac tctcacagtc tcctca 336

<210> SEQ ID NO 44
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44
gatgttgtga tgacccagac tccactcact ttgtcggtta ccattggaca accagcctcc 60
atctcttgca agtcaagtca gagcctctta gatagttatg gaaagacata tttgaattgg 120
ttgttacagc ggccaggcca gtctccaaag cgcctaatct atctggtgtc taaattggac 180
tctggagtcc ctgacaggtt cactggcagt ggatcaggga cagatttcac actgaaaatc 240
agcagagtgg aggctgagga tttgggaatt tattattgct ggcaaggtac acattttcct 300
cacacgttcg gctcggggac aaagttggaa ataaaa 336

<210> SEQ ID NO 45
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45
caggttcagc tgcagcagtc tggagctgag ctggcgaggc ctggggcttc agtgaaactg 60
tcctgcaagg cttctggcta caccttcaca agctatggta taagctgggt gaaacagaga 120
actggacagg gccttgagtg gattggagag atttttccta gaagtagtaa tacttactat 180
aatgagaagt tcaagggcaa ggccacactg actgcagaca agtcctccag cacagtgtac 240
atggagttcc gcagcctgac atctgaggac tctgcggtct atttctgtgc aagagagggg 300
ggcctggcct ggtttgctta ctggggccaa gggactctgg tcactgtctc tgca 354

<210> SEQ ID NO 46
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46
gatgttgtga tgacccagac tccactcact ttgtcggtta ccattggaca accagcttcc 60
atctcttgca agtcaagtca gagcctctta tatactaatg gaaacaccta tttgaattgg 120
ttattacaga ggccaggcca gtctccaaaa cgcctaatct atctggtgtc taaattggac 180
tctggaatcc ctgacaggtt cagtggcagt ggatcaggga cagatttcac actgagaatc 240
agcagagtgg aggctgagga tttgggagtt tattactgct tgcagagtac acattttcca 300
ttcacgttcg gctcggggac aaagttggaa ataaaa 336

<210> SEQ ID NO 47
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
gaggtccagc tgcaacaatc tggacctgag ctggtgaagc ctggggcttc agtgaagatg     60
tcctgtaagg cttctggata cacaatcact gactactaca tgatgtggtt gaagcagagt    120
catggaaaga gccttgaatg gattggagat attaatcctt acactggtgg tactagctac    180
aaccagaagt tcaagggcaa ggccacattg actgtagaca aatcctccag cacagcctac    240
ctgcagctcc acagcctgac atctgaggac tctgcagtct attactgtgc aagaggggcc    300
tactggggcc aaggcaccac tctcacagtc tcctca                              336

<210> SEQ ID NO 48
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
gatgttgtga tgacccagac tccactcact ttgtcggtta ccattggaca accagcctcc     60
atctcttgca agtcaagtca gagcctctta gatagtgatg gaaagacata tttgaattgg    120
ttgttacaga ggccaggcca gtctccaaag cgcctaatct atctggtgtc taaactggac    180
tctggagtcc ctgacaggtt cactggcagt ggatcaggga cagatttcac actgaaaatc    240
agcagagtgg aggctgagga tttgggagtt tattattgct ggcaaggtac acattttccg    300
tacacgttcg gaggggggac caagctggaa ataaaa                              336

<210> SEQ ID NO 49
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gaggtccagc tgcaacaatc tggacctgag ctggtgaagc ctggggcttc agtgaagatg     60
tcctgtaagg cttctggata cacaatcact gactactaca tgatgtggtt gaagcagagt    120
catggaaaga gccttgaatg gattggagat attaatcctt acactggtgg tactagctac    180
aaccagaagt tcaagggcaa ggccacattg actgtagaca aatcctccag cacagcctac    240
atgcagctca acagcctgac atctgaggac tctgcagtct attactgtgc aagaggggcc    300
tactggggcc aaggcaccac tctcacagtc tcctca                              336

<210> SEQ ID NO 50
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gatgttgtga tgacccagac tccactcact ttgtcggtta ccattggaca accagcctcc     60
atctcttgca agtcaagtca gagcctctta gatagtgatg gaaagacata tttgaattgg    120
ttgttacaga ggccaggcca gtctccaaag cgcctaatct atctggtgtc taaactggac 180
tctggagtcc ctgacaggtt cactggcagt ggatcaggga cagatttcac actgaaaatc 240
agcagagtgg aggctgagga tttgggagtt tattattgct ggcaaggtac acattttccg 300
tacacgttcg gaggggggac caagctggaa ataaaa 336

<210> SEQ ID NO 51
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 51
gaggtccagc tgcaacaatc tggacctgag ctggtgaagc ctggggcttc agtgaagata 60
tcctgtaagg cttctggata cacgttcact gactactaca tgaactgggt gaagcagagc 120
catggcagga gccttgagtt gattggagat attaatccta acaatggtgg ttctaacttc 180
aaccagaagt tcaggggcaa ggccacattg actgtagaca agtcctccag cacagcctat 240
atggagctcc gcagcctgac atctgaggac tctgcaatct attactgtgc aagaatgggt 300
tactggggcc aagggactct ggtcactgtc tctgca 336

<210> SEQ ID NO 52
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 52
gatgttgtga tgacccagac tccactcact ttgtcggtta ccattggaca accagcctcc 60
atctcttgca agtcaagtca gagcctctta catagtgatg gaaagacata tttgaattgg 120
atgttccaga ggccaggcca gtctccaaag cgcctaatct atctggtgtc taaactggac 180
tctggagtcc cttacaggtt cactggcggt ggatcaggga cagatttcac actgcaaatc 240
agcagagtgg agactgagga tttgggagtt tattattgct ggcaaggtac acattttcct 300
cggacgttcg gtggaggcac caagctggaa atcaaa 336

<210> SEQ ID NO 53
<211> LENGTH: 342
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 53
gaggtccagc tgcagcagtc tggacctgaa ctggtcaagc ctggggcttc agtgaagatg 60
tcctgcaagg cttctggata cacattcact gactactaca tacactgggt gaagcagaag 120
cctgggcagg gccttgagta cattggagag atttatcctg gaagtggtaa tacttactac 180
aatgggaagt tcaggggcaa ggccacactg actgcagaca agtcctccag cacagcctac 240
atgcagctca gcagcctgac atctgaggac tctgcagtct atttctgtgg tagtggctac 300
tttgactact ggggccaagg caccactctc acagtctcct ca 342

<210> SEQ ID NO 54

<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 54
gatgttgtga tgacccagac tccactcact ttgtctgtta ccattggaca gccagcttcc 60
atttcttgca agtcaagtca gagcctctta tatagtaatg gaaaaaccta tttgaattgg 120
ttattacaga gtccaggcca gtctccaaag ctcctaatct atctggtgtc taaactggaa 180
tctggagtcc ctgacagatt cagtggcagt ggatcaggga cagattttac actgaaactc 240
agcagagtgg aggctgagga tttgggagta tattactgcg tgcaaggtac acatttccca 300
ttcacgttcg gctcggggac aaagttggaa ataaaa 336

<210> SEQ ID NO 55
<211> LENGTH: 1368
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 55
atggagactg ggctgcgctg gcttctcctg gtcgctgtgt tcaaaggtgt ccagtgtcag 60
gagcaactgg tggagtccgg gggagacctg gtcaagcctg gggcatccct gacactcacc 120
tgcacagcct ctggattctc cttcaataag aattattgga tgtgctgggt ccgccaggct 180
ccagggaagg ggctggagtg gatcggatgc atttataatg gtgatggcaa cacatactac 240
gcgagctggg tgaatggccg attcaccatc tccaaaacct cgtcgaccac ggtgactctg 300
caaatgacca gtctgacagt cgcggacacg gccatctatt tctgtgcgag actacttaat 360
atgtggggcc caggcaccct ggtcaccgtc tcctcagggc aacctaaggc tccatcagtc 420
ttcccactgg ccccctgctg cggggacaca cccagctcca cggtgaccct gggctgcctg 480
gtcaaaggct acctcccgga gccagtgacc gtgacctgga actcgggcac cctcaccaat 540
ggggtacgca ccttcccgtc cgtccggcag tcctcaggcc tctactcgct gagcagcgtg 600
gtgagcgtga cctcaagcag ccagcccgtc acctgcaacg tggcccaccc agccaccaac 660
accaaagtgg acaagaccgt tgcgccctcg acatgcagca agcccatgtg cccaccccct 720
gaactcccgg ggggaccgtc tgtcttcatc ttccccccaa aacccaagga caccctcatg 780
atctcacgca cccccgaggt cacatgcgtg gtggtggacg tgagccagga tgaccccgag 840
gtgcagttca catggtacat aaacaacgag caggtgcgca ccgcccggcc gccgctacgg 900
gagcagcagt tcaacagcac gatccgcgtg gtcagcaccc tccccatcgc gcaccaggac 960
tggctgaggg gcaaggagtt caagtgcaaa gtccacaaca aggcactccc ggcccccatc 1020
gagaaaacca tctccaaagc cagagggcag cccctggagc cgaaggtcta caccatgggc 1080
cctccccggg aggagctgag cagcaggtcg gtcagcctga cctgcatgat caacggcttc 1140
tacccttccg acatctcggt ggagtgggag aagaacggga aggcagagga caactacaag 1200
accacgccga ccgtgctgga cagcgacggc tcctacttcc tctacagcaa gctctcagtg 1260
cccacgagtg agtggcagcg gggcgacgtc ttcacctgct ccgtgatgca cgaggccttg 1320
cacaaccact acacgcagaa gtccatctcc cgctctccgg gtaaatag 1368

<210> SEQ ID NO 56
<211> LENGTH: 720
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

```
atggacacga gggcccccac tcagctgctg gggctcctac tgctctggct cccaggtgcc     60

agatgtgctg acattgtgat gacccagact ccagcctccg tggaggcagc tgtgggaggc    120

acagtcacca tcaagtgcca ggccagtgag agcattggca atgcattagc ctggtatcag    180

cagaaaccag ggcagcctcc caagctcctg atctatactg cagccactct ggcatctggg    240

gtcccatcgc ggttcagcgg cagtggatct gggacagagt tcactctcac catcagtggc    300

gtgcagtgtg acgatgctgc cacttactac tgtcaaagct attattttac tagtgttagt    360

agttatggca atgctttcgg cggagggacc gaggtggtgg tcaaaggtga tccagttgca    420

cctactgtcc tcatcttccc accagctgct gatcaggtgg caactggaac agtcaccatc    480

gtgtgtgtgg cgaataaata ctttcccgat gtcaccgtca cctgggaggt ggatggcacc    540

acccaaacaa ctggcatcga gaacagtaaa acaccgcaga attctgcaga ttgtacctac    600

aacctcagca gcactctgac actgaccagc acacagtaca acagccacaa agagtacacc    660

tgcaaggtga cccagggcac gacctcagtc gtccagagct tcaatagggg tgactgttag    720
```

<210> SEQ ID NO 57
<211> LENGTH: 1401
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57

```
atggagactg ggctgcgctg gcttctcctg gtcgctgtgc tcaaaggtgt ccagtgtcag     60

tcgttggagg agtccggggg agacctggtc aagcctgggg catccctgac actcacctgc    120

agagtctctg gattctcctt cagtagcagt tattatatgt gttgggtccg ccaggctcca    180

gggaaggggc tggaatggat cgcatgtatt ggtactactc gtggtagcac ttactacgcg    240

acctgggcga aaggccgatt caccatttct aaaatctcgt cgaccacggt gactctacaa    300

atgaccagtc tgacagacgc ggacacggcc acctatttct gtgcgagaga tgctactggt    360

tataggatta acacgattgg cctctatttt aatttgtggg gcccaggcac cctggtcacc    420

gtctcctcag ggcaacctaa ggctccatca gtcttcccac tggcccccctg ctgcggggac    480

acacccagct ccacggtgac cctgggctgc ctggtcaaag gctacctccc ggagccagtg    540

accgtgacct ggaactcggg caccctcacc aatggggtac gcaccttccc gtccgtccgg    600

cagtcctcag gcctctactc gctgagcagc gtggtgagcg tgacctcaag cagccagccc    660

gtcacctgca acgtggccca cccagccacc aacaccaaag tggacaagac cgttgcgccc    720

tcgacatgca gcaagcccat gtgcccaccc cctgaactcc cggggggacc gtctgtcttc    780

atcttccccc caaaacccaa ggacaccctc atgatctcac gcacccccga ggtcacatgc    840

gtggtggtgg acgtgagcca ggatgacccc gaggtgcagt tcacatggta cataaacaac    900

gagcaggtgc gcaccgcccg gccgccgcta cgggagcagc agttcaacag cacgatccgc    960

gtggtcagca ccctccccat cgcgcaccag gactggctga ggggcaagga gttcaagtgc   1020
```

aaagtccaca acaaggcact cccggccccc atcgagaaaa ccatctccaa agccagaggg 1080
cagcccctgg agccgaaggt ctacaccatg ggccctcccc gggaggagct gagcagcagg 1140
tcggtcagcc tgacctgcat gatcaacggc ttctaccctt ccgacatctc ggtggagtgg 1200
gagaagaacg ggaaggcaga ggacaactac aagaccacgc cgaccgtgct ggacagcgac 1260
ggctcctact tcctctacag caagctctca gtgcccacga gtgagtggca gcggggcgac 1320
gtcttcacct gctccgtgat gcacgaggcc ttgcacaacc actacacgca gaagtccatc 1380
tcccgctctc cgggtaaata g 1401

<210> SEQ ID NO 58
<211> LENGTH: 714
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 58
atggacacga gggcccccac tcagctgctg gggctcctgc tgctctggct cccaggtgcc 60
agatgtgcgt tcgaattgac ccagactcca tcctccgtgg aggctgctgt gggaggcacg 120
cccaccatca agtgccaggc cagtcagacc atttacagtt acttatcctg gtatcagcag 180
aaaccagggc agcctcccaa gctcctgatc tatgaagcgt ccaaactggc ctctggggtc 240
ccatcgcggt tcagcggcag tggatctggg acagactaca ctctcaccat cagcgacctg 300
gagtgtgccg atgctgccac ttactactgt caaagctatc atggtactgc tagtactgaa 360
tataatactt tcggcggggg gaccgaggtg gtggtcagag gtgatccagt tgcacctact 420
gtcctcatct tcccaccagc tgctgatcag gtggcaactg gaacagtcac catcgtgtgt 480
gtggcgaata aatactttcc cgatgtcacc gtcacctggg aggtggatgg caccacccaa 540
acaactggca tcgagaacag taaaacaccg cagaattctg cagattgtac ctacaacctc 600
agcagcactc tgacactgac cagcacacag tacaacagcc acaaagagta cacctgcaag 660
gtgacccagg gcacgacctc agtcgtccag agcttcaata ggggtgactg ttag 714

<210> SEQ ID NO 59
<211> LENGTH: 1401
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 59
atggagactg ggctgcgctg gcttctcctg gtcgctgtgc tcaaaggtgt ccagtgtcag 60
cagcagctgg tggagtccgg gggaggcctg gtcaagcctg gggcagccct gacattcacc 120
tgcacagcct ctggattctc cttcagtggc aattattgga tatgctgggt ccgccaggct 180
ccagggaagg ggttggagtg gatcgcgtgc attggtacta ttactagtag gacatactac 240
gcgagctggg cgaaaggccg attcaccatt tccaaaacct cgtcgaccac ggtgactctg 300
caaatgacca gtctgacagc cgcggacacg gccacgtatt tctgtgcgag aggtgcggtt 360
gttagtagtg gtaatgctcc ctactacttt accttgtggg gcccaggcac cctggtcacc 420
gtctcctcag ggcaacctaa ggctccatca gtcttcccac tggcccccctg ctgcggggac 480 acacccagct ccacggtgac cctgggctgc ctggtcaaag gctacctccc ggagccagtg 540
accgtgacct ggaactcggg caccctcacc aatggggtac gcaccttccc gtccgtccgg 600
cagtcctcag gcctctactc gctgagcagc gtggtgagcg tgacctcaag cagccagccc 660
gtcacctgca acgtggccca cccagccacc aacaccaaag tggacaagac cgttgcgccc 720
tcgacatgca gcaagcccat gtgcccaccc cctgaactcc cgggggggacc gtctgtcttc 780 atcttccccc caaaacccaa ggacaccctc atgatctcac gcacccccga ggtcacatgc 840
gtggtggtgg acgtgagcca ggatgacccc gaggtgcagt tcacatggta cataaacaac 900
gagcaggtgc gcaccgcccg gccgccgcta cgggagcagc agttcaacag cacgatccgc 960
gtggtcagca ccctccccat cgcgcaccag gactggctga ggggcaagga gttcaagtgc 1020
aaagtccaca acaaggcact cccggccccc atcgagaaaa ccatctccaa agccagaggg 1080
cagcccctgg agccgaaggt ctacaccatg ggccctcccc gggaggagct gagcagcagg 1140
tcggtcagcc tgacctgcat gatcaacggc ttctaccctt ccgacatctc ggtggagtgg 1200
gagaagaacg ggaaggcaga ggacaactac aagaccacgc cgaccgtgct ggacagcgac 1260
ggctcctact tcctctacag caagctctca gtgcccacga gtgagtggca gcggggcgac 1320
gtcttcacct gctccgtgat gcacgaggcc ttgcacaacc actacacgca gaagtccatc 1380
tcccgctctc cgggtaaata g 1401

<210> SEQ ID NO 60
<211> LENGTH: 711
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 60
atggacacga gggcccccac tcagctgctg gggctcctgc tgctctggct cccaggtgcc 60
agatgtgcat tcgaattgac gcagactcca tcctccgtgg aggcagctgt gggaggcaca 120
gtcaccatca agtgccaggc cagtcagagc attagtagtt acttatcctg gtatcagcag 180
aaaccagggc agcctcccaa gctcctgatc tacagggcat ccactctgga atctggggtc 240
ccatcgcggt ttaaaggcag tggatctggg acagagttca ctctcaccat cagcgacctg 300
gagtgtgccg atgctgccac ttacttctgt caaagctatt atggtgttac ttttagtggt 360
tttgctttcg gcggagggac cgaggtggtg gtcaaaggtg atccagttgc acctactgtc 420
ctcatcttcc caccagctgc tgatcaggtg gcaactggaa cagtcaccat cgtgtgtgtg 480
gcgaataaat actttcccga tgtcaccgtc acctgggagg tggatggcac cacccaaaca 540
actggcatcg agaacagtaa aacaccgcag aattctgcag attgtaccta caacctcagc 600
agcactctga cactgaccag cacacagtac aacagccaca aagagtacac ctgcaaggtg 660
acccagggca cgacctcagt cgtccagagc ttcaataggg gtgactgtta g 711

<210> SEQ ID NO 61
<211> LENGTH: 1383
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 61
atggagactg ggctgcgctg gcttctcctg gtcgctgtgc tcaaaggtgt ccagtgtcag 60
tcgttggagg agtccggggg agacctggtc aagcctgggg catccctgac actcacctgc 120
aaagcctctg gaatcgactt caataactat tggataacct gggtccgcca ggctccaggg 180
aaggggctgg agtggatcgc atgcatttat gttggaatta ccggccgcac atggtacgcg 240
aactgggcga aaggccgatt caccatctcc aaggcctcga gcacggtgga tctgaaaatg 300
accagtctga cagccgcgga cacggccacc tatttctgtg cgaggaatgg tgatggtggt 360
atttatgctc ttaacttgtg gggcccaggc accctggtca ccgtctcctc agggcaacct 420
aaggctccat cagtcttccc actggccccc tgctgcgggg acacacccag ctccacggtg 480
accctgggct gcctggtcaa aggctacctc ccggagccag tgaccgtgac ctggaactcg 540
ggcaccctca ccaatggggt acgcaccttc ccgtccgtcc ggcagtcctc aggcctctac 600
tcgctgagca gcgtggtgag cgtgacctca agcagccagc ccgtcacctg caacgtggcc 660
cacccagcca ccaacaccaa agtggacaag accgttgcgc cctcgacatg cagcaagccc 720
atgtgcccac cccctgaact cccgggggga ccgtctgtct tcatcttccc cccaaaaccc 780
aaggacaccc tcatgatctc acgcaccccc gaggtcacat gcgtggtggt ggacgtgagc 840
caggatgacc ccgaggtgca gttcacatgg tacataaaca acgagcaggt gcgcaccgcc 900
cggccgccgc tacgggagca gcagttcaac agcacgatcc gcgtggtcag caccctcccc 960
atcgcgcacc aggactggct gaggggcaag gagttcaagt gcaaagtcca caacaaggca 1020
ctcccggccc ccatcgagaa aaccatctcc aaagccagag ggcagcccct ggagccgaag 1080
gtctacacca tgggccctcc ccgggaggag ctgagcagca ggtcggtcag cctgacctgc 1140
atgatcaacg gcttctaccc ttccgacatc tcggtggagt gggagaagaa cgggaaggca 1200
gaggacaact acaagaccac gccgaccgtg ctggacagcg acggctccta cttcctctac 1260
agcaagctct cagtgcccac gagtgagtgg cagcggggcg acgtcttcac ctgctccgtg 1320
atgcacgagg ccttgcacaa ccactacacg cagaagtcca tctcccgctc tccgggtaaa 1380
tag 1383

<210> SEQ ID NO 62
<211> LENGTH: 717
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 62
atggacacga gggcccccac tcagctgctg gggctcctgc tgctctggct cccaggtgcc 60
acatttgcac aagtgctgac ccagactgca tcgtccgtgt ctgcagctgt gggaggcaca 120
gtcaccatca gttgccagtc cagtcagagt gtttataata ataattggtt agcctggtat 180
cagcagaaac cagggcagcc tcccaagctc ctgatctaca gggcatccac tctgacatct 240
ggggtcccat cgcggttcaa aggcagtgga tctgggacac agttcactct caccatcagc 300
gacctggagt gtgacgatgc tgccacttac tactgtgcag gcggttatag tggtaatatt 360
tacgtaaatg atttcggcgg agggaccgag gtggtggtca aaggtgatcc agttgcacct 420
actgtcctca tcttcccacc agctgctgat caggtggcaa ctggaacagt caccatcgtg 480
tgtgtggcga ataaatactt tcccgatgtc accgtcacct gggaggtgga tggcaccacc 540
caaacaactg gcatcgagaa cagtaaaaca ccgcagaatt ctgcagattg tacctacaac 600
ctcagcagca ctctgacact gaccagcaca cagtacaaca gccacaaaga gtacacctgc 660
aaggtgaccc agggcacgac ctcagtcgtc cagagcttca ataggggtga ctgttag 717

<210> SEQ ID NO 63
<211> LENGTH: 1380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
atggagactg ggctgcgctg gcttctcctg gtcgctgtgc tcaaaggtgt ccagtgtcag 60
gagcagctgg aggagtccgg gggagacctg gtcaagcctg ggggatccct gacactcacc 120
tgcaaagcct ctggattctc cttcagtaat acctactggg catgctgggt ccgccaggct 180
ccagggaagg ggctggagtg gatcgcatgc atgaatcctg ctagtagtgg tagctcttac 240
tacgcgagct gggcgaaagg ccgattcacc atctccaaaa cctcgtcgac cacggtgact 300
ctgcacatgc ccagtctgac agccgcggac acggccacct atttctgtgc gaaatgggat 360
actgctttcg atgtgtgggg cccaggcacc ctggtcaccg tctcctcagg gcaacctaag 420
gctccatcag tcttcccact ggccccctgc tgcggggaca cacccagctc cacggtgacc 480
ctgggctgcc tggtcaaagg ctacctcccg gagccagtga ccgtgacctg gaactcgggc 540
accctcacca atggggtacg caccttcccg tccgtccggc agtcctcagg cctctactcg 600
ctgagcagcg tggtgagcgt gacctcaagc agccagcccg tcacctgcaa cgtggcccac 660
ccagccacca acaccaaagt ggacaagacc gttgcgccct cgacatgcag caagcccatg 720
tgcccacccc ctgaactccc gggggaccg tctgtcttca tcttcccccc aaaacccaag 780
gacaccctca tgatctcacg cacccccgag gtcacatgcg tggtggtgga cgtgagccag 840
gatgaccccg aggtgcagtt cacatggtac ataaacaacg agcaggtgcg caccgcccgg 900
ccgccgctac gggagcagca gttcaacagc acgatccgcg tggtcagcac cctccccatc 960
gcgcaccagg actggctgag gggcaaggag ttcaagtgca aagtccacaa caaggcactc 1020
ccggccccca tcgagaaaac catctccaaa gccagagggc agcccctgga gccgaaggtc 1080
tacaccatgg gccctccccg ggaggagctg agcagcaggt cggtcagcct gacctgcatg 1140
atcaacggct tctacccttc cgacatctcg gtggagtggg agaagaacgg gaaggcagag 1200
gacaactaca agaccacgcc gaccgtgctg gacagcgacg gctcctactt cctctacagc 1260
aagctctcag tgcccacgag tgagtggcag cggggcgacg tcttcacctg ctccgtgatg 1320
cacgaggcct tgcacaacca ctacacgcag aagtccatct cccgctctcc gggtaaatag 1380

<210> SEQ ID NO 64
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
atggacacga gggcccccac tcagctgctg gggctcctgc tgctctggct cccaggtgcc 60
agatgtgccg atgttgtgat gacccagact ccatcctccg tggaggcagc tgtgggaggc 120
acagtcacca tcaagtgcca ggccagtcag agcattagta gctacttagc ctggtatcag 180
cagaaaccag ggcagcctcc caagctcctg atctatggtg catccaatct ggagtctggg 240
gtcccatcgc ggttcaaagg cagtggatct gggacagagt acactctcac catcagcggc 300
gtgcagtgtg acgatgctgc cacttactac tgtcaaaact attatgctat tgatacttat 360
ggtcatgctt tcggcggagg gaccgaggtg gtggtcaaag gtgatccagt tgcacctact 420
gtcctcatct tcccaccagc tgctgatcag gtggcaactg gaacagtcac catcgtgtgt 480
gtggcgaata aatactttcc cgatgtcacc gtcacctggg aggtggatgg caccacccaa 540
acaactggca tcgagaacag taaaacaccg cagaattctg cagattgtac ctacaacctc 600
agcagcactc tgacactgac cagcacacag tacaacagcc acaaagagta cacctgcaag 660
gtgacccagg gcacgacctc agtcgtccag agcttcaata ggggtgactg ttag 714

<210> SEQ ID NO 65
<211> LENGTH: 1368
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65
atggagactg ggctgcgctg gcttctcctg gtcgctgtgc tcaaaggtgt ccagtgtcag 60
gagcagctgg aggagtccgg gggagacctg gtcaagcctg gggcatccct gacactcacc 120
tgcacagcct ctggattctc ctttagtagc aactatcaca tctgctgggt ccgccaggct 180
ccaggaaagg ggctggagtt gatcgcatgc atttatgttg gtgatggcag cacatactac 240
gcgagctggg cgaaaggccg attcaccatc tccaaatcct cgtcgaccac ggtagctctg 300
caaatgacca gtctgacagc cgcggacacg gccacctatt tctgtgggag aatgtttaac 360
ttgtggggcc caggcaccct ggtcaccgtc tcctcagggc aacctaaggc tccatcagtc 420
ttcccactgg ccccctgctg cggggacaca cccagctcca cggtgaccct gggctgcctg 480
gtcaaaggct acctcccgga gccagtgacc gtgacctgga actcgggcac cctcaccaat 540
ggggtacgca ccttcccgtc cgtccggcag tcctcaggcc tctactcgct gagcagcgtg 600
gtgagcgtga cctcaagcag ccagcccgtc acctgcaacg tggcccaccc agccaccaac 660
accaaagtgg acaagaccgt tgcgccctcg acatgcagca agcccatgtg cccacccccct 720 gaactcccgg ggggaccgtc tgtcttcatc ttccccccaa aacccaagga caccctcatg 780
atctcacgca cccccgaggt cacatgcgtg gtggtggacg tgagccagga tgaccccgag 840
gtgcagttca catggtacat aaacaacgag caggtgcgca ccgcccggcc gccgctacgg 900
gagcagcagt tcaacagcac gatccgcgtg gtcagcaccc tccccatcgc gcaccaggac 960
tggctgaggg gcaaggagtt caagtgcaaa gtccacaaca aggcactccc ggcccccatc 1020
gagaaaacca tctccaaagc cagagggcag cccctggagc cgaaggtcta caccatgggc 1080
cctccccggg aggagctgag cagcaggtcg gtcagcctga cctgcatgat caacggcttc 1140 taccccttccg acatctcggt ggagtgggag aagaacggga aggcagagga caactacaag 1200
accacgccga ccgtgctgga cagcgacggc tcctacttcc tctacagcaa gctctcagtg 1260
cccacgagtg agtggcagcg gggcgacgtc ttcacctgct ccgtgatgca cgaggccttg 1320
cacaaccact acacgcagaa gtccatctcc cgctctccgg gtaaatag 1368

<210> SEQ ID NO 66
<211> LENGTH: 708
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66
atggacacga gggcccccac tcagctgctg gggctcctgc tgctctggct cccaggtgcc 60
atatgtgacc ctgtgctgac ccagactcca tcctccgtgt ctgcggctgt gggagtcaca 120
gtcaccatca actgccagtc cagtccgagt gtttatagta actacttatc ctggtatcag 180
cagaaaccag ggcagcctcc caagctcctc atctatctgg catctactct ggcatctggg 240
gtcccatcgc ggttcaaagg cagtggatct gggacacagt tcactctcac catcagcgac 300
gtgcagtgtg acgatgctgc cacttactac tgtgcaggca cttatagtgg taatatttgg 360
tctttcggcg gagggaccga ggtggtggtc aaaggtgatc cagttgcacc tactgtcctc 420
atcttcccac cagctgctga tcaggtggca actggaacag tcaccatcgt gtgtgtggcg 480
aataaatact ttcccgatgt caccgtcacc tgggaggtgg atggcaccac ccaaacaact 540
ggcatcgaga acagtaaaac accgcagaat tctgcagatt gtacctacaa cctcagcagc 600
actctgacac tgaccagcac acagtacaac agccacaaag agtacacctg caaggtgacc 660
cagggcacga cctcagtcgt ccagagcttc aataggggtg actgttag 708

<210> SEQ ID NO 67
<211> LENGTH: 1383
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
atggagactg ggctgcgctg gcttctcctg gtcgctgtgc tcaaaggtgt ccagtgtcag 60
cagcagctgg tggagtccgg gggaggcctg gtcaagcctg gggcatccct gacactcacc 120
tgcacagcct ctggattctc cttcagtagc ggctatcaca tgtgctgggt ccgccaggct 180
ccagggaagg ggctggagtg gatcgcatgc tttggtgttt atactggtac cactacctac 240
gcgagctggg cgaaaggtcg attcaccatc tccaaaacct cgtcgaccac ggtgactcta 300
caaatgacca gtctaacagt cgcggacacg gccacctatt tctgtgcgag aatcagtgct 360
gaaaatggtg gggacttgtg gggcccaggc accctggtca ccgtctcctc agggcaacct 420
aaggctccat cagtcttccc actggccccc tgctgcgggg acacacccag ctccacggtg 480
accctgggct gcctggtcaa aggctacctc ccggagccag tgaccgtgac ctggaactcg 540
ggcaccctca ccaatggggt acgcaccttc ccgtccgtcc ggcagtcctc aggcctctac 600
tcgctgagca gcgtggtgag cgtgacctca agcagccagc ccgtcacctg caacgtggcc 660
cacccagcca ccaacaccaa agtggacaag accgttgcgc cctcgacatg cagcaagccc 720
atgtgcccac cccctgaact cccgggggga ccgtctgtct tcatcttccc cccaaaaccc 780
aaggacaccc tcatgatctc acgcaccccc gaggtcacat gcgtggtggt ggacgtgagc 840
caggatgacc ccgaggtgca gttcacatgg tacataaaca acgagcaggt gcgcaccgcc 900
cggccgccgc tacgggagca gcagttcaac agcacgatcc gcgtggtcag caccctcccc 960
atcgcgcacc aggactggct gaggggcaag gagttcaagt gcaaagtcca caacaaggca 1020
ctcccggccc ccatcgagaa aaccatctcc aaagccagag ggcagcccct ggagccgaag 1080
gtctacacca tgggccctcc ccgggaggag ctgagcagca ggtcggtcag cctgacctgc 1140
atgatcaacg gcttctaccc ttccgacatc tcggtggagt gggagaagaa cgggaaggca 1200
gaggacaact acaagaccac gccgaccgtg ctggacagcg acggctccta cttcctctac 1260
agcaagctct cagtgcccac gagtgagtgg cagcggggcg acgtcttcac ctgctccgtg 1320
atgcacgagg ccttgcacaa ccactacacg cagaagtcca tctcccgctc tccgggtaaa 1380
tag 1383

<210> SEQ ID NO 68
<211> LENGTH: 711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68
atggacacga gggcccccac tcagctgctg gggctcctgc tgctctggct cccaggtgcc 60
agatgtgatg ttgtgatgac ccagactcca gcctccgtgg aggcagctgt gggaggcaca 120
gtcaccatca agtgccaggc cagtcagagc attagcaact acttttcttg gtatcagcag 180
aaaccagggc agcctcccaa gctcctgatc tacagggcgt ccactctggc atctggggtc 240
ccatcgcggt tcagcggcag tggatctggg acagagttca ctctcaccat cagcgacctg 300
gagtgtgccg attctgccac ttactactgt cagtgcactt atggtagtag tagtactggt 360
tttggtttcg gcggagggac cgaggtggtg gtcaaaggtg atccagttgc acctactgtc 420
cccatcttcc caccagctgc tgatcaggtg gcaactggaa cagtcaccat cgtgtgtgtg 480
gcgaataaat actttcccga tgtcaccgtc acctgggagg tggatggcac cacccaaaca 540
actggcatcg agaacagtaa aacaccgcag aattctgcag attgtaccta caacctcagc 600
agcactctga cactgaccag cacacagtac aacagccaca aagagtacac ctgcaaggtg 660
acccagggca cgacctcagt cgtccagagc ttcaataggg gtgactgtta g 711

<210> SEQ ID NO 69
<211> LENGTH: 1371
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 69
atggagactg ggctgcgctg gcttctcctg gtcgctgtgc tcaaaggtgt ccagtgtcag 60
tcgttggagg agtccggggg agacctggtc aagcctgggg catccctgac actcacctgc 120
atggcctctg gaatcgactt cagtagcggc tacggcatgt ggtgggtccg ccaggctcca 180
gggaagggac tggagtatat cggatacatt gatactggtg atgataacac atactacgcg 240
aactgggcga aaggccgatt caccatctcc aaaacctcgt cgaccacggt gactctgcaa 300
atgaccagtc tgacagtcgc ggacacggcc acctatttct gtgcgaaagg gggcgccata 360
gacctctggg gcccagggac cctcgtcacc gtctcttcag ggcaacctaa ggctccatca 420
gtcttcccac tggcccccctg ctgcggggac acacccagct ccacggtgac cctgggctgc 480
ctggtcaaag gctacctccc ggagccagtg accgtgacct ggaactcggg caccctcacc 540
aatggggtac gcaccttccc gtccgtccgg cagtcctcag gcctctactc gctgagcagc 600
gtggtgagcg tgacctcaag cagccagccc gtcacctgca acgtggccca cccagccacc 660
aacaccaaag tggacaagac cgttgcgccc tcgacatgca gcaagcccat gtgcccaccc 720
cctgaactcc cgggggggacc gtctgtcttc atcttccccc caaaacccaa ggacaccctc 780
atgatctcac gcacccccga ggtcacatgc gtggtggtgg acgtgagcca ggatgacccc 840
gaggtgcagt tcacatggta cataaacaac gagcaggtgc gcaccgcccg gccgccgcta 900
cgggagcagc agttcaacag cacgatccgc gtggtcagca ccctccccat cgcgcaccag 960
gactggctga ggggcaagga gttcaagtgc aaagtccaca acaaggcact cccggccccc 1020
atcgagaaaa ccatctccaa agccagaggg cagcccctgg agccgaaggt ctacaccatg 1080
ggccctcccc gggaggagct gagcagcagg tcggtcagcc tgacctgcat gatcaacggc 1140
ttctaccctt ccgacatctc ggtggagtgg gagaagaacg ggaaggcaga ggacaactac 1200
aagaccacgc cgaccgtgct ggacagcgac ggctcctact tcctctacag caagctctca 1260
gtgcccacga gtgagtggca gcggggcgac gtcttcacct gctccgtgat gcacgaggcc 1320
ttgcacaacc actacacgca gaagtccatc tcccgctctc cgggtaaata g 1371

<210> SEQ ID NO 70
<211> LENGTH: 720
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 70
atggacacga gggcccccac tcagctgctg ggactcctac tgctctggct cccaggtgcc 60
agatgtgctg acattgtgat gacccagact ccagcctccg tggaggcagc tgtgggaggc 120
acagtcacca tcaagtgcca ggccagtcag agcattagta gttacttagc ctggtatcag 180
cagaaaccag ggcagcgtcc caagctcctg atctacaggg catccactct aaaatctggg 240
gtcccatcgc ggttcaaagg cagtggatct gggacagagt acactctcac catcagcgac 300
ctggagtgtg ccgatgctgc cacttattat tgtcaagcgt attatcttag tagtagtatc 360
agttatggta atactttcgg cggagggacc gaggtggtgg tcaaaggtga tccagttgca 420
cctactgtcc tcatcttccc accagctgct gatcaggtgg caactggaac agtcaccatc 480
gtgtgtgtgg cgaataaata ctttcccgat gtcaccgtca cctgggaggt ggatggcacc 540
acccaaacaa ctggcatcga gaacagtaaa acaccgcaga attctgcaga ttgtacctac 600
aacctcagca gcactctgac actgaccagc acacagtaca acagccacaa agagtacacc 660
tgcaaggtga cccagggcac gacctcagtc gtccagagct tcaatagggg tgactgttag 720

<210> SEQ ID NO 71
<211> LENGTH: 1371
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 71
atggagactg ggctgcgctg gcttctcctg gtcgctgtgc tcaaaggtgt ccagtgtcag 60
tcgttggagg agtccggggg agacctggtc aagcctgggg cgtccctgac actcacctgc 120
acagcctctg gattctccct cagtagcggg tatggcatgt gctgggtccg ccaggctcca 180
gggaagggac tggagtggat cggatacact gatactgcta ctggtaccat tcactacgcg 240
agctgggcga aaggccgatt caccatctcc aaaacctcgt cgaccacggt gactctgcaa 300
atgaccagtc tgacagccgc ggacacggcc acctatttct gtgcgaaagg gggcgccatg 360
gacctctggg gcccagggac cctcgtcacc gtctcttcag ggcaacctaa ggctccatca 420
gtcttcccac tggcccctg ctgcggggac acacccagct ccacggtgac cctgggctgc 480
ctggtcaaag gctacctccc ggagccagtg accgtgacct ggaactcggg caccctcacc 540
aatggggtac gcaccttccc gtccgtccgg cagtcctcag gcctctactc gctgagcagc 600
gtggtgagcg tgacctcaag cagccagccc gtcacctgca acgtggccca cccagccacc 660
aacaccaaag tggacaagac cgttgcgccc tcgacatgca gcaagcccat gtgcccaccc 720
cctgaactcc cgggggacc gtctgtcttc atcttcccc caaaacccaa ggacaccctc 780
atgatctcac gcaccccga ggtcacatgc gtggtggtgg acgtgagcca ggatgacccc 840
gaggtgcagt tcacatggta cataaacaac gagcaggtgc gcaccgcccg gccgccgcta 900
cgggagcagc agttcaacag cacgatccgc gtggtcagca ccctccccat cgcgcaccag 960
gactggctga ggggcaagga gttcaagtgc aaagtccaca acaaggcact cccggcccc 1020 atcgagaaaa ccatctccaa agccagaggg cagcccctgg agccgaaggt ctacaccatg 1080
ggccctcccc gggaggagct gagcagcagg tcggtcagcc tgacctgcat gatcaacggc 1140
ttctaccctt ccgacatctc ggtggagtgg gagaagaacg ggaaggcaga ggacaactac 1200
aagaccacgc cgaccgtgct ggacagcgac ggctcctact tcctctacag caagctctca 1260
gtgcccacga gtgagtggca gcggggcgac gtcttcacct gctccgtgat gcacgaggcc 1320
ttgcacaacc actacacgca gaagtccatc tcccgctctc cgggtaaata g 1371

<210> SEQ ID NO 72
<211> LENGTH: 720
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72
atggacacga gggcccccac tcagctgctg gggctcctac tgctctggct cccaggtgcc 60
agatgtgctg acattgtgat gacccagact ccagcctccg tggaggcagc tgtgggaggc 120
acagtcacca tcaagtgcca ggccagtcag agcattagta gctacttagc ctggtatcag 180
cagaaaccag ggcagcctcc caagctcctg atctacagga catccactct ggcatctggg 240
gtcccatcgc ggttcaaagg cagtggatct gggacagagt acactctcac catcagcgac 300
ctggagtgtg ccgatgctgc cacttactat tgtcaaagct atgcttatag tagtagtagc 360
agttatggta atgctttcgg cggagggacc gaggtggtgg tcaaaggtga tccagttgca 420
cctactgtcc tcatcttccc accagctgct gatcaggtgg caactggaac agtcaccatc 480
gtgtgtgtgg cgaataaata ctttcccgat gtcaccgtca cctgggaggt ggatggcacc 540
acccaaacaa ctggcatcga gaacagtaaa acaccgcaga attctgcaga ttgtacctac 600
aacctcagca gcactctgac actgaccagc acacagtaca acagccacaa agagtacacc 660
tgcaaggtga cccagggcac gacctcagtc gtccagagct tcaatagggg tgactgttag 720

<210> SEQ ID NO 73
<211> LENGTH: 1365
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 73
atggagactg ggctgcgctg gcttctcctg gtcgctgtgc tcaaaggtgt ccagtgtcag 60
tcgttggagg agtccggggg agacctggtc aagcctgggg catccctgac actcacctgc 120
acaggctctg gaatcgactt cagtagcagc tactggatat gctgggtccg ccaggctcca 180
gggaaggggc tggagtggat cgcatgcatc gatggtagtg atggtaacac ttactacgcg 240
agctgggcga gaggccgatt caccatctcc aaaacctcgt cgaccacggt gactctgcaa 300
atggccagtc tgacagccgc ggacacggcc acctatttct gtacgagaga tctcaggttg 360
tggggcccag gcaccctggt caccgtctcc tcagggcaac ctaaggctcc atcagtcttc 420
ccactggccc cctgctgcgg ggacacaccc agctccacgg tgaccctggg ctgcctggtc 480
aaaggctacc tcccggagcc agtgaccgtg acctggaact cgggcaccct caccaatggg 540
gtacgcacct tcccgtccgt ccggcagtcc tcaggcctct actcgctgag cagcgtggtg 600
agcgtgacct caagcagcca gcccgtcacc tgcaacgtgg cccacccagc caccaacacc 660
aaagtggaca agaccgttgc gccctcgaca tgcagcaagc ccatgtgccc acccccctgaa 720 ctcccggggg gaccgtctgt cttcatcttc cccccaaaac ccaaggacac cctcatgatc 780
tcacgcaccc ccgaggtcac atgcgtggtg gtggacgtga gccaggatga ccccgaggtg 840
cagttcacat ggtacataaa caacgagcag gtgcgcaccg cccggccgcc gctacgggag 900
cagcagttca acagcacgat ccgcgtggtc agcaccctcc ccatcgcgca ccaggactgg 960
ctgaggggca aggagttcaa gtgcaaagtc cacaacaagg cactcccggc ccccatcgag 1020
aaaaccatct ccaaagccag agggcagccc ctggagccga aggtctacac catgggccct 1080
ccccgggagg agctgagcag caggtcggtc agcctgacct gcatgatcaa cggcttctac 1140
ccttccgaca tctcggtgga gtgggagaag aacgggaagg cagaggacaa ctacaagacc 1200
acgccgaccg tgctggacag cgacggctcc tacttcctct acagcaagct ctcagtgccc 1260
acgagtgagt ggcagcgggg cgacgtcttc acctgctccg tgatgcacga ggccttgcac 1320
aaccactaca cgcagaagtc catctcccgc tctccgggta aatag 1365

<210> SEQ ID NO 74
<211> LENGTH: 723
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 74
atggacacga gggcccccac tcagctgctg gggctcctgc tgctctggct cccaggtgcc 60
agatgtgctg acattgtgct gacccagact ccagcctcgg tgtctgcagc tgtgggaggc 120
acagtcacca tcaactgcca ggccagtcag aatgtttata gtaacaatgc cttagcctgg 180
catcagcaga aaccagggca gcgtcccaac ctcctgatct acaaggcttc cactctggca 240
tctggggtcc catcgcggtt caaaggcagt ggatctggga cacagtttac tctcaccatc 300
agcgacgtgc agtgtgacga tgctgccact tactactgtc taggcgaatt tagttgtagt 360
agtggtgatt gttttgtttt cggcggaggg accgaggtgg tggtcaaagg tgatccagtt 420
gcacctactg tcctcatctt cccaccagct gctgatcagg tggcaactgg aacagtcacc 480
atcgtgtgtg tggcgaataa atactttccc gatgtcaccg tcacctggga ggtggatggc 540
accacccaaa caactggcat cgagaacagt aaaacaccgc agaattctgc agattgtacc 600
tacaacctca gcagcactct gacactgacc agcacacagt acaacagcca caaagagtac 660
acctgcaagg tgacccaggg cacgacctca gtcgtccaga gcttcaatag gggtgactgt 720

```
tag                                                                  723

<210> SEQ ID NO 75
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

atggagactg ggctgcgctg gcttctcctg gtcgctgtgc tcaaaggtgt ccagtgtcag     60

tcgttggagg agtccggggg agacctggtc aagcctgggg catccctgac actcacctgc    120

atggcctctg gaatcgactt cagtagcggc tacggcatgt ggtgggtccg ccaggctcca    180

gggaagggac tggagtatat cggatacatt gatactggtg atgataacac atactacgcg    240

aactgggcga aaggccgatt caccatctcc aaaacctcgt cgaccacggt gactctgcaa    300

atgaccagtc tgacagtcgc ggacacggcc acctatttct gtgcgaaagg gggcgccata    360

gacctctggg gcccagggac cctcgtcacc gtctcttcag ggcaacctaa ggctccatca    420

gtcttcccac tggccccctg ctgcggggac acacccagct ccacggtgac cctgggctgc    480

ctggtcaaag gctacctccc ggagccagtg accgtgacct ggaactcggg caccctcacc    540

aatggggtac gcaccttccc gtccgtccgg cagtcctcag gcctctactc gctgagcagc    600

gtggtgagcg tgacctcaag cagccagccc gtcacctgca acgtggccca cccagccacc    660

aacaccaaag tggacaagac cgttgcgccc tcgacatgca gcaagcccat gtgcccaccc    720

cctgaactcc cgggggggacc gtctgtcttc atcttccccc caaaacccaa ggacaccctc    780

atgatctcac gcacccccga ggtcacatgc gtggtggtgg acgtgagcca ggatgacccc    840

gaggtgcagt tcacatggta cataaacaac gagcaggtgc gcaccgcccg gccgccgcta    900

cgggagcagc agttcaacag cacgatccgc gtggtcagca ccctccccat cgcgcaccag    960

gactggctga ggggcaagga gttcaagtgc aaagtccaca acaaggcact cccggccccc   1020

atcgagaaaa ccatctccaa agccagaggg cagcccctgg agccgaaggt ctacaccatg   1080

ggccctcccc gggaggagct gagcagcagg tcggtcagcc tgacctgcat gatcaacggc   1140

ttctaccctt ccgacatctc ggtggagtgg gagaagaacg ggaaggcaga ggacaactac   1200

aagaccacgc cgaccgtgct ggacagcgac ggctcctact tcctctacag caagctctca   1260

gtgcccacga gtgagtggca gcggggcgac gtcttcacct gctccgtgat gcacgaggcc   1320

ttgcacaacc actacacgca gaagtccatc tcccgctctc cgggtaaata g             1371

<210> SEQ ID NO 76
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

atggacacga gggcccccac tcagctgctg ggactcctac tgctctggct cccaggtgcc     60

agatgtgctg acattgtgat gacccagact ccagcctccg tggaggcagc tgtgggaggc    120

acagtcacca tcaagtgcca ggccagtcag agcattagta gttacttagc ctggtatcag    180

cagaaaccag ggcagcgtcc caagctcctg atctacaggg catccactct aaaatctggg    240
```

```
gtcccatcgc ggttcaaagg cagtggatct gggacagagt acactctcac catcagcgac    300

ctggagtgtg ccgatgctgc cacttattat tgtcaagcgt attatcttag tagtagtatc    360

agttatggta atactttcgg cggagggacc gaggtggtgg tcaaaggtga tccagttgca    420

cctactgtcc tcatcttccc accagctgct gatcaggtgg caactggaac agtcaccatc    480

gtgtgtgtgg cgaataaata ctttcccgat gtcaccgtca cctgggaggt ggatggcacc    540

acccaaacaa ctggcatcga gaacagtaaa acaccgcaga attctgcaga ttgtacctac    600

aacctcagca gcactctgac actgaccagc acacagtaca acagccacaa agagtacacc    660

tgcaaggtga cccagggcac gacctcagtc gtccagagct tcaatagggg tgactgttag    720
```

<210> SEQ ID NO 77
<211> LENGTH: 1416
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 77

```
atggagactg ggctgcgctg gcttctcctg gtcgctgtgc tcaaaggtgt ccagtgtcag     60

cagcagctgg aggagtccgg gggaggcctg gtcaagcctg gaggaaccct gacactcacc    120

tgcaaagcct ctggagtcgc cctcaatccc tactactata tgtgctgggt ccgccaggct    180

ccagggaagg ggctggagtg gatcgcatgc gtggatgctg atagtagtgg tagcacttac    240

tacgcgagct gggcgaaagg ccgattcacc atctccaaaa cctcgtcgac cacggtgact    300

ctgaaaatga ccagtctgac agccgcggac acggccacct atttctgtgc gagagaatcg    360

gttgactata gttctgttgg tattggctat gtacatggta cggatggctt gtggggccca    420

ggcaccctgg tcaccgtctc ctcagggcaa cctaaggctc catcagtctt cccactggcc    480

ccctgctgcg gggacacacc cagctccacg gtgaccctgg gctgcctggt caaaggctac    540

ctcccggagc cagtgaccgt gacctggaac tcgggcaccc tcaccaatgg ggtacgcacc    600

ttcccgtccg tccggcagtc ctcaggcctc tactcgctga gcagcgtggt gagcgtgacc    660

tcaagcagcc agcccgtcac ctgcaacgtg gcccacccag ccaccaacac caaagtggac    720

aagaccgttg cgccctcgac atgcagcaag cccatgtgcc caccccctga actcccgggg    780

ggaccgtctg tcttcatctt ccccccaaaa cccaaggaca ccctcatgat ctcacgcacc    840

cccgaggtca catgcgtggt ggtggacgtg agccaggatg accccgaggt gcagttcaca    900

tggtacataa acaacgagca ggtgcgcacc gcccggccgc cgctacggga gcagcagttc    960

aacagcacga tccgcgtggt cagcaccctc cccatcgcgc accaggactg gctgaggggc   1020

aaggagttca agtgcaaagt ccacaacaag gcactcccgg cccccatcga gaaaaccatc   1080

tccaaagcca gagggcagcc cctggagccg aaggtctaca ccatgggccc tccccgggag   1140

gagctgagca gcaggtcggt cagcctgacc tgcatgatca acggcttcta cccttccgac   1200

atctcggtgg agtgggagaa gaacgggaag gcagaggaca actacaagac cacgccgacc   1260

gtgctggaca gcgacggctc ctacttcctc tacagcaagc tctcagtgcc cacgagtgag   1320

tggcagcggg gcgacgtctt cacctgctcc gtgatgcacg aggccttgca caaccactac   1380

acgcagaagt ccatctcccg ctctccgggt aaatag                             1416
```

<210> SEQ ID NO 78
<211> LENGTH: 720
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 78
atggacacga gggcccccac tcagctgctg gggctcctgc tgctctggct cccaggtgcc 60
agatgtgccg acatcgtggt gacccagact ccatcctccg tgtctgcagc tgtgggaggc 120
acagtcacca tcaagtgcca ggccagtcag agcattagca actacttttc ttggtatcag 180
cagaaaccag ggcagcctcc caagctcctg atctacaggg cgtccactct ggcatctggg 240
gtcccatcgc ggttcaaagg cagtggatct gggacagagt tcactctcac catcagcgac 300
ctggagtgtg ccgatgctgc cacttactac tgtcaatgca cttacggtag aagtaatagt 360
aatttttttt atggtttcgg cggagggacc gaggtggtgg tcaaaggtga tccagttgca 420
cctactgtcc tcatcttccc accagctgct gatcaggtgg caactggaac agtcaccatc 480
gtgtgtgtgg cgaataaata ctttcccgat gtcaccgtca cctgggaggt ggatggcacc 540
acccaaacaa ctggcatcga gaacagtaaa acaccgcaga attctgcaga ttgtacctac 600
aacctcagca gcactctgac actgaccagc acacagtaca acagccacaa agagtacacc 660
tgcaaggtga cccagggcac gacctcagtc gtccagagct tcaatagggg tgactgttag 720

<210> SEQ ID NO 79
<211> LENGTH: 1395
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 79
atggagactg ggctgcgctg gcttctcctg gtcgccgtgc tcaaaggtgt ccagtgtcag 60
tcgttggagg agtccggggg agacctggtc aagcctgggg cctccctgac actcacctgc 120
acagcctctg gatcctcctt cagtagtacc tactggaact gctgggtccg ccaggctcca 180
gggaaggggc tggagtggat cgcatgcatt aatgctggta gtggtaccac ttactacgcg 240
agctgggcga aaggccgatt caccgtctcc aaaacctcgt cgaccacggt gactctgcaa 300
atgaccagtc tgacagccgc ggacacggcc acctatttct gtacgagaga tagtgatggt 360
cgttttagta gtggctacta ttttaacttg tggggcccag gcaccctggt caccgtctcc 420
tcagggcaac ctaaggctcc atcagtcttc ccactggccc cctgctgcgg ggacacaccc 480
agctccacgg tgaccctggg ctgcctggtc aaaggctacc tcccggagcc agtgaccgtg 540
acctggaact cgggcaccct caccaatggg gtacgcacct tcccgtccgt ccggcagtcc 600
tcaggcctct actcgctgag cagcgtggtg agcgtgacct caagcagcca gcccgtcacc 660
tgcaacgtgg cccacccagc caccaacacc aaagtggaca agaccgttgc gccctcgaca 720
tgcagcaagc ccatgtgccc accccctgaa ctcccggggg gaccgtctgt cttcatcttc 780
cccccaaaac ccaaggacac cctcatgatc tcacgcaccc ccgaggtcac atgcgtggtg 840
gtggacgtga gccaggatga ccccgaggtg cagttcacat ggtacataaa caacgagcag 900
gtgcgcaccg cccggccgcc gctacgggag cagcagttca acagcacgat ccgcgtggtc 960
agcaccctcc ccatcgcgca ccaggactgg ctgaggggca aggagttcaa gtgcaaagtc 1020
cacaacaagg cactcccggc ccccatcgag aaaaccatct ccaaagccag agggcagccc 1080
ctggagccga aggtctacac catgggccct ccccgggagg agctgagcag caggtcggtc 1140
agcctgacct gcatgatcaa cggcttctac ccttccgaca tctcggtgga gtgggagaag 1200
aacgggaagg cagaggacaa ctacaagacc acgccgaccg tgctggacag cgacggctcc 1260
tacttcctct acagcaagct ctcagtgccc acgagtgagt ggcagcgggg cgacgtcttc 1320
acctgctccg tgatgcacga ggccttgcac aaccactaca cgcagaagtc catctcccgc 1380
tctccgggta aatag 1395

<210> SEQ ID NO 80
<211> LENGTH: 717
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 80
atggacacga gggcccccac tcagctgctg gggctcctgc tgctctggct cccaggtgcc 60
acatttgccc aagtgctgac ccagactgca tcccctgtgt ctgcagctgt gggaggcaca 120
gtcaccatca attgtcagtc cagtcagagt gtttatgata acaactggtt agcctggtat 180
cagcaaaaac cagggcagcc tcccaaactc ttgatcgacg atgcatccaa attgacatct 240
ggggtctcat cgcggttcaa aggcagtgga tctgggacgc agttcactct caccatcagc 300
ggcgtgcagt gtgacgatgc tgccacttac tactgtcaag gcgcttatta tagtagtggt 360
tggtactggg ctttcggcgg agggaccgag gtggtggtca aaggtgatcc agttgcacct 420
actgtcctca tcttcccacc agctgctgat caggtggcaa ctggaacagt caccatcgtg 480
tgtgtggcga ataaatactt tcccgatgtc accgtcacct gggaggtgga tggcaccacc 540
caaacaactg gcatcgagaa cagtaaaaca ccgcagaatt ctgcagattg tacctacaac 600
ctcagcagca ctctgacact gaccagcaca cagtacaaca gccacaaaga gtacacctgc 660
aaggtgaccc agggcacgac ctcagtcgtc cagagcttca ataggggtga ctgttag 717

<210> SEQ ID NO 81
<211> LENGTH: 1404
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81
atggagactg ggctgcgctg gcttctcctg gtcgctgtgc tcaaaggtgt ccagtgtcag 60
cagcagctgg aggagtccgg gggaggcctg gtcaagcctg gaggaaccct gacactcacc 120
tgcaaagcct ctggaatcga cttcagtagc tactactaca tgtgttgggt ccgccaggct 180
ccagggaagg ggctggagtt gatcgtatgt atttatacta gtagtggtgg cacatggtac 240
gcgagctggg tgaatggccg actcaccatc tccagaagca ccagcctaaa cacggtggat 300
ctgaaaatga ccagtctgac agccgcggac acggccacct atttctgtgc cagaggggtt 360
tattctggta gtagtgatta tccaactcgg ttggatctct ggggccaggg caccctggtc 420
accgtctcct tagggcaacc taaggctcca tcagtcttcc cactggcccc ctgctgcggg 480
gacacaccca gctccacggt gaccctgggc tgcctggtca aaggctacct cccggagcca 540
gtgaccgtga cctggaactc gggcaccctc accaatgggg tacgcacctt cccgtccgtc 600
cggcagtcct caggcctcta ctcgctgagc agcgtggtga gcgtgacctc aagcagccag 660

```
cccgtcacct gcaacgtggc ccacccagcc accaacacca aagtggacaa gaccgttgcg    720

ccctcgacat gcagcaagcc catgtgccca ccccctgaac tcccgggggg accgtctgtc    780

ttcatcttcc ccccaaaacc caaggacacc ctcatgatct cacgcacccc cgaggtcaca    840

tgcgtggtgg tggacgtgag ccaggatgac cccgaggtgc agttcacatg gtacataaac    900

aacgagcagg tgcgcaccgc ccggccgccg ctacgggagc agcagttcaa cagcacgatc    960

cgcgtggtca gcaccctccc catcgcgcac caggactggc tgaggggcaa ggagttcaag   1020

tgcaaagtcc acaacaaggc actcccggcc cccatcgaga aaaccatctc caaagccaga   1080

gggcagcccc tggagccgaa ggtctacacc atgggccctc cccgggagga gctgagcagc   1140

aggtcggtca gcctgacctg catgatcaac ggcttctacc cttccgacat ctcggtggag   1200

tgggagaaga acgggaaggc agaggacaac tacaagacca cgccgaccgt gctggacagc   1260

gacggctcct acttcctcta cagcaagctc tcagtgccca cgagtgagtg gcagcggggc   1320

gacgtcttca cctgctccgt gatgcacgag gccttgcaca accactacac gcagaagtcc   1380

atctcccgct ctccgggtaa atag                                          1404
```

```
<210> SEQ ID NO 82
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

atggacacga gcacctccac tgcgctcctg ggctcctgc tgctctggct cacaggtgcc      60

agatgtgcca tcgagatgac ccagtctcca ccctccctgt ctgcatctgt gggagaaact    120

gtcaggatta ggtgcctggc cagtgaggac atttacagtg gtatatcctg gtaccaacag    180

aagccagaga aacctcctac actcctgatc tctggtgcat ccaatttaga atctggggtc    240

ccaccacggt tcagtggcgg tggatccggg acagattaca ccctcaccat cggcggcgtg    300

caggctgaag atgttgccac ctactactgt ctaggcggtt atagtttcag tagtaccggt    360

ttgacttttg gagctggcac caaggtggaa atcaaacgtg atccagttgc gccttctgtc    420

ctcctcttcc caccatctaa ggaggagctg acaactggaa cagccaccat cgtgtgtgtg    480

gcgaataaat actttcccga tgtcaccgtc acctgggagg tggatggcac cacccaaaca    540

actggcatcg agaacagtaa aacaccgcag aattctgcag attgtaccta caacctcagc    600

agcactctga cactgaccag cacacagtac aacagccaca aagagtacac ctgcaaggtg    660

acccagggca cgacctcagt cgtccagagc ttcaataggg gtgactgtta g             711
```

```
<210> SEQ ID NO 83
<211> LENGTH: 1383
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

atggagactg ggctgcgctg gcttctcctg gtcgctgtgc tcaaaggtgt ccagtgtcag     60

caacatctgg tggagtccgg gggaggcctg gtcaagcctg ggcatccct gacactcacc    120

tgcacagcct ctggattctc cttcactacc ggctatcaca tgtgctgggt ccgccaggct    180

ccagggaagg ggctggagtg gatcgcatgt tttggtgttt atactagtac cactacctac    240
```

gcgagctggg cgaaaggtcg attcaccatc tccaaaacct cgtcgaccac ggtgactcta 300
caaatgacca gtctaacagt cgcggacacg gccacctatt tctgtgcgag aatcagtgct 360
gaagatggtg gggacttgtg gggcccaggc accctggtca ccgtctcctc agggcaacct 420
aaggctccat cagtcttccc actggccccc tgctgcgggg acacacccag ctccacggtg 480
accctgggct gcctggtcaa aggctacctc ccggagccag tgaccgtgac ctggaactcg 540
ggcaccctca ccaatggggt acgcaccttc ccgtccgtcc ggcagtcctc aggcctctac 600
tcgctgagca gcgtggtgag cgtgacctca agcagccagc ccgtcacctg caacgtggcc 660
cacccagcca ccaacaccaa agtggacaag accgttgcgc cctcgacatg cagcaagccc 720
atgtgcccac cccctgaact cccgggggga ccgtctgtct tcatcttccc cccaaaaccc 780
aaggacaccc tcatgatctc acgcaccccc gaggtcacat gcgtggtggt ggacgtgagc 840
caggatgacc ccgaggtgca gttcacatgg tacataaaca acgagcaggt gcgcaccgcc 900
cggccgccgc tacgggagca gcagttcaac agcacgatcc gcgtggtcag caccctcccc 960
atcgcgcacc aggactggct gaggggcaag gagttcaagt gcaaagtcca caacaaggca 1020
ctcccggccc ccatcgagaa aaccatctcc aaagccagag ggcagcccct ggagccgaag 1080
gtctacacca tgggccctcc ccgggaggag ctgagcagca ggtcggtcag cctgacctgc 1140
atgatcaacg gcttctaccc ttccgacatc tcggtggagt gggagaagaa cgggaaggca 1200
gaggacaact acaagaccac gccgaccgtg ctggacagcg acggctccta cttcctctac 1260
agcaagctct cagtgcccac gagtgagtgg cagcggggcg acgtcttcac ctgctccgtg 1320
atgcacgagg ccttgcacaa ccactacacg cagaagtcca tctcccgctc tccgggtaaa 1380
tag 1383

<210> SEQ ID NO 84
<211> LENGTH: 711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84
atggacacga gggcccccac tcagctgctg gggctcctgc tgctctggct cccaggtgcc 60
agatgtgatg ttgtgatgac ccagactcca gcctccgtgg aggcagctgt gggaggcaca 120
gtcaccatca cgtgccaggc cagtcagagc attagcaact acttttcttg gtatcagcag 180
aaaccagggc agcctcccaa gctcctgatc tacagggcgt ccactctggc atctggggtc 240
ccatcgcggt tcagcggcag tggatctggg acacagttca ctctcaccat cagcgacctg 300
gagtgtgccg attctgccac ttacgcctgt cagtgcactt atggtagtag tagtactggt 360
tttggtttcg gcggagggac cgaggtggtg gtcaaaggtg atccagttgc acctactgtc 420
ctcatcttcc caccagctgc tgatcaggtg gcaactggaa cagtcaccat cgtgtgtgtg 480
gcgaataaat actttcccga tgtcaccgtc acctgggagg tggatggcac cacccaaaca 540
actggcatcg agaacagtaa aacaccgcag aattctgcag attgtaccta caacctcagc 600
agcactctga cactgaccag cacacagtac aacagccaca aagagtacac ctgcaaggtg 660
acccagggca cgacctcagt cgtccagagc ttcaataggg gtgactgtta g 711

<210> SEQ ID NO 85
<211> LENGTH: 1389

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 85

```
atggagactg ggctgcgctg gcttctcctg gtcgctgtgc tcaaaggtgt ccagtgtcag     60

tcgttggagg agtccggggg agacctggtc aagcctgggg catccctgac actcacctgc    120

aaagcctctg gattctcctt cagtagttac ttctggatat gctgggtccg ccaggctcca    180

gggaaggggc tggagtggag cgcatgcatc tatggtgata gtagtggtag tagttactac    240

gcgagctggg cgaaaggccg attcaccatc tccaaaacct cgtcgaccac ggtgactctg    300

caaatgacca gtctgacagc cgcggacacg gccacctatt tctgtgcgag ttatggtagt    360

agtagttatt actactctaa tttatggggc ccaggcaccc tggtcaccgt ctcctcaggg    420

caacctaagg ctccatcagt cttcccactg gccccctgct gcggggacac acccagctcc    480

acggtgaccc tgggctgcct ggtcaaaggc tacctcccgg agccagtgac cgtgacctgg    540

aactcgggca ccctcaccaa tggggtacgc accttcccgt ccgtccggca gtcctcaggc    600

ctctactcgc tgagcagcgt ggtgagcgtg acctcaagca gccagcccgt cacctgcaac    660

gtggcccacc cagccaccaa caccaaagtg gacaagaccg ttgcgccctc gacatgcagc    720

aagcccatgt gcccaccccc tgaactcccg gggggaccgt ctgtcttcat cttcccccca    780

aaacccaagg acaccctcat gatctcacgc acccccgagg tcacatgcgt ggtggtggac    840

gtgagccagg atgaccccga ggtgcagttc acatggtaca taaacaacga gcaggtgcgc    900

accgcccggc cgccgctacg ggagcagcag ttcaacagca cgatccgcgt ggtcagcacc    960

ctccccatcg cgcaccagga ctggctgagg ggcaaggagt tcaagtgcaa agtccacaac   1020

aaggcactcc cggcccccat cgagaaaacc atctccaaag ccagagggca gcccctggag   1080

ccgaaggtct acaccatggg ccctccccgg gaggagctga gcagcaggtc ggtcagcctg   1140

acctgcatga tcaacggctt ctacccttcc gacatctcgg tggagtggga gaagaacggg   1200

aaggcagagg acaactacaa gaccacgccg accgtgctgg acagcgacgg ctcctacttc   1260

ctctacagca agctctcagt gcccacgagt gagtggcagc ggggcgacgt cttcacctgc   1320

tccgtgatgc acgaggcctt gcacaaccac tacacgcaga agtccatctc ccgctctccg   1380

ggtaaatag                                                           1389
```

<210> SEQ ID NO 86
<211> LENGTH: 708
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 86

```
atggacacga gggcccccac tcagctgctg gggctcctgc tgctctggct cccaggtgcc     60

atatgtgacc ctgtgatgac ccagactcca tcttccacgt ctgcggctgt gggaggcaca    120

gtcaccatca gttgccagtc cagtcagagt gtttataata acaactactt agcctggtat    180

cagcagaaac cagggcagcc tcccaaacgc ctgatctacg aatcatccaa actggcatct    240

ggggtcccat cgcggttcag aggcagtgga tctggggcac agttcactct caccatcagc    300

gacctggagt gtgacgatgc tgccacttac tactgtctag gcgcatatta tactactctt    360
```

gatttcggcg gagggaccga ggtggtggtc agaggtgatc cagttgcacc tactgtcctc 420
atcttcccac cagctgctga tcaggtggca actggaacag tcaccatcgt gtgtgtggcg 480
aataaatact ttcccgatgt caccgtcacc tgggaggtgg atggcaccac ccaaacaact 540
ggcatcgaga acagtaaaac accgcagaat tctgcagatt gtacctacaa cctcagcagc 600
actctgacac tgaccagcac acagtacaac agccacaaag agtacacctg caaggtgacc 660
cagggcacga cctcagtcgt ccagagcttc aataggggtg actgttag 708

<210> SEQ ID NO 87
<211> LENGTH: 1383
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
atggagactg ggctgcgctg gcttctcctg gtcgctgtgc tcaaaggtgt ccagtgtcag 60
gagcagttgg tggagtccgg gggaggcctg gtccagcctg agggatccct gacactcacc 120
tgcaaagcct ctggattcga cttcagtagc aatgcaatgt gctgggtccg ccaggctcca 180
gggaaggggc tggagtggat cgcatgcatt tataatggtg atggcagcac atactacgcg 240
agctgggtga atggccgatt caccatctcc aagacctcgt cgaccacggt gactctgcaa 300
atgaccagtc tgacagccgc ggacacggcc acctatttct gtgcgagagg tctctctaat 360
tggaataggg ataacttatg gggccctggc accctggtca ccgtctcctc agggcaacct 420
aaggctccat cagtcttccc actggccccc tgctgcgggg acacacccag ctccacggtg 480
accctgggct gcctggtcaa aggctacctc ccggagccag tgaccgtgac ctggaactcg 540
ggcaccctca ccaatggggt acgcaccttc ccgtccgtcc ggcagtcctc aggcctctac 600
tcgctgagca gcgtggtgag cgtgacctca agcagccagc ccgtcacctg caacgtggcc 660
cacccagcca ccaacaccaa agtggacaag accgttgcgc cctcgacatg cagcaagccc 720
atgtgcccac cccctgaact cccgggggga ccgtctgtct tcatcttccc cccaaaaccc 780
aaggacaccc tcatgatctc acgcaccccc gaggtcacat gcgtggtggt ggacgtgagc 840
caggatgacc ccgaggtgca gttcacatgg tacataaaca acgagcaggt gcgcaccgcc 900
cggccgccgc tacgggagca gcagttcaac agcacgatcc gcgtggtcag caccctcccc 960
atcgcgcacc aggactggct gaggggcaag gagttcaagt gcaaagtcca caacaaggca 1020
ctcccggccc ccatcgagaa aaccatctcc aaagccagag ggcagcccct ggagccgaag 1080
gtctacacca tgggccctcc ccgggaggag ctgagcagca ggtcggtcag cctgacctgc 1140
atgatcaacg gcttctaccc ttccgacatc tcggtggagt gggagaagaa cgggaaggca 1200
gaggacaact acaagaccac gccgaccgtg ctggacagcg acggctccta cttcctctac 1260
agcaagctct cagtgcccac gagtgagtgg cagcggggcg acgtcttcac ctgctccgtg 1320
atgcacgagg ccttgcacaa ccactacacg cagaagtcca tctcccgctc tccgggtaaa 1380
tag 1383

<210> SEQ ID NO 88
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
atggacacga gggcccccac tcagctgctg gggctcctgc tgctctggct cccaggtgcc 60
acatttgccc aagtgctgac ccagactcca tcctccgtgt ctgcagctgt gggaggcaca 120
gccaccatca actgccaggc cagtcagagt ctttatagtc ccaagaattt agcctggtat 180
cagcagacac cagggcagcc tcccaagctc ctgatctatt ctgcatcgaa actggcatct 240
ggggtcccat cgcggttcaa aggcagtgga tctgggacac agttcactct caccatcagc 300
ggcgtgcagt gtgacgatgc tgcaatttac tactgtcaag gcgaatttag ttgtactact 360
gctgcttgtt ttgcttttgg cggagggacc gaggtggtgg tcaaaggtga tccagttgca 420
cctactgtcc tcatcttccc accagctgct gatcaggtgg caactggaac agtcaccatc 480
gtgtgtgtgg cgaataaata ctttcccgat gtcaccgtca cctgggaggt ggatggcacc 540
acccaaacaa ctggcatcga gaacagtaaa acaccgcaga attctgcaga ttgtacctac 600
aacctcagca gcactctgac actgaccagc acacagtaca acagccacaa agagtacacc 660
tgcaaggtga cccagggcac gacctcagtc gtccagagct tcaatagggg tgactgttag 720

<210> SEQ ID NO 89
<211> LENGTH: 1386
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89
atggagactg ggctgcgctg gcttctcctg gtcgctgtgc tcaaaggtgt ccagtgtcag 60
tctttggagg agtccggggg aggcctggtc cagcctgagg gatccctgac actcgcctgc 120
acagcttcgg gattctcctt cagtagctac tactacatct gctgggtccg ccaggctcca 180
gggacggggc tggagtggat cggatgcatt aatactggta gtgatgacac tcactacgcg 240
agctggttga aaggccgatt caccttctcc aaggcctcgt cgaccacgtt gactctgcaa 300
atgaccagtc tgacagccgc ggacacggcc acctatttct gtgcgagatc atctggtagt 360
agtgatgatg cttatgatct ctggggccca ggcaccctgg tcactgtctc ctcagggcaa 420
cctaaggctc catcagtctt cccactggcc ccctgctgcg gggacacacc cagctccacg 480
gtgaccctgg gctgcctggt caaaggctac ctcccggagc cagtgaccgt gacctggaac 540
tcgggcaccc tcaccaatgg ggtacgcacc ttcccgtccg tccggcagtc ctcaggcctc 600
tactcgctga gcagcgtggt gagcgtgacc tcaagcagcc agcccgtcac ctgcaacgtg 660
gcccacccag ccaccaacac caaagtggac aagaccgttg cgccctcgac atgcagcaag 720
cccatgtgcc cacccccctga actcccgggg ggaccgtctg tcttcatctt ccccccaaaa 780
cccaaggaca ccctcatgat ctcacgcacc cccgaggtca catgcgtggt ggtggacgtg 840
agccaggatg accccgaggt gcagttcaca tggtacataa acaacgagca ggtgcgcacc 900
gcccggccgc cgctacggga gcagcagttc aacagcacga tccgcgtggt cagcaccctc 960
cccatcgcgc accaggactg gctgaggggc aaggagttca agtgcaaagt ccacaacaag 1020
gcactcccgg cccccatcga gaaaaccatc tccaaagcca gagggcagcc cctggagccg 1080
aaggtctaca ccatgggccc tccccgggag gagctgagca gcaggtcggt cagcctgacc 1140
tgcatgatca acggcttcta cccttccgac atctcggtgg agtgggagaa gaacgggaag 1200
gcagaggaca actacaagac cacgccgacc gtgctggaca gcgacggctc ctacttcctc 1260
tacagcaagc tctcagtgcc cacgagtgag tggcagcggg gcgacgtctt cacctgctcc 1320
gtgatgcacg aggccttgca caaccactac acgcagaagt ccatctcccg ctctccgggt 1380
aaatag 1386

<210> SEQ ID NO 90
<211> LENGTH: 708
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 90
atggacacga gggcccccac tcagctgctg gggctcctgc tgctctggct cccaggtgcc 60
agatgtgatg ttgtgatgac ccagactcca gcctccgtgt ctgaacctgt gggaggcgca 120
gtcaccatca agtgccaggc cagtcagagc attggtagta atttagcctg gtatcagcac 180
aaaccagggc agcctcccaa gctcctgatc tattttgcat ccagcctggc atctggggtc 240
tcgtcgcggt tcaagggcgg tagatctggg acacagttca ctctcaccat cagcgacctg 300
gagtgtgccg atgctgccac ttactactgt cactgtactt attatcctct tagttatgtt 360
actttcggcg gagggaccga ggtggtggtc aaaggtgatc cagttgcacc tactgtcctc 420
atcttcccac cagctgctga tcaggtggca actggaacag tcaccatcgt gtgtgtggcg 480
aataaatact ttcccgatgt caccgtcacc tgggaggtgg atggcaccac ccaaacaact 540
ggcatcgaga acagtaaaac accgcagaat tctgcagatt gtacctacaa cctcagcagc 600
actctgacac tgaccagcac acagtacaac agccacaaag agtacacctg caaggtgacc 660
cagggcacga cctcagtcgt ccagagcttc aataggggtg actgttag 708

<210> SEQ ID NO 91
<211> LENGTH: 1395
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 91
atggagactg ggctgcgctg gcttctcctg gtcgctgtgc tcaaaggtgt ccagtgtcag 60
tcgttggagg agtccggggg agacctggtc aagcctggga catccctgac actctcctgc 120
acagcctctg gattctcctt cggtagctat tattatatgt gctgggtccg ccaggctcca 180
gggaaggggc tggagtggat cgcatgcatt gatgttggta gtagtggtga cacatactac 240
gcgagctggg tgaatggccg attcaccatc tccaaaacct cgtcgaccac ggtgactctg 300
caaatgacca gtctgacagc cgcggacacg gccacctatt tctgtgcgag agatgatact 360
gctgctggtg gttttggtaa tttggaattg tggggcccag gcaccctggt caccgtctcc 420
tcagggcaac ctaaggctcc atcagtcttc ccactggccc cctgctgcgg ggacacaccc 480
agctccacgg tgaccctggg ctgcctggtc aaaggctacc tcccggagcc agtgaccgtg 540
acctggaact cgggcaccct caccaatggg gtacgcacct tcccgtccgt ccggcagtcc 600
tcaggcctct actcgctgag cagcgtggtg agcgtgacct caagcagcca gcccgtcacc 660
tgcaacgtgg cccacccagc caccaacacc aaagtggaca agaccgttgc gccctcgaca 720
tgcagcaagc ccatgtgccc accccctgaa ctcccggggg gaccgtctgt cttcatcttc 780
cccccaaaac ccaaggacac cctcatgatc tcacgcaccc ccgaggtcac atgcgtggtg 840
gtggacgtga gccaggatga ccccgaggtg cagttcacat ggtacataaa caacgagcag 900
gtgcgcaccg cccggccgcc gctacgggag cagcagttca acagcacgat ccgcgtggtc 960
agcaccctcc ccatcgcgca ccaggactgg ctgaggggca aggagttcaa gtgcaaagtc 1020
cacaacaagg cactcccggc ccccatcgag aaaaccatct ccaaagccag agggcagccc 1080
ctggagccga aggtctacac catgggccct ccccgggagg agctgagcag caggtcggtc 1140
agcctgacct gcatgatcaa cggcttctac ccttccgaca tctcggtgga gtgggagaag 1200
aacgggaagg cagaggacaa ctacaagacc acgccgaccg tgctggacag cgacggctcc 1260
tacttcctct acagcaagct ctcagtgccc acgagtgagt ggcagcgggg cgacgtcttc 1320
acctgctccg tgatgcacga ggccttgcac aaccactaca cgcagaagtc catctcccgc 1380
tctccgggta aatag 1395

<210> SEQ ID NO 92
<211> LENGTH: 717
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 92
atggacacga gggcccccac tcagctgctg gggctcctgc tgctctggct cccaggtgcc 60
agatgtgcat tcgaattgac ccagactcca tcctccgtgt ctgaacctgt gggaggcaca 120
gtcaccatca agtgccaggc cagtcagagc atttacagct acttttcctg gtatcagcag 180
aaaccagggc agcctcccaa gcgcctgatt taccaggcat ccactctggc ttctggggtc 240
ccatcgcggt tcaaaggcag tggatctggg acagatttca ctctcaccat cagcgacctg 300
gagtgtgccg atgctgccac ttactactgt caaaacaatt atggtagggg tagtggtagt 360
tatttttttg gtttcggcgg agggaccgag gtggtggtca aaggtgatcc agttgcacct 420
actgtcctca tcttcccacc agctgctgat caggtggcaa ctggaacagt caccatcgtg 480
tgtgtggcga ataaatactt tcccgatgtc accgtcacct gggaggtgga tggcaccacc 540
caaacaactg gcatcgagaa cagtaaaaca ccgcagaatt ctgcagattg tacctacaac 600
ctcagcagca ctctgacact gaccagcaca cagtacaaca gccacaaaga gtacacctgc 660
aaggtgaccc agggcacgac ctcagtcgtc cagagcttca ataggggtga ctgttag 717

<210> SEQ ID NO 93
<211> LENGTH: 1371
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93
atggagactg ggctgcgctg gcttctcctg gtcgctgtgc tcaaaggtgt ccagtgtcag 60
tcgttggagg agtccggggg agacctggtc aagcctgggg catccctgac actcacctgc 120
aaagcctctg gaatcgactt cagtagcggc tacggcatgt ggtgggtccg ccaggctcca 180
gggaagggac tggagtatat cggatacatt gatactggta gtggtagcac ttactacgcg 240
aactgggcga aaggccgatt caccatctcc aaaacctcgt cgaccatggt gactctgcaa 300
atgaccagtc tgacagtcgc ggacacggcc acctatttct gtgcgaaagg gggcgccata 360
gacctctggg gcccagggac cctcgtcacc gtctcttcag ggcaacctaa ggctccatca 420
gtcttcccac tggcccctg ctgcggggac acacccagct ccacggtgac cctgggctgc 480
ctggtcaaag gctacctccc ggagccagtg accgtgacct ggaactcggg caccctcacc 540
aatggggtac gcaccttccc gtccgtccgg cagtcctcag gcctctactc gctgagcagc 600
gtggtgagcg tgacctcaag cagccagccc gtcacctgca acgtggccca cccagccacc 660
aacaccaaag tggacaagac cgttgcgccc tcgacatgca gcaagcccat gtgcccaccc 720
cctgaactcc cgggggggacc gtctgtcttc atcttccccc caaaacccaa ggacaccctc 780
atgatctcac gcacccccga ggtcacatgc gtggtggtgg acgtgagcca ggatgacccc 840
gaggtgcagt tcacatggta cataaacaac gagcaggtgc gcaccgcccg gccgccgcta 900
cgggagcagc agttcaacag cacgatccgc gtggtcagca ccctccccat cgcgcaccag 960
gactggctga ggggcaagga gttcaagtgc aaagtccaca acaaggcact cccggccccc 1020
atcgagaaaa ccatctccaa agccagaggg cagcccctgg agccgaaggt ctacaccatg 1080
ggccctcccc gggaggagct gagcagcagg tcggtcagcc tgacctgcat gatcaacggc 1140
ttctaccctt ccgacatctc ggtggagtgg gagaagaacg ggaaggcaga ggacaactac 1200
aagaccacgc cgaccgtgct ggacagcgac ggctcctact tcctctacag caagctctca 1260
gtgcccacga gtgagtggca gcggggcgac gtcttcacct gctccgtgat gcacgaggcc 1320
ttgcacaacc actacacgca gaagtccatc tcccgctctc cgggtaaata g 1371

<210> SEQ ID NO 94
<211> LENGTH: 720
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 94
atggacacga gggcccccac tcagctgctg ggactcctac tgctctggct cccaggtgcc 60
agatgtgctg acattgtgat gacccagact ccagcctccg tggaggcagc tgtgggaggc 120
acagtcacca tcaagtgcca ggccagtcag agcattagta gttacttagc ctggtatcag 180
cagaaaccag ggcagcgtcc caagctcctg atctacaggg catccactct ggcatctggg 240
gtcccatcgc ggttcaaagg cagtggatct gggacagact acactctcac catcagcgac 300
ctggagtgtg ccgatgctgc cacttattat tgtcatacct attatcttag tagtagtatc 360
agttatggta atactttcgg cggagggacc gaggtggtgg tcaaaggtga tccagttgca 420
cctactgtcc tcatcttccc accagctgct gatcaggtgg caactggaac agtcaccatc 480
gtgtgtgtgg cgaataaata ctttcccgat gtcaccgtca cctgggaggt ggatggcacc 540
acccaaacaa ctggcatcga gaacagtaaa acaccgcaga attctgcaga ttgtacctac 600
aacctcagca gcactctgac actgaccagc acacagtaca acagccacaa agagtacacc 660
tgcaaggtga cccagggcac gacctcagtc gtccagagct tcaatagggg tgactgttag 720

<210> SEQ ID NO 95
<211> LENGTH: 1398
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 95
atggagactg ggctgcgctg gcttctcctg gtcgctgtgc tcaaaggtgt ccagtgtcag 60
gagcagctgg aggagtccgg gggagacctg gtcaagcctg agggatccct gacactcacc 120
tgcaaagcct ctggattctc cttcagtagc atctactgga tttgctgggt ccgccaggct 180
ccagggaagg ggctggagtg gatcgcatgc actactgttg tcaaaagtgg tagaacttac 240
tacgcgaact gggcgaaagg ccgattcacc atctccaaaa cctcgtcgac cacggtgact 300
ctgcaaatga ccagtctgac agccgcggac acggccacct atttctgtgc gagagaattt 360
gttgatggtg gtggtagtag tggtagggac ttgtggggcc caggcaccct ggtcaccgtc 420
tcctcagggc aacctaaggc tccatcagtc ttcccactgg ccccctgctg cggggacaca 480
cccagctcca cggtgaccct gggctgcctg gtcaaaggct acctcccgga gccagtgacc 540
gtgacctgga actcgggcac cctcaccaat ggggtacgca ccttcccgtc cgtccggcag 600
tcctcaggcc tctactcgct gagcagcgtg gtgagcgtga cctcaagcag ccagcccgtc 660
acctgcaacg tggcccaccc agccaccaac accaaagtgg acaagaccgt tgcgccctcg 720
acatgcagca agcccatgtg cccaccccct gaactcccgg ggggaccgtc tgtcttcatc 780
ttccccccaa aacccaagga caccctcatg atctcacgca cccccgaggt cacatgcgtg 840
gtggtggacg tgagccagga tgaccccgag gtgcagttca catggtacat aaacaacgag 900
caggtgcgca ccgcccggcc gccgctacgg gagcagcagt tcaacagcac gatccgcgtg 960
gtcagcaccc tccccatcgc gcaccaggac tggctgaggg gcaaggagtt caagtgcaaa 1020
gtccacaaca aggcactccc ggcccccatc gagaaaacca tctccaaagc cagagggcag 1080
cccctggagc cgaaggtcta caccatgggc cctccccggg aggagctgag cagcaggtcg 1140
gtcagcctga cctgcatgat caacggcttc taccettccg acatctcggt ggagtgggag 1200
aagaacggga aggcagagga caactacaag accacgccga ccgtgctgga cagcgacggc 1260
tcctacttcc tctacagcaa gctctcagtg cccacgagtg agtggcagcg gggcgacgtc 1320
ttcacctgct ccgtgatgca cgaggccttg cacaaccact acacgcagaa gtccatctcc 1380
cgctctccgg gtaaatag 1398

<210> SEQ ID NO 96
<211> LENGTH: 711
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 96
atggacacga gggcccccac tcagctgctg gggctcctgc tgctctggct cccaggtgcc 60
agatgtgcct atgatatgac ccagactcca gcctccgtgg aggcagctgt gggaggcaca 120
gtcaccatca agtgccaggc cagtcagagc attagtaggg acttatcctg gtatcagcag 180
aaacctggac agcctcccaa gcgcctaatc tacaaggcat ccactctggc atctggggtc 240
ccatcgcggt tcaaaggcag tggatctggg acagatttca ctctcaccat cagcgacctg 300
gagtgtgccg atgctgccac ttactactgt caacagggtt atagtagtat tgatgttgat 360
aatgatttcg gcggagggac cgaggtggtg gtcaaaggtg atccagttgc acctactgtc 420
ctcatcttcc caccagctgc tgatcaggtg gcaactggaa cagtcaccat cgtgtgtgtg 480
gcgaataaat actttcccga tgtcaccgtc acctgggagg tggatggcac cacccaaaca 540
actggcatcg agaacagtaa aacaccgcag aattctgcag attgtaccta caacctcagc 600
agcactctga cactgaccag cacacagtac aacagccaca aagagtacac ctgcaaggtg 660
acccagggca cgacctcagt cgtccagagc ttcaataggg gtgactgtta g 711

<210> SEQ ID NO 97
<211> LENGTH: 1404
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 97
atggagactg ggctgcgctg gcttctcctg gtcgctgtgc tcaaaggtgt ccagtgtcag 60
gagcagctgg aggagtccgg gggaggcctg gtcaagcctg agggatccct gacactcacc 120
tgcaaagcct ctggattcga cctcagtagc ggctatgaca tgtgctgggt ccgccaggct 180
ccagggaagg ggctggagtg gatcgcatgc atttatgctg attatagtgg tagcacatac 240
tacgcgagct gggtgaatgg ccgattcacc atctccagca gcaccagcct aaacacggtg 300
gatctgaaaa tgaccagtct gacagccgcg gacacggcca cctatttctg tgccagaggg 360
gctactggta atggtggtta tggatactac tttaacttgt ggggcccagg caccctggtc 420
accgtctcct cagggcaacc taaggctcca tcagtcttcc cactggcccc ctgctgcggg 480
gacacaccca gctccacggt gaccctgggc tgcctggtca aaggctacct cccggagcca 540
gtgaccgtga cctggaactc gggcaccctc accaatgggg tacgcacctt cccgtccgtc 600
cggcagtcct caggcctcta ctcgctgagc agcgtggtga gcgtgacctc aagcagccag 660
cccgtcacct gcaacgtggc ccacccagcc accaacacca aagtggacaa gaccgttgcg 720
ccctcgacat gcagcaagcc catgtgccca ccccctgaac tcccgggggg accgtctgtc 780
ttcatcttcc ccccaaaacc caaggacacc ctcatgatct cacgcacccc cgaggtcaca 840
tgcgtggtgg tggacgtgag ccaggatgac cccgaggtgc agttcacatg gtacataaac 900
aacgagcagg tgcgcaccgc ccggccgccg ctacgggagc agcagttcaa cagcacgatc 960
cgcgtggtca gcaccctccc catcgcgcac caggactggc tgaggggcaa ggagttcaag 1020
tgcaaagtcc acaacaaggc actcccggcc cccatcgaga aaaccatctc caaagccaga 1080
gggcagcccc tggagccgaa ggtctacacc atgggccctc cccgggagga gctgagcagc 1140
aggtcggtca gcctgacctg catgatcaac ggcttctacc cttccgacat ctcggtggag 1200
tgggagaaga acgggaaggc agaggacaac tacaagacca cgccgaccgt gctggacagc 1260
gacggctcct acttcctcta cagcaagctc tcagtgccca cgagtgagtg gcagcggggc 1320
gacgtcttca cctgctccgt gatgcacgag gccttgcaca accactacac gcagaagtcc 1380
atctcccgct ctccgggtaa atag 1404

<210> SEQ ID NO 98
<211> LENGTH: 717
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98
atggacacga gggcccccac tcagctgctg gggctcctac tgctctggct cccaggtgcc 60
agatgtgctg acattgtgat gacccagact ccagcctccg tgtctgaacc tgtgggaggc 120
acagtcacca tcaagtgtca ggccagtcag aacattaata gcggcttagc ctggtatcag 180
cagaaaccag ggcagcctcc caagctcctg atctacaagg catccactct ggcatctggg 240
gtctcatcgc ggttcaaagg cagtggatct gggacagaat tcactctcac catcagcgac 300
ctggagtgtg ccgatgctgc cacttactac tgtcaaacct attattatag tagtagtagt 360
agtgataatg ctttcggcgg agggaccgag gtggtggtca aaggtgatcc agttgcacct 420
actgtcctca tcttcccacc agctgctgat caggtggcaa ctggaacagt caccatcgtg 480
tgtgtggcga ataaatactt tcccgatgtc accgtcacct gggaggtgga tggcaccacc 540
caaacaactg gcatcgagaa cagtaaaaca ccgcagaatt ctgcagattg tacctacaac 600
ctcagcagca ctctgacact gaccagcaca cagtacaaca gccacaaaga gtacacctgc 660
aaggtgaccc agggcacgac ctcagtcgtc cagagcttca ataggggtga ctgttag 717

<210> SEQ ID NO 99
<211> LENGTH: 1389
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 99
atggagactg ggctgcgctg gcttctcctg gtcgctgtgc tcaaaggtgt ccagtgtcag 60
tcgttggagg agtccggggg agacctggtc aagcctgggg catccctgac actcacctgc 120
acagcttctg gattctcctt cagtagcagt tattggatat gctgggtccg ccaggctcca 180
gggaaggggc tggagtggat cgcatgtatt tatggtggta gtagtggtaa cattgcctac 240
gcgagctggg cgaaaggccg attcaccatc tccaaaacct cgtcgaccac ggtgactcta 300
caaatgacca gtctgacagc cgcggacacg gccacctatt tctgtgcgag agatattcct 360
agtgatgctt tcaccttaga cttgtggggc ccaggcaccc tggtcaccgt ctcctcaggg 420
caacctaagg ctccatcagt cttcccactg gccccctgct gcggggacac acccagctcc 480
acggtgaccc tgggctgcct ggtcaaaggc tacctcccgg agccagtgac cgtgacctgg 540
aactcgggca ccctcaccaa tggggtacgc accttcccgt ccgtccggca gtcctcaggc 600
ctctactcgc tgagcagcgt ggtgagcgtg acctcaagca gccagcccgt cacctgcaac 660
gtggcccacc cagccaccaa caccaaagtg gacaagaccg ttgcgccctc gacatgcagc 720
aagcccatgt gcccaccccc tgaactcccg gggggaccgt ctgtcttcat cttcccccca 780
aaacccaagg acaccctcat gatctcacgc acccccgagg tcacatgcgt ggtggtggac 840
gtgagccagg atgaccccga ggtgcagttc acatggtaca taaacaacga gcaggtgcgc 900
accgcccggc cgccgctacg ggagcagcag ttcaacagca cgatccgcgt ggtcagcacc 960
ctccccatcg cgcaccagga ctggctgagg ggcaaggagt tcaagtgcaa agtccacaac 1020
aaggcactcc cggcccccat cgagaaaacc atctccaaag ccagagggca gcccctggag 1080
ccgaaggtct acaccatggg ccctccccgg gaggagctga gcagcaggtc ggtcagcctg 1140
acctgcatga tcaacggctt ctacccttcc gacatctcgg tggagtggga gaagaacggg 1200
aaggcagagg acaactacaa gaccacgccg accgtgctgg acagcgacgg ctcctacttc 1260
ctctacagca agctctcagt gcccacgagt gagtggcagc ggggcgacgt cttcacctgc 1320
tccgtgatgc acgaggcctt gcacaaccac tacacgcaga agtccatctc ccgctctccg 1380
ggtaaatag 1389

<210> SEQ ID NO 100
<211> LENGTH: 720
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 100
atggacacga gggcccccac tcagctgctg gggctcctgc tgctctggct cccaggtgcc 60
acatttgccc aagtgctgac ccagactcca tcctccgtgt ctgcagctgt gggaagcaca 120
gtcaccatca attgccaggc cagtcagagt gtttataaag acaacaattt agcctggtat 180
cagcagaaac cagggcagcc tcccaagctc ctgatctaca aggcttccac tctggcatct 240
ggggtcccat cgcggttcaa aggcagtgga tctgggacac agttcactct caccatcagc 300
ggcgtgcagt gtgaagatgc tgccacttac tactgtcaag gcgaattcag ttgtggtagt 360
gctgattgta ttgctttcgg cggagggacc gaggtggtgg tcaaaggtga tccagttgca 420
cctactgtcc tcatcttccc accagctgct gatcaggtgg caactggaac agtcaccatc 480
gtgtgtgtgg cgaataaata ctttcccgat gtcaccgtca cctgggaggt ggatggcacc 540
acccaaacaa ctggcatcga gaacagtaaa acaccgcaga attctgcaga ttgtacctac 600
aacctcagca gcactctgac actgaccagc acacagtaca acagccacaa agagtacacc 660
tgcaaggtga cccagggcac gacctcagtc gtccagagct tcaatagggg tgactgttag 720

<210> SEQ ID NO 101
<211> LENGTH: 1371
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 101
atggagactg ggctgcgctg gcttctcctg gtcgctgtgc tcaaaggtgt ccagtgtcag 60
tcgttggagg agtccggggg agacctggtc aagcctgggg catccctgac actcacctgc 120
aaaggctctg gaatcgactt cagtagcggc tacggcatgt ggtgggtccg ccaggctcca 180
gggaagggac tggagtatat cggatacatt gatactggtt atggtagcac ttactacgcg 240
agctgggcga aaggccgatt caccatctcc aagacctcgt cgaccacggt gactctgcaa 300
atgaccagtc tgacagtcgc ggacacggcc acctatttct gtgcgaaagg gggcgccata 360
gacctctggg gcccagggac cctcgtcacc gtctcttcag ggcaacctaa ggctccatca 420
gtcttcccac tggccccctg ctgcggggac acacccagct ccacggtgac cctgggctgc 480
ctggtcaaag gctacctccc ggagccagtg accgtgacct ggaactcggg caccctcacc 540
aatggggtac gcaccttccc gtccgtccgg cagtcctcag gcctctactc gctgagcagc 600
gtggtgagcg tgacctcaag cagccagccc gtcacctgca acgtggccca cccagccacc 660
aacaccaaag tggacaagac cgttgcgccc tcgacatgca gcaagcccat gtgcccaccc 720
cctgaactcc cggggggacc gtctgtcttc atcttccccc caaaacccaa ggacaccctc 780
atgatctcac gcacccccga ggtcacatgc gtggtggtgg acgtgagcca ggatgacccc 840
gaggtgcagt tcacatggta cataaacaac gagcaggtgc gcaccgcccg gccgccgcta 900
cgggagcagc agttcaacag cacgatccgc gtggtcagca ccctccccat cgcgcaccag 960
gactggctga ggggcaagga gttcaagtgc aaagtccaca acaaggcact cccggccccc 1020
atcgagaaaa ccatctccaa agccagaggg cagcccctgg agccgaaggt ctacaccatg 1080
ggccctcccc gggaggagct gagcagcagg tcggtcagcc tgacctgcat gatcaacggc 1140
ttctaccctt ccgacatctc ggtggagtgg gagaagaacg ggaaggcaga ggacaactac 1200
aagaccacgc cgaccgtgct ggacagcgac ggctcctact tcctctacag caagctctca 1260
gtgcccacga gtgagtggca gcggggcgac gtcttcacct gctccgtgat gcacgaggcc 1320
ttgcacaacc actacacgca gaagtccatc tcccgctctc cgggtaaata g 1371

<210> SEQ ID NO 102
<211> LENGTH: 717
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 102
atggacacga gggcccccac tcagctgctg gggctcctgc tgctctggct cccaggtgcc 60
acatttgcag ccgtgctgac ccagactccg gcttccacgt ctgcagctgt gggaggcaca 120
gtcaccatca attgtcagtc cagtcagagc gtgtatcgta gcaactggtt agcctggtat 180
cagcagaaac cagggcagcc tcccaagctc ctgatctatg atgtatttaa tttggcatct 240
ggggtcccat cccggttcaa gggcagtgga tctgggacac agttcactct caccatcagc 300
ggcgtgcagt gtgccgatgc tgccacttac tactgtcaag gcagttatta tagtggtaat 360
tggtacagtg ctttcggcgg agggaccgag gtggtggtca aaggtgatcc agttgcacct 420
actgtcctca tcttcccacc agctgctgat caggtggcaa ctggaacagt caccatcgtg 480
tgtgtggcga ataaatactt tcccgatgtc accgtcacct gggaggtgga tggcaccacc 540
caaacaactg gcatcgagaa cagtaaaaca ccgcagaatt ctgcagattg tacctacaac 600
ctcagcagca ctctgacact gaccagcaca cagtacaaca gccacaaaga gtacacctgc 660
aaggtgaccc agggcacgac ctcagtcgtc cagagcttca ataggggtga ctgttag 717

<210> SEQ ID NO 103
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 103

Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Pro Asp Tyr
            20                  25                  30

Asn Met Asp Trp Val Lys Gln Ser His Gly Lys Ser Leu Glu Trp Ile
        35                  40                  45

Gly Tyr Ile Asn Pro Asp Asn Gly Gly Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Leu Asp Ser Ser Gly Tyr Gly Tyr Tyr Ala Met Asp Tyr Trp

```
            100                 105                 110

Gly Gln Gly Thr Ser Val Thr Val Ser Ser
        115                 120


<210> SEQ ID NO 104
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met His Trp Tyr Gln Gln Lys Pro Gly Gln Pro Pro
        35                  40                  45

Lys Leu Leu Ile Tyr Arg Ala Ser Asn Leu Asp Ser Glu Ile Pro Ala
    50                  55                  60

Arg Phe Ser Gly Ser Gly Ser Arg Thr Asp Phe Thr Leu Thr Ile Asp
65                  70                  75                  80

Pro Val Glu Thr Asp Asp Val Ala Thr Tyr Tyr Cys Gln Gln Ser Tyr
                85                  90                  95

Lys Asp Pro Arg Thr Phe Gly Gly Gly Thr Lys Leu Glu Ile Lys
            100                 105                 110


<210> SEQ ID NO 105
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Lys Val Met Leu Val Glu Ser Gly Gly Ala Leu Val Lys Pro Gly Gly
1               5                   10                  15

Ser Leu Lys Leu Ser Cys Val Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Tyr Tyr Thr Tyr Tyr Pro Asp Ser Val
    50                  55                  60

Lys Gly Arg Phe Thr Ile Ser Arg Asp Asn Ala Arg Asn Thr Leu Phe
65                  70                  75                  80

Leu Gln Met Ser Ser Leu Arg Ser Glu Asp Thr Ala Met Phe Tyr Cys
                85                  90                  95

Ala Arg Glu Asp Asp Tyr Gly Arg Tyr Ser Tyr Thr Met Asp Tyr Trp
            100                 105                 110

Gly Gln Gly Thr Ser Val Thr Val Ser Ser
        115                 120


<210> SEQ ID NO 106
<211> LENGTH: 112
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 106

Asp Val Val Met Thr Gln Thr Pro Leu Ser Leu Pro Val Ser Leu Gly
1 5 10 15

Asp Gln Val Ser Ile Ser Cys Arg Cys Ser Gln Ser Leu Val His Ser
20 25 30

Asn Gly Asn Thr Tyr Leu His Trp Tyr Leu Gln Lys Pro Gly Gln Ser
35 40 45

Pro Gln Leu Leu Ile Tyr Lys Ile Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Phe Cys Ser Gln Ser
85 90 95

Thr His Val Pro Tyr Thr Phe Gly Gly Gly Thr Glu Leu Glu Ile Lys
100 105 110

<210> SEQ ID NO 107
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 107

Glu Val Gln Leu Gln Gln Ser Gly Pro Glu Leu Val Lys Pro Gly Ala
1 5 10 15

Ser Val Arg Ile Ser Cys Lys Ala Ser Gly Tyr Thr Phe Thr Asp Tyr
20 25 30

Tyr Ile His Trp Val Lys Gln Lys Pro Gly Gln Gly Leu Glu Cys Ile
35 40 45

Gly Glu Ile Tyr Pro Gly Thr Asp Asn Thr Tyr Tyr Ser Lys Lys Phe
50 55 60

Arg Gly Lys Ala Thr Leu Thr Ala Asp Lys Ser Ser Asp Thr Ala Tyr
65 70 75 80

Met Gln Leu Ser Ser Leu Thr Ser Glu Asp Ser Ala Val Tyr Phe Cys
85 90 95

Ala Arg Gly Asp Tyr Tyr Arg Gly Tyr Phe Asp Val Trp Gly Ala Gly
100 105 110

Thr Thr Val Thr Val Ser Ser
115

<210> SEQ ID NO 108
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 108

Asp Val Val Met Thr Gln Thr Ser Leu Thr Leu Ser Val Thr Ile Gly
1 5 10 15

Gln Pro Ala Ser Ile Ser Cys Lys Ser Ser Gln Ser Leu Leu His Ser
20 25 30

Asn Gly Lys Thr Tyr Leu Asn Trp Leu Leu Gln Arg Pro Gly Gln Ser
35 40 45

Pro Lys Phe Leu Ile Tyr Leu Val Ser Lys Leu Glu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ser
                85                  90                  95

Thr His Phe Pro Trp Thr Phe Gly Gly Gly Thr Lys Leu Glu Ile Lys
            100                 105                 110

<210> SEQ ID NO 109
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

Glu Val Gln Leu Gln Gln Ser Gly Pro Glu Leu Val Lys Pro Gly Ala
1               5                   10                  15

Ser Val Lys Lys Ser Cys Lys Ala Ser Gly Tyr Thr Phe Thr Asp Tyr
            20                  25                  30

Tyr Met His Trp Val Lys Gln Lys Pro Gly Gln Gly Leu Glu Trp Ile
        35                  40                  45

Gly Lys Ile Tyr Pro Gly Ser Gly Asn Thr His Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Thr Asn Tyr Tyr Gly Tyr Arg Ala Met Asn Tyr Trp Gly Gln Gly
            100                 105                 110

Ser Ser Val Thr Val Ser Ser
        115

<210> SEQ ID NO 110
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

Asp Ile His Leu Thr Gln Ser Pro Ser Ser Leu Ser Ala Ser Leu Gly
1               5                   10                  15

Glu Arg Ile Ser Leu Thr Cys Arg Ala Ser Gln Asp Ile Tyr Ile Ser
            20                  25                  30

Leu Asn Trp Phe Gln Gln Lys Pro Asp Gly Thr Ile Lys Leu Leu Ile
        35                  40                  45

Tyr Gly Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Ser Pro Tyr
                85                  90                  95

Thr Phe Gly Gly Gly Thr Lys Leu Glu Ile Lys
            100                 105

<210> SEQ ID NO 111
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met His Trp Val Lys Gln Lys Pro Gly Gln Gly Leu Glu Trp Ile
        35                  40                  45

Gly Glu Ile Tyr Pro Gly Ser Gly Asn Pro Tyr Tyr Asn Glu Lys Phe
    50                  55                  60

Lys Gly Lys Ala Thr Leu Thr Ala Asp Lys Ser Ser Ser Ser Ala Tyr
65                  70                  75                  80

Met Gln Leu Ser Ser Leu Thr Ser Glu Asp Ser Ala Val Tyr Phe Cys
                85                  90                  95

Ala Arg Thr Ser Tyr Gly Arg Val Gly Thr Gly Phe Ala Tyr Trp Gly
            100                 105                 110

Gln Gly Thr Leu Val Thr Val Ser Ala
        115                 120
```

<210> SEQ ID NO 112
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

```
Asn Phe Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Thr Glu Asp Leu Gly Ile Tyr Phe Cys Ser Gln Ser
                85                  90                  95

Ser His Val Pro Thr Phe Gly Ala Gly Thr Lys Leu Glu Leu Lys
            100                 105                 110
```

<210> SEQ ID NO 113
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Tyr Ile Asn Pro Asn Asn Gly Tyr Thr Glu Tyr Asn Gln Arg Phe
    50                  55                  60

Lys Asp Lys Ala Thr Leu Thr Ala Asp Arg Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Asp Ile Ile Thr Thr Asp Tyr Trp Gly Gln Gly Thr Thr
            100                 105                 110

Leu Thr Val Ser Ser
        115

<210> SEQ ID NO 114
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val Tyr Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 115
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Gln Gln Arg Pro Gly Gln Gly Leu Glu Trp Ile
        35                  40                  45

Gly Val Ile Asp Pro Ser Asp Ser Tyr Thr Asn Tyr Asn Gln Lys Phe
    50                  55                  60

```
Lys Gly Lys Ala Thr Leu Thr Val Asp Thr Ser Ser Ser Ser Ala Tyr
65                  70                  75                  80

Met Gln Leu Ser Ser Leu Thr Ser Glu Asp Ser Ala Val Tyr Tyr Cys
                85                  90                  95

Ala Arg Asp Asp Val Ala Met Asp Tyr Trp Gly Gln Gly Thr Ser Val
            100                 105                 110

Thr Val Ser Ser
        115


<210> SEQ ID NO 116
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Asp Ile Val Val Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Ile His Trp Tyr Gln Gln Lys Pro Gly Gln Pro Pro
        35                  40                  45

Lys Leu Leu Ile Tyr Arg Ala Ser Asn Leu Lys Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110


<210> SEQ ID NO 117
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Ala Gly Leu Glu Trp Val
        35                  40                  45

Ala Glu Ile Arg Asn Lys Ala His Asn Pro Ala Thr Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Thr Leu Val Ala Pro Asp Ala Met Asp Tyr Trp Gly Gln Gly
            100                 105                 110

Thr Ser Val Thr Val Ser Ser
        115
```

<210> SEQ ID NO 118
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 118

Asp Ile Val Met Ser Leu Ser Pro Ser Ser Leu Ala Val Ser Val Gly
1 5 10 15

Glu Lys Val Thr Met Ser Cys Lys Ser Ser Gln Ser Leu Leu Tyr Ser
20 25 30

Arg Asn Gln Lys Asn Tyr Leu Ala Trp Tyr Gln Gln Lys Pro Gly Gln
35 40 45

Ser Pro Lys Leu Leu Ile Tyr Trp Ala Ser Thr Arg Ala Ser Gly Val
50 55 60

Pro Asp Arg Phe Thr Gly Ser Gly Ser Gly Thr Asp Phe Thr Leu Thr
65 70 75 80

Ile Ser Ser Val Lys Ala Glu Asp Leu Ala Val Tyr Tyr Cys Gln Gln
85 90 95

Tyr Tyr Ser Tyr Pro Tyr Thr Phe Gly Gly Gly Thr Lys Leu Glu Ile
100 105 110

Lys

<210> SEQ ID NO 119
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 119

Gln Val Gln Leu Gln Gln Ser Gly Pro Glu Leu Val Arg Pro Gly Ala
1 5 10 15

Ser Val Lys Met Ser Cys Lys Ala Ser Gly Tyr Thr Phe Thr Ser Tyr
20 25 30

Trp Met His Trp Val Lys Gln Arg Pro Gly Gln Gly Leu Glu Trp Ile
35 40 45

Gly Met Ile Asp Pro Ser Asn Ser Glu Thr Trp Leu Asn Gln Lys Phe
50 55 60

Lys Asp Lys Ala Thr Leu Asn Val Asp Lys Ser Ser Asn Thr Ala Tyr
65 70 75 80

Met Gln Leu Ser Ser Leu Thr Ser Glu Asp Ser Ala Val Tyr Tyr Cys
85 90 95

Ala Arg Tyr Asp Gly Tyr Tyr Asp Tyr Trp Gly Gln Gly Thr Thr Leu
100 105 110

Thr Val Ser Ser
115

<210> SEQ ID NO 120
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 120

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Val Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Trp Thr Phe Gly Gly Gly Thr Lys Leu Glu Ile Lys
            100                 105                 110

<210> SEQ ID NO 121
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Val Gln Leu Gln Gln Pro Gly Ala Glu Leu Val Arg Pro Gly Ala
1               5                   10                  15

Ser Val Lys Leu Ser Cys Lys Pro Ser Gly Tyr Thr Phe Thr Ser Tyr
            20                  25                  30

Trp Met Asn Trp Val Lys Gln Arg Pro Gly Gln Gly Leu Glu Trp Ile
        35                  40                  45

Gly Met Ile Asp Pro Ser Asp Ser Glu Thr His Tyr Asn Gln Met Phe
    50                  55                  60

Lys Asp Lys Ala Thr Leu Thr Val Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Gln Ile Tyr Tyr Ala Tyr Asp Lys Ala Tyr Trp Gly Gln Gly Thr
            100                 105                 110

Leu Val Thr Val Ser Ala
        115

<210> SEQ ID NO 122
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser His Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Ser Leu Thr
65 70 75 80

Ile Ser Ser Val Lys Ala Glu Asp Leu Ala Val Tyr Tyr Cys Gln Glu
85 90 95

Tyr Tyr Ser Trp Thr Phe Gly Gly Gly Thr Lys Leu Glu Ile Lys
100 105 110

<210> SEQ ID NO 123
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 123

Glu Val Gln Leu Gln Gln Ser Gly Pro Glu Leu Val Lys Pro Gly Ala
1 5 10 15

Ser Val Lys Ile Ser Cys Lys Ala Ser Gly Tyr Thr Phe Thr Asp Tyr
20 25 30

Tyr Met Asn Trp Val Lys Gln Ser His Gly Lys Ser Leu Glu Trp Ile
35 40 45

Gly Asp Ile Asn Pro His Asn Gly Gly Thr Ser Phe Ile Gln Lys Phe
50 55 60

Lys Gly Lys Ala Thr Leu Thr Val Asp Lys Ser Ser Ser Thr Ala Tyr
65 70 75 80

Met Glu Leu Arg Ser Leu Thr Ser Glu Asp Ser Ala Val Tyr Tyr Cys
85 90 95

Ala Pro Leu Gly Arg Lys Glu Gly Phe Ala Tyr Trp Gly Gln Gly Thr
100 105 110

Leu Val Thr Val Ser Ala
115

<210> SEQ ID NO 124
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 124

Asp Thr Val Leu Thr Gln Ser Pro Ala Ser Leu Val Val Ser Leu Gly
1 5 10 15

Gln Arg Ala Thr Ile Ser Cys Arg Ala Ser Lys Ser Val Ser Thr Ser
20 25 30

Gly Tyr Ser Tyr Met His Trp Tyr Gln Gln Lys Pro Gly Gln Pro Pro
35 40 45

Lys Leu Leu Ile Tyr Leu Ala Ser Asn Leu Glu Ser Gly Val Pro Ala
50 55 60

Arg Phe Ser Gly Ser Gly Ser Gly Thr Ala Phe Thr Leu Asn Ile His
65 70 75 80

Pro Val Glu Glu Glu Asp Ala Ala Thr Tyr Tyr Cys Gln His Ser Arg
85 90 95

Glu Leu Pro Tyr Thr Phe Gly Gly Gly Thr Lys Leu Glu Ile Lys
100 105 110

<210> SEQ ID NO 125

<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 125

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Ser Thr Phe
20 25 30

Ala Met Gly Val Gly Trp Ile Arg Gln Pro Ser Gly Lys Gly Leu Glu
35 40 45

Trp Leu Ala His Ile Trp Trp Asp Asp Asp Lys Tyr Tyr Asn Pro Ala
50 55 60

Leu Lys Ser Arg Leu Thr Ile Ser Lys Asp Thr Ser Lys Asn His Val
65 70 75 80

Phe Leu Lys Ile Ala Asn Val Asp Thr Ala Asp Thr Ala Thr Tyr Tyr
85 90 95

Cys Ala Arg Met Pro Leu Thr Phe Tyr Phe Asp Tyr Trp Gly Gln Gly
100 105 110

Thr Thr Leu Thr Val Ser Ser
115

<210> SEQ ID NO 126
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 126

Asp Val Leu Leu Thr Gln Thr Pro Leu Ser Leu Pro Val Ser Leu Gly
1 5 10 15

Asp Gln Ala Ser Ile Ser Cys Arg Ser Ser Gln Ser Ile Val His Ser
20 25 30

Asn Gly His Thr Tyr Leu Glu Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser His Val Pro Phe Thr Phe Gly Gly Gly Thr Lys Leu Glu Ile Lys
100 105 110

<210> SEQ ID NO 127
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 127

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Arg Thr Phe
20 25 30

Ala Met Gly Val Gly Trp Ile Arg Gln Pro Ser Gly Lys Gly Leu Glu
35 40 45

Trp Leu Ala His Ile Trp Trp Asp Asp Asp Lys Tyr Tyr Asn Pro Ala
50 55 60

Leu Lys Ser Arg Leu Thr Ile Ser Lys Asp Thr Ser Lys Asn Gln Val
65 70 75 80

Phe Leu Lys Ile Ala Asn Val Asp Thr Ala Asp Thr Ala Thr Tyr Tyr
85 90 95

Cys Ala Arg Met Pro Leu Thr Phe Tyr Phe Asp Tyr Trp Gly Gln Gly
100 105 110

Thr Thr Leu Thr Val Ser Ser
115

<210> SEQ ID NO 128
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 128

Asp Val Leu Met Thr Gln Thr Pro Leu Ser Leu Pro Val Ser Leu Gly
1 5 10 15

Asp Gln Ala Ser Ile Ser Cys Arg Ser Ser Gln Ser Ile Val His Ser
20 25 30

Asn Gly Asn Thr Tyr Leu Glu Trp Tyr Leu Gln Lys Pro Gly Gln Ser
35 40 45

Pro Lys Leu Leu Ile Tyr Lys Val Ser Thr Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser His Val Pro Phe Thr Phe Gly Gly Gly Thr Lys Leu Glu Ile Lys
100 105 110

<210> SEQ ID NO 129
<211> LENGTH: 115
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 129

Gln Val Gln Leu Gln Gln Pro Gly Ala Glu Leu Val Met Pro Gly Ala
1 5 10 15

Ser Val Lys Leu Ser Cys Lys Ala Ser Gly Tyr Thr Phe Thr Asn Tyr
20 25 30

Trp Met His Trp Val Lys Gln Arg Pro Gly Gln Gly Leu Glu Trp Ile
35 40 45

Gly Glu Ile Asp Pro Ser Asp Ser Tyr Thr Asn Tyr Asn Gln Lys Phe
50 55 60

Lys Gly Lys Ala Thr Leu Thr Val Asp Lys Ser Ser Ser Thr Ala Tyr
65 70 75 80

```
Met Gln Leu Ser Ser Leu Thr Ser Glu Asp Ser Ala Val Tyr Tyr Cys
                85                  90                  95

Thr Arg Gln Gly Ser Thr Tyr Ala Trp Gly Gln Gly Thr Ser Val Thr
            100                 105                 110

Val Ser Ser
        115


<210> SEQ ID NO 130
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gly Gly Thr Lys Leu Glu Ile Lys
            100                 105                 110


<210> SEQ ID NO 131
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Met Trp Val Lys Gln Ser His Gly Lys Ser Leu Glu Trp Ile
        35                  40                  45

Gly Asp Ile Asn Pro Tyr Asn Gly Gly Ser Ser Tyr Asn Pro Lys Phe
    50                  55                  60

Lys Gly Arg Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Thr Tyr Trp Gly Gln Gly Thr Leu Val Thr Val Ser Ala
            100                 105                 110


<210> SEQ ID NO 132
<211> LENGTH: 112
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 132

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Ala Gly Lys Thr Tyr Leu Asn Trp Leu Leu Gln Arg Pro Gly Gln Ser
        35                  40                  45

Pro Lys Arg Leu Met Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

<210> SEQ ID NO 133
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 133

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Ile Lys Gln Arg Pro Gly Gln Gly Leu Glu Trp Ile
        35                  40                  45

Gly Glu Ile Asn Pro Ser Asn Gly Gly Ser Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr His Cys
                85                  90                  95

Lys Ser Arg Gly Tyr Trp Gly Gln Gly Thr Thr Leu Thr Val Ser Ser
            100                 105                 110

<210> SEQ ID NO 134
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 134

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Tyr Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro

```
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Ile Tyr Tyr Cys Trp Gln Gly
                85                  90                  95

Thr His Phe Pro His Thr Phe Gly Ser Gly Thr Lys Leu Glu Ile Lys
            100                 105                 110


<210> SEQ ID NO 135
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Ile
        35                  40                  45

Gly Glu Ile Phe Pro Arg Ser Ser Asn Thr Tyr Tyr Asn Glu Lys Phe
    50                  55                  60

Lys Gly Lys Ala Thr Leu Thr Ala Asp Lys Ser Ser Ser Thr Val Tyr
65                  70                  75                  80

Met Glu Phe Arg Ser Leu Thr Ser Glu Asp Ser Ala Val Tyr Phe Cys
                85                  90                  95

Ala Arg Glu Gly Gly Leu Ala Trp Phe Ala Tyr Trp Gly Gln Gly Thr
            100                 105                 110

Leu Val Thr Val Ser Ala
        115


<210> SEQ ID NO 136
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Thr
            20                  25                  30

Asn Gly Asn Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Ile Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Leu Gln Ser
                85                  90                  95

Thr His Phe Pro Phe Thr Phe Gly Ser Gly Thr Lys Leu Glu Ile Lys
            100                 105                 110
```

```
<210> SEQ ID NO 137
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Ile Thr Asp Tyr
            20                  25                  30

Tyr Met Met Trp Leu Lys Gln Ser His Gly Lys Ser Leu Glu Trp Ile
        35                  40                  45

Gly Asp Ile Asn Pro Tyr Thr Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Leu Gln Leu His Ser Leu Thr Ser Glu Asp Ser Ala Val Tyr Tyr Cys
                85                  90                  95

Ala Arg Gly Ala Tyr Trp Gly Gln Gly Thr Thr Leu Thr Val Ser Ser
            100                 105                 110


<210> SEQ ID NO 138
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110


<210> SEQ ID NO 139
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Ile Thr Asp Tyr
            20                  25                  30
```

```
Tyr Met Met Trp Leu Lys Gln Ser His Gly Lys Ser Leu Glu Trp Ile
        35                  40                  45

Gly Asp Ile Asn Pro Tyr Thr Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Ala Tyr Trp Gly Gln Gly Thr Thr Leu Thr Val Ser Ser
            100                 105                 110
```

<210> SEQ ID NO 140
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 140

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110
```

<210> SEQ ID NO 141
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 141

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Arg Ser Leu Glu Leu Ile
        35                  40                  45

Gly Asp Ile Asn Pro Asn Asn Gly Gly Ser Asn Phe Asn Gln Lys Phe
    50                  55                  60

Arg Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Ile Tyr Tyr Cys
                85                  90                  95

Ala Arg Met Gly Tyr Trp Gly Gln Gly Thr Leu Val Thr Val Ser Ala
            100                 105                 110
```

<210> SEQ ID NO 142
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 142

Asp Val Val Met Thr Gln Thr Pro Leu Thr Leu Ser Val Thr Ile Gly
1 5 10 15

Gln Pro Ala Ser Ile Ser Cys Lys Ser Ser Gln Ser Leu Leu His Ser
20 25 30

Asp Gly Lys Thr Tyr Leu Asn Trp Met Phe Gln Arg Pro Gly Gln Ser
35 40 45

Pro Lys Arg Leu Ile Tyr Leu Val Ser Lys Leu Asp Ser Gly Val Pro
50 55 60

Tyr Arg Phe Thr Gly Gly Gly Ser Gly Thr Asp Phe Thr Leu Gln Ile
65 70 75 80

Ser Arg Val Glu Thr Glu Asp Leu Gly Val Tyr Tyr Cys Trp Gln Gly
85 90 95

Thr His Phe Pro Arg Thr Phe Gly Gly Gly Thr Lys Leu Glu Ile Lys
100 105 110

<210> SEQ ID NO 143
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 143

Glu Val Gln Leu Gln Gln Ser Gly Pro Glu Leu Val Lys Pro Gly Ala
1 5 10 15

Ser Val Lys Met Ser Cys Lys Ala Ser Gly Tyr Thr Phe Thr Asp Tyr
20 25 30

Tyr Ile His Trp Val Lys Gln Lys Pro Gly Gln Gly Leu Glu Tyr Ile
35 40 45

Gly Glu Ile Tyr Pro Gly Ser Gly Asn Thr Tyr Tyr Asn Gly Lys Phe
50 55 60

Arg Gly Lys Ala Thr Leu Thr Ala Asp Lys Ser Ser Ser Thr Ala Tyr
65 70 75 80

Met Gln Leu Ser Ser Leu Thr Ser Glu Asp Ser Ala Val Tyr Phe Cys
85 90 95

Gly Ser Gly Tyr Phe Asp Tyr Trp Gly Gln Gly Thr Thr Leu Thr Val
100 105 110

Ser Ser

<210> SEQ ID NO 144
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 144

Asp Val Val Met Thr Gln Thr Pro Leu Thr Leu Ser Val Thr Ile Gly

```
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Ser Pro Gly Gln Ser
        35                  40                  45

Pro Lys Leu Leu Ile Tyr Leu Val Ser Lys Leu Glu Ser Gly Val Pro
    50                  55                  60

Asp Arg Phe Ser Gly Ser Gly Ser Gly Thr Asp Phe Thr Leu Lys Leu
65                  70                  75                  80

Ser Arg Val Glu Ala Glu Asp Leu Gly Val Tyr Tyr Cys Val Gln Gly
                85                  90                  95

Thr His Phe Pro Phe Thr Phe Gly Ser Gly Thr Lys Leu Glu Ile Lys
            100                 105                 110
```

<210> SEQ ID NO 145
<211> LENGTH: 139
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 145

```
Met Asp Trp Leu Trp Asn Leu Leu Phe Leu Met Val Val Ala Gln Ser
1               5                   10                  15

Ala Gln Ala Gln Ile Gln Leu Val Gln Ser Gly Pro Glu Val Lys Lys
            20                  25                  30

Pro Gly Glu Ser Val Lys Ile Ser Cys Lys Ala Ser Gly Tyr Thr Phe
        35                  40                  45

Thr Asp Tyr Ala Met Asn Trp Val Lys Gln Ala Pro Gly Asn Gly Leu
    50                  55                  60

Lys Trp Met Gly Trp Ile Asn Thr Gln Thr Gly Lys Pro Thr Tyr Ala
65                  70                  75                  80

Asp Asp Phe Lys Gln Arg Phe Val Phe Ser Leu Glu Thr Ser Ala Arg
                85                  90                  95

Thr Thr Tyr Leu Gln Ile Asn Asn Leu Asn Ile Glu Asp Thr Ala Thr
            100                 105                 110

Tyr Phe Cys Thr Arg Leu Gly Thr Gly Asn Thr Lys Gly Phe Ala Tyr
        115                 120                 125

Trp Gly Gln Gly Thr Leu Val Thr Val Ser Ser
    130                 135
```

<210> SEQ ID NO 146
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 146

```
Met Glu Ser Gln Thr His Val Leu Ile Ser Leu Leu Leu Cys Val Ser
1               5                   10                  15

Gly Thr Cys Gly Asp Ile Leu Ile Asn Gln Ser Pro Ala Ser Leu Thr
            20                  25                  30

Val Ser Ala Gly Glu Arg Val Thr Met Ser Cys Lys Ser Ser Gln Ser
        35                  40                  45

Leu Leu Tyr Ser Glu Asn Asn Gln Asp Tyr Leu Ala Trp Tyr Gln Gln
```

```
    50                  55                  60

Lys Pro Gly Gln Phe Pro Lys Leu Leu Ile Tyr Gly Ala Ser Asn Arg
65                  70                  75                  80

His Thr Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Asp Tyr
            100                 105                 110

Tyr Cys Glu Gln Thr Tyr Arg Tyr Pro Phe Thr Phe Gly Ser Gly Thr
        115                 120                 125

Lys Leu Glu Ile Lys
    130


<210> SEQ ID NO 147
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Met Glu Leu Glu Leu Ser Leu Ile Phe Ile Phe Ser Leu Leu Lys Asp
1               5                   10                  15

Val Gln Cys Glu Val Gln Leu Val Glu Ser Gly Gly Ser Leu Val Gln
            20                  25                  30

Pro Gly Gly Ser Leu Lys Leu Ser Cys Val Ala Ser Gly Tyr Thr Phe
        35                  40                  45

Ser Asn Tyr Trp Met Asp Trp Val Arg Gln Ser Pro Gly Lys Ser Leu
    50                  55                  60

Glu Trp Ile Gly Glu Ile Asn Thr Asp Gly Arg Arg Thr Asn Tyr Ala
65                  70                  75                  80

Pro Ser Ile Lys Asp Arg Phe Thr Ile Ser Arg Asp Asn Ala Lys Ser
                85                  90                  95

Thr Leu Tyr Leu Gln Met Ser Asn Val Lys Ser Asp Asp Thr Ala Ile
            100                 105                 110

Tyr Tyr Cys Thr Ile Leu Arg Val Tyr Pro His Tyr Phe Asp Tyr Trp
        115                 120                 125

Gly Gln Gly Val Met Val Thr Val Ser Ser
    130                 135


<210> SEQ ID NO 148
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Met Met Ser Pro Ala Gln Phe Leu Phe Leu Leu Met Leu Trp Ile Gln
1               5                   10                  15

Glu Ala Arg Gly Asp Val Val Met Thr Gln Thr Pro Pro Ser Leu Ser
            20                  25                  30

Val Ala Ile Gly Gln Ser Val Ser Ile Ser Cys Lys Ser Ser Gln Ser
        35                  40                  45

Leu Val Tyr Ser Asp Gly Glu Thr Tyr Leu His Trp Phe Leu Gln Ser
    50                  55                  60

Pro Gly Arg Ser Pro Lys Arg Leu Ile Tyr His Val Ser Asn Leu Gly
```

65 70 75 80

Ser Gly Val Pro Asp Arg Phe Ser Gly Thr Gly Ser Leu Thr Asp Phe
85 90 95

Thr Leu Arg Ile Ser Arg Val Glu Ala Glu Asp Leu Gly Val Tyr Tyr
100 105 110

Cys Ala Gln Thr Thr His Phe Pro Pro Thr Phe Gly Ala Gly Thr Lys
115 120 125

Leu Glu Leu Lys
130

<210> SEQ ID NO 149
<211> LENGTH: 135
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 149

Met Ala Val Leu Val Leu Leu Leu Cys Leu Val Thr Phe Pro Ser Cys
1 5 10 15

Ala Leu Ser Gln Val Gln Leu Lys Glu Ser Gly Pro Gly Leu Val Gln
20 25 30

Pro Ser Gln Thr Leu Ser Leu Thr Cys Thr Val Ser Gly Phe Ser Leu
35 40 45

Thr Ser Asn Ser Val Ser Trp Val Arg Gln Ala Pro Gly Lys Gly Leu
50 55 60

Glu Trp Met Gly Ala Ile Trp Ser Gly Gly Ser Thr Asp Tyr Asn Ser
65 70 75 80

Ala Leu Lys Ser Arg Leu Ser Ile Ser Arg Asp Thr Ser Lys Ser Gln
85 90 95

Val Phe Leu Lys Met Asn Ser Leu Gln Thr Glu Asp Thr Ala Ile Tyr
100 105 110

Phe Cys Thr Arg Ser His Trp Glu Pro Phe Asp Tyr Trp Gly Gln Gly
115 120 125

Val Met Val Thr Val Ser Ser
130 135

<210> SEQ ID NO 150
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 150

Met Glu Ser Gln Thr Gln Ala Leu Ile Ser Leu Leu Leu Trp Val Tyr
1 5 10 15

Gly Thr Cys Gly Asp Ile Val Met Thr Gln Ser Pro Phe Ser Leu Ala
20 25 30

Val Ser Glu Gly Glu Met Val Thr Ile Asn Cys Lys Ser Ser Gln Gly
35 40 45

Leu Leu Ser Ser Gly Asn Gln Lys Asn Tyr Leu Ala Trp Tyr Gln Gln
50 55 60

Arg Pro Gly Gln Ser Pro Lys Leu Leu Ile Tyr Tyr Ala Ser Thr Arg
65 70 75 80

Gln Ser Gly Val Pro Asp Arg Phe Ile Gly Gly Gly Ser Gly Thr Asp

```
                85                  90                  95

Phe Thr Leu Thr Ile Ser Asp Val Gln Ala Glu Asp Leu Ala Asp Tyr
            100                 105                 110

Tyr Cys Leu Gln His Tyr Ser Tyr Pro Pro Thr Phe Gly Ser Gly Thr
        115                 120                 125

Lys Leu Glu Ile Lys
    130


<210> SEQ ID NO 151
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Met Ala Val Leu Val Leu Leu Leu Cys Leu Val Thr Phe Pro Ser Cys
1               5                   10                  15

Ala Leu Ser Gln Val Gln Leu Arg Glu Ser Gly Pro Gly Leu Val Gln
            20                  25                  30

Pro Ser Gln Thr Leu Ser Leu Thr Cys Thr Val Ser Gly Phe Ser Leu
        35                  40                  45

Thr Ser Asn Ser Val Thr Trp Val Arg Gln Pro Pro Gly Lys Gly Leu
    50                  55                  60

Glu Trp Met Gly Ala Ile Trp Ser Asp Gly Ser Thr Asp Tyr Asn Ser
65                  70                  75                  80

Thr Leu Lys Ser Arg Leu Ser Ile Ser Arg Asp Thr Ser Lys Ser Gln
                85                  90                  95

Val Phe Leu Lys Met Ser Ser Leu Gln Thr Glu Asp Thr Ala Ile Tyr
            100                 105                 110

Phe Cys Thr Arg Ser His Trp Glu Pro Phe Asp Tyr Trp Gly Gln Gly
        115                 120                 125

Val Met Val Thr Val Ser Ser
    130                 135


<210> SEQ ID NO 152
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Met Glu Ser Gln Thr Gln Ala Leu Ile Ser Leu Leu Leu Trp Val Tyr
1               5                   10                  15

Gly Thr Cys Gly Asp Ile Val Met Thr Gln Ser Pro Leu Ser Leu Ala
            20                  25                  30

Val Ser Glu Gly Glu Thr Val Thr Met Asn Cys Lys Ser Ser Gln Ser
        35                  40                  45

Leu Phe Ser Ser Gly Asn Gln Lys Asn Tyr Leu Ala Trp Tyr Gln Gln
    50                  55                  60

Lys Pro Gly Gln Ser Pro Lys Leu Leu Ile Tyr Tyr Ala Ser Thr Arg
65                  70                  75                  80

Gln Ser Gly Val Pro Asp Arg Phe Ile Gly Ser Gly Ser Gly Thr Asp
                85                  90                  95

Phe Thr Leu Thr Ile Ser Asp Val Gln Thr Glu Asp Leu Ala Asp Tyr
```

```
            100                 105                 110

Tyr Cys Leu Gln His Tyr Asn Tyr Pro Pro Thr Phe Gly Ser Gly Thr
        115                 120                 125

Lys Leu Glu Ile Lys
    130


<210> SEQ ID NO 153
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Met Asp Leu Arg Leu Thr Tyr Val Phe Ile Val Ala Ile Leu Lys Gly
1               5                   10                  15

Val Leu Cys Glu Val Lys Leu Glu Glu Ser Gly Gly Gly Leu Val Gln
            20                  25                  30

Pro Gly Met Ser Val Lys Leu Ser Cys Ala Thr Ser Gly Phe Ile Phe
        35                  40                  45

Ser Asp Tyr Trp Met Glu Trp Val Arg Gln Ala Pro Gly Lys Gly Leu
    50                  55                  60

Glu Trp Val Ala Glu Ile Arg Asn Lys Ala Asn Asn Tyr Ala Thr Tyr
65                  70                  75                  80

Tyr Gly Lys Ser Met Lys Gly Arg Phe Thr Ile Ser Arg Asp Asp Ser
                85                  90                  95

Lys Ser Ile Val Tyr Leu Gln Val Asn Ser Ile Arg Ser Glu Asp Thr
            100                 105                 110

Ala Ile Tyr Tyr Cys Ala Pro Asn Phe Asp Tyr Trp Gly Gln Gly Val
        115                 120                 125

Met Val Thr Val Ser Ser
    130


<210> SEQ ID NO 154
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Met Ser Pro Val Gln Ser Leu Phe Leu Leu Leu Leu Trp Ile Leu Gly
1               5                   10                  15

Thr His Gly Asp Val Val Leu Thr Gln Thr Pro Pro Thr Leu Ser Ala
            20                  25                  30

Thr Ile Gly Gln Ser Val Ser Ile Ser Cys Arg Ser Ser Gln Ser Leu
        35                  40                  45

Leu His Ser Thr Gly Asn Thr Tyr Leu Asn Trp Leu Leu Gln Arg Pro
    50                  55                  60

Gly Gln Pro Pro Gln Leu Leu Ile Tyr Leu Val Ser Arg Leu Glu Ser
65                  70                  75                  80

Gly Val Pro Asn Arg Phe Ser Ala Ser Gly Ser Gly Thr Asp Phe Thr
                85                  90                  95

Leu Lys Ile Ser Gly Ile Glu Ala Glu Asp Leu Gly Val Tyr Tyr Cys
            100                 105                 110

Val Gln Ser Ser His Thr Pro Tyr Thr Phe Gly Thr Gly Thr Lys Leu
```

115 120 125

Glu Leu Lys
130

<210> SEQ ID NO 155
<211> LENGTH: 135
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 155

Met Asp Ile Arg Leu Ser Leu Val Phe Leu Val Leu Phe Met Lys Gly
1 5 10 15

Val Gln Cys Glu Val Gln Leu Val Glu Ser Gly Gly Gly Leu Val Gln
20 25 30

Pro Gly Arg Ser Leu Lys Leu Ser Cys Ala Ala Ser Arg Phe Thr Phe
35 40 45

Ser Asp Tyr Asn Met Ala Trp Val Arg Gln Ala Pro Lys Lys Gly Leu
50 55 60

Glu Trp Val Ala Thr Ile Tyr His Asp Asp Ser Gly Ser Tyr Tyr Arg
65 70 75 80

Asp Ser Val Lys Gly Arg Phe Thr Ile Ser Arg Asn Asn Ala Lys Ser
85 90 95

Thr Leu Tyr Leu Gln Met Asp Ser Leu Arg Ser Glu Asp Met Ala Thr
100 105 110

Tyr Tyr Cys Ala Arg His Asn Asn Gly Phe Asp Tyr Trp Gly Gln Gly
115 120 125

Val Met Val Thr Val Ala Ser
130 135

<210> SEQ ID NO 156
<211> LENGTH: 131
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 156

Met Lys Trp Pro Val Arg Leu Leu Val Leu Phe Phe Trp Ile Pro Ala
1 5 10 15

Ser Gly Gly Asp Val Val Met Thr Gln Thr Pro Val Ser Leu Pro Val
20 25 30

Arg Leu Gly Gly Gln Ala Ser Ile Ser Cys Arg Ser Ser Gln Ser Leu
35 40 45

Val His Ser Asn Gly Asn Thr Tyr Leu His Trp Tyr Leu Gln Lys Pro
50 55 60

Gly Gln Ser Pro Gln Leu Leu Ile Asn Arg Val Ser Asn Arg Phe Ser
65 70 75 80

Gly Val Pro Asp Arg Phe Ser Gly Ser Gly Ser Gly Thr Asp Phe Thr
85 90 95

Leu Lys Ile Asn Arg Val Glu Pro Glu Asp Leu Gly Asp Tyr Tyr Cys
100 105 110

Leu Gln Ser Thr His Phe Pro Leu Thr Phe Gly Ser Gly Thr Lys Leu
115 120 125

Glu Thr Lys

130

<210> SEQ ID NO 157
<211> LENGTH: 136
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 157

Met Asp Ile Arg Leu Ser Leu Gly Phe Leu Val Leu Phe Ile Lys Gly
1 5 10 15

Asp Gln Cys Ala Val Gln Leu Val Glu Ser Gly Gly Gly Leu Val Gln
20 25 30

Pro Gly Arg Ser Leu Lys Leu Ser Cys Ala Ala Ser Arg Ile Thr Phe
35 40 45

Thr Asp Tyr Tyr Met Ala Trp Val Arg Gln Ala Pro Thr Lys Gly Leu
50 55 60

Glu Trp Val Ala Thr Ile Ser Ser Asp Gly Gly Asp Thr Phe Tyr Arg
65 70 75 80

Asp Ser Val Lys Gly Arg Phe Thr Ile Ser Arg Asp Asn Ala Lys Ser
85 90 95

Thr Leu Tyr Leu Gln Met Val Ser Leu Arg Ser Glu Asp Thr Ala Thr
100 105 110

Tyr Tyr Cys Ser Thr Asp Arg Gly Ala Gln Phe Gly Tyr Trp Gly Gln
115 120 125

Gly Thr Leu Val Thr Val Ser Ser
130 135

<210> SEQ ID NO 158
<211> LENGTH: 126
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 158

Met Ala Pro Val Gln Leu Leu Gly Leu Leu Leu Ile Trp Leu Pro Ala
1 5 10 15

Met Arg Cys Asp Ile Gln Met Thr Gln Ser Pro Ser Phe Leu Ser Ala
20 25 30

Ser Val Gly Asp Arg Val Ser Ile Asn Cys Lys Ala Ser Gln Asn Val
35 40 45

His Glu Asn Leu Asn Trp Tyr Gln Gln Lys Leu Gly Glu Ala Pro Lys
50 55 60

Arg Leu Ile Tyr Asn Thr Asn Asn Leu Gln Thr Gly Ile Pro Ser Arg
65 70 75 80

Phe Ser Gly Ser Gly Ser Gly Ala Asp Tyr Thr Leu Thr Ile Ser Ser
85 90 95

Leu Gln Pro Glu Asp Phe Ala Thr Tyr Phe Cys Leu Gln His Asn Ala
100 105 110

Phe Pro Tyr Thr Phe Gly Pro Gly Thr Lys Leu Glu Leu Lys
115 120 125

<210> SEQ ID NO 159
<211> LENGTH: 455
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 159

Met Glu Thr Gly Leu Arg Trp Leu Leu Leu Val Ala Val Phe Lys Gly
1               5                   10                  15

Val Gln Cys Gln Glu Gln Leu Val Glu Ser Gly Gly Asp Leu Val Lys
            20                  25                  30

Pro Gly Ala Ser Leu Thr Leu Thr Cys Thr Ala Ser Gly Phe Ser Phe
        35                  40                  45

Asn Lys Asn Tyr Trp Met Cys Trp Val Arg Gln Ala Pro Gly Lys Gly
    50                  55                  60

Leu Glu Trp Ile Gly Cys Ile Tyr Asn Gly Asp Gly Asn Thr Tyr Tyr
65                  70                  75                  80

Ala Ser Trp Val Asn Gly Arg Phe Thr Ile Ser Lys Thr Ser Ser Thr
                85                  90                  95

Thr Val Thr Leu Gln Met Thr Ser Leu Thr Val Ala Asp Thr Ala Ile
            100                 105                 110

Tyr Phe Cys Ala Arg Leu Leu Asn Met Trp Gly Pro Gly Thr Leu Val
        115                 120                 125

Thr Val Ser Ser Gly Gln Pro Lys Ala Pro Ser Val Phe Pro Leu Ala
    130                 135                 140

Pro Cys Cys Gly Asp Thr Pro Ser Ser Thr Val Thr Leu Gly Cys Leu
145                 150                 155                 160

Val Lys Gly Tyr Leu Pro Glu Pro Val Thr Val Thr Trp Asn Ser Gly
                165                 170                 175

Thr Leu Thr Asn Gly Val Arg Thr Phe Pro Ser Val Arg Gln Ser Ser
            180                 185                 190

Gly Leu Tyr Ser Leu Ser Ser Val Val Ser Val Thr Ser Ser Ser Gln
        195                 200                 205

Pro Val Thr Cys Asn Val Ala His Pro Ala Thr Asn Thr Lys Val Asp
    210                 215                 220

Lys Thr Val Ala Pro Ser Thr Cys Ser Lys Pro Met Cys Pro Pro Pro
225                 230                 235                 240

Glu Leu Pro Gly Gly Pro Ser Val Phe Ile Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Asp Asp Pro Glu Val Gln Phe Thr Trp Tyr Ile Asn
        275                 280                 285

Asn Glu Gln Val Arg Thr Ala Arg Pro Pro Leu Arg Glu Gln Gln Phe
    290                 295                 300

Asn Ser Thr Ile Arg Val Val Ser Thr Leu Pro Ile Ala His Gln Asp
305                 310                 315                 320

Trp Leu Arg Gly Lys Glu Phe Lys Cys Lys Val His Asn Lys Ala Leu
                325                 330                 335

Pro Ala Pro Ile Glu Lys Thr Ile Ser Lys Ala Arg Gly Gln Pro Leu
            340                 345                 350

Glu Pro Lys Val Tyr Thr Met Gly Pro Pro Arg Glu Glu Leu Ser Ser
        355                 360                 365

Arg Ser Val Ser Leu Thr Cys Met Ile Asn Gly Phe Tyr Pro Ser Asp
    370                 375                 380
```

```
Ile Ser Val Glu Trp Glu Lys Asn Gly Lys Ala Glu Asp Asn Tyr Lys
385                 390                 395                 400

Thr Thr Pro Thr Val Leu Asp Ser Asp Gly Ser Tyr Phe Leu Tyr Ser
                405                 410                 415

Lys Leu Ser Val Pro Thr Ser Glu Trp Gln Arg Gly Asp Val Phe Thr
            420                 425                 430

Cys Ser Val Met His Glu Ala Leu His Asn His Tyr Thr Gln Lys Ser
        435                 440                 445

Ile Ser Arg Ser Pro Gly Lys
    450                 455
```

<210> SEQ ID NO 160
<211> LENGTH: 239
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 160

```
Met Asp Thr Arg Ala Pro Thr Gln Leu Leu Gly Leu Leu Leu Leu Trp
1               5                   10                  15

Leu Pro Gly Ala Arg Cys Ala Asp Ile Val Met Thr Gln Thr Pro Ala
            20                  25                  30

Ser Val Glu Ala Ala Val Gly Gly Thr Val Thr Ile Lys Cys Gln Ala
        35                  40                  45

Ser Glu Ser Ile Gly Asn Ala Leu Ala Trp Tyr Gln Gln Lys Pro Gly
    50                  55                  60

Gln Pro Pro Lys Leu Leu Ile Tyr Thr Ala Ala Thr Leu Ala Ser Gly
65                  70                  75                  80

Val Pro Ser Arg Phe Ser Gly Ser Gly Ser Gly Thr Glu Phe Thr Leu
                85                  90                  95

Thr Ile Ser Gly Val Gln Cys Asp Asp Ala Ala Thr Tyr Tyr Cys Gln
            100                 105                 110

Ser Tyr Tyr Phe Thr Ser Val Ser Ser Tyr Gly Asn Ala Phe Gly Gly
        115                 120                 125

Gly Thr Glu Val Val Val Lys Gly Asp Pro Val Ala Pro Thr Val Leu
    130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235
```

<210> SEQ ID NO 161
<211> LENGTH: 466
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 161

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Arg Val Ser Gly Phe Ser Phe Ser
        35                  40                  45

Ser Ser Tyr Tyr Met Cys Trp Val Arg Gln Ala Pro Gly Lys Gly Leu
    50                  55                  60

Glu Trp Ile Ala Cys Ile Gly Thr Thr Arg Gly Ser Thr Tyr Tyr Ala
65                  70                  75                  80

Thr Trp Ala Lys Gly Arg Phe Thr Ile Ser Lys Ile Ser Ser Thr Thr
                85                  90                  95

Val Thr Leu Gln Met Thr Ser Leu Thr Asp Ala Asp Thr Ala Thr Tyr
            100                 105                 110

Phe Cys Ala Arg Asp Ala Thr Gly Tyr Arg Ile Asn Thr Ile Gly Leu
        115                 120                 125

Tyr Phe Asn Leu Trp Gly Pro Gly Thr Leu Val Thr Val Ser Ser Gly
    130                 135                 140

Gln Pro Lys Ala Pro Ser Val Phe Pro Leu Ala Pro Cys Cys Gly Asp
145                 150                 155                 160

Thr Pro Ser Ser Thr Val Thr Leu Gly Cys Leu Val Lys Gly Tyr Leu
                165                 170                 175

Pro Glu Pro Val Thr Val Thr Trp Asn Ser Gly Thr Leu Thr Asn Gly
            180                 185                 190

Val Arg Thr Phe Pro Ser Val Arg Gln Ser Ser Gly Leu Tyr Ser Leu
        195                 200                 205

Ser Ser Val Val Ser Val Thr Ser Ser Ser Gln Pro Val Thr Cys Asn
    210                 215                 220

Val Ala His Pro Ala Thr Asn Thr Lys Val Asp Lys Thr Val Ala Pro
225                 230                 235                 240

Ser Thr Cys Ser Lys Pro Met Cys Pro Pro Pro Glu Leu Pro Gly Gly
                245                 250                 255

Pro Ser Val Phe Ile Phe Pro Pro Lys Pro Lys Asp Thr Leu Met Ile
            260                 265                 270

Ser Arg Thr Pro Glu Val Thr Cys Val Val Val Asp Val Ser Gln Asp
        275                 280                 285

Asp Pro Glu Val Gln Phe Thr Trp Tyr Ile Asn Asn Glu Gln Val Arg
    290                 295                 300

Thr Ala Arg Pro Pro Leu Arg Glu Gln Gln Phe Asn Ser Thr Ile Arg
305                 310                 315                 320

Val Val Ser Thr Leu Pro Ile Ala His Gln Asp Trp Leu Arg Gly Lys
                325                 330                 335

Glu Phe Lys Cys Lys Val His Asn Lys Ala Leu Pro Ala Pro Ile Glu
            340                 345                 350

Lys Thr Ile Ser Lys Ala Arg Gly Gln Pro Leu Glu Pro Lys Val Tyr
        355                 360                 365

Thr Met Gly Pro Pro Arg Glu Glu Leu Ser Ser Arg Ser Val Ser Leu
    370                 375                 380

Thr Cys Met Ile Asn Gly Phe Tyr Pro Ser Asp Ile Ser Val Glu Trp
385                 390                 395                 400

Glu Lys Asn Gly Lys Ala Glu Asp Asn Tyr Lys Thr Thr Pro Thr Val 405 410 415

Leu Asp Ser Asp Gly Ser Tyr Phe Leu Tyr Ser Lys Leu Ser Val Pro
420 425 430

Thr Ser Glu Trp Gln Arg Gly Asp Val Phe Thr Cys Ser Val Met His
435 440 445

Glu Ala Leu His Asn His Tyr Thr Gln Lys Ser Ile Ser Arg Ser Pro
450 455 460

Gly Lys
465

<210> SEQ ID NO 162
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 162

Met Asp Thr Arg Ala Pro Thr Gln Leu Leu Gly Leu Leu Leu Leu Trp
1 5 10 15

Leu Pro Gly Ala Arg Cys Ala Phe Glu Leu Thr Gln Thr Pro Ser Ser
20 25 30

Val Glu Ala Ala Val Gly Gly Thr Pro Thr Ile Lys Cys Gln Ala Ser
35 40 45

Gln Thr Ile Tyr Ser Tyr Leu Ser Trp Tyr Gln Gln Lys Pro Gly Gln
50 55 60

Pro Pro Lys Leu Leu Ile Tyr Glu Ala Ser Lys Leu Ala Ser Gly Val
65 70 75 80

Pro Ser Arg Phe Ser Gly Ser Gly Ser Gly Thr Asp Tyr Thr Leu Thr
85 90 95

Ile Ser Asp Leu Glu Cys Ala Asp Ala Ala Thr Tyr Tyr Cys Gln Ser
100 105 110

Tyr His Gly Thr Ala Ser Thr Glu Tyr Asn Thr Phe Gly Gly Gly Thr
115 120 125

Glu Val Val Val Arg Gly Asp Pro Val Ala Pro Thr Val Leu Ile Phe
130 135 140

Pro Pro Ala Ala Asp Gln Val Ala Thr Gly Thr Val Thr Ile Val Cys
145 150 155 160

Val Ala Asn Lys Tyr Phe Pro Asp Val Thr Val Thr Trp Glu Val Asp
165 170 175

Gly Thr Thr Gln Thr Thr Gly Ile Glu Asn Ser Lys Thr Pro Gln Asn
180 185 190

Ser Ala Asp Cys Thr Tyr Asn Leu Ser Ser Thr Leu Thr Leu Thr Ser
195 200 205

Thr Gln Tyr Asn Ser His Lys Glu Tyr Thr Cys Lys Val Thr Gln Gly
210 215 220

Thr Thr Ser Val Val Gln Ser Phe Asn Arg Gly Asp Cys
225 230 235

<210> SEQ ID NO 163
<211> LENGTH: 466
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 163

```
Met Glu Thr Gly Leu Arg Trp Leu Leu Leu Val Ala Val Leu Lys Gly
1               5                   10                  15

Val Gln Cys Gln Gln Gln Leu Val Glu Ser Gly Gly Gly Leu Val Lys
            20                  25                  30

Pro Gly Ala Ala Leu Thr Phe Thr Cys Thr Ala Ser Gly Phe Ser Phe
        35                  40                  45

Ser Gly Asn Tyr Trp Ile Cys Trp Val Arg Gln Ala Pro Gly Lys Gly
    50                  55                  60

Leu Glu Trp Ile Ala Cys Ile Gly Thr Ile Thr Ser Arg Thr Tyr Tyr
65                  70                  75                  80

Ala Ser Trp Ala Lys Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Phe Cys Ala Arg Gly Ala Val Val Ser Ser Gly Asn Ala Pro Tyr
        115                 120                 125

Tyr Phe Thr Leu Trp Gly Pro Gly Thr Leu Val Thr Val Ser Ser Gly
    130                 135                 140

Gln Pro Lys Ala Pro Ser Val Phe Pro Leu Ala Pro Cys Cys Gly Asp
145                 150                 155                 160

Thr Pro Ser Ser Thr Val Thr Leu Gly Cys Leu Val Lys Gly Tyr Leu
                165                 170                 175

Pro Glu Pro Val Thr Val Thr Trp Asn Ser Gly Thr Leu Thr Asn Gly
            180                 185                 190

Val Arg Thr Phe Pro Ser Val Arg Gln Ser Ser Gly Leu Tyr Ser Leu
        195                 200                 205

Ser Ser Val Val Ser Val Thr Ser Ser Ser Gln Pro Val Thr Cys Asn
    210                 215                 220

Val Ala His Pro Ala Thr Asn Thr Lys Val Asp Lys Thr Val Ala Pro
225                 230                 235                 240

Ser Thr Cys Ser Lys Pro Met Cys Pro Pro Pro Glu Leu Pro Gly Gly
                245                 250                 255

Pro Ser Val Phe Ile Phe Pro Pro Lys Pro Lys Asp Thr Leu Met Ile
            260                 265                 270

Ser Arg Thr Pro Glu Val Thr Cys Val Val Val Asp Val Ser Gln Asp
        275                 280                 285

Asp Pro Glu Val Gln Phe Thr Trp Tyr Ile Asn Asn Glu Gln Val Arg
    290                 295                 300

Thr Ala Arg Pro Pro Leu Arg Glu Gln Gln Phe Asn Ser Thr Ile Arg
305                 310                 315                 320

Val Val Ser Thr Leu Pro Ile Ala His Gln Asp Trp Leu Arg Gly Lys
                325                 330                 335

Glu Phe Lys Cys Lys Val His Asn Lys Ala Leu Pro Ala Pro Ile Glu
            340                 345                 350

Lys Thr Ile Ser Lys Ala Arg Gly Gln Pro Leu Glu Pro Lys Val Tyr
        355                 360                 365

Thr Met Gly Pro Pro Arg Glu Glu Leu Ser Ser Arg Ser Val Ser Leu
    370                 375                 380

Thr Cys Met Ile Asn Gly Phe Tyr Pro Ser Asp Ile Ser Val Glu Trp
385                 390                 395                 400

Glu Lys Asn Gly Lys Ala Glu Asp Asn Tyr Lys Thr Thr Pro Thr Val
                405                 410                 415
```

Leu Asp Ser Asp Gly Ser Tyr Phe Leu Tyr Ser Lys Leu Ser Val Pro
420 425 430

Thr Ser Glu Trp Gln Arg Gly Asp Val Phe Thr Cys Ser Val Met His
435 440 445

Glu Ala Leu His Asn His Tyr Thr Gln Lys Ser Ile Ser Arg Ser Pro
450 455 460

Gly Lys
465

<210> SEQ ID NO 164
<211> LENGTH: 236
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 164

Met Asp Thr Arg Ala Pro Thr Gln Leu Leu Gly Leu Leu Leu Leu Trp
1 5 10 15

Leu Pro Gly Ala Arg Cys Ala Phe Glu Leu Thr Gln Thr Pro Ser Ser
20 25 30

Val Glu Ala Ala Val Gly Gly Thr Val Thr Ile Lys Cys Gln Ala Ser
35 40 45

Gln Ser Ile Ser Ser Tyr Leu Ser Trp Tyr Gln Gln Lys Pro Gly Gln
50 55 60

Pro Pro Lys Leu Leu Ile Tyr Arg Ala Ser Thr Leu Glu Ser Gly Val
65 70 75 80

Pro Ser Arg Phe Lys Gly Ser Gly Ser Gly Thr Glu Phe Thr Leu Thr
85 90 95

Ile Ser Asp Leu Glu Cys Ala Asp Ala Ala Thr Tyr Phe Cys Gln Ser
100 105 110

Tyr Tyr Gly Val Thr Phe Ser Gly Phe Ala Phe Gly Gly Gly Thr Glu
115 120 125

Val Val Val Lys Gly Asp Pro Val Ala Pro Thr Val Leu Ile Phe Pro
130 135 140

Pro Ala Ala Asp Gln Val Ala Thr Gly Thr Val Thr Ile Val Cys Val
145 150 155 160

Ala Asn Lys Tyr Phe Pro Asp Val Thr Val Thr Trp Glu Val Asp Gly
165 170 175

Thr Thr Gln Thr Thr Gly Ile Glu Asn Ser Lys Thr Pro Gln Asn Ser
180 185 190

Ala Asp Cys Thr Tyr Asn Leu Ser Ser Thr Leu Thr Leu Thr Ser Thr
195 200 205

Gln Tyr Asn Ser His Lys Glu Tyr Thr Cys Lys Val Thr Gln Gly Thr
210 215 220

Thr Ser Val Val Gln Ser Phe Asn Arg Gly Asp Cys
225 230 235

<210> SEQ ID NO 165
<211> LENGTH: 460
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 165

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Lys Ala Ser Gly Ile Asp Phe Asn
        35                  40                  45

Asn Tyr Trp Ile Thr Trp Val Arg Gln Ala Pro Gly Lys Gly Leu Glu
    50                  55                  60

Trp Ile Ala Cys Ile Tyr Val Gly Ile Thr Gly Arg Thr Trp Tyr Ala
65                  70                  75                  80

Asn Trp Ala Lys Gly Arg Phe Thr Ile Ser Lys Ala Ser Ser Thr Val
                85                  90                  95

Asp Leu Lys Met Thr Ser Leu Thr Ala Ala Asp Thr Ala Thr Tyr Phe
            100                 105                 110

Cys Ala Arg Asn Gly Asp Gly Gly Ile Tyr Ala Leu Asn Leu Trp Gly
        115                 120                 125

Pro Gly Thr Leu Val Thr Val Ser Ser Gly Gln Pro Lys Ala Pro Ser
    130                 135                 140

Val Phe Pro Leu Ala Pro Cys Cys Gly Asp Thr Pro Ser Ser Thr Val
145                 150                 155                 160

Thr Leu Gly Cys Leu Val Lys Gly Tyr Leu Pro Glu Pro Val Thr Val
                165                 170                 175

Thr Trp Asn Ser Gly Thr Leu Thr Asn Gly Val Arg Thr Phe Pro Ser
            180                 185                 190

Val Arg Gln Ser Ser Gly Leu Tyr Ser Leu Ser Ser Val Val Ser Val
        195                 200                 205

Thr Ser Ser Ser Gln Pro Val Thr Cys Asn Val Ala His Pro Ala Thr
    210                 215                 220

Asn Thr Lys Val Asp Lys Thr Val Ala Pro Ser Thr Cys Ser Lys Pro
225                 230                 235                 240

Met Cys Pro Pro Pro Glu Leu Pro Gly Gly Pro Ser Val Phe Ile Phe
                245                 250                 255

Pro Pro Lys Pro Lys Asp Thr Leu Met Ile Ser Arg Thr Pro Glu Val
            260                 265                 270

Thr Cys Val Val Val Asp Val Ser Gln Asp Asp Pro Glu Val Gln Phe
        275                 280                 285

Thr Trp Tyr Ile Asn Asn Glu Gln Val Arg Thr Ala Arg Pro Pro Leu
    290                 295                 300

Arg Glu Gln Gln Phe Asn Ser Thr Ile Arg Val Val Ser Thr Leu Pro
305                 310                 315                 320

Ile Ala His Gln Asp Trp Leu Arg Gly Lys Glu Phe Lys Cys Lys Val
                325                 330                 335

His Asn Lys Ala Leu Pro Ala Pro Ile Glu Lys Thr Ile Ser Lys Ala
            340                 345                 350

Arg Gly Gln Pro Leu Glu Pro Lys Val Tyr Thr Met Gly Pro Pro Arg
        355                 360                 365

Glu Glu Leu Ser Ser Arg Ser Val Ser Leu Thr Cys Met Ile Asn Gly
    370                 375                 380

Phe Tyr Pro Ser Asp Ile Ser Val Glu Trp Glu Lys Asn Gly Lys Ala
385                 390                 395                 400

Glu Asp Asn Tyr Lys Thr Thr Pro Thr Val Leu Asp Ser Asp Gly Ser
                405                 410                 415
```

Tyr Phe Leu Tyr Ser Lys Leu Ser Val Pro Thr Ser Glu Trp Gln Arg
420 425 430

Gly Asp Val Phe Thr Cys Ser Val Met His Glu Ala Leu His Asn His
435 440 445

Tyr Thr Gln Lys Ser Ile Ser Arg Ser Pro Gly Lys
450 455 460

<210> SEQ ID NO 166
<211> LENGTH: 238
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 166

Met Asp Thr Arg Ala Pro Thr Gln Leu Leu Gly Leu Leu Leu Leu Trp
1 5 10 15

Leu Pro Gly Ala Thr Phe Ala Gln Val Leu Thr Gln Thr Ala Ser Ser
20 25 30

Val Ser Ala Ala Val Gly Gly Thr Val Thr Ile Ser Cys Gln Ser Ser
35 40 45

Gln Ser Val Tyr Asn Asn Asn Trp Leu Ala Trp Tyr Gln Gln Lys Pro
50 55 60

Gly Gln Pro Pro Lys Leu Leu Ile Tyr Arg Ala Ser Thr Leu Thr Ser
65 70 75 80

Gly Val Pro Ser Arg Phe Lys Gly Ser Gly Ser Gly Thr Gln Phe Thr
85 90 95

Leu Thr Ile Ser Asp Leu Glu Cys Asp Asp Ala Ala Thr Tyr Tyr Cys
100 105 110

Ala Gly Gly Tyr Ser Gly Asn Ile Tyr Val Asn Asp Phe Gly Gly Gly
115 120 125

Thr Glu Val Val Val Lys Gly Asp Pro Val Ala Pro Thr Val Leu Ile
130 135 140

Phe Pro Pro Ala Ala Asp Gln Val Ala Thr Gly Thr Val Thr Ile Val
145 150 155 160

Cys Val Ala Asn Lys Tyr Phe Pro Asp Val Thr Val Thr Trp Glu Val
165 170 175

Asp Gly Thr Thr Gln Thr Thr Gly Ile Glu Asn Ser Lys Thr Pro Gln
180 185 190

Asn Ser Ala Asp Cys Thr Tyr Asn Leu Ser Ser Thr Leu Thr Leu Thr
195 200 205

Ser Thr Gln Tyr Asn Ser His Lys Glu Tyr Thr Cys Lys Val Thr Gln
210 215 220

Gly Thr Thr Ser Val Val Gln Ser Phe Asn Arg Gly Asp Cys
225 230 235

<210> SEQ ID NO 167
<211> LENGTH: 459
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 167

Met Glu Thr Gly Leu Arg Trp Leu Leu Leu Val Ala Val Leu Lys Gly
1 5 10 15

```
Val Gln Cys Gln Glu Gln Leu Glu Glu Ser Gly Gly Asp Leu Val Lys
            20                  25                  30

Pro Gly Gly Ser Leu Thr Leu Thr Cys Lys Ala Ser Gly Phe Ser Phe
        35                  40                  45

Ser Asn Thr Tyr Trp Ala Cys Trp Val Arg Gln Ala Pro Gly Lys Gly
    50                  55                  60

Leu Glu Trp Ile Ala Cys Met Asn Pro Ala Ser Ser Gly Ser Ser Tyr
65                  70                  75                  80

Tyr Ala Ser Trp Ala Lys Gly Arg Phe Thr Ile Ser Lys Thr Ser Ser
                85                  90                  95

Thr Thr Val Thr Leu His Met Pro Ser Leu Thr Ala Ala Asp Thr Ala
            100                 105                 110

Thr Tyr Phe Cys Ala Lys Trp Asp Thr Ala Phe Asp Val Trp Gly Pro
        115                 120                 125

Gly Thr Leu Val Thr Val Ser Ser Gly Gln Pro Lys Ala Pro Ser Val
    130                 135                 140

Phe Pro Leu Ala Pro Cys Cys Gly Asp Thr Pro Ser Ser Thr Val Thr
145                 150                 155                 160

Leu Gly Cys Leu Val Lys Gly Tyr Leu Pro Glu Pro Val Thr Val Thr
                165                 170                 175

Trp Asn Ser Gly Thr Leu Thr Asn Gly Val Arg Thr Phe Pro Ser Val
            180                 185                 190

Arg Gln Ser Ser Gly Leu Tyr Ser Leu Ser Ser Val Val Ser Val Thr
        195                 200                 205

Ser Ser Ser Gln Pro Val Thr Cys Asn Val Ala His Pro Ala Thr Asn
    210                 215                 220

Thr Lys Val Asp Lys Thr Val Ala Pro Ser Thr Cys Ser Lys Pro Met
225                 230                 235                 240

Cys Pro Pro Pro Glu Leu Pro Gly Gly Pro Ser Val Phe Ile Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Asp Asp Pro Glu Val Gln Phe Thr
        275                 280                 285

Trp Tyr Ile Asn Asn Glu Gln Val Arg Thr Ala Arg Pro Pro Leu Arg
    290                 295                 300

Glu Gln Gln Phe Asn Ser Thr Ile Arg Val Val Ser Thr Leu Pro Ile
305                 310                 315                 320

Ala His Gln Asp Trp Leu Arg Gly Lys Glu Phe Lys Cys Lys Val His
                325                 330                 335

Asn Lys Ala Leu Pro Ala Pro Ile Glu Lys Thr Ile Ser Lys Ala Arg
            340                 345                 350

Gly Gln Pro Leu Glu Pro Lys Val Tyr Thr Met Gly Pro Pro Arg Glu
        355                 360                 365

Glu Leu Ser Ser Arg Ser Val Ser Leu Thr Cys Met Ile Asn Gly Phe
    370                 375                 380

Tyr Pro Ser Asp Ile Ser Val Glu Trp Glu Lys Asn Gly Lys Ala Glu
385                 390                 395                 400

Asp Asn Tyr Lys Thr Thr Pro Thr Val Leu Asp Ser Asp Gly Ser Tyr
                405                 410                 415

Phe Leu Tyr Ser Lys Leu Ser Val Pro Thr Ser Glu Trp Gln Arg Gly
            420                 425                 430

Asp Val Phe Thr Cys Ser Val Met His Glu Ala Leu His Asn His Tyr
```

```
        435                 440                 445

Thr Gln Lys Ser Ile Ser Arg Ser Pro Gly Lys
    450                 455


<210> SEQ ID NO 168
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Met Asp Thr Arg Ala Pro Thr Gln Leu Leu Gly Leu Leu Leu Leu Trp
1               5                   10                  15

Leu Pro Gly Ala Arg Cys Ala Asp Val Val Met Thr Gln Thr Pro Ser
            20                  25                  30

Ser Val Glu Ala Ala Val Gly Gly Thr Val Thr Ile Lys Cys Gln Ala
        35                  40                  45

Ser Gln Ser Ile Ser Ser Tyr Leu Ala Trp Tyr Gln Gln Lys Pro Gly
    50                  55                  60

Gln Pro Pro Lys Leu Leu Ile Tyr Gly Ala Ser Asn Leu Glu Ser Gly
65                  70                  75                  80

Val Pro Ser Arg Phe Lys Gly Ser Gly Ser Gly Thr Glu Tyr Thr Leu
                85                  90                  95

Thr Ile Ser Gly Val Gln Cys Asp Asp Ala Ala Thr Tyr Tyr Cys Gln
            100                 105                 110

Asn Tyr Tyr Ala Ile Asp Thr Tyr Gly His Ala Phe Gly Gly Gly Thr
        115                 120                 125

Glu Val Val Val Lys Gly Asp Pro Val Ala Pro Thr Val Leu Ile Phe
    130                 135                 140

Pro Pro Ala Ala Asp Gln Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235


<210> SEQ ID NO 169
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Met Glu Thr Gly Leu Arg Trp Leu Leu Leu Val Ala Val Leu Lys Gly
1               5                   10                  15

Val Gln Cys Gln Glu Gln Leu Glu Glu Ser Gly Gly Asp Leu Val Lys
            20                  25                  30

Pro Gly Ala Ser Leu Thr Leu Thr Cys Thr Ala Ser Gly Phe Ser Phe
```

```
        35                  40                  45

Ser Ser Asn Tyr His Ile Cys Trp Val Arg Gln Ala Pro Gly Lys Gly
    50                  55                  60

Leu Glu Leu Ile Ala Cys Ile Tyr Val Gly Asp Gly Ser Thr Tyr Tyr
65                  70                  75                  80

Ala Ser Trp Ala Lys Gly Arg Phe Thr Ile Ser Lys Ser Ser Ser Thr
                85                  90                  95

Thr Val Ala Leu Gln Met Thr Ser Leu Thr Ala Ala Asp Thr Ala Thr
            100                 105                 110

Tyr Phe Cys Gly Arg Met Phe Asn Leu Trp Gly Pro Gly Thr Leu Val
        115                 120                 125

Thr Val Ser Ser Gly Gln Pro Lys Ala Pro Ser Val Phe Pro Leu Ala
    130                 135                 140

Pro Cys Cys Gly Asp Thr Pro Ser Ser Thr Val Thr Leu Gly Cys Leu
145                 150                 155                 160

Val Lys Gly Tyr Leu Pro Glu Pro Val Thr Val Thr Trp Asn Ser Gly
                165                 170                 175

Thr Leu Thr Asn Gly Val Arg Thr Phe Pro Ser Val Arg Gln Ser Ser
            180                 185                 190

Gly Leu Tyr Ser Leu Ser Ser Val Val Ser Val Thr Ser Ser Ser Gln
        195                 200                 205

Pro Val Thr Cys Asn Val Ala His Pro Ala Thr Asn Thr Lys Val Asp
    210                 215                 220

Lys Thr Val Ala Pro Ser Thr Cys Ser Lys Pro Met Cys Pro Pro Pro
225                 230                 235                 240

Glu Leu Pro Gly Gly Pro Ser Val Phe Ile Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Asp Asp Pro Glu Val Gln Phe Thr Trp Tyr Ile Asn
        275                 280                 285

Asn Glu Gln Val Arg Thr Ala Arg Pro Pro Leu Arg Glu Gln Gln Phe
    290                 295                 300

Asn Ser Thr Ile Arg Val Val Ser Thr Leu Pro Ile Ala His Gln Asp
305                 310                 315                 320

Trp Leu Arg Gly Lys Glu Phe Lys Cys Lys Val His Asn Lys Ala Leu
                325                 330                 335

Pro Ala Pro Ile Glu Lys Thr Ile Ser Lys Ala Arg Gly Gln Pro Leu
            340                 345                 350

Glu Pro Lys Val Tyr Thr Met Gly Pro Pro Arg Glu Glu Leu Ser Ser
        355                 360                 365

Arg Ser Val Ser Leu Thr Cys Met Ile Asn Gly Phe Tyr Pro Ser Asp
    370                 375                 380

Ile Ser Val Glu Trp Glu Lys Asn Gly Lys Ala Glu Asp Asn Tyr Lys
385                 390                 395                 400

Thr Thr Pro Thr Val Leu Asp Ser Asp Gly Ser Tyr Phe Leu Tyr Ser
                405                 410                 415

Lys Leu Ser Val Pro Thr Ser Glu Trp Gln Arg Gly Asp Val Phe Thr
            420                 425                 430

Cys Ser Val Met His Glu Ala Leu His Asn His Tyr Thr Gln Lys Ser
        435                 440                 445

Ile Ser Arg Ser Pro Gly Lys
    450                 455
```

<210> SEQ ID NO 170
<211> LENGTH: 235
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 170

```
Met Asp Thr Arg Ala Pro Thr Gln Leu Leu Gly Leu Leu Leu Leu Trp
1               5                   10                  15

Leu Pro Gly Ala Ile Cys Asp Pro Val Leu Thr Gln Thr Pro Ser Ser
            20                  25                  30

Val Ser Ala Ala Val Gly Val Thr Val Thr Ile Asn Cys Gln Ser Ser
        35                  40                  45

Pro Ser Val Tyr Ser Asn Tyr Leu Ser Trp Tyr Gln Gln Lys Pro Gly
    50                  55                  60

Gln Pro Pro Lys Leu Leu Ile Tyr Leu Ala Ser Thr Leu Ala Ser Gly
65                  70                  75                  80

Val Pro Ser Arg Phe Lys Gly Ser Gly Ser Gly Thr Gln Phe Thr Leu
                85                  90                  95

Thr Ile Ser Asp Val Gln Cys Asp Asp Ala Ala Thr Tyr Tyr Cys Ala
            100                 105                 110

Gly Thr Tyr Ser Gly Asn Ile Trp Ser Phe Gly Gly Gly Thr Glu Val
        115                 120                 125

Val Val Lys Gly Asp Pro Val Ala Pro Thr Val Leu Ile Phe Pro Pro
    130                 135                 140

Ala Ala Asp Gln Val Ala Thr Gly Thr Val Thr Ile Val Cys Val Ala
145                 150                 155                 160

Asn Lys Tyr Phe Pro Asp Val Thr Val Thr Trp Glu Val Asp Gly Thr
                165                 170                 175

Thr Gln Thr Thr Gly Ile Glu Asn Ser Lys Thr Pro Gln Asn Ser Ala
            180                 185                 190

Asp Cys Thr Tyr Asn Leu Ser Ser Thr Leu Thr Leu Thr Ser Thr Gln
        195                 200                 205

Tyr Asn Ser His Lys Glu Tyr Thr Cys Lys Val Thr Gln Gly Thr Thr
    210                 215                 220

Ser Val Val Gln Ser Phe Asn Arg Gly Asp Cys
225                 230                 235
```

<210> SEQ ID NO 171
<211> LENGTH: 460
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 171

```
Met Glu Thr Gly Leu Arg Trp Leu Leu Leu Val Ala Val Leu Lys Gly
1               5                   10                  15

Val Gln Cys Gln Gln Gln Leu Val Glu Ser Gly Gly Gly Leu Val Lys
            20                  25                  30

Pro Gly Ala Ser Leu Thr Leu Thr Cys Thr Ala Ser Gly Phe Ser Phe
        35                  40                  45

Ser Ser Gly Tyr His Met Cys Trp Val Arg Gln Ala Pro Gly Lys Gly
    50                  55                  60
```

```
Leu Glu Trp Ile Ala Cys Phe Gly Val Tyr Thr Gly Thr Thr Thr Tyr
65                  70                  75                  80

Ala Ser Trp Ala Lys Gly Arg Phe Thr Ile Ser Lys Thr Ser Ser Thr
                85                  90                  95

Thr Val Thr Leu Gln Met Thr Ser Leu Thr Val Ala Asp Thr Ala Thr
            100                 105                 110

Tyr Phe Cys Ala Arg Ile Ser Ala Glu Asn Gly Gly Asp Leu Trp Gly
        115                 120                 125

Pro Gly Thr Leu Val Thr Val Ser Ser Gly Gln Pro Lys Ala Pro Ser
    130                 135                 140

Val Phe Pro Leu Ala Pro Cys Cys Gly Asp Thr Pro Ser Ser Thr Val
145                 150                 155                 160

Thr Leu Gly Cys Leu Val Lys Gly Tyr Leu Pro Glu Pro Val Thr Val
                165                 170                 175

Thr Trp Asn Ser Gly Thr Leu Thr Asn Gly Val Arg Thr Phe Pro Ser
            180                 185                 190

Val Arg Gln Ser Ser Gly Leu Tyr Ser Leu Ser Ser Val Val Ser Val
        195                 200                 205

Thr Ser Ser Ser Gln Pro Val Thr Cys Asn Val Ala His Pro Ala Thr
    210                 215                 220

Asn Thr Lys Val Asp Lys Thr Val Ala Pro Ser Thr Cys Ser Lys Pro
225                 230                 235                 240

Met Cys Pro Pro Pro Glu Leu Pro Gly Gly Pro Ser Val Phe Ile Phe
                245                 250                 255

Pro Pro Lys Pro Lys Asp Thr Leu Met Ile Ser Arg Thr Pro Glu Val
            260                 265                 270

Thr Cys Val Val Val Asp Val Ser Gln Asp Asp Pro Glu Val Gln Phe
        275                 280                 285

Thr Trp Tyr Ile Asn Asn Glu Gln Val Arg Thr Ala Arg Pro Pro Leu
    290                 295                 300

Arg Glu Gln Gln Phe Asn Ser Thr Ile Arg Val Val Ser Thr Leu Pro
305                 310                 315                 320

Ile Ala His Gln Asp Trp Leu Arg Gly Lys Glu Phe Lys Cys Lys Val
                325                 330                 335

His Asn Lys Ala Leu Pro Ala Pro Ile Glu Lys Thr Ile Ser Lys Ala
            340                 345                 350

Arg Gly Gln Pro Leu Glu Pro Lys Val Tyr Thr Met Gly Pro Pro Arg
        355                 360                 365

Glu Glu Leu Ser Ser Arg Ser Val Ser Leu Thr Cys Met Ile Asn Gly
    370                 375                 380

Phe Tyr Pro Ser Asp Ile Ser Val Glu Trp Glu Lys Asn Gly Lys Ala
385                 390                 395                 400

Glu Asp Asn Tyr Lys Thr Thr Pro Thr Val Leu Asp Ser Asp Gly Ser
                405                 410                 415

Tyr Phe Leu Tyr Ser Lys Leu Ser Val Pro Thr Ser Glu Trp Gln Arg
            420                 425                 430

Gly Asp Val Phe Thr Cys Ser Val Met His Glu Ala Leu His Asn His
        435                 440                 445

Tyr Thr Gln Lys Ser Ile Ser Arg Ser Pro Gly Lys
    450                 455                 460
```

<210> SEQ ID NO 172
<211> LENGTH: 236

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 172

Met Asp Thr Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ala Ser
            20                  25                  30

Val Glu Ala Ala Val Gly Gly Thr Val Thr Ile Lys Cys Gln Ala Ser
        35                  40                  45

Gln Ser Ile Ser Asn Tyr Phe Ser Trp Tyr Gln Gln Lys Pro Gly Gln
    50                  55                  60

Pro Pro Lys Leu Leu Ile Tyr Arg Ala Ser Thr Leu Ala Ser Gly Val
65                  70                  75                  80

Pro Ser Arg Phe Ser Gly Ser Gly Ser Gly Thr Glu Phe Thr Leu Thr
                85                  90                  95

Ile Ser Asp Leu Glu Cys Ala Asp Ser Ala Thr Tyr Tyr Cys Gln Cys
            100                 105                 110

Thr Tyr Gly Ser Ser Ser Thr Gly Phe Gly Phe Gly Gly Gly Thr Glu
        115                 120                 125

Val Val Val Lys Gly Asp Pro Val Ala Pro Thr Val Pro Ile Phe Pro
    130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Asn Arg Gly Asp Cys
225                 230                 235

<210> SEQ ID NO 173
<211> LENGTH: 456
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 173

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Met Ala Ser Gly Ile Asp Phe Ser
        35                  40                  45

Ser Gly Tyr Gly Met Trp Trp Val Arg Gln Ala Pro Gly Lys Gly Leu
    50                  55                  60

Glu Tyr Ile Gly Tyr Ile Asp Thr Gly Asp Asp Asn Thr Tyr Tyr Ala
65                  70                  75                  80

Asn Trp Ala Lys Gly Arg Phe Thr Ile Ser Lys Thr Ser Ser Thr Thr
85 90 95

Val Thr Leu Gln Met Thr Ser Leu Thr Val Ala Asp Thr Ala Thr Tyr
100 105 110

Phe Cys Ala Lys Gly Gly Ala Ile Asp Leu Trp Gly Pro Gly Thr Leu
115 120 125

Val Thr Val Ser Ser Gly Gln Pro Lys Ala Pro Ser Val Phe Pro Leu
130 135 140

Ala Pro Cys Cys Gly Asp Thr Pro Ser Ser Thr Val Thr Leu Gly Cys
145 150 155 160

Leu Val Lys Gly Tyr Leu Pro Glu Pro Val Thr Val Thr Trp Asn Ser
165 170 175

Gly Thr Leu Thr Asn Gly Val Arg Thr Phe Pro Ser Val Arg Gln Ser
180 185 190

Ser Gly Leu Tyr Ser Leu Ser Ser Val Val Ser Val Thr Ser Ser Ser
195 200 205

Gln Pro Val Thr Cys Asn Val Ala His Pro Ala Thr Asn Thr Lys Val
210 215 220

Asp Lys Thr Val Ala Pro Ser Thr Cys Ser Lys Pro Met Cys Pro Pro
225 230 235 240

Pro Glu Leu Pro Gly Gly Pro Ser Val Phe Ile Phe Pro Pro Lys Pro
245 250 255

Lys Asp Thr Leu Met Ile Ser Arg Thr Pro Glu Val Thr Cys Val Val
260 265 270

Val Asp Val Ser Gln Asp Asp Pro Glu Val Gln Phe Thr Trp Tyr Ile
275 280 285

Asn Asn Glu Gln Val Arg Thr Ala Arg Pro Pro Leu Arg Glu Gln Gln
290 295 300

Phe Asn Ser Thr Ile Arg Val Val Ser Thr Leu Pro Ile Ala His Gln
305 310 315 320

Asp Trp Leu Arg Gly Lys Glu Phe Lys Cys Lys Val His Asn Lys Ala
325 330 335

Leu Pro Ala Pro Ile Glu Lys Thr Ile Ser Lys Ala Arg Gly Gln Pro
340 345 350

Leu Glu Pro Lys Val Tyr Thr Met Gly Pro Pro Arg Glu Glu Leu Ser
355 360 365

Ser Arg Ser Val Ser Leu Thr Cys Met Ile Asn Gly Phe Tyr Pro Ser
370 375 380

Asp Ile Ser Val Glu Trp Glu Lys Asn Gly Lys Ala Glu Asp Asn Tyr
385 390 395 400

Lys Thr Thr Pro Thr Val Leu Asp Ser Asp Gly Ser Tyr Phe Leu Tyr
405 410 415

Ser Lys Leu Ser Val Pro Thr Ser Glu Trp Gln Arg Gly Asp Val Phe
420 425 430

Thr Cys Ser Val Met His Glu Ala Leu His Asn His Tyr Thr Gln Lys
435 440 445

Ser Ile Ser Arg Ser Pro Gly Lys
450 455

<210> SEQ ID NO 174
<211> LENGTH: 239
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 174

Met Asp Thr Arg Ala Pro Thr Gln Leu Leu Gly Leu Leu Leu Leu Trp
1 5 10 15

Leu Pro Gly Ala Arg Cys Ala Asp Ile Val Met Thr Gln Thr Pro Ala
20 25 30

Ser Val Glu Ala Ala Val Gly Gly Thr Val Thr Ile Lys Cys Gln Ala
35 40 45

Ser Gln Ser Ile Ser Ser Tyr Leu Ala Trp Tyr Gln Gln Lys Pro Gly
50 55 60

Gln Arg Pro Lys Leu Leu Ile Tyr Arg Ala Ser Thr Leu Lys Ser Gly
65 70 75 80

Val Pro Ser Arg Phe Lys Gly Ser Gly Ser Gly Thr Glu Tyr Thr Leu
85 90 95

Thr Ile Ser Asp Leu Glu Cys Ala Asp Ala Ala Thr Tyr Tyr Cys Gln
100 105 110

Ala Tyr Tyr Leu Ser Ser Ser Ile Ser Tyr Gly Asn Thr Phe Gly Gly
115 120 125

Gly Thr Glu Val Val Val Lys Gly Asp Pro Val Ala Pro Thr Val Leu
130 135 140

Ile Phe Pro Pro Ala Ala Asp Gln Val Ala Thr Gly Thr Val Thr Ile
145 150 155 160

Val Cys Val Ala Asn Lys Tyr Phe Pro Asp Val Thr Val Thr Trp Glu
165 170 175

Val Asp Gly Thr Thr Gln Thr Thr Gly Ile Glu Asn Ser Lys Thr Pro
180 185 190

Gln Asn Ser Ala Asp Cys Thr Tyr Asn Leu Ser Ser Thr Leu Thr Leu
195 200 205

Thr Ser Thr Gln Tyr Asn Ser His Lys Glu Tyr Thr Cys Lys Val Thr
210 215 220

Gln Gly Thr Thr Ser Val Val Gln Ser Phe Asn Arg Gly Asp Cys
225 230 235

<210> SEQ ID NO 175
<211> LENGTH: 456
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 175

Met Glu Thr Gly Leu Arg Trp Leu Leu Leu Val Ala Val Leu Lys Gly
1 5 10 15

Val Gln Cys Gln Ser Leu Glu Glu Ser Gly Gly Asp Leu Val Lys Pro
20 25 30

Gly Ala Ser Leu Thr Leu Thr Cys Thr Ala Ser Gly Phe Ser Leu Ser
35 40 45

Ser Gly Tyr Gly Met Cys Trp Val Arg Gln Ala Pro Gly Lys Gly Leu
50 55 60

Glu Trp Ile Gly Tyr Thr Asp Thr Ala Thr Gly Thr Ile His Tyr Ala
65 70 75 80

Ser Trp Ala Lys Gly Arg Phe Thr Ile Ser Lys Thr Ser Ser Thr Thr
85 90 95

Val Thr Leu Gln Met Thr Ser Leu Thr Ala Ala Asp Thr Ala Thr Tyr

```
            100                 105                 110

Phe Cys Ala Lys Gly Gly Ala Met Asp Leu Trp Gly Pro Gly Thr Leu
        115                 120                 125

Val Thr Val Ser Ser Gly Gln Pro Lys Ala Pro Ser Val Phe Pro Leu
    130                 135                 140

Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
                165                 170                 175

Gly Thr Leu Thr Asn Gly Val Arg Thr Phe Pro Ser Val Arg Gln Ser
            180                 185                 190

Ser Gly Leu Tyr Ser Leu Ser Ser Val Val Ser Val Thr Ser Ser Ser
        195                 200                 205

Gln Pro Val Thr Cys Asn Val Ala His Pro Ala Thr Asn Thr Lys Val
    210                 215                 220

Asp Lys Thr Val Ala Pro Ser Thr Cys Ser Lys Pro Met Cys Pro Pro
225                 230                 235                 240

Pro Glu Leu Pro Gly Gly Pro Ser Val Phe Ile Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Asp Asp Pro Glu Val Gln Phe Thr Trp Tyr Ile
        275                 280                 285

Asn Asn Glu Gln Val Arg Thr Ala Arg Pro Pro Leu Arg Glu Gln Gln
    290                 295                 300

Phe Asn Ser Thr Ile Arg Val Val Ser Thr Leu Pro Ile Ala His Gln
305                 310                 315                 320

Asp Trp Leu Arg Gly Lys Glu Phe Lys Cys Lys Val His Asn Lys Ala
                325                 330                 335

Leu Pro Ala Pro Ile Glu Lys Thr Ile Ser Lys Ala Arg Gly Gln Pro
            340                 345                 350

Leu Glu Pro Lys Val Tyr Thr Met Gly Pro Pro Arg Glu Glu Leu Ser
        355                 360                 365

Ser Arg Ser Val Ser Leu Thr Cys Met Ile Asn Gly Phe Tyr Pro Ser
    370                 375                 380

Asp Ile Ser Val Glu Trp Glu Lys Asn Gly Lys Ala Glu Asp Asn Tyr
385                 390                 395                 400

Lys Thr Thr Pro Thr Val Leu Asp Ser Asp Gly Ser Tyr Phe Leu Tyr
                405                 410                 415

Ser Lys Leu Ser Val Pro Thr Ser Glu Trp Gln Arg Gly Asp Val Phe
            420                 425                 430

Thr Cys Ser Val Met His Glu Ala Leu His Asn His Tyr Thr Gln Lys
        435                 440                 445

Ser Ile Ser Arg Ser Pro Gly Lys
    450                 455


<210> SEQ ID NO 176
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176
```

```
Met Asp Thr Arg Ala Pro Thr Gln Leu Leu Gly Leu Leu Leu Leu Trp
1               5                   10                  15

Leu Pro Gly Ala Arg Cys Ala Asp Ile Val Met Thr Gln Thr Pro Ala
            20                  25                  30

Ser Val Glu Ala Ala Val Gly Gly Thr Val Thr Ile Lys Cys Gln Ala
        35                  40                  45

Ser Gln Ser Ile Ser Ser Tyr Leu Ala Trp Tyr Gln Gln Lys Pro Gly
    50                  55                  60

Gln Pro Pro Lys Leu Leu Ile Tyr Arg Thr Ser Thr Leu Ala Ser Gly
65                  70                  75                  80

Val Pro Ser Arg Phe Lys Gly Ser Gly Ser Gly Thr Glu Tyr Thr Leu
                85                  90                  95

Thr Ile Ser Asp Leu Glu Cys Ala Asp Ala Ala Thr Tyr Tyr Cys Gln
            100                 105                 110

Ser Tyr Ala Tyr Ser Ser Ser Ser Ser Tyr Gly Asn Ala Phe Gly Gly
        115                 120                 125

Gly Thr Glu Val Val Val Lys Gly Asp Pro Val Ala Pro Thr Val Leu
    130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235
```

<210> SEQ ID NO 177
<211> LENGTH: 454
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 177

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Thr Gly Ser Gly Ile Asp Phe Ser
        35                  40                  45

Ser Ser Tyr Trp Ile Cys Trp Val Arg Gln Ala Pro Gly Lys Gly Leu
    50                  55                  60

Glu Trp Ile Ala Cys Ile Asp Gly Ser Asp Gly Asn Thr Tyr Tyr Ala
65                  70                  75                  80

Ser Trp Ala Arg Gly Arg Phe Thr Ile Ser Lys Thr Ser Ser Thr Thr
                85                  90                  95

Val Thr Leu Gln Met Ala Ser Leu Thr Ala Ala Asp Thr Ala Thr Tyr
            100                 105                 110

Phe Cys Thr Arg Asp Leu Arg Leu Trp Gly Pro Gly Thr Leu Val Thr
        115                 120                 125
```

Val Ser Ser Gly Gln Pro Lys Ala Pro Ser Val Phe Pro Leu Ala Pro
130 135 140

Cys Cys Gly Asp Thr Pro Ser Ser Thr Val Thr Leu Gly Cys Leu Val
145 150 155 160

Lys Gly Tyr Leu Pro Glu Pro Val Thr Val Thr Trp Asn Ser Gly Thr
165 170 175

Leu Thr Asn Gly Val Arg Thr Phe Pro Ser Val Arg Gln Ser Ser Gly
180 185 190

Leu Tyr Ser Leu Ser Ser Val Val Ser Val Thr Ser Ser Ser Gln Pro
195 200 205

Val Thr Cys Asn Val Ala His Pro Ala Thr Asn Thr Lys Val Asp Lys
210 215 220

Thr Val Ala Pro Ser Thr Cys Ser Lys Pro Met Cys Pro Pro Pro Glu
225 230 235 240

Leu Pro Gly Gly Pro Ser Val Phe Ile Phe Pro Pro Lys Pro Lys Asp
245 250 255

Thr Leu Met Ile Ser Arg Thr Pro Glu Val Thr Cys Val Val Val Asp
260 265 270

Val Ser Gln Asp Asp Pro Glu Val Gln Phe Thr Trp Tyr Ile Asn Asn
275 280 285

Glu Gln Val Arg Thr Ala Arg Pro Pro Leu Arg Glu Gln Gln Phe Asn
290 295 300

Ser Thr Ile Arg Val Val Ser Thr Leu Pro Ile Ala His Gln Asp Trp
305 310 315 320

Leu Arg Gly Lys Glu Phe Lys Cys Lys Val His Asn Lys Ala Leu Pro
325 330 335

Ala Pro Ile Glu Lys Thr Ile Ser Lys Ala Arg Gly Gln Pro Leu Glu
340 345 350

Pro Lys Val Tyr Thr Met Gly Pro Pro Arg Glu Glu Leu Ser Ser Arg
355 360 365

Ser Val Ser Leu Thr Cys Met Ile Asn Gly Phe Tyr Pro Ser Asp Ile
370 375 380

Ser Val Glu Trp Glu Lys Asn Gly Lys Ala Glu Asp Asn Tyr Lys Thr
385 390 395 400

Thr Pro Thr Val Leu Asp Ser Asp Gly Ser Tyr Phe Leu Tyr Ser Lys
405 410 415

Leu Ser Val Pro Thr Ser Glu Trp Gln Arg Gly Asp Val Phe Thr Cys
420 425 430

Ser Val Met His Glu Ala Leu His Asn His Tyr Thr Gln Lys Ser Ile
435 440 445

Ser Arg Ser Pro Gly Lys
450

<210> SEQ ID NO 178
<211> LENGTH: 240
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 178

Met Asp Thr Arg Ala Pro Thr Gln Leu Leu Gly Leu Leu Leu Leu Trp
1 5 10 15

Leu Pro Gly Ala Arg Cys Ala Asp Ile Val Leu Thr Gln Thr Pro Ala

```
            20                  25                  30

Ser Val Ser Ala Ala Val Gly Gly Thr Val Thr Ile Asn Cys Gln Ala
        35                  40                  45

Ser Gln Asn Val Tyr Ser Asn Asn Ala Leu Ala Trp His Gln Gln Lys
    50                  55                  60

Pro Gly Gln Arg Pro Asn Leu Leu Ile Tyr Lys Ala Ser Thr Leu Ala
65                  70                  75                  80

Ser Gly Val Pro Ser Arg Phe Lys Gly Ser Gly Ser Gly Thr Gln Phe
                85                  90                  95

Thr Leu Thr Ile Ser Asp Val Gln Cys Asp Asp Ala Ala Thr Tyr Tyr
            100                 105                 110

Cys Leu Gly Glu Phe Ser Cys Ser Ser Gly Asp Cys Phe Val Phe Gly
        115                 120                 125

Gly Gly Thr Glu Val Val Val Lys Gly Asp Pro Val Ala Pro Thr Val
    130                 135                 140

Leu Ile Phe Pro Pro Ala Ala Asp Gln Val Ala Thr Gly Thr Val Thr
145                 150                 155                 160

Ile Val Cys Val Ala Asn Lys Tyr Phe Pro Asp Val Thr Val Thr Trp
                165                 170                 175

Glu Val Asp Gly Thr Thr Gln Thr Thr Gly Ile Glu Asn Ser Lys Thr
            180                 185                 190

Pro Gln Asn Ser Ala Asp Cys Thr Tyr Asn Leu Ser Ser Thr Leu Thr
        195                 200                 205

Leu Thr Ser Thr Gln Tyr Asn Ser His Lys Glu Tyr Thr Cys Lys Val
    210                 215                 220

Thr Gln Gly Thr Thr Ser Val Val Gln Ser Phe Asn Arg Gly Asp Cys
225                 230                 235                 240


<210> SEQ ID NO 179
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Met Ala Ser Gly Ile Asp Phe Ser
        35                  40                  45

Ser Gly Tyr Gly Met Trp Trp Val Arg Gln Ala Pro Gly Lys Gly Leu
    50                  55                  60

Glu Tyr Ile Gly Tyr Ile Asp Thr Gly Asp Asp Asn Thr Tyr Tyr Ala
65                  70                  75                  80

Asn Trp Ala Lys Gly Arg Phe Thr Ile Ser Lys Thr Ser Ser Thr Thr
                85                  90                  95

Val Thr Leu Gln Met Thr Ser Leu Thr Val Ala Asp Thr Ala Thr Tyr
            100                 105                 110

Phe Cys Ala Lys Gly Gly Ala Ile Asp Leu Trp Gly Pro Gly Thr Leu
        115                 120                 125

Val Thr Val Ser Ser Gly Gln Pro Lys Ala Pro Ser Val Phe Pro Leu
    130                 135                 140
```

Ala Pro Cys Cys Gly Asp Thr Pro Ser Ser Thr Val Thr Leu Gly Cys
145 150 155 160

Leu Val Lys Gly Tyr Leu Pro Glu Pro Val Thr Val Thr Trp Asn Ser
165 170 175

Gly Thr Leu Thr Asn Gly Val Arg Thr Phe Pro Ser Val Arg Gln Ser
180 185 190

Ser Gly Leu Tyr Ser Leu Ser Ser Val Val Ser Val Thr Ser Ser Ser
195 200 205

Gln Pro Val Thr Cys Asn Val Ala His Pro Ala Thr Asn Thr Lys Val
210 215 220

Asp Lys Thr Val Ala Pro Ser Thr Cys Ser Lys Pro Met Cys Pro Pro
225 230 235 240

Pro Glu Leu Pro Gly Gly Pro Ser Val Phe Ile Phe Pro Pro Lys Pro
245 250 255

Lys Asp Thr Leu Met Ile Ser Arg Thr Pro Glu Val Thr Cys Val Val
260 265 270

Val Asp Val Ser Gln Asp Asp Pro Glu Val Gln Phe Thr Trp Tyr Ile
275 280 285

Asn Asn Glu Gln Val Arg Thr Ala Arg Pro Pro Leu Arg Glu Gln Gln
290 295 300

Phe Asn Ser Thr Ile Arg Val Val Ser Thr Leu Pro Ile Ala His Gln
305 310 315 320

Asp Trp Leu Arg Gly Lys Glu Phe Lys Cys Lys Val His Asn Lys Ala
325 330 335

Leu Pro Ala Pro Ile Glu Lys Thr Ile Ser Lys Ala Arg Gly Gln Pro
340 345 350

Leu Glu Pro Lys Val Tyr Thr Met Gly Pro Pro Arg Glu Glu Leu Ser
355 360 365

Ser Arg Ser Val Ser Leu Thr Cys Met Ile Asn Gly Phe Tyr Pro Ser
370 375 380

Asp Ile Ser Val Glu Trp Glu Lys Asn Gly Lys Ala Glu Asp Asn Tyr
385 390 395 400

Lys Thr Thr Pro Thr Val Leu Asp Ser Asp Gly Ser Tyr Phe Leu Tyr
405 410 415

Ser Lys Leu Ser Val Pro Thr Ser Glu Trp Gln Arg Gly Asp Val Phe
420 425 430

Thr Cys Ser Val Met His Glu Ala Leu His Asn His Tyr Thr Gln Lys
435 440 445

Ser Ile Ser Arg Ser Pro Gly Lys
450 455

<210> SEQ ID NO 180
<211> LENGTH: 239
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 180

Met Asp Thr Arg Ala Pro Thr Gln Leu Leu Gly Leu Leu Leu Leu Trp
1 5 10 15

Leu Pro Gly Ala Arg Cys Ala Asp Ile Val Met Thr Gln Thr Pro Ala
20 25 30

Ser Val Glu Ala Ala Val Gly Gly Thr Val Thr Ile Lys Cys Gln Ala
35 40 45

Ser Gln Ser Ile Ser Ser Tyr Leu Ala Trp Tyr Gln Gln Lys Pro Gly
    50                  55                  60

Gln Arg Pro Lys Leu Leu Ile Tyr Arg Ala Ser Thr Leu Lys Ser Gly
65                  70                  75                  80

Val Pro Ser Arg Phe Lys Gly Ser Gly Ser Gly Thr Glu Tyr Thr Leu
                85                  90                  95

Thr Ile Ser Asp Leu Glu Cys Ala Asp Ala Ala Thr Tyr Tyr Cys Gln
            100                 105                 110

Ala Tyr Tyr Leu Ser Ser Ser Ile Ser Tyr Gly Asn Thr Phe Gly Gly
        115                 120                 125

Gly Thr Glu Val Val Val Lys Gly Asp Pro Val Ala Pro Thr Val Leu
    130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235

<210> SEQ ID NO 181
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Met Glu Thr Gly Leu Arg Trp Leu Leu Leu Val Ala Val Leu Lys Gly
1               5                   10                  15

Val Gln Cys Gln Gln Gln Leu Glu Glu Ser Gly Gly Gly Leu Val Lys
            20                  25                  30

Pro Gly Gly Thr Leu Thr Leu Thr Cys Lys Ala Ser Gly Val Ala Leu
        35                  40                  45

Asn Pro Tyr Tyr Tyr Met Cys Trp Val Arg Gln Ala Pro Gly Lys Gly
    50                  55                  60

Leu Glu Trp Ile Ala Cys Val Asp Ala Asp Ser Ser Gly Ser Thr Tyr
65                  70                  75                  80

Tyr Ala Ser Trp Ala Lys Gly Arg Phe Thr Ile Ser Lys Thr Ser Ser
                85                  90                  95

Thr Thr Val Thr Leu Lys Met Thr Ser Leu Thr Ala Ala Asp Thr Ala
            100                 105                 110

Thr Tyr Phe Cys Ala Arg Glu Ser Val Asp Tyr Ser Ser Val Gly Ile
        115                 120                 125

Gly Tyr Val His Gly Thr Asp Gly Leu Trp Gly Pro Gly Thr Leu Val
    130                 135                 140

Thr Val Ser Ser Gly Gln Pro Lys Ala Pro Ser Val Phe Pro Leu Ala
145                 150                 155                 160

Pro Cys Cys Gly Asp Thr Pro Ser Ser Thr Val Thr Leu Gly Cys Leu

```
                165                 170                 175

Val Lys Gly Tyr Leu Pro Glu Pro Val Thr Val Thr Trp Asn Ser Gly
            180                 185                 190

Thr Leu Thr Asn Gly Val Arg Thr Phe Pro Ser Val Arg Gln Ser Ser
        195                 200                 205

Gly Leu Tyr Ser Leu Ser Ser Val Val Ser Val Thr Ser Ser Ser Gln
    210                 215                 220

Pro Val Thr Cys Asn Val Ala His Pro Ala Thr Asn Thr Lys Val Asp
225                 230                 235                 240

Lys Thr Val Ala Pro Ser Thr Cys Ser Lys Pro Met Cys Pro Pro Pro
                245                 250                 255

Glu Leu Pro Gly Gly Pro Ser Val Phe Ile Phe Pro Pro Lys Pro Lys
            260                 265                 270

Asp Thr Leu Met Ile Ser Arg Thr Pro Glu Val Thr Cys Val Val Val
        275                 280                 285

Asp Val Ser Gln Asp Asp Pro Glu Val Gln Phe Thr Trp Tyr Ile Asn
    290                 295                 300

Asn Glu Gln Val Arg Thr Ala Arg Pro Pro Leu Arg Glu Gln Gln Phe
305                 310                 315                 320

Asn Ser Thr Ile Arg Val Val Ser Thr Leu Pro Ile Ala His Gln Asp
                325                 330                 335

Trp Leu Arg Gly Lys Glu Phe Lys Cys Lys Val His Asn Lys Ala Leu
            340                 345                 350

Pro Ala Pro Ile Glu Lys Thr Ile Ser Lys Ala Arg Gly Gln Pro Leu
        355                 360                 365

Glu Pro Lys Val Tyr Thr Met Gly Pro Pro Arg Glu Glu Leu Ser Ser
    370                 375                 380

Arg Ser Val Ser Leu Thr Cys Met Ile Asn Gly Phe Tyr Pro Ser Asp
385                 390                 395                 400

Ile Ser Val Glu Trp Glu Lys Asn Gly Lys Ala Glu Asp Asn Tyr Lys
                405                 410                 415

Thr Thr Pro Thr Val Leu Asp Ser Asp Gly Ser Tyr Phe Leu Tyr Ser
            420                 425                 430

Lys Leu Ser Val Pro Thr Ser Glu Trp Gln Arg Gly Asp Val Phe Thr
        435                 440                 445

Cys Ser Val Met His Glu Ala Leu His Asn His Tyr Thr Gln Lys Ser
    450                 455                 460

Ile Ser Arg Ser Pro Gly Lys
465                 470


<210> SEQ ID NO 182
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Met Asp Thr Arg Ala Pro Thr Gln Leu Leu Gly Leu Leu Leu Leu Trp
1               5                   10                  15

Leu Pro Gly Ala Arg Cys Ala Asp Ile Val Val Thr Gln Thr Pro Ser
            20                  25                  30

Ser Val Ser Ala Ala Val Gly Gly Thr Val Thr Ile Lys Cys Gln Ala
        35                  40                  45
```

Ser Gln Ser Ile Ser Asn Tyr Phe Ser Trp Tyr Gln Gln Lys Pro Gly
50 55 60

Gln Pro Pro Lys Leu Leu Ile Tyr Arg Ala Ser Thr Leu Ala Ser Gly
65 70 75 80

Val Pro Ser Arg Phe Lys Gly Ser Gly Ser Gly Thr Glu Phe Thr Leu
85 90 95

Thr Ile Ser Asp Leu Glu Cys Ala Asp Ala Ala Thr Tyr Tyr Cys Gln
100 105 110

Cys Thr Tyr Gly Arg Ser Asn Ser Asn Phe Phe Tyr Gly Phe Gly Gly
115 120 125

Gly Thr Glu Val Val Val Lys Gly Asp Pro Val Ala Pro Thr Val Leu
130 135 140

Ile Phe Pro Pro Ala Ala Asp Gln Val Ala Thr Gly Thr Val Thr Ile
145 150 155 160

Val Cys Val Ala Asn Lys Tyr Phe Pro Asp Val Thr Val Thr Trp Glu
165 170 175

Val Asp Gly Thr Thr Gln Thr Thr Gly Ile Glu Asn Ser Lys Thr Pro
180 185 190

Gln Asn Ser Ala Asp Cys Thr Tyr Asn Leu Ser Ser Thr Leu Thr Leu
195 200 205

Thr Ser Thr Gln Tyr Asn Ser His Lys Glu Tyr Thr Cys Lys Val Thr
210 215 220

Gln Gly Thr Thr Ser Val Val Gln Ser Phe Asn Arg Gly Asp Cys
225 230 235

<210> SEQ ID NO 183
<211> LENGTH: 464
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 183

Met Glu Thr Gly Leu Arg Trp Leu Leu Leu Val Ala Val Leu Lys Gly
1 5 10 15

Val Gln Cys Gln Ser Leu Glu Glu Ser Gly Gly Asp Leu Val Lys Pro
20 25 30

Gly Ala Ser Leu Thr Leu Thr Cys Thr Ala Ser Gly Ser Ser Phe Ser
35 40 45

Ser Thr Tyr Trp Asn Cys Trp Val Arg Gln Ala Pro Gly Lys Gly Leu
50 55 60

Glu Trp Ile Ala Cys Ile Asn Ala Gly Ser Gly Thr Thr Tyr Tyr Ala
65 70 75 80

Ser Trp Ala Lys Gly Arg Phe Thr Val Ser Lys Thr Ser Ser Thr Thr
85 90 95

Val Thr Leu Gln Met Thr Ser Leu Thr Ala Ala Asp Thr Ala Thr Tyr
100 105 110

Phe Cys Thr Arg Asp Ser Asp Gly Arg Phe Ser Ser Gly Tyr Tyr Phe
115 120 125

Asn Leu Trp Gly Pro Gly Thr Leu Val Thr Val Ser Ser Gly Gln Pro
130 135 140

Lys Ala Pro Ser Val Phe Pro Leu Ala Pro Cys Cys Gly Asp Thr Pro
145 150 155 160

Ser Ser Thr Val Thr Leu Gly Cys Leu Val Lys Gly Tyr Leu Pro Glu
165 170 175

Pro Val Thr Val Thr Trp Asn Ser Gly Thr Leu Thr Asn Gly Val Arg
180 185 190

Thr Phe Pro Ser Val Arg Gln Ser Ser Gly Leu Tyr Ser Leu Ser Ser
195 200 205

Val Val Ser Val Thr Ser Ser Ser Gln Pro Val Thr Cys Asn Val Ala
210 215 220

His Pro Ala Thr Asn Thr Lys Val Asp Lys Thr Val Ala Pro Ser Thr
225 230 235 240

Cys Ser Lys Pro Met Cys Pro Pro Pro Glu Leu Pro Gly Gly Pro Ser
245 250 255

Val Phe Ile Phe Pro Pro Lys Pro Lys Asp Thr Leu Met Ile Ser Arg
260 265 270

Thr Pro Glu Val Thr Cys Val Val Val Asp Val Ser Gln Asp Asp Pro
275 280 285

Glu Val Gln Phe Thr Trp Tyr Ile Asn Asn Glu Gln Val Arg Thr Ala
290 295 300

Arg Pro Pro Leu Arg Glu Gln Gln Phe Asn Ser Thr Ile Arg Val Val
305 310 315 320

Ser Thr Leu Pro Ile Ala His Gln Asp Trp Leu Arg Gly Lys Glu Phe
325 330 335

Lys Cys Lys Val His Asn Lys Ala Leu Pro Ala Pro Ile Glu Lys Thr
340 345 350

Ile Ser Lys Ala Arg Gly Gln Pro Leu Glu Pro Lys Val Tyr Thr Met
355 360 365

Gly Pro Pro Arg Glu Glu Leu Ser Ser Arg Ser Val Ser Leu Thr Cys
370 375 380

Met Ile Asn Gly Phe Tyr Pro Ser Asp Ile Ser Val Glu Trp Glu Lys
385 390 395 400

Asn Gly Lys Ala Glu Asp Asn Tyr Lys Thr Thr Pro Thr Val Leu Asp
405 410 415

Ser Asp Gly Ser Tyr Phe Leu Tyr Ser Lys Leu Ser Val Pro Thr Ser
420 425 430

Glu Trp Gln Arg Gly Asp Val Phe Thr Cys Ser Val Met His Glu Ala
435 440 445

Leu His Asn His Tyr Thr Gln Lys Ser Ile Ser Arg Ser Pro Gly Lys
450 455 460

<210> SEQ ID NO 184
<211> LENGTH: 238
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 184

Met Asp Thr Arg Ala Pro Thr Gln Leu Leu Gly Leu Leu Leu Leu Trp
1 5 10 15

Leu Pro Gly Ala Thr Phe Ala Gln Val Leu Thr Gln Thr Ala Ser Pro
20 25 30

Val Ser Ala Ala Val Gly Gly Thr Val Thr Ile Asn Cys Gln Ser Ser
35 40 45

Gln Ser Val Tyr Asp Asn Asn Trp Leu Ala Trp Tyr Gln Gln Lys Pro
50 55 60

Gly Gln Pro Pro Lys Leu Leu Ile Asp Asp Ala Ser Lys Leu Thr Ser

```
65                  70                  75                  80

Gly Val Ser Ser Arg Phe Lys Gly Ser Gly Ser Gly Thr Gln Phe Thr
                85                  90                  95

Leu Thr Ile Ser Gly Val Gln Cys Asp Asp Ala Ala Thr Tyr Tyr Cys
            100                 105                 110

Gln Gly Ala Tyr Tyr Ser Ser Gly Trp Tyr Trp Ala Phe Gly Gly Gly
        115                 120                 125

Thr Glu Val Val Val Lys Gly Asp Pro Val Ala Pro Thr Val Leu Ile
    130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235


<210> SEQ ID NO 185
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Met Glu Thr Gly Leu Arg Trp Leu Leu Leu Val Ala Val Leu Lys Gly
1               5                   10                  15

Val Gln Cys Gln Gln Gln Leu Glu Glu Ser Gly Gly Gly Leu Val Lys
            20                  25                  30

Pro Gly Gly Thr Leu Thr Leu Thr Cys Lys Ala Ser Gly Ile Asp Phe
        35                  40                  45

Ser Ser Tyr Tyr Tyr Met Cys Trp Val Arg Gln Ala Pro Gly Lys Gly
    50                  55                  60

Leu Glu Leu Ile Val Cys Ile Tyr Thr Ser Ser Gly Gly Thr Trp Tyr
65                  70                  75                  80

Ala Ser Trp Val Asn Gly Arg Leu Thr Ile Ser Arg Ser Thr Ser Leu
                85                  90                  95

Asn Thr Val Asp Leu Lys Met Thr Ser Leu Thr Ala Ala Asp Thr Ala
            100                 105                 110

Thr Tyr Phe Cys Ala Arg Gly Val Tyr Ser Gly Ser Ser Asp Tyr Pro
        115                 120                 125

Thr Arg Leu Asp Leu Trp Gly Gln Gly Thr Leu Val Thr Val Ser Leu
    130                 135                 140

Gly Gln Pro Lys Ala Pro Ser Val Phe Pro Leu Ala Pro Cys Cys Gly
145                 150                 155                 160

Asp Thr Pro Ser Ser Thr Val Thr Leu Gly Cys Leu Val Lys Gly Tyr
                165                 170                 175

Leu Pro Glu Pro Val Thr Val Thr Trp Asn Ser Gly Thr Leu Thr Asn
            180                 185                 190
```

Gly Val Arg Thr Phe Pro Ser Val Arg Gln Ser Ser Gly Leu Tyr Ser
195 200 205

Leu Ser Ser Val Val Ser Val Thr Ser Ser Ser Gln Pro Val Thr Cys
210 215 220

Asn Val Ala His Pro Ala Thr Asn Thr Lys Val Asp Lys Thr Val Ala
225 230 235 240

Pro Ser Thr Cys Ser Lys Pro Met Cys Pro Pro Pro Glu Leu Pro Gly
245 250 255

Gly Pro Ser Val Phe Ile Phe Pro Pro Lys Pro Lys Asp Thr Leu Met
260 265 270

Ile Ser Arg Thr Pro Glu Val Thr Cys Val Val Val Asp Val Ser Gln
275 280 285

Asp Asp Pro Glu Val Gln Phe Thr Trp Tyr Ile Asn Asn Glu Gln Val
290 295 300

Arg Thr Ala Arg Pro Pro Leu Arg Glu Gln Gln Phe Asn Ser Thr Ile
305 310 315 320

Arg Val Val Ser Thr Leu Pro Ile Ala His Gln Asp Trp Leu Arg Gly
325 330 335

Lys Glu Phe Lys Cys Lys Val His Asn Lys Ala Leu Pro Ala Pro Ile
340 345 350

Glu Lys Thr Ile Ser Lys Ala Arg Gly Gln Pro Leu Glu Pro Lys Val
355 360 365

Tyr Thr Met Gly Pro Pro Arg Glu Glu Leu Ser Ser Arg Ser Val Ser
370 375 380

Leu Thr Cys Met Ile Asn Gly Phe Tyr Pro Ser Asp Ile Ser Val Glu
385 390 395 400

Trp Glu Lys Asn Gly Lys Ala Glu Asp Asn Tyr Lys Thr Thr Pro Thr
405 410 415

Val Leu Asp Ser Asp Gly Ser Tyr Phe Leu Tyr Ser Lys Leu Ser Val
420 425 430

Pro Thr Ser Glu Trp Gln Arg Gly Asp Val Phe Thr Cys Ser Val Met
435 440 445

His Glu Ala Leu His Asn His Tyr Thr Gln Lys Ser Ile Ser Arg Ser
450 455 460

Pro Gly Lys
465

<210> SEQ ID NO 186
<211> LENGTH: 236
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 186

Met Asp Thr Ser Thr Ser Thr Ala Leu Leu Gly Leu Leu Leu Leu Trp
1 5 10 15

Leu Thr Gly Ala Arg Cys Ala Ile Glu Met Thr Gln Ser Pro Pro Ser
20 25 30

Leu Ser Ala Ser Val Gly Glu Thr Val Arg Ile Arg Cys Leu Ala Ser
35 40 45

Glu Asp Ile Tyr Ser Gly Ile Ser Trp Tyr Gln Gln Lys Pro Glu Lys
50 55 60

Pro Pro Thr Leu Leu Ile Ser Gly Ala Ser Asn Leu Glu Ser Gly Val
65 70 75 80

Pro Pro Arg Phe Ser Gly Gly Gly Ser Gly Thr Asp Tyr Thr Leu Thr
85 90 95

Ile Gly Gly Val Gln Ala Glu Asp Val Ala Thr Tyr Tyr Cys Leu Gly
100 105 110

Gly Tyr Ser Phe Ser Ser Thr Gly Leu Thr Phe Gly Ala Gly Thr Lys
115 120 125

Val Glu Ile Lys Arg Asp Pro Val Ala Pro Ser Val Leu Leu Phe Pro
130 135 140

Pro Ser Lys Glu Glu Leu Thr Thr Gly Thr Ala Thr Ile Val Cys Val
145 150 155 160

Ala Asn Lys Tyr Phe Pro Asp Val Thr Val Thr Trp Glu Val Asp Gly
165 170 175

Thr Thr Gln Thr Thr Gly Ile Glu Asn Ser Lys Thr Pro Gln Asn Ser
180 185 190

Ala Asp Cys Thr Tyr Asn Leu Ser Ser Thr Leu Thr Leu Thr Ser Thr
195 200 205

Gln Tyr Asn Ser His Lys Glu Tyr Thr Cys Lys Val Thr Gln Gly Thr
210 215 220

Thr Ser Val Val Gln Ser Phe Asn Arg Gly Asp Cys
225 230 235

<210> SEQ ID NO 187
<211> LENGTH: 460
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 187

Met Glu Thr Gly Leu Arg Trp Leu Leu Leu Val Ala Val Leu Lys Gly
1 5 10 15

Val Gln Cys Gln Gln His Leu Val Glu Ser Gly Gly Gly Leu Val Lys
20 25 30

Pro Gly Ala Ser Leu Thr Leu Thr Cys Thr Ala Ser Gly Phe Ser Phe
35 40 45

Thr Thr Gly Tyr His Met Cys Trp Val Arg Gln Ala Pro Gly Lys Gly
50 55 60

Leu Glu Trp Ile Ala Cys Phe Gly Val Tyr Thr Ser Thr Thr Thr Tyr
65 70 75 80

Ala Ser Trp Ala Lys Gly Arg Phe Thr Ile Ser Lys Thr Ser Ser Thr
85 90 95

Thr Val Thr Leu Gln Met Thr Ser Leu Thr Val Ala Asp Thr Ala Thr
100 105 110

Tyr Phe Cys Ala Arg Ile Ser Ala Glu Asp Gly Gly Asp Leu Trp Gly
115 120 125

Pro Gly Thr Leu Val Thr Val Ser Ser Gly Gln Pro Lys Ala Pro Ser
130 135 140

Val Phe Pro Leu Ala Pro Cys Cys Gly Asp Thr Pro Ser Ser Thr Val
145 150 155 160

Thr Leu Gly Cys Leu Val Lys Gly Tyr Leu Pro Glu Pro Val Thr Val
165 170 175

Thr Trp Asn Ser Gly Thr Leu Thr Asn Gly Val Arg Thr Phe Pro Ser
180 185 190

Val Arg Gln Ser Ser Gly Leu Tyr Ser Leu Ser Ser Val Val Ser Val

```
        195                 200                 205

Thr Ser Ser Ser Gln Pro Val Thr Cys Asn Val Ala His Pro Ala Thr
    210                 215                 220

Asn Thr Lys Val Asp Lys Thr Val Ala Pro Ser Thr Cys Ser Lys Pro
225                 230                 235                 240

Met Cys Pro Pro Pro Glu Leu Pro Gly Gly Pro Ser Val Phe Ile Phe
                245                 250                 255

Pro Pro Lys Pro Lys Asp Thr Leu Met Ile Ser Arg Thr Pro Glu Val
            260                 265                 270

Thr Cys Val Val Val Asp Val Ser Gln Asp Asp Pro Glu Val Gln Phe
        275                 280                 285

Thr Trp Tyr Ile Asn Asn Glu Gln Val Arg Thr Ala Arg Pro Pro Leu
    290                 295                 300

Arg Glu Gln Gln Phe Asn Ser Thr Ile Arg Val Val Ser Thr Leu Pro
305                 310                 315                 320

Ile Ala His Gln Asp Trp Leu Arg Gly Lys Glu Phe Lys Cys Lys Val
                325                 330                 335

His Asn Lys Ala Leu Pro Ala Pro Ile Glu Lys Thr Ile Ser Lys Ala
            340                 345                 350

Arg Gly Gln Pro Leu Glu Pro Lys Val Tyr Thr Met Gly Pro Pro Arg
        355                 360                 365

Glu Glu Leu Ser Ser Arg Ser Val Ser Leu Thr Cys Met Ile Asn Gly
    370                 375                 380

Phe Tyr Pro Ser Asp Ile Ser Val Glu Trp Glu Lys Asn Gly Lys Ala
385                 390                 395                 400

Glu Asp Asn Tyr Lys Thr Thr Pro Thr Val Leu Asp Ser Asp Gly Ser
                405                 410                 415

Tyr Phe Leu Tyr Ser Lys Leu Ser Val Pro Thr Ser Glu Trp Gln Arg
            420                 425                 430

Gly Asp Val Phe Thr Cys Ser Val Met His Glu Ala Leu His Asn His
        435                 440                 445

Tyr Thr Gln Lys Ser Ile Ser Arg Ser Pro Gly Lys
    450                 455                 460


<210> SEQ ID NO 188
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Met Asp Thr Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ala Ser
            20                  25                  30

Val Glu Ala Ala Val Gly Gly Thr Val Thr Ile Thr Cys Gln Ala Ser
        35                  40                  45

Gln Ser Ile Ser Asn Tyr Phe Ser Trp Tyr Gln Gln Lys Pro Gly Gln
    50                  55                  60

Pro Pro Lys Leu Leu Ile Tyr Arg Ala Ser Thr Leu Ala Ser Gly Val
65                  70                  75                  80

Pro Ser Arg Phe Ser Gly Ser Gly Ser Gly Thr Gln Phe Thr Leu Thr
                85                  90                  95
```

```
Ile Ser Asp Leu Glu Cys Ala Asp Ser Ala Thr Tyr Ala Cys Gln Cys
            100                 105                 110

Thr Tyr Gly Ser Ser Ser Thr Gly Phe Gly Phe Gly Gly Gly Thr Glu
        115                 120                 125

Val Val Val Lys Gly Asp Pro Val Ala Pro Thr Val Leu Ile Phe Pro
    130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Asn Arg Gly Asp Cys
225                 230                 235


<210> SEQ ID NO 189
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Lys Ala Ser Gly Phe Ser Phe Ser
        35                  40                  45

Ser Tyr Phe Trp Ile Cys Trp Val Arg Gln Ala Pro Gly Lys Gly Leu
    50                  55                  60

Glu Trp Ser Ala Cys Ile Tyr Gly Asp Ser Ser Gly Ser Ser Tyr Tyr
65                  70                  75                  80

Ala Ser Trp Ala Lys Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Phe Cys Ala Ser Tyr Gly Ser Ser Ser Tyr Tyr Tyr Ser Asn Leu
        115                 120                 125

Trp Gly Pro Gly Thr Leu Val Thr Val Ser Ser Gly Gln Pro Lys Ala
    130                 135                 140

Pro Ser Val Phe Pro Leu Ala Pro Cys Cys Gly Asp Thr Pro Ser Ser
145                 150                 155                 160

Thr Val Thr Leu Gly Cys Leu Val Lys Gly Tyr Leu Pro Glu Pro Val
                165                 170                 175

Thr Val Thr Trp Asn Ser Gly Thr Leu Thr Asn Gly Val Arg Thr Phe
            180                 185                 190

Pro Ser Val Arg Gln Ser Ser Gly Leu Tyr Ser Leu Ser Ser Val Val
        195                 200                 205

Ser Val Thr Ser Ser Ser Gln Pro Val Thr Cys Asn Val Ala His Pro
    210                 215                 220
```

Ala Thr Asn Thr Lys Val Asp Lys Thr Val Ala Pro Ser Thr Cys Ser
225 230 235 240

Lys Pro Met Cys Pro Pro Pro Glu Leu Pro Gly Gly Pro Ser Val Phe
245 250 255

Ile Phe Pro Pro Lys Pro Lys Asp Thr Leu Met Ile Ser Arg Thr Pro
260 265 270

Glu Val Thr Cys Val Val Val Asp Val Ser Gln Asp Asp Pro Glu Val
275 280 285

Gln Phe Thr Trp Tyr Ile Asn Asn Glu Gln Val Arg Thr Ala Arg Pro
290 295 300

Pro Leu Arg Glu Gln Gln Phe Asn Ser Thr Ile Arg Val Val Ser Thr
305 310 315 320

Leu Pro Ile Ala His Gln Asp Trp Leu Arg Gly Lys Glu Phe Lys Cys
325 330 335

Lys Val His Asn Lys Ala Leu Pro Ala Pro Ile Glu Lys Thr Ile Ser
340 345 350

Lys Ala Arg Gly Gln Pro Leu Glu Pro Lys Val Tyr Thr Met Gly Pro
355 360 365

Pro Arg Glu Glu Leu Ser Ser Arg Ser Val Ser Leu Thr Cys Met Ile
370 375 380

Asn Gly Phe Tyr Pro Ser Asp Ile Ser Val Glu Trp Glu Lys Asn Gly
385 390 395 400

Lys Ala Glu Asp Asn Tyr Lys Thr Thr Pro Thr Val Leu Asp Ser Asp
405 410 415

Gly Ser Tyr Phe Leu Tyr Ser Lys Leu Ser Val Pro Thr Ser Glu Trp
420 425 430

Gln Arg Gly Asp Val Phe Thr Cys Ser Val Met His Glu Ala Leu His
435 440 445

Asn His Tyr Thr Gln Lys Ser Ile Ser Arg Ser Pro Gly Lys
450 455 460

<210> SEQ ID NO 190
<211> LENGTH: 235
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 190

Met Asp Thr Arg Ala Pro Thr Gln Leu Leu Gly Leu Leu Leu Leu Trp
1 5 10 15

Leu Pro Gly Ala Ile Cys Asp Pro Val Met Thr Gln Thr Pro Ser Ser
20 25 30

Thr Ser Ala Ala Val Gly Gly Thr Val Thr Ile Ser Cys Gln Ser Ser
35 40 45

Gln Ser Val Tyr Asn Asn Asn Tyr Leu Ala Trp Tyr Gln Gln Lys Pro
50 55 60

Gly Gln Pro Pro Lys Arg Leu Ile Tyr Glu Ser Ser Lys Leu Ala Ser
65 70 75 80

Gly Val Pro Ser Arg Phe Arg Gly Ser Gly Ser Gly Ala Gln Phe Thr
85 90 95

Leu Thr Ile Ser Asp Leu Glu Cys Asp Asp Ala Ala Thr Tyr Tyr Cys
100 105 110

Leu Gly Ala Tyr Tyr Thr Thr Leu Asp Phe Gly Gly Gly Thr Glu Val

```
        115                 120                 125

Val Val Arg Gly Asp Pro Val Ala Pro Thr Val Leu Ile Phe Pro Pro
    130                 135                 140

Ala Ala Asp Gln Val Ala Thr Gly Thr Val Thr Ile Val Cys Val Ala
145                 150                 155                 160

Asn Lys Tyr Phe Pro Asp Val Thr Val Thr Trp Glu Val Asp Gly Thr
                165                 170                 175

Thr Gln Thr Thr Gly Ile Glu Asn Ser Lys Thr Pro Gln Asn Ser Ala
            180                 185                 190

Asp Cys Thr Tyr Asn Leu Ser Ser Thr Leu Thr Leu Thr Ser Thr Gln
        195                 200                 205

Tyr Asn Ser His Lys Glu Tyr Thr Cys Lys Val Thr Gln Gly Thr Thr
    210                 215                 220

Ser Val Val Gln Ser Phe Asn Arg Gly Asp Cys
225                 230                 235


<210> SEQ ID NO 191
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Gln
            20                  25                  30

Pro Glu Gly Ser Leu Thr Leu Thr Cys Lys Ala Ser Gly Phe Asp Phe
        35                  40                  45

Ser Ser Asn Ala Met Cys Trp Val Arg Gln Ala Pro Gly Lys Gly Leu
    50                  55                  60

Glu Trp Ile Ala Cys Ile Tyr Asn Gly Asp Gly Ser Thr Tyr Tyr Ala
65                  70                  75                  80

Ser Trp Val Asn Gly Arg Phe Thr Ile Ser Lys Thr Ser Ser Thr Thr
                85                  90                  95

Val Thr Leu Gln Met Thr Ser Leu Thr Ala Ala Asp Thr Ala Thr Tyr
            100                 105                 110

Phe Cys Ala Arg Gly Leu Ser Asn Trp Asn Arg Asp Asn Leu Trp Gly
        115                 120                 125

Pro Gly Thr Leu Val Thr Val Ser Ser Gly Gln Pro Lys Ala Pro Ser
    130                 135                 140

Val Phe Pro Leu Ala Pro Cys Cys Gly Asp Thr Pro Ser Ser Thr Val
145                 150                 155                 160

Thr Leu Gly Cys Leu Val Lys Gly Tyr Leu Pro Glu Pro Val Thr Val
                165                 170                 175

Thr Trp Asn Ser Gly Thr Leu Thr Asn Gly Val Arg Thr Phe Pro Ser
            180                 185                 190

Val Arg Gln Ser Ser Gly Leu Tyr Ser Leu Ser Ser Val Val Ser Val
        195                 200                 205

Thr Ser Ser Ser Gln Pro Val Thr Cys Asn Val Ala His Pro Ala Thr
    210                 215                 220

Asn Thr Lys Val Asp Lys Thr Val Ala Pro Ser Thr Cys Ser Lys Pro
225                 230                 235                 240
```

```
Met Cys Pro Pro Pro Glu Leu Pro Gly Gly Pro Ser Val Phe Ile Phe
                245                 250                 255

Pro Pro Lys Pro Lys Asp Thr Leu Met Ile Ser Arg Thr Pro Glu Val
            260                 265                 270

Thr Cys Val Val Val Asp Val Ser Gln Asp Asp Pro Glu Val Gln Phe
        275                 280                 285

Thr Trp Tyr Ile Asn Asn Glu Gln Val Arg Thr Ala Arg Pro Pro Leu
    290                 295                 300

Arg Glu Gln Gln Phe Asn Ser Thr Ile Arg Val Val Ser Thr Leu Pro
305                 310                 315                 320

Ile Ala His Gln Asp Trp Leu Arg Gly Lys Glu Phe Lys Cys Lys Val
                325                 330                 335

His Asn Lys Ala Leu Pro Ala Pro Ile Glu Lys Thr Ile Ser Lys Ala
            340                 345                 350

Arg Gly Gln Pro Leu Glu Pro Lys Val Tyr Thr Met Gly Pro Pro Arg
        355                 360                 365

Glu Glu Leu Ser Ser Arg Ser Val Ser Leu Thr Cys Met Ile Asn Gly
    370                 375                 380

Phe Tyr Pro Ser Asp Ile Ser Val Glu Trp Glu Lys Asn Gly Lys Ala
385                 390                 395                 400

Glu Asp Asn Tyr Lys Thr Thr Pro Thr Val Leu Asp Ser Asp Gly Ser
                405                 410                 415

Tyr Phe Leu Tyr Ser Lys Leu Ser Val Pro Thr Ser Glu Trp Gln Arg
            420                 425                 430

Gly Asp Val Phe Thr Cys Ser Val Met His Glu Ala Leu His Asn His
        435                 440                 445

Tyr Thr Gln Lys Ser Ile Ser Arg Ser Pro Gly Lys
    450                 455                 460
```

<210> SEQ ID NO 192
<211> LENGTH: 239
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 192

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
            20                  25                  30

Val Ser Ala Ala Val Gly Gly Thr Ala Thr Ile Asn Cys Gln Ala Ser
        35                  40                  45

Gln Ser Leu Tyr Ser Pro Lys Asn Leu Ala Trp Tyr Gln Gln Thr Pro
    50                  55                  60

Gly Gln Pro Pro Lys Leu Leu Ile Tyr Ser Ala Ser Lys Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Gly Val Gln Cys Asp Asp Ala Ala Ile Tyr Tyr Cys
            100                 105                 110

Gln Gly Glu Phe Ser Cys Thr Thr Ala Ala Cys Phe Ala Phe Gly Gly
        115                 120                 125

Gly Thr Glu Val Val Val Lys Gly Asp Pro Val Ala Pro Thr Val Leu
    130                 135                 140
```

Ile Phe Pro Pro Ala Ala Asp Gln Val Ala Thr Gly Thr Val Thr Ile
145 150 155 160

Val Cys Val Ala Asn Lys Tyr Phe Pro Asp Val Thr Val Thr Trp Glu
165 170 175

Val Asp Gly Thr Thr Gln Thr Thr Gly Ile Glu Asn Ser Lys Thr Pro
180 185 190

Gln Asn Ser Ala Asp Cys Thr Tyr Asn Leu Ser Ser Thr Leu Thr Leu
195 200 205

Thr Ser Thr Gln Tyr Asn Ser His Lys Glu Tyr Thr Cys Lys Val Thr
210 215 220

Gln Gly Thr Thr Ser Val Val Gln Ser Phe Asn Arg Gly Asp Cys
225 230 235

<210> SEQ ID NO 193
<211> LENGTH: 461
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 193

Met Glu Thr Gly Leu Arg Trp Leu Leu Leu Val Ala Val Leu Lys Gly
1 5 10 15

Val Gln Cys Gln Ser Leu Glu Glu Ser Gly Gly Gly Leu Val Gln Pro
20 25 30

Glu Gly Ser Leu Thr Leu Ala Cys Thr Ala Ser Gly Phe Ser Phe Ser
35 40 45

Ser Tyr Tyr Tyr Ile Cys Trp Val Arg Gln Ala Pro Gly Thr Gly Leu
50 55 60

Glu Trp Ile Gly Cys Ile Asn Thr Gly Ser Asp Asp Thr His Tyr Ala
65 70 75 80

Ser Trp Leu Lys Gly Arg Phe Thr Phe Ser Lys Ala Ser Ser Thr Thr
85 90 95

Leu Thr Leu Gln Met Thr Ser Leu Thr Ala Ala Asp Thr Ala Thr Tyr
100 105 110

Phe Cys Ala Arg Ser Ser Gly Ser Ser Asp Asp Ala Tyr Asp Leu Trp
115 120 125

Gly Pro Gly Thr Leu Val Thr Val Ser Ser Gly Gln Pro Lys Ala Pro
130 135 140

Ser Val Phe Pro Leu Ala Pro Cys Cys Gly Asp Thr Pro Ser Ser Thr
145 150 155 160

Val Thr Leu Gly Cys Leu Val Lys Gly Tyr Leu Pro Glu Pro Val Thr
165 170 175

Val Thr Trp Asn Ser Gly Thr Leu Thr Asn Gly Val Arg Thr Phe Pro
180 185 190

Ser Val Arg Gln Ser Ser Gly Leu Tyr Ser Leu Ser Ser Val Val Ser
195 200 205

Val Thr Ser Ser Ser Gln Pro Val Thr Cys Asn Val Ala His Pro Ala
210 215 220

Thr Asn Thr Lys Val Asp Lys Thr Val Ala Pro Ser Thr Cys Ser Lys
225 230 235 240

Pro Met Cys Pro Pro Pro Glu Leu Pro Gly Gly Pro Ser Val Phe Ile
245 250 255

Phe Pro Pro Lys Pro Lys Asp Thr Leu Met Ile Ser Arg Thr Pro Glu

```
            260                 265                 270

Val Thr Cys Val Val Val Asp Val Ser Gln Asp Asp Pro Glu Val Gln
        275                 280                 285

Phe Thr Trp Tyr Ile Asn Asn Glu Gln Val Arg Thr Ala Arg Pro Pro
    290                 295                 300

Leu Arg Glu Gln Gln Phe Asn Ser Thr Ile Arg Val Val Ser Thr Leu
305                 310                 315                 320

Pro Ile Ala His Gln Asp Trp Leu Arg Gly Lys Glu Phe Lys Cys Lys
                325                 330                 335

Val His Asn Lys Ala Leu Pro Ala Pro Ile Glu Lys Thr Ile Ser Lys
            340                 345                 350

Ala Arg Gly Gln Pro Leu Glu Pro Lys Val Tyr Thr Met Gly Pro Pro
        355                 360                 365

Arg Glu Glu Leu Ser Ser Arg Ser Val Ser Leu Thr Cys Met Ile Asn
    370                 375                 380

Gly Phe Tyr Pro Ser Asp Ile Ser Val Glu Trp Glu Lys Asn Gly Lys
385                 390                 395                 400

Ala Glu Asp Asn Tyr Lys Thr Thr Pro Thr Val Leu Asp Ser Asp Gly
                405                 410                 415

Ser Tyr Phe Leu Tyr Ser Lys Leu Ser Val Pro Thr Ser Glu Trp Gln
            420                 425                 430

Arg Gly Asp Val Phe Thr Cys Ser Val Met His Glu Ala Leu His Asn
        435                 440                 445

His Tyr Thr Gln Lys Ser Ile Ser Arg Ser Pro Gly Lys
    450                 455                 460


<210> SEQ ID NO 194
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Met Asp Thr Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ala Ser
            20                  25                  30

Val Ser Glu Pro Val Gly Gly Ala Val Thr Ile Lys Cys Gln Ala Ser
        35                  40                  45

Gln Ser Ile Gly Ser Asn Leu Ala Trp Tyr Gln His Lys Pro Gly Gln
    50                  55                  60

Pro Pro Lys Leu Leu Ile Tyr Phe Ala Ser Ser Leu Ala Ser Gly Val
65                  70                  75                  80

Ser Ser Arg Phe Lys Gly Gly Arg Ser Gly Thr Gln Phe Thr Leu Thr
                85                  90                  95

Ile Ser Asp Leu Glu Cys Ala Asp Ala Ala Thr Tyr Tyr Cys His Cys
            100                 105                 110

Thr Tyr Tyr Pro Leu Ser Tyr Val Thr Phe Gly Gly Gly Thr Glu Val
        115                 120                 125

Val Val Lys Gly Asp Pro Val Ala Pro Thr Val Leu Ile Phe Pro Pro
    130                 135                 140

Ala Ala Asp Gln Val Ala Thr Gly Thr Val Thr Ile Val Cys Val Ala
145                 150                 155                 160
```

Asn Lys Tyr Phe Pro Asp Val Thr Val Thr Trp Glu Val Asp Gly Thr
165 170 175

Thr Gln Thr Thr Gly Ile Glu Asn Ser Lys Thr Pro Gln Asn Ser Ala
180 185 190

Asp Cys Thr Tyr Asn Leu Ser Ser Thr Leu Thr Leu Thr Ser Thr Gln
195 200 205

Tyr Asn Ser His Lys Glu Tyr Thr Cys Lys Val Thr Gln Gly Thr Thr
210 215 220

Ser Val Val Gln Ser Phe Asn Arg Gly Asp Cys
225 230 235

<210> SEQ ID NO 195
<211> LENGTH: 464
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 195

Met Glu Thr Gly Leu Arg Trp Leu Leu Leu Val Ala Val Leu Lys Gly
1 5 10 15

Val Gln Cys Gln Ser Leu Glu Glu Ser Gly Gly Asp Leu Val Lys Pro
20 25 30

Gly Thr Ser Leu Thr Leu Ser Cys Thr Ala Ser Gly Phe Ser Phe Gly
35 40 45

Ser Tyr Tyr Tyr Met Cys Trp Val Arg Gln Ala Pro Gly Lys Gly Leu
50 55 60

Glu Trp Ile Ala Cys Ile Asp Val Gly Ser Ser Gly Asp Thr Tyr Tyr
65 70 75 80

Ala Ser Trp Val Asn Gly Arg Phe Thr Ile Ser Lys Thr Ser Ser Thr
85 90 95

Thr Val Thr Leu Gln Met Thr Ser Leu Thr Ala Ala Asp Thr Ala Thr
100 105 110

Tyr Phe Cys Ala Arg Asp Asp Thr Ala Ala Gly Gly Phe Gly Asn Leu
115 120 125

Glu Leu Trp Gly Pro Gly Thr Leu Val Thr Val Ser Ser Gly Gln Pro
130 135 140

Lys Ala Pro Ser Val Phe Pro Leu Ala Pro Cys Cys Gly Asp Thr Pro
145 150 155 160

Ser Ser Thr Val Thr Leu Gly Cys Leu Val Lys Gly Tyr Leu Pro Glu
165 170 175

Pro Val Thr Val Thr Trp Asn Ser Gly Thr Leu Thr Asn Gly Val Arg
180 185 190

Thr Phe Pro Ser Val Arg Gln Ser Ser Gly Leu Tyr Ser Leu Ser Ser
195 200 205

Val Val Ser Val Thr Ser Ser Ser Gln Pro Val Thr Cys Asn Val Ala
210 215 220

His Pro Ala Thr Asn Thr Lys Val Asp Lys Thr Val Ala Pro Ser Thr
225 230 235 240

Cys Ser Lys Pro Met Cys Pro Pro Pro Glu Leu Pro Gly Gly Pro Ser
245 250 255

Val Phe Ile Phe Pro Pro Lys Pro Lys Asp Thr Leu Met Ile Ser Arg
260 265 270

Thr Pro Glu Val Thr Cys Val Val Val Asp Val Ser Gln Asp Asp Pro
275 280 285

Glu Val Gln Phe Thr Trp Tyr Ile Asn Asn Glu Gln Val Arg Thr Ala
290 295 300

Arg Pro Pro Leu Arg Glu Gln Gln Phe Asn Ser Thr Ile Arg Val Val
305 310 315 320

Ser Thr Leu Pro Ile Ala His Gln Asp Trp Leu Arg Gly Lys Glu Phe
325 330 335

Lys Cys Lys Val His Asn Lys Ala Leu Pro Ala Pro Ile Glu Lys Thr
340 345 350

Ile Ser Lys Ala Arg Gly Gln Pro Leu Glu Pro Lys Val Tyr Thr Met
355 360 365

Gly Pro Pro Arg Glu Glu Leu Ser Ser Arg Ser Val Ser Leu Thr Cys
370 375 380

Met Ile Asn Gly Phe Tyr Pro Ser Asp Ile Ser Val Glu Trp Glu Lys
385 390 395 400

Asn Gly Lys Ala Glu Asp Asn Tyr Lys Thr Thr Pro Thr Val Leu Asp
405 410 415

Ser Asp Gly Ser Tyr Phe Leu Tyr Ser Lys Leu Ser Val Pro Thr Ser
420 425 430

Glu Trp Gln Arg Gly Asp Val Phe Thr Cys Ser Val Met His Glu Ala
435 440 445

Leu His Asn His Tyr Thr Gln Lys Ser Ile Ser Arg Ser Pro Gly Lys
450 455 460

<210> SEQ ID NO 196
<211> LENGTH: 238
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 196

Met Asp Thr Arg Ala Pro Thr Gln Leu Leu Gly Leu Leu Leu Leu Trp
1 5 10 15

Leu Pro Gly Ala Arg Cys Ala Phe Glu Leu Thr Gln Thr Pro Ser Ser
20 25 30

Val Ser Glu Pro Val Gly Gly Thr Val Thr Ile Lys Cys Gln Ala Ser
35 40 45

Gln Ser Ile Tyr Ser Tyr Phe Ser Trp Tyr Gln Gln Lys Pro Gly Gln
50 55 60

Pro Pro Lys Arg Leu Ile Tyr Gln Ala Ser Thr Leu Ala Ser Gly Val
65 70 75 80

Pro Ser Arg Phe Lys Gly Ser Gly Ser Gly Thr Asp Phe Thr Leu Thr
85 90 95

Ile Ser Asp Leu Glu Cys Ala Asp Ala Ala Thr Tyr Tyr Cys Gln Asn
100 105 110

Asn Tyr Gly Arg Gly Ser Gly Ser Tyr Phe Phe Gly Phe Gly Gly Gly
115 120 125

Thr Glu Val Val Val Lys Gly Asp Pro Val Ala Pro Thr Val Leu Ile
130 135 140

Phe Pro Pro Ala Ala Asp Gln Val Ala Thr Gly Thr Val Thr Ile Val
145 150 155 160

Cys Val Ala Asn Lys Tyr Phe Pro Asp Val Thr Val Thr Trp Glu Val
165 170 175

Asp Gly Thr Thr Gln Thr Thr Gly Ile Glu Asn Ser Lys Thr Pro Gln

```
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235


<210> SEQ ID NO 197
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Lys Ala Ser Gly Ile Asp Phe Ser
        35                  40                  45

Ser Gly Tyr Gly Met Trp Trp Val Arg Gln Ala Pro Gly Lys Gly Leu
    50                  55                  60

Glu Tyr Ile Gly Tyr Ile Asp Thr Gly Ser Gly Ser Thr Tyr Tyr Ala
65                  70                  75                  80

Asn Trp Ala Lys Gly Arg Phe Thr Ile Ser Lys Thr Ser Ser Thr Met
                85                  90                  95

Val Thr Leu Gln Met Thr Ser Leu Thr Val Ala Asp Thr Ala Thr Tyr
            100                 105                 110

Phe Cys Ala Lys Gly Gly Ala Ile Asp Leu Trp Gly Pro Gly Thr Leu
        115                 120                 125

Val Thr Val Ser Ser Gly Gln Pro Lys Ala Pro Ser Val Phe Pro Leu
    130                 135                 140

Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
                165                 170                 175

Gly Thr Leu Thr Asn Gly Val Arg Thr Phe Pro Ser Val Arg Gln Ser
            180                 185                 190

Ser Gly Leu Tyr Ser Leu Ser Ser Val Val Ser Val Thr Ser Ser Ser
        195                 200                 205

Gln Pro Val Thr Cys Asn Val Ala His Pro Ala Thr Asn Thr Lys Val
    210                 215                 220

Asp Lys Thr Val Ala Pro Ser Thr Cys Ser Lys Pro Met Cys Pro Pro
225                 230                 235                 240

Pro Glu Leu Pro Gly Gly Pro Ser Val Phe Ile Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Asp Asp Pro Glu Val Gln Phe Thr Trp Tyr Ile
        275                 280                 285

Asn Asn Glu Gln Val Arg Thr Ala Arg Pro Pro Leu Arg Glu Gln Gln
    290                 295                 300
```

Phe Asn Ser Thr Ile Arg Val Val Ser Thr Leu Pro Ile Ala His Gln
305 310 315 320

Asp Trp Leu Arg Gly Lys Glu Phe Lys Cys Lys Val His Asn Lys Ala
325 330 335

Leu Pro Ala Pro Ile Glu Lys Thr Ile Ser Lys Ala Arg Gly Gln Pro
340 345 350

Leu Glu Pro Lys Val Tyr Thr Met Gly Pro Pro Arg Glu Glu Leu Ser
355 360 365

Ser Arg Ser Val Ser Leu Thr Cys Met Ile Asn Gly Phe Tyr Pro Ser
370 375 380

Asp Ile Ser Val Glu Trp Glu Lys Asn Gly Lys Ala Glu Asp Asn Tyr
385 390 395 400

Lys Thr Thr Pro Thr Val Leu Asp Ser Asp Gly Ser Tyr Phe Leu Tyr
405 410 415

Ser Lys Leu Ser Val Pro Thr Ser Glu Trp Gln Arg Gly Asp Val Phe
420 425 430

Thr Cys Ser Val Met His Glu Ala Leu His Asn His Tyr Thr Gln Lys
435 440 445

Ser Ile Ser Arg Ser Pro Gly Lys
450 455

<210> SEQ ID NO 198
<211> LENGTH: 239
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 198

Met Asp Thr Arg Ala Pro Thr Gln Leu Leu Gly Leu Leu Leu Leu Trp
1 5 10 15

Leu Pro Gly Ala Arg Cys Ala Asp Ile Val Met Thr Gln Thr Pro Ala
20 25 30

Ser Val Glu Ala Ala Val Gly Gly Thr Val Thr Ile Lys Cys Gln Ala
35 40 45

Ser Gln Ser Ile Ser Ser Tyr Leu Ala Trp Tyr Gln Gln Lys Pro Gly
50 55 60

Gln Arg Pro Lys Leu Leu Ile Tyr Arg Ala Ser Thr Leu Ala Ser Gly
65 70 75 80

Val Pro Ser Arg Phe Lys Gly Ser Gly Ser Gly Thr Asp Tyr Thr Leu
85 90 95

Thr Ile Ser Asp Leu Glu Cys Ala Asp Ala Ala Thr Tyr Tyr Cys His
100 105 110

Thr Tyr Tyr Leu Ser Ser Ser Ile Ser Tyr Gly Asn Thr Phe Gly Gly
115 120 125

Gly Thr Glu Val Val Val Lys Gly Asp Pro Val Ala Pro Thr Val Leu
130 135 140

Ile Phe Pro Pro Ala Ala Asp Gln Val Ala Thr Gly Thr Val Thr Ile
145 150 155 160

Val Cys Val Ala Asn Lys Tyr Phe Pro Asp Val Thr Val Thr Trp Glu
165 170 175

Val Asp Gly Thr Thr Gln Thr Thr Gly Ile Glu Asn Ser Lys Thr Pro
180 185 190

Gln Asn Ser Ala Asp Cys Thr Tyr Asn Leu Ser Ser Thr Leu Thr Leu
195 200 205

```
Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235


<210> SEQ ID NO 199
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Met Glu Thr Gly Leu Arg Trp Leu Leu Leu Val Ala Val Leu Lys Gly
1               5                   10                  15

Val Gln Cys Gln Glu Gln Leu Glu Glu Ser Gly Gly Asp Leu Val Lys
            20                  25                  30

Pro Glu Gly Ser Leu Thr Leu Thr Cys Lys Ala Ser Gly Phe Ser Phe
        35                  40                  45

Ser Ser Ile Tyr Trp Ile Cys Trp Val Arg Gln Ala Pro Gly Lys Gly
    50                  55                  60

Leu Glu Trp Ile Ala Cys Thr Thr Val Val Lys Ser Gly Arg Thr Tyr
65                  70                  75                  80

Tyr Ala Asn Trp Ala Lys Gly Arg Phe Thr Ile Ser Lys Thr Ser Ser
                85                  90                  95

Thr Thr Val Thr Leu Gln Met Thr Ser Leu Thr Ala Ala Asp Thr Ala
            100                 105                 110

Thr Tyr Phe Cys Ala Arg Glu Phe Val Asp Gly Gly Gly Ser Ser Gly
        115                 120                 125

Arg Asp Leu Trp Gly Pro Gly Thr Leu Val Thr Val Ser Ser Gly Gln
    130                 135                 140

Pro Lys Ala Pro Ser Val Phe Pro Leu Ala Pro Cys Cys Gly Asp Thr
145                 150                 155                 160

Pro Ser Ser Thr Val Thr Leu Gly Cys Leu Val Lys Gly Tyr Leu Pro
                165                 170                 175

Glu Pro Val Thr Val Thr Trp Asn Ser Gly Thr Leu Thr Asn Gly Val
            180                 185                 190

Arg Thr Phe Pro Ser Val Arg Gln Ser Ser Gly Leu Tyr Ser Leu Ser
        195                 200                 205

Ser Val Val Ser Val Thr Ser Ser Ser Gln Pro Val Thr Cys Asn Val
    210                 215                 220

Ala His Pro Ala Thr Asn Thr Lys Val Asp Lys Thr Val Ala Pro Ser
225                 230                 235                 240

Thr Cys Ser Lys Pro Met Cys Pro Pro Pro Glu Leu Pro Gly Gly Pro
                245                 250                 255

Ser Val Phe Ile Phe Pro Pro Lys Pro Lys Asp Thr Leu Met Ile Ser
            260                 265                 270

Arg Thr Pro Glu Val Thr Cys Val Val Val Asp Val Ser Gln Asp Asp
        275                 280                 285

Pro Glu Val Gln Phe Thr Trp Tyr Ile Asn Asn Glu Gln Val Arg Thr
    290                 295                 300

Ala Arg Pro Pro Leu Arg Glu Gln Gln Phe Asn Ser Thr Ile Arg Val
305                 310                 315                 320

Val Ser Thr Leu Pro Ile Ala His Gln Asp Trp Leu Arg Gly Lys Glu
```

-continued

```
                325                 330                 335

Phe Lys Cys Lys Val His Asn Lys Ala Leu Pro Ala Pro Ile Glu Lys
            340                 345                 350

Thr Ile Ser Lys Ala Arg Gly Gln Pro Leu Glu Pro Lys Val Tyr Thr
        355                 360                 365

Met Gly Pro Pro Arg Glu Glu Leu Ser Ser Arg Ser Val Ser Leu Thr
    370                 375                 380

Cys Met Ile Asn Gly Phe Tyr Pro Ser Asp Ile Ser Val Glu Trp Glu
385                 390                 395                 400

Lys Asn Gly Lys Ala Glu Asp Asn Tyr Lys Thr Thr Pro Thr Val Leu
                405                 410                 415

Asp Ser Asp Gly Ser Tyr Phe Leu Tyr Ser Lys Leu Ser Val Pro Thr
            420                 425                 430

Ser Glu Trp Gln Arg Gly Asp Val Phe Thr Cys Ser Val Met His Glu
        435                 440                 445

Ala Leu His Asn His Tyr Thr Gln Lys Ser Ile Ser Arg Ser Pro Gly
    450                 455                 460

Lys
465


<210> SEQ ID NO 200
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Ala Ala Val Gly Gly Thr Val Thr Ile Lys Cys Gln Ala Ser
        35                  40                  45

Gln Ser Ile Ser Arg Asp Leu Ser Trp Tyr Gln Gln Lys Pro Gly Gln
    50                  55                  60

Pro Pro Lys Arg Leu Ile Tyr Lys Ala Ser Thr Leu Ala Ser Gly Val
65                  70                  75                  80

Pro Ser Arg Phe Lys Gly Ser Gly Ser Gly Thr Asp Phe Thr Leu Thr
                85                  90                  95

Ile Ser Asp Leu Glu Cys Ala Asp Ala Ala Thr Tyr Tyr Cys Gln Gln
            100                 105                 110

Gly Tyr Ser Ser Ile Asp Val Asp Asn Asp Phe Gly Gly Gly Thr Glu
        115                 120                 125

Val Val Val Lys Gly Asp Pro Val Ala Pro Thr Val Leu Ile Phe Pro
    130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205
```

```
Gln Tyr Asn Ser His Lys Glu Tyr Thr Cys Lys Val Thr Gln Gly Thr
    210                 215                 220

Thr Ser Val Val Gln Ser Phe Asn Arg Gly Asp Cys
225                 230                 235


<210> SEQ ID NO 201
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Met Glu Thr Gly Leu Arg Trp Leu Leu Leu Val Ala Val Leu Lys Gly
1               5                   10                  15

Val Gln Cys Gln Glu Gln Leu Glu Glu Ser Gly Gly Gly Leu Val Lys
            20                  25                  30

Pro Glu Gly Ser Leu Thr Leu Thr Cys Lys Ala Ser Gly Phe Asp Leu
        35                  40                  45

Ser Ser Gly Tyr Asp Met Cys Trp Val Arg Gln Ala Pro Gly Lys Gly
    50                  55                  60

Leu Glu Trp Ile Ala Cys Ile Tyr Ala Asp Tyr Ser Gly Ser Thr Tyr
65                  70                  75                  80

Tyr Ala Ser Trp Val Asn Gly Arg Phe Thr Ile Ser Ser Ser Thr Ser
                85                  90                  95

Leu Asn Thr Val Asp Leu Lys Met Thr Ser Leu Thr Ala Ala Asp Thr
            100                 105                 110

Ala Thr Tyr Phe Cys Ala Arg Gly Ala Thr Gly Asn Gly Gly Tyr Gly
        115                 120                 125

Tyr Tyr Phe Asn Leu Trp Gly Pro Gly Thr Leu Val Thr Val Ser Ser
    130                 135                 140

Gly Gln Pro Lys Ala Pro Ser Val Phe Pro Leu Ala Pro Cys Cys Gly
145                 150                 155                 160

Asp Thr Pro Ser Ser Thr Val Thr Leu Gly Cys Leu Val Lys Gly Tyr
                165                 170                 175

Leu Pro Glu Pro Val Thr Val Thr Trp Asn Ser Gly Thr Leu Thr Asn
            180                 185                 190

Gly Val Arg Thr Phe Pro Ser Val Arg Gln Ser Ser Gly Leu Tyr Ser
        195                 200                 205

Leu Ser Ser Val Val Ser Val Thr Ser Ser Ser Gln Pro Val Thr Cys
    210                 215                 220

Asn Val Ala His Pro Ala Thr Asn Thr Lys Val Asp Lys Thr Val Ala
225                 230                 235                 240

Pro Ser Thr Cys Ser Lys Pro Met Cys Pro Pro Pro Glu Leu Pro Gly
                245                 250                 255

Gly Pro Ser Val Phe Ile Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Asp Asp Pro Glu Val Gln Phe Thr Trp Tyr Ile Asn Asn Glu Gln Val
    290                 295                 300

Arg Thr Ala Arg Pro Pro Leu Arg Glu Gln Gln Phe Asn Ser Thr Ile
305                 310                 315                 320

Arg Val Val Ser Thr Leu Pro Ile Ala His Gln Asp Trp Leu Arg Gly
                325                 330                 335
```

Lys Glu Phe Lys Cys Lys Val His Asn Lys Ala Leu Pro Ala Pro Ile
340 345 350

Glu Lys Thr Ile Ser Lys Ala Arg Gly Gln Pro Leu Glu Pro Lys Val
355 360 365

Tyr Thr Met Gly Pro Pro Arg Glu Glu Leu Ser Ser Arg Ser Val Ser
370 375 380

Leu Thr Cys Met Ile Asn Gly Phe Tyr Pro Ser Asp Ile Ser Val Glu
385 390 395 400

Trp Glu Lys Asn Gly Lys Ala Glu Asp Asn Tyr Lys Thr Thr Pro Thr
405 410 415

Val Leu Asp Ser Asp Gly Ser Tyr Phe Leu Tyr Ser Lys Leu Ser Val
420 425 430

Pro Thr Ser Glu Trp Gln Arg Gly Asp Val Phe Thr Cys Ser Val Met
435 440 445

His Glu Ala Leu His Asn His Tyr Thr Gln Lys Ser Ile Ser Arg Ser
450 455 460

Pro Gly Lys
465

<210> SEQ ID NO 202
<211> LENGTH: 238
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 202

Met Asp Thr Arg Ala Pro Thr Gln Leu Leu Gly Leu Leu Leu Leu Trp
1 5 10 15

Leu Pro Gly Ala Arg Cys Ala Asp Ile Val Met Thr Gln Thr Pro Ala
20 25 30

Ser Val Ser Glu Pro Val Gly Gly Thr Val Thr Ile Lys Cys Gln Ala
35 40 45

Ser Gln Asn Ile Asn Ser Gly Leu Ala Trp Tyr Gln Gln Lys Pro Gly
50 55 60

Gln Pro Pro Lys Leu Leu Ile Tyr Lys Ala Ser Thr Leu Ala Ser Gly
65 70 75 80

Val Ser Ser Arg Phe Lys Gly Ser Gly Ser Gly Thr Glu Phe Thr Leu
85 90 95

Thr Ile Ser Asp Leu Glu Cys Ala Asp Ala Ala Thr Tyr Tyr Cys Gln
100 105 110

Thr Tyr Tyr Tyr Ser Ser Ser Ser Ser Asp Asn Ala Phe Gly Gly Gly
115 120 125

Thr Glu Val Val Val Lys Gly Asp Pro Val Ala Pro Thr Val Leu Ile
130 135 140

Phe Pro Pro Ala Ala Asp Gln Val Ala Thr Gly Thr Val Thr Ile Val
145 150 155 160

Cys Val Ala Asn Lys Tyr Phe Pro Asp Val Thr Val Thr Trp Glu Val
165 170 175

Asp Gly Thr Thr Gln Thr Thr Gly Ile Glu Asn Ser Lys Thr Pro Gln
180 185 190

Asn Ser Ala Asp Cys Thr Tyr Asn Leu Ser Ser Thr Leu Thr Leu Thr
195 200 205

Ser Thr Gln Tyr Asn Ser His Lys Glu Tyr Thr Cys Lys Val Thr Gln 210 215 220

Gly Thr Thr Ser Val Val Gln Ser Phe Asn Arg Gly Asp Cys
225 230 235

<210> SEQ ID NO 203
<211> LENGTH: 462
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 203

Met Glu Thr Gly Leu Arg Trp Leu Leu Leu Val Ala Val Leu Lys Gly
1 5 10 15

Val Gln Cys Gln Ser Leu Glu Glu Ser Gly Gly Asp Leu Val Lys Pro
20 25 30

Gly Ala Ser Leu Thr Leu Thr Cys Thr Ala Ser Gly Phe Ser Phe Ser
35 40 45

Ser Ser Tyr Trp Ile Cys Trp Val Arg Gln Ala Pro Gly Lys Gly Leu
50 55 60

Glu Trp Ile Ala Cys Ile Tyr Gly Gly Ser Ser Gly Asn Ile Ala Tyr
65 70 75 80

Ala Ser Trp Ala Lys Gly Arg Phe Thr Ile Ser Lys Thr Ser Ser Thr
85 90 95

Thr Val Thr Leu Gln Met Thr Ser Leu Thr Ala Ala Asp Thr Ala Thr
100 105 110

Tyr Phe Cys Ala Arg Asp Ile Pro Ser Asp Ala Phe Thr Leu Asp Leu
115 120 125

Trp Gly Pro Gly Thr Leu Val Thr Val Ser Ser Gly Gln Pro Lys Ala
130 135 140

Pro Ser Val Phe Pro Leu Ala Pro Cys Cys Gly Asp Thr Pro Ser Ser
145 150 155 160

Thr Val Thr Leu Gly Cys Leu Val Lys Gly Tyr Leu Pro Glu Pro Val
165 170 175

Thr Val Thr Trp Asn Ser Gly Thr Leu Thr Asn Gly Val Arg Thr Phe
180 185 190

Pro Ser Val Arg Gln Ser Ser Gly Leu Tyr Ser Leu Ser Ser Val Val
195 200 205

Ser Val Thr Ser Ser Ser Gln Pro Val Thr Cys Asn Val Ala His Pro
210 215 220

Ala Thr Asn Thr Lys Val Asp Lys Thr Val Ala Pro Ser Thr Cys Ser
225 230 235 240

Lys Pro Met Cys Pro Pro Pro Glu Leu Pro Gly Gly Pro Ser Val Phe
245 250 255

Ile Phe Pro Pro Lys Pro Lys Asp Thr Leu Met Ile Ser Arg Thr Pro
260 265 270

Glu Val Thr Cys Val Val Val Asp Val Ser Gln Asp Asp Pro Glu Val
275 280 285

Gln Phe Thr Trp Tyr Ile Asn Asn Glu Gln Val Arg Thr Ala Arg Pro
290 295 300

Pro Leu Arg Glu Gln Gln Phe Asn Ser Thr Ile Arg Val Val Ser Thr
305 310 315 320

Leu Pro Ile Ala His Gln Asp Trp Leu Arg Gly Lys Glu Phe Lys Cys
325 330 335

```
Lys Val His Asn Lys Ala Leu Pro Ala Pro Ile Glu Lys Thr Ile Ser
            340                 345                 350

Lys Ala Arg Gly Gln Pro Leu Glu Pro Lys Val Tyr Thr Met Gly Pro
        355                 360                 365

Pro Arg Glu Glu Leu Ser Ser Arg Ser Val Ser Leu Thr Cys Met Ile
    370                 375                 380

Asn Gly Phe Tyr Pro Ser Asp Ile Ser Val Glu Trp Glu Lys Asn Gly
385                 390                 395                 400

Lys Ala Glu Asp Asn Tyr Lys Thr Thr Pro Thr Val Leu Asp Ser Asp
                405                 410                 415

Gly Ser Tyr Phe Leu Tyr Ser Lys Leu Ser Val Pro Thr Ser Glu Trp
            420                 425                 430

Gln Arg Gly Asp Val Phe Thr Cys Ser Val Met His Glu Ala Leu His
        435                 440                 445

Asn His Tyr Thr Gln Lys Ser Ile Ser Arg Ser Pro Gly Lys
    450                 455                 460


<210> SEQ ID NO 204
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
            20                  25                  30

Val Ser Ala Ala Val Gly Ser Thr Val Thr Ile Asn Cys Gln Ala Ser
        35                  40                  45

Gln Ser Val Tyr Lys Asp Asn Asn Leu Ala Trp Tyr Gln Gln Lys Pro
    50                  55                  60

Gly Gln Pro Pro Lys Leu Leu Ile Tyr Lys Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Gly Val Gln Cys Glu Asp Ala Ala Thr Tyr Tyr Cys
            100                 105                 110

Gln Gly Glu Phe Ser Cys Gly Ser Ala Asp Cys Ile Ala Phe Gly Gly
        115                 120                 125

Gly Thr Glu Val Val Val Lys Gly Asp Pro Val Ala Pro Thr Val Leu
    130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235
```

<210> SEQ ID NO 205
<211> LENGTH: 456
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 205

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Lys Gly Ser Gly Ile Asp Phe Ser
        35                  40                  45

Ser Gly Tyr Gly Met Trp Trp Val Arg Gln Ala Pro Gly Lys Gly Leu
    50                  55                  60

Glu Tyr Ile Gly Tyr Ile Asp Thr Gly Tyr Gly Ser Thr Tyr Tyr Ala
65                  70                  75                  80

Ser Trp Ala Lys Gly Arg Phe Thr Ile Ser Lys Thr Ser Ser Thr Thr
                85                  90                  95

Val Thr Leu Gln Met Thr Ser Leu Thr Val Ala Asp Thr Ala Thr Tyr
            100                 105                 110

Phe Cys Ala Lys Gly Gly Ala Ile Asp Leu Trp Gly Pro Gly Thr Leu
        115                 120                 125

Val Thr Val Ser Ser Gly Gln Pro Lys Ala Pro Ser Val Phe Pro Leu
    130                 135                 140

Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
                165                 170                 175

Gly Thr Leu Thr Asn Gly Val Arg Thr Phe Pro Ser Val Arg Gln Ser
            180                 185                 190

Ser Gly Leu Tyr Ser Leu Ser Ser Val Val Ser Val Thr Ser Ser Ser
        195                 200                 205

Gln Pro Val Thr Cys Asn Val Ala His Pro Ala Thr Asn Thr Lys Val
    210                 215                 220

Asp Lys Thr Val Ala Pro Ser Thr Cys Ser Lys Pro Met Cys Pro Pro
225                 230                 235                 240

Pro Glu Leu Pro Gly Gly Pro Ser Val Phe Ile Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Asp Asp Pro Glu Val Gln Phe Thr Trp Tyr Ile
        275                 280                 285

Asn Asn Glu Gln Val Arg Thr Ala Arg Pro Pro Leu Arg Glu Gln Gln
    290                 295                 300

Phe Asn Ser Thr Ile Arg Val Val Ser Thr Leu Pro Ile Ala His Gln
305                 310                 315                 320

Asp Trp Leu Arg Gly Lys Glu Phe Lys Cys Lys Val His Asn Lys Ala
                325                 330                 335

Leu Pro Ala Pro Ile Glu Lys Thr Ile Ser Lys Ala Arg Gly Gln Pro
            340                 345                 350

Leu Glu Pro Lys Val Tyr Thr Met Gly Pro Pro Arg Glu Glu Leu Ser
```

```
        355                 360                 365

Ser Arg Ser Val Ser Leu Thr Cys Met Ile Asn Gly Phe Tyr Pro Ser
    370                 375                 380

Asp Ile Ser Val Glu Trp Glu Lys Asn Gly Lys Ala Glu Asp Asn Tyr
385                 390                 395                 400

Lys Thr Thr Pro Thr Val Leu Asp Ser Asp Gly Ser Tyr Phe Leu Tyr
                405                 410                 415

Ser Lys Leu Ser Val Pro Thr Ser Glu Trp Gln Arg Gly Asp Val Phe
            420                 425                 430

Thr Cys Ser Val Met His Glu Ala Leu His Asn His Tyr Thr Gln Lys
        435                 440                 445

Ser Ile Ser Arg Ser Pro Gly Lys
    450                 455


<210> SEQ ID NO 206
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ala Ser
            20                  25                  30

Thr Ser Ala Ala Val Gly Gly Thr Val Thr Ile Asn Cys Gln Ser Ser
        35                  40                  45

Gln Ser Val Tyr Arg Ser Asn Trp Leu Ala Trp Tyr Gln Gln Lys Pro
    50                  55                  60

Gly Gln Pro Pro Lys Leu Leu Ile Tyr Asp Val Phe Asn Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Gly Val Gln Cys Ala Asp Ala Ala Thr Tyr Tyr Cys
            100                 105                 110

Gln Gly Ser Tyr Tyr Ser Gly Asn Trp Tyr Ser Ala Phe Gly Gly Gly
        115                 120                 125

Thr Glu Val Val Val Lys Gly Asp Pro Val Ala Pro Thr Val Leu Ile
    130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235


<210> SEQ ID NO 207
<211> LENGTH: 13
```

<212> TYPE: PRT
<213> ORGANISM: Artificial Sequence
<220> FEATURE:
<223> OTHER INFORMATION: Description of Artificial Sequence: Synthetic peptide

<400> SEQUENCE: 207

Ala Ala Trp Asp Asp Ser Leu Asn Gly Leu Asn Trp Val
1 5 10

<210> SEQ ID NO 208
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 208

Gln Val Gln Leu Val Glu Ser Gly Gly Gly Val Val Gln Pro Gly Arg
1 5 10 15

Ser Leu Arg Leu Ser Cys Ala Ala Ser
20 25

<210> SEQ ID NO 209
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 209

Gly Phe Thr Phe Ser Asn Tyr Gly
1 5

<210> SEQ ID NO 210
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 210

Met Asn Trp Val Arg Gln Ala Pro Gly Lys Gly Leu Glu Trp Val Ser
1 5 10 15

Tyr

<210> SEQ ID NO 211
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 211

Ile Ser Ser Ser Gly Ser Thr Val
1 5

<210> SEQ ID NO 212
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 212

Tyr Tyr Ala Asp Ser Val Lys Gly Arg Phe Thr Ile Ser Arg Asp Asn
1 5 10 15

Ala Lys Asn Ser Leu Tyr Leu Gln Met Asn Ser Leu Arg Asp Glu Asp
20 25 30

Thr Ala Val Tyr Tyr Cys Ala Ser
35 40

<210> SEQ ID NO 213
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 213

Gly Gln Leu Asp Thr Ser Asp Ala Phe Asp Ile
1 5 10

<210> SEQ ID NO 214
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 214

Trp Gly Gln Gly Thr Leu Val Thr Val Ser Ser
1 5 10

<210> SEQ ID NO 215
<211> LENGTH: 26
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 215

Asp Ile Glu Met Thr Gln Ser Pro Ser Ser Pro Ser Ala Ser Val Gly
1 5 10 15

Asp Arg Val Thr Ile Thr Cys Arg Ala Ser
20 25

<210> SEQ ID NO 216
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 216

Gln Ser Ile Ser Ser Tyr
1 5

<210> SEQ ID NO 217
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 217

Leu Asn Trp Tyr Gln Gln Lys Pro Gly Lys Ala Pro Lys Leu Leu Ile
1 5 10 15

Tyr

<210> SEQ ID NO 218
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 218

Ala Ala Ser
1

<210> SEQ ID NO 219
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 219

Ser Leu Gln Ser Gly Val Pro Ser Arg Phe Ser Gly Ser Gly Ser Gly
1 5 10 15

Thr Asp Phe Thr Leu Thr Ile Ser Ser Leu Gln Pro Glu Asp Phe Ala
20 25 30

Thr Tyr Tyr Cys
35

<210> SEQ ID NO 220
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 220

Gln Gln Ser Tyr Ser Thr Pro Leu Thr
1 5

<210> SEQ ID NO 221
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 221

Phe Gly Gly Gly Thr Lys Val Glu Ile Lys
1 5 10

<210> SEQ ID NO 222
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 222

Glu Val Gln Leu Leu Glu Ser Gly Gly Gly Val Val Gln Ser Gly Arg
1 5 10 15

Ser Leu Arg Val Ser Cys Ala Ala Ser
20 25

<210> SEQ ID NO 223
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 223

Gly Phe Ser Phe Ser Ser Tyr Gly
1 5

<210> SEQ ID NO 224
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 224

Met His Trp Val Arg Gln Ala Pro Gly Lys Gly Leu Glu Trp Val Ser
1 5 10 15

Tyr

<210> SEQ ID NO 225
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 225

Ile Ser Ser Ser Gly Ser Thr Ile
1 5

<210> SEQ ID NO 226
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 226

Tyr Tyr Ala Asp Ser Val Lys Gly Arg Phe Thr Ile Ser Arg Asp Asn
1 5 10 15

Ala Glu Asn Ser Leu Tyr Leu Gln Met Asn Ser Leu Arg Ala Glu Asp
20 25 30

Thr Ala Val Tyr Tyr Cys Ala Arg
35 40

<210> SEQ ID NO 227
<211> LENGTH: 26
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 227

Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 228
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gln Gly Ile Ser Asn Tyr
1               5

<210> SEQ ID NO 229
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Leu Ala Trp Tyr Gln Gln Lys Pro Gly Lys Val Pro Lys Leu Leu Ile
1               5                   10                  15

Tyr

<210> SEQ ID NO 230
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Thr Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 231
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Phe Gly Gly Gly Thr Lys Val Glu Val Lys
1               5                   10

<210> SEQ ID NO 232
<211> LENGTH: 25
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 232

Glu Val Gln Leu Leu Glu Ser Gly Gly Gly Val Val Gln Pro Gly Arg
1               5                   10                  15

Ser Leu Arg Leu Ser Cys Ala Ala Ser
            20                  25

<210> SEQ ID NO 233
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ile Ser Ser Ser Ser Ser Thr Ile
1               5

<210> SEQ ID NO 234
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 234

Gly Gln Xaa Asp Xaa Ser Asp Ala Phe Asp Ile
1               5                   10

<210> SEQ ID NO 235
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (16)..(16)
<223> OTHER INFORMATION: Any amino acid

<400> SEQUENCE: 235

Leu Asn Xaa Tyr Gln Gln Lys Pro Gly Lys Ala Pro Lys Leu Leu Xaa
1               5                   10                  15

Tyr

<210> SEQ ID NO 236
<211> LENGTH: 3
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 236

Xaa Ala Ser
1


<210> SEQ ID NO 237
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Any amino acid

<400> SEQUENCE: 237

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Xaa Ala
            20                  25                  30

Thr Tyr Tyr Cys
        35


<210> SEQ ID NO 238
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 238

Phe Gly Gly Gly Xaa Lys Xaa Glu Ile Lys
1               5                   10


<210> SEQ ID NO 239
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Tyr Tyr Ala Asp Ser Val Lys Gly Arg Phe Ala Ile Ser Arg Asp Asn
1               5                   10                  15

Ala Lys Asn Thr Leu Tyr Leu Gln Met Asn Ser Leu Arg Ala Glu Asp
            20                  25                  30

Thr Ala Leu Tyr Tyr Cys Ala Lys
        35                  40
```

<210> SEQ ID NO 240
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 240

Ala Thr Arg Tyr Asp Ile Leu Thr Gly Tyr Ser Asp Gly Val Asp Tyr
1 5 10 15

Phe Asp Tyr

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 241

His Gln Ser Tyr Ser Thr Pro Tyr Thr
1 5

<210> SEQ ID NO 242
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 242

Phe Gly Gln Gly Thr Lys Leu Glu Ile Lys
1 5 10

<210> SEQ ID NO 243
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 243

Gln Val Gln Leu Val Glu Ser Gly Gly Gly Leu Val Gln Pro Gly Gly
1 5 10 15

Ser Leu Arg Leu Ser Cys Ala Ala Ser
20 25

<210> SEQ ID NO 244
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 244

Met Ser Trp Val Arg Gln Ala Pro Gly Lys Gly Leu Glu Trp Val Ala
1 5 10 15

Asn

<210> SEQ ID NO 245
<211> LENGTH: 8

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ile Lys Gln Asp Gly Ser Glu Lys
1               5

<210> SEQ ID NO 246
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Tyr Tyr Val Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys Ala Arg
        35                  40

<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Val Thr Ser Pro His Ala Phe Asp Ile
1               5

<210> SEQ ID NO 248
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Trp Gly Arg Gly Thr Leu Val Thr Val Ser Ser
1               5                   10

<210> SEQ ID NO 249
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Asp Ile Gln Met Thr Gln Ser Pro Ser Ala Met Ser Ala Ser Val Gly
1               5                   10                  15

Asp Arg Val Thr Ile Thr Cys Arg Ala Ser
            20                  25

<210> SEQ ID NO 250
<211> LENGTH: 17

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Leu Ala Trp Phe Gln Gln Lys Pro Gly Lys Val Pro Lys Arg Leu Ile
1               5                   10                  15

Tyr

<210> SEQ ID NO 251
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Gln Val Gln Leu Val Glu Ser Gly Gly Gly Val Val Arg Pro Gly Gly
1               5                   10                  15

Ser Leu Arg Leu Ser Cys Ala Ala Ser
            20                  25

<210> SEQ ID NO 252
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Met Ser Trp Val Arg Gln Ala Pro Gly Lys Gly Leu Glu Trp Val Ser
1               5                   10                  15

Gly

<210> SEQ ID NO 253
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Ile Asn Trp Asn Gly Gly Ser Thr
1               5

<210> SEQ ID NO 254
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Gly Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Gly Glu Asp
            20                  25                  30

Thr Ala Val Tyr Tyr Cys Val Thr
        35                  40

<210> SEQ ID NO 255
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 255

Gln Gly Ser Ala Phe Asp Ile
1 5

<210> SEQ ID NO 256
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 256

Ser Tyr Glu Leu Thr Gln Pro Pro Ser Leu Ser Val Ser Pro Gly Gln
1 5 10 15

Thr Ala Arg Ile Thr Cys Ser Gly Asp
20 25

<210> SEQ ID NO 257
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 257

Ala Leu Ala Lys Gln Tyr
1 5

<210> SEQ ID NO 258
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 258

Ala Tyr Trp Tyr Gln Gln Thr Pro Gly Gln Ala Pro Val Leu Val Ile
1 5 10 15

Tyr

<210> SEQ ID NO 259
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 259

Lys Asp Thr
1

<210> SEQ ID NO 260
<211> LENGTH: 36

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 260

```
Glu Arg Pro Ser Gly Ile Pro Glu Arg Phe Ser Gly Ser Ser Ser Gly
1               5                   10                  15

Thr Thr Val Thr Leu Thr Ile Ser Gly Val Gln Ala Glu Asp Glu Val
            20                  25                  30

Asp Tyr Tyr Cys
        35
```

<210> SEQ ID NO 261
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 261

```
Gln Ser Thr Asp Ser Ser Gly Thr Tyr Gln Val
1               5                   10
```

<210> SEQ ID NO 262
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 262

```
Phe Gly Gly Gly Thr Lys Leu Thr Val Leu
1               5                   10
```

<210> SEQ ID NO 263
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 263

```
Gln Val Gln Leu Val Gln Ser Gly Ala Glu Val Lys Lys Pro Gly Ala
1               5                   10                  15

Ser Val Lys Val Ser Cys Lys Ala Ser
            20                  25
```

<210> SEQ ID NO 264
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 264

```
Ile Ser Trp Val Arg Gln Ala Pro Gly Gln Gly Leu Glu Trp Met Gly
1               5                   10                  15

Trp
```

<210> SEQ ID NO 265
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 265

Ile Ser Ala Tyr Asn Gly Asn Thr
1 5

<210> SEQ ID NO 266
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 266

Asn Tyr Ala Gln Lys Leu Gln Gly Arg Val Thr Met Thr Thr Asp Thr
1 5 10 15

Ser Thr Ser Thr Ala Tyr Met Glu Leu Arg Ser Leu Arg Ser Asp Asp
20 25 30

Thr Ala Ala Tyr Tyr Cys Ala Arg
35 40

<210> SEQ ID NO 267
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 267

Val Thr Gly Ile Thr Gly Thr Thr Ile Asp Pro
1 5 10

<210> SEQ ID NO 268
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 268

Trp Gly Gln Gly Thr Met Val Thr Val Ser Ser
1 5 10

<210> SEQ ID NO 269
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 269

Asp Ala Ser
1

<210> SEQ ID NO 270
<211> LENGTH: 36
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 270

```
Ser Leu Glu Ser Gly Val Pro Ser Arg Phe Ser Gly Ser Gly Ser Gly
1               5                   10                  15

Thr Glu Phe Thr Leu Thr Ile Ser Ser Leu Gln Pro Asp Asp Phe Ala
            20                  25                  30

Val Tyr Tyr Cys
        35
```

<210> SEQ ID NO 271
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

```
Gln Gln Tyr Asn Asn Trp Pro Gln Thr
1               5
```

<210> SEQ ID NO 272
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

```
Phe Gly Gln Gly Thr Lys Val Glu Ile Lys
1               5                   10
```

<210> SEQ ID NO 273
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

```
Gln Val Gln Leu Val Glu Ser Gly Gly Gly Leu Val Lys Pro Gly Gly
1               5                   10                  15

Ser Leu Arg Leu Ser Cys Ala Ala Ser
            20                  25
```

<210> SEQ ID NO 274
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

```
Met Ser Trp Val Arg Gln Ala Pro Gly Lys Gly Leu Glu Trp Val Ser
1               5                   10                  15

Ala
```

<210> SEQ ID NO 275

<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Ile Ser Gly Ser Gly Gly Ser Thr
1               5

<210> SEQ ID NO 276
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys Ala Arg
        35                  40

<210> SEQ ID NO 277
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Asp Tyr Gly Gly Tyr Asp Gly Val Tyr Phe Asp Tyr
1               5                   10

<210> SEQ ID NO 278
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Ser Tyr Glu Leu Thr Gln Asp Pro Ala Val Ser Val Ala Leu Gly Gln
1               5                   10                  15

Thr Val Arg Ile Thr Cys Gln Gly Asp
            20                  25

<210> SEQ ID NO 279
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Ser Leu Arg Ser Tyr Tyr
1               5

<210> SEQ ID NO 280

<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 280

Ala Ser Trp Tyr Gln Gln Lys Pro Gly Gln Ala Pro Val Leu Val Ile
1 5 10 15

Tyr

<210> SEQ ID NO 281
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 281

Gly Lys Asn
1

<210> SEQ ID NO 282
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 282

Asn Arg Pro Ser Gly Ile Pro Asp Arg Phe Ser Gly Ser Ser Ser Gly
1 5 10 15

Asn Thr Ala Ser Leu Thr Ile Thr Gly Ala Gln Ala Glu Asp Glu Ala
20 25 30

Asp Tyr Tyr Cys
35

<210> SEQ ID NO 283
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 283

Asn Ser Arg Asp Ser Ser Gly Asn His Val Val
1 5 10

<210> SEQ ID NO 284
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 284

Phe Gly Gly Gly Thr Lys Val Thr Val Leu
1 5 10

<210> SEQ ID NO 285
<211> LENGTH: 25

<212> TYPE: PRT
<213> ORGANISM: Artificial Sequence
<220> FEATURE:
<223> OTHER INFORMATION: Description of Artificial Sequence: Synthetic peptide

<400> SEQUENCE: 285

Glu Val Gln Leu Leu Glu Ser Gly Gly Gly Leu Val Lys Pro Gly Gly
1               5                   10                  15

Ser Leu Arg Leu Ser Cys Ala Ala Ser
            20                  25

<210> SEQ ID NO 286
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 286

Met His Trp Val Arg Gln Ala Pro Gly Lys Gly Leu Glu Trp Val Ala
1               5                   10                  15

Val

<210> SEQ ID NO 287
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 287

Ile Ser Tyr Asp Gly Ser Asn Lys
1               5

<210> SEQ ID NO 288
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 288

Tyr Tyr Ala Asp Ser Val Lys Gly Arg Phe Ala Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys Ala Arg
        35                  40

<210> SEQ ID NO 289
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 289

Asp Arg Asp Val Gly Pro Thr Tyr Tyr Tyr Tyr Gly Met Asp Val
1               5                   10                  15

<210> SEQ ID NO 290
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 290

```
Ser Tyr Glu Leu Thr Gln Pro Pro Ser Leu Ser Val Ser Pro Gly Gln
1               5                   10                  15

Thr Ala Arg Ile Thr Cys Ser Gly His
            20                  25
```

<210> SEQ ID NO 291
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 291

```
Ala Leu Pro Lys Gln Tyr
1               5
```

<210> SEQ ID NO 292
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 292

```
Glu Arg Pro Ser Gly Ile Pro Glu Arg Phe Ser Gly Ser Ser Ser Gly
1               5                   10                  15

Thr Thr Val Thr Leu Thr Ile Ser Gly Val Gln Ala Glu Asp Glu Ala
            20                  25                  30

Asp Tyr Tyr Cys
        35
```

<210> SEQ ID NO 293
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 293

```
Gln Ser Ala Asp Ser Ser Gly Pro Tyr Gln Val
1               5                   10
```

<210> SEQ ID NO 294
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 294

```
Phe Gly Gly Gly Thr Gln Leu Thr Val Leu
1               5                   10
```

<210> SEQ ID NO 295
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

```
Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys Ala Lys
        35                  40
```

<210> SEQ ID NO 296
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

```
Asp Arg Glu Tyr Ile Ala Val Ala Ala Asp Tyr
1               5                   10
```

<210> SEQ ID NO 297
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

```
Trp Gly Gln Gly Thr Thr Val Thr Val Ser Ser
1               5                   10
```

<210> SEQ ID NO 298
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

```
Asp Ile Gln Met Thr Gln Ser Pro Ser Ser Leu Ser Ala Ser Val Gly
1               5                   10                  15

Asp Thr Ile Ser Ile Thr Cys Arg Ala Ser
            20                  25
```

<210> SEQ ID NO 299
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

```
Ser Leu Gln Ser Gly Val Pro Ser Arg Phe Ser Gly Ser Gly Ser Arg
1               5                   10                  15

Thr Asp Phe Thr Leu Thr Ile Ser Ser Val Gln Pro Glu Asp Phe Ala
```

```
            20                  25                  30

Thr Tyr Tyr Cys
        35


<210> SEQ ID NO 300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Gln Gln Ser Tyr Ser Thr Pro Phe Thr
1               5


<210> SEQ ID NO 301
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Phe Gly Pro Gly Thr Lys Val Glu Ile Lys
1               5                   10


<210> SEQ ID NO 302
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Glu Val Gln Leu Val Glu Ser Gly Ala Glu Val Lys Lys Pro Gly Ala
1               5                   10                  15

Ser Val Lys Val Ser Cys Lys Ala Ser
            20                  25


<210> SEQ ID NO 303
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Met His Trp Val Arg Gln Ala Pro Gly Gln Gly Leu Glu Trp Met Gly
1               5                   10                  15

Ile


<210> SEQ ID NO 304
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Ile Asn Pro Ser Gly Gly Ser Thr
1               5
```

<210> SEQ ID NO 305
<211> LENGTH: 40
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 305

Ile Tyr Ala Gln Lys Phe Gln Gly Arg Val Thr Met Thr Arg Asp Thr
1 5 10 15

Ser Thr Ser Thr Val Tyr Met Glu Leu Ser Ser Leu Arg Ser Glu Asp
20 25 30

Thr Ala Val Tyr Tyr Cys Ala Arg
35 40

<210> SEQ ID NO 306
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 306

Ser Leu Arg Asp Gly Tyr Asn Tyr Ile Gly Ser Leu Gly Tyr
1 5 10

<210> SEQ ID NO 307
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 307

Gln Ser Glu Leu Thr Gln Pro Pro Ser Ala Ser Gly Thr Pro Gly Gln
1 5 10 15

Arg Val Thr Ile Ser Cys Ser Gly Ser
20 25

<210> SEQ ID NO 308
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 308

Ser Ser Asn Ile Gly Ser Asn Tyr
1 5

<210> SEQ ID NO 309
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 309

Val Tyr Trp Tyr Gln Gln Leu Pro Gly Thr Ala Pro Lys Leu Leu Ile
1 5 10 15

Tyr

<210> SEQ ID NO 310
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Arg Asn Asn
1

<210> SEQ ID NO 311
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Gln Arg Pro Ser Gly Val Pro Asp Arg Phe Ser Gly Ser Lys Ser Gly
1               5                   10                  15

Thr Ser Ala Ser Leu Ala Ile Arg Gly Leu Gln Ser Glu Asp Glu Ala
            20                  25                  30

Gly Tyr Tyr Cys
        35

<210> SEQ ID NO 312
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Gly Phe Thr Phe Asp Asp Tyr Ala
1               5

<210> SEQ ID NO 313
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Met His Trp Val Arg Gln Ala Pro Gly Lys Gly Leu Glu Trp Val Ser
1               5                   10                  15

Gly

<210> SEQ ID NO 314
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Ile Ser Trp Asn Ser Gly Ser Thr 1 5

<210> SEQ ID NO 315
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 315

Tyr Tyr Ala Asp Ser Val Lys Gly Arg Phe Thr Ile Ser Arg Asp Asn
1 5 10 15

Ser Lys Asn Thr Leu Tyr Leu Gln Met Asn Ser Leu Arg Ala Glu Asp
20 25 30

Thr Ala Val Tyr Tyr Cys Ala Gly
35 40

<210> SEQ ID NO 316
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 316

Gly Ser Arg Arg Tyr Asp Ser Ser Gly Tyr Tyr Tyr Glu Ser Phe Asp
1 5 10 15

Tyr

<210> SEQ ID NO 317
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 317

Asn Leu Glu Thr Gly Val Pro Ser Arg Phe Ser Gly Ser Gly Ser Gly
1 5 10 15

Thr Asp Phe Thr Leu Thr Ile Ser Ser Leu Gln Pro Glu Asp Phe Ala
20 25 30

Thr Tyr Tyr Cys
35

<210> SEQ ID NO 318
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 318

Gln Gln Ser Tyr His Thr Pro Tyr Thr
1 5

<210> SEQ ID NO 319
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 319

Gln Met Gln Leu Val Gln Ser Gly Ala Glu Val Lys Lys Pro Gly Ser
1 5 10 15

Ser Val Lys Val Ser Cys Lys Ala Ser
20 25

<210> SEQ ID NO 320
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 320

Gly Gly Thr Phe Ser Ser Tyr Ala
1 5

<210> SEQ ID NO 321
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 321

Ile Ser Trp Val Arg Gln Ala Pro Gly Gln Gly Leu Glu Trp Met Gly
1 5 10 15

Arg

<210> SEQ ID NO 322
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 322

Ile Ile Pro Ile Leu Gly Ile Ala
1 5

<210> SEQ ID NO 323
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 323

Asn Tyr Ala Gln Lys Phe Gln Gly Arg Val Thr Ile Thr Ala Asp Lys
1 5 10 15

Ser Thr Ser Thr Ala Tyr Met Glu Leu Ser Ser Leu Arg Ser Glu Asp
20 25 30

Thr Ala Val Tyr Tyr Cys Ala Arg
35 40

<210> SEQ ID NO 324
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 324

Asp Ile Asn Arg Tyr Asn Trp Asn Phe Arg Ala Phe Asp Ile
1 5 10

<210> SEQ ID NO 325
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 325

Gln Ser Val Leu Tyr Ser Ser Asn Asn Lys Asn Tyr
1 5 10

<210> SEQ ID NO 326
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 326

Leu Ala Trp Tyr Gln Gln Lys Pro Arg Gln Pro Pro Lys Leu Leu Ile
1 5 10 15

Tyr

<210> SEQ ID NO 327
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 327

Trp Ala Ser
1

<210> SEQ ID NO 328
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 328

Thr Arg Glu Ser Gly Val Pro Asp Arg Phe Ser Gly Asn Gly Ser Gly
1 5 10 15

Thr Asp Phe Thr Leu Thr Ile Ser Ser Leu Gln Ala Glu Asp Val Ala
20 25 30

Ala Tyr Tyr Cys
35

<210> SEQ ID NO 329
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 329

Gln Gln His Tyr Ser Thr Pro Leu Thr
1               5

<210> SEQ ID NO 330
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 331
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Asn Tyr Ala Gln Lys Leu Gln Gly Arg Val Thr Met Thr Thr Asn Thr
1               5                   10                  15

Ser Thr Ser Thr Ala Tyr Met Glu Leu Arg Ser Leu Arg Ser Asp Asp
            20                  25                  30

Thr Ala Val Tyr Tyr Cys Ala Arg
        35                  40

<210> SEQ ID NO 332
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Leu Asn Trp Tyr Arg Gln Lys Pro Gly Lys Ala Pro Lys Leu Leu Ile
1               5                   10                  15

Tyr

<210> SEQ ID NO 333
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Ala Ala
            20                  25                  30

Thr Tyr Tyr Cys

35

<210> SEQ ID NO 334
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 334

Gln Gln Tyr Asp Ser Gln Ser Gly Thr
1 5

<210> SEQ ID NO 335
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 335

Glu Val Gln Leu Val Glu Ser Gly Gly Gly Val Val Gln Pro Gly Arg
1 5 10 15

Ser Leu Arg Leu Ser Cys Ala Ala Ser
20 25

<210> SEQ ID NO 336
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 336

Ile Ser Tyr Asp Gly Val Lys Lys
1 5

<210> SEQ ID NO 337
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 337

Tyr Tyr Ala Asp Ser Val Lys Gly Arg Phe Thr Ile Ser Arg Asp Asn
1 5 10 15

Ser Lys Ser Thr Leu Tyr Leu Gln Met Asn Ser Leu Arg Val Asp Asp
20 25 30

Thr Ala Val Tyr Tyr Cys Ala Lys
35 40

<210> SEQ ID NO 338
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 338

Asp Leu Gly Trp Gln Asn Asp Tyr 1               5

<210> SEQ ID NO 339
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 339

Gln Ser Val Leu Thr Gln Pro Ala Ser Val Ser Gly Ser Pro Gly Gln
1               5                   10                  15

Ser Ile Thr Ile Ser Cys Thr Gly Thr Asp Leu Gly Trp Gln Asn Asp
            20                  25                  30

Tyr

<210> SEQ ID NO 340
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 340

Ser Ser Asp Val Gly Gly His Asn Tyr
1               5

<210> SEQ ID NO 341
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 341

Val Ser Trp Tyr Gln Gln His Pro Gly Lys Ala Pro Lys Leu Met Ile
1               5                   10                  15

Tyr

<210> SEQ ID NO 342
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 342

Asp Val Ser
1

<210> SEQ ID NO 343
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 343

Asn Arg Pro Ser Gly Val Ser Asn Arg Phe Ser Gly Ser Lys Ser Gly
1               5                   10                  15

Asn Thr Ala Ser Leu Thr Ile Ser Gly Leu Gln Ala Glu Asp Glu Ala
20 25 30

Asp Tyr Tyr Cys
35

<210> SEQ ID NO 344
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 344

Ser Ser Tyr Thr Ser Ser Ser Pro Trp Val
1 5 10

<210> SEQ ID NO 345
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 345

Phe Gly Gly Gly Thr Lys Leu Thr Val Leu Gly
1 5 10

<210> SEQ ID NO 346
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 346

Glu Val Gln Leu Val Glu Ser Gly Gly Gly Leu Val Gln Pro Gly Gly
1 5 10 15

Ser Leu Arg Leu Ser Cys Ala Ala Ser
20 25

<210> SEQ ID NO 347
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 347

Tyr Tyr Ala Asp Ser Val Lys Gly Arg Phe Thr Ile Ser Arg Asp Asn
1 5 10 15

Ser Lys Asn Ala Leu Tyr Leu Gln Met Asn Ser Leu Arg Ala Glu Asp
20 25 30

Thr Ala Val Tyr Tyr Cys Arg Gly
35 40

<210> SEQ ID NO 348
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 348

Tyr Cys Ser Ser Thr Ser Cys Tyr Gly Arg Arg Gly Ala Phe Asp Ile
1 5 10 15

<210> SEQ ID NO 349
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 349

Ser Gly Gln Gly Thr Leu Val Thr Val Ser Ser
1 5 10

<210> SEQ ID NO 350
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 350

Gln Ala Val Leu Thr Gln Pro Pro Ser Ala Ser Gly Thr Pro Gly Gln
1 5 10 15

Arg Val Thr Ile Ser Cys Ser Gly Arg
20 25

<210> SEQ ID NO 351
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 351

Asn Ser Asn Ile Gly Ser Asn Asn
1 5

<210> SEQ ID NO 352
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 352

Val Asn Trp Tyr Gln His Leu Pro Gly Thr Ala Pro Lys Leu Leu Ile
1 5 10 15

Tyr

<210> SEQ ID NO 353
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 353

Ser Asn Asn

1

<210> SEQ ID NO 354
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 354

Gln Arg Pro Ser Gly Val Pro Asp Arg Phe Ser Ala Ser Lys Ser Gly
1 5 10 15

Thr Ser Ala Ser Leu Ala Ile Ser Gly Leu Gln Ser Glu Asp Glu Ala
20 25 30

Asp Tyr Tyr Cys
35

<210> SEQ ID NO 355
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 355

Ala Ala Trp Asp Asp Arg Met Asn Gly Pro Val
1 5 10

<210> SEQ ID NO 356
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 356

Ile Gly Gly Gly Thr Lys Val Thr Val Leu Gly
1 5 10

<210> SEQ ID NO 357
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 357

Met His Trp Val Arg Gln Ala Pro Ala Lys Gly Leu Val Trp Val Ser
1 5 10 15

Arg

<210> SEQ ID NO 358
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 358

Ile Asn Ser Asp Gly Ser Ser Thr
1 5

<210> SEQ ID NO 359
<211> LENGTH: 40
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 359

Ser Tyr Ala Asp Ser Val Lys Gly Arg Phe Thr Ile Ser Arg Asp Asn
1 5 10 15

Ser Lys Asn Thr Leu Tyr Leu Gln Met Asn Ser Leu Arg Ala Glu Asp
20 25 30

Thr Ala Val Tyr Tyr Cys Ala Arg
35 40

<210> SEQ ID NO 360
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 360

Asp Phe Trp Ser Gly Arg Pro Tyr Tyr Tyr Tyr Met Asp Val
1 5 10

<210> SEQ ID NO 361
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 361

Gln Asp Ile Gly Asp Asp
1 5

<210> SEQ ID NO 362
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 362

Leu Ala Trp Phe Gln Gln Lys Pro Gly Lys Ala Pro Lys Arg Leu Ile
1 5 10 15

Tyr

<210> SEQ ID NO 363
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 363

Thr Leu Gln Gly Gly Val Pro Ser Arg Phe Ser Gly Ser Gly Ser Gly
1 5 10 15

Thr Asp Phe Thr Leu Thr Ile Ser Ser Leu Gln Pro Glu Asp Phe Ala
20 25 30

Thr Tyr Tyr Cys
35

<210> SEQ ID NO 364
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 364

Gln Gln Ser Tyr Ser Thr Pro Arg Thr
1 5

<210> SEQ ID NO 365
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 365

Tyr Tyr Ala Asp Ser Val Lys Gly Arg Phe Thr Ile Ser Arg Asp Asn
1 5 10 15

Ser Lys Asn Thr Leu Tyr Leu Gln Met Asn Ser Arg Arg Ala Glu Asp
20 25 30

Thr Ala Val Tyr Tyr Cys Ala Arg
35 40

<210> SEQ ID NO 366
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 366

Trp Gly Ile Val Ala Ala Arg Pro Asn Tyr Tyr Tyr Gly Met Asp Val
1 5 10 15

<210> SEQ ID NO 367
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 367

Gln Ser Ala Leu Thr Gln Pro Arg Ser Val Ser Gly Ser Pro Gly Gln
1 5 10 15

Ser Val Thr Ile Ser Cys Thr Gly Thr
20 25

<210> SEQ ID NO 368
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 368

Ser Ser Asp Val Gly Gly Tyr Asn Tyr
1 5

<210> SEQ ID NO 369
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 369

Ser Ser Tyr Ala Asn Asn Ser Pro Trp Val
1 5 10

<210> SEQ ID NO 370
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 370

Phe Gly Gly Gly Thr Lys Val Thr Val Leu Gly
1 5 10

<210> SEQ ID NO 371
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 371

Gln Val Gln Leu Val Gln Ser Gly Ala Glu Val Arg Lys Pro Gly Ala
1 5 10 15

Ser Val Lys Val Ser Cys Lys Ala Ser
20 25

<210> SEQ ID NO 372
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 372

Asn Tyr Ala Gln Lys Leu Gln Gly Arg Val Thr Met Thr Thr Asp Thr
1 5 10 15

Ser Thr Ser Thr Ala Tyr Met Glu Leu Arg Ser Leu Arg Ser Asp Asp
20 25 30

Thr Ala Val Tyr Tyr Cys Ala Arg
35 40

<210> SEQ ID NO 373
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 373

```
Asp Ile Gln Met Thr Gln Ser Pro Ser Ser Leu Ser Ala Ser Val Gly
1               5                   10                  15

Asp Arg Val Thr Ile Thr Cys Gln Ala Ser
            20                  25
```

<210> SEQ ID NO 374
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 374

```
Gln Asp Ile Ser Asn Tyr
1               5
```

<210> SEQ ID NO 375
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 375

```
Asn Leu Glu Thr Gly Val Pro Ser Arg Phe Ser Gly Ser Gly Ser Gly
1               5                   10                  15

Thr Asp Phe Thr Phe Thr Ile Ser Ser Leu Gln Pro Glu Asp Ile Ala
            20                  25                  30

Thr Tyr Tyr Cys
        35
```

<210> SEQ ID NO 376
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 376

```
Gln Gln Tyr Ala Asn Leu Pro Leu Thr
1               5
```

<210> SEQ ID NO 377
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 377

```
Gly Phe Thr Val Ser Ser Asn Tyr
1               5
```

<210> SEQ ID NO 378
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 378

Met Ser Trp Val Arg Gln Ala Pro Gly Lys Gly Leu Glu Trp Val Ser
1               5                   10                  15

Val

<210> SEQ ID NO 379
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Ile Tyr Ser Gly Gly Ser Thr
1               5

<210> SEQ ID NO 380
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Gly Gly Leu Thr Gly Asp Asp Ala Phe Asp Ile
1               5                   10

<210> SEQ ID NO 381
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Gln Ser Ile Ser Ser Phe
1               5

<210> SEQ ID NO 382
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Leu Asn Trp Tyr Gln Gln Lys Pro Gly Thr Ala Pro Lys Leu Leu Ile
1               5                   10                  15

Tyr

<210> SEQ ID NO 383
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Thr Thr Ser
1

<210> SEQ ID NO 384
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 384

Gln Gln Gly Asn Ser Leu Pro Leu Thr
1 5

<210> SEQ ID NO 385
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 385

Asp Lys Glu Leu Ser Tyr
1 5

<210> SEQ ID NO 386
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 386

Gln Ser Gly Leu Thr Gln Pro Ala Ser Val Ser Gly Ser Pro Gly Gln
1 5 10 15

Ser Ile Thr Ile Ser Cys Thr Gly Thr
20 25

<210> SEQ ID NO 387
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 387

Glu Val Ser
1

<210> SEQ ID NO 388
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 388

Asn Arg Pro Ser Gly Val Pro Asp Arg Phe Ser Gly Ser Lys Ser Gly
1 5 10 15

Asn Thr Ala Ser Leu Thr Ile Ser Gly Leu Gln Ala Glu Asp Glu Ala
20 25 30

Asp Tyr Tyr Cys
35

<210> SEQ ID NO 389
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 389

Lys Thr Ser
1

<210> SEQ ID NO 390
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 390

```
Asn Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35
```

<210> SEQ ID NO 391
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 391

```
Met Ser Trp Val Arg Gln Ala Pro Ala Lys Gly Leu Glu Trp Val Ser
1               5                   10                  15

Ala
```

<210> SEQ ID NO 392
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 392

```
Asp Arg Pro Tyr Ser Tyr Gly Lys Asn Asp Ala Phe Asp Ile
1               5                   10
```

<210> SEQ ID NO 393
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 393

```
Gln Asp Val Ser Asn Tyr
1               5
```

<210> SEQ ID NO 394
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 394

Phe Gly Gly Gly Thr Lys Leu Glu Ile Lys
1 5 10

<210> SEQ ID NO 395
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 395

Glu Val Gln Leu Val Gln Ser Gly Ala Glu Val Lys Lys Pro Gly Ala
1 5 10 15

Ser Val Lys Val Ser Cys Lys Ala Ser
20 25

<210> SEQ ID NO 396
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 396

Gly Tyr Thr Phe Thr Ser Tyr Tyr
1 5

<210> SEQ ID NO 397
<211> LENGTH: 40
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 397

Ser Tyr Ala Gln Lys Phe Gln Gly Arg Val Thr Met Thr Arg Asp Thr
1 5 10 15

Ser Thr Ser Thr Val Tyr Met Glu Leu Ser Ser Leu Arg Ser Glu Asp
20 25 30

Thr Ala Val Tyr Tyr Cys Ala Arg
35 40

<210> SEQ ID NO 398
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 398

Ala Gly Gly Tyr Tyr Tyr Tyr Tyr Met Asp Val
1 5 10

```
<210> SEQ ID NO 399
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Gln Ser Gly Leu Thr Gln Pro Pro Ser Ala Ser Gly Thr Pro Gly Gln
1               5                   10                  15

Arg Val Thr Ile Ser Cys Ser Gly Ser
            20                  25


<210> SEQ ID NO 400
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Gly Pro Asn Ile Gly Asn Asn Tyr
1               5


<210> SEQ ID NO 401
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Val Tyr Trp Tyr Gln Gln Leu Pro Gly Thr Ala Pro Lys Leu Leu Met
1               5                   10                  15

Tyr


<210> SEQ ID NO 402
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Ser Pro Trp Leu Ile Thr Phe Gly Gly Val Ile Ala Met Gly Tyr
1               5                   10                  15


<210> SEQ ID NO 403
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Gln Ser Val Leu Thr Gln Pro Pro Ser Ala Ser Gly Thr Pro Gly Gln
1               5                   10                  15

Arg Val Thr Ile Ser Cys Ser Gly Ser
            20                  25
```

<210> SEQ ID NO 404
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 404

Gln Arg Pro Ser Gly Val Pro Asp Arg Phe Ser Gly Ser Lys Ser Gly
1 5 10 15

Thr Ser Ala Ser Leu Ala Ile Ser Gly Leu Arg Ser Glu Asp Glu Ala
20 25 30

Asp Tyr Tyr Cys
35

<210> SEQ ID NO 405
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 405

Ala Ala Trp Asp Asp Ser Leu Ser Gly Val Val
1 5 10

<210> SEQ ID NO 406
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 406

Phe Gly Gly Gly Thr Gln Leu Thr Val Leu Gly
1 5 10

<210> SEQ ID NO 407
<211> LENGTH: 26
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 407

Asp Ile Val Met Thr Gln Ser Pro Ser Ser Leu Ser Ala Ser Val Gly
1 5 10 15

Asp Arg Val Thr Ile Thr Cys Arg Ala Ser
20 25

<210> SEQ ID NO 408
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 408

Gln Gln Phe Asn Asn Tyr Pro Leu Thr
1 5

<210> SEQ ID NO 409
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 409

Gln Val Gln Leu Val Glu Ser Gly Ala Glu Val Lys Lys Pro Gly Ala
1               5                   10                  15

Ser Val Lys Val Ser Cys Lys Ala Ser
            20                  25

<210> SEQ ID NO 410
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 410

Gln Arg Pro Ser Gly Val Pro Asp Arg Phe Ser Gly Ser Lys Ser Gly
1               5                   10                  15

Thr Ser Ala Ser Leu Ala Ile Ser Gly Leu Gln Ser Glu Asp Glu Ala
            20                  25                  30

Asp Tyr Tyr Cys
        35

<210> SEQ ID NO 411
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 411

Ala Ala Trp Asp Asp Ser Leu Asn Gly Tyr Val
1               5                   10

<210> SEQ ID NO 412
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 412

Phe Gly Thr Gly Thr Lys Leu Thr Val Leu Gly
1               5                   10

<210> SEQ ID NO 413
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 413

Gln Ile Gln Leu Val Gln Ser Gly Ala Glu Val Lys Lys Pro Gly Glu
1               5                   10                  15

Ser Leu Lys Ile Ser Cys Lys Ala Ser Gly Tyr Thr Phe Thr Asp Tyr 20 25 30

Ala Ile Gly Trp Val Arg Gln Met Pro Gly Lys Gly Leu Glu Trp Met
35 40 45

Gly Ile Ile Asn Thr Gln Thr Gly Lys Pro Lys Tyr Ser Pro Ser Phe
50 55 60

Gln Gly Gln Phe Ile Phe Ser Leu Asp Thr Ser Ile Asn Thr Thr Tyr
65 70 75 80

Leu Gln Trp Ser Ser Leu Lys Ala Ser Asp Thr Ala Ile Tyr Phe Cys
85 90 95

Thr Arg Leu Gly Thr Gly Asn Thr Lys Gly Phe Ala Tyr Trp Gly Gln
100 105 110

Gly Thr Thr Val Thr Val Ser Ser
115 120

<210> SEQ ID NO 414
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 414

Asp Ile Gln Ile Thr Gln Ser Pro Ser Ser Leu Ser Ala Ser Leu Gly
1 5 10 15

Asp Lys Val Thr Ile Thr Cys Arg Ser Ser Gln Ser Leu Leu Tyr Ser
20 25 30

Glu Asn Asn Gln Asp Tyr Leu Ala Trp Tyr Gln Gln Lys Pro Gly Lys
35 40 45

Ala Pro Lys Leu Leu Ile Tyr Gly Ala Ser Asn Leu Gln Ser Gly Val
50 55 60

Pro Ser Arg Phe Ser Gly Arg Gly Ser Gly Thr Asp Phe Thr Leu Thr
65 70 75 80

Ile Ser Ser Leu Gln Pro Glu Asp Phe Ala Thr Tyr Tyr Cys Glu Gln
85 90 95

Thr Tyr Arg Tyr Pro Phe Thr Phe Gly Pro Gly Thr Lys Val Asp Ile
100 105 110

Lys Arg

<210> SEQ ID NO 415
<211> LENGTH: 471
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 415

Met Gly Trp Ser Cys Ile Ile Leu Phe Leu Val Ala Thr Ala Thr Gly
1 5 10 15

Val His Ser Gln Val Gln Leu Val Gln Ser Gly Ala Glu Val Lys Lys
20 25 30

Pro Gly Ala Ser Val Lys Val Ser Cys Lys Ala Ser Gly Tyr Thr Phe
35 40 45

Pro Asp Tyr Asn Met Asp Trp Val Arg Gln Ala Pro Gly Gln Arg Leu
50 55 60

Glu Trp Met Gly Tyr Ile Asn Pro Asp Asn Gly Gly Thr Ile Tyr Asn
65 70 75 80

```
Gln Lys Phe Lys Gly Arg Val Thr Leu Thr Val Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Leu Asp Ser Ser Gly Tyr Gly Tyr Tyr Ala Met
        115                 120                 125

Asp Tyr Trp Gly Gln Gly Thr Ser Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Ala Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470
```

<210> SEQ ID NO 416
<211> LENGTH: 471

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 416

Met Gly Trp Ser Cys Ile Ile Leu Phe Leu Val Ala Thr Ala Thr Gly
1 5 10 15

Val His Ser Gln Val Gln Leu Val Gln Ser Gly Ala Glu Val Lys Lys
20 25 30

Pro Gly Ala Ser Val Lys Val Ser Cys Lys Ala Ser Gly Tyr Thr Phe
35 40 45

Pro Asp Tyr Asn Met Asp Trp Val Arg Gln Ala Pro Gly Gln Arg Leu
50 55 60

Glu Trp Ile Gly Tyr Ile Asn Pro Asp Asn Gly Gly Thr Ile Tyr Asn
65 70 75 80

Gln Lys Phe Lys Gly Arg Val Thr Leu Thr Val Asp Thr Ser Ala Ser
85 90 95

Thr Ala Tyr Met Glu Leu Ser Ser Leu Arg Ser Glu Asp Thr Ala Val
100 105 110

Tyr Tyr Cys Ala Arg Leu Asp Ser Ser Gly Tyr Gly Tyr Tyr Ala Met
115 120 125

Asp Tyr Trp Gly Gln Gly Thr Ser Val Thr Val Ser Ser Ala Ser Thr
130 135 140

Lys Gly Pro Ser Val Phe Pro Leu Ala Pro Ser Ser Lys Ser Thr Ser
145 150 155 160

Gly Gly Thr Ala Ala Leu Gly Cys Leu Val Lys Asp Tyr Phe Pro Glu
165 170 175

Pro Val Thr Val Ser Trp Asn Ser Gly Ala Leu Thr Ser Gly Val His
180 185 190

Thr Phe Pro Ala Val Leu Gln Ser Ser Gly Leu Tyr Ser Leu Ser Ser
195 200 205

Val Val Thr Val Pro Ser Ser Ser Leu Gly Thr Gln Thr Tyr Ile Cys
210 215 220

Asn Val Asn His Lys Pro Ser Asn Thr Lys Val Asp Lys Lys Val Glu
225 230 235 240

Pro Lys Ser Cys Asp Lys Thr His Thr Cys Pro Pro Cys Pro Ala Pro
245 250 255

Glu Leu Leu Gly Gly Pro Ser Val Phe Leu Phe Pro Pro Lys Pro Lys
260 265 270

Asp Thr Leu Met Ile Ser Arg Thr Pro Glu Val Thr Cys Val Val Val
275 280 285

Asp Val Ser His Glu Asp Pro Glu Val Lys Phe Asn Trp Tyr Val Asp
290 295 300

Gly Val Glu Val His Asn Ala Lys Thr Lys Pro Arg Glu Glu Gln Tyr
305 310 315 320

Ala Ser Thr Tyr Arg Val Val Ser Val Leu Thr Val Leu His Gln Asp
325 330 335

Trp Leu Asn Gly Lys Glu Tyr Lys Cys Lys Val Ser Asn Lys Ala Leu
340 345 350

Pro Ala Pro Ile Glu Lys Thr Ile Ser Lys Ala Lys Gly Gln Pro Arg
355 360 365

Glu Pro Gln Val Tyr Thr Leu Pro Pro Ser Arg Asp Glu Leu Thr Lys
370 375 380

```
Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470


<210> SEQ ID NO 417
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 417

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Pro Asp Tyr Asn Met Asp Trp Val Arg Gln Ala Pro Gly Gln Arg Leu
    50                  55                  60

Glu Trp Met Gly Tyr Ile Asn Pro Asp Asn Gly Gly Thr Ile Tyr Asn
65                  70                  75                  80

Gln Lys Phe Lys Gly Arg Ala Thr Leu Thr Val Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Leu Asp Ser Ser Gly Tyr Gly Tyr Tyr Ala Met
        115                 120                 125

Asp Tyr Trp Gly Gln Gly Thr Ser Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
```

```
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Ala Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470


<210> SEQ ID NO 418
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 418

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Pro Asp Tyr Asn Met Asp Trp Val Arg Gln Ala Pro Gly Gln Ser Leu
    50                  55                  60

Glu Trp Ile Gly Tyr Ile Asn Pro Asp Asn Gly Gly Thr Ile Tyr Asn
65                  70                  75                  80

Gln Lys Phe Lys Gly Arg Ala Thr Leu Thr Val Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Leu Asp Ser Ser Gly Tyr Gly Tyr Tyr Ala Met
        115                 120                 125

Asp Tyr Trp Gly Gln Gly Thr Ser Val Thr Val Ser Ser Ala Ser Thr
    130                 135                 140
```

Lys Gly Pro Ser Val Phe Pro Leu Ala Pro Ser Ser Lys Ser Thr Ser
145 150 155 160

Gly Gly Thr Ala Ala Leu Gly Cys Leu Val Lys Asp Tyr Phe Pro Glu
165 170 175

Pro Val Thr Val Ser Trp Asn Ser Gly Ala Leu Thr Ser Gly Val His
180 185 190

Thr Phe Pro Ala Val Leu Gln Ser Ser Gly Leu Tyr Ser Leu Ser Ser
195 200 205

Val Val Thr Val Pro Ser Ser Ser Leu Gly Thr Gln Thr Tyr Ile Cys
210 215 220

Asn Val Asn His Lys Pro Ser Asn Thr Lys Val Asp Lys Lys Val Glu
225 230 235 240

Pro Lys Ser Cys Asp Lys Thr His Thr Cys Pro Pro Cys Pro Ala Pro
245 250 255

Glu Leu Leu Gly Gly Pro Ser Val Phe Leu Phe Pro Pro Lys Pro Lys
260 265 270

Asp Thr Leu Met Ile Ser Arg Thr Pro Glu Val Thr Cys Val Val Val
275 280 285

Asp Val Ser His Glu Asp Pro Glu Val Lys Phe Asn Trp Tyr Val Asp
290 295 300

Gly Val Glu Val His Asn Ala Lys Thr Lys Pro Arg Glu Glu Gln Tyr
305 310 315 320

Ala Ser Thr Tyr Arg Val Val Ser Val Leu Thr Val Leu His Gln Asp
325 330 335

Trp Leu Asn Gly Lys Glu Tyr Lys Cys Lys Val Ser Asn Lys Ala Leu
340 345 350

Pro Ala Pro Ile Glu Lys Thr Ile Ser Lys Ala Lys Gly Gln Pro Arg
355 360 365

Glu Pro Gln Val Tyr Thr Leu Pro Pro Ser Arg Asp Glu Leu Thr Lys
370 375 380

Asn Gln Val Ser Leu Thr Cys Leu Val Lys Gly Phe Tyr Pro Ser Asp
385 390 395 400

Ile Ala Val Glu Trp Glu Ser Asn Gly Gln Pro Glu Asn Asn Tyr Lys
405 410 415

Thr Thr Pro Pro Val Leu Asp Ser Asp Gly Ser Phe Phe Leu Tyr Ser
420 425 430

Lys Leu Thr Val Asp Lys Ser Arg Trp Gln Gln Gly Asn Val Phe Ser
435 440 445

Cys Ser Val Met His Glu Ala Leu His Asn His Tyr Thr Gln Lys Ser
450 455 460

Leu Ser Leu Ser Pro Gly Lys
465 470

<210> SEQ ID NO 419
<211> LENGTH: 237
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 419

Met Gly Trp Ser Cys Ile Ile Leu Phe Leu Val Ala Thr Ala Thr Gly
1 5 10 15

Val His Ser Asp Ile Val Met Thr Gln Ser Pro Asp Ser Leu Ala Val
20 25 30

```
Ser Leu Gly Glu Arg Ala Thr Ile Asn Cys Arg Ala Ser Glu Ser Val
        35                  40                  45

Asp Asn Tyr Gly Ile Ser Phe Met His Trp Tyr Gln Gln Lys Pro Gly
    50                  55                  60

Gln Pro Pro Lys Leu Leu Ile Tyr Arg Ala Ser Asn Leu Asp Ser Gly
65                  70                  75                  80

Val Pro Asp Arg Phe Ser Gly Ser Gly Ser Gly Thr Asp Phe Thr Leu
                85                  90                  95

Thr Ile Ser Ser Leu Gln Ala Glu Asp Val Ala Thr Tyr Tyr Cys Gln
            100                 105                 110

Gln Ser Tyr Lys Asp Pro Arg Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 420
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 420

```
Met Gly Trp Ser Cys Ile Ile Leu Phe Leu Val Ala Thr Ala Thr Gly
1               5                   10                  15

Val His Ser Asp Ile Val Leu Thr Gln Ser Pro Ala Ser Leu Ala Val
            20                  25                  30

Ser Pro Gly Gln Arg Ala Thr Ile Thr Cys Arg Ala Ser Glu Ser Val
        35                  40                  45

Asp Asn Tyr Gly Ile Ser Phe Met His Trp Tyr Gln Gln Lys Pro Gly
    50                  55                  60

Gln Pro Pro Lys Leu Leu Ile Tyr Arg Ala Ser Asn Leu Asp Ser Glu
65                  70                  75                  80

Val Pro Ala Arg Phe Ser Gly Ser Gly Ser Arg Thr Asp Phe Thr Leu
                85                  90                  95

Thr Ile Asn Pro Val Glu Ala Asn Asp Thr Ala Thr Tyr Tyr Cys Gln
            100                 105                 110

Gln Ser Tyr Lys Asp Pro Arg Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
```

145 150 155 160

Asn Phe Tyr Pro Arg Glu Ala Lys Val Gln Trp Lys Val Asp Asn Ala
165 170 175

Leu Gln Ser Gly Asn Ser Gln Glu Ser Val Thr Glu Gln Asp Ser Lys
180 185 190

Asp Ser Thr Tyr Ser Leu Ser Ser Thr Leu Thr Leu Ser Lys Ala Asp
195 200 205

Tyr Glu Lys His Lys Val Tyr Ala Cys Glu Val Thr His Gln Gly Leu
210 215 220

Ser Ser Pro Val Thr Lys Ser Phe Asn Arg Gly Glu Cys
225 230 235

<210> SEQ ID NO 421
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 421

Gln Ser Leu Glu Glu Ser Gly Gly Asp Leu Val Lys Pro Gly Ala Ser
1 5 10 15

Leu Thr Leu Thr Cys Arg Val Ser Gly Phe Ser Phe Ser Ser Ser Tyr
20 25 30

Tyr Met Cys Trp Val Arg Gln Ala Pro Gly Lys Gly Leu Glu Trp Ile
35 40 45

Ala Cys Ile Gly Thr Thr Arg Gly Ser Thr Tyr Tyr Ala Thr Trp Ala
50 55 60

Lys Gly Arg Phe Thr Ile Ser Lys Ile Ser Ser Thr Thr Val Thr Leu
65 70 75 80

Gln Met Thr Ser Leu Thr Asp Ala Asp Thr Ala Thr Tyr Phe Cys Ala
85 90 95

Arg Asp Ala Thr Gly Tyr Arg Ile Asn Thr Ile Gly Leu Tyr Phe Asn
100 105 110

Leu Trp Gly Pro Gly Thr Leu Val Thr Val Ser Ser
115 120

<210> SEQ ID NO 422
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 422

Gln Ser Leu Leu Glu Ser Gly Gly Gly Leu Val Lys Pro Gly Gly Ser
1 5 10 15

Leu Arg Leu Ser Cys Ala Val Ser Gly Phe Ser Phe Ser Ser Ser Tyr
20 25 30

Tyr Met Cys Trp Val Arg Gln Ala Pro Gly Lys Gly Leu Glu Trp Val
35 40 45

Ser Cys Ile Gly Thr Thr Arg Gly Ser Thr Tyr Tyr Ala Asp Ser Ala
50 55 60

Lys Gly Arg Phe Thr Ile Ser Lys Ile Ser Lys Asn Thr Val Tyr Leu
65 70 75 80

Gln Met Thr Ser Leu Arg Ala Glu Asp Thr Ala Val Tyr Phe Cys Ala

```
                85                  90                  95

Arg Asp Ala Thr Gly Tyr Arg Ile Asn Thr Ile Gly Leu Tyr Phe Asn
            100                 105                 110

Leu Trp Gly Pro Gly Thr Leu Val Thr Val Ser Ser
        115                 120


<210> SEQ ID NO 423
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Glu Val Gln Leu Leu Glu Ser Gly Gly Gly Leu Val Lys Pro Gly Gly
1               5                   10                  15

Ser Leu Arg Leu Ser Cys Ala Val Ser Gly Phe Ser Phe Ser Ser Ser
            20                  25                  30

Tyr Tyr Met Cys Trp Val Arg Gln Ala Pro Gly Lys Gly Leu Glu Trp
        35                  40                  45

Val Ser Cys Ile Gly Thr Thr Arg Gly Ser Thr Tyr Tyr Ala Asp Ser
    50                  55                  60

Ala Lys Gly Arg Phe Thr Ile Ser Lys Asp Asn Ser Lys Asn Thr Val
65                  70                  75                  80

Tyr Leu Gln Met Thr Ser Leu Arg Ala Glu Asp Thr Ala Val Tyr Phe
                85                  90                  95

Cys Ala Arg Asp Ala Thr Gly Tyr Arg Ile Asn Thr Ile Gly Leu Tyr
            100                 105                 110

Phe Asn Leu Trp Gly Gln Gly Thr Leu Val Thr Val Ser Ser
        115                 120                 125


<210> SEQ ID NO 424
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Gln Ser Leu Leu Glu Ser Gly Gly Gly Leu Val Lys Pro Gly Gly Ser
1               5                   10                  15

Leu Arg Leu Ser Cys Ala Val Ser Gly Phe Ser Phe Ser Ser Ser Tyr
            20                  25                  30

Tyr Met Cys Trp Val Arg Gln Ala Pro Gly Lys Gly Leu Glu Trp Val
        35                  40                  45

Ser Cys Ile Gly Thr Thr Arg Gly Ser Thr Tyr Tyr Ala Asp Ser Ala
    50                  55                  60

Lys Gly Arg Phe Thr Ile Ser Lys Glu Ser Lys Asn Thr Val Tyr Leu
65                  70                  75                  80

Gln Met Ser Ser Leu Arg Ala Glu Asp Thr Ala Val Tyr Phe Cys Ala
                85                  90                  95

Arg Asp Ala Thr Gly Tyr Arg Ile Asn Thr Ile Gly Leu Tyr Phe Asn
            100                 105                 110

Leu Trp Gly Pro Gly Thr Leu Val Thr Val Ser Ser
        115                 120
```

<210> SEQ ID NO 425
<211> LENGTH: 126
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 425

Glu Val Gln Leu Leu Glu Ser Gly Gly Gly Leu Val Lys Pro Gly Gly
1 5 10 15

Ser Leu Arg Leu Ser Cys Ala Val Ser Gly Phe Ser Phe Ser Ser Ser
20 25 30

Tyr Tyr Met Cys Trp Val Arg Gln Ala Pro Gly Lys Gly Leu Glu Trp
35 40 45

Val Ser Cys Ile Gly Thr Thr Arg Gly Ser Thr Tyr Tyr Ala Asp Ser
50 55 60

Ala Lys Gly Arg Phe Thr Ile Ser Lys Asp Asn Ser Lys Asn Thr Val
65 70 75 80

Tyr Leu Gln Met Ser Ser Leu Arg Ala Glu Asp Thr Ala Val Tyr Phe
85 90 95

Cys Ala Arg Asp Ala Thr Gly Tyr Arg Ile Asn Thr Ile Gly Leu Tyr
100 105 110

Phe Asn Leu Trp Gly Gln Gly Thr Leu Val Thr Val Ser Ser
115 120 125

<210> SEQ ID NO 426
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 426

Gln Ser Leu Leu Glu Ser Gly Gly Gly Leu Val Lys Pro Gly Gly Ser
1 5 10 15

Leu Arg Leu Ser Cys Ala Val Ser Gly Phe Ser Phe Ser Ser Ser Tyr
20 25 30

Tyr Met Cys Trp Val Arg Gln Ala Pro Gly Lys Gly Leu Glu Trp Val
35 40 45

Ser Cys Ile Gly Thr Thr Arg Gly Ser Thr Tyr Tyr Ala Asp Ser Ala
50 55 60

Lys Gly Arg Phe Thr Ile Ser Lys Glu Ser Lys Asn Thr Val Tyr Leu
65 70 75 80

Gln Met Ser Ser Leu Arg Ala Glu Asp Thr Ala Val Tyr Phe Cys Ala
85 90 95

Arg Asp Ala Thr Gly Tyr Arg Ile Gln Thr Ile Gly Leu Tyr Phe Asn
100 105 110

Leu Trp Gly Pro Gly Thr Leu Val Thr Val Ser Ser
115 120

<210> SEQ ID NO 427
<211> LENGTH: 126
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 427

Glu Val Gln Leu Leu Glu Ser Gly Gly Gly Leu Val Lys Pro Gly Gly
1 5 10 15

Ser Leu Arg Leu Ser Cys Ala Val Ser Gly Phe Ser Phe Ser Ser Ser
20 25 30

Tyr Tyr Met Cys Trp Val Arg Gln Ala Pro Gly Lys Gly Leu Glu Trp
35 40 45

Val Ser Cys Ile Gly Thr Thr Arg Gly Ser Thr Tyr Tyr Ala Asp Ser
50 55 60

Ala Lys Gly Arg Phe Thr Ile Ser Lys Asp Asn Ser Lys Asn Thr Val
65 70 75 80

Tyr Leu Gln Met Ser Ser Leu Arg Ala Glu Asp Thr Ala Val Tyr Phe
85 90 95

Cys Ala Arg Asp Ala Thr Gly Tyr Arg Ile Gln Thr Ile Gly Leu Tyr
100 105 110

Phe Asn Leu Trp Gly Gln Gly Thr Leu Val Thr Val Ser Ser
115 120 125

<210> SEQ ID NO 428
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 428

Glu Leu Thr Gln Thr Pro Ser Ser Val Glu Ala Ala Val Gly Gly Thr
1 5 10 15

Pro Thr Ile Lys Cys Gln Ala Ser Gln Thr Ile Tyr Ser Tyr Leu Ser
20 25 30

Trp Tyr Gln Gln Lys Pro Gly Gln Pro Pro Lys Leu Leu Ile Tyr Glu
35 40 45

Ala Ser Lys Leu Ala Ser Gly Val Pro Ser Arg Phe Ser Gly Ser Gly
50 55 60

Ser Gly Thr Asp Tyr Thr Leu Thr Ile Ser Asp Leu Glu Cys Ala Asp
65 70 75 80

Ala Ala Thr Tyr Tyr Cys Gln Ser Tyr His Gly Thr Ala Ser Thr Glu
85 90 95

Tyr Asn Thr Phe Gly Gly Gly Thr Glu Val Val Val Lys
100 105

<210> SEQ ID NO 429
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 429

Gln Leu Thr Gln Ser Pro Ser Ser Leu Ser Ala Ser Val Gly Asp Arg
1 5 10 15

Val Thr Ile Thr Cys Gln Ala Ser Gln Thr Ile Tyr Ser Tyr Leu Ser
20 25 30

Trp Tyr Gln Gln Lys Pro Gly Lys Pro Pro Lys Leu Leu Ile Tyr Glu
35 40 45

Ala Ser Lys Leu Ala Ser Gly Val Pro Ser Arg Phe Ser Gly Ser Gly
50 55 60

Ser Gly Thr Asp Tyr Thr Leu Thr Ile Ser Ser Leu Gln Pro Glu Asp
65 70 75 80

Phe Ala Thr Tyr Tyr Cys Gln Ser Tyr His Gly Thr Ala Ser Thr Glu
85 90 95

Tyr Asn Thr Phe Gly Gly Gly Thr Lys Val Glu Ile Lys
100 105

<210> SEQ ID NO 430
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 430

Asp Ile Gln Leu Thr Gln Ser Pro Ser Ser Leu Ser Ala Ser Val Gly
1 5 10 15

Asp Arg Val Thr Ile Thr Cys Gln Ala Ser Gln Thr Ile Tyr Ser Tyr
20 25 30

Leu Ser Trp Tyr Gln Gln Lys Pro Gly Lys Pro Pro Lys Leu Leu Ile
35 40 45

Tyr Glu Ala Ser Lys Leu Ala Ser Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Gln Ser Tyr His Gly Thr Ala Ser
85 90 95

Thr Glu Tyr Asn Thr Phe Gly Gly Gly Thr Lys Val Glu Ile Lys
100 105 110

<210> SEQ ID NO 431
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 431

Gln Leu Thr Gln Ser Pro Ser Ser Leu Ser Ala Ser Val Gly Asp Arg
1 5 10 15

Val Thr Ile Thr Cys Gln Ala Ser Gln Thr Ile Tyr Ser Tyr Leu Ser
20 25 30

Trp Tyr Gln Gln Lys Pro Gly Lys Pro Pro Lys Leu Leu Ile Tyr Glu
35 40 45

Ala Ser Lys Leu Ala Ser Gly Val Pro Ser Arg Phe Ser Gly Ser Gly
50 55 60

Ser Gly Thr Asp Tyr Thr Leu Thr Ile Ser Ser Leu Gln Pro Glu Asp
65 70 75 80

Thr Ala Thr Tyr Tyr Cys Gln Ser Tyr His Gly Thr Ala Ser Thr Glu
85 90 95

Tyr Asn Thr Phe Gly Gly Gly Thr Lys Val Glu Ile Lys
100 105

<210> SEQ ID NO 432
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 432

Asp Ile Gln Leu Thr Gln Ser Pro Ser Ser Leu Ser Ala Ser Val Gly
1 5 10 15

Asp Arg Val Thr Ile Thr Cys Gln Ala Ser Gln Thr Ile Tyr Ser Tyr
20 25 30

Leu Ser Trp Tyr Gln Gln Lys Pro Gly Lys Pro Pro Lys Leu Leu Ile
35 40 45

Tyr Glu Ala Ser Lys Leu Ala Ser Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Thr Ala Thr Tyr Tyr Cys Gln Ser Tyr His Gly Thr Ala Ser
85 90 95

Thr Glu Tyr Asn Thr Phe Gly Gly Gly Thr Lys Val Glu Ile Lys
100 105 110

<210> SEQ ID NO 433
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 433

Gln Leu Thr Gln Ser Pro Ser Ser Leu Ser Ala Ser Val Gly Asp Arg
1 5 10 15

Val Thr Ile Thr Cys Gln Ala Ser Gln Thr Ile Tyr Ser Tyr Leu Ser
20 25 30

Trp Tyr Gln Gln Lys Pro Gly Lys Pro Pro Lys Leu Leu Ile Tyr Glu
35 40 45

Ala Ser Lys Leu Ala Ser Gly Val Pro Ser Arg Phe Ser Gly Ser Gly
50 55 60

Ser Gly Thr Asp Tyr Thr Leu Thr Ile Ser Ser Leu Gln Pro Glu Asp
65 70 75 80

Thr Ala Thr Tyr Tyr Cys Gln Ser Tyr His Gly Thr Ala Ser Thr Glu
85 90 95

Tyr Gln Thr Phe Gly Gly Gly Thr Lys Val Glu Ile Lys
100 105

<210> SEQ ID NO 434
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 434

Asp Ile Gln Leu Thr Gln Ser Pro Ser Ser Leu Ser Ala Ser Val Gly
1 5 10 15

Asp Arg Val Thr Ile Thr Cys Gln Ala Ser Gln Thr Ile Tyr Ser Tyr
20 25 30

Leu Ser Trp Tyr Gln Gln Lys Pro Gly Lys Pro Pro Lys Leu Leu Ile
35 40 45

Tyr Glu Ala Ser Lys Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Thr Ala Thr Tyr Tyr Cys Gln Ser Tyr His Gly Thr Ala Ser
                85                  90                  95

Thr Glu Tyr Gln Thr Phe Gly Gly Gly Thr Lys Val Glu Ile Lys
            100                 105                 110

<210> SEQ ID NO 435
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Asp Ile Val Met Thr Gln Ser Pro Asp Ser Leu Ala Val Ser Leu Gly
1               5                   10                  15

Glu Arg Ala Thr Ile Asn Cys Lys Ser Ser
            20                  25

<210> SEQ ID NO 436
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Gly Phe Thr Phe Ser Thr Tyr Gly
1               5

<210> SEQ ID NO 437
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Gly Phe Thr Phe Ser Ser Tyr Trp
1               5

<210> SEQ ID NO 438
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Gly Phe Thr Phe Asp Asp Tyr Gly
1               5

<210> SEQ ID NO 439
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 439

Gly Tyr Thr Phe Thr Ser Tyr Gly
1               5


<210> SEQ ID NO 440
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Gly Phe Thr Phe Ser Ser Tyr Ala
1               5


<210> SEQ ID NO 441
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Gly Tyr Thr Phe Thr Arg Tyr Tyr
1               5


<210> SEQ ID NO 442
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Asp Leu Gly His Phe Asp Ser Gly Ser Ser Tyr Phe Asp Tyr
1               5                   10


<210> SEQ ID NO 443
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 443

Lys Arg Pro Ser Gly Val Pro Asp Arg Phe Ser Gly Ser Lys Ser Gly
1               5                   10                  15

Asn Thr Ala Ser Leu Thr Ile Ser Gly Leu Gln Ala Glu Asp Glu Ala
            20                  25                  30

Asp Tyr His Cys
        35
```